US011654161B2

(12) United States Patent
Hartung et al.

(10) Patent No.: US 11,654,161 B2
(45) Date of Patent: *May 23, 2023

(54) COMPOSITIONS AND METHODS FOR NEURALGENESIS

(71) Applicant: The Johns Hopkins University, Baltimore, MD (US)

(72) Inventors: Thomas Hartung, Baltimore, MD (US); David Pamies, Baltimore, MD (US); Helena T. Hogberg, Nottingham, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/700,750

(22) Filed: Dec. 2, 2019

(65) Prior Publication Data

US 2020/0121725 A1 Apr. 23, 2020

Related U.S. Application Data

(63) Continuation of application No. 16/077,411, filed as application No. PCT/US2017/017464 on Feb. 10, 2017.

(60) Provisional application No. 62/294,112, filed on Feb. 11, 2016.

(51) Int. Cl.

| | |
|---|---|
| ***A61K 35/30*** | (2015.01) |
| ***A61K 38/41*** | (2006.01) |
| ***C12N 5/074*** | (2010.01) |
| ***G01N 33/68*** | (2006.01) |
| ***G01N 33/50*** | (2006.01) |
| ***C12N 5/00*** | (2006.01) |
| ***G01N 33/58*** | (2006.01) |

(52) U.S. Cl.

CPC .............. *A61K 35/30* (2013.01); *A61K 38/41* (2013.01); *C12N 5/0062* (2013.01); *C12N 5/0696* (2013.01); *G01N 33/50* (2013.01); *G01N 33/58* (2013.01); *G01N 33/6893* (2013.01); *C12N 2501/11* (2013.01); *C12N 2501/115* (2013.01); *C12N 2501/13* (2013.01); *C12N 2501/22* (2013.01)

(58) Field of Classification Search

CPC ...... A61K 35/30; A61K 38/41; C12N 5/0062; C12N 5/0696; C12N 5/0697; C12N 2501/22; G01N 33/58

See application file for complete search history.

(56) References Cited

U.S. PATENT DOCUMENTS

| | | | |
|---|---|---|---|
| 2006/0270032 A1 | 11/2006 | Bhatia et al. |
| 2007/0015210 A1 | 1/2007 | Ezekiel |
| 2015/0267164 A1 | 9/2015 | Laukkanen et al. |

OTHER PUBLICATIONS

Nunes, Marta C., et al. "Identification and isolation of multipotential neural progenitor cells from the subcortical white matter of the adult human brain." Nature medicine 9.4 (2003): 439-447 (9 pages).

Uroukov, Ivan S., et al. "Electrophysiological measurements in three-dimensional in vivo-mimetic organotypic cell cultures: Preliminary studies with hen embryo brain spheroids." Neuroscience letters 404.1-2 (2006): 33-38 (6 pages).

Douvaras, Panagiotis, et al. "Efficient generation of myelinating oligodendrocytes from primary progressive multiple sclerosis patients by induced pluripotent stem cells." Stem cell reports 3.2 (2014): 250-259 (10 pages).

Hayase, Makoto, et al. "Committed neural progenitor cells derived from genetically modified bone marrow stromal cells ameliorate deficits in a rat model of stroke." Journal of Cerebral Blood Flow & Metabolism 29.8 (2009): 1409-1420 (12 pages).

Hopkins, Amy M., et al. "3D in vitro modeling of the central nervous system." Progress in neurobiology 125 (2015): 1-25.

Pamies, David, et al. "A human brain microphysiological system derived from induced pluripotent stem cells to study neurological diseases and toxicity." Altex 34.3 (2017): 362 (27 pages).

European Search Report of counterpart EP Application No. 17 75 0868, dated Dec. 19, 2020 (11 pages).

Written Opinion of International Application No. PCT/US2017/017464, dated Jun. 20, 2017 (9 pages).

Dingle et al., "Three-Dimensional Neural Spheroid Culture: An In Vitro Model for Cortical Studies", Tissue Eng Part C Methods, 21(12):1274-83 (2015).

*Primary Examiner* — Olga N Chernyshev

(74) *Attorney, Agent, or Firm* — Fox Rothschild LLP

(57) ABSTRACT

The present invention relates to novel compositions and methods to produce 3D organ equivalents of the brain (i.e. "mini-brains"). The invention also relates to methods of using human induced pluripotent stem cells, a combination of growth and other soluble factors and gyratory shaking. Cells from healthy or diseased donors or animals can be used to allow testing different genetic backgrounds. The model can be further enhanced by using genetically modified cells, adding micro-glia or their precursors or indicator cells (e.g. with reporter genes or tracers) as well as adding endothelial cells to form a blood-brain-barrier.

22 Claims, 40 Drawing Sheets
(32 of 40 Drawing Sheet(s) Filed in Color)

Specification includes a Sequence Listing.

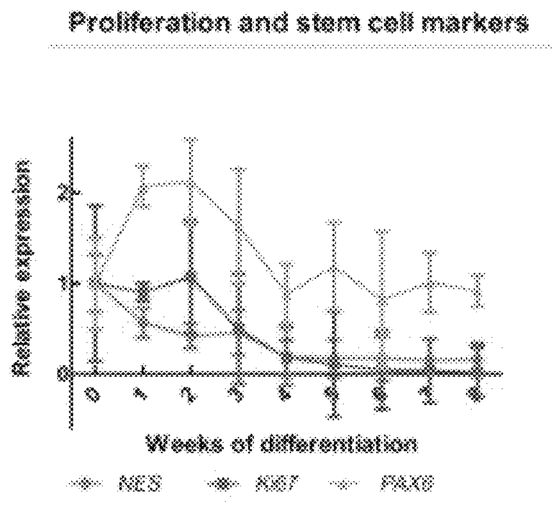
FIG. 1C1
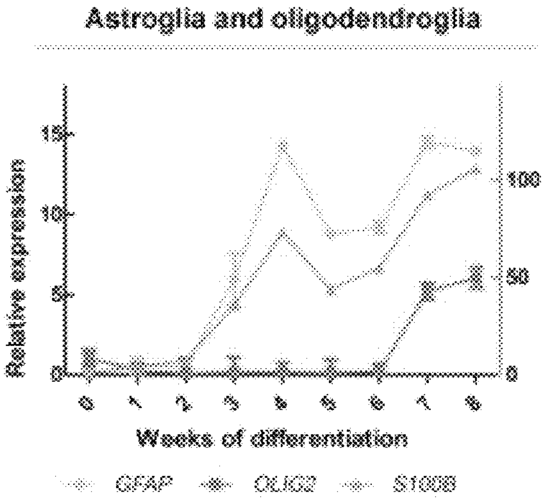
FIG. 1C2

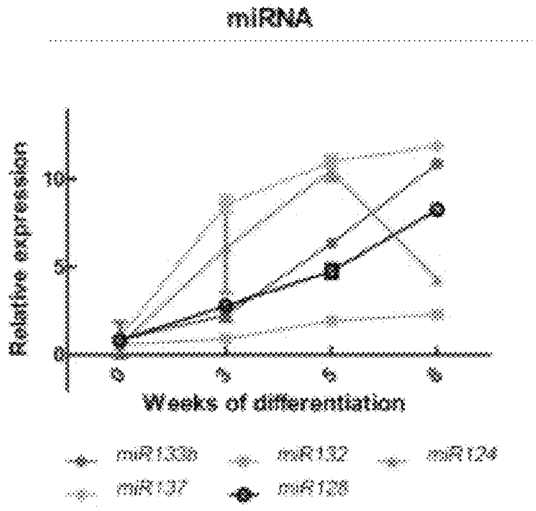
FIG. 1C3
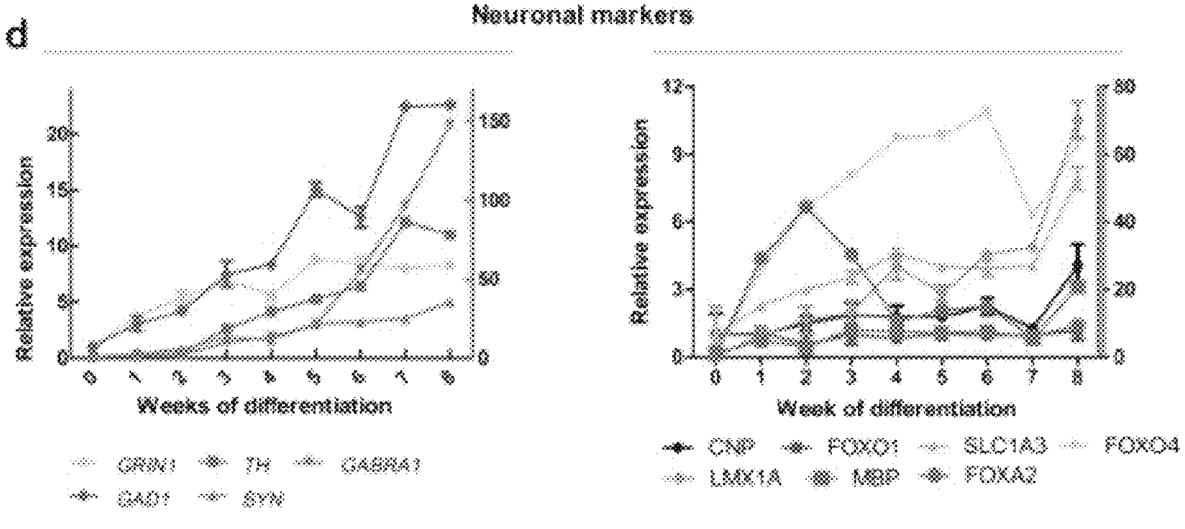
FIG. 1C4

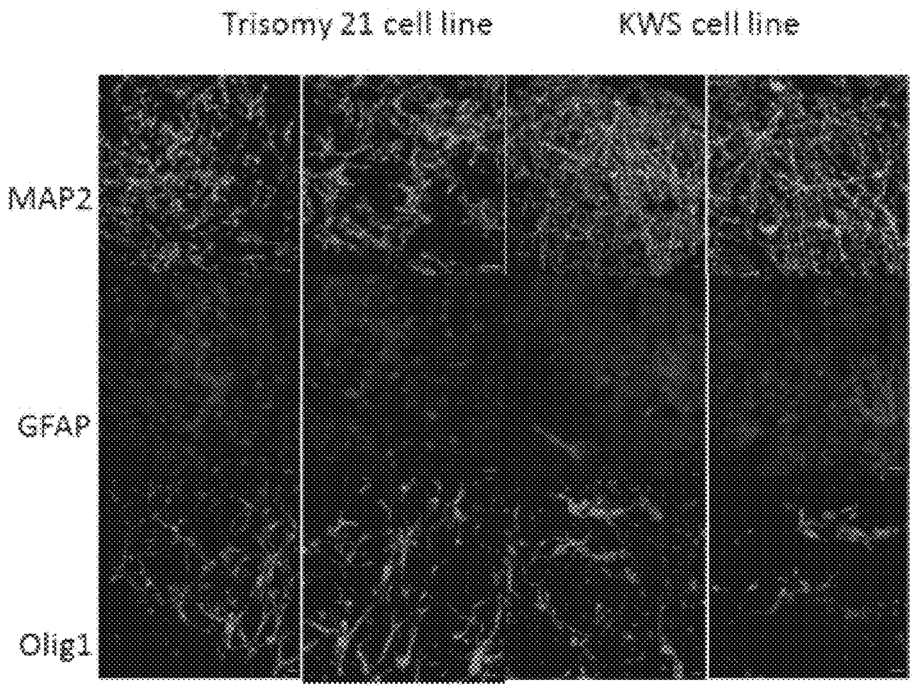
FIG. 1C5

| Amp/Deletion Table | | | | | | | | |
|---|---|---|---|---|---|---|---|---|
| Chr | Amp/Del | Start-Stop (bp) | Size(kb) | Chr Band | # Probes | Log2 Ratio | Genes[a] | Overlap Normal CNVs?[β] |
| 2 | GAIN | 44,479,791-49,652,038 | 5,172 | p21 - p16.3 | 219 | 0.328063 | SLC2A1, SIX3, SIX2, PRKCE, EPAS1, PIGF, SOCS5, MCFD2, TTC7A, CALM2, MSH2, KCNK12, MSH6, FBXO11, LHCGR, FSHR, PREPL, CAMKMT, UNQ6975, SRBD1, LOC388946, ATP6V1E2, RHOQ, CRIPT, LOC388948, LOC100134259, C2orf61, EPCAM, MIR559, FOXN2, KLRAQ1, STON1-GTF2A1L, STON1, GTF2A1L | No |
| 10 | GAIN | 124,347,670-124,351,275 | 3 | q26.13 | 6 | 0.782955 | DMBT1 | Yes |
| 11 | GAIN | 54,872,150-55,032,155 | 160 | q11 | 5 | 0.619389 | TRIM48 | Yes |
| 14 | GAIN | 19,265,142-20,421,677 | 1,157 | q11.2 | 22 | 0.490838 | OR11H12, POTEG, POTEM, OR11H2, OR4Q3, OR4M1, OR4N2, OR4K2, OR4K5, OR4K1 | Yes |
| 14 | GAIN | 67,306,385-67,514,841 | 208 | q23.3 | 28 | 0.555366 | GPHN | Yes |
| 18 | LOSS | 132,387-14,158,122 | 14,026 | p11.32 - p11.21 | 541 | -0.89217 | Too Numerous | No |
| 18 | DEL | 7,694,140-7,821,430 | 127 | p11.23 | 6 | -4.90876 | PTPRM | Yes |
| 18 | LOSS | 14,556,513-15,047,825 | 491 | p11.21 | 14 | -0.5347 | ANKRD30B, MIR3156-2 | Yes |
| X | GAIN | 58,141,950-58,428,287 | 286 | p11.1 | 9 | 0.478356 | | Yes |

FIG. 5C

Glial cell population

FIG. 13A
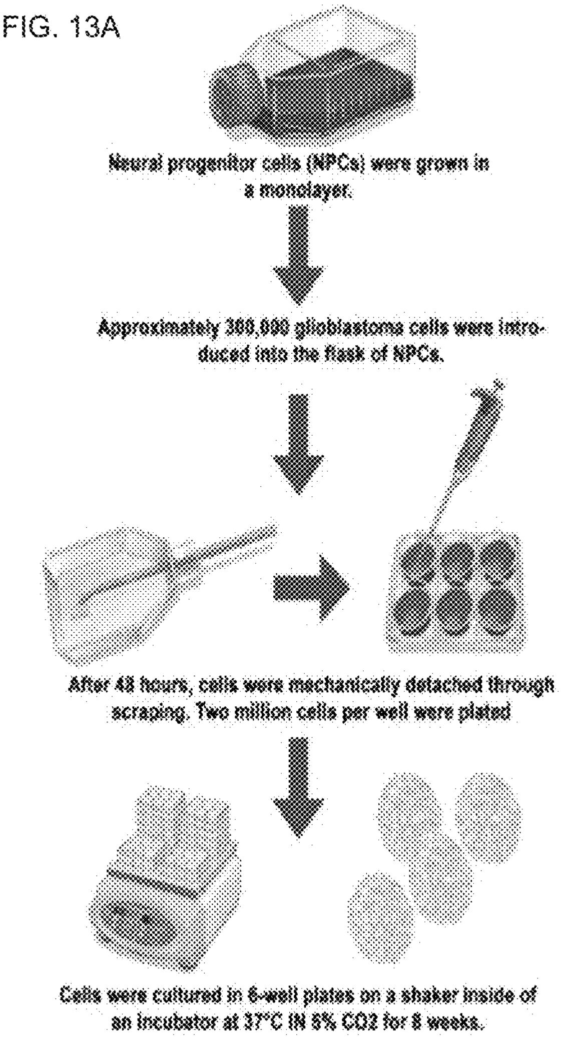
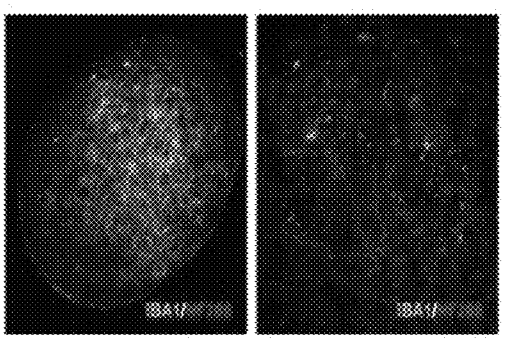
FIG. 13B
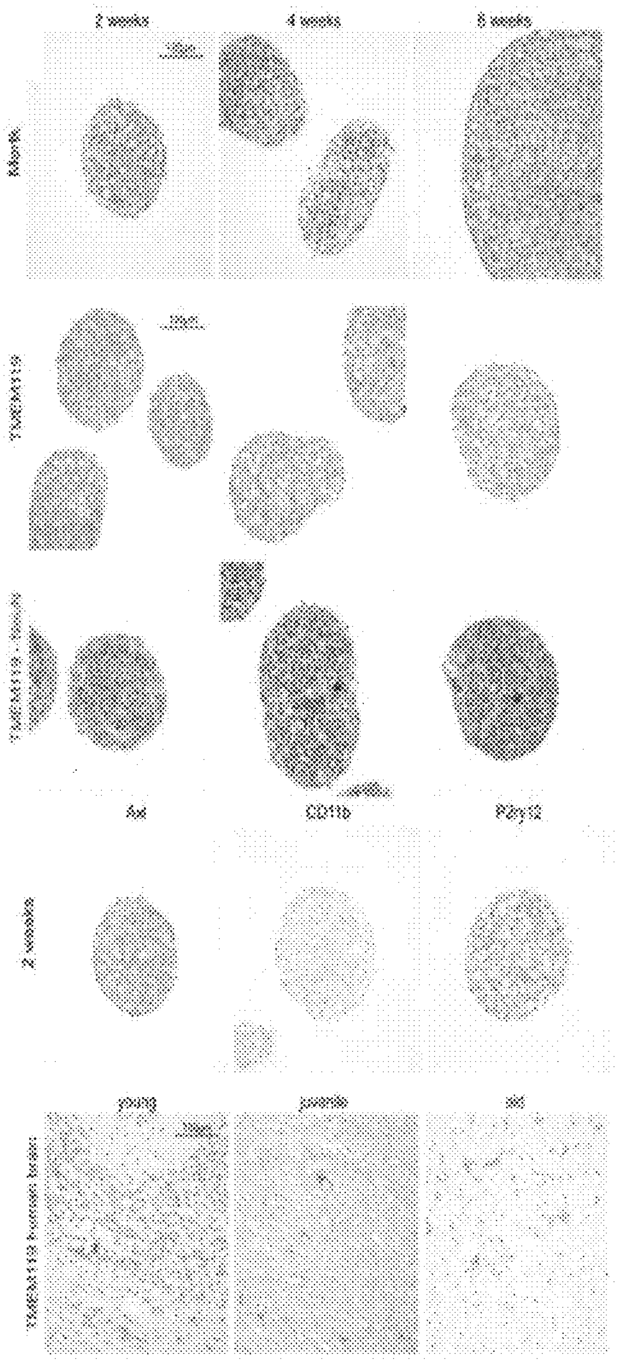
FIG. 13C

SEQUENCE LISTING

```
<160> NUMBER OF SEQ ID NOS: 70

<210> SEQ ID NO 1
<211> LENGTH: 938
<212> TYPE: PRT
<213> ORGANISM: Homo sapiens

<400> SEQUENCE: 1

Met Ser Thr Met Arg Leu Leu Thr Leu Ala Leu Leu Phe Ser Cys Ser
1               5                   10                  15

Val Ala Arg Ala Ala Cys Asp Pro Lys Ile Val Asn Ile Gly Ala Val
            20                  25                  30

Leu Ser Thr Arg Lys His Glu Gln Met Phe Arg Glu Ala Val Asn Gln
        35                  40                  45

Ala Asn Lys Arg His Gly Ser Trp Lys Ile Gln Leu Asn Ala Thr Ser
    50                  55                  60

Val Thr His Lys Pro Asn Ala Ile Gln Met Ala Leu Ser Val Cys Glu
65                  70                  75                  80

Asp Leu Ile Ser Ser Gln Val Tyr Ala Ile Leu Val Ser His Pro Pro
                85                  90                  95

Thr Pro Asn Asp His Phe Thr Pro Thr Pro Val Ser Tyr Thr Ala Gly
            100                 105                 110

Phe Tyr Arg Ile Pro Val Leu Gly Leu Thr Thr Arg Met Ser Ile Tyr
        115                 120                 125

Ser Asp Lys Ser Ile His Leu Ser Phe Leu Arg Thr Val Pro Pro Tyr
    130                 135                 140

Ser His Gln Ser Ser Val Trp Phe Glu Met Met Arg Val Tyr Ser Trp
145                 150                 155                 160

Asn His Ile Ile Leu Leu Val Ser Asp Asp His Glu Gly Arg Ala Ala
                165                 170                 175

Gln Lys Arg Leu Glu Thr Leu Leu Glu Glu Arg Glu Ser Lys Ala Glu
            180                 185                 190
```

```
Lys Val Leu Gln Phe Asp Pro Gly Thr Lys Asn Val Thr Ala Leu Leu
        195                 200                 205

Met Glu Ala Lys Glu Leu Glu Ala Arg Val Ile Ile Leu Ser Ala Ser
    210                 215                 220

Glu Asp Asp Ala Ala Thr Val Tyr Arg Ala Ala Ala Met Leu Asn Met
225                 230                 235                 240

Thr Gly Ser Gly Tyr Val Trp Leu Val Gly Glu Arg Glu Ile Ser Gly
                245                 250                 255

Asn Ala Leu Arg Tyr Ala Pro Asp Gly Ile Leu Gly Leu Gln Leu Ile
            260                 265                 270

Asn Gly Lys Asn Glu Ser Ala His Ile Ser Asp Ala Val Gly Val Val
        275                 280                 285

Ala Gln Ala Val His Glu Leu Leu Glu Lys Glu Asn Ile Thr Asp Pro
    290                 295                 300

Pro Arg Gly Cys Val Gly Asn Thr Asn Ile Trp Lys Thr Gly Pro Leu
305                 310                 315                 320

Phe Lys Arg Val Leu Met Ser Ser Lys Tyr Ala Asp Gly Val Thr Gly
                325                 330                 335

Arg Val Glu Phe Asn Glu Asp Gly Asp Arg Lys Phe Ala Asn Tyr Ser
            340                 345                 350

Ile Met Asn Leu Gln Asn Arg Lys Leu Val Gln Val Gly Ile Tyr Asn
        355                 360                 365

Gly Thr His Val Ile Pro Asn Asp Arg Lys Ile Ile Trp Pro Gly Gly
    370                 375                 380

Glu Thr Glu Lys Pro Arg Gly Tyr Gln Met Ser Thr Arg Leu Lys Ile
385                 390                 395                 400

Val Thr Ile His Gln Glu Pro Phe Val Tyr Val Lys Pro Thr Leu Ser
                405                 410                 415

Asp Gly Thr Cys Lys Glu Glu Phe Thr Val Asn Gly Asp Pro Val Lys
            420                 425                 430

Lys Val Ile Cys Thr Gly Pro Asn Asp Thr Ser Pro Gly Ser Pro Arg
        435                 440                 445

His Thr Val Pro Gln Cys Cys Tyr Gly Phe Cys Ile Asp Leu Leu Ile
    450                 455                 460

Lys Leu Ala Arg Thr Met Asn Phe Thr Tyr Glu Val His Leu Val Ala
465                 470                 475                 480

Asp Gly Lys Phe Gly Thr Gln Glu Arg Val Asn Asn Ser Asn Lys Lys
                485                 490                 495

Glu Trp Asn Gly Met Met Gly Glu Leu Leu Ser Gly Gln Ala Asp Met
            500                 505                 510

Ile Val Ala Pro Leu Thr Ile Asn Asn Glu Arg Ala Gln Tyr Ile Glu
        515                 520                 525

Phe Ser Lys Pro Phe Lys Tyr Gln Gly Leu Thr Ile Leu Val Lys Lys
    530                 535                 540

Glu Ile Pro Arg Ser Thr Leu Asp Ser Phe Met Gln Pro Phe Gln Ser
545                 550                 555                 560

Thr Leu Trp Leu Leu Val Gly Leu Ser Val His Val Val Ala Val Met
                565                 570                 575

Leu Tyr Leu Leu Asp Arg Phe Ser Pro Phe Gly Arg Phe Lys Val Asn
            580                 585                 590

Ser Glu Glu Glu Glu Glu Asp Ala Leu Thr Leu Ser Ser Ala Met Trp
        595                 600                 605
```

Phe Ser Trp Gly Val Leu Leu Asn Ser Gly Ile Gly Glu Gly Ala Pro
    610                 615                 620

Arg Ser Phe Ser Ala Arg Ile Leu Gly Met Val Trp Ala Gly Phe Ala
625                 630                 635                 640

Met Ile Ile Val Ala Ser Tyr Thr Ala Asn Leu Ala Ala Phe Leu Val
                645                 650                 655

Leu Asp Arg Pro Glu Glu Arg Ile Thr Gly Ile Asn Asp Pro Arg Leu
            660                 665                 670

Arg Asn Pro Ser Asp Lys Phe Ile Tyr Ala Thr Val Lys Gln Ser Ser
        675                 680                 685

Val Asp Ile Tyr Phe Arg Arg Gln Val Glu Leu Ser Thr Met Tyr Arg
    690                 695                 700

His Met Glu Lys His Asn Tyr Glu Ser Ala Ala Glu Ala Ile Gln Ala
705                 710                 715                 720

Val Arg Asp Asn Lys Leu His Ala Phe Ile Trp Asp Ser Ala Val Leu
                725                 730                 735

Glu Phe Glu Ala Ser Gln Lys Cys Asp Leu Val Thr Thr Gly Glu Leu
            740                 745                 750

Phe Phe Arg Ser Gly Phe Gly Ile Gly Met Arg Lys Asp Ser Pro Trp
        755                 760                 765

Lys Gln Asn Val Ser Leu Ser Ile Leu Lys Ser His Glu Asn Gly Phe
    770                 775                 780

Met Glu Asp Leu Asp Lys Thr Trp Val Arg Tyr Gln Glu Cys Asp Ser
785                 790                 795                 800

Arg Ser Asn Ala Pro Ala Thr Leu Thr Phe Glu Asn Met Ala Gly Val
                805                 810                 815

Phe Met Leu Val Ala Gly Gly Ile Val Ala Gly Ile Phe Leu Ile Phe
            820                 825                 830

Ile Glu Ile Ala Tyr Lys Arg His Lys Asp Ala Arg Arg Lys Gln Met
        835                 840                 845

Gln Leu Ala Phe Ala Ala Val Asn Val Trp Arg Lys Asn Leu Gln Asp
    850                 855                 860

Arg Lys Ser Gly Arg Ala Glu Pro Asp Pro Lys Lys Lys Ala Thr Phe
865                 870                 875                 880

Arg Ala Ile Thr Ser Thr Leu Ala Ser Ser Phe Lys Arg Arg Arg Ser
                885                 890                 895

Ser Lys Asp Thr Ser Thr Gly Gly Gly Arg Gly Ala Leu Gln Asn Gln
            900                 905                 910

Lys Asp Thr Val Leu Pro Arg Arg Ala Ile Glu Arg Glu Glu Gly Gln
        915                 920                 925

Leu Gln Leu Cys Ser Arg His Arg Glu Ser
    930                 935

<210> SEQ ID NO 2
<211> LENGTH: 4400
<212> TYPE: DNA
<213> ORGANISM: Homo sapiens

<400> SEQUENCE: 2
gtcgccgcag cgtccggacc ggaaccagcg ccgtccgcgg agccgccgcc gccgccgccg 60
ggccctttcc aagccgggcg ctcggagctg tgcccggccc cgcttcagca ccgcggacag 120
cgccggccgc gtggggctga gccccgagcc cccgcgcacg cttcagcgcc ccttccctcg 180
gccgacgtcc cgggaccgcc gctccggggg agacgtggcg tccgcagccc gcggggccgg 240

-continued

```
gcgagcgcag gacggcccgg aagccccgcg ggggatgcgc cgagggcccc gcgttcgcgc    300
cgcgcagagc caggcccgcg gcccgagccc atgagcacca tgcgcctgct gacgctcgcc    360
ctgctgttct cctgctccgt cgcccgtgcc gcgtgcgacc ccaagatcgt caacattggc    420
gcggtgctga gcacgcggaa gcacgagcag atgttccgcg aggccgtgaa ccaggccaac    480
aagcggcacg gctcctggaa gattcagctc aatgccacct ccgtcacgca caagcccaac    540
gccatccaga tggctctgtc ggtgtgcgag gacctcatct ccagccaggt ctacgccatc    600
ctagttagcc atccacctac ccccaacgac cacttcactc ccacccctgt ctcctacaca    660
gccggcttct accgcatacc cgtgctgggg ctgaccaccc gcatgtccat ctactcggac    720
aagagcatcc acctgagctt cctgcgcacc gtgccgccct actcccacca gtccagcgtg    780
tggtttgaga tgatgcgtgt ctacagctgg aaccacatca tcctgctggt cagcgacgac    840
cacgagggcc gggcggctca gaaacgcctg gagacgctgc tggaggagcg tgagtccaag    900
gcagagaagg tgctgcagtt tgacccaggg accaagaacg tgacggccct gctgatggag    960
gcgaaagagc tggaggcccg ggtcatcatc ctttctgcca gcgaggacga tgctgccact   1020
gtataccgcg cagccgcgat gctgaacatg acgggctccg ggtacgtgtg gctggtcggc   1080
gagcgcgaga tctcggggaa cgccctgcgc tacgccccag acggcatcct cgggctgcag   1140
ctcatcaacg gcaagaacga gtcggcccac atcagcgacg ccgtgggcgt ggtggcccag   1200
gccgtgcacg agctcctcga gaaggagaac atcaccgacc cgccgcgggg ctgcgtgggc   1260
aacaccaaca tctggaagac cgggccgctc ttcaagagag tgctgatgtc ttccaagtat   1320
gcggatgggg tgactggtcg cgtggagttc aatgaggatg gggaccggaa gttcgccaac   1380
tacagcatca tgaacctgca gaaccgcaag ctggtgcaag tgggcatcta caatggcacc   1440
cacgtcatcc ctaatgacag gaagatcatc tggccaggcg gagagacaga gaagcctcga   1500
gggtaccaga tgtccaccag actgaagatt gtgacgatcc accaggagcc cttcgtgtac   1560
gtcaagccca cgctgagtga tgggacatgc aaggaggagt tcacagtcaa cggcgaccca   1620
gtcaagaagg tgatctgcac cgggcccaac gacacgtcgc cgggcagccc ccgccacacg   1680
gtgcctcagt gttgctacgg cttttgcatc gacctgctca tcaagctggc acggaccatg   1740
aacttcacct acgaggtgca cctggtggca gatggcaagt tcggcacaca ggagcgggtg   1800
aacaacagca acaagaagga gtggaatggg atgatgggcg agctgctcag cgggcaggca   1860
gacatgatcg tggcgccgct aaccataaac aacgagcgcg cgcagtacat cgagttttcc   1920
aagcccttca agtaccaggg cctgactatt ctggtcaaga aggagattcc ccggagcacg   1980
ctggactcgt tcatgcagcc gttccagagc acactgtggc tgctggtggg gctgtcggtg   2040
cacgtggtgg ccgtgatgct gtacctgctg gaccgcttca gccccttcgg ccggttcaag   2100
gtgaacagcg aggaggagga ggaggacgca ctgaccctgt cctcggccat gtggttctcc   2160
tggggcgtcc tgctcaactc cggcatcggg gaaggcgccc ccagaagctt ctcagcgcgc   2220
atcctgggca tggtgtgggc cggctttgcc atgatcatcg tggcctccta caccgccaac   2280
ctggcggcct tcctggtgct ggaccggccg gaggagcgca tcacgggcat caacgaccct   2340
cggctgagga accccctcgga caagtttatc tacgccacgg tgaagcagag ctccgtggat   2400
atctacttcc ggcgccaggt ggagctgagc accatgtacc ggcatatgga gaagcacaac   2460
tacgagagtg cggcggaggc catccaggcc gtgagagaca acaagctgca tgccttcatc   2520
tgggactcgg cggtgctgga gttcgaggcc tcgcagaagt gcgacctggt gacgactgga   2580
gagctgtttt tccgctcggg cttcggcata ggcatgcgca aagacagccc ctggaagcag   2640
```

-continued

```
aacgtctccc tgtccatcct caagtcccac gagaatggct tcatggaaga cctggacaag   2700

acgtgggttc ggtatcagga atgtgactcg cgcagcaacg cccctgcgac ccttactttt   2760

gagaacatgg ccggggtctt catgctggta gctgggggca tcgtggccgg gatcttcctg   2820

attttcatcg agattgccta caagcggcac aaggatgctc gccggaagca gatgcagctg   2880

gcctttgccg ccgttaacgt gtggcggaag aacctgcagg atagaaagag tggtagagca   2940

gagcctgacc ctaaaaagaa agccacattt agggctatca cctccaccct ggcttccagc   3000

ttcaagaggc gtaggtcctc caaagacacg agcaccgggg gtggacgcgg cgctttgcaa   3060

aaccaaaaag acacagtgct gccgcgacgc gctattgaga gggaggaggg ccagctgcag   3120

ctgtgttccc gtcataggga gagctgagac tccccgcccg ccctcctctg ccccctcccc   3180

cgcagacaga cagacagacg gacgggacag cggcccggcc cacgcagagc cccggagcac   3240

cacggggtcg ggggaggagc acccccagcc tcccccaggc tgcgcctgcc cgcccgccgg   3300

ttggccggct ggccggtcca ccccgtcccg gccccgcgcg tgcccccagc gtggggctaa   3360

cgggcgcctt gtctgtgtat ttctattttg cagcagtacc atcccactga tatcacgggc   3420

ccgctcaacc tctcagatcc ctcggtcagc accgtggtgt gaggcccccg gaggcgccca   3480

cctgcccagt tagcccggcc aaggacactg atgggtcctg ctgctcggga aggcctgagg   3540

gaagcccacc cgccccagag actgcccacc ctgggcctcc cgtccgtccg cccgcccacc   3600

ccgctgcctg gcgggcagcc cctgctggac caaggtgcgg accggagcgg ctgaggacgg   3660

ggcagagctg agtcggctgg gcagggccgc agggcgctcc ggcagaggca gggccctggg   3720

gtctctgagc agtggggagc gggggctaac tggccccagg cggaggggct tggagcagag   3780

acggcagccc catccttccc gcagcaccag cctgagccac agtggggccc atggccccag   3840

ctggctgggt cgcccctcct cgggcgcctg cgctcctctg cagcctgagc tccaccctcc   3900

cctcttcttg cggcaccgcc cacccacacc ccgtctgccc cttgacccca cacgccgggg   3960

ctggccctgc cctcccccac ggccgtccct gacttcccag ctggcagcgc ctcccgccgc   4020

ctcgggccgc ctcctccaga ctcgagaggg ctgagcccct cctctcctcg tccggcctgc   4080

agcccagaac gggcctcccc gggggtcccc ggacgctggc tcgggactgt cttcaaccct   4140

gccctgcacc ttgggcacgg gagagcgcca cccgcccgcc cccgccctcg ctccgggtgc   4200

gtgaccggcc cgccaccttg tacagaacca gcactcccag ggcccgagcg cgtgccttcc   4260

ccgtgcggcc cgtgcgcagc cgcgctctgc ccctccgtcc ccagggtgca ggcgcgcacc   4320

gcccaacccc cacctcccgg tgtatgcagt ggtgatgcct aaaggaatgt cacgcagttt   4380

tcaaaaaaaa aaaaaaaaaa                                               4400
```

<210> SEQ ID NO 3
<211> LENGTH: 594
<212> TYPE: PRT
<213> ORGANISM: Homo sapiens

<400> SEQUENCE: 3

```
Met Ala Ser Ser Thr Pro Ser Ser Ser Ala Thr Ser Ser Asn Ala Gly
1               5                   10                  15

Ala Asp Pro Asn Thr Thr Asn Leu Arg Pro Thr Thr Tyr Asp Thr Trp
            20                  25                  30

Cys Gly Val Ala His Gly Cys Thr Arg Lys Leu Gly Leu Lys Ile Cys
        35                  40                  45

Gly Phe Leu Gln Arg Thr Asn Ser Leu Glu Glu Lys Ser Arg Leu Val
    50                  55                  60
```

-continued

```
Ser Ala Phe Lys Glu Arg Gln Ser Ser Lys Asn Leu Leu Ser Cys Glu
65                  70                  75                  80

Asn Ser Asp Arg Asp Ala Arg Phe Arg Arg Thr Glu Thr Asp Phe Ser
                85                  90                  95

Asn Leu Phe Ala Arg Asp Leu Leu Pro Ala Lys Asn Gly Glu Glu Gln
            100                 105                 110

Thr Val Gln Phe Leu Leu Glu Val Val Asp Ile Leu Leu Asn Tyr Val
        115                 120                 125

Arg Lys Thr Phe Asp Arg Ser Thr Lys Val Leu Asp Phe His His Pro
    130                 135                 140

His Gln Leu Leu Glu Gly Met Glu Gly Phe Asn Leu Glu Leu Ser Asp
145                 150                 155                 160

His Pro Glu Ser Leu Glu Gln Ile Leu Val Asp Cys Arg Asp Thr Leu
                165                 170                 175

Lys Tyr Gly Val Arg Thr Gly His Pro Arg Phe Phe Asn Gln Leu Ser
            180                 185                 190

Thr Gly Leu Asp Ile Ile Gly Leu Ala Gly Glu Trp Leu Thr Ser Thr
        195                 200                 205

Ala Asn Thr Asn Met Phe Thr Tyr Glu Ile Ala Pro Val Phe Val Leu
    210                 215                 220

Met Glu Gln Ile Thr Leu Lys Lys Met Arg Glu Ile Val Gly Trp Ser
225                 230                 235                 240

Ser Lys Asp Gly Asp Gly Ile Phe Ser Pro Gly Gly Ala Ile Ser Asn
                245                 250                 255

Met Tyr Ser Ile Met Ala Ala Arg Tyr Lys Tyr Phe Pro Glu Val Lys
            260                 265                 270

Thr Lys Gly Met Ala Ala Val Pro Lys Leu Val Leu Phe Thr Ser Glu
        275                 280                 285

Gln Ser His Tyr Ser Ile Lys Lys Ala Gly Ala Ala Leu Gly Phe Gly
    290                 295                 300

Thr Asp Asn Val Ile Leu Ile Lys Cys Asn Glu Arg Gly Lys Ile Ile
305                 310                 315                 320

Pro Ala Asp Phe Glu Ala Lys Ile Leu Glu Ala Lys Gln Lys Gly Tyr
                325                 330                 335

Val Pro Phe Tyr Val Asn Ala Thr Ala Gly Thr Thr Val Tyr Gly Ala
            340                 345                 350

Phe Asp Pro Ile Gln Glu Ile Ala Asp Ile Cys Glu Lys Tyr Asn Leu
        355                 360                 365

Trp Leu His Val Asp Ala Ala Trp Gly Gly Gly Leu Leu Met Ser Arg
    370                 375                 380

Lys His Arg His Lys Leu Asn Gly Ile Glu Arg Ala Asn Ser Val Thr
385                 390                 395                 400

Trp Asn Pro His Lys Met Met Gly Val Leu Leu Gln Cys Ser Ala Ile
                405                 410                 415

Leu Val Lys Glu Lys Gly Ile Leu Gln Gly Cys Asn Gln Met Cys Ala
            420                 425                 430

Gly Tyr Leu Phe Gln Pro Asp Lys Gln Tyr Asp Val Ser Tyr Asp Thr
        435                 440                 445

Gly Asp Lys Ala Ile Gln Cys Gly Arg His Val Asp Ile Phe Lys Phe
    450                 455                 460

Trp Leu Met Trp Lys Ala Lys Gly Thr Val Gly Phe Glu Asn Gln Ile
465                 470                 475                 480
```

-continued

```
Asn Lys Cys Leu Glu Leu Ala Glu Tyr Leu Tyr Ala Lys Ile Lys Asn
                485                 490                 495

Arg Glu Glu Phe Glu Met Val Phe Asn Gly Glu Pro Glu His Thr Asn
            500                 505                 510

Val Cys Phe Trp Tyr Ile Pro Gln Ser Leu Arg Gly Val Pro Asp Ser
        515                 520                 525

Pro Gln Arg Arg Glu Lys Leu His Lys Val Ala Pro Lys Ile Lys Ala
    530                 535                 540

Leu Met Met Glu Ser Gly Thr Thr Met Val Gly Tyr Gln Pro Gln Gly
545                 550                 555                 560

Asp Lys Ala Asn Phe Phe Arg Met Val Ile Ser Asn Pro Ala Ala Thr
                565                 570                 575

Gln Ser Asp Ile Asp Phe Leu Ile Glu Glu Ile Glu Arg Leu Gly Gln
            580                 585                 590

Asp Leu


<210> SEQ ID NO 4
<211> LENGTH: 4007
<212> TYPE: DNA
<213> ORGANISM: Homo sapiens

<400> SEQUENCE: 4

agcgtgtggt agaggagaaa cgctgaaacc ggaccgaaac ctcgccctag gcttagcgat      60

ggctaaaaac cggctgggac aagagggagg caagcaacat tccgactcgc tgctttctgg     120

ctgtctggag tgcaaggtga ctgtggttct tctctggcca agtccgaggg agaacgtaaa     180

gatatgggcc tttttccccc tctcaccttg tctcaccaaa gtccctagtc cccggagcag     240

ttagcctctt tctttccagg gaattagcca gacacaacaa cgggaaccag acaccgaacc     300

agacatgccc gccccgtgcg ccctccccccc gctggcccac acgccggctg ctgagtgccc     360

aatggggctt gtagcggctc ggctggaaaa tcgctcactg agcgctcccc tgtgctccta     420

gcccagtccc ccacaccctt gcgtcttgta ctggccttgg acccccaccc cgaccccgac     480

cccgcctcgt ctcggcgctt cactccaggt cgcgccgatg caccgccaga ctcgagagcg     540

gcccagggct acgctccctg cgccccagta ccggagctag cgcgcacgtc tcctccgctg     600

cccccacccc tgcgcacccc taccaggcag gctcgctgcc tttcctccct cttgtctctc     660

cagagccgga tcttcaaggg gagcctccgt gccccccggct gctcagtccc tccggtgtgc     720

aggaccccgg aagtcctccc cgcacagctc tcgcttctct ttgcagcctg tttctgcgcc     780

ggaccagtcg aggactctgg acagtagagg ccccgggacg accgagctga tggcgtcttc     840

gaccccatct tcgtccgcaa cctcctcgaa cgcgggagcg gaccccaata ccactaacct     900

gcgccccaca acgtacgata cctggtgcgg cgtggcccat ggatgcacca gaaaactggg     960

gctcaagatc tgcggcttct tgcaaaggac caacagcctg gaagagaaga gtcgccttgt    1020

gagtgccttc aaggagaggc aatcctccaa gaacctgctt tcctgtgaaa acagcgaccg    1080

ggatgcccgc ttccggcgca cagagactga cttctctaat ctgtttgcta gagatctgct    1140

tccggctaag aacggtgagg agcaaaccgt gcaattcctc ctggaagtgg tggacatact    1200

cctcaactat gtccgcaaga catttgatcg ctccaccaag gtgctggact ttcatcaccc    1260

acaccagttg ctggaaggca tggagggctt caacttggag ctctctgacc accccgagtc    1320

cctggagcag atcctggttg actgcagaga caccttgaag tatggggttc gcacaggtca    1380

tcctcgattt ttcaaccagc tctccactgg attggatatt attggcctag ctggagaatg    1440
```

-continued

```
gctgacatca acggccaata ccaacatgtt tacatatgaa attgcaccag tgtttgtcct   1500
catggaacaa ataacactta agaagatgag agagatagtt ggatggtcaa gtaaagatgg   1560
tgatgggata ttttctcctg ggggcgccat atccaacatg tacagcatca tggctgctcg   1620
ctacaagtac ttcccggaag ttaagacaaa gggcatggcg gctgtgccta aactggtcct   1680
cttcacctca gaacagagtc actattccat aaagaaagct ggggctgcac ttggctttgg   1740
aactgacaat gtgattttga taaagtgcaa tgaaaggggg aaaataattc cagctgattt   1800
tgaggcaaaa attcttgaag ccaaacagaa gggatatgtt cccttttatg tcaatgcaac   1860
tgctggcacg actgtttatg gagcttttga tccgatacaa gagattgcag atatatgtga   1920
gaaatataac ctttggttgc atgtcgatgg atttaacttc tcacaattgg ccaataggat   1980
catctgcctt gctactgaac taatgactaa caaaggctgt gtcacgtggc atcccaacta   2040
ttcagtaaac atgcatcatg gctgcctggg gaggtgggct gctcatgtcc aggaagcacc   2100
accataaact caacggcata gaaagggcca actcagtcac ctggaaccct cacaagatga   2160
tgggcgtgct gttgcagtgc tctgccattc tcgtcaagga aaagggtata ctccaaggat   2220
gcaaccagat gtgtgcagga tacctcttcc agccagacaa gcagtatgat gtctcctacg   2280
acaccgggga caaggcaatt cagtgtggcc gccacgtgga tatcttcaag ttctggctga   2340
tgtggaaagc aaagggcaca gtgggatttg aaaaccagat caacaaatgc ctggaactgg   2400
ctgaatacct ctatgccaag attaaaaaca gagaagaatt tgagatggtt ttcaatggcg   2460
agcctgagca cacaaacgtc tgtttttggt atattccaca aagcctcagg ggtgtgccag   2520
acagccctca acgacgggaa aagctacaca aggtggctcc aaaaatcaaa gccctgatga   2580
tggagtcagg tacgaccatg gttggctacc agccccaagg ggacaaggcc aacttcttcc   2640
ggatggtcat ctccaaccca gccgctaccc agtctgacat tgacttcctc attgaggaga   2700
tagaaagact gggccaggat ctgtaatcat ccttcgcaga acatgagttt atgggaatgc   2760
cttttccctc tggcactcca gaacaaacct ctatatgttg ctgaaacaca caggccattt   2820
cattgaggga aaacataata tcttgaagaa tattgttaaa accttactta aagcttgttt   2880
gttctagtta gcaggaaata gtgttctttt taaaaagttg cacattagga acagagtata   2940
tatgtacagt tatacatacc tctctctata tatacatgta tagtgagtgt ggcttagtaa   3000
tagatcacgg catgtttccc gctccaagag aattcacttt accttcagca gttaccgagg   3060
agctaaacat gctgccaacc agcttgtcca acaactccag gaaaactgtt tttcaaaacg   3120
ccatgtccta ggggccaagg gaaatgctgt tggtgagaat cgacctcact gtcagcgttt   3180
ctccacctga agtgatgatg gatgagaaaa aacaccacca aatgacaagt cacaccctcc   3240
ccattagtat cctgttaggg gaaaatagta gcagagtcat tgttacaggt gtactatggc   3300
tgtattttta gagattaatt tgtgtagatt gtgtaaattc ctgttgtctg accttggtgg   3360
tgggaggggg agactatgtg tcatgatttc aatgattgtt taattgtagg tcaatgaaat   3420
atttgcttat ttatattcag agatgtacca tgttaaagag gcgtcttgta ttttcttccc   3480
atttgtaatg tatcttattt atatatgaag taagttctga aaactgttta tggtattttc   3540
gtgcatttgt gagccaaaga gaaaagatta aaattagtga gatttgtatt tatattagag   3600
tgcccttaaa ataatgattt aagcatttta ctgtctgtaa gagaattcta agattgtaca   3660
taaagtcata tatatggaaa tcctgttact taaatagcat ctgctcttct cttacgctct   3720
ctgtctggct gtacgtctgg tgttctcaat gcttttctag caactgttgg ataataacta   3780
gatctcctgt aattttgtag tagttgatga ccaatctctg ttactcgctt agctgaaacc   3840
```

taaggcaaca tttccgaaga ccttctgaag atctcagata aagtgaccag gctcacaact 3900
gtttttgaag aagggaaatt cacactgtgc gttttagagt atgcaagaag aatataaata 3960
aataaaaata ttctccatgg agaatttgaa caaaaaaaaa aaaaaaa 4007

<210> SEQ ID NO 5
<211> LENGTH: 599
<212> TYPE: PRT
<213> ORGANISM: Homo sapiens

<400> SEQUENCE: 5

Met Ala Thr Asn Gly Ser Lys Val Ala Asp Gly Gln Ile Ser Thr Glu
1 5 10 15

Val Ser Glu Ala Pro Val Ala Asn Asp Lys Pro Lys Thr Leu Val Val
20 25 30

Lys Val Gln Lys Lys Ala Ala Asp Leu Pro Asp Arg Asp Thr Trp Lys
35 40 45

Gly Arg Phe Asp Phe Leu Met Ser Cys Val Gly Tyr Ala Ile Gly Leu
50 55 60

Gly Asn Val Trp Arg Phe Pro Tyr Leu Cys Gly Lys Asn Gly Gly Gly
65 70 75 80

Ala Phe Leu Ile Pro Tyr Phe Leu Thr Leu Ile Phe Ala Gly Val Pro
85 90 95

Leu Phe Leu Leu Glu Cys Ser Leu Gly Gln Tyr Thr Ser Ile Gly Gly
100 105 110

Leu Gly Val Trp Lys Leu Ala Pro Met Phe Lys Gly Val Gly Leu Ala
115 120 125

Ala Ala Val Leu Ser Phe Trp Leu Asn Ile Tyr Tyr Ile Val Ile Ile
130 135 140

Ser Trp Ala Ile Tyr Tyr Leu Tyr Asn Ser Phe Thr Thr Thr Leu Pro
145 150 155 160

Trp Lys Gln Cys Asp Asn Pro Trp Asn Thr Asp Arg Cys Phe Ser Asn
165 170 175

Tyr Ser Met Val Asn Thr Thr Asn Met Thr Ser Ala Val Val Glu Phe
180 185 190

Trp Glu Arg Asn Met His Gln Met Thr Asp Gly Leu Asp Lys Pro Gly
195 200 205

Gln Ile Arg Trp Pro Leu Ala Ile Thr Leu Ala Ile Ala Trp Ile Leu
210 215 220

Val Tyr Phe Cys Ile Trp Lys Gly Val Gly Trp Thr Gly Lys Val Val
225 230 235 240

Tyr Phe Ser Ala Thr Tyr Pro Tyr Ile Met Leu Ile Ile Leu Phe Phe
245 250 255

Arg Gly Val Thr Leu Pro Gly Ala Lys Glu Gly Ile Leu Phe Tyr Ile
260 265 270

Thr Pro Asn Phe Arg Lys Leu Ser Asp Ser Glu Val Trp Leu Asp Ala
275 280 285

Ala Thr Gln Ile Phe Phe Ser Tyr Gly Leu Gly Leu Gly Ser Leu Ile
290 295 300

Ala Leu Gly Ser Tyr Asn Ser Phe His Asn Asn Val Tyr Arg Asp Ser
305 310 315 320

Ile Ile Val Cys Cys Ile Asn Ser Cys Thr Ser Met Phe Ala Gly Phe
325 330 335

Val Ile Phe Ser Ile Val Gly Phe Met Ala His Val Thr Lys Arg Ser
340 345 350

```
Ile Ala Asp Val Ala Ala Ser Gly Pro Gly Leu Ala Phe Leu Ala Tyr
        355                 360                 365

Pro Glu Ala Val Thr Gln Leu Pro Ile Ser Pro Leu Trp Ala Ile Leu
    370                 375                 380

Phe Phe Ser Met Leu Leu Met Leu Gly Ile Asp Ser Gln Phe Cys Thr
385                 390                 395                 400

Val Glu Gly Phe Ile Thr Ala Leu Val Asp Glu Tyr Pro Arg Leu Leu
                405                 410                 415

Arg Asn Arg Arg Glu Leu Phe Ile Ala Ala Val Cys Ile Ile Ser Tyr
            420                 425                 430

Leu Ile Gly Leu Ser Asn Ile Thr Gln Gly Gly Ile Tyr Val Phe Lys
        435                 440                 445

Leu Phe Asp Tyr Tyr Ser Ala Ser Gly Met Ser Leu Leu Phe Leu Val
    450                 455                 460

Phe Phe Glu Cys Val Ser Ile Ser Trp Phe Tyr Gly Val Asn Arg Phe
465                 470                 475                 480

Tyr Asp Asn Ile Gln Glu Met Val Gly Ser Arg Pro Cys Ile Trp Trp
                485                 490                 495

Lys Leu Cys Trp Ser Phe Phe Thr Pro Ile Ile Val Ala Gly Val Phe
            500                 505                 510

Ile Phe Ser Ala Val Gln Met Thr Pro Leu Thr Met Gly Asn Tyr Val
        515                 520                 525

Phe Pro Lys Trp Gly Gln Gly Val Gly Trp Leu Met Ala Leu Ser Ser
    530                 535                 540

Met Val Leu Ile Pro Gly Tyr Met Ala Tyr Met Phe Leu Thr Leu Lys
545                 550                 555                 560

Gly Ser Leu Lys Gln Arg Ile Gln Val Met Val Gln Pro Ser Glu Asp
                565                 570                 575

Ile Val Arg Pro Glu Asn Gly Pro Glu Gln Pro Gln Ala Gly Ser Ser
            580                 585                 590

Thr Ser Lys Glu Ala Tyr Ile
        595
```

<210> SEQ ID NO 6
<211> LENGTH: 1981
<212> TYPE: DNA
<213> ORGANISM: Homo sapiens
<220> FEATURE:
<221> NAME/KEY: modified_base
<222> LOCATION: (68)..(68)
<223> OTHER INFORMATION: a, c, t, g, unknown or other

<400> SEQUENCE: 6

```
gtagcttcac taaggtggga tggatagcag ggtctcaggc acaaccagta atggagagac      60

aaaaccantg tatcacaaga tggagtttgt gctgtcagtg gctggggaga tcattggctt     120

aggcaacgtc tggaggtttc cctatctctg ctacaaaaat gggggaggtg ccttcttcat     180

cccctacctc gtcttcctct ttacctgtgg cattcctgtc ttccttctgg agacagcact     240

aggccagtac actagccagg gaggcgtcac agcctggagg aagatctgcc ccatctttga     300

gggcattggc tatgcctccc agatgatcgt catcctcctc aacgtctact acatcattgt     360

gttggcctgg gccctgttct acctcttcag cagcttcacc atcgacctgc cctggggcgg     420

ctgctaccat gagtggaaca cagaacactg tatggagttc cagaagacca acggctccct     480

gaatggtacc tctgagaatg ccacctctcc tgtcatcgag ttctgggagc ggcgggtctt     540

gaagatctct gatgggatcc agcacctggg ggccctgcgc tgggagctgg ctctgtgcct     600
```

```
cctgctggcc tgggtcatct gctacttctg catctggaag ggggtgaagt ccacaggcaa    660

ggtggtgtac ttcacggcca catttcctta cctcatgctg gtggtcctgt taattcgagg    720

ggtgacgttg cctggggcag cccaaggaat tcagttttac ctgtacccaa acctcacgcg    780

tctgtgggat ccccaggtgt ggatggatgc aggcacccag atattcttct ccttcgccat    840

ctgtcttggg tgcctgacag ccctgggcag ctacaacaag taccacaaca actgctacag    900

cggcaccagc tttgtggccg gctttgccat cttctccatc ctgggcttca tgtctcagga    960

gcagggggtg cccatttctg aggtggccga gtcaggccct ggcctggctt tcatcgctta   1020

cccgcgggct gtggtgatgc tgcccttctc tcctctctgg gcctgctgtt tcttcttcat   1080

ggtcgttctc ctgggactgg atagccagtt tgtgtgtgta gaaagcctgg tgacagcgct   1140

ggtggacatg taccctcacg tgttccgcaa gaagaaccgg agggaagtcc tcatccttgg   1200

agtatctgtc gtctccttcc ctgtggggct gatcatgctc acagagggcg gaatgtacgt   1260

gttccagctc tttgactact atgcggccag tggcatgtgc ctcctgttcg tggccatctt   1320

cgagtccctc tgtgtggctt gggtttacgg agccaagcgc ttctacgaca acatcgaaga   1380

catgattggg tacaggccat ggcctcttat caaatactgt tggctcttcc tcacaccagc   1440

tgtgtgcaca gccacctttc tcttctccct gataaagtac actccgctga cctacaacaa   1500

gaagtacacg tacccgtggt ggggcgatgc cctgggctgg ctcctggctc tgtcctcctg   1560

gtctgcattc ctgcctggag cctctacaga ctcggaaccc tcaagggccc cttcagagag   1620

agaatccgtc agctcatgtg cccagccgag gacctgcccc agcggaaccc agcaggaccc   1680

tcggctcccg ccaccccag gacctcactg ctcagactca cagagctaga gtctcactgc   1740

taggggcag gcccttggat ggtgcctgtg tgcctggcct tggggatggc tgtggaggga   1800

acgtggcaga agcagcccca tgtgttccct gcccccgacc tggagtggat aagacaagag   1860

gggtattttg gagtccacct gctgagctgg aggcctccca ctgcaacttt tcagctcagg   1920

ggttgttgaa cagatgtgaa aaggccagtg ccaagagtgt ccctcggaga cccttgaagg   1980

c                                                                   1981
```

<210> SEQ ID NO 7
<211> LENGTH: 528
<212> TYPE: PRT
<213> ORGANISM: Homo sapiens

<400> SEQUENCE: 7

```
Met Pro Thr Pro Asp Ala Thr Thr Pro Gln Ala Lys Gly Phe Arg Arg
1               5                   10                  15

Ala Val Ser Glu Leu Asp Ala Lys Gln Ala Glu Ala Ile Met Val Arg
            20                  25                  30

Gly Gln Gly Ala Pro Gly Pro Ser Leu Thr Gly Ser Pro Trp Pro Gly
        35                  40                  45

Thr Ala Ala Pro Ala Ala Ser Tyr Thr Pro Thr Pro Arg Ser Pro Arg
    50                  55                  60

Phe Ile Gly Arg Arg Gln Ser Leu Ile Glu Asp Ala Arg Lys Glu Arg
65                  70                  75                  80

Glu Ala Ala Val Ala Ala Ala Ala Ala Ala Val Pro Ser Glu Pro Gly
                85                  90                  95

Asp Pro Leu Glu Ala Val Ala Phe Glu Glu Lys Glu Gly Lys Ala Val
            100                 105                 110

Leu Asn Leu Leu Phe Ser Pro Arg Ala Thr Lys Pro Ser Ala Leu Ser
        115                 120                 125
```

-continued

```
Arg Ala Val Lys Val Phe Glu Thr Phe Glu Ala Lys Ile His His Leu
    130                 135                 140

Glu Thr Arg Pro Ala Gln Arg Pro Arg Ala Gly Gly Pro His Leu Glu
145                 150                 155                 160

Tyr Phe Val Arg Leu Glu Val Arg Arg Gly Asp Leu Ala Ala Leu Leu
                165                 170                 175

Ser Gly Val Arg Gln Val Ser Glu Asp Val Arg Ser Pro Ala Gly Pro
            180                 185                 190

Lys Val Pro Trp Phe Pro Arg Lys Val Ser Glu Leu Asp Lys Cys His
        195                 200                 205

His Leu Val Thr Lys Phe Asp Pro Asp Leu Asp Leu Asp His Pro Gly
    210                 215                 220

Phe Ser Asp Gln Val Tyr Arg Gln Arg Arg Lys Leu Ile Ala Glu Ile
225                 230                 235                 240

Ala Phe Gln Tyr Arg His Gly Asp Pro Ile Pro Arg Val Glu Tyr Thr
                245                 250                 255

Ala Glu Glu Ile Ala Thr Trp Lys Glu Val Tyr Thr Thr Leu Lys Gly
            260                 265                 270

Leu Tyr Ala Thr His Ala Cys Gly Glu His Leu Glu Ala Phe Ala Leu
        275                 280                 285

Leu Glu Arg Phe Ser Gly Tyr Arg Glu Asp Asn Ile Pro Gln Leu Glu
    290                 295                 300

Asp Val Ser Arg Phe Leu Lys Glu Arg Thr Gly Phe Gln Leu Arg Pro
305                 310                 315                 320

Val Ala Gly Leu Leu Ser Ala Arg Asp Phe Leu Ala Ser Leu Ala Phe
                325                 330                 335

Arg Val Phe Gln Cys Thr Gln Tyr Ile Arg His Ala Ser Ser Pro Met
            340                 345                 350

His Ser Pro Glu Pro Asp Cys Cys His Glu Leu Leu Gly His Val Pro
        355                 360                 365

Met Leu Ala Asp Arg Thr Phe Ala Gln Phe Ser Gln Asp Ile Gly Leu
    370                 375                 380

Ala Ser Leu Gly Ala Ser Asp Glu Glu Ile Glu Lys Leu Ser Thr Leu
385                 390                 395                 400

Tyr Trp Phe Thr Val Glu Phe Gly Leu Cys Lys Gln Asn Gly Glu Val
                405                 410                 415

Lys Ala Tyr Gly Ala Gly Leu Leu Ser Ser Tyr Gly Glu Leu Leu His
            420                 425                 430

Cys Leu Ser Glu Glu Pro Glu Ile Arg Ala Phe Asp Pro Glu Ala Ala
        435                 440                 445

Ala Val Gln Pro Tyr Gln Asp Gln Thr Tyr Gln Ser Val Tyr Phe Val
    450                 455                 460

Ser Glu Ser Phe Ser Asp Ala Lys Asp Lys Leu Arg Ser Tyr Ala Ser
465                 470                 475                 480

Arg Ile Gln Arg Pro Phe Ser Val Lys Phe Asp Pro Tyr Thr Leu Ala
                485                 490                 495

Ile Asp Val Leu Asp Ser Pro Gln Ala Val Arg Arg Ser Leu Glu Gly
            500                 505                 510

Val Gln Asp Glu Leu Asp Thr Leu Ala His Ala Leu Ser Ala Ile Gly
        515                 520                 525
```

<210> SEQ ID NO 8
<211> LENGTH: 14877
<212> TYPE: DNA
<213> ORGANISM: Homo sapiens

<400> SEQUENCE: 8

```
gcgggggggc agtgtgtgct ccagcatgtg tgtgtgtgtg tgcatgtaca cgtgtgcacc     60
tgtatcgcct gtgtgtgtgc atgtgatgtg tacacgtgtc atgcatgcac gcacatgtgt    120
agtgtgtgct cgtgtgtggt gtgtgcctgt gtcatgtatg agcacacttg tatatgttgt    180
gtgtactgtg tcatatatga gtgtgtttgc ctgtgtagtg catgcacatc cgtgtgtgca    240
tctggtgtgt ccgtgggtca ttacgagtgc atcgtatgtg tatcgtgtac atgagtacac    300
ttgtatgtgt ggtgtgtaca ggtgccatgt aagtgtgctt gtacatatat gcatgcatgt    360
gtcatatgca tctgtgtgtg catgtgtgtg gtgcacacat gtgttatgtc tgagtgtgcc    420
tgtatgtgtg ctatgtacac gtcatgtgtg agtgtgcttg catgtgcagt gtgtggatgc    480
tgcttgtacc tgtggtgtgt acctgtgtca tgggtgctca cacgtgcatg gagtgttgtg    540
tgtgtgcttg tgtgccccat gtgtgcatgt gtgtgtgcct cacacagatg cctgcatttg    600
cctaggcact tgcaagagga caccatgctg gctctcaaag atcacagggc cacctgagcc    660
ctgtgcacac cacagccagg ccatggctag accctgcaga gccacagggc gatgcctgtc    720
agccagggga cccagaacac ctcctgggct cctccccagc acatggctgg gctcctccag    780
caggcctgga tttgggaagg gcccgtggtg ggcaaggctg gtgctgggga gcaggcctgg    840
tggcctcaga gactcgccct gtgggcggag cagcctcaca gccaggtcga agtcagcact    900
ctgaccctgc cccacgcggg gagtgggcac cagtcccagg gcacagacgt gctgggtgat    960
taatctgggt gattaagcct cgggctgaga ggctgttgag agagaacacg ctccattgtg   1020
gagctggctc agcattcctt acggccatgg tggcaggggc tgtaaccaca gggacggcgg   1080
aagtggtgga gggtggtggg gtatggaggg aagcccagag ggctccgtgc aggaaggtgg   1140
agcctggtgc aatggagggg acagcaaggg ctcctcagac ctctgcgggg cccccactcc   1200
cctggtcacc tgttttgtct ctgatctggc ctgggtcggc cctcactcct ggccccacct   1260
catagccccc cctggtgggg ctccgctcca gcccttctcc ttcccagggg ccagtatgct   1320
ggccccaggg gtctcttggg gcgtgacctc ggcctccaga gaaccctgtc ccagctctgc   1380
ccttccctct ggggtctctg tagatgggac gctggtcaca gcagcctgtc tgatttgttc   1440
cctgtggcct aggttcctga gccccacagt gccaggggat ggatgccacc ggatctttga   1500
aagaccagtg tcaggccggg cgcagtggct cacgcctgta atcccagcac tttgggaggc   1560
cgaggtgggc ggatcacgaa gtcaggagat cgagaccatc ctggctaaca cagtgaaacc   1620
ccgtctccac taaaaataca aaaagttagc tgggcgtggt ggtgggcgcc tgtagtccca   1680
gctacttggg aggctgaggc aggagaatgg cgtgaaccgg ggaggcggag cttgcagtga   1740
gccgagatcg cgccattgca ctccagcctg ggtgacagag cgagactcgg tctcaaaaaa   1800
aaagaaaaaa aggaaagacc agtgtcttgg gagttgggaa acctgggctg gagactcact   1860
gcatgacccc tgagaagttg cacctcagaa cctcagtcct cgcatctgca gaatgggtct   1920
gtgaacacct cagctgcccg aacgtggatg ccgcaggctg acccagcact gagctctacc   1980
aagaccaggg gccagccgtg tgctccctcc aggcctgtgc ccagcgtgga gaggcctcgt   2040
cccgtgggcg ctggagtgga gccttcctgg tgtttgtgga catctctgga gagggccaga   2100
ggcaggtggg tgacacgggg catggctcaa tcatgggtgg tccagactgg agaggtaccc   2160
```

-continued

```
tcgggctggg agcggggagg ctggccaggg tagacttttg gggcctccat ggataccctc   2220
accatctgga atcggagagg ggcacggcac aaaggagggc ggggccaggg ccaggactgg   2280
agtcggggc acctctgtgc caacaggggc cttggatctg gggtacagca tggttccccg   2340
gccctgaagg ggctggcgtg tgggacaggc ttcccaggaa tggataggca gggatggatg   2400
ctgcctgatt ggggcgggag gctggaggca gggcaggtgc aggcacctga gggcagcact   2460
cacctccaca ggggtccagg ggcctcccca gcctcagcac ctggcctggg ctcctgcctc   2520
cagagagcct ggccccaagg aagagtctag taagcttagt tcccatcggg cttccatgaa   2580
agcacaactg gcccggcagg aaaccgaatt aaaaagcaat atttgtatca gtggaagaca   2640
tttgctgaaa ggttaaatcc acatccggca gtgtgggcca tgagcctccg gcgtggtgtt   2700
catcaggcat gtctctcctc ctggcctggg cacctgagca ctggggccgc cctgggcaga   2760
gctggggcgg ggtgctgggg ggcctggagc tgcctcaccg agggatcctc agcagccgac   2820
cctgggggag gcaaatgaga ctctttctgg ggaccttgag gggagctcgg gggagccatg   2880
cagagcttca ccaggcctgg acactgggca tggaggctgg gccacccaag ggccatcacc   2940
agggactcag gtgggtgggc ctcagccctg ggtgacagaa gctcacgggc cgcagggcga   3000
ggccagaggc tgagccttca ggctgaggtc ttggaggcaa atccctccaa cgcccttctg   3060
agcaggcacc cagacctact gtgggcagga cccacaggag gtggaggcct ttggggaaca   3120
ctgtggaggg gcatagcatc tccgagagag gacagggtct gcactgggtg ctgagagaca   3180
gcaggggccg agcggtaggc ttccctgccc ccagggatgt tccagaggag cgcaagggag   3240
gggcattaat atcgtggcaa gaaagggcag gcattgcaga gtgagcagcg acggaactgg   3300
gttttgtggg atgcatagga gttcacccgg ataagaggtg ggtgaggaat gacactgcaa   3360
accggggatc acggagcccc aaatccttct gggccaggaa gtgggaaggg ttggggggtc   3420
ttccctttgc tttgactgag cactcagcct gcctgcagag ggcagcgagg agccacggag   3480
gggtgtggga cagggatgcc atggctgaag cagttttagg aaaggtccca ggggctattg   3540
ttgaagagag aacggggagc ggggagtccc acagctgaca ggagcagagt gggccctgag   3600
agatgccagc tctggctgcc acagtgacca gccggggtag gccttcgaga agtcagggag   3660
cgtctagggc ttctggctcc tgctgggccc agggtgtcat cttgggctgc caacaccaga   3720
aagcccagca gatacaggaa gccccaagcc ctgtcggaaa cggttcttct ccaggaggga   3780
cagcggtggc agcgttcagc cgcaggccat gcactctggg gccacgtcct tccctctgta   3840
cagtccagca ttgtcaaggc aggctctggc catctctgct gaccccagag ggatggggag   3900
gcctcccctt ccaccagaag ggccagaagc caccctgggc aggggcatca ctctccctgg   3960
gtggggcagc ggctgggagc aggaggtgcc agtgggcgtg ggctggatgc gggtgcctgc   4020
ggggcggaca tggaacttgg gggaggctct aggctggggt tgtcctcaag ggagttctca   4080
ggtcacccca gggtcaccct caacccgggg cctggtgggg tagaggagaa actgcaaagg   4140
tctctccaag gggaaggcat cagggccctc agcactgagg gacgtgcgtg ctctttaaag   4200
aaggggccac aggaccccga gggaagccag gagctagcag tgggccatag aggggctgag   4260
tggggtgggt ggaagccgtc cctggccctg gtcgccctgg caaccctggt ggggactgtg   4320
atgcaggagg tggcagccat ttggaaacgc gtggcgtctc cttagagatg tcttcttcag   4380
cctcccaggg tcctccacac tggacaggtg ggccctcctg ggacattctg gaccccacgg   4440
ggcgagcttg ggaagccgct gcaagggcca cacctgcagg gcccgggggc tgtgggcaga   4500
tggcactcct aggaaccacg tctatgagac acacggcctg gaatcttctg gagaagcaaa   4560
```

-continued

```
caaattgcct cctgacatct gaggctggag gctggattcc ccgtcttggg gctttctggg   4620
tcggtctgcc acgaggttct ggtgttcatt aaaagtgtgc ccctgggctg ccagaaagcc   4680
cctccctgtg tgctctcttg agggctgtgg ggccaagggg accctggctg tctcagcccc   4740
ccgcagagca cgagcccctg gtccccgcaa gcccgcgggc tgaggatgat tcagacaggg   4800
ctggggagtg aaggcaatta gattccacgg acgagccctt tctcctgcgc ctccctcctt   4860
cctcacccac ccccgcctcc atcaggcaca gcaggcaggg gtgggggatg taaggagggg   4920
aaggtggggg acccagaggg ggctttgacg tcagctcagc ttataagagg ctgctgggcc   4980
agggctgtgg agacggagcc cggacctcca cactgagcca tgcccacccc cgacgccacc   5040
acgccacagg ccaagggctt ccgcagggcc gtgtctgagc tggacgccaa gcaggcagag   5100
gccatcatgg taagagggca ggtaggtgcc cggcggccgc agtggaccgg agcccagggc   5160
tggtgccagc tgcctctgct actccccagc ctggctggca gccccaggct cagggtccat   5220
gcaaacccct gggacgcggc gtggatgtgg aggcctgggc acagcggcat cccctgtgcc   5280
tggtgtttga gtccctgttg ggggagggtg aggtgatgcc tgtccctgtg tgtgcccctc   5340
ttaggccgac ctctctcggg ggtcgtgtgg gtctctgtgt cttgtttcat cttgaatctt   5400
aacgatcgga atgtggaaac aaatccatcc aaaaaatcca agatggccag aggtccccgg   5460
ctgctgcacc cagcccccac cctactccca cctgcccctg cctccctctg ccccagctgc   5520
cctagtcagc accccaacca gcctgcctgc ttggggaggc agccccaagg cccttcccag   5580
gctctagcag cagctcatgg tggggggtcc tgggcaaata gggggcaaaa ttcaaagggt   5640
atctgggctc tggggtgatt cccattggcc tgttcctccc ttatttccct cattcattca   5700
ttcattcatt cattcattca ccatggagtc tgtgttccct gtgacctgca ctcggaagcc   5760
ctgtgtacag gggactgtgt gggccaggct ggataatcgg gagcttttca gcccacagga   5820
ggggtcttcg gtgcctcctt gggcactcag aaccttgggc tccctggcac atttaaaatg   5880
ggtttttatt tatggacctt gattgaaatg tggtgtgagt tgtagcagtg tcatttccag   5940
gtaccttctc agggacacag ggcgccctcc cccgtcctcc cccgccctcc cctaccctcc   6000
cccaccaggc tccccatcag gcatcccctc cccagggcgc cccggggccc agcctcacag   6060
gctctccgtg gcctggaact gcagccccag ctgcatccta cacccccacc ccaagggtaa   6120
gtaagagggg actctgggag gggcttctgc tgctcccctt catgttccac aaccctggaa   6180
gctcaggatg aagctgattc ttctcttaca aggggcccag agccttcttg ggagttcagc   6240
tccaagggat gagccccagg tgtctgccaa gtccccctct gtccaggcct gggacggctc   6300
tgggatcgag gggtcagagg cgctgagccc agggagagac acctgcgccc agagctatga   6360
caaagggtgg agggatgaca aggcagccag gagcgggcgc ctgcggggtg gcacagaggg   6420
gcagggcccg aggacaggtg tcctgatggg agtgtgagaa agggtcccct gtgcggcagc   6480
caggagggta ggggggttgt tcactggggc cctgtggggg cagctccttc ctgagctgcc   6540
gttccctccc cggcagccga tgccactgtc catcaagaca tcgccctctt cccatcacta   6600
atccagttag cgcctggcct ggggatgagt gacacagcgt ctctgtctgt ctgctcgcca   6660
cagagtgggg agcaggcgag caccttccca gcccccactc ctccccccacc accactgctt   6720
ctgactgggc tgcccccatc gggaagggcg tgcaatgccc gcaggcacct cggctagcat   6780
ctgccccagc aggcacacag taggcgctca aaaacgtgct ctcatcccct gcctctgtgt   6840
gccatcagcg ctgcccgact gtgggaccag ctgtgggtgg aggtccccgg gtctcagcag   6900
gtggaggagg catgggtgcc ccttgtcccc acagtccccg cggttcattg ggcgcaggca   6960
```

gagcctcatc gaggacgccc gcaaggagcg ggaggcggcg gtggcagcag cggccgctgc 7020
agtcccctcg gagcccgggg accccctgga ggctgtggcc tttgaggaga aggaggggaa 7080
ggccgtgcta aacctgctct tctccccgag ggccaccaag ccctcggcgc tgtcccgagc 7140
tgtgaaggtg tttgaggtga gctggtggcc ttcgtgtccc tggggcaagt tcacctgtgg 7200
gtggggctgt gtgggctgag ttcctgaccc ctctatagca gaggtgcagc tgcccaggcc 7260
cccgaggccg gcacaggatg cagcagggga gtctcaggcc tcagctcagc ccccatggca 7320
tctagccaca cccccgtgtt tttgagggat cctgagccca cccctagggc tgaggctacc 7380
aagccccact gtgcctcttg ccttgcccat cccctggatc cccctcaccc accatttccc 7440
acgtgggggg ctcccagcag ggcagcacaa gaggcagggg cagggcagtg tgccctctcc 7500
cacccaccca gcacagtggc tcaggtgacc actgattgca ttagtcactc cggccccact 7560
gtgccccggg aggcaggtga cccagctccc ggaagaagct cccaaatgac attaaagcca 7620
gactccccgc cccccagctc ccagagccag ttttgtggcc cgagggccac tgcgacccac 7680
cgcccttgtt gctaggcaac aggaggtggg ggtggagcgg acccttctgg ccagtgtcct 7740
ggacgctcag gggccagtga gactcagggc ccatcctaca aacctggatg aggccaccag 7800
ggttgggggc accttctgac cagtggctga ggagccggac tgtgtggcat ggccttggga 7860
cacacacacc gagccgccca gaaccaggtt aagcctcaag cggtgacaac tcctggttag 7920
gcacgtaaca caaaatccaa cttgccagtg gcaaaccctg gcctggtggc cgacagctga 7980
cctgagcctg gaagaacggg atctgtgtgc tgctagcaca aaagtcaagg gcagggcctg 8040
gccagccagc cagatgtgcc tcctccccgc ccaccccacc ctctctctcc atctctgtct 8100
ctttctcctt ctctctctct tcctgctttt gctccctaag acgtttgaag ccaaaatcca 8160
ccatctagag acccggcccg cccagaggcc gcgagctggg ggcccccacc tggagtactt 8220
cgtgcgcctc gaggtgcgcc gaggggacct ggccgccctg ctcagtggtg tgcgccaggt 8280
gtcagaggac gtgcgcagcc ccgcggggcc caagggtgag gcggttttct gtccttgagg 8340
gccaccaaat gaccttgaga ggctggggtg caggggctcc tgcagggga ccctacagtg 8400
accacgtggt ggtggcctgg ttccctctct gcgggctcca ctccgcaccc cgttttgcta 8460
cacatccgtg tccgggcctg gggccactcc aggatccccc cgcagctctc acagccccgg 8520
ctgcctctgc cccccggaag tcttgtaggg gaggctgctt caaggtgggt gacacagccc 8580
cacggctccg agctcaccaa gatctcttcc tccatcaccc ataaagtccc ctggttccca 8640
agaaaagtgt cagagctgga caagtgtcat cacctggtca ccaagttcga ccctgacctg 8700
gacttggacc acccggtgag tggtgcgccc ctcactcagg cctcctgccc ctgatcacat 8760
cccctaccct tagcccaacc ctggacagga gtctgtcggc tccaggagcc tccgtggcct 8820
gtgcccccac cccagcacag cctcctgacc cgtgcatccc ctctgccctc agggcttctc 8880
ggaccaggtg taccgccagc gcaggaagct gattgctgag atcgccttcc agtacaggca 8940
gtgaggggcc cctgcgctcg ggacccagac tccgtcctgc aggctgacgc tggacctggg 9000
gggtgggagg gaaggacaaa ggggaggacc catcttgtca ccagcatcag tgcctcctgc 9060
caggcagctc tgctccaggg ctttccatgt ccccaaatcc cagtggggaa actgaggccc 9120
agggggcta gagcaacctg ccgaggccac atagccggct cacggcacag tcagctgggg 9180
tgcaccctcc tgtccatcct ccaacccaaa ggcctcgctg cactaggcgg gtgtggacct 9240
gtgcccagtg aagctccctc cctccctcct gcccttctca ctccccgagg ggacctgctg 9300
accactggcc ccctccccag cggcgacccg attccccgtg tggagtacac cgccgaggag 9360
attgccacct ggtgagacct ccgtgcagct aggggctggg gaggagcccg ggggatgcct 9420
cctggaatcc tggcgtgtga gggccgcctc cagggacctt ggcacaacag gagagactaa 9480
ggccgggaag aagagggact tgcagggctc agaatgttgg gttgggagga agaggctacc 9540
catcctgtcg ggccatcccc agtgtgctga gggaccgccc ctcatggccc cctatcccct 9600
gggattccct aaagccacca gcaaaagccc ctcccggggg cctgggtctt caggggtccc 9660
caagaggcct gcgttggtag ggctcaggc aggcagaggc acccacagtt caggaggggg 9720
gtttcgggca ctggggtggg gcattagagg gccctgagcc tggctgcccg caggaaggag 9780
gtctacacca cgctgaaggg cctctacgcc acgcacgcct gcggggagca cctggaggcc 9840
tttgctttgc tggagcgctt cagcggctac cgggaagaca atatccccca gctggaggac 9900
gtctcccgct tcctgaaggg tgtgcccaga cgggaggggc gcagagccgg ggggccgggg 9960
atggtcagcc aagcgcccca ccccagcgcg gctccagccc gtcccggctc ggcagtgacc 10020
cgcgtggccc cttgcagagc gcacgggctt ccagctgcgg cctgtggccg gcctgctgtc 10080
cgcccgggac ttcctggcca gcctggcctt ccgcgtgttc cagtgcaccc agtatatccg 10140
ccacgcgtcc tcgcccatgc actcccctga gccgtgagtg cgcgccctgg ccgccagccc 10200
gagggtgggg ggtgcgacgg gcggcccctc agccccttc tccctcctac gcgcagggac 10260
tgctgccacg agctgctggg gcacgtgccc atgctggccg accgcacctt cgcgcagttc 10320
tcgcaggtac gccgcggcct cggagggagc cggggtcacc caggggctgg cttggcgccg 10380
ggggcgggcg gggatcgatg tgcgggtggg tgaagtgtgc tgcctgctcc cgggccccgc 10440
caaggaggct cggcgccccg agggtcgcgc ggcatagggc ggggctggag cggagcctcc 10500
cacggcctgt gctgccacct gccggctacc tgggaacggc gcccacgggc ttaggaatgt 10560
ggtcaaggag ggctgcctgg aggaggaggc ccggtggagg tgcggatcct gggcggccag 10620
ggaaggtctc tgccgccagg gaagtgtccc agagacccct ggaggggctg ctgacacccc 10680
cggtgccccc acctcgagca tgacccaggg ctgcctctcc ccatccttca tcctccctgc 10740
tccacaggac attggcctgg cgtccctggg ggcctcggat gaggaaattg agaagctgtc 10800
cacggtgggt tgacccctcc ctgcagggcc tggggtgtgg gtttgggggt ctgaatccag 10860
gcctcaccct cttgccgtcc aggctgaggc ctctccttcc acccacgaat tgtgaccctc 10920
accctggcct gcctgcatcc tggcctggcc tccctggggg tggtatcctg gtcacgggtg 10980
accaggggct gcccggtggg cggcagctgt ctctgggctg atgctgcccg gcttccccgc 11040
agctgtactg gttcacggtg gagttcgggc tgtgtaagca gaacggggag gtgaaggcct 11100
atggtgccgg gctgctgtcc tcctacgggg agctcctggt gagagtctct ccttgctgca 11160
gcccccagca gaggggcagg gctgggggac ggtgcaggga ggggacaggc tcccagtggg 11220
aggaaactga ggcctggacc tccaggactc aggctctgtt tgggagaagg cttgtctctg 11280
cccagtcctc accccacatt atcccaggcc tccgaaggcc cggcggggga gatgggggtg 11340
actctaccca aggaacccac ccagcgtcag gccacggtgc cccagttccc tcggggacct 11400
gggtgcagtg gagtcagtga tgccattggc ctcctgccag cactgcctgt ctgaggagcc 11460
tgagattcgg gccttcgacc ctgaggctgc ggccgtgcag ccctaccaag accagacgta 11520
ccagtcagtc tacttcgtgt ctgagagctt cagtgacgcc aaggacaagc tcaggtgggc 11580
taggctgcta gggcaagccc cccatggtgc ccccaaactg ggccagccag gccttccttc 11640
tggccttgag cagggctgga cctgtgagcc caggtcacag atgagaaaac cgacccctgg 11700
ttgcagcagc ccccacacag cagggacacc atccgtgaga aggaccccag cgtctgggga 11760
ggggcagacc tacaggactg ggggctgctg ggtggccggg tcaaggccag tcttggaggt 11820
gctgacagag cctgagcttt gtgaggacgt cctgtggaac ctgtcccggc cccctgccct 11880
gggatgggga gaagtcaggg ggatagacag agtcaaggtg ggggacaggg cgggagtggg 11940
gtccccaggg ctgggggcct ttggtgcagt gaccagagtg tcaggagagg ggagcaaagc 12000
cctctagcct catcctcata aaaggtctca tcattttccc tccagcctct tatgcactgg 12060
ggaaactgag gccaggggct atgtgtccag cggacagggg tgctgaattc cacccacagg 12120
cttagggata tggtcaagga aagcttcctg gaggaggccc agtggaggtt cagggaggga 12180
tggggtgccc ggcagtctct agtggaaaag gcgcctagcc tatctccccc atgaaccccc 12240
tcacccagcc ctggaagagg cctcagtgtc ccgcctgtga ccagttggct cagaaaagcc 12300
ctgggagctc tgagccactg tgaaggtgga aacgcggccc ctggcctccc ctctcctgga 12360
ggctgcagac tctgcccgcc agttgacgag ggctctgccg ctctcctccc caggagctat 12420
gcctcacgca tccagcgccc cttctccgtg aagttcgacc cgtacacgct ggccatcgac 12480
gtgctggaca gcccccaggc cgtgcggcgc tccctggagg gtgtccagga tgagctggac 12540
acccttgccc atgcgctgag tgccattggc taggtgcacg gcgtccctga gggcccttcc 12600
caacctcccc tggtcctgca ctgtcccgga gctcaggccc tggtgagggg ctgggtcccg 12660
ggtgcccccc atgccctccc tgctgccagg ctcccactgc ccctgcacct gcttctcagc 12720
gcaacagctg tgtgtgcccg tggtgaggtt gtgctgcctg tggtgaggtc ctgtcctggc 12780
tcccagggtc ctgggggctg ctgcactgcc ctccgccctt ccctgacact gtctgctgcc 12840
ccaatcaccg tcacaataaa agaaactgtg gtctctacac ctgcctggcc ccacatctgt 12900
gccacagaga cagaccctgg gatcctcaga ctcccacacc cccaccccag cctcactcag 12960
aggtttcgcc ctggcctcct tcctcctctg ggagatggct ggccgccctg gccaggcagc 13020
tggcccctcc gggcctggtt tccccgctca ccctgaggcc ccgcccagct ctgagcccca 13080
agcagctcca gaggctcggg caccctggcc gagctgcccc atctccgtgg ggtgccctcc 13140
caaggtgggg agccacgtga cagtgggagg gcctctctca ggcctggcag ggagcagggg 13200
tcacaaactg tgctggctgg gggtggtctc agaggtgggc ctgcaggcct aaccctccct 13260
gctgacaggg ctcccagccc ttgagagaaa cagggatgga ggaacagctg ccctgatgcc 13320
ctcacccacc cggagcaggc cctgcgaacc aaggggaacc tcagtgtggc ccccagcatg 13380
tgtgctgatg gggagggtct ggctgagctg gtgcccaggc agatggtctg ggcctgtctc 13440
cccagcgagg caggatgggg gctggatttc agactctgta agatgcccct ggcttactcg 13500
aggggcctgg acattgccct ccagagagag cacccaacac cctccaggct tgaccggcca 13560
gggtgtcccc ttcctacctt ggagagagca gccccagggc atcctgcagg gggtgctggg 13620
acaccagctg gccttcaagg tctctgcctc cctccagcca ccccactaca cgctgctggg 13680
atcctggatc tcagctcccc ggccgacaac actggcaaac tcctactcat ccacgaaggc 13740
cctcctgggc atggtggtcc ttcccagcct ggcagtctgt tcctcacaca ccttgttagt 13800
gcccagcccc tgaggttgca gctgggggtg tctctgaagg gctgtgagcc cccaggaagc 13860
cctggggaag tgcctgcctt gcctcccccc ggccctgcca gcgcctggct ctgccctcct 13920
acctgggctc cccccatcca gcctccctcc ctacacactc ctctcaagga ggcacccatg 13980
tcctctccag ctgccgggcc tcagagcact gtggcgtcct ggggcagcca ccgcatgtcc 14040
tgctgtggca tggctcaggg tggaaagggc ggaagggagg ggtcctgcag atagctggtg 14100
cccactacca aacccgctcg gggcaggaga gccaaaggct gggtgtgtgc agagcggccc 14160

```
cgagaggttc cgaggctgag gccagggtgg gacataggga tgcgaggggc cggggcacag  14220

gatactccaa cctgcctgcc cccatggtct catcctcctg cttctgggac ctcctgatcc  14280

tgcccctggt gctaagaggc aggtaggggc tgcaggcagc agggctcgga gcccatgccc  14340

cctcaccatg ggtcaggctg gacctccagg tgcctgttct ggggagctgg gagggccgga  14400

ggggtgtacc ccaggggctc agcccagatg acactatggg ggtgatggtg tcatgggacc  14460

tggccaggag aggggagatg ggctcccaga agaggagtgg gggctgagag ggtgcctggg  14520

gggccaggac ggagctgggc cagtgcacag cttcccacac ctgcccaccc ccagagtcct  14580

gccgccaccc ccagatcaca cggaagatga ggtccgagtg gcctgctgag gacttgctgc  14640

ttgtccccag gtccccaggt catgccctcc ttctgccacc ctggggagct gagggcctca  14700

gctggggctg ctgtcctaag gcagggtggg aactaggcag ccagcaggga ggggacccct  14760

ccctcactcc cactctccca cccccaccac cttggcccat ccatggcggc atcttgggcc  14820

atccgggact ggggacaggg gtcctgggga caggggtgtg gggacagggg tcctggg     14877
```

<210> SEQ ID NO 9
<211> LENGTH: 382
<212> TYPE: PRT
<213> ORGANISM: Homo sapiens

<400> SEQUENCE: 9

```
Met Leu Asp Gly Leu Lys Met Glu Glu Asn Phe Gln Ser Ala Ile Asp
1               5                   10                  15

Thr Ser Ala Ser Phe Ser Ser Leu Leu Gly Arg Ala Val Ser Pro Lys
            20                  25                  30

Ser Val Cys Glu Gly Cys Gln Arg Val Ile Leu Asp Arg Phe Leu Leu
        35                  40                  45

Arg Leu Asn Asp Ser Phe Trp His Glu Gln Cys Val Gln Cys Ala Ser
    50                  55                  60

Cys Lys Glu Pro Leu Glu Thr Thr Cys Phe Tyr Arg Asp Lys Lys Leu
65                  70                  75                  80

Tyr Cys Lys Tyr Asp Tyr Glu Lys Leu Phe Ala Val Lys Cys Gly Gly
                85                  90                  95

Cys Phe Glu Ala Ile Ala Pro Asn Glu Phe Val Met Arg Ala Gln Lys
            100                 105                 110

Ser Val Tyr His Leu Ser Cys Phe Cys Cys Cys Val Cys Glu Arg Gln
        115                 120                 125

Leu Gln Lys Gly Asp Glu Phe Val Leu Lys Glu Gly Gln Leu Leu Cys
    130                 135                 140

Lys Gly Asp Tyr Glu Lys Glu Arg Glu Leu Leu Ser Leu Val Ser Pro
145                 150                 155                 160

Ala Ala Ser Asp Ser Gly Lys Ser Asp Asp Glu Glu Ser Leu Cys Lys
                165                 170                 175

Ser Ala His Gly Ala Gly Lys Gly Thr Ala Glu Glu Gly Lys Asp His
            180                 185                 190

Lys Arg Pro Lys Arg Pro Arg Thr Ile Leu Thr Thr Gln Gln Arg Arg
        195                 200                 205

Ala Phe Lys Ala Ser Phe Glu Val Ser Ser Lys Pro Cys Arg Lys Val
    210                 215                 220

Arg Glu Thr Leu Ala Ala Glu Thr Gly Leu Ser Val Arg Val Val Gln
225                 230                 235                 240

Val Trp Phe Gln Asn Gln Arg Ala Lys Met Lys Lys Leu Ala Arg Arg
                245                 250                 255
```

```
Gln Gln Gln Gln Gln Gln Asp Gln Gln Asn Thr Gln Arg Leu Ser Ser
            260                 265                 270

Ala Gln Thr Asn Gly Gly Gly Ser Ala Gly Met Glu Gly Ile Met Asn
        275                 280                 285

Pro Tyr Thr Ala Leu Pro Thr Pro Gln Gln Leu Leu Ala Ile Glu Gln
    290                 295                 300

Ser Val Tyr Ser Ser Asp Pro Phe Arg Gln Gly Leu Thr Pro Pro Gln
305                 310                 315                 320

Met Pro Gly Asp His Met His Pro Tyr Gly Ala Glu Pro Leu Phe His
                325                 330                 335

Asp Leu Asp Ser Asp Asp Thr Ser Leu Ser Asn Leu Gly Asp Cys Phe
            340                 345                 350

Leu Ala Thr Ser Glu Ala Gly Pro Leu Gln Ser Arg Val Gly Asn Pro
        355                 360                 365

Ile Asp His Leu Tyr Ser Met Gln Asn Ser Tyr Phe Thr Ser
    370                 375                 380


<210> SEQ ID NO 10
<211> LENGTH: 5310
<212> TYPE: DNA
<213> ORGANISM: Homo sapiens
<220> FEATURE:
<221> NAME/KEY: modified_base
<222> LOCATION: (901)..(1000)
<223> OTHER INFORMATION: a, c, t, g, unknown or other
<220> FEATURE:
<221> NAME/KEY: modified_base
<222> LOCATION: (1301)..(1400)
<223> OTHER INFORMATION: a, c, t, g, unknown or other
<220> FEATURE:
<221> NAME/KEY: modified_base
<222> LOCATION: (1821)..(1920)
<223> OTHER INFORMATION: a, c, t, g, unknown or other
<220> FEATURE:
<221> NAME/KEY: modified_base
<222> LOCATION: (2881)..(2980)
<223> OTHER INFORMATION: a, c, t, g, unknown or other
<220> FEATURE:
<221> NAME/KEY: modified_base
<222> LOCATION: (3461)..(3560)
<223> OTHER INFORMATION: a, c, t, g, unknown or other
<220> FEATURE:
<221> NAME/KEY: modified_base
<222> LOCATION: (4401)..(4500)
<223> OTHER INFORMATION: a, c, t, g, unknown or other
<220> FEATURE:
<221> NAME/KEY: modified_base
<222> LOCATION: (4801)..(4900)
<223> OTHER INFORMATION: a, c, t, g, unknown or other

<400> SEQUENCE: 10

gtataggttg gggcggagtc ggattcggga tggaaaacct ggggcaaggg atgtaggtgg     60

gggtgagggg ggcaggagaa ggagaaacgc agttgggggg cggaggccta agtacataac    120

gtgttgactt caagtgaaat cagatcagcc agagcagttc gctgtgactg atctctcctc    180

ccaccctaca ttctcttggc tggaccctat cctcctggct gattctggtc gccctggaca    240

ctccctcagt tctttcccag gagtgcggtg gctgctggcg ccgagtccca gcgggcacgg    300

acgtcagacg catcgtttct tctcctctac aggtcctccc ggcccggccc gaacatgctg    360

gacggcctaa agatggagga gaacttccaa agcgcgatcg acacctcggc ctccttctcc    420

tcgctgctgg gtgagtgttc aggccgtgcg tcctgggcgc actctctttc cgcttggcgc    480

tgagctctgg agccccgctc tctgggacct ggtccgcgat agggaagcta gcgcccctct    540

tcatacacta aattgagccc catcactatc tgtccgtcag tgcttgtggg tcgtccctac    600
```

```
ccaaataaat ccaacaagcc gccccaggcc tcacgcactg ggcaccgaat tccccaaagc    660
cgcgaggggc gggcgagctt gttcgtaggc gtctgagtgg caagtgatta aaaataccca    720
gggctggatt tttaatctcg gagctgatcg acgtctcata aatgccgccc tcttctcgcg    780
gcctagaggc aatagcatcc gagacccgag gcctggagcg cccaagttcg aggaggcttc    840
tctcccccac caactccagc cccaatttca gccatgggca aggccgagag agacttttct    900
nnnnnnnnnn nnnnnnnnnn nnnnnnnnnn nnnnnnnnnn nnnnnnnnnn nnnnnnnnnn    960
nnnnnnnnnn nnnnnnnnnn nnnnnnnnnn nnnnnnnnnn gggtcccggc caggtttggc   1020
atggtctacc tgcccgggct gctcacccgc caacgtctgt tgtggctaca ggcagagcgg   1080
tgagccccaa gtctgtctgc gagggctgtc agcgggtcat cttggacagg tttctgctgc   1140
ggctcaacga cagcttctgg catgagcagt gcgtgcagtg cgcctcctgc aaagagcccc   1200
tggagaccac ctgcttctac cgggacaaga agctgtactg caagtatgac tacgagaagt   1260
aagtggccgc acccccgcag cgctccccgc gcactggcat nnnnnnnnnn nnnnnnnnnn   1320
nnnnnnnnnn nnnnnnnnnn nnnnnnnnnn nnnnnnnnnn nnnnnnnnnn nnnnnnnnnn   1380
nnnnnnnnnn nnnnnnnnnn atcccagttc ttgaagttcc ttttgctgtt gacttcaggg   1440
gagacccagg accaagccag attttactca tggtgcatgt acttcctttc tccctgctgc   1500
caggctgttt gctgttaaat gtgggggctg cttcgaggcc atcgctccca atgagtttgt   1560
tatgcgggcc cagaagagtg tataccacct gagctgcttc tgctgctgtg tctgcgagcg   1620
acagcttcag aagggtgatg agtttgtcct gaaggagggg cagctgctct gcaaagggga   1680
ctatgagaag gagcgggagc tgctcagcct ggtgagccca gcagcctcag actcaggtga   1740
gtgccaggtg gtgggcaggg ctgcggtggg gtgggtagag tggagttggg tggctgtctg   1800
cattgtttct tccctagatg nnnnnnnnnn nnnnnnnnnn nnnnnnnnnn nnnnnnnnnn   1860
nnnnnnnnnn nnnnnnnnnn nnnnnnnnnn nnnnnnnnnn nnnnnnnnnn nnnnnnnnnn   1920
catacagctc caggaactgg ctttcaggga ctcacaacat tgtcttttgc ttctttcagg   1980
taaaagtgat gatgaagaaa gtctctgcaa gtcagcccat ggggcaggga aaggaactgc   2040
tgaggaaggc aaggaccata agcgccccaa acgtccgaga accatcttga caactcaaca   2100
gaggcgagca ttcaaggcct catttgaagt atcctccaag ccctgcagga aggtatagga   2160
gggagcaggg aggaaaagga gctgggcccc acttctctgt gtgcactcag acccctctgg   2220
gatctcagtg ggcattgggg gtcacagtgg tgaggaaggc tgttcagaca gagcctgcac   2280
aggcggctca agcctgttgg agactccaga gatcactaag ctgtggccag ggtgtgatag   2340
actctcctga agctttcatg catgcacacc aactccaaat ggcccctgtc acacctttca   2400
tttcatagag cacaatggga acagtaataa tgataggtgt ccattgtggt gtagacccag   2460
atgctgtaaa gcaaagagta taaaaacaca gtggcttgca gtactctttt ttgagtctgg   2520
ctttttccac ttggtgtggt ggtttgggga ttcattcatt cctatttcag cattccactg   2580
tataggtgtg ccatgattgg tttgtccatg cacctgttga tgggtgtttg gggttgtttc   2640
tagtttggga ctgtttcaaa taggactgct atggacattc atgtaaaaaa aaatacagtg   2700
gtttaatgag acaggagttt attctcttct gtcacagtcc agaggtgagc aaggcaaggc   2760
tggtgggtgg ctctgttatc catctcctgt gtccaagcga ctgctccagt tgtcaccatg   2820
tttccagtca ccaggtagag aaagaggaaa tggagggcaa gcgccctgct ttttaaggat   2880
nnnnnnnnnn nnnnnnnnnn nnnnnnnnnn nnnnnnnnnn nnnnnnnnnn nnnnnnnnnn   2940
nnnnnnnnnn nnnnnnnnnn nnnnnnnnnn nnnnnnnnnn atgcatatgc atggcttata   3000
```

```
gctaaagcac aacaatagac taaagtctaa accacttgaa ggcctaattt ccagagcaag   3060
agaaatccag aaacacctct tgggaatgca catgtaaatt aataattatt attttgtttc   3120
tttacctggt gaaggacttt ctttctacct gaagggaagc aatgttctcg tgtttgtgtg   3180
tatgctcaac attaaaaact attcagctcc taaagcagat acagtctttt ggcctcctca   3240
agtattatat aggagatgtt ctacctccta ccctgagatg ccagtgtgtc tacatttctc   3300
gttcaatttt tccaaggtga gagagactct ggctgcagag acagggctga gtgtccgtgt   3360
cgtccaggtg tggttccaaa accagagagc gaaggtaacc tgcttcttac ttttatctgt   3420
ccccatgttg ctggtttcct gaaataatca cagtaggaca nnnnnnnnnn nnnnnnnnnn   3480
nnnnnnnnnn nnnnnnnnnn nnnnnnnnnn nnnnnnnnnn nnnnnnnnnn nnnnnnnnnn   3540
nnnnnnnnnn nnnnnnnnnn agccctctcc cggggaaggt gtcacttcca ggcccccccct   3600
tactttgtga acatgctgca ggccacctga cttctaatcc tatggtcctc tccttatcag   3660
atgaagaagc tggccaggcg acagcagcag cagcagcaag atcagcagaa cacccagagg   3720
ctgagctctg gtaagctggt gcctcctccc aggcagttct ggctggaatc caggctgttc   3780
ctaccagagg cctcccacta cccagctctt tggatgacat atctggactc agtgaagcct   3840
agaccacacc cactggagaa ataaggcctt caagggaaga ctgagccacg aggaacttgt   3900
gagagggttg agggctcctg agctgcaggc ttagaactgc tgattgggga tggcactgac   3960
cttatccaca gcgtccaggc ctggatccca ccacagcgtc agggactgct tgcagagtca   4020
cagatacgtt cagtttctca tcttgcttag ttctccttcc aggctaattg atttaataga   4080
agacacctcg gtgacttggc tctttccaaa ataacataaa gtagtaaaaa taatgatagt   4140
aaaataacaa tgccttcctt tgttgaacac tcttatagat tggtgttctc atacatgctg   4200
acttgacttt tacaacaccc attcctggag gcgagtggag aagttgttat tatccctatg   4260
tcacagatga gcaaacaaag gctctgcaag attgaatgtg gccctagatc ggtaagggca   4320
gggggctggg actagaactc taactgtgtt ccacaggcca tgggccttct catctctacc   4380
cagatgtgct tttgaaaaag nnnnnnnnnn nnnnnnnnnn nnnnnnnnnn nnnnnnnnnn   4440
nnnnnnnnnn nnnnnnnnnn nnnnnnnnnn nnnnnnnnnn nnnnnnnnnn nnnnnnnnnn   4500
cacgttgaga atgacctggc ttcttctttg ttccacagct cagacaaacg gtggtgggag   4560
tgctgggatg gaaggaatca tgaaccccta cacggctctg cccaccccac agcagctcct   4620
ggccatcgag cagagtgtct acagctcaga tcccttccga cagggtctca ccccacccca   4680
gatgcctgga gaccacatgc acccttatgg taagagggac ttaagcccct cgggccctct   4740
cataacttgt gtgggtttct cattccctcc taaacacatc taggcagttc ccagatgctc   4800
nnnnnnnnnn nnnnnnnnnn nnnnnnnnnn nnnnnnnnnn nnnnnnnnnn nnnnnnnnnn   4860
nnnnnnnnnn nnnnnnnnnn nnnnnnnnnn nnnnnnnnnn aaatgagtca cttcttcaag   4920
accctcatgc cagtgtttca tctccatttc aggtgccgag ccccttttcc atgacctgga   4980
tagcgacgac acctccctca gtaacctggg tgattgtttc ctagcaacct cagaagctgg   5040
gcctctgcag tccagagtgg gaaaccccat tgaccatctg tactccatgc agaattctta   5100
cttcacatct tgagtcttcc cctagagttc tgtgactagg ctcccatatg gaacaaccat   5160
attctttgag gggtcactgg ctttaggaca gggaggccag ggaagaggtg ggttggggag   5220
ggagttttgt tggggatgct gttgtataat gatatggtgt agctcagcat ttccaaagac   5280
tgaatacatt atggattgca tagtttaatg                                    5310
```

-continued

<210> SEQ ID NO 11
<211> LENGTH: 655
<212> TYPE: PRT
<213> ORGANISM: Homo sapiens

<400> SEQUENCE: 11

```
Met Ala Glu Ala Pro Gln Val Val Glu Ile Asp Pro Asp Phe Glu Pro
1               5                   10                  15

Leu Pro Arg Pro Arg Ser Cys Thr Trp Pro Leu Pro Arg Pro Glu Phe
            20                  25                  30

Ser Gln Ser Asn Ser Ala Thr Ser Ser Pro Ala Pro Ser Gly Ser Ala
        35                  40                  45

Ala Ala Asn Pro Asp Ala Ala Ala Gly Leu Pro Ser Ala Ser Ala Ala
    50                  55                  60

Ala Val Ser Ala Asp Phe Met Ser Asn Leu Ser Leu Leu Glu Glu Ser
65                  70                  75                  80

Glu Asp Phe Pro Gln Ala Pro Gly Ser Val Ala Ala Ala Val Ala Ala
                85                  90                  95

Ala Ala Ala Ala Ala Ala Thr Gly Gly Leu Cys Gly Asp Phe Gln Gly
            100                 105                 110

Pro Glu Ala Gly Cys Leu His Pro Ala Pro Pro Gln Pro Pro Pro Pro
        115                 120                 125

Gly Pro Leu Ser Gln His Pro Pro Val Pro Pro Ala Ala Ala Gly Pro
    130                 135                 140

Leu Ala Gly Gln Pro Arg Lys Ser Ser Ser Ser Arg Arg Asn Ala Trp
145                 150                 155                 160

Gly Asn Leu Ser Tyr Ala Asp Leu Ile Thr Lys Ala Ile Glu Ser Ser
                165                 170                 175

Ala Glu Lys Arg Leu Thr Leu Ser Gln Ile Tyr Glu Trp Met Val Lys
            180                 185                 190

Ser Val Pro Tyr Phe Lys Asp Lys Gly Asp Ser Asn Ser Ser Ala Gly
        195                 200                 205

Trp Lys Asn Ser Ile Arg His Asn Leu Ser Leu His Ser Lys Phe Ile
    210                 215                 220

Arg Val Gln Asn Glu Gly Thr Gly Lys Ser Ser Trp Trp Met Leu Asn
225                 230                 235                 240

Pro Glu Gly Gly Lys Ser Gly Lys Ser Pro Arg Arg Arg Ala Ala Ser
                245                 250                 255

Met Asp Asn Asn Ser Lys Phe Ala Lys Ser Arg Ser Arg Ala Ala Lys
            260                 265                 270

Lys Lys Ala Ser Leu Gln Ser Gly Gln Glu Gly Ala Gly Asp Ser Pro
        275                 280                 285

Gly Ser Gln Phe Ser Lys Trp Pro Ala Ser Pro Gly Ser His Ser Asn
    290                 295                 300

Asp Asp Phe Asp Asn Trp Ser Thr Phe Arg Pro Arg Thr Ser Ser Asn
305                 310                 315                 320

Ala Ser Thr Ile Ser Gly Arg Leu Ser Pro Ile Met Thr Glu Gln Asp
                325                 330                 335

Asp Leu Gly Glu Gly Asp Val His Ser Met Val Tyr Pro Pro Ser Ala
            340                 345                 350

Ala Lys Met Ala Ser Thr Leu Pro Ser Leu Ser Glu Ile Ser Asn Pro
        355                 360                 365

Glu Asn Met Glu Asn Leu Leu Asp Asn Leu Asn Leu Leu Ser Ser Pro
    370                 375                 380
```

-continued

```
Thr Ser Leu Thr Val Ser Thr Gln Ser Ser Pro Gly Thr Met Met Gln
385                 390                 395                 400

Gln Thr Pro Cys Tyr Ser Phe Ala Pro Pro Asn Thr Ser Leu Asn Ser
                405                 410                 415

Pro Ser Pro Asn Tyr Gln Lys Tyr Thr Tyr Gly Gln Ser Ser Met Ser
            420                 425                 430

Pro Leu Pro Gln Met Pro Ile Gln Thr Leu Gln Asp Asn Lys Ser Ser
        435                 440                 445

Tyr Gly Gly Met Ser Gln Tyr Asn Cys Ala Pro Gly Leu Leu Lys Glu
    450                 455                 460

Leu Leu Thr Ser Asp Ser Pro Pro His Asn Asp Ile Met Thr Pro Val
465                 470                 475                 480

Asp Pro Gly Val Ala Gln Pro Asn Ser Arg Val Leu Gly Gln Asn Val
                485                 490                 495

Met Met Gly Pro Asn Ser Val Met Ser Thr Tyr Gly Ser Gln Ala Ser
            500                 505                 510

His Asn Lys Met Met Asn Pro Ser Ser His Thr His Pro Gly His Ala
        515                 520                 525

Gln Gln Thr Ser Ala Val Asn Gly Arg Pro Leu Pro His Thr Val Ser
    530                 535                 540

Thr Met Pro His Thr Ser Gly Met Asn Arg Leu Thr Gln Val Lys Thr
545                 550                 555                 560

Pro Val Gln Val Pro Leu Pro His Pro Met Gln Met Ser Ala Leu Gly
                565                 570                 575

Gly Tyr Ser Ser Val Ser Ser Cys Asn Gly Tyr Gly Arg Met Gly Leu
            580                 585                 590

Leu His Gln Glu Lys Leu Pro Ser Asp Leu Asp Gly Met Phe Ile Glu
        595                 600                 605

Arg Leu Asp Cys Asp Met Glu Ser Ile Ile Arg Asn Asp Leu Met Asp
    610                 615                 620

Gly Asp Thr Leu Asp Phe Asn Phe Asp Asn Val Leu Pro Asn Gln Ser
625                 630                 635                 640

Phe Pro His Ser Val Lys Thr Thr Thr His Ser Trp Val Ser Gly
                645                 650                 655
```

<210> SEQ ID NO 12
<211> LENGTH: 5738
<212> TYPE: DNA
<213> ORGANISM: Homo sapiens

<400> SEQUENCE: 12

```
gcagccgcca cattcaacag gcagcagcgc agcgggcgcg ccgctgggga gagcaagcgg      60

cccgcggcgt ccgtccgtcc ttccgtccgc ggccctgtca gctggagcgc ggcgcaggct     120

ctgccccggc ccggcggctc tggccggccg tccagtccgt gcggcggacc ccgaggagcc     180

tcgatgtgga tggccccgcg aagttaagtt ctgggctcgc gcttccactc cgccgcgcct     240

tcctcccagt ttccgtccgc tcgccgcacc ggcttcgttc ccccaaatct cggaccgtcc     300

cttcgcgccc cctccccgtc cgcccccagt gctgcgttct ccccctcttg gctctcctgc     360

ggctggggga ggggcggggg tcaccatggc cgaggcgcct caggtggtgg agatcgaccc     420

ggacttcgag ccgctgcccc ggccgcgctc gtgcacctgg ccgctgccca ggccggagtt     480

tagccagtcc aactcggcca cctccagccc ggcgccgtcg ggcagcgcgg ctgccaaccc     540

cgacgccgcg gcgggcctgc cctcggcctc ggctgccgct gtcagcgccg acttcatgag     600
```

-continued

```
caacctgagc ttgctggagg agagcgagga cttcccgcag gcgcccggct ccgtggcggc    660
ggcggtggcg gcggcggccg ccgcggccgc caccgggggg ctgtgcgggg acttccaggg    720
cccggaggcg ggctgcctgc acccagcgcc accgcagccc ccgccgcccg ggccgctgtc    780
gcagcacccg ccggtgcccc ccgccgccgc tgggccgctc gcggggcagc cgcgcaagag    840
cagctcgtcc cgccgcaacg cgtggggcaa cctgtcctac gccgacctca tcaccaaggc    900
catcgagagc tcggcggaga agcggctcac gctgtcgcag atctacgagt ggatggtcaa    960
gagcgtgccc tacttcaagg ataagggtga cagcaacagc tcggcgggct ggaagaattc   1020
aattcgtcat aatctgtccc tacacagcaa gttcattcgt gtgcagaatg aaggaactgg   1080
aaaaagttct tggtggatgc tcaatccaga gggtggcaag agcgggaaat ctcctaggag   1140
aagagctgca tccatggaca acaacagtaa atttgctaag agccgaagcc gagctgccaa   1200
gaagaaagca tctctccagt ctggccagga gggtgctggg gacagccctg gatcacagtt   1260
ttccaaatgg cctgcaagcc ctggctctca cagcaatgat gactttgata actggagtac   1320
atttcgccct cgaactagct caaatgctag tactattagt gggagactct cacccattat   1380
gaccgaacag gatgatcttg gagaagggga tgtgcattct atggtgtacc cgccatctgc   1440
cgcaaagatg gcctctactt tacccagtct gtctgagata agcaatcccg aaaacatgga   1500
aaatcttttg gataatctca accttctctc atcaccaaca tcattaactg tttcgaccca   1560
gtcctcacct ggcaccatga tgcagcagac gccgtgctac tcgtttgcgc caccaaacac   1620
cagtttgaat tcacccagcc caaactacca aaaatataca tatggccaat ccagcatgag   1680
ccctttgccc cagatgccta tacaaacact tcaggacaat aagtcgagtt atggaggtat   1740
gagtcagtat aactgtgcgc ctggactctt gaaggagttg ctgacttctg actctcctcc   1800
ccataatgac attatgacac cagttgatcc tggggtagcc cagcccaaca gccgggttct   1860
gggccagaac gtcatgatgg gccctaattc ggtcatgtca acctatggca gccaggcatc   1920
tcataacaaa atgatgaatc ccagctccca tacccaccct ggacatgctc agcagacatc   1980
tgcagttaac gggcgtcccc tgccccacac ggtaagcacc atgccccaca cctcgggtat   2040
gaaccgcctg acccaagtga agacacctgt acaagtgcct ctgccccacc ccatgcagat   2100
gagtgccctg gggggctact cctccgtgag cagctgcaat ggctatggca gaatgggcct   2160
tctccaccag gagaagctcc caagtgactt ggatggcatg ttcattgagc gcttagactg   2220
tgacatggaa tccatcattc ggaatgacct catggatgga gatacattgg attttaactt   2280
tgacaatgtg ttgcccaacc aaagcttccc acacagtgtc aagacaacga cacatagctg   2340
ggtgtcaggc tgagggttag tgagcaggtt acacttaaaa gtacttcaga ttgtctgaca   2400
gcaggaactg agagaagcag tccaaagatg tctttcacca actccctttt agttttcttg   2460
gttaaaaaaa aaaacaaaaa aaaaaaccct cctttttttcc tttcgtcaga cttggcagca   2520
aagacatttt tcctgtacag gatgtttgcc caatgtgtgc aggttatgtg ctgctgtaga   2580
taaggactgt gccattggaa atttcattac aatgaagtgc caaactcact acaccatata   2640
attgcagaaa agattttcag atcctggtgt gctttcaagt tttgtatata agcagtagat   2700
acagattgta tttgtgtgtg tttttggttt ttctaaatat ccaattggtc caaggaaagt   2760
ttatactctt tttgtaatac tgtgatgggc ctcatgtctt gataagttaa acttttgttt   2820
gtactacctg ttttctgcgg aactgacgga tcacaaagaa ctgaatctcc attctgcatc   2880
tccattgaac agccttggac ctgttcacgt tgccacagaa ttcacatgag aaccaagtag   2940
cctgttatca atctgctaaa ttaatggact tgttaaactt ttggaaaaaa aaagattaaa   3000
```

```
tgccagcttt gtacaggtct tttctatttt tttttgttta ttttgttatt tgcaaatttg   3060
tacaaacatt taaatggttc taatttccag ataaatgatt tttgatgtta ttgttgggac   3120
ttaagaacat ttttggaata gatattgaac tgtaataatg ttttcttaaa actagagtct   3180
actttgttac atagtcagct tgtaaatttt gtggaaccac aggtatttgg ggcagcattc   3240
ataattttca ttttgtattc taactggatt agtactaatt ttatacatgc ttaactggtt   3300
tgtacacttt gggatgctac ttagtgatgt ttctgactaa tcttaaatca ttgtaattag   3360
tacttgcata ttcaacgttt caggccctgg ttgggcagga aagtgatgta tagttatgga   3420
cactttgcgt ttcttattta ggataactta atatgttttt atgtatgtat tttaaagaaa   3480
tttcatctgc ttctactgaa ctatgcgtac tgcatagcat caagtcttct ctagagacct   3540
ctgtagtcct gggaggcctc ataatgtttg tagatcagaa aagggagatc tgcatctaaa   3600
gcaatggtcc tttgtcaaac gagggatttt gatccacttc accattttga gttgagcttt   3660
agcaaaagtt tcccctcata attctttgct cttgtttcag tccaggtgga ggttggtttt   3720
gtagttctgc cttgaggaat tatgtcaaca ctcatacttc atctcattct cccttctgcc   3780
ctgcagatta gattacttag cacactgtgg aagtttaagt ggaaggaggg aatttaaaaa   3840
tgggacttga gtggtttgta gaatttgtgt tcataagttc agatgggtag caaatggaat   3900
agaacttact taaaaattgg ggagatttat ttgaaaacca gctgtaagtt gtgcattgag   3960
attatgttaa aagccttggc ttaagaattt gaaaatttct ttagcctgta gcaacctaaa   4020
ctgtaattcc tatcattatg ttttattact ttccaattac ctgtaactga cagaccaaat   4080
taattggctt tgtgtcctat ttagtccatc agtattttca agtcatgtgg aaagcccaaa   4140
gtcatcacaa tgaagagaac aggtgcacag cactgttcct cttgtgttct tgagaaggat   4200
ctaatttttc tgtatatagc ccacatcaca cttgctttgt cttgtatgtt aattgcatct   4260
tcattggctt ggtatttcct aaatgtttaa caagaacaca agtgttcctg ataagatttc   4320
ctacagtaag ccagctctat tgtaagcttc ccactgtgat gatcattttt ttgaagattc   4380
attgaacagc caccactcta tcatcctcat tttggggcag tccaagacat agctggtttt   4440
agaaacccaa gttcctctaa gcacagcctc ccgggtatgt aactgaactt ggtgccaaag   4500
tacttgtgta ctaatttcta ttactacgta ctgtcacttt cctcccgtgc cattactgca   4560
tcataataca aggaacctca gagcccccat ttgttcatta aagaggcaac tacagccaaa   4620
atcactgtta aaatcttact acttcatgga gtagctctta ggaaaatata tcttcctcct   4680
gagtctgggt aattatacct ctcccaagcc cccattgtgt gttgaaatcc tgtcatgaat   4740
ccttggtagc tctctgagaa cagtgaagtc cagggaaagg catctggtct gtctggaaag   4800
caaacattat gtggcctctg gtagtttttt tcctgtaaga atactgactt tctggagtaa   4860
tgagtatata tcagttattg tacatgattg ctttgtgaaa tgtgcaaatg atatcaccta   4920
tgcagccttg tttgatttat tttctctggt ttgtactgtt attaaaagca tattgtatta   4980
tagagctatt cagatatttt aaatataaag atgtattgtt tccgtaatat agacgtatgg   5040
aatatattta ggtaatagat gtattacttg gaaagttctg ctttgacaaa ctgacaaagt   5100
ctaaatgagc acatgtatcc cagtgagcag taaatcaatg gaacatccca agaagaggat   5160
aaggatgctt aaaatggaaa tcattctcca acgatataca aattggactt gttcaactgc   5220
tggatatatg ctaccaataa ccccagcccc aacttaaaat tcttacattc aagctcctaa   5280
gagttcttaa tttataacta attttaaaag agaagtttct tttctggttt tagtttggga   5340
ataatcattc attaaaaaaa atgtattgtg gtttatgcga acagaccaac ctggcattac   5400
```

-continued agttggcctc tccttgaggt gggcacagcc tggcagtgtg gccaggggtg gccatgtaag 5460
tcccatcagg acgtagtcat gcctcctgca tttcgctacc cgagtttagt aacagtgcag 5520
attccacgtt cttgttccga tactctgaga agtgcctgat gttgatgtac ttacagacac 5580
aagaacaatc tttgctataa ttgtataaag ccataaatgt acataaatta tgtttaaatg 5640
gcttggtgtc tttcttttct aattatgcag aataagctct ttattaggaa tttttgtga 5700 agctattaaa tacttgagtt aagtcttgtc agccacaa 5738

<210> SEQ ID NO 13
<211> LENGTH: 457
<212> TYPE: PRT
<213> ORGANISM: Homo sapiens

<400> SEQUENCE: 13

Met Leu Gly Ala Val Lys Met Glu Gly His Glu Pro Ser Asp Trp Ser
1 5 10 15

Ser Tyr Tyr Ala Glu Pro Glu Gly Tyr Ser Ser Val Ser Asn Met Asn
20 25 30

Ala Gly Leu Gly Met Asn Gly Met Asn Thr Tyr Met Ser Met Ser Ala
35 40 45

Ala Ala Met Gly Ser Gly Ser Gly Asn Met Ser Ala Gly Ser Met Asn
50 55 60

Met Ser Ser Tyr Val Gly Ala Gly Met Ser Pro Ser Leu Ala Gly Met
65 70 75 80

Ser Pro Gly Ala Gly Ala Met Ala Gly Met Gly Gly Ser Ala Gly Ala
85 90 95

Ala Gly Val Ala Gly Met Gly Pro His Leu Ser Pro Ser Leu Ser Pro
100 105 110

Leu Gly Gly Gln Ala Ala Gly Ala Met Gly Gly Leu Ala Pro Tyr Ala
115 120 125

Asn Met Asn Ser Met Ser Pro Met Tyr Gly Gln Ala Gly Leu Ser Arg
130 135 140

Ala Arg Asp Pro Lys Thr Tyr Arg Arg Ser Tyr Thr His Ala Lys Pro
145 150 155 160

Pro Tyr Ser Tyr Ile Ser Leu Ile Thr Met Ala Ile Gln Gln Ser Pro
165 170 175

Asn Lys Met Leu Thr Leu Ser Glu Ile Tyr Gln Trp Ile Met Asp Leu
180 185 190

Phe Pro Phe Tyr Arg Gln Asn Gln Gln Arg Trp Gln Asn Ser Ile Arg
195 200 205

His Ser Leu Ser Phe Asn Asp Cys Phe Leu Lys Val Pro Arg Ser Pro
210 215 220

Asp Lys Pro Gly Lys Gly Ser Phe Trp Thr Leu His Pro Asp Ser Gly
225 230 235 240

Asn Met Phe Glu Asn Gly Cys Tyr Leu Arg Arg Gln Lys Arg Phe Lys
245 250 255

Cys Glu Lys Gln Leu Ala Leu Lys Glu Ala Ala Gly Ala Ala Gly Ser
260 265 270

Gly Lys Lys Ala Ala Ala Gly Ala Gln Ala Ser Gln Ala Gln Leu Gly
275 280 285

Glu Ala Ala Gly Pro Ala Ser Glu Thr Pro Ala Gly Thr Glu Ser Pro
290 295 300

His Ser Ser Ala Ser Pro Cys Gln Glu His Lys Arg Gly Gly Leu Gly
305 310 315 320

-continued

```
Glu Leu Lys Gly Thr Pro Ala Ala Ala Leu Ser Pro Pro Glu Pro Ala
                325                 330                 335

Pro Ser Pro Gly Gln Gln Gln Gln Ala Ala Ala His Leu Leu Gly Pro
            340                 345                 350

Pro His His Pro Gly Leu Pro Pro Glu Ala His Leu Lys Pro Glu His
        355                 360                 365

His Tyr Ala Phe Asn His Pro Phe Ser Ile Asn Asn Leu Met Ser Ser
    370                 375                 380

Glu Gln Gln His His His Ser His His His His Gln Pro His Lys Met
385                 390                 395                 400

Asp Leu Lys Ala Tyr Glu Gln Val Met His Tyr Pro Gly Tyr Gly Ser
                405                 410                 415

Pro Met Pro Gly Ser Leu Ala Met Gly Pro Val Thr Asn Lys Thr Gly
            420                 425                 430

Leu Asp Ala Ser Pro Leu Ala Ala Asp Thr Ser Tyr Tyr Gln Gly Val
        435                 440                 445

Tyr Ser Arg Pro Ile Met Asn Ser Ser
    450                 455


<210> SEQ ID NO 14
<211> LENGTH: 2428
<212> TYPE: DNA
<213> ORGANISM: Homo sapiens

<400> SEQUENCE: 14

cccgcccact tccaactacc gcctccggcc tgcccaggga gagagaggga gtggagccca      60

gggagaggga gcgcgagaga gggagggagg aggggacggt gctttggctg actttttttt     120

aaaagagggt gggggtgggg ggtgattgct ggtcgtttgt tgtggctgtt aaattttaaa     180

ctgccatgca ctcggcttcc agtatgctgg gagcggtgaa gatggaaggg cacgagccgt     240

ccgactggag cagctactat gcagagcccg agggctactc ctccgtgagc aacatgaacg     300

ccggcctggg gatgaacggc atgaacacgt acatgagcat gtcggcggcc gccatgggca     360

gcggctcggg caacatgagc gcgggctcca tgaacatgtc gtcgtacgtg ggcgctggca     420

tgagcccgtc cctggcgggg atgtcccccg gcgcgggcgc catggcgggc atgggcggct     480

cggccggggc ggccggcgtg gcgggcatgg ggccgcactt gagtcccagc ctgagcccgc     540

tcggggggca ggcggccggg gccatgggcg gcctggcccc ctacgccaac atgaactcca     600

tgagccccat gtacgggcag gcgggcctga gccgcgcccg cgaccccaag acctacaggc     660

gcagctacac gcacgcaaag ccgccctact cgtacatctc gctcatcacc atggccatcc     720

agcagagccc caacaagatg ctgacgctga gcgagatcta ccagtggatc atggacctct     780

tccccttcta ccggcagaac cagcagcgct ggcagaactc catccgccac tcgctctcct     840

tcaacgactg tttcctgaag gtgccccgct cgcccgacaa gcccggcaag ggctccttct     900

ggaccctgca ccctgactcg ggcaacatgt tcgagaacgg ctgctacctg cgccgccaga     960

agcgcttcaa gtgcgagaag cagctggcgc tgaaggaggc cgcaggcgcc gccggcagcg    1020

gcaagaaggc ggccgccgga gcccaggcct cacaggctca actcggggag gccgccgggc    1080

cggcctccga gactccggcg ggcaccgagt cgcctcactc gagcgcctcc ccgtgccagg    1140

agcacaagcg agggggcctg ggagagctga aggggacgcc ggctgcggcg ctgagccccc    1200

cagagccggc gccctctccc gggcagcagc agcaggccgc ggcccacctg ctgggcccgc    1260

cccaccaccc gggcctgccg cctgaggccc acctgaagcc ggaacaccac tacgccttca    1320
```

accacccgtt ctccatcaac aacctcatgt cctcggagca gcagcaccac cacagccacc 1380
accaccacca accccacaaa atggacctca aggcctacga acaggtgatg cactaccccg 1440
gctacggttc ccccatgcct ggcagcttgg ccatgggccc ggtcacgaac aaaacgggcc 1500
tggacgcctc gcccctggcc gcagatacct cctactacca gggggtgtac tcccggccca 1560
ttatgaactc ctcttaagaa gacgacggct tcaggcccgg ctaactctgg caccccggat 1620
cgaggacaag tgagagagca agtgggggtc gagactttgg ggagacggtg ttgcagagac 1680
gcaagggaga agaaatccat aacacccccca ccccaacacc cccaagacag cagtcttctt 1740
cacccgctgc agccgttccg tcccaaacag agggccacac agatacccca cgttctatat 1800
aaggaggaaa acgggaaaga atataaagtt aaaaaaaagc ctccggtttc cactactgtg 1860
tagactcctg cttcttcaag cacctgcaga ttctgatttt tttgttgttg ttgttctcct 1920
ccattgctgt tgttgcaggg aagtcttact taaaaaaaaa aaaaaatttt gtgagtgact 1980
cggtgtaaaa ccatgtagtt ttaacagaac cagagggttg tactattgtt taaaaacagg 2040
aaaaaaaata atgtaagggt ctgttgtaaa tgaccaagaa aaagaaaaaa aaagcattcc 2100
caatcttgac acggtgaaat ccaggtctcg ggtccgatta atttatggtt tctgcgtgct 2160
ttatttatgg cttataaatg tgtattctgg ctgcaagggc cagagttcca caaatctata 2220
ttaaagtgtt atacccggtt ttatcccttg aatcttttct tccagatttt tcttttcttt 2280
acttggctta caaaatatac aggcttggaa attatttcaa gaaggaggga gggataccct 2340
gtctggttgc aggttgtatt ttattttggc ccagggagtg ttgctgtttt cccaacattt 2400
tattaataaa attttcagac ataaaaaa 2428

<210> SEQ ID NO 15
<211> LENGTH: 505
<212> TYPE: PRT
<213> ORGANISM: Homo sapiens

<400> SEQUENCE: 15

Met Asp Pro Gly Asn Glu Asn Ser Ala Thr Glu Ala Ala Ala Ile Ile
1 5 10 15

Asp Leu Asp Pro Asp Phe Glu Pro Gln Ser Arg Pro Arg Ser Cys Thr
20 25 30

Trp Pro Leu Pro Arg Pro Glu Ile Ala Asn Gln Pro Ser Glu Pro Pro
35 40 45

Glu Val Glu Pro Asp Leu Gly Glu Lys Val His Thr Glu Gly Arg Ser
50 55 60

Glu Pro Ile Leu Leu Pro Ser Arg Leu Pro Glu Pro Ala Gly Gly Pro
65 70 75 80

Gln Pro Gly Ile Leu Gly Ala Val Thr Gly Pro Arg Lys Gly Gly Ser
85 90 95

Arg Arg Asn Ala Trp Gly Asn Gln Ser Tyr Ala Glu Leu Ile Ser Gln
100 105 110

Ala Ile Glu Ser Ala Pro Glu Lys Arg Leu Thr Leu Ala Gln Ile Tyr
115 120 125

Glu Trp Met Val Arg Thr Val Pro Tyr Phe Lys Asp Lys Gly Asp Ser
130 135 140

Asn Ser Ser Ala Gly Trp Lys Asn Ser Ile Arg His Asn Leu Ser Leu
145 150 155 160

His Ser Lys Phe Ile Lys Val His Asn Glu Ala Thr Gly Lys Ser Ser
165 170 175

Trp Trp Met Leu Asn Pro Glu Gly Gly Lys Ser Gly Lys Ala Pro Arg
180 185 190

Arg Arg Ala Ala Ser Met Asp Ser Ser Ser Lys Leu Leu Arg Gly Arg
195 200 205

Ser Lys Ala Pro Lys Lys Lys Pro Ser Val Leu Pro Ala Pro Pro Glu
210 215 220

Gly Ala Thr Pro Thr Ser Pro Val Gly His Phe Ala Lys Trp Ser Gly
225 230 235 240

Ser Pro Cys Ser Arg Asn Arg Glu Glu Ala Asp Met Trp Thr Thr Phe
245 250 255

Arg Pro Arg Ser Ser Ser Asn Ala Ser Ser Val Ser Thr Arg Leu Ser
260 265 270

Pro Leu Arg Pro Glu Ser Glu Val Leu Ala Glu Glu Ile Pro Ala Ser
275 280 285

Val Ser Ser Tyr Ala Gly Gly Val Pro Pro Thr Leu Asn Glu Gly Leu
290 295 300

Glu Leu Leu Asp Gly Leu Asn Leu Thr Ser Ser His Ser Leu Leu Ser
305 310 315 320

Arg Ser Gly Leu Ser Gly Phe Ser Leu Gln His Pro Gly Val Thr Gly
325 330 335

Pro Leu His Thr Tyr Ser Ser Ser Leu Phe Ser Pro Ala Glu Gly Pro
340 345 350

Leu Ser Ala Gly Glu Gly Cys Phe Ser Ser Ser Gln Ala Leu Glu Ala
355 360 365

Leu Leu Thr Ser Asp Thr Pro Pro Pro Pro Ala Asp Val Leu Met Thr
370 375 380

Gln Val Asp Pro Ile Leu Ser Gln Ala Pro Thr Leu Leu Leu Leu Gly
385 390 395 400

Gly Leu Pro Ser Ser Ser Lys Leu Ala Thr Gly Val Gly Leu Cys Pro
405 410 415

Lys Pro Leu Glu Ala Pro Gly Pro Ser Ser Leu Val Pro Thr Leu Ser
420 425 430

Met Ile Ala Pro Pro Pro Val Met Ala Ser Ala Pro Ile Pro Lys Ala
435 440 445

Leu Gly Thr Pro Val Leu Thr Pro Pro Thr Glu Ala Ala Ser Gln Asp
450 455 460

Arg Met Pro Gln Asp Leu Asp Leu Asp Met Tyr Met Glu Asn Leu Glu
465 470 475 480

Cys Asp Met Asp Asn Ile Ile Ser Asp Leu Met Asp Glu Gly Glu Gly
485 490 495

Leu Asp Phe Asn Phe Glu Pro Asp Pro
500 505

<210> SEQ ID NO 16
<211> LENGTH: 3365
<212> TYPE: DNA
<213> ORGANISM: Homo sapiens

<400> SEQUENCE: 16
aaaaggggga gggaactgcg gctaaggaga cgttcggtga tgggagcgca atatatgagg 60
ggatacagtg cctcaggttt aaaagagcag gaagctgagt gagaggttgc agaaaaagtg 120
tcttcgctcg gcagaggtta caggtggcat ctcagaaaga gctttgaggc tacaggctgt 180
agtcgggaag gggatcggag aactgtgtga agggacagct tagggactag cgtcctggga 240
ctagggggaa gttcgcgact ttctgaagac tggcaggaat gtgcctcctg gccctcgatg 300
cttcccccct gaggggaggc atcgtgaggg actgtggcag gcttcactga acgctgagcc 360
ggggaggtcc aactccacgt atggatccgg ggaatgagaa ttcagccaca gaggctgccg 420
cgatcataga cctagatccc gacttcgaac cccagagccg tccccgctcc tgcacctggc 480
cccttccccg accagagatc gctaaccagc cgtccgagcc gcccgaggtg gagccagatc 540
tgggggaaaa ggtacacacg gaggggcgct cagagccgat cctgttgccc tctcggctcc 600
cagagccggc cgggggcccc cagcccggaa tcctgggggc tgtaacaggt cctcggaagg 660
gaggctcccg ccggaatgcc tggggaaatc agtcatatgc agaactcatc agccaggcca 720
ttgaaagcgc ccccggagaag cgactgacac ttgcccagat ctacgagtgg atggtccgta 780
ctgtacccta cttcaaggac aagggtgaca gcaacagctc agcaggatgg aagaactcga 840
tccgccacaa cctgtccctg cacagcaagt tcatcaaggt tcacaacgag gccaccggca 900
aaagctcttg gtggatgctg aaccctgagg gaggcaagag cggcaaagcc ccccgccgcc 960
gggccgcctc catggatagc agcagcaagc tgctccgggg ccgcagtaaa gcccccaaga 1020
agaaaccatc tgtgctgcca gctccacccg aaggtgccac tccaacgagc cctgtcggcc 1080
actttgccaa gtggtcaggc agcccttgct ctcgaaaccg tgaagaagcc gatatgtgga 1140
ccaccttccg tccacgaagc agttcaaatg ccagcagtgt cagcacccgg ctgtccccct 1200
tgaggccaga gtctgaggtg ctggcggagg aaataccagc ttcagtcagc agttatgcag 1260
ggggtgtccc tcccaccctc aatgaaggtc tagagctgtt agatgggctc aatctcacct 1320
cttcccattc cctgctatct cggagtggtc tctctggctt ctctttgcag catcctgggg 1380
ttaccggccc cttacacacc tacagcagct cccttttcag cccagcagag ggccccctgt 1440
cagcaggaga agggtgcttc tccagctccc aggctctgga ggccctgctc acctctgata 1500
cgccaccacc ccctgctgac gtcctcatga cccaggtaga tcccattctg tcccaggctc 1560
cgactcttct gttgctgggg gggcttcctt cctccagtaa gctggccacg ggcgtcggcc 1620
tgtgtcccaa gcccctagag gctccaggcc ccagcagtct ggttcccacc ctttctatga 1680
tagcaccacc tccagtcatg gcaagtgccc ccatccccaa ggctctgggg actcctgtgc 1740
tcacaccccc tactgaagct gcaagccaag acagaatgcc tcaggatcta gatcttgata 1800
tgtatatgga gaacctggag tgtgacatgg ataacatcat cagtgacctc atggatgagg 1860
gcgagggact ggacttcaac tttgagccag atccctgagt catgcctgga agctttgtcc 1920
cctgcttcag atgtggagcc aggcgtgttc atatctactc tttacccttg agccctcccc 1980
aggaatttgg gaccctgctt tagagctagg gtggggtctg gtcacacaca ggtgttgaag 2040
aaattataaa gataaagctg ccccatctgg ggacgatatg gggagggaga tgggaggggga 2100
aaggggagag ggtttttctc actgtgccaa ttagggggta aggccccctc tcaggagcca 2160
tcatcggctt tccccattcc tacccactta ggctttgtag caagatgagc aatgctgttg 2220
gaaatgtgaa gtcaccagtg gccttacccc tgcctttggg agcaggattt ttttgtagag 2280
agtcttatct gagctgagcc aggctagctg gagcctggga tttctatgca gtggcccctt 2340

```
aggccagtga tgtgcggtgg gtgggctgtt taggggatct ggaagggcca aggtctgagc   2400

actggagtgg ctcgccaggc caaatcaccc ttagaaggct gcagataaca gaaaggcttt   2460

ttataaactt ttaaagaaat ataaacacaa atatagagat tttttaacca tggcagggtg   2520

ctagtggtgg gcagaatgct tttttttctt tctgaaggct ttgtgatagt gacatgatac   2580

aaacactaca gacaataaat attaggagac acagggaagt ggggagaggt ggggagtaat   2640

agtaaacaca gggaagagct cccctacgga ccaggtatag agaaaggtct atgcagaaat   2700

aggttagagt ttccctaaca aaaaagctaa cccaggtccc ctcattcctt caacttgtgc   2760

ctgggagtgt gtggtgttag ggtgcagcca cactcttcta tgacccagca tgggttagtg   2820

ctatggtggg agagtacatt gaaggcctgg aattagcttg gggccaggga agggactggg   2880

aggggagaga agagaaggag ggaaggattt aggatggtaa agttaggtac agagacctcc   2940

ctgttcaagg cccctgacag ctgtccctgc ccttcttccc cttccctgac tgcaggggtt   3000

atgtggaagt gtgtgtggca gcaggcagcg gggaggggag gaacagggaa gggggagctg   3060

gggagcttgg ctgagggtct gggaaatgag cagggatggg gggggatgtg gatcaggttt   3120

actagcacct gccagggagg ccatctgggg ctccttctcc accccagccc ccaaagcagc   3180

ccttccccca gtgccctttg catcgtcccc tcccccaccc ctgctgtggg ttcccatcat   3240

ttcctgtgtc agcgcctggc ctacccagat tgtatcatgt gctagattgg agtggggaag   3300

tgtgtcaaat caataaatga ataaattcaa taaatgccta taaccagcaa aaaaaaaaaa   3360

aaaaa                                                               3365
```

<210> SEQ ID NO 17
<211> LENGTH: 421
<212> TYPE: PRT
<213> ORGANISM: Homo sapiens

<400> SEQUENCE: 17

```
Met Asn Arg Gly Phe Ser Arg Lys Ser His Thr Phe Leu Pro Lys Ile
1               5                   10                  15

Phe Phe Arg Lys Met Ser Ser Ser Gly Ala Lys Asp Lys Pro Glu Leu
            20                  25                  30

Gln Phe Pro Phe Leu Gln Asp Glu Asp Thr Val Ala Thr Leu Leu Glu
        35                  40                  45

Cys Lys Thr Leu Phe Ile Leu Arg Gly Leu Pro Gly Ser Gly Lys Ser
    50                  55                  60

Thr Leu Ala Arg Val Ile Val Asp Lys Tyr Arg Asp Gly Thr Lys Met
65                  70                  75                  80

Val Ser Ala Asp Ala Tyr Lys Ile Thr Pro Gly Ala Arg Gly Ala Phe
                85                  90                  95

Ser Glu Glu Tyr Lys Arg Leu Asp Glu Asp Leu Ala Ala Tyr Cys Arg
            100                 105                 110

Arg Arg Asp Ile Arg Ile Leu Val Leu Asp Asp Thr Asn His Glu Arg
        115                 120                 125

Glu Arg Leu Glu Gln Leu Phe Glu Met Ala Asp Gln Tyr Gln Tyr Gln
    130                 135                 140

Val Val Leu Val Glu Pro Lys Thr Ala Trp Arg Leu Asp Cys Ala Gln
145                 150                 155                 160

Leu Lys Glu Lys Asn Gln Trp Gln Leu Ser Ala Asp Asp Leu Lys Lys
                165                 170                 175

Leu Lys Pro Gly Leu Glu Lys Asp Phe Leu Pro Leu Tyr Phe Gly Trp
            180                 185                 190
```

```
Phe Leu Thr Lys Lys Ser Ser Glu Thr Leu Arg Lys Ala Gly Gln Val
        195                 200                 205

Phe Leu Glu Glu Leu Gly Asn His Lys Ala Phe Lys Lys Glu Leu Arg
    210                 215                 220

Gln Phe Val Pro Gly Asp Glu Pro Arg Glu Lys Met Asp Leu Val Thr
225                 230                 235                 240

Tyr Phe Gly Lys Arg Pro Pro Gly Val Leu His Cys Thr Thr Lys Phe
                245                 250                 255

Cys Asp Tyr Gly Lys Ala Pro Gly Ala Glu Glu Tyr Ala Gln Gln Asp
            260                 265                 270

Val Leu Lys Lys Ser Tyr Ser Lys Ala Phe Thr Leu Thr Ile Ser Ala
        275                 280                 285

Leu Phe Val Thr Pro Lys Thr Thr Gly Ala Arg Val Glu Leu Ser Glu
    290                 295                 300

Gln Gln Leu Gln Leu Trp Pro Ser Asp Val Asp Lys Leu Ser Pro Thr
305                 310                 315                 320

Asp Asn Leu Pro Arg Gly Ser Arg Ala His Ile Thr Leu Gly Cys Ala
                325                 330                 335

Ala Asp Val Glu Ala Val Gln Thr Gly Leu Asp Leu Leu Glu Ile Leu
            340                 345                 350

Arg Gln Glu Lys Gly Gly Ser Arg Gly Glu Glu Val Gly Glu Leu Ser
        355                 360                 365

Arg Gly Lys Leu Tyr Ser Leu Gly Asn Gly Arg Trp Met Leu Thr Leu
    370                 375                 380

Ala Lys Asn Met Glu Val Arg Ala Ile Phe Thr Gly Tyr Tyr Gly Lys
385                 390                 395                 400

Gly Lys Pro Val Pro Thr Gln Gly Ser Arg Lys Gly Gly Ala Leu Gln
                405                 410                 415

Ser Cys Thr Ile Ile
            420
```

<210> SEQ ID NO 18
<211> LENGTH: 2598
<212> TYPE: DNA
<213> ORGANISM: Homo sapiens

<400> SEQUENCE: 18

```
ctccgcgcag gcgggcggcc ccggagcgct ggtgccggca gaggcggcga cggtggcgcc     60

cctcctcatc atgaggcttc tcccgaaaaa gccacacatt cctgcccaag atcttcttcc    120

gcaagatgtc atcctcaggg gccaaggaca agcctgagct gcagtttccc ttccttcagg    180

atgaggacac agtggccacg ctgctagagt gcaagacgct cttcatcttg cgcggcctgc    240

caggaagcgg caagtccacg ctggcacggg tcatcgtgga caagtaccgt gatggcacca    300

agatggtgtc ggctgacgct tacaagatca cccccggcgc tcgaggagcc ttctccgagg    360

agtacaagcg gctcgatgag gacctggctg cctactgccg ccgccgggac atcagaattc    420

ttgtgcttga tgacaccaac cacgaacggg aacggctgga gcagctcttt gaaatggccg    480

accagtacca gtaccaggtg gtgctggtgg agcccaagac ggcgtggcgg ctggactgtg    540

cccagctcaa ggagaagaac cagtggcagc tgtcggctga tgacctgaag aagctgaagc    600

ctgggctgga gaaggacttc ctgccgctct acttcggctg gttcctgacc aagaagagct    660

ctgagaccct ccgcaaagcc ggccaggtct tcctggaaga gctggggaac cacaaggcct    720

tcaagaagga gctgcgacaa ttcgtccctg gggatgagcc cagggagaag atggacttgg    780
```

-continued

```
tcacctactt tggaaagaga cccccaggcg tgctgcattg cacaaccaag ttttgtgact    840

acgggaaggc tcccggggca gaggagtacg ctcaacaaga tgtgttaaag aaatcttact    900

ccaaggcctt cacgctgacc atctctgccc tctttgtgac acccaagacg actggggccc    960

gggtggagtt aagcgagcag caactgcagt tgtggccgag tgatgtggac aagctgtcac   1020

ccactgacaa cctgccgcgg gggagccgcg cccacatcac cctcggctgt gcagctgacg   1080

tagaggccgt gcagacgggc cttgacctct tagagattct gcggcaggag aagggggggca   1140

gccgaggcga ggaggtgggc gagctaagcc ggggcaagct ctattccttg ggcaatgggc   1200

gctggatgct gaccctggcc aagaacatgg aggtcagggc catcttcacg ggtactacg    1260

ggaaaggcaa acctgtgccc acgcaaggta gccggaaggg gggcgccttg cagtcctgca   1320

ccatcatatg agtgttctca ccaccactta tgcccctaga agggaagggg agagggaaac   1380

gtgccctctg tttgatcctt gttttgtgac attttttttt ttttttttt tactcaaagt    1440

taacctacct gtaacttttt aaaaacttgt aaaataactg accctccctt cctgtccgcc   1500

ctcttcccct ctaatgctca cgctcccaac acaaggtggg cagggaggca ccattcagga   1560

acctggacca aagctgacga ggctgggcca agccagggat ggggccacag ccagaacccc   1620

gagccctact tccaggttct ggttagctca gccccagccc agcccagctg ctctgcccag   1680

agctgggtga gtggggagac acctcagagc cccgcaaaac ccactgaccg gaggcaaaag   1740

gcagtggggc tgggggtagt tttccatggt cacagagaac tagtggtggc tctgagaagg   1800

ggaggacctc tgggctttga ttccatctcc ttgtcttttt tctttgtttt tagagacagg   1860

gtcctgctat ttcccaagct ggagtgcagt ggtgcgatca tggctcactg cagcctcgaa   1920

ctcctgggct caagcaatcc tcctgagtga tcccatttct taatcagtgt agccccaaga   1980

aggctggggc tatttaccag ggtagaaaaa ggagcttacc tcccaccttt ggtcctaagt   2040

ccctgccccc tccccttcac accataacta ggtaacagtt tgataactag ggaagaaagc   2100

agaacagtta agcagccgcc acatccccgc tggctggggg cctcactcca ggaaggggct   2160

ggactggctg tcctttccag tggcctggct ccgctgtgtg gatggggaga tcggggccag   2220

aggcagaacc ctggtgagga agctccagtc ctgctctcta cccagcccat cttgcctcca   2280

tggtgcctct ggaggcctct gggcctcctc taacaggggc tggtgggcac caagagccaa   2340

tggagtagac ccctggctgg taagggccaa gtcccaccgg ttgcttctgg gaaggggttt   2400

ctaacactag tctgtgtgct gtggttcctg ggtgccctc cactgccctc tgttcagtaa    2460

cagggccttg ctaatcgggt tgtcactcaa caaaagtgct ttggatttaa gttactatcc   2520

tggctttgcc caacctcagc aacctgtaag actgataatg aaataaatca tgttaatcct   2580

agcaaaaaaa aaaaaaaa                                                 2598
```

<210> SEQ ID NO 19
<211> LENGTH: 304
<212> TYPE: PRT
<213> ORGANISM: Homo sapiens

<400> SEQUENCE: 19

```
Met Gly Asn His Ala Gly Lys Arg Glu Leu Asn Ala Glu Lys Ala Ser
1               5                   10                  15

Thr Asn Ser Glu Thr Asn Arg Gly Glu Ser Glu Lys Lys Arg Asn Leu
            20                  25                  30

Gly Glu Leu Ser Arg Thr Thr Ser Glu Asp Asn Glu Val Phe Gly Glu
        35                  40                  45
```

```
Ala Asp Ala Asn Gln Asn Asn Gly Thr Ser Ser Gln Asp Thr Ala Val
    50                  55                  60

Thr Asp Ser Lys Arg Thr Ala Asp Pro Lys Asn Ala Trp Gln Asp Ala
65                  70                  75                  80

His Pro Ala Asp Pro Gly Ser Arg Pro His Leu Ile Arg Leu Phe Ser
                85                  90                  95

Arg Asp Ala Pro Gly Arg Glu Asp Asn Thr Phe Lys Asp Arg Pro Ser
            100                 105                 110

Glu Ser Asp Glu Leu Gln Thr Ile Gln Glu Asp Ser Ala Ala Thr Ser
        115                 120                 125

Glu Ser Leu Asp Val Met Ala Ser Gln Lys Arg Pro Ser Gln Arg His
    130                 135                 140

Gly Ser Lys Tyr Leu Ala Thr Ala Ser Thr Met Asp His Ala Arg His
145                 150                 155                 160

Gly Phe Leu Pro Arg His Arg Asp Thr Gly Ile Leu Asp Ser Ile Gly
                165                 170                 175

Arg Phe Phe Gly Gly Asp Arg Gly Ala Pro Lys Arg Gly Ser Gly Lys
            180                 185                 190

Asp Ser His His Pro Ala Arg Thr Ala His Tyr Gly Ser Leu Pro Gln
        195                 200                 205

Lys Ser His Gly Arg Thr Gln Asp Glu Asn Pro Val Val His Phe Phe
    210                 215                 220

Lys Asn Ile Val Thr Pro Arg Thr Pro Pro Pro Ser Gln Gly Lys Gly
225                 230                 235                 240

Arg Gly Leu Ser Leu Ser Arg Phe Ser Trp Gly Ala Glu Gly Gln Arg
                245                 250                 255

Pro Gly Phe Gly Tyr Gly Gly Arg Ala Ser Asp Tyr Lys Ser Ala His
            260                 265                 270

Lys Gly Phe Lys Gly Val Asp Ala Gln Gly Thr Leu Ser Lys Ile Phe
        275                 280                 285

Lys Leu Gly Gly Arg Asp Ser Arg Ser Gly Ser Pro Met Ala Arg Arg
    290                 295                 300
```

<210> SEQ ID NO 20
<211> LENGTH: 2139
<212> TYPE: DNA
<213> ORGANISM: Homo sapiens

<400> SEQUENCE: 20

```
gaaaacagtg cagccacctc cgagagcctg gatgtgatgg cgtcacagaa gagaccctcc      60

cagaggcacg gatccaagta cctggccaca gcaagtacca tggaccatgc caggcatggc     120

ttcctcccaa ggcacagaga cacgggcatc cttgactcca tcgggcgctt ctttggcggt     180

gacaggggtg cgccaaagcg gggctctggc aaggactcac accacccggc aagaactgct     240

cactatggct ccctgcccca gaagtcacac ggccggaccc aagatgaaaa ccccgtagtc     300

cacttcttca agaacattgt gacgcctcgc acaccacccc cgtcgcaggg aaaggggaga     360

ggactgtccc tgagcagatt tagctggggg gccgaaggcc agagaccagg atttggctac     420

ggaggcagag cgtccgacta taaatcggct cacaagggat tcaagggagt cgatgcccag     480

ggcacgcttt ccaaaatttt taagctggga ggaagagata gtcgctctgg atcacccatg     540

gctagacgct gaaaacccac ctggttccgg aatcctgtcc tcagcttctt aatataactg     600

ccttaaaact ttaatcccac ttgcccctgt tacctaatta gagcagatga cccctcccct     660

aatgcctgcg gagttgtgca cgtagtaggg tcaggccacg gcagcctacc ggcaatttcc     720
```

```
ggccaacagt taaatgagaa catgaaaaca gaaaacggtt aaaactgtcc ctttctgtgt     780

gaagatcacg ttccttcccc cgcaatgtgc ccccagacgc acgtgggtct tcagggggcc     840

aggtgcacag acgtccctcc acgttcaccc ctccaccctt ggactttctt ttcgccgtgg     900

ctcggcaccc ttgcgctttt gctggtcact gccatggagg cacacagctg cagagacaga     960

gaggacgtgg gcggcagaga ggactgttga catccaagct tcctttgttt tttttcctg     1020

tccttctctc acctcctaaa gtagacttca tttttcctaa caggattaga cagtcaagga    1080

gtggcttact acatgtggga gctttttggt atgtgacatg cgggctgggc agctgttaga    1140

gtccaacgtg gggcagcaca gagagggggc cacctcccca ggccgtggct gcccacacac    1200

cccaattagc tgaattcgcg tgtggcagag ggaggaaaag gaggcaaacg tgggctgggc    1260

aatggcctca cataggaaac aggtcttcc tggagatttg gtgatggaga tgtcaagcag     1320

gtggcctctg gacgtcaccg ttgccctgca tggtggcccc agagcagcct ctatgaacaa    1380

cctcgtttcc aaaccacagc ccacagccgg agagtccagg aagacttgcg cactcagagc    1440

agaagggtag gagtcctcta gacagcctcg cagccgcgcc agtcgcccat agacactggc    1500

tgtgaccggg cgtgctggca gcggcagtgc acagtggcca gcactaaccc tccctgagaa    1560

gataaccggc tcattcactt cctcccagaa gacgcgtggt agcgagtagg cacaggcgtg    1620

cacctgctcc cgaattactc accgagacac acgggctgag cagacggccc ctgtgatgga    1680

gacaaagagc tcttctgacc atatccttct taacacccgc tggcatctcc tttcgcgcct    1740

ccctccctaa cctactgacc caccttttga ttttagcgca cctgtgattg ataggccttc    1800

caaagagtcc cacgctggca tcaccctccc cgaggacgga gatgaggagt agtcagcgtg    1860

atgccaaaac gcgtcttctt aatccaattc taattctgaa tgtttcgtgt gggcttaata    1920

ccatgtctat taatatatag cctcgatgat gagagagtta caaagaacaa aactccagac    1980

acaaacctcc aaatttttca gcagaagcac tctgcgtcgc tgagctgagg tcggctctgc    2040

gatccatacg tggccgcacc cacacagcac gtgctgtgac gatggctgaa cggaaagtgt    2100

acactgttcc tgaatattga aataaaacaa taaacttttt                          2139
```

<210> SEQ ID NO 21
<211> LENGTH: 378
<212> TYPE: PRT
<213> ORGANISM: Homo sapiens

<400> SEQUENCE: 21

```
Met Asp Ser Val Arg Ser Gly Ala Phe Gly His Leu Phe Arg Pro Asp
1               5                   10                  15

Asn Phe Ile Phe Gly Gln Ser Gly Ala Gly Asn Asn Trp Ala Lys Gly
            20                  25                  30

His Tyr Thr Glu Gly Ala Glu Leu Val Asp Ser Val Leu Asp Val Val
        35                  40                  45

Arg Lys Glu Cys Glu Asn Cys Asp Cys Leu Gln Gly Phe Gln Leu Thr
    50                  55                  60

His Ser Leu Gly Gly Gly Thr Gly Ser Gly Met Gly Thr Leu Leu Ile
65                  70                  75                  80

Ser Lys Val Arg Glu Glu Tyr Pro Asp Arg Ile Met Asn Thr Phe Ser
                85                  90                  95

Val Val Pro Ser Pro Lys Val Ser Asp Thr Val Val Glu Pro Tyr Asn
            100                 105                 110

Ala Thr Leu Ser Ile His Gln Leu Val Glu Asn Thr Asp Glu Thr Tyr
        115                 120                 125
```

```
Cys Ile Asp Asn Glu Ala Leu Tyr Asp Ile Cys Phe Arg Thr Leu Lys
    130                 135                 140

Leu Ala Thr Pro Thr Tyr Gly Asp Leu Asn His Leu Val Ser Ala Thr
145                 150                 155                 160

Met Ser Gly Val Thr Thr Ser Leu Arg Phe Pro Gly Gln Leu Asn Ala
                165                 170                 175

Asp Leu Arg Lys Leu Ala Val Asn Met Val Pro Phe Pro Arg Leu His
            180                 185                 190

Phe Phe Met Pro Gly Phe Ala Pro Leu Thr Ala Arg Gly Ser Gln Gln
        195                 200                 205

Tyr Arg Ala Leu Thr Val Pro Glu Leu Thr Gln Gln Met Phe Asp Ala
    210                 215                 220

Lys Asn Met Met Ala Ala Cys Asp Pro Arg His Gly Arg Tyr Leu Thr
225                 230                 235                 240

Val Ala Thr Val Phe Arg Gly Arg Met Ser Met Lys Glu Val Asp Glu
                245                 250                 255

Gln Met Leu Ala Ile Gln Ser Lys Asn Ser Ser Tyr Phe Val Glu Trp
            260                 265                 270

Ile Pro Asn Asn Val Lys Val Ala Val Cys Asp Ile Pro Pro Arg Gly
        275                 280                 285

Leu Lys Met Ser Ser Thr Phe Ile Gly Asn Ser Thr Ala Ile Gln Glu
    290                 295                 300

Leu Phe Lys Arg Ile Ser Glu Gln Phe Thr Ala Met Phe Arg Arg Lys
305                 310                 315                 320

Ala Phe Leu His Trp Tyr Thr Gly Glu Gly Met Asp Glu Met Glu Phe
                325                 330                 335

Thr Glu Ala Glu Ser Asn Met Asn Asp Leu Val Ser Glu Tyr Gln Gln
            340                 345                 350

Tyr Gln Asp Ala Thr Ala Glu Glu Glu Gly Glu Met Tyr Glu Asp Asp
        355                 360                 365

Glu Glu Glu Ser Glu Ala Gln Gly Pro Lys
    370                 375
```

<210> SEQ ID NO 22
<211> LENGTH: 1720
<212> TYPE: DNA
<213> ORGANISM: Homo sapiens

<400> SEQUENCE: 22

```
gcccggcccg cccgcgcccg tccgcagccg cccgccagac gcgcccagta tgagggagat      60

cgtgcacatc caggccggcc agtgcggcaa ccagatcggg gccaagttct gggaagtcat     120

cagtgatgag catggcatcg accccagcgg caactacgtg ggcgactcgg acttgcagct     180

ggagcggatc agcgtctact acaacgaggc ctcttctcac aagtacgtgc ctcgagccat     240

tctggtggac ctggaacccg gaaccatgga cagtgtccgc tcaggggcct ttggacatct     300

cttcaggcct gacaatttca tctttggtca gagtggggcc ggcaacaact gggccaaggg     360

tcactacacg gagggggcgg agctggtgga ttcggtcctg gatgtggtgc ggaaggagtg     420

tgaaaactgc gactgcctgc agggcttcca gctgacccac tcgctggggg gcggcacggg     480

ctccggcatg ggcacgttgc tcatcagcaa ggtgcgtgag gagtatcccg accgcatcat     540

gaacaccttc agcgtcgtgc cctcacccaa ggtgtcagac acggtggtgg agccctacaa     600

cgccacgctg tccatccacc agctggtgga gaacacggat gagacctact gcatcgacaa     660

cgaggcgctc tacgacatct gcttccgcac cctcaagctg gccacgccca cctacgggga     720
```

-continued

```
cctcaaccac ctggtatcgg ccaccatgag cggagtcacc acctccttgc gcttcccggg    780

ccagctcaac gctgacctgc gcaagctggc cgtcaacatg gtgcccttcc cgcgcctgca    840

cttcttcatg cccggcttcg ccccccctcac agcccggggc agccagcagt accgggccct    900

gaccgtgccc gagctcaccc agcagatgtt cgatgccaag aacatgatgg ccgcctgcga    960

cccgcgccac ggccgctacc tgacggtggc caccgtgttc cggggccgca tgtccatgaa   1020

ggaggtggac gagcagatgc tggccatcca gagcaagaac agcagctact tcgtggagtg   1080

gatccccaac aacgtgaagg tggccgtgtg tgacatcccg ccccgcggcc tcaagatgtc   1140

ctccaccttc atcgggaaca gcacggccat ccaggagctg ttcaagcgca tctccgagca   1200

gttcacggcc atgttccggc gcaaggcctt cctgcactgg tacacgggcg agggcatgga   1260

cgagatggag ttcaccgagg ccgagagcaa catgaacgac ctggtgtccg agtaccagca   1320

gtaccaggac gccacggccg aggaagaggg cgagatgtac gaagacgacg aggaggagtc   1380

ggaggcccag ggccccaagt gaagctgctc gcagctggag tgagaggcag gtggcggccg   1440

gggccgaagc cagcagtgtc taaacccccg gagccatctt gctgccgaca ccctgctttc   1500

ccctcgccct agggctccct tgccgccctc ctgcagtatt tatggcctcg tcctccccac   1560

ctaggccacg tgtgagctgc tcctgtctct gtcttattgc agctccaggc ctgacgtttt   1620

acggttttgt tttttactgg tttgtgttta tattttcggg gatacttaat aaatctattg   1680

ctgtcagata cccttaaaaa aaaaaaaaaa aaaaaaaaaa                         1720
```

<210> SEQ ID NO 23
<211> LENGTH: 312
<212> TYPE: PRT
<213> ORGANISM: Homo sapiens

<400> SEQUENCE: 23

```
Met Ala Gln Pro Tyr Pro Pro Ala Gln Tyr Pro Pro Pro Pro Gln Asn
1               5                   10                  15

Gly Ile Pro Ala Glu Tyr Ala Pro Pro Pro Pro His Pro Thr Gln Asp
            20                  25                  30

Tyr Ser Gly Gln Thr Pro Val Pro Thr Glu His Gly Met Thr Leu Tyr
        35                  40                  45

Thr Pro Ala Gln Thr His Pro Glu Gln Pro Gly Ser Glu Ala Ser Thr
    50                  55                  60

Gln Pro Ile Ala Gly Thr Gln Thr Val Pro Gln Thr Asp Glu Ala Ala
65                  70                  75                  80

Gln Thr Asp Ser Gln Pro Leu His Pro Ser Asp Pro Thr Glu Lys Gln
                85                  90                  95

Gln Pro Lys Arg Leu His Val Ser Asn Ile Pro Phe Arg Phe Arg Asp
            100                 105                 110

Pro Asp Leu Arg Gln Met Phe Gly Gln Phe Gly Lys Ile Leu Asp Val
        115                 120                 125

Glu Ile Ile Phe Asn Glu Arg Gly Ser Lys Gly Phe Gly Phe Val Thr
    130                 135                 140

Phe Glu Thr Ser Ser Asp Ala Asp Arg Ala Arg Glu Lys Leu Asn Gly
145                 150                 155                 160

Thr Ile Val Glu Gly Arg Lys Ile Glu Val Asn Asn Ala Thr Ala Arg
                165                 170                 175

Val Met Thr Asn Lys Lys Thr Gly Asn Pro Tyr Thr Asn Gly Trp Lys
            180                 185                 190
```

```
Leu Asn Pro Val Val Gly Ala Val Tyr Gly Pro Glu Phe Tyr Ala Val
        195                 200                 205

Thr Gly Phe Pro Tyr Pro Thr Thr Gly Thr Ala Val Ala Tyr Arg Gly
    210                 215                 220

Ala His Leu Arg Gly Arg Gly Arg Ala Val Tyr Asn Thr Phe Arg Ala
225                 230                 235                 240

Ala Pro Pro Pro Pro Pro Ile Pro Thr Tyr Gly Ala Val Val Tyr Gln
                245                 250                 255

Asp Gly Phe Tyr Gly Ala Glu Ile Tyr Gly Gly Tyr Ala Ala Tyr Arg
            260                 265                 270

Tyr Ala Gln Pro Ala Ala Ala Ala Ala Ala Tyr Ser Asp Ser Tyr Gly
        275                 280                 285

Arg Val Tyr Ala Ala Ala Asp Pro Tyr His His Thr Ile Gly Pro Ala
    290                 295                 300

Ala Thr Tyr Ser Ile Gly Thr Met
305                 310


<210> SEQ ID NO 24
<211> LENGTH: 3007
<212> TYPE: DNA
<213> ORGANISM: Homo sapiens

<400> SEQUENCE: 24

gatacagcag cagctggtgc tcctggccag gctgtgcgtg ctctctctgc ctctctctct     60

cggactctct gctctctctc tctgactctc tcctctctct ctgttggcct ggtgaaatgt    120

tcttggctgt aggcacacag agccttggac tcaaggctgt tggagtcgag gacaccttga    180

cttcggtcct ggaggttgaa attctgcctc tgagaagcta acagtcttcc tgtggtcgcc    240

actcctcccc agcagccccc tccttgccaa ggacggtcca gaaggagccc cactggggcc    300

tccccgctca gcaaagcaga cctcacctcc cactaccagc ttgaagtcac agcagccaga    360

ggaaattctg ccaccatttt cccaggtctg cagcccctcc agctgggaac ctgctcctgg    420

agccatccct ctgcaaacag agagcccaga gtgcctcggg gaaaattggc tgaataaaag    480

agcgatcagg acgccacggc tccgcctgaa gcgatggccc agccctaccc ccccgcccag    540

taccccccctc cgccacagaa cggcatccct gccgagtacg ccccgccccc accgcacccc    600

acgcaggact actccggcca gacccccggtc cccacagagc atggcatgac cctgtacaca    660

ccagcacaga cccaccccga gcagccaggc tccgaggcca gcacacagcc catcgccggg    720

acccagacag tgccgcagac agacgaggcg gcacagacgg acagccagcc gctccacccc    780

tccgacccta cagagaagca gcagcccaag cggctacacg tctccaacat cccctccgg    840

ttcagggacc ccgacttgcg gcaaatgttc gggcaattcg gaaaaatttt agacgtggag    900

atcattttta acgagcgggg ctccaagggt tttgggtttg taacttttga aactagctca    960

gatgctgacc gagcccggga gaagctgaat gggacgatcg tagagggacg gaaaattgag   1020

gtcaataatg ccacggcccg agtgatgacc aacaagaaga cggggaaccc ctacaccaac   1080

ggctggaagc taaatccagt ggtcggcgca gtctacgggc ctgaattcta tgcagtgacg   1140

gggttcccct accccaccac cggcacagcc gttgcctacc ggggcgcaca tcttcggggc   1200

cggggccggg ccgtgtataa tacatttcgg gctgcgccac ccccaccccc catcccgact   1260

tacggagcgg tcgtgtatca ggatggattt tatggtgctg agatttatgg aggctacgca   1320

gcctacagat acgctcagcc cgctgcagcg gcggcagcct acagcgacag ttacggcaga   1380

gtctacgcag ctgccgaccc gtaccatcac accatcgggc ccgcggcgac ctacagcatt   1440
```

```
ggaaccatgt gaaaccttcc accgtttcct tctcggacca tgaagggcaa aaacaaaaaa   1500

acaaaaaaaa tcacaaaaca aaaaaaacaa aaaaagatgt taagatccaa gcaacaaaaa   1560

aaaaaccaac caaaccaaga ggcatccaac caagtccaag tcccgcgtcc tggccacacg   1620

cccgcaccga gggagcacgc cggcaggggc gccgaggagc ggccccagga caggacggcc   1680

ccaccgcgtc ctggctggca gcacagtggg aacacgcccc tccgtctcag gcagtggggg   1740

agttggaggg gaaggggcct cccttgtggg acccgtgggg ggctctgttt tccatccagt   1800

cttcctttcc cagcccccaa ctcccaagac agacagtgtg gagcccagcg gcggcggagc   1860

aggcccgggc ctgagcaggc aggcgctgct agcaagactt gatctttgtg gccagctgtg   1920

ccagggggcc ggcggggctg aggggtgcgg gcagctttca tcccaggggc tccactgggc   1980

cccgtcaccc tcctgtcgcg tcccctgcgt cccacctccc tcctgcccgg cagtcccgcc   2040

cgtgccccca gcctggcgag gaagccgtcc aacagtagcc ccggggccag ctcccaacag   2100

aaagggctga cgtggctcca ggactcaggg gcgctccatg ggaggacgaa ggaagcccag   2160

ccagccagga gccactcctc acacctccaa gtgtggccaa gtgggccctg aggccaagga   2220

cttacttgct cttcctggcc atctctccct ttctggagga ggcccggggc ctgtgtacac   2280

caaggctgac ctcgtgctgc ctgctgggac ccagccctcc ctgccgctcc cctgtgagcc   2340

cagtccaccg tgggcgccca gggccaggga cgggccagcg cccggctgca tcgcgaggtt   2400

gggagtcaca gtggctgtgg gcctggacgg gcacagccag agcaggggcc catgggaagg   2460

gcaagggatg gggaagcctg ggccggcccc ttccctgctc ccaaggcagg tgtccaggtg   2520

gcgggagcag caccaaggac agccaggctt acccggtggg aggagcagga gcagagcagg   2580

tggcagggag gaacccctgg cgaggcaggg agcactgaag tagggaagca gcaaaaaata   2640

caggctccca acgtggctcc actgtctcat gaagtgtcaa aaatttaaaa atacacctca   2700

ctttctattc agcatcagct attgaaatgg aattctcctt ttctattccc gttgtacata   2760

gccccacgcc ctgcctccgg ctttgtcctc tgtacagagc cccctgtccc ctctgctgtt   2820

ccggaccctt ttcttgcagc agctcaaccc cccgactcac tcagatcccc aggactgcag   2880

ccgagccccg ggcttccttt cttaccattc tgtatgcttc caaggtgtga ccattcaaac   2940

taacagtatt attaagatta ttaataaaga tttctttctt caaaccagga aaaaaaaaaa   3000

aaaaaaa                                                             3007
```

<210> SEQ ID NO 25
<211> LENGTH: 564
<212> TYPE: PRT
<213> ORGANISM: Homo sapiens

<400> SEQUENCE: 25

```
Met Ser Ser His Gly Asn Ser Leu Phe Leu Arg Glu Ser Gly Gln Arg
1               5                   10                  15

Leu Gly Arg Val Gly Trp Leu Gln Arg Leu Gln Glu Ser Leu Gln Gln
            20                  25                  30

Arg Ala Leu Arg Thr Arg Leu Arg Leu Gln Thr Met Thr Leu Glu His
        35                  40                  45

Val Leu Arg Phe Leu Arg Arg Asn Ala Phe Ile Leu Leu Thr Val Ser
    50                  55                  60

Ala Val Val Ile Gly Val Ser Leu Ala Phe Ala Leu Arg Pro Tyr Gln
65                  70                  75                  80

Leu Thr Tyr Arg Gln Ile Lys Tyr Phe Ser Phe Pro Gly Glu Leu Leu
                85                  90                  95
```

-continued

```
Met Arg Met Leu Gln Met Leu Val Leu Pro Leu Ile Val Ser Ser Leu
            100                 105                 110

Val Thr Gly Met Ala Ser Leu Asp Asn Lys Ala Thr Gly Arg Met Gly
        115                 120                 125

Met Arg Ala Ala Val Tyr Tyr Met Val Thr Thr Ile Ile Ala Val Phe
    130                 135                 140

Ile Gly Ile Leu Met Val Thr Ile Ile His Pro Gly Lys Gly Ser Lys
145                 150                 155                 160

Glu Gly Leu His Arg Glu Gly Arg Ile Glu Thr Ile Pro Thr Ala Asp
                165                 170                 175

Ala Phe Met Asp Leu Ile Arg Asn Met Phe Pro Pro Asn Leu Val Glu
            180                 185                 190

Ala Cys Phe Lys Gln Phe Lys Thr Gln Tyr Ser Thr Arg Val Val Thr
        195                 200                 205

Arg Thr Met Val Arg Thr Glu Asn Gly Ser Glu Pro Gly Ala Ser Met
    210                 215                 220

Pro Pro Pro Phe Ser Val Glu Asn Gly Thr Ser Phe Leu Glu Asn Val
225                 230                 235                 240

Thr Arg Ala Leu Gly Thr Leu Gln Glu Met Leu Ser Phe Glu Glu Thr
                245                 250                 255

Val Pro Val Pro Gly Ser Ala Asn Gly Ile Asn Ala Leu Gly Leu Val
            260                 265                 270

Val Phe Ser Val Ala Phe Gly Leu Val Ile Gly Gly Met Lys His Lys
        275                 280                 285

Gly Arg Val Leu Arg Asp Phe Phe Asp Ser Leu Asn Glu Ala Ile Met
    290                 295                 300

Arg Leu Val Gly Ile Ile Ile Trp Tyr Ala Pro Val Gly Ile Leu Phe
305                 310                 315                 320

Leu Ile Ala Gly Lys Ile Leu Glu Met Glu Asp Met Ala Val Leu Gly
                325                 330                 335

Gly Gln Leu Gly Met Tyr Thr Leu Thr Val Ile Val Gly Leu Phe Leu
            340                 345                 350

His Ala Gly Ile Val Leu Pro Leu Ile Tyr Phe Leu Val Thr His Arg
        355                 360                 365

Asn Pro Phe Pro Phe Ile Gly Gly Met Leu Gln Ala Leu Ile Thr Ala
    370                 375                 380

Met Gly Thr Ser Ser Ser Ser Ala Thr Leu Pro Ile Thr Phe Arg Cys
385                 390                 395                 400

Leu Glu Glu Gly Leu Gly Val Asp Arg Arg Ile Thr Arg Phe Val Leu
                405                 410                 415

Pro Val Gly Ala Thr Val Asn Met Asp Gly Thr Ala Leu Tyr Glu Ala
            420                 425                 430

Leu Ala Ala Ile Phe Ile Ala Gln Val Asn Asn Tyr Glu Leu Asn Leu
        435                 440                 445

Gly Gln Ile Thr Thr Ile Ser Ile Thr Ala Thr Ala Ala Ser Val Gly
    450                 455                 460

Ala Ala Gly Ile Pro Gln Ala Gly Leu Val Thr Met Val Ile Val Leu
465                 470                 475                 480

Thr Ser Val Gly Leu Pro Thr Glu Asp Ile Thr Leu Ile Ile Ala Val
                485                 490                 495

Asp Trp Phe Leu Asp Arg Leu Arg Thr Met Thr Asn Val Leu Gly Asp
            500                 505                 510
```

```
Ser Ile Gly Ala Ala Val Ile Glu His Leu Ser Gln Arg Glu Leu Glu
        515                 520                 525

Leu Gln Glu Ala Glu Leu Thr Leu Pro Ser Leu Gly Lys Pro Tyr Lys
    530                 535                 540

Ser Leu Met Ala Gln Glu Lys Gly Ala Ser Arg Gly Arg Gly Gly Asn
545                 550                 555                 560

Glu Ser Ala Met


<210> SEQ ID NO 26
<211> LENGTH: 2990
<212> TYPE: DNA
<213> ORGANISM: Homo sapiens

<400> SEQUENCE: 26

ggcatagcgc gtcccggctc cgcgccggtg cctccacggt ccggtccccg cgccggtgct     60

gcacagtccc tggcgggtcc ccgcggcccc ggccgggcgc ttcgccgggc tccggctcct    120

gcatccgggc gcagcgcgca ggccgaggcg cgggcaggcc gcccccgccg ctccggacgc    180

cgggatgtaa gaggctccga aaagcagccc acgcatctca tcagatctaa gtgtctagag    240

gtcgggagaa ccaagtggga aagacccacc ctcacccctc accttgtaga aactgggaac    300

actagaaggg acattttctg agcaggaaac ccaagagaca gggttttacg ctgtcaccca    360

agttggagtg cagtggtacg atcatagctc attgcagcct caaactcctg ggttcaagcg    420

atcctcctgc tttagcctct tgagtagcta ggactacagg cacaggccac cgtgcctggc    480

taatttttaa tttttaaaaa agagacaggg tctggctatg ttgcccaggc tggccatgaa    540

ctcctgggct caagcggttc tccagccttc acctcccaaa gtgttgggat tgcaggcatg    600

agccactgcg tctggcccac agatgctaag tgctgtctgc tcttctccag gggtcagcaa    660

attttttcag caaatggccc aagagtaaat attttgagct ttgtggcccg tacaatctct    720

gtcccaacaa ctcaactcag gcattgtagc ttgaaagcag ctgtagacaa taggtaatcc    780

atgagtgtgg ctgtgtgcca ataaaacttt atttacaaaa acaagcagta ggctgaattt    840

gactagcaga ccatagtttg tcaataccgt attatgtctt gtaaggaaga gaaaggaacc    900

agacaaaact ctagcctcgg gagttttcct gactgttcag atcttagctg aatgatctcc    960

cttggtatct acaggcaact tcctgctgtg gcttagggac tggaaacata atatcccaga   1020

gggattccct gtgtagtctg tggttcactc tttgggattt tttttttttt tttcacagca   1080

aggagaagca gcattgtggt ttcaggagat gggtccattt ggagcaggat cctaagtggg   1140

gcttggcatt gggaatttgg attagctcta gaggacgcag gatctggaaa atcagggcag   1200

atttcccatc ccttggatat ggtggggagt tgaggagggc aaggaagatc ccagaaaagc   1260

cagtggcagc aaaacacaaa ggccagggac ctacgtactg gtaaaactga gacctccaag   1320

aaacctgcag ctcgacctgg ttgaattcag atagaccatg agcagccatg gcaacagcct   1380

gttccttcgg gagagcggcc agcggctggg ccgggtgggc tggctgcagc ggctgcagga   1440

aagcctgcag cagagagcac tgcgcacgcg cctgcgcctg cagaccatga ccctcgagca   1500

cgtgctgcgc ttcctgcgcc gaaacgcctt cattctgctg acggtcagcg ccgtggtcat   1560

tggggtcagc ctggcctttg ccctgcgccc atatcagctc acctaccgcc agatcaagta   1620

cttctctttt cctggagagc ttctgatgag gatgctgcag atgctggtgt tacctctcat   1680

tgtctccagc ctggtcacag gtatggcatc cctggacaac aaggccacgg ggcggatggg   1740

gatgcgggca gctgtgtact acatggtgac caccatcatc gcggtcttca tcggcatcct   1800
```

```
catggtcacc atcatccatc ccgggaaggg ctccaaggag gggctgcacc gggagggccg   1860

gatcgagacc atccccacag ctgatgcctt catggacctg atcagaaata tgtttccacc   1920

aaaccttgtg gaggcctgct tcaaacagtt caagacgcag tacagcacga gggtggtaac   1980

caggaccatg gtgaggacag agaacgggtc tgagccgggt gcctccatgc ctcctccatt   2040

ctcagtggag aacggaacca gcttcctgga aaatgtcact cgggccttgg gtaccctgca   2100

ggagatgctg agctttgagg agactgtacc cgtgcctggc tccgccaatg gcatcaacgc   2160

cctgggcctc gtggtcttct ctgtggcctt tgggctggtc attggtggca tgaaacacaa   2220

gggcagagtc ctcagggact tcttcgacag cctcaatgag gctattatga ggctggtggg   2280

catcattatc tggtgagtcc tggtctgtgc ccacgggaag gtggagccag agctgggaag   2340

tcaggctgtg ggaagctgc cgaagggctt gctggggacc tttggtcatt catttacgta   2400

ttgggtgatt cacttaccca ctcaccaact cattcattca tgtctttctg ggatgatttc   2460

atcactagtt cacttccttg ttcatctgtt cattcattca ttcttctatg cattggttag   2520

ttcatggaat atctcactct ttcattcatt catgtccttc tgcaatgatt cattcactgc   2580

tttgttcatc tgttcattca ctcattcttc tatgcattga tgaaatcact cattcagtga   2640

tttattcatc tatactcatg cttcaatgca ttgatttact catttcctca tgcatttatt   2700

cattcatcta tgcattggtt aaatcactgg ccaactcact aactcattca ttcattcaca   2760

cttttctgca atgatttgtt cacttgttca ctcccttgct tatctgttca ttcactcatt   2820

cttcaataca ttgaccaagc cattcactga catttattca gctacattta ttctttcatg   2880

cattggtctg gatttatttg gtcattcatt tatttatttt gcaaaattaa tgtattttta   2940

attgacaaat aaaaactgta tatattttca tgtgcaaaaa aaaaaaaaaa              2990
```

<210> SEQ ID NO 27
<211> LENGTH: 1192
<212> TYPE: PRT
<213> ORGANISM: Homo sapiens

<400> SEQUENCE: 27

```
Met Glu Asp Leu Asp Gln Ser Pro Leu Val Ser Ser Ser Asp Ser Pro
1               5                   10                  15

Pro Arg Pro Gln Pro Ala Phe Lys Tyr Gln Phe Val Arg Glu Pro Glu
            20                  25                  30

Asp Glu Glu Glu Glu Glu Glu Glu Glu Glu Glu Asp Glu Asp Glu Asp
        35                  40                  45

Leu Glu Glu Leu Glu Val Leu Glu Arg Lys Pro Ala Ala Gly Leu Ser
    50                  55                  60

Ala Ala Pro Val Pro Thr Ala Pro Ala Ala Gly Ala Pro Leu Met Asp
65                  70                  75                  80

Phe Gly Asn Asp Phe Val Pro Pro Ala Pro Arg Gly Pro Leu Pro Ala
                85                  90                  95

Ala Pro Pro Val Ala Pro Glu Arg Gln Pro Ser Trp Asp Pro Ser Pro
            100                 105                 110

Val Ser Ser Thr Val Pro Ala Pro Ser Pro Leu Ser Ala Ala Ala Val
        115                 120                 125

Ser Pro Ser Lys Leu Pro Glu Asp Asp Glu Pro Pro Ala Arg Pro Pro
    130                 135                 140

Pro Pro Pro Pro Ala Ser Val Ser Pro Gln Ala Glu Pro Val Trp Thr
145                 150                 155                 160
```

-continued

```
Pro Pro Ala Pro Ala Pro Ala Ala Pro Pro Ser Thr Pro Ala Ala Pro
                165                 170                 175

Lys Arg Arg Gly Ser Ser Gly Ser Val Asp Glu Thr Leu Phe Ala Leu
            180                 185                 190

Pro Ala Ala Ser Glu Pro Val Ile Arg Ser Ser Ala Glu Asn Met Asp
        195                 200                 205

Leu Lys Glu Gln Pro Gly Asn Thr Ile Ser Ala Gly Gln Glu Asp Phe
    210                 215                 220

Pro Ser Val Leu Leu Glu Thr Ala Ala Ser Leu Pro Ser Leu Ser Pro
225                 230                 235                 240

Leu Ser Ala Ala Ser Phe Lys Glu His Glu Tyr Leu Gly Asn Leu Ser
                245                 250                 255

Thr Val Leu Pro Thr Glu Gly Thr Leu Gln Glu Asn Val Ser Glu Ala
            260                 265                 270

Ser Lys Glu Val Ser Glu Lys Ala Lys Thr Leu Leu Ile Asp Arg Asp
        275                 280                 285

Leu Thr Glu Phe Ser Glu Leu Glu Tyr Ser Glu Met Gly Ser Ser Phe
    290                 295                 300

Ser Val Ser Pro Lys Ala Glu Ser Ala Val Ile Val Ala Asn Pro Arg
305                 310                 315                 320

Glu Glu Ile Ile Val Lys Asn Lys Asp Glu Glu Glu Lys Leu Val Ser
                325                 330                 335

Asn Asn Ile Leu His Asn Gln Gln Glu Leu Pro Thr Ala Leu Thr Lys
            340                 345                 350

Leu Val Lys Glu Asp Glu Val Val Ser Ser Glu Lys Ala Lys Asp Ser
        355                 360                 365

Phe Asn Glu Lys Arg Val Ala Val Glu Ala Pro Met Arg Glu Glu Tyr
    370                 375                 380

Ala Asp Phe Lys Pro Phe Glu Arg Val Trp Glu Val Lys Asp Ser Lys
385                 390                 395                 400

Glu Asp Ser Asp Met Leu Ala Ala Gly Gly Lys Ile Glu Ser Asn Leu
                405                 410                 415

Glu Ser Lys Val Asp Lys Lys Cys Phe Ala Asp Ser Leu Glu Gln Thr
            420                 425                 430

Asn His Glu Lys Asp Ser Glu Ser Ser Asn Asp Asp Thr Ser Phe Pro
        435                 440                 445

Ser Thr Pro Glu Gly Ile Lys Asp Arg Ser Gly Ala Tyr Ile Thr Cys
    450                 455                 460

Ala Pro Phe Asn Pro Ala Ala Thr Glu Ser Ile Ala Thr Asn Ile Phe
465                 470                 475                 480

Pro Leu Leu Gly Asp Pro Thr Ser Glu Asn Lys Thr Asp Glu Lys Lys
                485                 490                 495

Ile Glu Glu Lys Lys Ala Gln Ile Val Thr Glu Lys Asn Thr Ser Thr
            500                 505                 510

Lys Thr Ser Asn Pro Phe Leu Val Ala Ala Gln Asp Ser Glu Thr Asp
        515                 520                 525

Tyr Val Thr Thr Asp Asn Leu Thr Lys Val Thr Glu Glu Val Val Ala
    530                 535                 540

Asn Met Pro Glu Gly Leu Thr Pro Asp Leu Val Gln Glu Ala Cys Glu
545                 550                 555                 560

Ser Glu Leu Asn Glu Val Thr Gly Thr Lys Ile Ala Tyr Glu Thr Lys
                565                 570                 575
```

-continued

```
Met Asp Leu Val Gln Thr Ser Glu Val Met Gln Glu Ser Leu Tyr Pro
            580                 585                 590

Ala Ala Gln Leu Cys Pro Ser Phe Glu Glu Ser Glu Ala Thr Pro Ser
        595                 600                 605

Pro Val Leu Pro Asp Ile Val Met Glu Ala Pro Leu Asn Ser Ala Val
    610                 615                 620

Pro Ser Ala Gly Ala Ser Val Ile Gln Pro Ser Ser Ser Pro Leu Glu
625                 630                 635                 640

Ala Ser Ser Val Asn Tyr Glu Ser Ile Lys His Glu Pro Glu Asn Pro
                645                 650                 655

Pro Pro Tyr Glu Glu Ala Met Ser Val Ser Leu Lys Lys Val Ser Gly
            660                 665                 670

Ile Lys Glu Glu Ile Lys Glu Pro Glu Asn Ile Asn Ala Ala Leu Gln
        675                 680                 685

Glu Thr Glu Ala Pro Tyr Ile Ser Ile Ala Cys Asp Leu Ile Lys Glu
    690                 695                 700

Thr Lys Leu Ser Ala Glu Pro Ala Pro Asp Phe Ser Asp Tyr Ser Glu
705                 710                 715                 720

Met Ala Lys Val Glu Gln Pro Val Pro Asp His Ser Glu Leu Val Glu
                725                 730                 735

Asp Ser Ser Pro Asp Ser Glu Pro Val Asp Leu Phe Ser Asp Asp Ser
            740                 745                 750

Ile Pro Asp Val Pro Gln Lys Gln Asp Glu Thr Val Met Leu Val Lys
        755                 760                 765

Glu Ser Leu Thr Glu Thr Ser Phe Glu Ser Met Ile Glu Tyr Glu Asn
    770                 775                 780

Lys Glu Lys Leu Ser Ala Leu Pro Pro Glu Gly Gly Lys Pro Tyr Leu
785                 790                 795                 800

Glu Ser Phe Lys Leu Ser Leu Asp Asn Thr Lys Asp Thr Leu Leu Pro
                805                 810                 815

Asp Glu Val Ser Thr Leu Ser Lys Lys Glu Lys Ile Pro Leu Gln Met
            820                 825                 830

Glu Glu Leu Ser Thr Ala Val Tyr Ser Asn Asp Asp Leu Phe Ile Ser
        835                 840                 845

Lys Glu Ala Gln Ile Arg Glu Thr Glu Thr Phe Ser Asp Ser Ser Pro
    850                 855                 860

Ile Glu Ile Ile Asp Glu Phe Pro Thr Leu Ile Ser Ser Lys Thr Asp
865                 870                 875                 880

Ser Phe Ser Lys Leu Ala Arg Glu Tyr Thr Asp Leu Glu Val Ser His
                885                 890                 895

Lys Ser Glu Ile Ala Asn Ala Pro Asp Gly Ala Gly Ser Leu Pro Cys
            900                 905                 910

Thr Glu Leu Pro His Asp Leu Ser Leu Lys Asn Ile Gln Pro Lys Val
        915                 920                 925

Glu Glu Lys Ile Ser Phe Ser Asp Asp Phe Ser Lys Asn Gly Ser Ala
    930                 935                 940

Thr Ser Lys Val Leu Leu Leu Pro Pro Asp Val Ser Ala Leu Ala Thr
945                 950                 955                 960

Gln Ala Glu Ile Glu Ser Ile Val Lys Pro Lys Val Leu Val Lys Glu
                965                 970                 975

Ala Glu Lys Lys Leu Pro Ser Asp Thr Glu Lys Glu Asp Arg Ser Pro
            980                 985                 990
```

```
Ser Ala Ile Phe Ser Ala Glu Leu  Ser Lys Thr Ser Val  Val Asp Leu
        995                 1000                 1005

Leu Tyr  Trp Arg Asp Ile Lys  Lys Thr Gly Val Val  Phe Gly Ala
    1010                 1015                 1020

Ser Leu  Phe Leu Leu Leu Ser  Leu Thr Val Phe Ser  Ile Val Ser
    1025                 1030                 1035

Val Thr  Ala Tyr Ile Ala Leu  Ala Leu Leu Ser Val  Thr Ile Ser
    1040                 1045                 1050

Phe Arg  Ile Tyr Lys Gly Val  Ile Gln Ala Ile Gln  Lys Ser Asp
    1055                 1060                 1065

Glu Gly  His Pro Phe Arg Ala  Tyr Leu Glu Ser Glu  Val Ala Ile
    1070                 1075                 1080

Ser Glu  Glu Leu Val Gln Lys  Tyr Ser Asn Ser Ala  Leu Gly His
    1085                 1090                 1095

Val Asn  Cys Thr Ile Lys Glu  Leu Arg Arg Leu Phe  Leu Val Asp
    1100                 1105                 1110

Asp Leu  Val Asp Ser Leu Lys  Phe Ala Val Leu Met  Trp Val Phe
    1115                 1120                 1125

Thr Tyr  Val Gly Ala Leu Phe  Asn Gly Leu Thr Leu  Leu Ile Leu
    1130                 1135                 1140

Ala Leu  Ile Ser Leu Phe Ser  Val Pro Val Ile Tyr  Glu Arg His
    1145                 1150                 1155

Gln Ala  Gln Ile Asp His Tyr  Leu Gly Leu Ala Asn  Lys Asn Val
    1160                 1165                 1170

Lys Asp  Ala Met Ala Lys Ile  Gln Ala Lys Ile Pro  Gly Leu Lys
    1175                 1180                 1185

Arg Lys  Ala Glu
    1190
```

<210> SEQ ID NO 28
<211> LENGTH: 4871
<212> TYPE: DNA
<213> ORGANISM: Homo sapiens

<400> SEQUENCE: 28

```
agtccctgcc ctcccctggg gagggtgagt cacgccaaac tgggcggaga gtccgctggc     60

ctcactccta gctcatctgg gcggcggcgg caagtgggga cagggcgggt ggcgcatcac    120

cggcgcggag gcaggaggag cagtctcatt gttccgggag ccgtcaccac agtaggtccc    180

tcggctcagt cggcccagcc cctctcagtc ctccccaacc cccacaaccg cccgcggctc    240

tgagacgcgg ccccggcggc ggcggcagca gctgcagcat catctccacc ctccagccat    300

ggaagacctg gaccagtctc ctctggtctc gtcctcggac agcccacccc ggccgcagcc    360

cgcgttcaag taccagttcg tgagggagcc cgaggacgag gaggaagaag aggaggagga    420

agaggaggac gaggacgaag acctggagga gctggaggtg ctggagagga agcccgccgc    480

cgggctgtcc gcggccccag tgcccaccgc ccctgccgcc ggcgcgcccc tgatggactt    540

cggaaatgac ttcgtgccgc cggcgccccg gggacccctg ccggccgctc cccccgtcgc    600

cccggagcgg cagccgtctt gggacccgag cccggtgtcg tcgaccgtgc ccgcgccatc    660

cccgctgtct gctgccgcag tctcgccctc caagctccct gaggacgacg agcctccggc    720

ccggcctccc cctcctcccc cggccagcgt gagcccccag gcagagcccg tgtggacccc    780

gccagccccg gctcccgccg cgcccccctc caccccggcc gcgcccaagc gcaggggctc    840

ctcgggctca gtggatgaga ccctttttgc tcttcctgct gcatctgagc ctgtgatacg    900
```

```
ctcctctgca gaaaatatgg acttgaagga gcagccaggt aacactattt cggctggtca    960
agaggatttc ccatctgtcc tgcttgaaac tgctgcttct cttccttctc tgtctcctct   1020
ctcagccgct tctttcaaag aacatgaata ccttggtaat ttgtcaacag tattacccac   1080
tgaaggaaca cttcaagaaa atgtcagtga agcttctaaa gaggtctcag agaaggcaaa   1140
aactctactc atagatagag atttaacaga gttttcagaa ttagaatact cagaaatggg   1200
atcatcgttc agtgtctctc caaaagcaga atctgccgta atagtagcaa atcctaggga   1260
agaaataatc gtgaaaaata aagatgaaga agagaagtta gttagtaata acatccttca   1320
taatcaacaa gagttaccta cagctcttac taaattggtt aaagaggatg aagttgtgtc   1380
ttcagaaaaa gcaaaagaca gttttaatga aaagagagtt gcagtggaag ctcctatgag   1440
ggaggaatat gcagacttca aaccatttga gcgagtatgg gaagtgaaag atagtaagga   1500
agatagtgat atgttggctg ctggaggtaa aatcgagagc aacttggaaa gtaaagtgga   1560
taaaaaatgt tttgcagata gccttgagca aactaatcac gaaaaagata gtgagagtag   1620
taatgatgat acttctttcc ccagtacgcc agaaggtata aaggatcgtt caggagcata   1680
tatcacatgt gctcccttta acccagcagc aactgagagc attgcaacaa acatttttcc   1740
tttgttagga gatcctactt cagaaaataa gaccgatgaa aaaaaaatag aagaaaagaa   1800
ggcccaaata gtaacagaga agaatactag caccaaaaca tcaaaccctt ttcttgtagc   1860
agcacaggat tctgagacag attatgtcac aacagataat ttaacaaagg tgactgagga   1920
agtcgtggca aacatgcctg aaggcctgac tccagattta gtacaggaag catgtgaaag   1980
tgaattgaat gaagttactg gtacaaagat tgcttatgaa acaaaaatgg acttggttca   2040
aacatcagaa gttatgcaag agtcactcta tcctgcagca cagctttgcc catcatttga   2100
agagtcagaa gctactcctt caccagtttt gcctgacatt gttatggaag caccattgaa   2160
ttctgcagtt cctagtgctg gtgcttccgt gatacagccc agctcatcac cattagaagc   2220
ttcttcagtt aattatgaaa gcataaaaca tgagcctgaa aaccccccac catatgaaga   2280
ggccatgagt gtatcactaa aaaaagtatc aggaataaag gaagaaatta aagagcctga   2340
aaatattaat gcagctcttc aagaaacaga agctccttat atatctattg catgtgattt   2400
aattaaagaa acaaagcttt ctgctgaacc agctccggat ttctctgatt attcagaaat   2460
ggcaaaagtt gaacagccag tgcctgatca ttctgagcta gttgaagatt cctcacctga   2520
ttctgaacca gttgacttat ttagtgatga ttcaatacct gacgttccac aaaaacaaga   2580
tgaaactgtg atgcttgtga aagaaagtct cactgagact tcatttgagt caatgataga   2640
atatgaaaat aaggaaaaac tcagtgcttt gccacctgag ggaggaaagc catatttgga   2700
atcttttaag ctcagtttag ataacacaaa agataccctg ttacctgatg aagtttcaac   2760
attgagcaaa aaggagaaaa ttcctttgca gatggaggag ctcagtactg cagtttattc   2820
aaatgatgac ttatttattt ctaaggaagc acagataaga gaaactgaaa cgttttcaga   2880
ttcatctcca attgaaatta tagatgagtt ccctacattg atcagttcta aaactgattc   2940
attttctaaa ttagccaggg aatatactga cctagaagta tcccacaaaa gtgaaattgc   3000
taatgccccg gatggagctg ggtcattgcc ttgcacagaa ttgccccatg acctttcttt   3060
gaagaacata caacccaaag ttgaagagaa aatcagtttc tcagatgact tttctaaaaa   3120
tgggtctgct acatcaaagg tgctcttatt gcctccagat gtttctgctt tggccactca   3180
agcagagata gagagcatag ttaaacccaa agttcttgtg aaagaagctg agaaaaaact   3240
tccttccgat acagaaaaag aggacagatc accatctgct atattttcag cagagctgag   3300
```

```
taaaacttca gttgttgacc tcctgtactg gagagacatt aagaagactg gagtggtgtt   3360
tggtgccagc ctattcctgc tgctttcatt gacagtattc agcattgtga gcgtaacagc   3420
ctacattgcc ttggccctgc tctctgtgac catcagcttt aggatataca agggtgtgat   3480
ccaagctatc cagaaatcag atgaaggcca cccattcagg gcatatctgg aatctgaagt   3540
tgctatatct gaggagttgg ttcagaagta cagtaattct gctcttggtc atgtgaactg   3600
cacgataaag gaactcaggc gcctcttctt agttgatgat ttagttgatt ctctgaagtt   3660
tgcagtgttg atgtgggtat ttacctatgt tggtgccttg tttaatggtc tgacactact   3720
gattttggct ctcatttcac tcttcagtgt tcctgttatt tatgaacggc atcaggcaca   3780
gatagatcat tatctaggac ttgcaaataa gaatgttaaa gatgctatgg ctaaaatcca   3840
agcaaaaatc cctggattga agcgcaaagc tgaatgaaaa cgcccaaaat aattagtagg   3900
agttcatctt taaaggggat attcatttga ttatacgggg gagggtcagg gaagaacgaa   3960
ccttgacgtt gcagtgcagt ttcacagatc gttgttagat ctttattttt agccatgcac   4020
tgttgtgagg aaaaattacc tgtcttgact gccatgtgtt catcatctta agtattgtaa   4080
gctgctatgt atggatttaa accgtaatca tatctttttc ctatctatct gaggcactgg   4140
tggaataaaa aacctgtata ttttactttg ttgcagatag tcttgccgca tcttggcaag   4200
ttgcagagat ggtggagcta gaaaaaaaaa aaaaaaagcc cttttcagtt tgtgcactgt   4260
gtatggtccg tgtagattga tgcagatttt ctgaaatgaa atgtttgttt agacgagatc   4320
ataccggtaa agcaggaatg acaaagcttg cttttctggt atgttctagg tgtattgtga   4380
cttttactgt tatattaatt gccaatataa gtaaatatag attatatatg tatagtgttt   4440
cacaaagctt agacctttac cttccagcca ccccacagtg cttgatattt cagagtcagt   4500
cattggttat acatgtgtag ttccaaagca cataagctag aagaagaaat atttctagga   4560
gcactaccat ctgttttcaa catgaaatgc cacacacata gaactccaac atcaatttca   4620
ttgcacagac tgactgtagt taattttgtc acagaatcta tggactgaat ctaatgcttc   4680
caaaaatgtt gtttgtttgc aaatatcaaa cattgttatg caagaaatta ttaattacaa   4740
aatgaagatt tataccattg tggtttaagc tgtactgaac taaatctgtg gaatgcattg   4800
tgaactgtaa aagcaaagta tcaataaagc ttatagactt aaaaaaaaaa aaaaaaaaaa   4860
aaaaaaaaaa a                                                        4871
```

<210> SEQ ID NO 29
<211> LENGTH: 271
<212> TYPE: PRT
<213> ORGANISM: Homo sapiens

<400> SEQUENCE: 29

```
Met Tyr Tyr Ala Val Ser Gln Ala Arg Val Asn Ala Val Pro Gly Thr
1               5                   10                  15

Met Leu Arg Pro Gln Arg Pro Gly Asp Leu Gln Leu Gly Ala Ser Leu
            20                  25                  30

Tyr Glu Leu Val Gly Tyr Arg Gln Pro Pro Ser Ser Ser Ser Ser Ser
        35                  40                  45

Thr Ser Ser Thr Ser Ser Thr Ser Ser Ser Ser Thr Thr Ala Pro Leu
    50                  55                  60

Leu Pro Lys Ala Ala Arg Glu Lys Pro Glu Ala Pro Ala Glu Pro Pro
65                  70                  75                  80

Gly Pro Gly Pro Gly Ser Gly Ala His Pro Gly Gly Ser Ala Arg Pro
                85                  90                  95
```

```
Asp Ala Lys Glu Glu Gln Gln Gln Gln Leu Arg Arg Lys Ile Asn Ser
            100                 105                 110

Arg Glu Arg Lys Arg Met Gln Asp Leu Asn Leu Ala Met Asp Ala Leu
        115                 120                 125

Arg Glu Val Ile Leu Pro Tyr Ser Ala Ala His Cys Gln Gly Ala Pro
    130                 135                 140

Gly Arg Lys Leu Ser Lys Ile Ala Thr Leu Leu Leu Ala Arg Asn Tyr
145                 150                 155                 160

Ile Leu Leu Leu Gly Ser Ser Leu Gln Glu Leu Arg Arg Ala Leu Gly
                165                 170                 175

Glu Gly Ala Gly Pro Ala Ala Pro Arg Leu Leu Leu Ala Gly Leu Pro
            180                 185                 190

Leu Leu Ala Ala Ala Pro Gly Ser Val Leu Leu Ala Pro Gly Ala Val
        195                 200                 205

Gly Pro Pro Asp Ala Leu Arg Pro Ala Lys Tyr Leu Ser Leu Ala Leu
    210                 215                 220

Asp Glu Pro Pro Cys Gly Gln Phe Ala Leu Pro Gly Gly Gly Ala Gly
225                 230                 235                 240

Gly Pro Gly Leu Cys Thr Cys Ala Val Cys Lys Phe Pro His Leu Val
                245                 250                 255

Pro Ala Ser Leu Gly Leu Ala Ala Val Gln Ala Gln Phe Ser Lys
            260                 265                 270


<210> SEQ ID NO 30
<211> LENGTH: 2298
<212> TYPE: DNA
<213> ORGANISM: Homo sapiens

<400> SEQUENCE: 30

gttctagatc gtttccccgc gcgcaggtcc gcggggaggg gcggcctgcc gaccggccca      60

ccccagggcg ttcctgaagg gcgtcctcgg ccgcccccac cgcctcccag atgtactatg     120

cggtttccca ggcgcgcgtg aacgcggtcc ccgggaccat gctgcggcca cagcggcccg     180

gagacttgca gctcggggcc tccctctacg agctggtggg ctacaggcag ccgccctcct     240

cctcctcctc ctccacctcc tccacctcct ccacttcctc ctcctccacg acggcccccc     300

tcctccccaa ggctgcgcgc gagaagccgg aggcgccggc cgagcctcca ggccccgggc     360

ccgggtcagg cgcgcacccg ggcggcagcg cccggccgga cgccaaggag gagcagcagc     420

agcagctgcg gcgcaagatc aacagccgcg agcggaagcg catgcaggac ctgaacctgg     480

ccatggacgc cctgcgcgag gtcatcctgc cctactcagc ggcgcactgc cagggcgcgc     540

ccggccgcaa gctctccaag atagccacgc tgctgctcgc ccgcaactac atcctactgc     600

tgggcagctc gctgcaggag ctgcgccgcg cgctgggcga gggcgccggg cccgccgcgc     660

cgcgcctgct gctggccggg ctgcccctgc tcgccgccgc gcccggctcc gtgctgctgg     720

cgcccggcgc cgtaggaccc cccgacgcgc tgcgccccgc caagtacctg tcgctggcgc     780

tggacgagcc gccgtgcggc cagttcgctc tccccggcgg cggcgcaggc ggccccggcc     840

tctgcacctg cgccgtgtgc aagttcccgc acctggtccc ggccagcctg ggcctggccg     900

ccgtgcaggc gcaattctcc aagtgagggc gggtctgggc ctggggcgcg acctcggccc     960

ggcctccctt cgctcagctt ctccgcgccc ctgctccctg cgtctgggag agcgaggccg    1020

agcaaggaaa gcatttcgaa ccttccagtc cagaggaagg gactgtcggg cacccccttc    1080

cccgccccca cccctgggac gttaaagtga ccagagcgga tgttcgatgg cgcctcgggg    1140
```

```
cagtttgggg ttctgggtcg gttccagcgg ctttaggcag aaagtgctcg ctctcaccca   1200

gcacatctct ctccttgtcc ctggagttgc gcgcttcgcg gggccgatgt agaacttagg   1260

gcgccttgcc gtggttggcg cgccccgggt gcagcgagag gccatccccg agcgctacct   1320

ccccggagcg gagcacgcgg gctcccagta ctaggggctg cgctcgagca gtggcggggg   1380

cggaggggtg gttcttttcc ttctcctccg ccagaggcca cgggcgccct tgttcccgcc   1440

ggccaggtcc tatcaaagga ggctgccgga actcaagagg cagaaaaaga ccagttaggc   1500

ggtgcagacg gtctgggacg tggcagacgg acggaccctc ggcggacagg tggtcggcgt   1560

cggggtgcgg tgggtagggg cgaggacaac gcagggtgcg ctgggttggg acgtgggtcc   1620

acttttgtag accagctgtt tggagagctg tatttaagac tcgcgtatcc agtgttttgt   1680

cgcagagagt tttcactctt aaatcctggg ggtttcttag aaagcaactt agaactcgag   1740

attcaccttt cgtttccctt tccccaaaag tagcgtaacc aacatttaag cttgcttaaa   1800

aacgaaaacc aaccgccttg catccagtgt tcccgattta ctaaaatagg taaccaggcg   1860

tctcacagtc gccgtcctgt caagagcgct aatgaacgtt ctcattaaca cgcaggagta   1920

ccgggagccc tgaaccgccc gctgctcggc ggatcccagc tgcggtggcg acggcgggaa   1980

ggcgctttcc gctgttcctc agcgggccgg gcccttgacc agcgcggccc gcaggtcttc   2040

cttctcgccg tcttgcagtt gaagagctac atacgtagtc agtttcgatt tgttacagac   2100

gttaacaaat tcctttaccc aaggttatgc tatgaccttt ccgcagttta ctttgatttt   2160

ctatgtttaa ggttttggtt gttggtagta gccgaattta actggcactt tattttactt   2220

ctaaccttgt ttcctgacgg tgtacagaat caacaaaata aaacatttaa agtctgattt   2280

tttaaaaaaa aaaaaaaa                                                 2298
```

```
<210> SEQ ID NO 31
<211> LENGTH: 323
<212> TYPE: PRT
<213> ORGANISM: Homo sapiens

<400> SEQUENCE: 31

Met Asp Ser Asp Ala Ser Leu Val Ser Ser Arg Pro Ser Ser Pro Glu
1               5                   10                  15

Pro Asp Asp Leu Phe Leu Pro Ala Arg Ser Lys Gly Ser Ser Gly Ser
            20                  25                  30

Ala Phe Thr Gly Gly Thr Val Ser Ser Ser Thr Pro Ser Asp Cys Pro
        35                  40                  45

Pro Glu Leu Ser Ala Glu Leu Arg Gly Ala Met Gly Ser Ala Gly Ala
    50                  55                  60

His Pro Gly Asp Lys Leu Gly Gly Ser Gly Phe Lys Ser Ser Ser Ser
65                  70                  75                  80

Ser Thr Ser Ser Ser Thr Ser Ser Ala Ala Ala Ser Ser Thr Lys Lys
                85                  90                  95

Asp Lys Lys Gln Met Thr Glu Pro Glu Leu Gln Gln Leu Arg Leu Lys
            100                 105                 110

Ile Asn Ser Arg Glu Arg Lys Arg Met His Asp Leu Asn Ile Ala Met
        115                 120                 125

Asp Gly Leu Arg Glu Val Met Pro Tyr Ala His Gly Pro Ser Val Arg
    130                 135                 140

Lys Leu Ser Lys Ile Ala Thr Leu Leu Leu Ala Arg Asn Tyr Ile Leu
145                 150                 155                 160
```

-continued

```
Met Leu Thr Asn Ser Leu Glu Glu Met Lys Arg Leu Val Ser Glu Ile
                165                 170                 175

Tyr Gly Gly His His Ala Gly Phe His Pro Ser Ala Cys Gly Gly Leu
            180                 185                 190

Ala His Ser Ala Pro Leu Pro Ala Ala Thr Ala His Pro Ala Ala Ala
        195                 200                 205

Ala His Ala Ala His His Pro Ala Val His His Pro Ile Leu Pro Pro
    210                 215                 220

Ala Ala Ala Ala Ala Ala Ala Ala Ala Ala Ala Ala Ala Val Ser Ser
225                 230                 235                 240

Ala Ser Leu Pro Gly Ser Gly Leu Pro Ser Val Gly Ser Ile Arg Pro
                245                 250                 255

Pro His Gly Leu Leu Lys Ser Pro Ser Ala Ala Ala Ala Ala Pro Leu
            260                 265                 270

Gly Gly Gly Gly Gly Gly Ser Gly Ala Ser Gly Gly Phe Gln His Trp
        275                 280                 285

Gly Gly Met Pro Cys Pro Cys Ser Met Cys Gln Val Pro Pro Pro His
    290                 295                 300

His His Val Ser Ala Met Gly Ala Gly Ser Leu Pro Arg Leu Thr Ser
305                 310                 315                 320

Asp Ala Lys


<210> SEQ ID NO 32
<211> LENGTH: 3275
<212> TYPE: DNA
<213> ORGANISM: Homo sapiens

<400> SEQUENCE: 32

gggtgcttat tatagatcga cgcgacacca gcgcccggtg ccaggttctc ccctgaggct     60

tttcggagcg agctcctcaa atcgcatcca gagtaagtgt ccccgcccca cagcagccgc    120

agcctagatc ccagggacag actctcctca actcggctgt gacccagaat gctccgatac    180

agggggtctg gatccctact ctgcgggcca tttctccaga gcgactttgc tcttctgtcc    240

tccccacact caccgctgca tctccctcac caaaagcgag aagtcggagc gacaacagct    300

ctttctgccc aagccccagt cagctggtga gctccccgtg gtctccagat gcagcacatg    360

gactctgggc cccgcgccgg ctctgggtgc atgtgcgtgt gcgtgtgttt gctgcgtggt    420

gtcgatggag ataaggtgga tccgtttgag gaaccaaatc attagttctc tatttagatc    480

tccattctcc ccaaagaaag gccctcactt cccactcgtt tattccagcc cgggggctca    540

gttttcccac acctaactga aagcccgaag cctctagaat gccacccgca ccccgagggt    600

caccaacgct ccctgaaata acctgttgca tgagagcaga ggggagatag agagagctta    660

attataggta cccgcgtgca gctaaaagga gggccagaga tagtagcgag gggacgaggg    720

agccacgggc cacctgtgcc gggaccccgc gctgtggtac tgcggtgcag gcgggagcag    780

cttttctgtc tctcactgac tcactctctc tctctctccc tctctctctc tctcattctc    840

tctcttttct cctcctctcc tggaagtttt cgggtccgag ggaaggagga ccctgcgaaa    900

gctgcgacga ctatcttccc ctggggccat ggactcggac gccagcctgg tgtccagccg    960

cccgtcgtcg ccagagcccg atgacctttt tctgccggcc cggagtaagg gcagcagcgg   1020

cagcgccttc actgggggca ccgtgtcctc gtccaccccg agtgactgcc cgccggagct   1080

gagcgccgag ctgcgcggcg ctatgggctc tgcgggcgcg catcctgtgg acaagctagg   1140

aggcagtggc ttcaagtcat cctcgtccag cacctcgtcg tctacgtcgt cggcggctgc   1200
```

-continued

```
gtcgtccacc aagaaggaca agaagcaaat gacagagccg gagctgcagc agctgcgtct   1260

caagatcaac agccgcgagc gcaagcgcat gcacgacctc aacatcgcca tggatggcct   1320

ccgcgaggtc atgccgtacg cacacggccc ttcggtgcgc aagctttcca agatcgccac   1380

gctgctgctg gcgcgcaact acatcctcat gctcaccaac tcgctggagg agatgaagcg   1440

actggtgagc gagatctacg ggggccacca cgctggcttc cacccgtcgg cctgcggcgg   1500

cctggcgcac tccgcgcccc tgcccgccgc caccgcgcac ccggcagcag cagcgcacgc   1560

cgcacatcac cccgcggtgc accaccccat cctgccgccc gccgccgcag cggctgctgc   1620

cgccgctgca gccgcggctg tgtccagcgc ctctctgccc ggatccgggc tgccgtcggt   1680

cggctccatc cgtccaccgc acggcctact caagtctccg tctgctgccg cggccgcccc   1740

gctggggggc gggggcggcg gcagtggggc gagcgggggc ttccagcact ggggcggcat   1800

gccctgcccc tgcagcatgt gccaggtgcc gccgccgcac caccacgtgt cggctatggg   1860

cgccggcagc ctgccgcgcc tcacctccga cgccaagtga gcctactggc gccggcgcgt   1920

tctggcgaca ggggagccag gggccgcggg gaagcgagga ctggcctgcg ctgggctcgg   1980

gagctctgtc gcgaggaggg gcgcaggacc atggactggg ggtggggcat ggtggggatt   2040

tcagcatctg cgaacccaag caatgggggc gcccacagag cagtggggag tgaggggatg   2100

ttctctccgg gacctgatcg agcgctgtct ggctttaacc tgagctggtc cagtagacat   2160

cgttttatga aaaggtaccg ctgtgtgcat tcctcactag aactcatccg acccccgacc   2220

cccacctccg ggaaaagatt ctaaaaactt ctttccctga gagcgtggcc tgacttgcag   2280

actcggcttg ggcagcactt cggggggga gggggtgtta tgggaggggg acacattggg   2340

gccttgctcg tcttcctcct ttcttggcgg gtgggagact ccgggtagcc gcactgcaga   2400

agcaacagcc cgaccgcgcc ctccagggtc gtccctggcc caaggccagg ggccacaagt   2460

tagttggaag ccggcgttcg gtatcagaag cgctgatggt catatccaat ctcaatatct   2520

gggtcaatcc acaccctctt agaactgtgg ccgttcctcc ctgtctctcg ttgatttggg   2580

agaatatggt tttctaataa atctgtggat gttccttctt caacagtatg agcaagttta   2640

tagacattca gagtagaacc acttgtggat tggaataacc caaaactgcc gatttcaggg   2700

gcgggtgcat tgtagttatt attttaaaat agaaactacc ccaccgactc atctttcctt   2760

ctctaagcac aaagtgattt ggttattttg gtacctgaga acgtaacaga attaaaaggc   2820

agttgctgtg gaaacagttt gggttatttg gggttctgt tggcttttta aaattttctt   2880

ttttggatgt gtaaatttat caatgatgag gtaagtgcgc aatgctaagc tgtttgctca   2940

cgtgactgcc agccccatcg gagtctaagc cggctttcct ctattttggt ttatttttgc   3000

cacgtttaac acaaatggta aactcctcca cgtgcttcct gcgttccgtg caagccgcct   3060

cggcgctgcc tgcgttgcaa actgggcttt gtagcgtctg ccgtgtaaca cccttcctct   3120

gatcgcaccg cccctcgcag agagtgtatc atctgtttta tttttgtaaa aacaaagtgc   3180

taaataatat ttattacttg tttggttgca aaaacggaat aaatgactga gtgttgagat   3240

tttaaataaa atttaaagca aaaaaaaaaa aaaaa                              3275
```

<210> SEQ ID NO 33
<211> LENGTH: 432
<212> TYPE: PRT
<213> ORGANISM: Homo sapiens

<400> SEQUENCE: 33

Met Glu Arg Arg Arg Ile Thr Ser Ala Ala Arg Arg Ser Tyr Val Ser
1               5                   10                  15

Ser Gly Glu Met Met Val Gly Gly Leu Ala Pro Gly Arg Arg Leu Gly
            20                  25                  30

Pro Gly Thr Arg Leu Ser Leu Ala Arg Met Pro Pro Pro Leu Pro Thr
        35                  40                  45

Arg Val Asp Phe Ser Leu Ala Gly Ala Leu Asn Ala Gly Phe Lys Glu
    50                  55                  60

Thr Arg Ala Ser Glu Arg Ala Glu Met Met Glu Leu Asn Asp Arg Phe
65                  70                  75                  80

Ala Ser Tyr Ile Glu Lys Val Arg Phe Leu Glu Gln Gln Asn Lys Ala
                85                  90                  95

Leu Ala Ala Glu Leu Asn Gln Leu Arg Ala Lys Glu Pro Thr Lys Leu
            100                 105                 110

Ala Asp Val Tyr Gln Ala Glu Leu Arg Glu Leu Arg Leu Arg Leu Asp
        115                 120                 125

Gln Leu Thr Ala Asn Ser Ala Arg Leu Glu Val Glu Arg Asp Asn Leu
    130                 135                 140

Ala Gln Asp Leu Ala Thr Val Arg Gln Lys Leu Gln Asp Glu Thr Asn
145                 150                 155                 160

Leu Arg Leu Glu Ala Glu Asn Asn Leu Ala Ala Tyr Arg Gln Glu Ala
                165                 170                 175

Asp Glu Ala Thr Leu Ala Arg Leu Asp Leu Glu Arg Lys Ile Glu Ser
            180                 185                 190

Leu Glu Glu Glu Ile Arg Phe Leu Arg Lys Ile His Glu Glu Glu Val
        195                 200                 205

Arg Glu Leu Gln Glu Gln Leu Ala Arg Gln Gln Val His Val Glu Leu
    210                 215                 220

Asp Val Ala Lys Pro Asp Leu Thr Ala Ala Leu Lys Glu Ile Arg Thr
225                 230                 235                 240

Gln Tyr Glu Ala Met Ala Ser Ser Asn Met His Glu Ala Glu Glu Trp
                245                 250                 255

Tyr Arg Ser Lys Phe Ala Asp Leu Thr Asp Ala Ala Ala Arg Asn Ala
            260                 265                 270

Glu Leu Leu Arg Gln Ala Lys His Glu Ala Asn Asp Tyr Arg Arg Gln
        275                 280                 285

Leu Gln Ser Leu Thr Cys Asp Leu Glu Ser Leu Arg Gly Thr Asn Glu
    290                 295                 300

Ser Leu Glu Arg Gln Met Arg Glu Gln Glu Glu Arg His Val Arg Glu
305                 310                 315                 320

Ala Ala Ser Tyr Gln Glu Ala Leu Ala Arg Leu Glu Glu Glu Gly Gln
                325                 330                 335

Ser Leu Lys Asp Glu Met Ala Arg His Leu Gln Glu Tyr Gln Asp Leu
            340                 345                 350

Leu Asn Val Lys Leu Ala Leu Asp Ile Glu Ile Ala Thr Tyr Arg Lys
        355                 360                 365

Leu Leu Glu Gly Glu Glu Asn Arg Ile Thr Ile Pro Val Gln Thr Phe
    370                 375                 380

Ser Asn Leu Gln Ile Arg Glu Thr Ser Leu Asp Thr Lys Ser Val Ser
385                 390                 395                 400

Glu Gly His Leu Lys Arg Asn Ile Val Val Lys Thr Val Glu Met Arg
405 410 415

Asp Gly Glu Val Ile Lys Glu Ser Lys Gln Glu His Lys Asp Val Met
420 425 430

<210> SEQ ID NO 34
<211> LENGTH: 1488
<212> TYPE: DNA
<213> ORGANISM: Homo sapiens

<400> SEQUENCE: 34
gcaggatgga gaggagacgc atcacctccg ctgctcgccg ctcctacgtc tcctcagggg 60
agatgatggt ggggggcctg gctcctggcc gccgtctggg tcctggcacc cgcctctccc 120
tggctcgaat gccccctcca ctcccgaccc gagtggattt ctccctggct ggggcactca 180
atgctggctt caaggagacc cgggccagtg agcgggcaga gatgatggag ctcaatgacc 240
gctttgccag ctacatcgag aaggttcgct tcctggaaca gcaaaacaag gcgctggctg 300
ctgagctgaa ccagctgcgg gccaaggagc ccaccaagct ggcagacgtc taccaggctg 360
agctgcgaga gctgcggctg cggctcgatc aactcaccgc caacagcgcc cggctggagg 420
ttgagaggga caatctggca caggacctgg ccactgtgag gcagaagctc caggatggaa 480
ccaacctgag gctggaagcc gagaacaacc tggctgccta tagacaggaa gcagatgaag 540
ccaccctggc ccgtctggat ctggagagga agattgagtc gctggaggag gagatccggt 600
tcttgaggaa gatccacgag gaggaggttc gggaactcca ggagcagctg gcccgacagc 660
aggtccatgt ggagcttgac gtggccaagc cagacctcac cgcagccctg aaagagatcc 720
gcacgcagta tgaggcaatg gcgtccagca acatgcatga agccgaagag tggtaccgct 780
ccaagtttgc agacctgaca gacgctgctg cccgcaacgc ggagctgctc cgccaggcca 840
agcacgaagc caacgactac cggcgccagt tgcagtcctt gacctgcgac ctggagtctc 900
tgcgcggcac gaacgagtcc ctggagaggc agatgcgcga gcaggaggag cggcacgtgc 960
gggaggcggc cagttatcag gaggcgctgg cgcggctgga ggaagagggg cagagcctca 1020
aggacgagat ggcccgccac ttgcaggagt accaggacct gctcaatgtc aagctggccc 1080
tggacatcga gatcgccacc tacaggaagc tgctagaggg cgaggagaac cggatcacca 1140
ttcccgtgca gaccttctcc aacctgcaga ttcgagaaac cagcctggac accaagtctg 1200
tgtcagaagg ccacctcaag aggaacatcg tggtgaagac cgtggagatg cgggatggag 1260
aggtcattaa ggagtccaag caggagcaca aggatgtgat gtgaggcagg acccacctgg 1320
tggcctctgc cccgtctcat gaggggcccg agcagaagca ggatagttgc tccgcctctg 1380
ctggcacatt tccccagacc tgagctcccc accaccccag ctgctcccct ccctcctctg 1440
tccctaggtc agcttgctgc cctaggctcc gtcagtatca ggcctgcc 1488

<210> SEQ ID NO 35
<211> LENGTH: 92
<212> TYPE: PRT
<213> ORGANISM: Homo sapiens

<400> SEQUENCE: 35

Met Ser Glu Leu Glu Lys Ala Met Val Ala Leu Ile Asp Val Phe His
1 5 10 15

Gln Tyr Ser Gly Arg Glu Gly Asp Lys His Lys Leu Lys Lys Ser Glu
20 25 30

```
Leu Lys Glu Leu Ile Asn Asn Glu Leu Ser His Phe Leu Glu Glu Ile
        35                  40                  45

Lys Glu Gln Glu Val Val Asp Lys Val Met Glu Thr Leu Asp Asn Asp
    50                  55                  60

Gly Asp Gly Glu Cys Asp Phe Gln Glu Phe Met Ala Phe Val Ala Met
65                  70                  75                  80

Val Thr Thr Ala Cys His Glu Phe Phe Glu His Glu
                85                  90


<210> SEQ ID NO 36
<211> LENGTH: 1135
<212> TYPE: DNA
<213> ORGANISM: Homo sapiens

<400> SEQUENCE: 36

gggcagaggg aataagaggc tgcctctgcc caccagtcct gccgcccagg acccgcagca     60

gagacgacgc ctgcagcaag gagaccagga aggggtgaga caaggaagag gatgtctgag    120

ctggagaagg ccatggtggc cctcatcgac gttttccacc aatattctgg aagggaggga    180

gacaagcaca agctgaagaa atccgaactg aaggagctca tcaacaatga gctttcccat    240

ttcttagagg aaatcaaaga gcaggaggtt gtggacaaag tcatggaaac actggacaat    300

gatggagacg gcgaatgtga cttccaggaa ttcatggcct ttgttgccat ggttactact    360

gcctgccacg agttctttga acatgagtga gattagaaag cagccaaacc tttcctgtaa    420

cagagacggt catgcaagaa agcagacagc aagggcttgc agcctagtag gagctgagct    480

ttccagccgt gttgtagcta attaggaagc ttgatttgct ttgtgattga aaaattgaaa    540

acctctttcc aaaggctgtt ttaacggcct gcatcattct ttctgctata ttaggcctgt    600

gtgtaagctg actggcccca gggactcttg ttaacagtaa cttaggagtc aggtctcagt    660

gataaagcgt gcaccgtgca gcccgccatg gccgtgtaga ccctaacccg gagggaaccc    720

tgactacaga aattaccccg gggcaccctt aaaacttcca ctacctttaa aaaacaaagc    780

cttatccagc attatttgaa aacactgctg ttctttaaat gcgttcctca tccatgcaga    840

taacagctgg ttggccggtg tggccctgca agggcgtggt ggcttcggcc tgcttcccgg    900

gatgcgcctg atcaccaggt gaacgctcag cgctggcagc gctcctggaa aaagcaactc    960

catcagaact cgcaatccga gccagctctg gggctccag cgtggcctcc gtgacccatg    1020

cgattcaagt cgcggctgca ggatccttgc ctccaacgtg cctccagcac atgcggcttc   1080

cgagggcact accgggggct ctgagccacc gcgagggcct gcgttcaata aaaag        1135


<210> SEQ ID NO 37
<211> LENGTH: 466
<212> TYPE: PRT
<213> ORGANISM: Homo sapiens

<400> SEQUENCE: 37

Met Ala Glu Glu Gln Asp Leu Ser Glu Val Glu Leu Ser Pro Val Gly
1               5                   10                  15

Ser Glu Glu Pro Arg Cys Leu Ser Pro Gly Ser Ala Pro Ser Leu Gly
            20                  25                  30

Pro Asp Gly Gly Gly Gly Gly Ser Gly Leu Arg Ala Ser Pro Gly Pro
        35                  40                  45

Gly Glu Leu Gly Lys Val Lys Lys Glu Gln Gln Asp Gly Glu Ala Asp
    50                  55                  60
```

-continued

```
Asp Asp Lys Phe Pro Val Cys Ile Arg Glu Ala Val Ser Gln Val Leu
65                  70                  75                  80

Ser Gly Tyr Asp Trp Thr Leu Val Pro Met Pro Val Arg Val Asn Gly
                85                  90                  95

Ala Ser Lys Ser Lys Pro His Val Lys Arg Pro Met Asn Ala Phe Met
            100                 105                 110

Val Trp Ala Gln Ala Ala Arg Arg Lys Leu Ala Asp Gln Tyr Pro His
        115                 120                 125

Leu His Asn Ala Glu Leu Ser Lys Thr Leu Gly Lys Leu Trp Arg Leu
    130                 135                 140

Leu Asn Glu Ser Asp Lys Arg Pro Phe Ile Glu Glu Ala Glu Arg Leu
145                 150                 155                 160

Arg Met Gln His Lys Lys Asp His Pro Asp Tyr Lys Tyr Gln Pro Arg
                165                 170                 175

Arg Arg Lys Asn Gly Lys Ala Ala Gln Gly Glu Ala Glu Cys Pro Gly
            180                 185                 190

Gly Glu Ala Glu Gln Gly Gly Thr Ala Ala Ile Gln Ala His Tyr Lys
        195                 200                 205

Ser Ala His Leu Asp His Arg His Pro Gly Glu Gly Ser Pro Met Ser
    210                 215                 220

Asp Gly Asn Pro Glu His Pro Ser Gly Gln Ser His Gly Pro Pro Thr
225                 230                 235                 240

Pro Pro Thr Thr Pro Lys Thr Glu Leu Gln Ser Gly Lys Ala Asp Pro
                245                 250                 255

Lys Arg Asp Gly Arg Ser Met Gly Glu Gly Gly Lys Pro His Ile Asp
            260                 265                 270

Phe Gly Asn Val Asp Ile Gly Glu Ile Ser His Glu Val Met Ser Asn
        275                 280                 285

Met Glu Thr Phe Asp Val Ala Glu Leu Asp Gln Tyr Leu Pro Pro Asn
    290                 295                 300

Gly His Pro Gly His Val Ser Ser Tyr Ser Ala Ala Gly Tyr Gly Leu
305                 310                 315                 320

Gly Ser Ala Leu Ala Val Ala Ser Gly His Ser Ala Trp Ile Ser Lys
                325                 330                 335

Pro Pro Gly Val Ala Leu Pro Thr Val Ser Pro Pro Gly Val Asp Ala
            340                 345                 350

Lys Ala Gln Val Lys Thr Glu Thr Ala Gly Pro Gln Gly Pro Pro His
        355                 360                 365

Tyr Thr Asp Gln Pro Ser Thr Ser Gln Ile Ala Tyr Thr Ser Leu Ser
    370                 375                 380

Leu Pro His Tyr Gly Ser Ala Phe Pro Ser Ile Ser Arg Pro Gln Phe
385                 390                 395                 400

Asp Tyr Ser Asp His Gln Pro Ser Gly Pro Tyr Tyr Gly His Ser Gly
                405                 410                 415

Gln Ala Ser Gly Leu Tyr Ser Ala Phe Ser Tyr Met Gly Pro Ser Gln
            420                 425                 430

Arg Pro Leu Tyr Thr Ala Ile Ser Asp Pro Ser Pro Ser Gly Pro Gln
        435                 440                 445

Ser His Ser Pro Thr His Trp Glu Gln Pro Val Tyr Thr Thr Leu Ser
    450                 455                 460

Arg Pro
465
```

<210> SEQ ID NO 38
<211> LENGTH: 2882
<212> TYPE: DNA
<213> ORGANISM: Homo sapiens

<400> SEQUENCE: 38
gtccggccag ggtggttggt ggtaaggatt caggctccgt cctaacgagg ccgtggcctg 60
aggctcaggg ccccccgccc ctccctccca gcccaccagc gtcacctccc agccccgagc 120
tggaccgcac accttgggac acggttttcc acttcctaag gacgagcccc agactggagg 180
agaggtccga ggaggtgggc gttggactct ttgcgaggac cccggcggct ggcccggggg 240
aggcggccga ggcggcggcg gcggcggccg gggcgacat ggcggaggag caggacctat 300
cggaggtgga gctgagcccc gtgggctcgg aggagccccg ctgcctgtcc ccggggagcg 360
cgccctcgct agggcccgac ggcggcggcg gcggatcggg cctgcgagcc agcccggggc 420
caggcgagct gggcaaggtc aagaaggagc agcaggacgg cgaggcggac gatgacaagt 480
tccccgtgtg catccgcgag gccgtcagcc aggtgctcag cggctacgac tggacgctgg 540
tgcccatgcc cgtgcgcgtc aacggcgcca gcaaaagcaa gccgcacgtc aagcggccca 600
tgaacgcctt catggtgtgg gctcaggcag cgcgcaggaa gctcgcggac cagtacccgc 660
acctgcacaa cgctgagctc agcaagacgc tgggcaagct ctggaggctg ctgaacgaaa 720
gtgacaagcg ccccttcatc gaggaggctg agcggctccg tatgcagcac aagaaagacc 780
acccggacta caagtaccag cccaggcggc ggaagaacgg gaaggccgcc cagggcgagg 840
cggagtgccc cggtggggag gccgagcaag gtgggaccgc cgccatccag gcccactaca 900
agagcgccca cttggaccac cggcacccag gagagggctc ccccatgtca gatgggaacc 960
ccgagcaccc ctcaggccag agccatggcc cacccacccc tccaaccacc ccgaagacag 1020
agctgcagtc gggcaaggca gacccgaagc gggacgggcg ctccatgggg gagggcggga 1080
agcctcacat cgacttcggc aacgtggaca ttggtgagat cagccacgag gtaatgtcca 1140
acatggagac ctttgatgtg gctgagttgg accagtacct gccgcccaat gggcacccag 1200
gccatgtgag cagctactca gcagccggct atgggctggg cagtgccctg gccgtggcca 1260
gtggacactc cgcctggatc tccaagccac caggcgtggc tctgcccacg gtctcaccac 1320
ctggtgtgga tgccaaagcc caggtgaaga cagagaccgc ggggccccag gggcccccac 1380
actacaccga ccagccatcc acctcacaga tcgcctacac ctccctcagc ctgccccact 1440
atggctcagc cttcccctcc atctcccgcc cccagtttga ctactctgac catcagccct 1500
caggacccta ttatggccac tcgggccagg cctctggcct ctactcggcc ttctcctata 1560
tggggccctc gcagcggccc ctctacacgg ccatctctga ccccagcccc tcagggcccc 1620
agtcccacag ccccacacac tgggagcagc cagtatatac gacactgtcc cggccctaaa 1680
gggggccctg tcgccaccac cccccgccca gcccctgccc ccagcctgtg tgccctgttc 1740
cttgcccacc tcaggcctgg tggtggcagt ggaggaggct gaggaggctg aagaggctga 1800
caggtcgggg ggctttctgt ctggctcact gccctgatga cccacccgcc ccatccaggc 1860
tccagcagca aagccccagg agaacaggct ggacagagga gaaggaggtt gactgttgca 1920
cccacactga aagatgaggg gctgcacctt cccccaggaa tgaccctcta tcccaggacc 1980
tgagaagggc ctgctcaccc tcctcgggga ggggaagcac cagggttggt ggcatcggag 2040
gccttaccac tcctatgact cctgttttct ctctcacaga tagtgagggt ctgacatgcc 2100
catgccacct atgccacagt gcctaagggc taggccaccc agagactgtg cccggagctg 2160

```
gccgtgtctc ccactcaggg gctgagagta gctttgagga gcctcattgg ggagtggggg   2220

gttcgaggga cttagtggag ttctcatccc ttcaatgccc cctccctttc tgaaggcagg   2280

aaggagttgg cacagaggcc ccctgatcca attctgtgcc aataacctca ttctttgtct   2340

gagaaacagc ccccagtcct cctccactac aacctccatg accttgagac gcatcccagg   2400

aggtgacgag gcaggggctc caggaaagga atcagagaca attcacagag cctccctccc   2460

tgggctcctt gccagctccc tcttccctta ctaggctcta tggcccctgc tcagtcagcc   2520

ccactccctg ggcttcccag agagtgacag ctgctcaggc cctaaccctt ggctccagga   2580

gacacagggc ccagcaccca ggttgctgtc ggcaggctga agacactaga atcctgacct   2640

gtacattctg cccttgcctc ttaccccttg cctcccagtg gtatttgaat aaagtatgta   2700

gctatatctg cccctatttt cctgttctgc agcccccaa atccacatgt aactcattac   2760

tgtctcctgt tatttatctc agtagtcccc tctcctagcc actctagccc ctattaactc   2820

tgcattaagc attccacata ataaaattaa aggttccggt taaaaaaaaa aaaaaaaaaa   2880

aa                                                                  2882
```

<210> SEQ ID NO 39
<211> LENGTH: 705
<212> TYPE: PRT
<213> ORGANISM: Homo sapiens

<400> SEQUENCE: 39

```
Met Asn Tyr Leu Arg Arg Arg Leu Ser Asp Ser Asn Phe Met Ala Asn
1               5                   10                  15

Leu Pro Asn Gly Tyr Met Thr Asp Leu Gln Arg Pro Gln Pro Pro Pro
            20                  25                  30

Pro Pro Pro Gly Ala His Ser Pro Gly Ala Thr Pro Gly Pro Gly Thr
        35                  40                  45

Ala Thr Ala Glu Arg Ser Ser Gly Val Ala Pro Ala Ala Ser Pro Ala
    50                  55                  60

Ala Pro Ser Pro Gly Ser Ser Gly Gly Gly Gly Phe Phe Ser Ser Leu
65                  70                  75                  80

Ser Asn Ala Val Lys Gln Thr Thr Ala Ala Ala Ala Ala Thr Phe Ser
                85                  90                  95

Glu Gln Val Gly Gly Gly Ser Gly Gly Ala Gly Arg Gly Gly Ala Ala
            100                 105                 110

Ser Arg Val Leu Leu Val Ile Asp Glu Pro His Thr Asp Trp Ala Lys
        115                 120                 125

Tyr Phe Lys Gly Lys Lys Ile His Gly Gly Ile Asp Ile Lys Val Glu
    130                 135                 140

Gln Ala Glu Phe Ser Asp Leu Asn Leu Val Ala His Ala Asn Gly Gly
145                 150                 155                 160

Phe Ser Val Asp Met Glu Val Leu Arg Asn Gly Val Lys Val Val Arg
                165                 170                 175

Ser Leu Lys Pro Asp Phe Val Leu Ile Arg Gln His Ala Phe Ser Met
            180                 185                 190

Ala Arg Asn Gly Asp Tyr Arg Ser Leu Val Ile Gly Leu Gln Tyr Ala
        195                 200                 205

Gly Ile Pro Ser Val Asn Ser Leu His Ser Val Tyr Asn Phe Cys Asp
    210                 215                 220

Lys Pro Trp Val Phe Ala Gln Met Val Arg Leu His Lys Lys Leu Gly
225                 230                 235                 240
```

-continued

```
Thr Glu Glu Phe Pro Leu Ile Asp Gln Thr Phe Tyr Pro Asn His Lys
                245                 250                 255

Glu Met Leu Ser Ser Thr Thr Tyr Pro Val Val Val Lys Met Gly His
            260                 265                 270

Ala His Ser Gly Met Gly Lys Val Lys Val Asp Asn Gln His Asp Phe
        275                 280                 285

Gln Asp Ile Ala Ser Val Val Ala Leu Thr Lys Thr Tyr Ala Thr Ala
    290                 295                 300

Glu Pro Phe Ile Asp Ala Lys Tyr Asp Val Arg Val Gln Lys Ile Gly
305                 310                 315                 320

Gln Asn Tyr Lys Ala Tyr Met Arg Thr Ser Val Ser Gly Asn Trp Lys
                325                 330                 335

Thr Asn Thr Gly Ser Ala Met Leu Glu Gln Ile Ala Met Ser Asp Arg
            340                 345                 350

Tyr Lys Leu Trp Val Asp Thr Cys Ser Glu Ile Phe Gly Gly Leu Asp
        355                 360                 365

Ile Cys Ala Val Glu Ala Leu His Gly Lys Asp Gly Arg Asp His Ile
    370                 375                 380

Ile Glu Val Val Gly Ser Ser Met Pro Leu Ile Gly Asp His Gln Asp
385                 390                 395                 400

Glu Asp Lys Gln Leu Ile Val Glu Leu Val Val Asn Lys Met Ala Gln
                405                 410                 415

Ala Leu Pro Arg Gln Arg Gln Arg Asp Ala Ser Pro Gly Arg Gly Ser
            420                 425                 430

His Gly Gln Thr Pro Ser Pro Gly Ala Leu Pro Leu Gly Arg Gln Thr
        435                 440                 445

Ser Gln Gln Pro Ala Gly Pro Pro Ala Gln Gln Arg Pro Pro Pro Gln
    450                 455                 460

Gly Gly Pro Pro Gln Pro Gly Pro Gly Pro Gln Arg Gln Gly Pro Pro
465                 470                 475                 480

Leu Gln Gln Arg Pro Pro Pro Gln Gly Gln Gln His Leu Ser Gly Leu
                485                 490                 495

Gly Pro Pro Ala Gly Ser Pro Leu Pro Gln Arg Leu Pro Ser Pro Thr
            500                 505                 510

Ser Ala Pro Gln Gln Pro Ala Ser Gln Ala Ala Pro Pro Thr Gln Gly
        515                 520                 525

Gln Gly Arg Gln Ser Arg Pro Val Ala Gly Gly Pro Gly Ala Pro Pro
    530                 535                 540

Ala Ala Arg Pro Pro Ala Ser Pro Ser Pro Gln Arg Gln Ala Gly Pro
545                 550                 555                 560

Pro Gln Ala Thr Arg Gln Thr Ser Val Ser Gly Pro Ala Pro Pro Lys
                565                 570                 575

Ala Ser Gly Ala Pro Pro Gly Gly Gln Gln Arg Gln Gly Pro Pro Gln
            580                 585                 590

Lys Pro Pro Gly Pro Ala Gly Pro Thr Arg Gln Ala Ser Gln Ala Gly
        595                 600                 605

Pro Val Pro Arg Thr Gly Pro Pro Thr Thr Gln Gln Pro Arg Pro Ser
    610                 615                 620

Gly Pro Gly Pro Ala Gly Ala Pro Lys Pro Gln Leu Ala Gln Lys Pro
625                 630                 635                 640

Ser Gln Asp Val Pro Pro Pro Ala Thr Ala Ala Ala Gly Gly Pro Pro
                645                 650                 655
```

```
His Pro Gln Leu Asn Lys Ser Gln Ser Leu Thr Asn Ala Phe Asn Leu
            660                 665                 670

Pro Glu Pro Ala Pro Pro Arg Pro Ser Leu Ser Gln Asp Glu Val Lys
        675                 680                 685

Ala Glu Thr Ile Arg Ser Leu Arg Lys Ser Phe Ala Ser Leu Phe Ser
    690                 695                 700

Asp
705


<210> SEQ ID NO 40
<211> LENGTH: 2470
<212> TYPE: DNA
<213> ORGANISM: Homo sapiens

<400> SEQUENCE: 40

ctcgagagag aaggagagga cattcctggc agaagttaca acacatgcaa aggtacagag      60

gttgcccccct tcctacccct ctccttagag gtgggttaga gatgtatcct ttttacagat    120

gaggaaacca aatctcagaa agattaagtc actttcccaa gtgtatggtg gaggccccac    180

ttgaacccag gcactgtgtc tccagacccc acactattac tgccttgttt aaaccagcca    240

actgatttaa tgaataaagg atgaacaaat gaataagtgg atgagtcacc tgaaaattct    300

gcaggcaaag agactccata tctacttact tcttgcctat cttctgccac ctctcctagt    360

ccaccatcac tgctcactat ggtcaaggtc ctacccaatc tggcccctgc taccacaacc    420

cccttcagct tgttccagcc acattggcac tggatgtttc ctcttcctgg cacattctta    480

aaaaaatgtg ttgatcataa agtgaacatg accctttggg aattaactgg agttcttgta    540

ttccctcatc tgtaaaatag acattatatt atccacccca ctggattgtt gtgagggtgg    600

gatgaaatga tgcatgtaaa cacgcttagc ttaagagttg ggtacaatca gtgaacaaat    660

gattatgaat tagtgctttt attgtagtca gaatcataaa gatttgacag gttcccatat    720

cccacctctg cttggactac ctcatttgct catatgcaaa gattatttgg tacctactgt    780

gtgtgcacca tgggatgggc ctgcctctgt ggaaagttct tgggtgcagg gggagacagc    840

catgggcact gatgacatca ggtagttatc gtgagttttg gcggtgtcca gagcaaaggg    900

atggtggcgt atataccaag tgtgttctgg tgtgggggtg gacacgcacc agggctaggg    960

ctgcagagaa tgtctgtgtt gcagatctag gtttctccat gatcatcggt gggaatgtgt   1020

tttgtctgca agtgtatgct catatgagtt tccctgggtc tctgtgtgtc agtgtgttac   1080

ctgtgtgtgt gggggtatgg gtgtatgcat gcatgtatgt aacatgccca tgtgtgttac   1140

tctggacttg tatgtctgta tgtataccta gattggcgtg tgttctgtct gtacatgccc   1200

tcgtatgttt cctcactttt gtgtgtgttt atatgtgtgt catttcttgt gtgccctcca   1260

ggccccccctt gccaccttgg gcaagggtgt gtacaccacc caagtgtcca cctccgcttg   1320

tctgatgctg tctgtgacgc ccccgctctc tgcctagctg agcctgtgtg gatgtgggag   1380

actaatctcc ccgcgggcac tgcgtgtgac ctcacccccc tctgtgaggg ggttatttct   1440

ctactttcgt gtctctgagt gtgcttccag tgccccccctc cccccaaaaa atgccttctg   1500

agttgaatat caacactaca aaccgagtat ctgcagactg cagagggccc tgcgtatgag   1560

tgcaagtggg ttttaggacc aggatgaggc ggggtggggg tgcctacctg acgaccgacc   1620

ccgacccact ggacaagcac ccaaccccca ttccccaaat tgcgcatccc ctatcagaga   1680

gggggagggg aaacaggatg cggcgaggcg cgtcgcgact gccagcttca gcaccgcgga   1740

cagtgccttc gcccccgcct ggcggcgcgc gccaccgccg cctcagcact gaaggcgcgc   1800
```

```
tgacgtcact cgccggtccc ccgcaaactc cccttcccgg ccaccttggt cgcgtccgcg   1860

ccgccgccgg cccagccgga ccgcaccacg cgaggcgcga gatagggggg cacgggcgcg   1920

accatctgcg ctgcggcgcc ggcgactcag cgctgcctca gtctgcggtg ggcagcggag   1980

gagtcgtgtc gtgcctgaga gcgcagctgt gctcctgggc accgcgcagt ccgccccccgc  2040

ggctcctggc cagaccaccc ctaggacccc ctgccccaag tcgcagccat gaactacctg   2100

cggcgccgcc tgtcggacag caactttatg gccaatctgc caaatgggta catgacagac   2160

ctgcagcgtc cgcagccgcc cccaccgccg cccggtgccc acagccccgg agccacgccc   2220

ggtcccggga ccgccactgc cgagaggtcc tccggggtcg ccccagcggc ctctccggcc   2280

gcccctagcc ccgggtcctc ggggggcggt ggcttcttct cgtcgctgtc caacgcggtc   2340

aagcagacca cggcggcggc agctgccacc ttcagcgagc aggtgggcgg cggctctggg   2400

ggcgcaggcc gcgggggagc cgcctccagg gtgctgctgg tcatcgacga gccgcacacc   2460

gactggtaag                                                          2470
```

```
<210> SEQ ID NO 41
<211> LENGTH: 313
<212> TYPE: PRT
<213> ORGANISM: Homo sapiens

<400> SEQUENCE: 41

Met Leu Leu Leu Ala Asp Met Asp Val Val Asn Gln Leu Val Ala Gly
1               5                   10                  15

Gly Gln Phe Arg Val Val Lys Glu Pro Leu Gly Phe Val Lys Val Leu
            20                  25                  30

Gln Trp Val Phe Ala Ile Phe Ala Phe Ala Thr Cys Gly Ser Tyr Ser
        35                  40                  45

Gly Glu Leu Gln Leu Ser Val Asp Cys Ala Asn Lys Thr Glu Ser Asp
    50                  55                  60

Leu Ser Ile Glu Val Glu Phe Glu Tyr Pro Phe Arg Leu His Gln Val
65                  70                  75                  80

Tyr Phe Asp Ala Pro Thr Cys Arg Gly Gly Thr Thr Lys Val Phe Leu
                85                  90                  95

Val Gly Asp Tyr Ser Ser Ser Ala Glu Phe Phe Val Thr Val Ala Val
            100                 105                 110

Phe Ala Phe Leu Tyr Ser Met Gly Ala Leu Ala Thr Tyr Ile Phe Leu
        115                 120                 125

Gln Asn Lys Tyr Arg Glu Asn Asn Lys Gly Pro Met Leu Asp Phe Leu
    130                 135                 140

Ala Thr Ala Val Phe Ala Phe Met Trp Leu Val Ser Ser Ser Ala Trp
145                 150                 155                 160

Ala Lys Gly Leu Ser Asp Val Lys Met Ala Thr Asp Pro Glu Asn Ile
                165                 170                 175

Ile Lys Glu Met Pro Val Cys Arg Gln Thr Gly Asn Thr Cys Lys Glu
            180                 185                 190

Leu Arg Asp Pro Val Thr Ser Gly Leu Asn Thr Ser Val Val Phe Gly
        195                 200                 205

Phe Leu Asn Leu Val Leu Trp Val Gly Asn Leu Trp Phe Val Phe Lys
    210                 215                 220

Glu Thr Gly Trp Ala Ala Pro Phe Leu Arg Ala Pro Pro Gly Ala Pro
225                 230                 235                 240

Glu Lys Gln Pro Ala Pro Gly Asp Ala Tyr Gly Asp Ala Gly Tyr Gly
                245                 250                 255
```

```
Gln Gly Pro Gly Gly Tyr Gly Pro Gln Asp Ser Tyr Gly Pro Gln Gly
            260                 265                 270

Gly Tyr Gln Pro Asp Tyr Gly Gln Pro Ala Gly Ser Gly Gly Ser Gly
        275                 280                 285

Tyr Gly Pro Gln Gly Asp Tyr Gly Gln Gln Gly Tyr Gly Pro Gln Gly
    290                 295                 300

Ala Pro Thr Ser Phe Ser Asn Gln Met
305                 310


<210> SEQ ID NO 42
<211> LENGTH: 2449
<212> TYPE: DNA
<213> ORGANISM: Homo sapiens

<400> SEQUENCE: 42

gccccctgca ttgctgatgc tgctgctggc ggacatggac gtggtgaatc agctggtggc      60

tgggggtcag ttccgggtgg tcaaggagcc cctcggcttt gtgaaggtgc tgcaatgggt     120

cttcgccatc ttcgcctttg ccacatgcgg cagctacagt ggggagctcc agctgagcgt     180

ggattgtgcc aacaagaccg agagtgacct cagcatcgag gtcgagttcg agtacccctt     240

caggctgcac caagtgtact ttgatgcacc cacctgccga gggggcacca ccaaggtctt     300

cttagttggg gactactcct cgtcagccga attctttgtc accgtggccg tgtttgcctt     360

cctctactcc atgggggctc tggccaccta catcttcctg cagaacaagt accgagagaa     420

taacaaaggg cccatgctgg actttctggc cacggctgtg ttcgccttca tgtggctagt     480

tagctcatcg gcatgggcca aggggctgtc agatgtgaag atggccacag acccagagaa     540

cattatcaag gagatgcctg tctgccgcca gacagggaac acatgcaagg agctgagaga     600

ccctgtgacc tcgggactca acacctcggt ggtgttcggc ttcctgaacc tggtgctctg     660

ggtcggcaac ctgtggttcg tgtttaagga gacaggctgg gccgccccgt tcctgcgcgc     720

gcctcccggc gcccccgaga aacaaccggc acccggggac gcctacggcg atgcaggcta     780

cgggcagggc cccggcgggt acgggcccca ggattcctac gggcctcagg gcggctacca     840

gcctgactat ggtcaaccag ccggcagcgg tggcagtggc tacgggcctc agggcgacta     900

tgggcagcaa ggctacggcc cgcagggtgc acccacctcc ttctccaatc agatgtagtc     960

tggtcagtga agcccaggag gacctggggg gggcaagagc tcaggagaag gcctgccccc    1020

cttcccaccc ctatacccta ggtctccacc cctcaagcca ggagaccctg tctttgctgt    1080

ttatatatat atatattata tataaatatc tatttatctg tctgagccct gccctcactc    1140

cactcccctc atccactagg tgcccagtct tgagtgggcc ccctctctta ccccgtccct    1200

ttccctgcat cccttggccc ctctctgttt accctccctg tcccctgagg ttaaggggat    1260

ctaaaaggag gacagggagg gaacagacct cggctgtgtg gggagggtgg gcgtgacttc    1320

agactctctc ctctctctcc ctccactcct cccaactctg gccttggttc ctccagcaat    1380

gcctgcctga acaaaggccg ttagggaaat ccaactccag ggttaaagaa aggcagagat    1440

tggggggggct tggggtagag aggacagttt aggacccaag gtggtcttgg agaggaggtg    1500

tggagtggag gggtcagcag gggggttggg ttccagacag agtggatctg gagtctgaag    1560

gagaggagtg cgctagagca ttctggggtg gggcttggaa gggcgctgag ggcagggttc    1620

tagaaggggc gaggctttaa gcgaggcaga atggtgggct ccagagtagg tgggtcttgg    1680

attggtacca gagcctatgg aaagggtgtg gcttggaaca tttgggagac tgagcttgat    1740

tctaaagggg acagatcttg agcaaggcaa gaagtgggat tcaggaatgg gccaagccag    1800
```

```
ggttccagac agggtggggc ttagaatggg gcttccatgg tggtttcaga aagggcagcc   1860

cctccccatg gtgcagtgaa gaaaatgttt tacaatggct gggtttgggc agtggagagg   1920

ggacttggat aggagcttcc agatgggttt tgttaggggt gggggagaat ggctctggct   1980

acgacttggg acggaagtgg cctgagaaga gtcgagtgat atggcttgta gggtgaggcg   2040

tgggatccag agagaagcac cccaccacac acacccttcc ccactcccgt gatgaaacag   2100

ctaggttaat aggaggacag aaccaacggg tctgtgggac tggcccaccc ctcttccccc   2160

ttcccctgcg ccctccctcc ctccacacct ccacccgtcc tggggtggtt ggaggcctgg   2220

tctggagccc ctatcctgca ccctctgcta tgtctgtgat gtcagtagtg cctgtgatcg   2280

tgtgttgcca ttttgtctgg ctgtggcccc tccttctccc ctccagaccc ctaccctttc   2340

ccaaaccctt cggtattgtt caaagaaccc ccctccccaa ggaagaacaa atatgattct   2400

cctctcccaa ataaactcct taaccaccta gtcaaaaaaa aaaaaaaaa               2449


<210> SEQ ID NO 43
<211> LENGTH: 1192
<212> TYPE: PRT
<213> ORGANISM: Homo sapiens

<400> SEQUENCE: 43

Met Glu Asp Leu Asp Gln Ser Pro Leu Val Ser Ser Ser Asp Ser Pro
1               5                   10                  15

Pro Arg Pro Gln Pro Ala Phe Lys Tyr Gln Phe Val Arg Glu Pro Glu
            20                  25                  30

Asp Glu Glu Glu Glu Glu Glu Glu Glu Glu Glu Asp Glu Asp Glu Asp
        35                  40                  45

Leu Glu Glu Leu Glu Val Leu Glu Arg Lys Pro Ala Ala Gly Leu Ser
    50                  55                  60

Ala Ala Pro Val Pro Thr Ala Pro Ala Ala Gly Ala Pro Leu Met Asp
65                  70                  75                  80

Phe Gly Asn Asp Phe Val Pro Pro Ala Pro Arg Gly Pro Leu Pro Ala
                85                  90                  95

Ala Pro Pro Val Ala Pro Glu Arg Gln Pro Ser Trp Asp Pro Ser Pro
            100                 105                 110

Val Ser Ser Thr Val Pro Ala Pro Ser Pro Leu Ser Ala Ala Ala Val
        115                 120                 125

Ser Pro Ser Lys Leu Pro Glu Asp Asp Glu Pro Pro Ala Arg Pro Pro
    130                 135                 140

Pro Pro Pro Pro Ala Ser Val Ser Pro Gln Ala Glu Pro Val Trp Thr
145                 150                 155                 160

Pro Pro Ala Pro Ala Pro Ala Ala Pro Pro Ser Thr Pro Ala Ala Pro
                165                 170                 175

Lys Arg Arg Gly Ser Ser Gly Ser Val Asp Glu Thr Leu Phe Ala Leu
            180                 185                 190

Pro Ala Ala Ser Glu Pro Val Ile Arg Ser Ser Ala Glu Asn Met Asp
        195                 200                 205

Leu Lys Glu Gln Pro Gly Asn Thr Ile Ser Ala Gly Gln Glu Asp Phe
    210                 215                 220

Pro Ser Val Leu Leu Glu Thr Ala Ala Ser Leu Pro Ser Leu Ser Pro
225                 230                 235                 240

Leu Ser Ala Ala Ser Phe Lys Glu His Glu Tyr Leu Gly Asn Leu Ser
                245                 250                 255
```

```
Thr Val Leu Pro Thr Glu Gly Thr Leu Gln Glu Asn Val Ser Glu Ala
            260                 265                 270

Ser Lys Glu Val Ser Glu Lys Ala Lys Thr Leu Leu Ile Asp Arg Asp
        275                 280                 285

Leu Thr Glu Phe Ser Glu Leu Glu Tyr Ser Glu Met Gly Ser Ser Phe
    290                 295                 300

Ser Val Ser Pro Lys Ala Glu Ser Ala Val Ile Val Ala Asn Pro Arg
305                 310                 315                 320

Glu Glu Ile Ile Val Lys Asn Lys Asp Glu Glu Glu Lys Leu Val Ser
                325                 330                 335

Asn Asn Ile Leu His Asn Gln Gln Glu Leu Pro Thr Ala Leu Thr Lys
            340                 345                 350

Leu Val Lys Glu Asp Glu Val Val Ser Ser Glu Lys Ala Lys Asp Ser
        355                 360                 365

Phe Asn Glu Lys Arg Val Ala Val Glu Ala Pro Met Arg Glu Glu Tyr
    370                 375                 380

Ala Asp Phe Lys Pro Phe Glu Arg Val Trp Glu Val Lys Asp Ser Lys
385                 390                 395                 400

Glu Asp Ser Asp Met Leu Ala Ala Gly Gly Lys Ile Glu Ser Asn Leu
                405                 410                 415

Glu Ser Lys Val Asp Lys Lys Cys Phe Ala Asp Ser Leu Glu Gln Thr
            420                 425                 430

Asn His Glu Lys Asp Ser Glu Ser Ser Asn Asp Asp Thr Ser Phe Pro
        435                 440                 445

Ser Thr Pro Glu Gly Ile Lys Asp Arg Ser Gly Ala Tyr Ile Thr Cys
    450                 455                 460

Ala Pro Phe Asn Pro Ala Ala Thr Glu Ser Ile Ala Thr Asn Ile Phe
465                 470                 475                 480

Pro Leu Leu Gly Asp Pro Thr Ser Glu Asn Lys Thr Asp Glu Lys Lys
                485                 490                 495

Ile Glu Glu Lys Lys Ala Gln Ile Val Thr Glu Lys Asn Thr Ser Thr
            500                 505                 510

Lys Thr Ser Asn Pro Phe Leu Val Ala Ala Gln Asp Ser Glu Thr Asp
        515                 520                 525

Tyr Val Thr Thr Asp Asn Leu Thr Lys Val Thr Glu Glu Val Val Ala
    530                 535                 540

Asn Met Pro Glu Gly Leu Thr Pro Asp Leu Val Gln Glu Ala Cys Glu
545                 550                 555                 560

Ser Glu Leu Asn Glu Val Thr Gly Thr Lys Ile Ala Tyr Glu Thr Lys
                565                 570                 575

Met Asp Leu Val Gln Thr Ser Glu Val Met Gln Glu Ser Leu Tyr Pro
            580                 585                 590

Ala Ala Gln Leu Cys Pro Ser Phe Glu Glu Ser Glu Ala Thr Pro Ser
        595                 600                 605

Pro Val Leu Pro Asp Ile Val Met Glu Ala Pro Leu Asn Ser Ala Val
    610                 615                 620

Pro Ser Ala Gly Ala Ser Val Ile Gln Pro Ser Ser Ser Pro Leu Glu
625                 630                 635                 640

Ala Ser Ser Val Asn Tyr Glu Ser Ile Lys His Glu Pro Glu Asn Pro
                645                 650                 655

Pro Pro Tyr Glu Glu Ala Met Ser Val Ser Leu Lys Lys Val Ser Gly
            660                 665                 670
```

```
Ile Lys Glu Glu Ile Lys Glu Pro Glu Asn Ile Asn Ala Ala Leu Gln
        675                 680                 685

Glu Thr Glu Ala Pro Tyr Ile Ser Ile Ala Cys Asp Leu Ile Lys Glu
    690                 695                 700

Thr Lys Leu Ser Ala Glu Pro Ala Pro Asp Phe Ser Asp Tyr Ser Glu
705                 710                 715                 720

Met Ala Lys Val Glu Gln Pro Val Pro Asp His Ser Glu Leu Val Glu
                725                 730                 735

Asp Ser Ser Pro Asp Ser Glu Pro Val Asp Leu Phe Ser Asp Asp Ser
            740                 745                 750

Ile Pro Asp Val Pro Gln Lys Gln Asp Glu Thr Val Met Leu Val Lys
        755                 760                 765

Glu Ser Leu Thr Glu Thr Ser Phe Glu Ser Met Ile Glu Tyr Glu Asn
    770                 775                 780

Lys Glu Lys Leu Ser Ala Leu Pro Pro Glu Gly Gly Lys Pro Tyr Leu
785                 790                 795                 800

Glu Ser Phe Lys Leu Ser Leu Asp Asn Thr Lys Asp Thr Leu Leu Pro
                805                 810                 815

Asp Glu Val Ser Thr Leu Ser Lys Lys Glu Lys Ile Pro Leu Gln Met
            820                 825                 830

Glu Glu Leu Ser Thr Ala Val Tyr Ser Asn Asp Asp Leu Phe Ile Ser
        835                 840                 845

Lys Glu Ala Gln Ile Arg Glu Thr Glu Thr Phe Ser Asp Ser Ser Pro
    850                 855                 860

Ile Glu Ile Ile Asp Glu Phe Pro Thr Leu Ile Ser Ser Lys Thr Asp
865                 870                 875                 880

Ser Phe Ser Lys Leu Ala Arg Glu Tyr Thr Asp Leu Glu Val Ser His
                885                 890                 895

Lys Ser Glu Ile Ala Asn Ala Pro Asp Gly Ala Gly Ser Leu Pro Cys
            900                 905                 910

Thr Glu Leu Pro His Asp Leu Ser Leu Lys Asn Ile Gln Pro Lys Val
        915                 920                 925

Glu Glu Lys Ile Ser Phe Ser Asp Asp Phe Ser Lys Asn Gly Ser Ala
    930                 935                 940

Thr Ser Lys Val Leu Leu Leu Pro Pro Asp Val Ser Ala Leu Ala Thr
945                 950                 955                 960

Gln Ala Glu Ile Glu Ser Ile Val Lys Pro Lys Val Leu Val Lys Glu
                965                 970                 975

Ala Glu Lys Lys Leu Pro Ser Asp Thr Glu Lys Glu Asp Arg Ser Pro
            980                 985                 990

Ser Ala Ile Phe Ser Ala Glu Leu  Ser Lys Thr Ser Val  Val Asp Leu
        995                 1000                1005

Leu Tyr  Trp Arg Asp Ile Lys  Lys Thr Gly Val Val  Phe Gly Ala
    1010                1015                1020

Ser Leu  Phe Leu Leu Leu Ser  Leu Thr Val Phe Ser  Ile Val Ser
    1025                1030                1035

Val Thr  Ala Tyr Ile Ala Leu  Ala Leu Leu Ser Val  Thr Ile Ser
    1040                1045                1050

Phe Arg  Ile Tyr Lys Gly Val  Ile Gln Ala Ile Gln  Lys Ser Asp
    1055                1060                1065

Glu Gly  His Pro Phe Arg Ala  Tyr Leu Glu Ser Glu  Val Ala Ile
    1070                1075                1080
```

```
Ser Glu  Glu Leu Val Gln Lys  Tyr Ser Asn Ser Ala  Leu Gly His
    1085                 1090                 1095

Val Asn  Cys Thr Ile Lys Glu  Leu Arg Arg Leu Phe  Leu Val Asp
    1100                 1105                 1110

Asp Leu  Val Asp Ser Leu Lys  Phe Ala Val Leu Met  Trp Val Phe
    1115                 1120                 1125

Thr Tyr  Val Gly Ala Leu Phe  Asn Gly Leu Thr Leu  Leu Ile Leu
    1130                 1135                 1140

Ala Leu  Ile Ser Leu Phe Ser  Val Pro Val Ile Tyr  Glu Arg His
    1145                 1150                 1155

Gln Ala  Gln Ile Asp His Tyr  Leu Gly Leu Ala Asn  Lys Asn Val
    1160                 1165                 1170

Lys Asp  Ala Met Ala Lys Ile  Gln Ala Lys Ile Pro  Gly Leu Lys
    1175                 1180                 1185

Arg Lys  Ala Glu
    1190
```

<210> SEQ ID NO 44
<211> LENGTH: 4871
<212> TYPE: DNA
<213> ORGANISM: Homo sapiens

<400> SEQUENCE: 44

```
agtccctgcc ctcccctggg gagggtgagt cacgccaaac tgggcggaga gtccgctggc     60

ctcactccta gctcatctgg gcggcggcgg caagtgggga cagggcgggt ggcgcatcac    120

cggcgcggag gcaggaggag cagtctcatt gttccgggag ccgtcaccac agtaggtccc    180

tcggctcagt cggcccagcc cctctcagtc ctccccaacc cccacaaccg cccgcggctc    240

tgagacgcgg ccccggcggc ggcggcagca gctgcagcat catctccacc ctccagccat    300

ggaagacctg gaccagtctc ctctggtctc gtcctcggac agcccacccc ggccgcagcc    360

cgcgttcaag taccagttcg tgagggagcc cgaggacgag gaggaagaag aggaggagga    420

agaggaggac gaggacgaag acctggagga gctggaggtg ctggagagga agcccgccgc    480

cgggctgtcc gcggccccag tgcccaccgc ccctgccgcc ggcgcgcccc tgatggactt    540

cggaaatgac ttcgtgccgc cggcgccccg gggacccctg ccggccgctc cccccgtcgc    600

cccggagcgg cagccgtctt gggacccgag cccggtgtcg tcgaccgtgc ccgcgccatc    660

cccgctgtct gctgccgcag tctcgccctc caagctccct gaggacgacg agcctccggc    720

ccggcctccc cctcctcccc cggccagcgt gagcccccag gcagagcccg tgtggacccc    780

gccagccccg gctcccgccg cgccccctc caccccggcc gcgcccaagc gcaggggctc    840

ctcgggctca gtggatgaga cccttttgc tcttcctgct gcatctgagc ctgtgatacg    900

ctcctctgca gaaaatatgg acttgaagga gcagccaggt aacactattt cggctggtca    960

agaggatttc ccatctgtcc tgcttgaaac tgctgcttct cttccttctc tgtctcctct   1020

ctcagccgct tctttcaaag aacatgaata ccttggtaat ttgtcaacag tattacccac   1080

tgaaggaaca cttcaagaaa atgtcagtga agcttctaaa gaggtctcag agaaggcaaa   1140

aactctactc atagatagag atttaacaga gttttcagaa ttagaatact cagaaatggg   1200

atcatcgttc agtgtctctc caaaagcaga atctgccgta atagtagcaa atcctaggga   1260

agaaataatc gtgaaaaata aagatgaaga agagaagtta gttagtaata acatccttca   1320

taatcaacaa gagttaccta cagctcttac taaattggtt aaagaggatg aagttgtgtc   1380

ttcagaaaaa gcaaaagaca gttttaatga aaagagagtt gcagtggaag ctcctatgag   1440
```

```
ggaggaatat gcagacttca aaccatttga gcgagtatgg gaagtgaaag atagtaagga   1500
agatagtgat atgttggctg ctggaggtaa aatcgagagc aacttggaaa gtaaagtgga   1560
taaaaaatgt tttgcagata gccttgagca aactaatcac gaaaaagata gtgagagtag   1620
taatgatgat acttctttcc ccagtacgcc agaaggtata aaggatcgtt caggagcata   1680
tatcacatgt gctccctta acccagcagc aactgagagc attgcaacaa acatttttcc   1740
tttgttagga gatcctactt cagaaaataa gaccgatgaa aaaaaaatag aagaaaagaa   1800
ggcccaaata gtaacagaga agaatactag caccaaaaca tcaaaccctt ttcttgtagc   1860
agcacaggat tctgagacag attatgtcac aacagataat ttaacaaagg tgactgagga   1920
agtcgtggca aacatgcctg aaggcctgac tccagattta gtacaggaag catgtgaaag   1980
tgaattgaat gaagttactg gtacaaagat tgcttatgaa acaaaaatgg acttggttca   2040
aacatcagaa gttatgcaag agtcactcta tcctgcagca cagctttgcc catcatttga   2100
agagtcagaa gctactcctt caccagtttt gcctgacatt gttatggaag caccattgaa   2160
ttctgcagtt cctagtgctg gtgcttccgt gatacagccc agctcatcac cattagaagc   2220
ttcttcagtt aattatgaaa gcataaaaca tgagcctgaa aaccccccac catatgaaga   2280
ggccatgagt gtatcactaa aaaaagtatc aggaataaag gaagaaatta aagagcctga   2340
aaatattaat gcagctcttc aagaaacaga agctccttat atatctattg catgtgattt   2400
aattaaagaa acaaagcttt ctgctgaacc agctccggat ttctctgatt attcagaaat   2460
ggcaaaagtt gaacagccag tgcctgatca ttctgagcta gttgaagatt cctcacctga   2520
ttctgaacca gttgacttat ttagtgatga ttcaatacct gacgttccac aaaaacaaga   2580
tgaaactgtg atgcttgtga aagaaagtct cactgagact tcatttgagt caatgataga   2640
atatgaaaat aaggaaaaac tcagtgcttt gccacctgag ggaggaaagc catatttgga   2700
atcttttaag ctcagtttag ataacacaaa agataccctg ttacctgatg aagtttcaac   2760
attgagcaaa aaggagaaaa ttcctttgca gatggaggag ctcagtactg cagtttattc   2820
aaatgatgac ttatttattt ctaaggaagc acagataaga gaaactgaaa cgttttcaga   2880
ttcatctcca attgaaatta tagatgagtt ccctacattg atcagttcta aaactgattc   2940
attttctaaa ttagccaggg aatatactga cctagaagta tcccacaaaa gtgaaattgc   3000
taatgccccg gatggagctg ggtcattgcc ttgcacagaa ttgccccatg acctttcttt   3060
gaagaacata caacccaaag ttgaagagaa aatcagtttc tcagatgact tttctaaaaa   3120
tgggtctgct acatcaaagg tgctcttatt gcctccagat gtttctgctt tggccactca   3180
agcagagata gagagcatag ttaaacccaa agttcttgtg aaagaagctg agaaaaaact   3240
tccttccgat acagaaaaag aggacagatc accatctgct atattttcag cagagctgag   3300
taaaacttca gttgttgacc tcctgtactg gagagacatt aagaagactg gagtggtgtt   3360
tggtgccagc ctattcctgc tgctttcatt gacagtattc agcattgtga gcgtaacagc   3420
ctacattgcc ttggccctgc tctctgtgac catcagcttt aggatataca agggtgtgat   3480
ccaagctatc cagaaatcag atgaaggcca cccattcagg gcatatctgg aatctgaagt   3540
tgctatatct gaggagttgg ttcagaagta cagtaattct gctcttggtc atgtgaactg   3600
cacgataaag gaactcaggc gcctcttctt agttgatgat ttagttgatt ctctgaagtt   3660
tgcagtgttg atgtgggtat ttacctatgt tggtgccttg tttaatggtc tgacactact   3720
gattttggct ctcatttcac tcttcagtgt tcctgttatt tatgaacggc atcaggcaca   3780
gatagatcat tatctaggac ttgcaaataa gaatgttaaa gatgctatgg ctaaaatcca   3840
```

```
agcaaaaatc cctggattga agcgcaaagc tgaatgaaaa cgcccaaaat aattagtagg   3900

agttcatctt taaaggggat attcatttga ttatacgggg gagggtcagg gaagaacgaa   3960

ccttgacgtt gcagtgcagt ttcacagatc gttgttagat ctttattttt agccatgcac   4020

tgttgtgagg aaaaattacc tgtcttgact gccatgtgtt catcatctta agtattgtaa   4080

gctgctatgt atggatttaa accgtaatca tatctttttc ctatctatct gaggcactgg   4140

tggaataaaa aacctgtata ttttactttg ttgcagatag tcttgccgca tcttggcaag   4200

ttgcagagat ggtggagcta gaaaaaaaaa aaaaaaagcc cttttcagtt tgtgcactgt   4260

gtatggtccg tgtagattga tgcagatttt ctgaaatgaa atgtttgttt agacgagatc   4320

ataccggtaa agcaggaatg acaaagcttg cttttctggt atgttctagg tgtattgtga   4380

cttttactgt tatattaatt gccaatataa gtaaatatag attatatatg tatagtgttt   4440

cacaaagctt agacctttac cttccagcca ccccacagtg cttgatattt cagagtcagt   4500

cattggttat acatgtgtag ttccaaagca cataagctag aagaagaaat atttctagga   4560

gcactaccat ctgttttcaa catgaaatgc cacacacata gaactccaac atcaatttca   4620

ttgcacagac tgactgtagt taattttgtc acagaatcta tggactgaat ctaatgcttc   4680

caaaaatgtt gtttgtttgc aaatatcaaa cattgttatg caagaaatta ttaattacaa   4740

aatgaagatt tataccattg tggtttaagc tgtactgaac taaatctgtg gaatgcattg   4800

tgaactgtaa aagcaaagta tcaataaagc ttatagactt aaaaaaaaaa aaaaaaaaaa   4860

aaaaaaaaaa a                                                        4871
```

<210> SEQ ID NO 45
<211> LENGTH: 432
<212> TYPE: PRT
<213> ORGANISM: Homo sapiens

<400> SEQUENCE: 45

```
Met Glu Arg Arg Arg Ile Thr Ser Ala Ala Arg Arg Ser Tyr Val Ser
1               5                   10                  15

Ser Gly Glu Met Met Val Gly Gly Leu Ala Pro Gly Arg Arg Leu Gly
            20                  25                  30

Pro Gly Thr Arg Leu Ser Leu Ala Arg Met Pro Pro Pro Leu Pro Thr
        35                  40                  45

Arg Val Asp Phe Ser Leu Ala Gly Ala Leu Asn Ala Gly Phe Lys Glu
    50                  55                  60

Thr Arg Ala Ser Glu Arg Ala Glu Met Met Glu Leu Asn Asp Arg Phe
65                  70                  75                  80

Ala Ser Tyr Ile Glu Lys Val Arg Phe Leu Glu Gln Gln Asn Lys Ala
                85                  90                  95

Leu Ala Ala Glu Leu Asn Gln Leu Arg Ala Lys Glu Pro Thr Lys Leu
            100                 105                 110

Ala Asp Val Tyr Gln Ala Glu Leu Arg Glu Leu Arg Leu Arg Leu Asp
        115                 120                 125

Gln Leu Thr Ala Asn Ser Ala Arg Leu Glu Val Glu Arg Asp Asn Leu
    130                 135                 140

Ala Gln Asp Leu Ala Thr Val Arg Gln Lys Leu Gln Asp Glu Thr Asn
145                 150                 155                 160

Leu Arg Leu Glu Ala Glu Asn Asn Leu Ala Ala Tyr Arg Gln Glu Ala
                165                 170                 175

Asp Glu Ala Thr Leu Ala Arg Leu Asp Leu Glu Arg Lys Ile Glu Ser
            180                 185                 190
```

```
Leu Glu Glu Glu Ile Arg Phe Leu Arg Lys Ile His Glu Glu Glu Val
        195                 200                 205

Arg Glu Leu Gln Glu Gln Leu Ala Arg Gln Gln Val His Val Glu Leu
    210                 215                 220

Asp Val Ala Lys Pro Asp Leu Thr Ala Ala Leu Lys Glu Ile Arg Thr
225                 230                 235                 240

Gln Tyr Glu Ala Met Ala Ser Ser Asn Met His Glu Ala Glu Glu Trp
                245                 250                 255

Tyr Arg Ser Lys Phe Ala Asp Leu Thr Asp Ala Ala Ala Arg Asn Ala
            260                 265                 270

Glu Leu Leu Arg Gln Ala Lys His Glu Ala Asn Asp Tyr Arg Arg Gln
        275                 280                 285

Leu Gln Ser Leu Thr Cys Asp Leu Glu Ser Leu Arg Gly Thr Asn Glu
    290                 295                 300

Ser Leu Glu Arg Gln Met Arg Glu Gln Glu Glu Arg His Val Arg Glu
305                 310                 315                 320

Ala Ala Ser Tyr Gln Glu Ala Leu Ala Arg Leu Glu Glu Glu Gly Gln
                325                 330                 335

Ser Leu Lys Asp Glu Met Ala Arg His Leu Gln Glu Tyr Gln Asp Leu
            340                 345                 350

Leu Asn Val Lys Leu Ala Leu Asp Ile Glu Ile Ala Thr Tyr Arg Lys
        355                 360                 365

Leu Leu Glu Gly Glu Glu Asn Arg Ile Thr Ile Pro Val Gln Thr Phe
    370                 375                 380

Ser Asn Leu Gln Ile Arg Glu Thr Ser Leu Asp Thr Lys Ser Val Ser
385                 390                 395                 400

Glu Gly His Leu Lys Arg Asn Ile Val Val Lys Thr Val Glu Met Arg
                405                 410                 415

Asp Gly Glu Val Ile Lys Glu Ser Lys Gln Glu His Lys Asp Val Met
            420                 425                 430
```

<210> SEQ ID NO 46
<211> LENGTH: 3097
<212> TYPE: DNA
<213> ORGANISM: Homo sapiens

<400> SEQUENCE: 46

```
atcgccagtc tagcccactc cttcataaag ccctcgcatc ccaggagcga gcagagccag     60

agcaggatgg agaggagacg catcacctcc gctgctcgcc gctcctacgt ctcctcaggg    120

gagatgatgg tgggggcct ggctcctggc cgccgtctgg gtcctggcac ccgcctctcc    180

ctggctcgaa tgccccctcc actcccgacc cgggtggatt tctccctggc tggggcactc    240

aatgctggct tcaaggagac ccgggccagt gagcgggcag agatgatgga gctcaatgac    300

cgctttgcca gctacatcga gaaggttcgc ttcctggaac agcaaaacaa ggcgctggct    360

gctgagctga accagctgcg ggccaaggag cccaccaagc tggcagacgt ctaccaggct    420

gagctgcgag agctgcggct gcggctcgat caactcaccg ccaacagcgc ccggctggag    480

gttgagaggg acaatctggc acaggacctg gccactgtga ggcagaagct ccaggatgaa    540

accaacctga ggctggaagc cgagaacaac ctggctgcct atagacagga agcagatgaa    600

gccaccctgg cccgtctgga tctggagagg aagattgagt cgctggagga ggagatccgg    660

ttcttgagga agatccacga ggaggaggtt cgggaactcc aggagcagct ggcccgacag    720

caggtccatg tggagcttga cgtggccaag ccagacctca ccgcagccct gaaagagatc    780
```

```
cgcacgcagt atgaggcaat ggcgtccagc aacatgcatg aagccgaaga gtggtaccgc    840
tccaagtttg cagacctgac agacgctgct gcccgcaacg cggagctgct ccgccaggcc    900
aagcacgaag ccaacgacta ccggcgccag ttgcagtcct tgacctgcga cctggagtct    960
ctgcgcggca cgaacgagtc cctggagagg cagatgcgcg agcaggagga gcggcacgtg   1020
cgggaggcgg ccagttatca ggaggcgctg gcgcggctgg aggaagaggg gcagagcctc   1080
aaggacgaga tggcccgcca cttgcaggag taccaggacc tgctcaatgt caagctggcc   1140
ctggacatcg agatcgccac ctacaggaag ctgctagagg gcgaggagaa ccggatcacc   1200
attcccgtgc agaccttctc caacctgcag attcgagaaa ccagcctgga caccaagtct   1260
gtgtcagaag gccacctcaa gaggaacatc gtggtgaaga ccgtggagat gcgggatgga   1320
gaggtcatta aggagtccaa gcaggagcac aaggatgtga tgtgaggcag gacccacctg   1380
gtggcctctg ccccgtctca tgaggggccc gagcagaagc aggatagttg ctccgcctct   1440
gctggcacat ttccccagac ctgagctccc caccacccca gctgctcccc tccctcctct   1500
gtccctaggt cagcttgctg ccctaggctc cgtcagtatc aggcctgcca gacggcaccc   1560
acccagcacc cagcaactcc aactaacaag aaactcaccc ccaaggggca gtctggaggg   1620
gcatggccag cagcttgcgt tagaatgagg aggaaggaga gaaggggagg agggcggggg   1680
gcacctacta catcgccctc cacatccctg attcctgttg ttatggaaac tgttgccaga   1740
gatggaggtt ctctcggagt atctgggaac tgtgcctttg agtttcctca ggctgctgga   1800
ggaaaactga gactcagaca ggaaagggaa ggccccacag acaaggtagc cctggccaga   1860
ggcttgtttt gtcttttggt ttttatgagg tgggatatcc ctatgctgcc taggctgacc   1920
ttgaactcct gggctcaagc agtctaccca cctcagcctc ctgtgtagct gggattatag   1980
attggagcca ccatgcccag ctcagagggt tgttctccta gactgaccct gatcagtcta   2040
agatgggtgg ggacgtcctg ccacctgggg cagtcacctg cccagatccc agaaggacct   2100
cctgagcgat gactcaagtg tctcagtcca cctgagctgc catccaggga tgccatctgt   2160
gggcacgctg tgggcaggtg ggagcttgat tctcagcact tgggggatct gttgtgtacg   2220
tggagaggga tgaggtgctg ggagggatag aggggggctg cctggccccc agctgtgggt   2280
acagagaggt caagcccagg aggactgccc cgtgcagact ggaggggacg ctggtagaga   2340
tggaggagga ggcaattggg atggcgctag gcatacaagt aggggttgtg ggtgaccagt   2400
tgcacttggc ctctggattg tgggaattaa ggaagtgact catcctcttg aagatgctga   2460
aacaggagag aaaggggatg tatccatggg ggcagggcat gactttgtcc catttctaaa   2520
ggcctcttcc ttgctgtgtc ataccaggcc gccccagcct ctgagcccct gggactgctg   2580
cttcttaacc ccagtaagcc actgccacac gtctgaccct ctccacccca tagtgaccgg   2640
ctgcttttcc ctaagccaag ggcctcttgc ggtcccttct tactcacaca caaaatgtac   2700
ccagtattct aggtagtgcc ctattttaca attgtaaaac tgaggcacga gcaaagtgaa   2760
gacactggct catattcctg cagcctggag gccgggtgct cagggctgac acgtccaccc   2820
cagtgcaccc actctgcttt gactgagcag actggtgagc agactggtgg gatctgtgcc   2880
cagagatggg actgggaggg cccacttcag ggttctcctc tcccctctaa ggccgaagaa   2940
gggtccttcc ctctccccaa gacttggtgt cctttccctc cactccttcc tgccacctgc   3000
tgctgctgct gctgctaatc ttcagggcac tgctgctgcc tttagtcgct gaggaaaaat   3060
aaagacaaat gctgcgccct tccccaaaaa aaaaaaa                            3097
```

<210> SEQ ID NO 47
<211> LENGTH: 92
<212> TYPE: PRT
<213> ORGANISM: Homo sapiens

<400> SEQUENCE: 47

Met Ser Glu Leu Glu Lys Ala Met Val Ala Leu Ile Asp Val Phe His
1               5                   10                  15

Gln Tyr Ser Gly Arg Glu Gly Asp Lys His Lys Leu Lys Lys Ser Glu
            20                  25                  30

Leu Lys Glu Leu Ile Asn Asn Glu Leu Ser His Phe Leu Glu Glu Ile
        35                  40                  45

Lys Glu Gln Glu Val Val Asp Lys Val Met Glu Thr Leu Asp Asn Asp
    50                  55                  60

Gly Asp Gly Glu Cys Asp Phe Gln Glu Phe Met Ala Phe Val Ala Met
65                  70                  75                  80

Val Thr Thr Ala Cys His Glu Phe Phe Glu His Glu
                85                  90

<210> SEQ ID NO 48
<211> LENGTH: 1135
<212> TYPE: DNA
<213> ORGANISM: Homo sapiens

<400> SEQUENCE: 48
gggcagaggg aataagaggc tgcctctgcc caccagtcct gccgcccagg acccgcagca 60
gagacgacgc ctgcagcaag gagaccagga aggggtgaga caaggaagag gatgtctgag 120
ctggagaagg ccatggtggc cctcatcgac gttttccacc aatattctgg aagggaggga 180
gacaagcaca agctgaagaa atccgaactg aaggagctca tcaacaatga gctttcccat 240
ttcttagagg aaatcaaaga gcaggaggtt gtggacaaag tcatggaaac actggacaat 300
gatggagacg gcgaatgtga cttccaggaa ttcatggcct ttgttgccat ggttactact 360
gcctgccacg agttctttga acatgagtga gattagaaag cagccaaacc tttcctgtaa 420
cagagacggt catgcaagaa agcagacagc aagggcttgc agcctagtag gagctgagct 480
ttccagccgt gttgtagcta attaggaagc ttgatttgct ttgtgattga aaaattgaaa 540
acctctttcc aaaggctgtt ttaacggcct gcatcattct ttctgctata ttaggcctgt 600
gtgtaagctg actggcccca gggactcttg ttaacagtaa cttaggagtc aggtctcagt 660
gataaagcgt gcaccgtgca gcccgccatg gccgtgtaga ccctaacccg gagggaaccc 720
tgactacaga aattaccccg gggcaccctt aaaacttcca ctacctttaa aaaacaaagc 780
cttatccagc attatttgaa aacactgctg ttctttaaat gcgttcctca tccatgcaga 840
taacagctgg ttggccggtg tggccctgca agggcgtggt ggcttcggcc tgcttcccgg 900
gatgcgcctg atcaccaggt gaacgctcag cgctggcagc gctcctggaa aaagcaactc 960
catcagaact cgcaatccga gccagctctg ggggctccag cgtggcctcc gtgacccatg 1020
cgattcaagt cgcggctgca ggatccttgc ctccaacgtg cctccagcac atgcggcttc 1080
cgagggcact accgggggct ctgagccacc gcgagggcct gcgttcaata aaaag 1135

<210> SEQ ID NO 49
<211> LENGTH: 422
<212> TYPE: PRT
<213> ORGANISM: Homo sapiens

<400> SEQUENCE: 49

```
Met Gln Asn Ser His Ser Gly Val Asn Gln Leu Gly Gly Val Phe Val
1               5                   10                  15

Asn Gly Arg Pro Leu Pro Asp Ser Thr Arg Gln Lys Ile Val Glu Leu
            20                  25                  30

Ala His Ser Gly Ala Arg Pro Cys Asp Ile Ser Arg Ile Leu Gln Val
        35                  40                  45

Ser Asn Gly Cys Val Ser Lys Ile Leu Gly Arg Tyr Tyr Glu Thr Gly
    50                  55                  60

Ser Ile Arg Pro Arg Ala Ile Gly Gly Ser Lys Pro Arg Val Ala Thr
65                  70                  75                  80

Pro Glu Val Val Ser Lys Ile Ala Gln Tyr Lys Arg Glu Cys Pro Ser
                85                  90                  95

Ile Phe Ala Trp Glu Ile Arg Asp Arg Leu Leu Ser Glu Gly Val Cys
            100                 105                 110

Thr Asn Asp Asn Ile Pro Ser Val Ser Ser Ile Asn Arg Val Leu Arg
        115                 120                 125

Asn Leu Ala Ser Glu Lys Gln Gln Met Gly Ala Asp Gly Met Tyr Asp
    130                 135                 140

Lys Leu Arg Met Leu Asn Gly Gln Thr Gly Ser Trp Gly Thr Arg Pro
145                 150                 155                 160

Gly Trp Tyr Pro Gly Thr Ser Val Pro Gly Gln Pro Thr Gln Asp Gly
                165                 170                 175

Cys Gln Gln Gln Glu Gly Gly Gly Glu Asn Thr Asn Ser Ile Ser Ser
            180                 185                 190

Asn Gly Glu Asp Ser Asp Glu Ala Gln Met Arg Leu Gln Leu Lys Arg
        195                 200                 205

Lys Leu Gln Arg Asn Arg Thr Ser Phe Thr Gln Glu Gln Ile Glu Ala
    210                 215                 220

Leu Glu Lys Glu Phe Glu Arg Thr His Tyr Pro Asp Val Phe Ala Arg
225                 230                 235                 240

Glu Arg Leu Ala Ala Lys Ile Asp Leu Pro Glu Ala Arg Ile Gln Val
                245                 250                 255

Trp Phe Ser Asn Arg Arg Ala Lys Trp Arg Arg Glu Glu Lys Leu Arg
            260                 265                 270

Asn Gln Arg Arg Gln Ala Ser Asn Thr Pro Ser His Ile Pro Ile Ser
        275                 280                 285

Ser Ser Phe Ser Thr Ser Val Tyr Gln Pro Ile Pro Gln Pro Thr Thr
    290                 295                 300

Pro Val Ser Ser Phe Thr Ser Gly Ser Met Leu Gly Arg Thr Asp Thr
305                 310                 315                 320

Ala Leu Thr Asn Thr Tyr Ser Ala Leu Pro Pro Met Pro Ser Phe Thr
                325                 330                 335

Met Ala Asn Asn Leu Pro Met Gln Pro Pro Val Pro Ser Gln Thr Ser
            340                 345                 350

Ser Tyr Ser Cys Met Leu Pro Thr Ser Pro Ser Val Asn Gly Arg Ser
        355                 360                 365

Tyr Asp Thr Tyr Thr Pro Pro His Met Gln Thr His Met Asn Ser Gln
    370                 375                 380

Pro Met Gly Thr Ser Gly Thr Thr Ser Thr Gly Leu Ile Ser Pro Gly
385                 390                 395                 400
```

Val Ser Val Pro Val Gln Val Pro Gly Ser Glu Pro Asp Met Ser Gln
405 410 415

Tyr Trp Pro Arg Leu Gln
420

<210> SEQ ID NO 50
<211> LENGTH: 1399
<212> TYPE: DNA
<213> ORGANISM: Homo sapiens

<400> SEQUENCE: 50
agggggaaga ctttaactag gggcgcgcag atgtgtgagg ccttttattg tgagagtgga 60
cagacatccg agatttcaga gccccatatt cgagccccgt ggaatcccgc ggcccccagc 120
cagagccagc atgcagaaca gtcacagcgg agtgaatcag ctcggtggtg tctttgtcaa 180
cgggcggcca ctgccggact ccacccggca gaagattgta gagctagctc acagcggggc 240
ccggccgtgc gacatttccc gaattctgca ggtgtccaac ggatgtgtga gtaaaattct 300
gggcaggtat tacgagactg gctccatcag acccagggca atcggtggta gtaaaccgag 360
agtagcgact ccagaagttg taagcaaaat agcccagtat aagcgggagt gcccgtccat 420
ctttgcttgg gaaatccgag acagattact gtccgagggg gtctgtacca acgataacat 480
accaagcgtg tcatcaataa acagagttct tcgcaacctg gctagcgaaa agcaacagat 540
gggcgcagac ggcatgtatg ataaactaag gatgttgaac gggcagaccg gaagctgggg 600
cacccgccct ggttggtatc cggggacttc ggtgccaggg caacctacgc aagatggctg 660
ccagcaacag gaaggagggg gagagaatac caactccatc agttccaacg gagaagattc 720
agatgaggct caaatgcgac ttcagctgaa gcggaagctg caaagaaata gaacatcctt 780
tacccaagag caaattgagg ccctggagaa agagtttgag agaacccatt atccagatgt 840
gtttgcccga gaaagactag cagccaaaat agatctacct gaagcaagaa tacaggtatg 900
gttttctaat cgaagggcca aatggagaag agaagaaaaa ctgaggaatc agagaagaca 960
ggccagcaac acacctagtc atattcctat cagcagtagt ttcagcacca gtgtctacca 1020
accaattcca caacccacca caccggtttc ctccttcaca tctggctcca tgttgggccg 1080
aacagacaca gccctcacaa acacctacag cgctctgccg cctatgccca gcttcaccat 1140
ggcaaataac ctgcctatgc aacccccagt ccccagccag acctcctcat actcctgcat 1200
gctgcccacc agcccttcgg tgaatgggcg gagttatgat acctacaccc ccccacatat 1260
gcagacacac atgaacagtc agccaatggg cacctcgggc accacttcaa caggactcat 1320
ttcccctggt gtgtcagttc cagttcaagt tcccggaagt gaacctgata tgtctcaata 1380
ctggccaaga ttacagtaa 1399

<210> SEQ ID NO 51
<211> LENGTH: 1621
<212> TYPE: PRT
<213> ORGANISM: Homo sapiens

<400> SEQUENCE: 51

Met Glu Gly Cys Met Gly Glu Glu Ser Phe Gln Met Trp Glu Leu Asn
1 5 10 15

Arg Arg Leu Glu Ala Tyr Leu Ala Arg Val Lys Ala Leu Glu Glu Gln
20 25 30

Asn Glu Leu Leu Ser Ala Glu Leu Gly Gly Leu Arg Ala Gln Ser Ala
35 40 45

-continued

```
Asp Thr Ser Trp Arg Ala His Ala Asp Asp Glu Leu Ala Ala Leu Arg
    50                  55                  60

Ala Leu Val Asp Gln Arg Trp Arg Glu Lys His Ala Ala Glu Val Ala
65                  70                  75                  80

Arg Asp Asn Leu Ala Glu Glu Leu Glu Gly Val Ala Gly Arg Cys Gln
                85                  90                  95

Gln Leu Arg Leu Ala Arg Glu Arg Thr Thr Glu Glu Val Ala Arg Asn
            100                 105                 110

Arg Arg Ala Val Glu Ala Glu Lys Cys Ala Arg Ala Trp Leu Ser Ser
        115                 120                 125

Gln Val Ala Glu Leu Glu Arg Glu Leu Glu Ala Leu Arg Val Ala His
    130                 135                 140

Glu Glu Glu Arg Val Gly Leu Asn Ala Gln Ala Ala Cys Ala Pro Arg
145                 150                 155                 160

Cys Pro Ala Pro Pro Arg Gly Pro Pro Ala Pro Ala Pro Glu Val Glu
                165                 170                 175

Glu Leu Ala Arg Arg Leu Gly Glu Ala Trp Arg Gly Ala Val Arg Gly
            180                 185                 190

Tyr Gln Glu Arg Val Ala His Met Glu Thr Ser Leu Gly Gln Ala Arg
        195                 200                 205

Glu Arg Leu Gly Arg Ala Val Gln Gly Ala Arg Glu Gly Arg Leu Glu
    210                 215                 220

Leu Gln Gln Leu Gln Ala Glu Arg Gly Gly Leu Leu Glu Arg Arg Ala
225                 230                 235                 240

Ala Leu Glu Gln Arg Leu Glu Gly Arg Trp Gln Glu Arg Leu Arg Ala
                245                 250                 255

Thr Glu Lys Phe Gln Leu Ala Val Glu Ala Leu Glu Gln Glu Lys Gln
            260                 265                 270

Gly Leu Gln Ser Gln Ile Ala Gln Val Leu Glu Gly Arg Gln Gln Leu
        275                 280                 285

Ala His Leu Lys Met Ser Leu Ser Leu Glu Val Ala Thr Tyr Arg Thr
    290                 295                 300

Leu Leu Glu Ala Glu Asn Ser Arg Leu Gln Thr Pro Gly Gly Gly Ser
305                 310                 315                 320

Lys Thr Ser Leu Ser Phe Gln Asp Pro Lys Leu Glu Leu Gln Phe Pro
                325                 330                 335

Arg Thr Pro Glu Gly Arg Arg Leu Gly Ser Leu Leu Pro Val Leu Ser
            340                 345                 350

Pro Thr Ser Leu Pro Ser Pro Leu Pro Ala Thr Leu Glu Thr Pro Val
        355                 360                 365

Pro Ala Phe Leu Lys Asn Gln Glu Phe Leu Gln Ala Arg Thr Pro Thr
    370                 375                 380

Leu Ala Ser Thr Pro Ile Pro Pro Thr Pro Gln Ala Pro Ser Pro Ala
385                 390                 395                 400

Val Asp Ala Glu Ile Arg Ala Gln Asp Ala Pro Leu Ser Leu Leu Gln
                405                 410                 415

Thr Gln Gly Gly Arg Lys Gln Ala Pro Glu Pro Leu Arg Ala Glu Ala
            420                 425                 430

Arg Val Ala Ile Pro Ala Ser Val Leu Pro Gly Pro Glu Glu Pro Gly
        435                 440                 445

Gly Gln Arg Gln Glu Ala Ser Thr Gly Gln Ser Pro Glu Asp His Ala
    450                 455                 460
```

-continued

```
Ser Leu Ala Pro Pro Leu Ser Pro Asp His Ser Ser Leu Glu Ala Lys
465                 470                 475                 480

Asp Gly Glu Ser Gly Gly Ser Arg Val Phe Ser Ile Cys Arg Gly Glu
                485                 490                 495

Gly Glu Gly Gln Ile Trp Gly Leu Val Glu Lys Glu Thr Ala Ile Glu
            500                 505                 510

Gly Lys Val Val Ser Ser Leu Gln Gln Glu Ile Trp Glu Glu Glu Asp
        515                 520                 525

Leu Asn Arg Lys Glu Ile Gln Asp Ser Gln Val Pro Leu Glu Lys Glu
    530                 535                 540

Thr Leu Lys Ser Leu Gly Glu Glu Ile Gln Glu Ser Leu Lys Thr Leu
545                 550                 555                 560

Glu Asn Gln Ser His Glu Thr Leu Glu Arg Glu Asn Gln Glu Cys Pro
                565                 570                 575

Arg Ser Leu Glu Glu Asp Leu Glu Thr Leu Lys Ser Leu Glu Lys Glu
            580                 585                 590

Asn Lys Glu Leu Leu Lys Asp Val Glu Val Val Arg Pro Leu Glu Lys
        595                 600                 605

Glu Ala Val Gly Gln Leu Lys Pro Thr Gly Lys Glu Asp Thr Gln Thr
    610                 615                 620

Leu Gln Ser Leu Gln Lys Glu Asn Gln Glu Leu Met Lys Ser Leu Glu
625                 630                 635                 640

Gly Asn Leu Glu Thr Phe Leu Phe Pro Gly Thr Glu Asn Gln Glu Leu
                645                 650                 655

Val Ser Ser Leu Gln Glu Asn Leu Glu Ser Leu Thr Ala Leu Glu Lys
            660                 665                 670

Glu Asn Gln Glu Pro Leu Arg Ser Pro Glu Val Gly Asp Glu Glu Ala
        675                 680                 685

Leu Arg Pro Leu Thr Lys Glu Asn Gln Glu Pro Leu Arg Ser Leu Glu
    690                 695                 700

Asp Glu Asn Lys Glu Ala Phe Arg Ser Leu Glu Lys Glu Asn Gln Glu
705                 710                 715                 720

Pro Leu Lys Thr Leu Glu Glu Glu Asp Gln Ser Ile Val Arg Pro Leu
                725                 730                 735

Glu Thr Glu Asn His Lys Ser Leu Arg Ser Leu Glu Glu Gln Asp Gln
            740                 745                 750

Glu Thr Leu Arg Thr Leu Glu Lys Glu Thr Gln Gln Arg Arg Arg Ser
        755                 760                 765

Leu Gly Glu Gln Asp Gln Met Thr Leu Arg Pro Pro Glu Lys Val Asp
    770                 775                 780

Leu Glu Pro Leu Lys Ser Leu Asp Gln Glu Ile Ala Arg Pro Leu Glu
785                 790                 795                 800

Asn Glu Asn Gln Glu Phe Leu Lys Ser Leu Lys Glu Glu Ser Val Glu
                805                 810                 815

Ala Val Lys Ser Leu Glu Thr Glu Ile Leu Glu Ser Leu Lys Ser Ala
            820                 825                 830

Gly Gln Glu Asn Leu Glu Thr Leu Lys Ser Pro Glu Thr Gln Ala Pro
        835                 840                 845

Leu Trp Thr Pro Glu Glu Ile Asn Gln Gly Ala Met Asn Pro Leu Glu
    850                 855                 860

Lys Glu Ile Gln Glu Pro Leu Glu Ser Val Glu Val Asn Gln Glu Thr
865                 870                 875                 880
```

-continued

```
Phe Arg Leu Leu Glu Glu Glu Asn Gln Glu Ser Leu Arg Ser Leu Gly
                885                 890                 895

Ala Trp Asn Leu Glu Asn Leu Arg Ser Pro Glu Glu Val Asp Lys Glu
            900                 905                 910

Ser Gln Arg Asn Leu Glu Glu Glu Glu Asn Leu Gly Lys Gly Glu Tyr
        915                 920                 925

Gln Glu Ser Leu Arg Ser Leu Glu Glu Glu Gly Gln Glu Leu Pro Gln
    930                 935                 940

Ser Ala Asp Val Gln Arg Trp Glu Asp Thr Val Glu Lys Asp Gln Glu
945                 950                 955                 960

Leu Ala Gln Glu Ser Pro Pro Gly Met Ala Gly Val Glu Asn Glu Asp
                965                 970                 975

Glu Ala Glu Leu Asn Leu Arg Glu Gln Asp Gly Phe Thr Gly Lys Glu
            980                 985                 990

Glu Val Val Glu Gln Gly Glu Leu  Asn Ala Thr Glu Glu  Val Trp Ile
        995                 1000                1005

Pro Gly  Glu Gly His Pro Glu  Ser Pro Glu Pro Lys  Glu Gln Arg
    1010                1015                1020

Gly Leu  Val Glu Gly Ala Ser  Val Lys Gly Gly Ala  Glu Gly Leu
    1025                1030                1035

Gln Asp  Pro Glu Gly Gln Ser  Gln Gln Val Gly Ala  Pro Gly Leu
    1040                1045                1050

Gln Ala  Pro Gln Gly Leu Pro  Glu Ala Ile Glu Pro  Leu Val Glu
    1055                1060                1065

Asp Asp  Val Ala Pro Gly Gly  Asp Gln Ala Ser Pro  Glu Val Met
    1070                1075                1080

Leu Gly  Ser Glu Pro Ala Met  Gly Glu Ser Ala Ala  Gly Ala Glu
    1085                1090                1095

Pro Gly  Pro Gly Gln Gly Val  Gly Gly Leu Gly Asp  Pro Gly His
    1100                1105                1110

Leu Thr  Arg Glu Glu Val Met  Glu Pro Pro Leu Glu  Glu Glu Ser
    1115                1120                1125

Leu Glu  Ala Lys Arg Val Gln  Gly Leu Glu Gly Pro  Arg Lys Asp
    1130                1135                1140

Leu Glu  Glu Ala Gly Gly Leu  Gly Thr Glu Phe Ser  Glu Leu Pro
    1145                1150                1155

Gly Lys  Ser Arg Asp Pro Trp  Glu Pro Pro Arg Glu  Gly Arg Glu
    1160                1165                1170

Glu Ser  Glu Ala Glu Ala Pro  Arg Gly Ala Glu Glu  Ala Phe Pro
    1175                1180                1185

Ala Glu  Thr Leu Gly His Thr  Gly Ser Asp Ala Pro  Ser Pro Trp
    1190                1195                1200

Pro Leu  Gly Ser Glu Glu Ala  Glu Glu Asp Val Pro  Pro Val Leu
    1205                1210                1215

Val Ser  Pro Ser Pro Thr Tyr  Thr Pro Ile Leu Glu  Asp Ala Pro
    1220                1225                1230

Gly Pro  Gln Pro Gln Ala Glu  Gly Ser Gln Glu Ala  Ser Trp Gly
    1235                1240                1245

Val Gln  Gly Arg Ala Glu Ala  Leu Gly Lys Val Glu  Ser Glu Gln
    1250                1255                1260

Glu Glu  Leu Gly Ser Gly Glu  Ile Pro Glu Gly Pro  Gln Glu Glu
    1265                1270                1275
```

```
Gly Glu  Glu Ser Arg Glu Glu  Ser Glu Glu Asp Glu  Leu Gly Glu
    1280                 1285                 1290

Thr Leu  Pro Asp Ser Thr Pro  Leu Gly Phe Tyr Leu  Arg Ser Pro
    1295                 1300                 1305

Thr Ser  Pro Arg Trp Asp Pro  Thr Gly Glu Gln Arg  Pro Pro Pro
    1310                 1315                 1320

Gln Gly  Glu Thr Gly Lys Glu  Gly Trp Asp Pro Ala  Val Leu Ala
    1325                 1330                 1335

Ser Glu  Gly Leu Glu Ala Pro  Pro Ser Glu Lys Glu  Glu Gly Glu
    1340                 1345                 1350

Glu Gly  Glu Glu Glu Cys Gly  Arg Asp Ser Asp Leu  Ser Glu Glu
    1355                 1360                 1365

Phe Glu  Asp Leu Gly Thr Glu  Ala Pro Phe Leu Pro  Gly Val Pro
    1370                 1375                 1380

Gly Glu  Val Ala Glu Pro Leu  Gly Gln Val Pro Gln  Leu Leu Leu
    1385                 1390                 1395

Asp Pro  Ala Ala Trp Asp Arg  Asp Gly Glu Ser Asp  Gly Phe Ala
    1400                 1405                 1410

Asp Glu  Glu Glu Ser Gly Glu  Glu Gly Glu Glu Asp  Gln Glu Glu
    1415                 1420                 1425

Gly Arg  Glu Pro Gly Ala Gly  Arg Trp Gly Pro Gly  Ser Ser Val
    1430                 1435                 1440

Gly Ser  Leu Gln Ala Leu Ser  Ser Ser Gln Arg Gly  Glu Phe Leu
    1445                 1450                 1455

Glu Ser  Asp Ser Val Ser Val  Ser Val Pro Trp Asp  Asp Ser Leu
    1460                 1465                 1470

Arg Gly  Ala Val Ala Gly Ala  Pro Lys Thr Ala Leu  Glu Thr Glu
    1475                 1480                 1485

Ser Gln  Asp Ser Ala Glu Pro  Ser Gly Ser Glu Glu  Glu Ser Asp
    1490                 1495                 1500

Pro Val  Ser Leu Glu Arg Glu  Asp Lys Val Pro Gly  Pro Leu Glu
    1505                 1510                 1515

Ile Pro  Ser Gly Met Glu Asp  Ala Gly Pro Gly Ala  Asp Ile Ile
    1520                 1525                 1530

Gly Val  Asn Gly Gln Gly Pro  Asn Leu Glu Gly Lys  Ser Gln His
    1535                 1540                 1545

Val Asn  Gly Gly Val Met Asn  Gly Leu Glu Gln Ser  Glu Glu Val
    1550                 1555                 1560

Gly Gln  Gly Met Pro Leu Val  Ser Glu Gly Asp Arg  Gly Ser Pro
    1565                 1570                 1575

Phe Gln  Glu Glu Glu Gly Ser  Ala Leu Lys Thr Ser  Trp Ala Gly
    1580                 1585                 1590

Ala Pro  Val His Leu Gly Gln  Gly Gln Phe Leu Lys  Phe Thr Gln
    1595                 1600                 1605

Arg Glu  Gly Asp Arg Glu Ser  Trp Ser Ser Gly Glu  Asp
    1610                 1615                 1620
```

<210> SEQ ID NO 52
<211> LENGTH: 5591
<212> TYPE: DNA
<213> ORGANISM: Homo sapiens

<400> SEQUENCE: 52
gctactccca ccccgccccg ccccgtcatt gtccccgtcg gtctcttttc tcttccgtcc 60
taaaagctct gcgagccgct cccttctccc ggtgccccgc gtctgtccat cctcagtggg 120
tcagacgagc aggatggagg gctgcatggg ggaggagtcg tttcagatgt gggagctcaa 180
tcggcgcctg gaggcctacc tggcccgggt caaggcgctg gaggagcaga atgagctgct 240
cagcgcggag ctcggggggc tccgggcaca atccgcggac acctcctggc gggcgcatgc 300
cgacgacgag ctggcggccc tgcgggccct cgttgaccaa cgctggcggg agaagcacgc 360
ggccgaggtg gcgcgcgaca acctggctga agagctggag ggcgtggcag gccgatgcca 420
gcagctgcgg ctggcccggg agcggacgac ggaggaggta gcccgcaacc ggcgcgccgt 480
cgaggcagag aaatgcgccc gggcctggct gagtagccag gtggcagagc tggagcgcga 540
gctagaggct ctacgcgtgg cgcacgagga ggagcgcgtc ggcctgaacg cgcaggctgc 600
ctgtgccccc cgctgccccg cgccgccccg cgggcctccc gcgccggccc cggaggtaga 660
ggagctggca aggcgactgg gcgaggcgtg gcgcggggca gtgcgcggct accaggagcg 720
cgtggcacac atggagacgt cgctgggcca ggcccgcgag cggctgggcc gggcggtgca 780
gggtgcccgc gagggccgcc tggagctgca gcagctccag gctgagcgcg gaggcctcct 840
ggagcgcagg gcagcgttgg aacagaggtt ggagggccgc tggcaggagc ggctgcgggc 900
tactgaaaag ttccagctgg ctgtggaggc cctggagcag gagaaacagg gcctacagag 960
ccagatcgct caggtcctgg aaggtcggca gcagctggcg cacctcaaga tgtccctcag 1020
cctggaggtg gccacgtaca ggaccctcct ggaggctgag aactcccggc tgcaaacacc 1080
tggcggtggc tccaagactt ccctcagctt tcaggacccc aagctggagc tgcaattccc 1140
taggacccca gagggccggc gtcttggatc tttgctccca gtcctgagcc caacttccct 1200
cccctcaccc ttgcctgcta cccttgagac acctgtgcca gcctttctta agaaccaaga 1260
attcctccag gcccgtaccc ctaccttggc cagcaccccc atcccccccca cacctcaggc 1320 accctctcct gctgtagatg cagagatcag agcccaggat gctcctctct ctctgctcca 1380
gacacagggt gggaggaaac aggctccaga gcccctgcgg gctgaagcca gggtggccat 1440
tcctgccagc gtcctgcctg gaccagagga gcctgggggc cagcggcaag aggccagtac 1500
aggccagtcc ccagaggacc atgcctcctt ggcaccaccc ctcagccctg accactccag 1560
tttagaggct aaggatggag aatccggtgg gtctagagtg ttcagcatat gccgagggga 1620
aggtgaaggg caaatctggg ggttggtaga gaaagaaaca gccatagagg gcaaagtggt 1680
aagcagcttg cagcaggaaa tatgggaaga agaggatcta aacaggaagg aaatccagga 1740
ctcccaggtt cctttggaaa aagaaaccct gaagtctctg ggagaggaga ttcaagagtc 1800
actgaagact ctggaaaacc agagccatga gacactagaa agggagaatc aagaatgtcc 1860
gaggtcttta gaagaagact tagaaacact aaaaagtcta gaaaaggaaa ataaagagct 1920
attaaaggat gtggaggtag tgagacctct agaaaaagag gctgtaggcc aacttaagcc 1980
tacaggaaaa gaggacacac agacattgca atccctgcaa aaggagaatc aagaactaat 2040
gaaatctctt gaaggtaatc tagagacatt tttatttcca ggaacggaaa atcaagaatt 2100
agtaagttct ctgcaagaga acttagagtc attgacagct ctggaaaagg agaatcaaga 2160
gccactgaga tctccagaag taggggatga ggaggcactg agacctctga caaaggagaa 2220
tcaggaaccc ctgaggtctc ttgaagatga gaacaaagag gcctttagat ctctagaaaa 2280
agagaaccag gagccactga agactctaga agaagaggac cagagtattg tgagacctct 2340
agaaacagag aatcacaaat cactgaggtc tttagaagaa caggaccaag agacattgag 2400
aactcttgaa aaagagactc aacagcgacg gaggtctcta ggggaacagg atcagatgac 2460
attaagaccc ccagaaaaag tggatctaga accactgaag tctcttgacc aggagatagc 2520
tagacctctt gaaaatgaga atcaagagtt cttaaagtca ctcaaagaag agagcgtaga 2580
ggcagtaaaa tctttagaaa cagagatcct agaatcactg aagtctgcgg gacaagagaa 2640
cctggaaaca ctgaaatctc cagaaactca agcaccactg tggactccag aagaaataaa 2700
tcagggggca atgaatcctc tagaaaagga aattcaagaa ccactggagt ctgtggaagt 2760
gaaccaagag acattcagac tcctggaaga ggagaatcag gaatcattga gatctctggg 2820
agcatggaac ctggagaatt tgagatctcc agaggaggta gacaaggaaa gtcaaaggaa 2880
tctggaagag gaagagaacc tgggaaaggg agagtaccaa gagtcactga ggtctctgga 2940
ggaggaggga caggagctgc cgcagtctgc agatgtgcag aggtgggaag atacggtgga 3000
gaaggaccaa gaactggctc aggaaagccc tcctgggatg gctggagtgg aaaatgagga 3060
tgaggcagag ctgaatctga gggagcagga tggcttcact gggaaggagg aggtggtaga 3120
gcagggagag ctgaatgcca cagaggaggt ctggatccca ggcgaggggc acccagagag 3180
ccctgagccc aaagagcaga gaggcctggt tgagggagcc agtgtgaagg gaggggctga 3240
gggcctccag gaccctgaag ggcaatcaca acaggtgggg gccccaggcc tccaggctcc 3300
ccaggggctg ccagaggcga tagagcccct ggtggaagat gatgtggccc caggggggtga 3360
ccaagcctcc ccagaggtca tgttggggtc agagcctgcc atgggtgagt ctgctgcggg 3420
agctgagcca ggcccggggc agggggtggg agggctgggg gacccaggcc atctgaccag 3480
ggaagaggtg atggaaccac ccctggaaga ggagagtttg gaggcaaaga gggttcaggg 3540
cttggaaggg cctagaaagg acctagagga ggcaggtggt ctggggacag agttctccga 3600
gctgcctggg aagagcagag acccttggga gcctcccagg gagggtaggg aggagtcaga 3660
ggctgaggcc cccaggggag cagaggaggc gttccctgct gagaccctgg gccacactgg 3720
aagtgatgcc ccttcacctt ggcctctggg gtcagaggaa gctgaggagg atgtaccacc 3780
agtgctggtc tcccccagcc caacgtacac cccgatcctg gaagatgccc ctgggcctca 3840
gcctcaggct gaagggagtc aggaggctag ctggggggtg caggggaggg ctgaagccct 3900
ggggaaagta gagagcgagc aggaggagtt gggttctggg gagatccccg agggccccca 3960
ggaggaaggg gaggagagca gagaagagag cgaggaggat gagctcgggg agacccttcc 4020
agactccact cccctgggct tctacctcag gtcccccacc tcccccaggt gggaccccac 4080
tggagagcag aggccacccc ctcaagggga gactggaaag gagggctggg atcctgctgt 4140
cctggcttcc gagggccttg aggccccacc ctcagaaaag gaggaggggg aggagggaga 4200
agaggagtgt ggccgtgact ctgacctgtc agaagaattt gaggacctgg ggactgaggc 4260
accttttctt cctggggtcc ctggggaggt ggcagaacct ctgggccagg tgccccagct 4320
gctactggat cctgcagcct gggatcgaga tggggagtcc gatgggtttg cagatgagga 4380
agaaagtggg gaggagggag aggaggatca ggaggagggg agggagccag gggctgggcg 4440
gtgggggcca gggtcttctg ttggcagcct ccaggccctg agtagctccc agagagggga 4500
attcctggag tctgattctg tgagtgtcag tgtcccctgg gatgacagct tgaggggtgc 4560
agtggctggt gcccccaaga ctgccctgga aacggagtcc caggacagtg ctgagccttc 4620
tggctcagag gaagagtctg accctgtttc cttggagagg gaggacaaag tccctggccc 4680
tctagagatc cccagtggga tggaggatgc aggcccaggg gcagacatca ttggtgttaa 4740

-continued

```
tggccagggt cccaacttgg aggggaagtc acagcatgtg aatgggggag tgatgaacgg   4800

gctggagcag tctgaggaag tggggcaagg aatgccgcta gtctctgagg gagaccgagg   4860

gagccccttt caggaggagg aggggagtgc tctgaagacc tcttgggcag gggctcctgt   4920

tcacctgggc cagggtcagt tcctgaagtt cactcagagg gaaggagata gagagtcctg   4980

gtcctcaggg gaggactagg aaaagaccat ctgcccggca ctggggactt aggggtgcgg   5040

ggaggggaag gacgcctcca agcccgctcc ctgctcagga gcagcactct taacttacga   5100

tctcttgaca tatggtttct ggctgagagg cctggcccgc taaggtgaaa aggggtgtgg   5160

caaaggagcc tactccaaga atggaggctg taggaatata acctcccacc ctgcaaaggg   5220

aatctcttgc ctgctccatc tcataggcta agtcagctga atcccgatag tactaggtcc   5280

ccttccctcc gcatcccgtc agctggaaaa ggcctgtggc ccagaggctt ctccaaaggg   5340

agggtgacat gctggctttt gtgcccaagc tcaccagccc tgcgccacct cactgcagta   5400

gtgcaccatc tcactgcagt agcacgccct cctgggccgt ctggcctgtg gctaatggag   5460

gtgacggcac tcccatgtgc tgactccccc catccctgcc acgctgtggc cctgcctggc   5520

tagtccctgc ctgaataaag taatgcctcc gcttcaaaaa aaaaaaaaaa aaaaaaaaaa   5580

aaaaaaaaaa a                                                        5591


<210> SEQ ID NO 53
<211> LENGTH: 348
<212> TYPE: PRT
<213> ORGANISM: Homo sapiens

<400> SEQUENCE: 53

Met Ala Gln Pro Gly Ser Gly Cys Lys Ala Thr Thr Arg Cys Leu Glu
1               5                   10                  15

Gly Thr Ala Pro Pro Ala Met Ala Gln Ser Asp Ala Glu Ala Leu Ala
            20                  25                  30

Gly Ala Leu Asp Lys Asp Glu Gly Gln Ala Ser Pro Cys Thr Pro Ser
        35                  40                  45

Thr Pro Ser Val Cys Ser Pro Pro Ser Ala Ala Ser Ser Val Pro Ser
    50                  55                  60

Ala Gly Lys Asn Ile Cys Ser Ser Cys Gly Leu Glu Ile Leu Asp Arg
65                  70                  75                  80

Tyr Leu Leu Lys Val Asn Asn Leu Ile Trp His Val Arg Cys Leu Glu
                85                  90                  95

Cys Ser Val Cys Arg Thr Ser Leu Arg Gln Gln Asn Ser Cys Tyr Ile
            100                 105                 110

Lys Asn Lys Glu Ile Phe Cys Lys Met Asp Tyr Phe Ser Arg Phe Gly
        115                 120                 125

Thr Lys Cys Ala Arg Cys Gly Arg Gln Ile Tyr Ala Ser Asp Trp Val
    130                 135                 140

Arg Arg Ala Arg Gly Asn Ala Tyr His Leu Ala Cys Phe Ala Cys Phe
145                 150                 155                 160

Ser Cys Lys Arg Gln Leu Ser Thr Gly Glu Glu Phe Gly Leu Val Glu
                165                 170                 175

Glu Lys Val Leu Cys Arg Ile His Tyr Asp Thr Met Ile Glu Asn Leu
            180                 185                 190

Lys Arg Ala Ala Glu Asn Gly Asn Gly Leu Thr Leu Glu Gly Ala Val
        195                 200                 205

Pro Ser Glu Gln Asp Ser Gln Pro Lys Pro Ala Lys Arg Ala Arg Thr
    210                 215                 220
```

-continued

```
Ser Phe Thr Ala Glu Gln Leu Gln Val Met Gln Ala Gln Phe Ala Gln
225                 230                 235                 240

Asp Asn Asn Pro Asp Ala Gln Thr Leu Gln Lys Leu Ala Asp Met Thr
                245                 250                 255

Gly Leu Ser Arg Arg Val Ile Gln Val Trp Phe Gln Asn Cys Arg Ala
            260                 265                 270

Arg His Lys Lys His Thr Pro Gln His Pro Val Pro Pro Ser Gly Ala
        275                 280                 285

Pro Pro Ser Arg Leu Pro Ser Ala Leu Ser Asp Asp Ile His Tyr Thr
    290                 295                 300

Pro Phe Ser Ser Pro Glu Arg Ala Arg Met Val Thr Leu His Gly Tyr
305                 310                 315                 320

Ile Glu Ser His Pro Phe Ser Val Leu Thr Leu Pro Ala Leu Pro His
                325                 330                 335

Leu Pro Val Gly Ala Pro Gln Leu Pro Leu Ser Arg
            340                 345
```

<210> SEQ ID NO 54
<211> LENGTH: 2835
<212> TYPE: DNA
<213> ORGANISM: Homo sapiens

<400> SEQUENCE: 54

```
cccgccaccg accaggtgat ggcccagcca gggtccggct gcaaagcgac cacccgctgt      60

cttgaaggga ccgcgccgcc cgccatggct cagtctgacg ccgaggccct ggcaggagct     120

ctggacaagg acgagggtca ggcctcccca tgtacgccca gcacgccatc tgtctgctca     180

ccgccctctg ccgcctcctc cgtgccgtct gcaggcaaga acatctgctc cagctgcggc     240

ctcgagatcc tggaccgata tctgctcaag gtcaacaacc tcatctggca cgtgcggtgc     300

ctcgagtgct ccgtgtgtcg cacgtcgctg aggcagcaga acagctgcta catcaagaac     360

aaggagatct tctgcaagat ggactacttc agccgattcg ggaccaagtg tgcccggtgc     420

ggccgacaga tctacgccag cgactgggtg cggagagctc gcggcaacgc ctaccacctg     480

gcctgcttcg cctgcttctc gtgcaagcgc cagctgtcca ctggtgagga gttcggcctg     540

gtcgaggaga aggtgctctg ccgcatccac tacgacacca tgattgagaa cctcaagagg     600

gccgccgaga acgggaacgg cctcacgttg gagggggcag tgccctcgga acaggacagt     660

caacccaagc cggccaagcg cgcgcggacg tccttcaccg cggaacagct gcaggttatg     720

caggcgcagt tcgcgcagga caacaacccc gacgctcaga cgctgcagaa gctggcggac     780

atgacgggcc tcagccggag agtcatccag gtgtggtttc aaaactgccg ggcgcgtcat     840

aaaaagcaca cgccgcaaca cccagtgccg ccctcggggg cgccccgtc ccgccttccc      900

tccgccctgt ccgacgacat ccactacacc ccgttcagca gccccgagcg ggcgcgcatg     960

gtcaccctgc acggctacat tgagagtcat ccttttcag tactaacgct gccggcactt     1020

ccgcatctgc ccgtgggcgc cccacagctg cccctcagcc gctgagatcc agtgtccaag    1080

ctgcggccag gagtccaccc acctccgcat ccaccccgt ccgccatcct gcccaccacc     1140

aggtcggttc ccgaggcctg gcctttccct ctcctgctga gaaccagaac ccaccaggag    1200

caccacagag tcctcctctt ggaaggcaga actccctgaa atctggaatc agggtggaaa    1260

cagcctgttt ttcccattta aacaggagtc ctcttcaact tcagctgatt acaataacaa    1320

aaggcggaat tgaattgtgc gatgccaacg gccttctcat ttacaggttt ttttccccca    1380

cattggcctt tatttactac ttccttggaa ccatctctga attctgaata gctgacaacc    1440
```

```
cccaatgtta tccactctgt tgcttttgtc tggaaaactc tacagtgttt gtgggatgtc   1500

cccaaaggta agctatgttc taattttatc atttccatct gtctggttat gtcaagttaa   1560

ttcagaaaga gaagagacag tgaccaaccc tgagaggcct aatagggcag agatggaggc   1620

ctgcccagac taggaggcag cggggataga cagggaatgg ggagaagaaa gacccccatt   1680

ggtttggaaa tcaaggagag ggcggtgaca tattggacca gaagaggcac tagccatttt   1740

aaggagagga aagagaaaac tctggggtca gggagagacc ctacccccac ctaattatcc   1800

agcatatatg taagaaacat agcagcgatg gtattcgatc tgtgccatga ctcttctgaa   1860

tgtttggaca ggttagagtt ggggacccct gttggccact tgttgacctc tcatagtggt   1920

gcttgggcca ggtcttctca atggaagggg aatcccttat aggggagagg gaacagagcc   1980

cagtgaaatg gcagtcagaa tgttaaccct ggatccatct ctaagtagag agagggtgcc   2040

cattgcctag gtgagtgtgc caagctcagg attccaactg gtgcctctga gcttcccaat   2100

caatacttcc tggagccagc cccacccacc cctgagaaca gaggtcagac acagctgcgt   2160

aacatccatc ctgctacaac tcttccaccc caaacaaaag ggctcaggct acacacgacc   2220

atgatttatg ttttcagggg atgcccattt gtcccaagct tatcctgtaa ttctagaatt   2280

acctggtgtc ctgatgcatt ttccactaga ggttgctaat cagcatgttt tagcccaagt   2340

ccaccttcct gctgtggtta acctgttatg ttgcttttgg aaggagactc taagacaggg   2400

aaagcaagtt catggtacat acgcagccat tgtctctgtt tttacccatg gcagacattg   2460

ctaatcaatg gcagctctat ttcactgagt ctggataagg tttcagagtt caaatgcttg   2520

acgttggcac ttaacatgaa agcctatagg tcattcttgc tctgggatct acaggcaggg   2580

taggcacagg tgcagcctaa gaagggaacc tgcttcctct cccttccaaa gacagtgaca   2640

gctgactgag ggcaaagagc aggcaccact cagaacgtgg tgagtacagc tcagctcagc   2700

actcagtcag tggtaacttg tgcccagccc tgtgctaggc gctgacatta acaggagcaa   2760

ccagggccca attcctggcc ttggagctca aatctttcct ttgatttttg ctcctgatca   2820

tcaaggcccc agtgg                                                    2835
```

```
<210> SEQ ID NO 55
<211> LENGTH: 356
<212> TYPE: PRT
<213> ORGANISM: Homo sapiens

<400> SEQUENCE: 55

Met Gln Ile Leu Ser Arg Cys Gln Gly Leu Met Ser Glu Glu Cys Gly
1               5                   10                  15

Arg Thr Thr Ala Leu Ala Ala Gly Arg Thr Arg Lys Gly Ala Gly Glu
            20                  25                  30

Glu Gly Leu Val Ser Pro Glu Gly Ala Gly Asp Glu Asp Ser Cys Ser
        35                  40                  45

Ser Ser Ala Pro Leu Ser Pro Ser Ser Ser Pro Arg Ser Met Ala Ser
    50                  55                  60

Gly Ser Gly Cys Pro Pro Gly Lys Cys Val Cys Asn Ser Cys Gly Leu
65                  70                  75                  80

Glu Ile Val Asp Lys Tyr Leu Leu Lys Val Asn Asp Leu Cys Trp His
                85                  90                  95

Val Arg Cys Leu Ser Cys Ser Val Cys Arg Thr Ser Leu Gly Arg His
            100                 105                 110

Thr Ser Cys Tyr Ile Lys Asp Lys Asp Ile Phe Cys Lys Leu Asp Tyr
        115                 120                 125
```

-continued

```
Phe Arg Arg Tyr Gly Thr Arg Cys Ser Arg Cys Gly Arg His Ile His
    130                 135                 140

Ser Thr Asp Trp Val Arg Arg Ala Lys Gly Asn Val Tyr His Leu Ala
145                 150                 155                 160

Cys Phe Ala Cys Phe Ser Cys Lys Arg Gln Leu Ser Thr Gly Glu Glu
                165                 170                 175

Phe Ala Leu Val Glu Glu Lys Val Leu Cys Arg Val His Tyr Asp Cys
            180                 185                 190

Met Leu Asp Asn Leu Lys Arg Glu Val Glu Asn Gly Asn Gly Ile Ser
        195                 200                 205

Val Glu Gly Ala Leu Leu Thr Glu Gln Asp Val Asn His Pro Lys Pro
    210                 215                 220

Ala Lys Arg Ala Arg Thr Ser Phe Thr Ala Asp Gln Leu Gln Val Met
225                 230                 235                 240

Gln Ala Gln Phe Ala Gln Asp Asn Asn Pro Asp Ala Gln Thr Leu Gln
                245                 250                 255

Lys Leu Ala Glu Arg Thr Gly Leu Ser Arg Arg Val Ile Gln Val Trp
            260                 265                 270

Phe Gln Asn Cys Arg Ala Arg His Lys Lys His Val Ser Pro Asn His
        275                 280                 285

Ser Ser Ser Thr Pro Val Thr Ala Ala Pro Pro Ser Arg Leu Ser Pro
    290                 295                 300

Pro Met Leu Glu Glu Met Ala Tyr Ser Ala Tyr Val Pro Gln Asp Gly
305                 310                 315                 320

Thr Met Leu Thr Ala Leu His Ser Tyr Met Asp Ala His Ser Pro Thr
                325                 330                 335

Thr Leu Gly Leu Gln Pro Leu Leu Pro His Ser Met Thr Gln Leu Pro
            340                 345                 350

Ile Ser His Thr
        355
```

<210> SEQ ID NO 56
<211> LENGTH: 2411
<212> TYPE: DNA
<213> ORGANISM: Homo sapiens

<400> SEQUENCE: 56

```
agcggcaaga ggctagcggc tggaccactt gtgctggagt ggtaaagaac tatcatgaat      60

ccatttactg aaagtgtcca tttctgaact caccctaaag aggacaaaca ccgcaaagta     120

gttaaaagtc aggcattcgc gtcggacgtc tgggtttgaa ttctgccctg gcttgactgg     180

aaacgcttcc cctatttctt ccgtagcgga ccgggagagc ttactggcgc tctgcgaacc     240

ggctggaaag aaacaccgag tcactcgtac agactcttgg tcgcagaact tggctttccg     300

ctattggtcc tccagaaccg cttgaaacaa ctggccccag ctggcgcatc agaccgcagt     360

gaggaatgcc gcggggcggg tggcgaaggc agggtctgcc cgccagtgga ttcccgggtg     420

tcccgcgtgg agcaggcttg cccagctggg aagcccatca aacctcagtc ttggcccaca     480

gtgggagaga gaccagtggg tcccagacgg aggccatcgc ccgcttttgg cgacctccac     540

tggcgtgaat aaaagcaccc ctctcttacc ctcagaaact gtgggtagca aggtataaaa     600

cggagtctgg gaccggtaag tcccaaggtg agcccgtata cagctctgcc atctctgagg     660

ggttatgcag attctgagca ggtgtcaggg gctcatgtca gaggagtgcg ggcggactac     720

agccctggcg gccgggagga ctcgcaaagg cgccggggaa gagggactgg tgagccccga     780
```

```
gggagcgggg gacgaggact cgtgctcctc ctcggccccg ctgtccccgt cgtcctcgcc    840
ccggtccatg gcctcgggct ccggctgccc tcctggcaag tgtgtgtgca acagttgcgg    900
cctggagatc gtggacaaat accttctcaa ggtgaatgac ctatgctggc atgtccggtg    960
tctctcctgc agtgtttgca gaacctccct aggaaggcac accagctgtt atattaaaga   1020
caaagacatt ttctgcaaac ttgattattt cagaaggtat ggaactcgct gctctcgatg   1080
tgggagacac atccattcta ctgactgggt ccggagagcc aaggggaatg tctatcactt   1140
ggcatgcttt gcctgctttt cctgcaaaag gcaactttcc acaggagagg agtttgcttt   1200
ggtggaagag aaagtcctct gcagagtaca ttatgactgc atgctggata atttaaaaag   1260
agaagtagaa aatgggaatg ggattagtgt ggaaggtgcc ctcctcacag agcaagatgt   1320
taaccatcca aaaccagcaa aaagagctcg gaccagcttt acagcagatc agcttcaggt   1380
tatgcaagca caatttgctc aggacaacaa cccagatgca cagacactcc agaaattggc   1440
agaaaggaca ggcttgagca gacgtgtgat acaggtgtgg tttcagaatt gtagagcacg   1500
ccacaagaaa cacgtcagtc ctaatcactc atcctccacc ccagtcacag cagccccacc   1560
ctccaggctg tctccaccca tgttagaaga aatggcttat tctgcctacg tgccccaaga   1620
tggaacgatg ttaactgcgc tgcatagtta tatggatgct cattcaccaa caactcttgg   1680
actccagccc ttgttacccc attcaatgac acaactgcca ataagtcata cctaattctt   1740
ttttcaggga tagacttgat taaggatata aatttgtcat ttattatgta taaaatacca   1800
ttgaaaagat attactgtta attttttatt taacacctaa agcatttcca acatcacttt   1860
gctgcccagg tatgtatcta tagttggcct gcaagacact tttattaatt cttcattttt   1920
tgtaaaactt atgtttacaa gaagaaaaca aatcaaaaca ttttttgtat tgtctggaaa   1980
tagttcactc tagtgtgtat ctgttaattt atttgtcatc aaaagagcac tttgcctaaa   2040
agaaaggact gacaagtgtg caaaatgttt acaatctttt gtgaaattgt agtttatcat   2100
tagtttgtat ctgtaagtta ttgtaataaa tattacctgt atttttgtt  atatacaact   2160
ttatactttg aagcttgtat ctgtgaattt gcaactgaaa tttattttgc caatgttttc   2220
tgaatgaact gaataaagct tctgttgtag catgccatgc aaacacatta ttgtgtttgt   2280
ggttgatgaa ttatggctgt aaataacact atagtttaat aagcccacca ttctgagttt   2340
attaaacatt ttccattctt gtgaaaattt caaaaaaaaa aaaaaaaaaa aaagaaaaaa   2400
aaaaaaaaaa a                                                        2411
```

<210> SEQ ID NO 57
<211> LENGTH: 682
<212> TYPE: PRT
<213> ORGANISM: Homo sapiens

<400> SEQUENCE: 57

```
Met Gln Leu Glu His Cys Leu Ser Pro Ser Ile Met Leu Ser Lys Lys
1               5                   10                  15

Phe Leu Asn Val Ser Ser Ser Tyr Pro His Ser Gly Gly Ser Glu Leu
            20                  25                  30

Val Leu His Asp His Pro Ile Ile Ser Thr Thr Asp Asn Leu Glu Arg
        35                  40                  45

Ser Ser Pro Leu Lys Lys Ile Thr Arg Gly Met Thr Asn Gln Ser Asp
    50                  55                  60

Thr Asp Asn Phe Pro Asp Ser Lys Asp Ser Pro Gly Asp Val Gln Arg
65                  70                  75                  80
```

```
Ser Lys Leu Ser Pro Val Leu Asp Gly Val Ser Glu Leu Arg His Ser
                85                  90                  95

Phe Asp Gly Ser Ala Ala Asp Arg Tyr Leu Leu Ser Gln Ser Ser Gln
            100                 105                 110

Pro Gln Ser Ala Ala Thr Ala Pro Ser Ala Met Phe Pro Tyr Pro Gly
        115                 120                 125

Gln His Gly Pro Ala His Pro Ala Phe Ser Ile Gly Ser Pro Ser Arg
    130                 135                 140

Tyr Met Ala His His Pro Val Ile Thr Asn Gly Ala Tyr Asn Ser Leu
145                 150                 155                 160

Leu Ser Asn Ser Ser Pro Gln Gly Tyr Pro Thr Ala Gly Tyr Pro Tyr
                165                 170                 175

Pro Gln Gln Tyr Gly His Ser Tyr Gln Gly Ala Pro Phe Tyr Gln Phe
            180                 185                 190

Ser Ser Thr Gln Pro Gly Leu Val Pro Gly Lys Ala Gln Val Tyr Leu
        195                 200                 205

Cys Asn Arg Pro Leu Trp Leu Lys Phe His Arg His Gln Thr Glu Met
    210                 215                 220

Ile Ile Thr Lys Gln Gly Arg Arg Met Phe Pro Phe Leu Ser Phe Asn
225                 230                 235                 240

Ile Ser Gly Leu Asp Pro Thr Ala His Tyr Asn Ile Phe Val Asp Val
                245                 250                 255

Ile Leu Ala Asp Pro Asn His Trp Arg Phe Gln Gly Gly Lys Trp Val
            260                 265                 270

Pro Cys Gly Lys Ala Asp Thr Asn Val Gln Gly Asn Arg Val Tyr Met
        275                 280                 285

His Pro Asp Ser Pro Asn Thr Gly Ala His Trp Met Arg Gln Glu Ile
    290                 295                 300

Ser Phe Gly Lys Leu Lys Leu Thr Asn Asn Lys Gly Ala Ser Asn Asn
305                 310                 315                 320

Asn Gly Gln Met Val Val Leu Gln Ser Leu His Lys Tyr Gln Pro Arg
                325                 330                 335

Leu His Val Val Glu Val Asn Glu Asp Gly Thr Glu Asp Thr Ser Gln
            340                 345                 350

Pro Gly Arg Val Gln Thr Phe Thr Phe Pro Glu Thr Gln Phe Ile Ala
        355                 360                 365

Val Thr Ala Tyr Gln Asn Thr Asp Ile Thr Gln Leu Lys Ile Asp His
    370                 375                 380

Asn Pro Phe Ala Lys Gly Phe Arg Asp Asn Tyr Asp Thr Ile Tyr Thr
385                 390                 395                 400

Gly Cys Asp Met Asp Arg Leu Thr Pro Ser Pro Asn Asp Ser Pro Arg
                405                 410                 415

Ser Gln Ile Val Pro Gly Ala Arg Tyr Ala Met Ala Gly Ser Phe Leu
            420                 425                 430

Gln Asp Gln Phe Val Ser Asn Tyr Ala Lys Ala Arg Phe His Pro Gly
        435                 440                 445

Ala Gly Ala Gly Pro Gly Pro Gly Thr Asp Arg Ser Val Pro His Thr
    450                 455                 460

Asn Gly Leu Leu Ser Pro Gln Gln Ala Glu Asp Pro Gly Ala Pro Ser
465                 470                 475                 480

Pro Gln Arg Trp Phe Val Thr Pro Ala Asn Asn Arg Leu Asp Phe Ala
                485                 490                 495
```

-continued

```
Ala Ser Ala Tyr Asp Thr Ala Thr Asp Phe Ala Gly Asn Ala Ala Thr
            500                 505                 510

Leu Leu Ser Tyr Ala Ala Ala Gly Val Lys Ala Leu Pro Leu Gln Ala
        515                 520                 525

Ala Gly Cys Thr Gly Arg Pro Leu Gly Tyr Tyr Ala Asp Pro Ser Gly
    530                 535                 540

Trp Gly Ala Arg Ser Pro Pro Gln Tyr Cys Gly Thr Lys Ser Gly Ser
545                 550                 555                 560

Val Leu Pro Cys Trp Pro Asn Ser Ala Ala Ala Ala Ala Arg Met Ala
                565                 570                 575

Gly Ala Asn Pro Tyr Leu Gly Glu Glu Ala Glu Gly Leu Ala Ala Glu
            580                 585                 590

Arg Ser Pro Leu Pro Pro Gly Ala Ala Glu Asp Ala Lys Pro Lys Asp
        595                 600                 605

Leu Ser Asp Ser Ser Trp Ile Glu Thr Pro Ser Ser Ile Lys Ser Ile
    610                 615                 620

Asp Ser Ser Asp Ser Gly Ile Tyr Glu Gln Ala Lys Arg Arg Arg Ile
625                 630                 635                 640

Ser Pro Ala Asp Thr Pro Val Ser Glu Ser Ser Ser Pro Leu Lys Ser
                645                 650                 655

Glu Val Leu Ala Gln Arg Asp Cys Glu Lys Asn Cys Ala Lys Asp Ile
            660                 665                 670

Ser Gly Tyr Tyr Gly Phe Tyr Ser His Ser
        675                 680


<210> SEQ ID NO 58
<211> LENGTH: 4006
<212> TYPE: DNA
<213> ORGANISM: Homo sapiens

<400> SEQUENCE: 58

gtcgctacca ggagccaggt gattatccta attaatgtct atctaattaa attactgtca      60

gcagctaacc aatggcagga gccgtttcat cggctgcaca agcagcaaga tcaaaagtga     120

gccttttctg attgctgcat agtgtcaatt ggccaatctc ttctcccagg gaaaaaaaaa     180

agtaaatcaa acctttgaga agcatttgct ggttgaagtg ctttctgtct agtgaggggg     240

tctgtggatt tctagtttat gataaatagg actttaaaaa ccagggacgg gagggcgagt     300

gttcaggttc tagagctatg cagctggagc actgcctttc tccttctatc atgctctcca     360

agaaatttct caatgtgagc agcagctacc cacattcagg cggatccgag cttgtcttgc     420

acgatcatcc cattatctcg accactgaca acctggagag aagttcacct ttgaaaaaaa     480

ttaccagggg gatgacgaat cagtcagata cagacaattt tcctgactcc aaggactcac     540

caggggacgt ccagagaagt aaactctctc ctgtcttgga cggggtctct gagcttcgtc     600

acagtttcga tggctctgct gcagatcgct acctcctctc tcagtccagc cagccacagt     660

ctgcggccac tgctcccagt gccatgttcc cgtaccccgg ccagcacgga ccggcgcacc     720

ccgccttctc catcggcagc cctagccgct acatggccca ccacccggtc atcaccaacg     780

gagcctacaa cagcctcctg tccaactcct cgccgcaggg ataccccacg gccggctacc     840

cctacccaca gcagtacggc cactcctacc aaggagctcc gttctaccag ttctcctcca     900

cccagccggg gctggtgccc ggcaaagcac aggtgtacct gtgcaacagg cccctttggc     960

tgaaatttca ccggcaccaa acggagatga tcatcaccaa acagggaagg cgcatgtttc    1020

ctttttaag ttttaacatt tctggtctcg atcccacggc tcattacaat atttttgtgg    1080
```

-continued

```
atgtgatttt ggcggatccc aatcactgga ggtttcaagg aggcaaatgg gttccttgcg   1140
gcaaagcgga caccaatgtg caaggaaatc gggtctatat gcatccggat tcccccaaca   1200
ctggggctca ctggatgcgc caagaaatct cttttggaaa attaaaactt acgaacaaca   1260
aaggagcttc aaataacaat gggcagatgg tggttttaca gtccttgcac aagtaccagc   1320
cccgcctgca tgtggtggaa gtgaacgagg acggcacgga ggacactagc cagcccggcc   1380
gcgtgcagac gttcactttc cctgagactc agttcatcgc cgtcaccgcc taccagaaca   1440
cggatattac acaactgaaa atagatcaca acccttttgc aaaaggattt cgggataatt   1500
atgacacgat ctacaccggc tgtgacatgg accgcctgac cccctcgccc aacgactcgc   1560
cgcgctcgca gatcgtgccc ggggcccgct acgccatggc cggctctttc ctgcaggacc   1620
agttcgtgag caactacgcc aaggcccgct tccacccggg cgcgggcgcg ggccccgggc   1680
cgggtacgga ccgcagcgtg ccgcacacca acgggctgct gtcgccgcag caggccgagg   1740
acccgggcgc gccctcgccg caacgctggt ttgtgacgcc ggccaacaac cggctggact   1800
tcgcggcctc ggcctatgac acggccacgg acttcgcggg caacgcggcc acgctgctct   1860
cttacgcggc ggcgggcgtg aaggcgctgc cgctgcaggc tgcaggctgc actggccgcc   1920
cgctcggcta ctacgccgac ccgtcgggct ggggcgcccg cagtccccccg cagtactgcg   1980
gcaccaagtc gggctcggtg ctgccctgct ggcccaacag cgccgcggcc gccgcgcgca   2040
tggccggcgc caatccctac ctgggcgagg aggccgaggg cctggccgcc gagcgctcgc   2100
cgctgccgcc cggcgccgcc gaggacgcca agcccaagga cctgtccgat tccagctgga   2160
tcgagacgcc ctcctcgatc aagtccatcg actccagcga ctcggggatt tacgagcagg   2220
ccaagcggag gcggatctcg ccggccgaca cgcccgtgtc cgagagttcg tccccgctca   2280
agagcgaggt gctggcccag cgggactgcg agaagaactg cgccaaggac attagcggct   2340
actatggctt ctactcgcac agctaggccg cccctgcccg cccggccccg ccgcggcccg   2400
gacccccagc cagcccctca cagctcttcc ccagctccgc ctccccacac tcctccttgc   2460
gcacccactc attttatttg accctcgatg gccgtctgca gcgaataagt gcaggtctcc   2520
gagcgtgatt ttaacctttt ttgcacagca gtctctgcaa ttagctcacc gaccttcaac   2580
tttgctgtaa accttttggt tttcctactt actcttcttc tgtggagtta tcctcctaca   2640
attcccctcc ccctcgtctt tctcttacct cctacttctc tttcttgtaa tgaaactctt   2700
cacctttagg agacctgggc agtcctgtca ggcagcagcg attccgaccc gccaagtctc   2760
ggcctccaca ttaaccatag gatgttgact ctagaacctg gacccaccca gcgcgtcctt   2820
tcttatcccc gagtggatgg atggatggat ggatggtagg gatgttaata attttagtgg   2880
aacaaagcct gtgaaatgat tgtacatagt gttaatttat tgtaacgaat ggctagtttt   2940
tattctcgtc aaggcacaaa accagttcat gcttaacctt tttttccttt cctttctttg   3000
cttttctttc tctcctctca tactttctct tctctctctt ttaattttct tgtgagataa   3060
tattctaaga ggctctagaa acatgaaata ctcagtagtg atgggtttcc cacttctcct   3120
caatccgttg catgaaataa ttactatgtg ccctaatgca cacaaatagc taaggagaat   3180
ccacccaaac acctttaaag gataggtgtc tgttcatagg caagtcgatt aagtggcatg   3240
atgcctgcaa agcaaagtca actggagttg tatgttcccc ccaccttcta aatagaatag   3300
ctcgacatca gcaatattat tttgccttat ttgtttttcc ccaaagtgcc aaatccatta   3360
ctggtctgtg caggtgccaa atatgctgac aaactgtttc tgaatatctt tcagtacccc   3420
ttcaccttta tatgctgtaa atctttgtaa tgaatactct attaatgata tagatgactg   3480
```

```
aattgttggt aactatagtg tagtctagtg aagatgaatt gtgtgagttg tatattttac   3540

tgcattttag ttttgaaaat gacttcccca ccacctagaa acagctgaaa tttgacttcc   3600

ttgggagaac actagcatta atgcaagtaa gactgatttt cccctaagtc ttgttatatt   3660

tgataaggag cattaatccc cctggaaata gattagtagg atttctaatg ttgtgtagca   3720

aacctatact tttttgtatt taaaaattaa tgtgaaatat gcatcataca caatattcaa   3780

tctagattcc agtccatggg gggatttttc ctaataggaa ttcagggtct aaacgtgtgt   3840

atattttggc tcttctgtaa atctaatgtt gtgattttta tatttgtttc gttttgtctg   3900

tgaactgaat aatttataca agaacacact ccattgagaa acgttttgtt ttttgctcgt   3960

ttgtatcgtc tgtgtataac aagtaaaata aacctggtaa aaacgc                  4006


<210> SEQ ID NO 59
<211> LENGTH: 542
<212> TYPE: PRT
<213> ORGANISM: Homo sapiens

<400> SEQUENCE: 59

Met Thr Lys Ser Asn Gly Glu Glu Pro Lys Met Gly Gly Arg Met Glu
1               5                   10                  15

Arg Phe Gln Gln Gly Val Arg Lys Arg Thr Leu Leu Ala Lys Lys Lys
            20                  25                  30

Val Gln Asn Ile Thr Lys Glu Asp Val Lys Ser Tyr Leu Phe Arg Asn
        35                  40                  45

Ala Phe Val Leu Leu Thr Val Thr Ala Val Ile Val Gly Thr Ile Leu
    50                  55                  60

Gly Phe Thr Leu Arg Pro Tyr Arg Met Ser Tyr Arg Glu Val Lys Tyr
65                  70                  75                  80

Phe Ser Phe Pro Gly Glu Leu Leu Met Arg Met Leu Gln Met Leu Val
                85                  90                  95

Leu Pro Leu Ile Ile Ser Ser Leu Val Thr Gly Met Ala Ala Leu Asp
            100                 105                 110

Ser Lys Ala Ser Gly Lys Met Gly Met Arg Ala Val Val Tyr Tyr Met
        115                 120                 125

Thr Thr Thr Ile Ile Ala Val Val Ile Gly Ile Ile Ile Val Ile Ile
    130                 135                 140

Ile His Pro Gly Lys Gly Thr Lys Glu Asn Met His Arg Glu Gly Lys
145                 150                 155                 160

Ile Val Arg Val Thr Ala Ala Asp Ala Phe Leu Asp Leu Ile Arg Asn
                165                 170                 175

Met Phe Pro Pro Asn Leu Val Glu Ala Cys Phe Lys Gln Phe Lys Thr
            180                 185                 190

Asn Tyr Glu Lys Arg Ser Phe Lys Val Pro Ile Gln Ala Asn Glu Thr
        195                 200                 205

Leu Val Gly Ala Val Ile Asn Asn Val Ser Glu Ala Met Glu Thr Leu
    210                 215                 220

Thr Arg Ile Thr Glu Glu Leu Val Pro Val Pro Gly Ser Val Asn Gly
225                 230                 235                 240

Val Asn Ala Leu Gly Leu Val Val Phe Ser Met Cys Phe Gly Phe Val
                245                 250                 255

Ile Gly Asn Met Lys Glu Gln Gly Gln Ala Leu Arg Glu Phe Phe Asp
            260                 265                 270

Ser Leu Asn Glu Ala Ile Met Arg Leu Val Ala Val Ile Met Trp Tyr
        275                 280                 285
```

-continued

```
Ala Pro Val Gly Ile Leu Phe Leu Ile Ala Gly Lys Ile Val Glu Met
    290                 295                 300

Glu Asp Met Gly Val Ile Gly Gly Gln Leu Ala Met Tyr Thr Val Thr
305                 310                 315                 320

Val Ile Val Gly Leu Leu Ile His Ala Val Ile Val Leu Pro Leu Leu
                325                 330                 335

Tyr Phe Leu Val Thr Arg Lys Asn Pro Trp Val Phe Ile Gly Gly Leu
            340                 345                 350

Leu Gln Ala Leu Ile Thr Ala Leu Gly Thr Ser Ser Ser Ser Ala Thr
        355                 360                 365

Leu Pro Ile Thr Phe Lys Cys Leu Glu Glu Asn Asn Gly Val Asp Lys
    370                 375                 380

Arg Val Thr Arg Phe Val Leu Pro Val Gly Ala Thr Ile Asn Met Asp
385                 390                 395                 400

Gly Thr Ala Leu Tyr Glu Ala Leu Ala Ala Ile Phe Ile Ala Gln Val
                405                 410                 415

Asn Asn Phe Glu Leu Asn Phe Gly Gln Ile Ile Thr Ile Ser Ile Thr
            420                 425                 430

Ala Thr Ala Ala Ser Ile Gly Ala Ala Gly Ile Pro Gln Ala Gly Leu
        435                 440                 445

Val Thr Met Val Ile Val Leu Thr Ser Val Gly Leu Pro Thr Asp Asp
    450                 455                 460

Ile Thr Leu Ile Ile Ala Val Asp Trp Phe Leu Asp Arg Leu Arg Thr
465                 470                 475                 480

Thr Thr Asn Val Leu Gly Asp Ser Leu Gly Ala Gly Ile Val Glu His
                485                 490                 495

Leu Ser Arg His Glu Leu Lys Asn Arg Asp Val Glu Met Gly Asn Ser
            500                 505                 510

Val Ile Glu Glu Asn Glu Met Lys Lys Pro Tyr Gln Leu Ile Ala Gln
        515                 520                 525

Asp Asn Glu Thr Glu Lys Pro Ile Asp Ser Glu Thr Lys Met
    530                 535                 540
```

<210> SEQ ID NO 60
<211> LENGTH: 1873
<212> TYPE: DNA
<213> ORGANISM: Homo sapiens

<400> SEQUENCE: 60

```
gatagtaact tgcagtttca gagcacatgc acactgtcag ggctagcctg cctgcttacg     60

cgcgctgcgg attgttgctc cgttgtacct gctggggaat tcacctcgtt actgcttgat    120

atcttccacc ccttacaaaa tcagaaaagt tgtgttttct aataccaaag aggaggtttg    180

gctttctgtg ggtgattccc agacactgaa gtgcaaagaa gagaccctcc tagaaaagta    240

aaatatgact aaaagcaatg gagaagagcc caagatgggg ggcaggatgg agagattcca    300

gcagggagtc cgtaaacgca cacttttggc caagaagaaa gtgcagaaca ttacaaagga    360

ggatgttaaa agttacctgt ttcggaatgc ttttgtgctg ctcacagtca ccgctgtcat    420

tgtgggtaca atccttggat ttaccctccg accatacaga atgagctacc gggaagtcaa    480

gtacttctcc tttcctgggg aacttctgat gaggatgtta cagatgctgg tcttaccact    540

tatcatctcc agtcttgtca caggaatggc ggcgctagat agtaaggcat cagggaagat    600

gggaatgcga gctgtagtct attatatgac taccaccatc attgctgtgg tgattggcat    660

aatcattgtc atcatcatcc atcctgggaa gggcacaaag gaaaacatgc acagagaagg    720
```

```
caaaattgta cgagtgacag ctgcagatgc cttcctggac ttgatcagga acatgttccc    780

tccaaatctg gtagaagcct gctttaaaca gtttaaaacc aactatgaga agagaagctt    840

taaagtgccc atccaggcca acgaaacgct tgtgggtgct gtgataaaca atgtgtctga    900

ggccatggag actcttaccc gaatcacaga ggagctggtc ccagttccag gatctgtgaa    960

tggagtcaat gccctgggtc tagttgtctt ctccatgtgc ttcggttttg tgattggaaa   1020

catgaaggaa caggggcagg ccctgagaga gttctttgat tctcttaacg aagccatcat   1080

gagactggta gcagtaataa tgtggtatgc ccccgtgggt attctcttcc tgattgctgg   1140

gaagattgtg gagatggaag acatgggtgt gattgggggg cagcttgcca tgtacaccgt   1200

gactgtcatt gttggcttac tcattcacgc agtcatcgtc ttgccactcc tctacttctt   1260

ggtaacacgg aaaaaccctt gggtttttat tggagggttg ctgcaagcac tcatcaccgc   1320

tctggggacc tcttcaagtt ctgccaccct acccatcacc ttcaagtgcc tggaagagaa   1380

caatggcgtg gacaagcgcg tcaccagatt cgtgctcccc gtaggagcca ccattaacat   1440

ggatgggact gccctctatg aggctttggc tgccattttc attgctcaag ttaacaactt   1500

tgaactgaac ttcggacaaa ttattacaat cagcatcaca gccacagctg ccagtattgg   1560

ggcagctgga attcctcagg cgggcctggt cactatggtc attgtgctga catctgtcgg   1620

cctgcccact gacgacatca cgctcatcat cgcggtggac tggttcctgg atcgcctccg   1680

gaccaccacc aacgtactgg gagactccct gggagctggg attgtggagc acttgtcacg   1740

acatgaactg aagaacagag atgttgaaat gggtaactca gtgattgaag agaatgaaat   1800

gaagaaacca tatcaactga ttgcacagga caatgaaact gagaaaccca tcgacagtga   1860

aaccaagatg tag                                                      1873
```

<210> SEQ ID NO 61
<211> LENGTH: 497
<212> TYPE: PRT
<213> ORGANISM: Homo sapiens

<400> SEQUENCE: 61

```
Met Pro Thr Pro Asp Ala Thr Thr Pro Gln Ala Lys Gly Phe Arg Arg
1               5                   10                  15

Ala Val Ser Glu Leu Asp Ala Lys Gln Ala Glu Ala Ile Met Ser Pro
            20                  25                  30

Arg Phe Ile Gly Arg Arg Gln Ser Leu Ile Glu Asp Ala Arg Lys Glu
        35                  40                  45

Arg Glu Ala Ala Val Ala Ala Ala Ala Ala Ala Val Pro Ser Glu Pro
    50                  55                  60

Gly Asp Pro Leu Glu Ala Val Ala Phe Glu Glu Lys Glu Gly Lys Ala
65                  70                  75                  80

Val Leu Asn Leu Leu Phe Ser Pro Arg Ala Thr Lys Pro Ser Ala Leu
                85                  90                  95

Ser Arg Ala Val Lys Val Phe Glu Thr Phe Glu Ala Lys Ile His His
            100                 105                 110

Leu Glu Thr Arg Pro Ala Gln Arg Pro Arg Ala Gly Gly Pro His Leu
        115                 120                 125

Glu Tyr Phe Val Arg Leu Glu Val Arg Arg Gly Asp Leu Ala Ala Leu
    130                 135                 140

Leu Ser Gly Val Arg Gln Val Ser Glu Asp Val Arg Ser Pro Ala Gly
145                 150                 155                 160
```

```
Pro Lys Val Pro Trp Phe Pro Arg Lys Val Ser Glu Leu Asp Lys Cys
                165                 170                 175

His His Leu Val Thr Lys Phe Asp Pro Asp Leu Asp Leu Asp His Pro
            180                 185                 190

Gly Phe Ser Asp Gln Val Tyr Arg Gln Arg Arg Lys Leu Ile Ala Glu
        195                 200                 205

Ile Ala Phe Gln Tyr Arg His Gly Asp Pro Ile Pro Arg Val Glu Tyr
    210                 215                 220

Thr Ala Glu Glu Ile Ala Thr Trp Lys Glu Val Tyr Thr Thr Leu Lys
225                 230                 235                 240

Gly Leu Tyr Ala Thr His Ala Cys Gly Glu His Leu Glu Ala Phe Ala
                245                 250                 255

Leu Leu Glu Arg Phe Ser Gly Tyr Arg Glu Asp Asn Ile Pro Gln Leu
            260                 265                 270

Glu Asp Val Ser Arg Phe Leu Lys Glu Arg Thr Gly Phe Gln Leu Arg
        275                 280                 285

Pro Val Ala Gly Leu Leu Ser Ala Arg Asp Phe Leu Ala Ser Leu Ala
    290                 295                 300

Phe Arg Val Phe Gln Cys Thr Gln Tyr Ile Arg His Ala Ser Ser Pro
305                 310                 315                 320

Met His Ser Pro Glu Pro Asp Cys Cys His Glu Leu Leu Gly His Val
                325                 330                 335

Pro Met Leu Ala Asp Arg Thr Phe Ala Gln Phe Ser Gln Asp Ile Gly
            340                 345                 350

Leu Ala Ser Leu Gly Ala Ser Asp Glu Glu Ile Glu Lys Leu Ser Thr
        355                 360                 365

Leu Tyr Trp Phe Thr Val Glu Phe Gly Leu Cys Lys Gln Asn Gly Glu
    370                 375                 380

Val Lys Ala Tyr Gly Ala Gly Leu Leu Ser Ser Tyr Gly Glu Leu Leu
385                 390                 395                 400

His Cys Leu Ser Glu Glu Pro Glu Ile Arg Ala Phe Asp Pro Glu Ala
                405                 410                 415

Ala Ala Val Gln Pro Tyr Gln Asp Gln Thr Tyr Gln Ser Val Tyr Phe
            420                 425                 430

Val Ser Glu Ser Phe Ser Asp Ala Lys Asp Lys Leu Arg Ser Tyr Ala
        435                 440                 445

Ser Arg Ile Gln Arg Pro Phe Ser Val Lys Phe Asp Pro Tyr Thr Leu
    450                 455                 460

Ala Ile Asp Val Leu Asp Ser Pro Gln Ala Val Arg Arg Ser Leu Glu
465                 470                 475                 480

Gly Val Gln Asp Glu Leu Asp Thr Leu Ala His Ala Leu Ser Ala Ile
                485                 490                 495

Gly


<210> SEQ ID NO 62
<211> LENGTH: 1629
<212> TYPE: DNA
<213> ORGANISM: Homo sapiens

<400> SEQUENCE: 62

acccagaggg ggctttgacg tcagctcagc ttataagagg ctgctgggcc agggctgtgg      60

agacggagcc cggacctcca cactgagcca tgcccacccc cgacgccacc acgccacagg     120

ccaagggctt ccgcagggcc gtgtctgagc tggacgccaa gcaggcagag gccatcatgt     180
```

```
ccccgcggtt cattgggcgc aggcagagcc tcatcgagga cgcccgcaag gagcgggagg    240

cggcggtggc agcagcggcc gctgcagtcc cctcggagcc cggggacccc ctggaggctg    300

tggcctttga ggagaaggag gggaaggccg tgctaaacct gctcttctcc ccgagggcca    360

ccaagccctc ggcgctgtcc cgagctgtga aggtgtttga gacgtttgaa gccaaaatcc    420

accatctaga gacccggccc gcccagaggc cgcgagctgg gggcccccac ctggagtact    480

tcgtgcgcct cgaggtgcgc cgaggggacc tggccgccct gctcagtggt gtgcgccagg    540

tgtcagagga cgtgcgcagc cccgcggggc ccaaggtccc ctggttccca agaaaagtgt    600

cagagctgga caagtgtcat cacctggtca ccaagttcga ccctgacctg gacttggacc    660

acccgggctt ctcggaccag gtgtaccgcc agcgcaggaa gctgattgct gagatcgcct    720

tccagtacag gcacggcgac ccgattcccc gtgtggagta caccgccgag gagattgcca    780

cctggaagga ggtctacacc acgctgaagg gcctctacgc cacgcacgcc tgcggggagc    840

acctggaggc ctttgctttg ctggagcgct tcagcggcta ccgggaagac aatatccccc    900

agctggagga cgtctcccgc ttcctgaagg agcgcacggg cttccagctg cggcctgtgg    960

ccggcctgct gtccgcccgg gacttcctgg ccagcctggc cttccgcgtg ttccagtgca   1020

cccagtatat ccgccacgcg tcctcgccca tgcactcccc tgagccggac tgctgccacg   1080

agctgctggg gcacgtgccc atgctggccg accgcacctt cgcgcagttc tcgcaggaca   1140

ttggcctggc gtccctgggg gcctcggatg aggaaattga gaagctgtcc acgctgtact   1200

ggttcacggt ggagttcggg ctgtgtaagc agaacgggga ggtgaaggcc tatggtgccg   1260

ggctgctgtc ctcctacggg gagctcctgc actgcctgtc tgaggagcct gagattcggg   1320

ccttcgaccc tgaggctgcg gccgtgcagc cctaccaaga ccagacgtac cagtcagtct   1380

acttcgtgtc tgagagcttc agtgacgcca aggacaagct caggagctat gcctcacgca   1440

tccagcgccc cttctccgtg aagttcgacc cgtacacgct ggccatcgac gtgctggaca   1500

gcccccaggc cgtgcggcgc tccctggagg gtgtccagga tgagctggac acccttgccc   1560

atgcgctgag tgccattggc taggtgcacg gcgtccctga gggcccttcc caacctcccc   1620

tggtcctgc                                                           1629
```

```
<210> SEQ ID NO 63
<211> LENGTH: 1020
<212> TYPE: PRT
<213> ORGANISM: Homo sapiens

<400> SEQUENCE: 63

Met Met Ser Phe Gly Gly Ala Asp Ala Leu Leu Gly Ala Pro Phe Ala
1               5                   10                  15

Pro Leu His Gly Gly Gly Ser Leu His Tyr Ala Leu Ala Arg Lys Gly
            20                  25                  30

Gly Ala Gly Gly Thr Arg Ser Ala Ala Gly Ser Ser Ser Gly Phe His
        35                  40                  45

Ser Trp Thr Arg Thr Ser Val Ser Ser Val Ser Ala Ser Pro Ser Arg
    50                  55                  60

Phe Arg Gly Ala Gly Ala Ala Ser Ser Thr Asp Ser Leu Asp Thr Leu
65                  70                  75                  80

Ser Asn Gly Pro Glu Gly Cys Met Val Ala Val Ala Thr Ser Arg Ser
                85                  90                  95

Glu Lys Glu Gln Leu Gln Ala Leu Asn Asp Arg Phe Ala Gly Tyr Ile
            100                 105                 110
```

```
Asp Lys Val Arg Gln Leu Glu Ala His Asn Arg Ser Leu Glu Gly Glu
        115                 120                 125

Ala Ala Ala Leu Arg Gln Gln Gln Ala Gly Arg Ser Ala Met Gly Glu
    130                 135                 140

Leu Tyr Glu Arg Glu Val Arg Glu Met Arg Gly Ala Val Leu Arg Leu
145                 150                 155                 160

Gly Ala Ala Arg Gly Gln Leu Arg Leu Glu Gln Glu His Leu Leu Glu
                165                 170                 175

Asp Ile Ala His Val Arg Gln Arg Leu Asp Asp Glu Ala Arg Gln Arg
            180                 185                 190

Glu Glu Ala Glu Ala Ala Ala Arg Ala Leu Ala Arg Phe Ala Gln Glu
        195                 200                 205

Ala Glu Ala Ala Arg Val Asp Leu Gln Lys Lys Ala Gln Ala Leu Gln
    210                 215                 220

Glu Glu Cys Gly Tyr Leu Arg Arg His His Gln Glu Glu Val Gly Glu
225                 230                 235                 240

Leu Leu Gly Gln Ile Gln Gly Ser Gly Ala Ala Gln Ala Gln Met Gln
                245                 250                 255

Ala Glu Thr Arg Asp Ala Leu Lys Cys Asp Val Thr Ser Ala Leu Arg
            260                 265                 270

Glu Ile Arg Ala Gln Leu Glu Gly His Ala Val Gln Ser Thr Leu Gln
        275                 280                 285

Ser Glu Glu Trp Phe Arg Val Arg Leu Asp Arg Leu Ser Glu Ala Ala
    290                 295                 300

Lys Val Asn Thr Asp Ala Met Arg Ser Ala Gln Glu Glu Ile Thr Glu
305                 310                 315                 320

Tyr Arg Arg Gln Leu Gln Ala Arg Thr Thr Glu Leu Glu Ala Leu Lys
                325                 330                 335

Ser Thr Lys Asp Ser Leu Glu Arg Gln Arg Ser Glu Leu Glu Asp Arg
            340                 345                 350

His Gln Ala Asp Ile Ala Ser Tyr Gln Glu Ala Ile Gln Gln Leu Asp
        355                 360                 365

Ala Glu Leu Arg Asn Thr Lys Trp Glu Met Ala Ala Gln Leu Arg Glu
    370                 375                 380

Tyr Gln Asp Leu Leu Asn Val Lys Met Ala Leu Asp Ile Glu Ile Ala
385                 390                 395                 400

Ala Tyr Arg Lys Leu Leu Glu Gly Glu Glu Cys Arg Ile Gly Phe Gly
                405                 410                 415

Pro Ile Pro Phe Ser Leu Pro Glu Gly Leu Pro Lys Ile Pro Ser Val
            420                 425                 430

Ser Thr His Ile Lys Val Lys Ser Glu Glu Lys Ile Lys Val Val Glu
        435                 440                 445

Lys Ser Glu Lys Glu Thr Val Ile Val Glu Glu Gln Thr Glu Glu Thr
    450                 455                 460

Gln Val Thr Glu Glu Val Thr Glu Glu Glu Lys Glu Ala Lys Glu
465                 470                 475                 480

Glu Glu Gly Lys Glu Glu Glu Gly Gly Glu Glu Glu Glu Ala Glu Gly
                485                 490                 495

Gly Glu Glu Glu Thr Lys Ser Pro Pro Ala Glu Glu Ala Ala Ser Pro
            500                 505                 510

Glu Lys Glu Ala Lys Ser Pro Val Lys Glu Glu Ala Lys Ser Pro Ala
        515                 520                 525
```

```
Glu Ala Lys Ser Pro Glu Lys Glu Glu Ala Lys Ser Pro Ala Glu Val
    530                 535                 540

Lys Ser Pro Glu Lys Ala Lys Ser Pro Ala Lys Glu Glu Ala Lys Ser
545                 550                 555                 560

Pro Pro Glu Ala Lys Ser Pro Glu Lys Glu Glu Ala Lys Ser Pro Ala
                565                 570                 575

Glu Val Lys Ser Pro Glu Lys Ala Lys Ser Pro Ala Lys Glu Glu Ala
            580                 585                 590

Lys Ser Pro Ala Glu Ala Lys Ser Pro Glu Lys Ala Lys Ser Pro Val
        595                 600                 605

Lys Glu Glu Ala Lys Ser Pro Ala Glu Ala Lys Ser Pro Val Lys Glu
    610                 615                 620

Glu Ala Lys Ser Pro Ala Glu Val Lys Ser Pro Glu Lys Ala Lys Ser
625                 630                 635                 640

Pro Thr Lys Glu Glu Ala Lys Ser Pro Glu Lys Ala Lys Ser Pro Glu
                645                 650                 655

Lys Glu Glu Ala Lys Ser Pro Glu Lys Ala Lys Ser Pro Val Lys Ala
            660                 665                 670

Glu Ala Lys Ser Pro Glu Lys Ala Lys Ser Pro Val Lys Ala Glu Ala
        675                 680                 685

Lys Ser Pro Glu Lys Ala Lys Ser Pro Val Lys Glu Glu Ala Lys Ser
    690                 695                 700

Pro Glu Lys Ala Lys Ser Pro Val Lys Glu Glu Ala Lys Ser Pro Glu
705                 710                 715                 720

Lys Ala Lys Ser Pro Val Lys Glu Glu Ala Lys Thr Pro Glu Lys Ala
                725                 730                 735

Lys Ser Pro Val Lys Glu Glu Ala Lys Ser Pro Glu Lys Ala Lys Ser
            740                 745                 750

Pro Glu Lys Ala Lys Thr Leu Asp Val Lys Ser Pro Glu Ala Lys Thr
        755                 760                 765

Pro Ala Lys Glu Glu Ala Arg Ser Pro Ala Asp Lys Phe Pro Glu Lys
    770                 775                 780

Ala Lys Ser Pro Val Lys Glu Glu Val Lys Ser Pro Glu Lys Ala Lys
785                 790                 795                 800

Ser Pro Leu Lys Glu Asp Ala Lys Ala Pro Glu Lys Glu Ile Pro Lys
                805                 810                 815

Lys Glu Glu Val Lys Ser Pro Val Lys Glu Glu Glu Lys Pro Gln Glu
            820                 825                 830

Val Lys Val Lys Glu Pro Pro Lys Lys Ala Glu Glu Glu Lys Ala Pro
        835                 840                 845

Ala Thr Pro Lys Thr Glu Glu Lys Lys Asp Ser Lys Lys Glu Glu Ala
    850                 855                 860

Pro Lys Lys Glu Ala Pro Lys Pro Lys Val Glu Glu Lys Lys Glu Pro
865                 870                 875                 880

Ala Val Glu Lys Pro Lys Glu Ser Lys Val Glu Ala Lys Lys Glu Glu
                885                 890                 895

Ala Glu Asp Lys Lys Lys Val Pro Thr Pro Glu Lys Glu Ala Pro Ala
            900                 905                 910

Lys Val Glu Val Lys Glu Asp Ala Lys Pro Lys Glu Lys Thr Glu Val
        915                 920                 925

Ala Lys Lys Glu Pro Asp Asp Ala Lys Ala Lys Glu Pro Ser Lys Pro
    930                 935                 940
```

```
Ala Glu Lys Lys Glu Ala Ala Pro Glu Lys Lys Asp Thr Lys Glu Glu
945                 950                 955                 960

Lys Ala Lys Lys Pro Glu Glu Lys Pro Lys Thr Glu Ala Lys Ala Lys
                965                 970                 975

Glu Asp Asp Lys Thr Leu Ser Lys Glu Pro Ser Lys Pro Lys Ala Glu
            980                 985                 990

Lys Ala Glu Lys Ser Ser Ser Thr  Asp Gln Lys Asp Ser  Lys Pro Pro
        995                 1000                 1005

Glu Lys  Ala Thr Glu Asp Lys  Ala Ala Lys Gly Lys
    1010                 1015                 1020
```

<210> SEQ ID NO 64
<211> LENGTH: 3721
<212> TYPE: DNA
<213> ORGANISM: Homo sapiens

<400> SEQUENCE: 64

```
aaaagggccg gcgccctggt gctgccgcag tgcctcccgc cccgtcccgg cctcgcgcac     60
ctgctcaggc catgatgagc ttcggcggcg cggacgcgct gctgggcgcc ccgttcgcgc    120
cgctgcatgg cggcggcagc ctccactacg cgctagcccg aaagggtggc gcaggcggga    180
cgcgctccgc cgctggctcc tccagcggct tccactcgtg gacacggacg tccgtgagct    240
ccgtgtccgc ctcgcccagc cgcttccgtg gcgcaggcgc cgcctcaagc accgactcgc    300
tggacacgct gagcaacggg ccggagggct gcatggtggc ggtggccacc tcacgcagtg    360
agaaggagca gctgcaggcg ctgaacgacc gcttcgccgg gtacatcgac aaggtgcggc    420
agctggaggc gcacaaccgc agcctggagg gcgaggctgc ggcgctgcgg cagcagcagg    480
cgggccgctc cgctatgggc gagctgtacg agcgcgaggt ccgcgagatg cgcggcgcgg    540
tgctgcgcct gggcgcggcg cgcggtcagc tacgcctgga gcaggagcac ctgctcgagg    600
acatcgcgca cgtgcgccag cgcctagacg acgaggcccg gcagcgagag gaggccgagg    660
cggcggcccg cgcgctggcg cgcttcgcgc aggaggccga ggcggcgcgc gtggacctgc    720
agaagaaggc gcaggcgctg caggaggagt gcggctacct gcggcgccac caccaggaag    780
aggtgggcga gctgctcggc cagatccagg gctccggcgc cgcgcaggcg cagatgcagg    840
ccgagacgcg cgacgccctg aagtgcgacg tgacgtcggc gctgcgcgag attcgcgcgc    900
agcttgaagg ccacgcggtg cagagcacgc tgcagtccga ggagtggttc cgagtgaggc    960
tggaccgact gtcggaggca gccaaggtga acacagacgc tatgcgctca gcgcaggagg   1020
agataactga gtaccggcgt cagctgcagg ccaggaccac agagctggag gcactgaaaa   1080
gcaccaagga ctcactggag aggcagcgct ctgagctgga ggaccgtcat caggccgaca   1140
ttgcctccta ccaggaagcc attcagcagc tggacgctga gctgaggaac accaagtggg   1200
agatggccgc ccagctgcga gaataccagg acctgctcaa tgtcaagatg gctctggata   1260
tagagatagc cgcttacaga aaactcctgg aaggtgaaga gtgtcggatt ggctttggcc   1320
caattccttt ctcgcttcca gaaggactcc ccaaaattcc ctctgtgtcc actcacataa   1380
aggtgaaaag cgaagagaag atcaaagtgg tggagaagtc tgagaaagaa actgtgattg   1440
tggaggaaca gacagaggag acccaagtga ctgaagaagt gactgaagaa gaggagaaag   1500
aggccaaaga ggaggagggc aaggaggaag aagggggtga agaagaggag gcagaagggg   1560
gagaagaaga aacaaagtct cccccagcag aagaggctgc atccccagag aaggaagcca   1620
agtcaccagt aaaggaagag gcaaagtcac cggctgaggc caagtcccca gagaaggagg   1680
```

-continued

```
aagcaaaatc cccagccgaa gtcaagtccc ctgagaaggc caagtctcca gcaaaggaag   1740
aggcaaagtc accgcctgag gccaagtccc cagagaagga ggaagcaaaa tctccagctg   1800
aggtcaagtc ccccgagaag gccaagtccc cagcaaagga agaggcaaag tcaccggctg   1860
aggccaagtc tccagagaag gccaagtccc cagtgaagga agaagcaaag tcaccggctg   1920
aggccaagtc cccagtgaag gaagaagcaa aatctccagc tgaggtcaag tccccggaaa   1980
aggccaagtc tccaacgaag gaggaagcaa agtcccctga gaaggccaag tccccagaga   2040
aggaagaggc caagtcccct gagaaggcca agtccccagt gaaggcagaa gcaaagtccc   2100
ctgagaaggc caagtcccca gtgaaggcag aagcaaagtc ccctgagaag gccaagtccc   2160
cagtgaagga agaagcaaag tcccctgaga aggccaagtc cccagtgaag gaagaagcaa   2220
agtcccctga gaaggccaag tccccagtga aggaagaagc aaagaccccc gagaaggcca   2280
agtccccagt gaaggaagaa gctaagtccc cagagaaggc caagtcccca gagaaggcca   2340
agactcttga tgtgaagtct ccagaagcca agactccagc gaaggaggaa gcaaggtccc   2400
ctgcagacaa attccctgaa aaggccaaaa gccctgtcaa ggaggaggtc aagtccccag   2460
agaaggcgaa atctcccctg aaggaggatg ccaaggcccc tgagaaggag atcccaaaaa   2520
aggaagaggt gaagtcccca gtgaaggagg aggagaagcc ccaggaggtg aaagtcaaag   2580
agcccccaaa gaaggcagag gaagagaaag cccctgccac accaaaaaca gaggagaaga   2640
aggacagcaa gaaagaggag gcacccaaga aggaggctcc aaagcccaag gtggaggaga   2700
agaaggaacc tgctgtcgaa aagcccaaag aatccaaagt tgaagccaag aaggaagagg   2760
ctgaagataa gaaaaaagtc cccaccccag agaaggaggc tcctgccaag gtggaggtga   2820
aggaagacgc taaacccaaa gaaaagacag aggtagccaa gaaggaacca gatgatgcca   2880
aggccaagga acccagcaaa ccagcagaga agaaggaggc agcaccggag aaaaaagaca   2940
ccaaggagga gaaggccaag aagcctgagg agaaacccaa gacagaggcc aaagccaagg   3000
aagatgacaa gaccctctca aaagagccta gcaagcctaa ggcagaaaag gctgaaaaat   3060
cctccagcac agaccaaaaa gacagcaagc ctccagagaa ggccacagaa gacaaggccg   3120
ccaaggggaa gtaaggcagg gagaaaggaa catccggaac agccaaagaa actcagaaga   3180
gtcccggagc tcaaggatca gagtaacaca attttcactt tttctgtctt tatgtaagaa   3240
gaaactgctt agatgacggg gcctccttct tcaaacagga atttctgtta gcaatatgtt   3300
agcaagagag ggcactccca ggcccctgcc cccaggccct ccccaggcga tggacaatta   3360
tgatagctta tgtagctgaa tgtgatacat gccgaatgcc acacgtaaac acttgactat   3420
aaaaactgcc cccctccttt ccaaataagt gcatttattg cctctatgtg caactgacag   3480
atgaccgcaa taatgaatga gcagttagaa atacattatg cttgagatgt cttaacctat   3540
tcccaaatgc cttctgtttt ccaaaggagt ggtcaagccc ttgcccagag ctctctattc   3600
tggaagagcg gtccaggtgg ggccggggac tggccactga attatgccag ggcgcacttt   3660
ccactggagt tcactttcaa ttgcttctgt gcaataaaac caagtgctta taaaatgaaa   3720
a                                                                   3721
```

<210> SEQ ID NO 65
<211> LENGTH: 559
<212> TYPE: PRT
<213> ORGANISM: Homo sapiens

<400> SEQUENCE: 65

Met Ala Asp Glu Arg Lys Asp Glu Ala Lys Ala Pro His Trp Thr Ser
1               5                   10                  15

Ala Pro Leu Thr Glu Ala Ser Ala His Ser His Pro Pro Glu Ile Lys
            20                  25                  30

Asp Gln Gly Gly Ala Gly Glu Gly Leu Val Arg Ser Ala Asn Gly Phe
        35                  40                  45

Pro Tyr Arg Glu Asp Glu Glu Gly Ala Phe Gly Glu His Gly Ser Gln
    50                  55                  60

Gly Thr Tyr Ser Asn Thr Lys Glu Asn Gly Ile Asn Gly Glu Leu Thr
65                  70                  75                  80

Ser Ala Asp Arg Glu Thr Ala Glu Glu Val Ser Ala Arg Ile Val Gln
                85                  90                  95

Val Val Thr Ala Glu Ala Val Ala Val Leu Lys Gly Glu Gln Glu Lys
            100                 105                 110

Glu Ala Gln His Lys Asp Gln Thr Ala Ala Leu Pro Leu Ala Ala Glu
        115                 120                 125

Glu Thr Ala Asn Leu Pro Pro Ser Pro Pro Pro Ser Pro Ala Ser Glu
    130                 135                 140

Gln Thr Val Thr Val Glu Glu Ala Ala Gly Gly Glu Ser Ala Leu Ala
145                 150                 155                 160

Pro Ser Val Phe Lys Gln Ala Lys Asp Lys Val Ser Asn Ser Thr Leu
                165                 170                 175

Ser Lys Ile Pro Ala Leu Gln Gly Ser Thr Lys Ser Pro Arg Tyr Ser
            180                 185                 190

Ser Ala Cys Pro Ser Thr Thr Lys Arg Ala Thr Phe Ser Asp Ser Leu
        195                 200                 205

Leu Ile Gln Pro Thr Ser Ala Gly Ser Thr Asp Arg Leu Pro Tyr Ser
    210                 215                 220

Lys Ser Gly Asn Lys Asp Gly Val Thr Lys Ser Pro Glu Lys Arg Ser
225                 230                 235                 240

Ser Leu Pro Arg Pro Ser Ser Ile Leu Pro Pro Arg Arg Gly Val Ser
                245                 250                 255

Gly Asp Arg Asp Glu Asn Ser Phe Ser Leu Asn Ser Ser Ile Ser Ser
            260                 265                 270

Ser Ala Arg Arg Thr Thr Arg Ser Glu Pro Ile Arg Arg Ala Gly Lys
        275                 280                 285

Ser Gly Thr Ser Thr Pro Thr Thr Pro Gly Ser Thr Ala Ile Thr Pro
    290                 295                 300

Gly Thr Pro Pro Ser Tyr Ser Ser Arg Thr Pro Gly Thr Pro Gly Thr
305                 310                 315                 320

Pro Ser Tyr Pro Arg Thr Pro His Thr Pro Gly Thr Pro Lys Ser Ala
                325                 330                 335

Ile Leu Val Pro Ser Glu Lys Lys Val Ala Ile Ile Arg Thr Pro Pro
            340                 345                 350

Lys Ser Pro Ala Thr Pro Lys Gln Leu Arg Leu Ile Asn Gln Pro Leu
        355                 360                 365

Pro Asp Leu Lys Asn Val Lys Ser Lys Ile Gly Ser Thr Asp Asn Ile
    370                 375                 380

Lys Tyr Gln Pro Lys Gly Gly Gln Val Arg Ile Leu Asn Lys Lys Ile
385                 390                 395                 400

Asp Phe Ser Lys Val Gln Ser Arg Cys Gly Ser Lys Asp Asn Ile Lys
                405                 410                 415

```
His Ser Ala Gly Gly Gly Asn Val Gln Ile Val Thr Lys Lys Ile Asp
            420                 425                 430

Leu Ser His Val Thr Ser Lys Cys Gly Ser Leu Lys Asn Ile Arg His
        435                 440                 445

Arg Pro Gly Gly Gly Arg Val Lys Ile Glu Ser Val Lys Leu Asp Phe
    450                 455                 460

Lys Glu Lys Ala Gln Ala Lys Val Gly Ser Leu Asp Asn Ala His His
465                 470                 475                 480

Val Pro Gly Gly Gly Asn Val Lys Ile Asp Ser Gln Lys Leu Asn Phe
                485                 490                 495

Arg Glu His Ala Lys Ala Arg Val Asp His Gly Ala Glu Ile Ile Thr
            500                 505                 510

Gln Ser Pro Gly Arg Ser Ser Val Ala Ser Pro Arg Arg Leu Ser Asn
        515                 520                 525

Val Ser Ser Ser Gly Ser Ile Asn Leu Leu Glu Ser Pro Gln Leu Ala
    530                 535                 540

Thr Leu Ala Glu Asp Val Thr Ala Ala Leu Ala Lys Gln Gly Leu
545                 550                 555
```

<210> SEQ ID NO 66
<211> LENGTH: 2286
<212> TYPE: DNA
<213> ORGANISM: Homo sapiens

<400> SEQUENCE: 66

```
ggcgctcggg ctgcgcgggc tctgggcagc agcagcagca gcagcagcat cctctcttcc     60

tttacttccc ttccgcttct ttctcttcct tctccttctt tttccccccc ctccccttct    120

tcccctaacc cttctacccc tctccttttt ctccggaggg cgctaagtcc gtgagcggtg    180

gcagtcgcga ccgcgggtgc atccagtttc tgcgcccaga ttttattgat ctaatccaaa    240

gtatcttata acttctggct ggaattaaga ttcttcagct tgtctctaac cgaggaagca    300

ttgattggga gctactcatt cagaaaatta aaagaaagaa gccagaaaat attatcaacc    360

ctttgagaac acgacacaac gaactttata ttttaccact tccttgaata gttgcaggag    420

aaataacaag gcattgaaga atggcagatg aacggaaaga cgaagcaaag gcacctcact    480

ggacctcagc accgctaaca gaggcatctg cacactcaca tccacctgag attaaggatc    540

aaggcggagc aggggaagga cttgtccgaa gcgccaatgg attcccatac agggaggatg    600

aagagggtgc ctttggagag catgggtcac agggcaccta ttcaaatacc aaagagaatg    660

ggatcaacgg agagctgacc tcagctgaca gagaaacagc agaggaggtg tctgcaagga    720

tagttcaagt agtcactgct gaggctgtag cagtcctgaa aggtgaacaa gagaaagaag    780

ctcaacataa agaccagact gcagctctgc ctttagcagc tgaagaaaca gctaatctgc    840

ctccttctcc acccccatca cctgcctcag aacagactgt cacagtggag gaagcagcag    900

gtggggaatc agctctggct cccagtgtat ttaaacaggc aaaggacaaa gtctctaatt    960

ctaccttgtc aaagattcct gctttacagg gtagcacaaa gtccccaaga tacagctcag   1020

cctgccctag cacgactaaa agggctacat tttctgacag tttattaata cagcccacct   1080

cagcaggctc cacagaccgt ttgccatact caaaatcagg gaacaaggac ggagtaacca   1140

agagcccaga aaagcgctct tctctcccaa gaccttcctc cattctccct cctcggcgag   1200

gtgtgtcagg agacagagat gagaattcct tctctctcaa cagttctatc tcttcttcag   1260

cacggcggac caccaggtca gagccaattc gcagagcagg gaagagtggt acctcaacac   1320
```

-continued

```
ccactacccc tgggtctact gccatcactc ctggcacccc accaagttat tcttcacgca   1380

caccaggcac tcctggaacc cctagctatc ccaggacccc tcacacacca ggaacccccca  1440

agtctgccat cttggtgccg agtgagaaga aggtcgccat catacgtact cctccaaaat   1500

ctcctgcgac tcccaagcag cttcggctta ttaaccaacc actgccagac ctgaagaatg   1560

tcaaatccaa aatcggatca acagacaaca tcaaatacca gcctaaaggg gggcaggtta   1620

ggattttaaa caagaagatc gattttagca aagttcagtc cagatgtggt tccaaggata   1680

acatcaaaca ttcggctggg ggcggaaatg tacaaattgt taccaagaaa atagacctaa   1740

gccatgtgac atccaaatgt ggctctctga agaacatccg ccacaggcca ggtggcggac   1800

gtgtgaaaat tgagagtgta aaactagatt tcaaagaaaa ggcccaagct aaagttggtt   1860

ctcttgataa tgctcatcat gtacctggag gtggtaatgt caagattgac agccaaaagt   1920

tgaacttcag agagcatgct aaagcccgtg tggaccatgg ggctgagatc attacacagt   1980

ccccaggcag atccagcgtg gcatcacccc gacgactcag caatgtctcc tcgtctggaa   2040

gcatcaacct gctcgaatct cctcagcttg ccactttggc tgaggatgtc actgctgcac   2100

tcgctaagca gggcttgtga atatttctca tttagcattg aaataataat atttaggcat   2160

gagctcttgg caggagtggg ctctgagcag ttgttatatt cattctttat aaaccataaa   2220

ataaataatc tcatccccaa aaaaaaaaaa aaaaaaaaaa aaaaaaaaaa aaaaaaaaaa   2280

aaaaaa                                                              2286
```

<210> SEQ ID NO 67
<211> LENGTH: 360
<212> TYPE: PRT
<213> ORGANISM: Homo sapiens

<400> SEQUENCE: 67

```
Met Glu Leu Asp Phe Gly His Phe Asp Glu Arg Asp Lys Thr Ser Arg
1               5                   10                  15

Asn Met Arg Gly Ser Arg Met Asn Gly Leu Pro Ser Pro Thr His Ser
            20                  25                  30

Ala His Cys Ser Phe Tyr Arg Thr Arg Thr Leu Gln Ala Leu Ser Asn
        35                  40                  45

Glu Lys Lys Ala Lys Lys Val Arg Phe Tyr Arg Asn Gly Asp Arg Tyr
    50                  55                  60

Phe Lys Gly Ile Val Tyr Ala Val Ser Ser Asp Arg Phe Arg Ser Phe
65                  70                  75                  80

Asp Ala Leu Leu Ala Asp Leu Thr Arg Ser Leu Ser Asp Asn Ile Asn
                85                  90                  95

Leu Pro Gln Gly Val Arg Tyr Ile Tyr Thr Ile Asp Gly Ser Arg Lys
            100                 105                 110

Ile Gly Ser Met Asp Glu Leu Glu Glu Gly Glu Ser Tyr Val Cys Ser
        115                 120                 125

Ser Asp Asn Phe Phe Lys Lys Val Glu Tyr Thr Lys Asn Val Asn Pro
    130                 135                 140

Asn Trp Ser Val Asn Val Lys Thr Ser Ala Asn Met Lys Ala Pro Gln
145                 150                 155                 160

Ser Leu Ala Ser Ser Asn Ser Ala Gln Ala Arg Glu Asn Lys Asp Phe
                165                 170                 175

Val Arg Pro Lys Leu Val Thr Ile Ile Arg Ser Gly Val Lys Pro Arg
            180                 185                 190
```

```
Lys Ala Val Arg Val Leu Leu Asn Lys Lys Thr Ala His Ser Phe Glu
        195                 200                 205

Gln Val Leu Thr Asp Ile Thr Glu Ala Ile Lys Leu Glu Thr Gly Val
    210                 215                 220

Val Lys Lys Leu Tyr Thr Leu Asp Gly Lys Gln Val Thr Cys Leu His
225                 230                 235                 240

Asp Phe Phe Gly Asp Asp Asp Val Phe Ile Ala Cys Gly Pro Glu Lys
                245                 250                 255

Phe Arg Tyr Ala Gln Asp Asp Phe Ser Leu Asp Glu Asn Glu Cys Arg
            260                 265                 270

Val Met Lys Gly Asn Pro Ser Ala Thr Ala Gly Pro Lys Ala Ser Pro
        275                 280                 285

Thr Pro Gln Lys Thr Ser Ala Lys Ser Pro Gly Pro Met Arg Arg Ser
    290                 295                 300

Lys Ser Pro Ala Asp Ser Ala Asn Gly Thr Ser Ser Ser Gln Leu Ser
305                 310                 315                 320

Thr Pro Lys Ser Lys Gln Ser Pro Ile Ser Thr Pro Thr Ser Pro Gly
                325                 330                 335

Ser Leu Arg Lys His Lys Asp Leu Tyr Leu Pro Leu Ser Leu Asp Asp
            340                 345                 350

Ser Asp Ser Leu Gly Asp Ser Met
        355                 360
```

<210> SEQ ID NO 68
<211> LENGTH: 9135
<212> TYPE: DNA
<213> ORGANISM: Homo sapiens

<400> SEQUENCE: 68

```
ctggcaggaa tttcttgctt ggagctcaga caacaaaggc atagagagat tggttttctt     60

tctctcagca tctccaccca accagcagaa aaccggtctc tgaggttcca ccaaaatatg    120

gaacttgatt ttggacactt tgacgaaaga gataagacat ccaggaacat gcgaggctcc    180

cggatgaatg ggttgcctag ccccactcac agcgcccact gtagcttcta ccgaaccaga    240

accttgcagg cactgagtaa tgagaagaaa gccaagaagg tacgtttcta ccgcaatggg    300

gaccgctact tcaaggggat tgtgtacgct gtgtcctctg accgttttcg cagctttgac    360

gccttgctgg ctgacctgac gcgatctctg tctgacaaca tcaacctgcc tcagggagtg    420

cgttacattt acaccattga tggatccagg aagatcggaa gcatggatga actggaggaa    480

ggggaaagct atgtctgttc ctcagacaac ttctttaaaa aggtggagta caccaagaat    540

gtcaatccca actggtctgt caacgtaaaa acatctgcca atatgaaagc cccccagtcc    600

ttggctagca gcaacagtgc acaggccagg gagaacaagg actttgtgcg ccccaagctg    660

gttaccatca tccgcagtgg ggtgaagcct cggaaggctg tgcgtgtgct tctgaacaag    720

aagacagccc actcttttga gcaagtcctc actgatatca cagaagccat caaactggag    780

accggggttg tcaaaaaact ctacactctg gatggaaaac aggtaacttg tctccatgat    840

ttctttggtg atgatgatgt gtttattgcc tgtggtcctg aaaaatttcg ctatgctcag    900

gatgattttt ctctggatga aaatgaatgc cgagtcatga agggaaaccc atcagccaca    960

gctggcccaa aggcatcccc aacacctcag aagacttcag ccaagagccc tggtcctatg   1020

cgccgaagca agtctccagc tgactcagca aacggaacct ccagcagcca gctctctacc   1080

cccaagtcta agcagtctcc catctctacg cccaccagtc ctggcagcct ccggaagcac   1140
```

-continued

```
aaggacctgt acctgcctct gtccttggat gactcggact cgcttggtga ttccatgtaa   1200
aggaggggag agtgctcaga gtccagagta caaatccaag cctatcattg tagtagggta   1260
cttctgctca agtgtccaac agggctattg gtgctttcaa gtttttattt tgttgttgtt   1320
gttattttga aaaacacatt gtaatatgtt gggtttattt tcctgtgatt tctcctctgg   1380
gccactgatc cacagttacc aattatgaga gatagattga taaccatcct ttggggcagc   1440
attccaggga tgcaaaatgt gctagtccat gacctttcaa tggaaagctt aggtgcctgc   1500
gttatatttg ccctgtctaa ttttgcccat acagtcttcc ttctgtagag ggctgtttac   1560
atatacagca cttaaaatgt ttgtgtggga aaaaaaaaac tcattggcag atccaagaat   1620
gacaaacaca agtgcccctt ttctctggat ctcaagaatg gtggaggacc ctggaaggac   1680
agcaaggcag ctccccagcc tcactcttca ctcctgattg aggcccgggt ttgttgtcca   1740
gcaccaattc tggctgtcaa tggggagaaa taaaccaaca acttataatt gtgacaccag   1800
atgcttagga tcctggtgct gggttagcta agagaataga cagaattgga aaatactgca   1860
gacatttccg aagagtttat aaagcacagt gaattcctgg tcaatctctc cactgaggca   1920
atttggaatc aataagcaat tgataatagt ttggagtaag ggacttcata tacctgattc   1980
ctctagaagg ctgtctaaca taccacatga ttacatgaac tgtatggtat ccatctatct   2040
ctgttctatt gaatgccttg ttaacagcca acactgaaaa cactgtgaga atttgttttc   2100
aggtctgaca cctttcagtc tctttttata gcaagaaatc aatatccttt ttataaaaat   2160
tcatgtctgt atttcaggag caaactcttc aggctccttt tttataaact ggtgattttt   2220
cttttgtcta aaaaacacat gaagaaaatt taccaaaaaa aaaaaaaaaa gcagaagaat   2280
aatgtagttt agaaattatg ctgtcactgc caaacagtaa cctccaggag aaaacaagat   2340
gaatagcaga ggccaattca atagaatcag tttttgata gctttttaac agttatgctt    2400
gcattaataa tttcaatgtg gaccagacat tctaattata ttttaaatga aatgttacag   2460
catattttaa gcaactcttt ttatctataa tcctaatatt tcatactgaa gacacagaaa   2520
tctttcactt gtctttaaca ttagaaagga tttctcttta ctaaggactg atcatttgaa   2580
atagttttca gtcttttgag atacaggttt ataacactgc tttttttttt ctgtaatcat   2640
agcccataat ggcaaagaca actaaattta agtgaaggtc atgcatgcca attctgtgtt   2700
tgcttttagc agatatgaag atttccttat ttctttgtaa ttgtgcagat attttgaaag   2760
gcacagcatt cgaagccaag ctgctgtttg gctactgaat ggcttgcagt tgttcctcca   2820
ctctaaatgg aatgagcttg ctgtgtgtgt gtgtggtggt ggtgggaggg ggtggtgcat   2880
gtgtgtgtgt gtgtgtgcat ctgcagctgc ttcaaaatta ggaaatacta caggacaccc   2940
ctgtaatgga ttggtggcaa ctgggtggca ctgctgatgt gcactgtgta ggggggaacc   3000
cagtggtggt ggggtagctc agatgcccct agacaagctt cagatgtctg tagctaccag   3060
aaacattttc ggttcaggaa aagtgagatg atggtagtac tggtttctgg tgaaattgaa   3120
gaaccccaaa tgatgaggat ctctttttgc cccctctcct tttttgtag acccattcaa    3180
aaccattaat aagcccattt tactaagccc ctatttcttt ctagaagctc agggttttct   3240
tagtgcctcc cagaacattt tgtagttaat tgggaaaaag tgatacttgg attagggggt   3300
gtgggcataa agaatggtgg gaggcctgat tttaaacttc aggccagaac cccccaatgac  3360
tccacccata gtctcacttt aggtctcatt tagtccatca cctttatttt aagttgagga   3420
agtggaggct ggtaaagagc aggaccagag gaagaatcca gatttcctta tgcttgggcc   3480
tcacactagc tctctgagta tttccttgat tgcggtatat gtactactag aaaataccaa   3540
```

-continued

```
atggatatat tttctttagg ataacctttg aaccaacaat cttcaataac aatagtacat   3600
cttccatctt acttttaatc gagtataagg aaatgtttct ttatggccat tttggaggga   3660
gcaggggatg aggcttggca tagtccaaaa tttaagtctc caataattaa ttgcatttta   3720
aattggccca ctttcaaggc aatttttttt gtgtgtctgt aactgagctc ctccacccct   3780
gtcattcact tccaatttta cccaatccaa ttttagcact caagttccat tgtgttaatt   3840
tctgcacggt caacaaacat caagtcagca agcatttgcc accactccct atacttctcc   3900
ctccttctta cacacacaca cacacacaca cacacaatcc atctcttgct tgttcctacc   3960
tcctgatttt tcttccctac agaaatagaa atagggacaa agaaggggaa aatgtatata   4020
ttggggctgg gctgaacaac taacttcata agtagtatta actaggggta aattgagaga   4080
aaagctcctt ttctcttcac tgttttggaa aggatagcca ttagcatgac tgctttgtgt   4140
ccttatggac tttagtatta gcctagattg aattatagcg ttttctagct ggaaggaacc   4200
ttaagatcac atcatctact cctctactcc aaatttctca ttcttcaggc caggaaaccg   4260
agacacagag gtaaagtaat ttccccaagg tcacacagct ggctggggca ggattgggtt   4320
tacaacccac atctcctggc tcttattcca gggccttttc ccactaagta gtattgcctt   4380
ccattaggct cctgagagtt atttctcagg gtcatgttgc atcttggagc cacatgctgc   4440
tgccctgatc tcagtgggaa atccacccag caacctaata cagccccttt tccctgcatt   4500
cacctggttc ccatccacat gggttgcaga tgtccttgaa gagagtgagg cattgagggc   4560
caataggagc aatggggtcc ctggccttgt ccatctgatt caggagatca ctgctccatc   4620
gtgaggagcc ctctgaatag ccccccactg aatgcttgcc ttgcccaaat ggaatggagg   4680
aagattgatt ttctccatca gttcaccttg tgtcatctca taatggttgg tctttccagg   4740
ctgagggaaa tgtttcttgt ttccagagta gaaaaagaaa gagtggaaca atagctttgt   4800
tcatcctaac tttctgagat ggcttttcaa cattttaaaa aaactagtgt ggctaccatt   4860
cactggcaat gatttctttt agaatatggg agtaagatga gctagagaaa ataacctggt   4920
ctcactgtgg ttgccctcat ccacaatgtc cccaaagcca tcctgctctg atgaggacaa   4980
tttccaggta taagcaaggg gctttgtgac aaaaatgtac cctggctgat gttaaacatt   5040
ggctcctgtg tttgcaccaa aatagcaagc tgtgtgctct atacactctt cccatcgtct   5100
tgtgtacact gctcctgtgg ccttccacag cagaaaccag ggcaaaaggg tccaaacaca   5160
tggttttcct tgctgcaagg ctcttcctgg gaactaaggg ggtatttatt agttcagttc   5220
taagagacct ccttctgggc ttaccccact cctcaggtac ttctctctcc ttcctccttc   5280
tcctccacag tcacaagtaa ccaaggaacc tgaaagtgga tgtgtagcta tttgaagaag   5340
gcaaggaacc ctgagattct tctttgaatc ctctagtcca agtcttagac cagtgattgg   5400
tgcttacctt gaacaaaatt ttgtctgtgt tcctaatccc ttcaatactc tgggtacaat   5460
gctcccaatc accctgcaca tttgattcta aatggctttt attttttaaa aatccatatc   5520
cctaggacaa gagaacagga tgcctatatc cccaaaatga gctccaggac actgatggga   5580
atgatcccaa agatcacccc acctcagaaa cgtctgtgcc aagagacttc cccagataga   5640
aacactggga cagtggtttg aacgacttct tttatggttg tccagtttgc tatggaaata   5700
aaaggcattg atttttaaa aagatgattg gaacctgtct ttggccacat agggccactt   5760
ggatccattt ccaggcctta ctcatatatt gccttcactg aagggctttg gctttaagtc   5820
ccagactggt ctcccaagtg aaccataagt gttttggagc tcatctgggg tgaggcatga   5880
gaatgttgcc ccatctatcc cttcaggaaa aggtgccttc cctccctttc tcctaaagcc   5940
```

```
tggtccccag aaattgtttt tgtctccaaa agtctagtat ggtctttata cacccagact   6000
cttagtgttg cgtcctgcct tgtttccttg ttaaggatct atgcagacct cccgctttgg   6060
cttagctagc gtgacattgg ctatcatttg acaagactaa cttttttttt tttttttttt   6120
tgactgagtc tccctctgtc acctaggctg gagtgcagtg gcacaatctt ggctcgctgc   6180
aaccttcacc cttcacctcc caggtcgaag cgattctcct gcctcagtct cccgagtagc   6240
tgggattaca ggcgtgcgcc accaaatctg gctatttttt tattattatt atttttagta   6300
gagatggggt ttcaccatgt tggccagact ggtcttgaac tcttggcctc aaattatctg   6360
cccacctcgg cctcccaaag tgctgggatt acaggcatga gccaccatgc ccagctgaca   6420
agactaattt tttatccctt ggtttattgg cttcaacatc ttctggaatc agaggtgatt   6480
ttttcttacc ttggatgcct gagactaggg gagtatagaa ttccaattgg taattaaggc   6540
atctttctgc tcctgatcag aagggcaggt tagttgggag aggtcagatg gcacaacaga   6600
agtcaccttg taagtaaggc aaagacttga aggcattagc gtttctcatt actaggtcaa   6660
taacctgagg gaatcaatgg ctttttgccg ctctacctct tgtgtatctc tttgactttt   6720
ctttctctgt ctagtttcct ctgttctcag tttatattct atgttatcag tctctctttc   6780
cacagtacaa acatccatcc tttctcctgt gcaattctgt ctctccctct tattatcttt   6840
atttgtactt tttccttcct ccctgtctag gcattgggca tgtgcctctt cttagcctgt   6900
gattttgcct tgggactgat gataaattat ttccagattc aatcagccct ggtcctaccc   6960
cagtccaatc agaagtatgt tggtgggaat caacctgatc ctggcccttt cttcttctcc   7020
attttcattc gtaatccccc tcagcagatc tttacaagca gtttccttat agctcatgta   7080
tctttaggtc tttgccttcc aagcactgta cagaatactt tgtggttcct ttttagtctg   7140
acattttgtg gagcagtgaa gcgtgctcag agacataatc agctgaagag aaaaaatcca   7200
cccatggatt tatatcagct aaatactaat aattgatttt gtttgatgtg cccataattt   7260
ttaaagctgc aatataatat aatgagggac cacaggtaat ttctcctgtc atttgttttg   7320
gctggatggg ggtgggggag taattgctta aagttttacc attacacatt aaactctcta   7380
taataatctt gtttggggct tgctaactgt tgagctgttt taactaaact ggtaggcaat   7440
cggagttgat ttaaatgaaa agataattta acaaatctat actataaaaa gagacatttg   7500
cttaattgac atgtattttt tccttctgag tcacctaaac atttactctt gacaccaact   7560
gttcatgata ctgaatagac agtccatata agagaaatta gtggacctaa agaagccaga   7620
ttgtaggtgt taatttatta aacagagtgc aaagcccttg gaaatgtcac tgcttggcaa   7680
taccatatgg aatgccaaaa tttacaatga cttttcttta taagttatcc aaaagggatt   7740
tgaacaagta agaggttatg ccaaaatgtc tccaatgtat ggtcctgtaa tatattgcag   7800
cttgaagcca atgatccctt atgacttgta tacaactaat gcatgtttta ttgaattttg   7860
catttcccac gtgtggtaag ttctttaaaa tgtttttgat caccttttttg tgccattaaa   7920
cttgtacaga aaatgttttt atggccattt tcaaagggag aaagtttaaa atggaaacag   7980
cccacccttt ctgccctata gctgtagtta gaattgagta cctgtagcaa aacagctgta   8040
attggtggtt gtagtgttag aggtgttagc ttgctagtga ctagctttgg agagtaaatg   8100
catggtattg tacatcacat ttcttaactc gttttaacct ctgaaaagaa tatattcttc   8160
tttgtagtcc ttcttcccac ccccttgccc tctccctctc cctgctccca gttgtcttac   8220
agttgtaaat atctgatttg aggcccaata actcttgcca agtaaagtca gcaaacaaca   8280
aacaaaccaa aatgtgggga aaaggcattt ctcaaccatc tctcagcagt tattgatcat   8340
```

```
ttcttaagga acagcattgt gatcaaagac tcaactttac gtaaaaatca gtggtaaatt    8400

ggggttgtat ttggccattt gattacattt caggattgaa tagttttcag aatcacatgt    8460

aatccaaaga cagtaggtag tgatgtccct tatccctgca gctgttttaa gatagagacc    8520

tcagaagact ctgcttgacc gatgaccaat aattatttga aaaaaaaaga aaaaatgaga    8580

gaaataaaac agatatttaa gaactttagc cacctattta gaatagttat agccagaaaa    8640

aaaaacaagg gcatgagttc aaatgcatta ctatcagtgt cctaggcaat acctaaccta    8700

ctctgaaatt gtgattcaaa agcagtattt caagaggcat tctccttttt tggtttgctg    8760

accccacttg gactggtagg tttggtgagg cccccataaa ccagctggag cagacccttt    8820

tcatctcctg tgcctgtaac acccctcttc ccccaccccc tccgcaattc aatgagggct    8880

ttcttgggtc agaggacttc aaggttgtct agagaagttt gccatgtgtg taaggtgctg    8940

tgaactgtga gtgctgaaga ttcgcagcat tcaataccag gcagccaaag agctgctctt    9000

gcaattattt tggctctcaa gctctgttct tcatcgcatt ctcatttctg tgtacatttg    9060

caagatgtgt gtaatgtcat tttccaaaaa taaaatttga tttcaataaa aaaaaaaaaa    9120

aaaaaaaaaa aaaaa                                                     9135
```

<210> SEQ ID NO 69
<211> LENGTH: 456
<212> TYPE: PRT
<213> ORGANISM: Homo sapiens

<400> SEQUENCE: 69

```
Met Arg Lys Ser Pro Gly Leu Ser Asp Cys Leu Trp Ala Trp Ile Leu
1               5                   10                  15

Leu Leu Ser Thr Leu Thr Gly Arg Ser Tyr Gly Gln Pro Ser Leu Gln
            20                  25                  30

Asp Glu Leu Lys Asp Asn Thr Thr Val Phe Thr Arg Ile Leu Asp Arg
        35                  40                  45

Leu Leu Asp Gly Tyr Asp Asn Arg Leu Arg Pro Gly Leu Gly Glu Arg
    50                  55                  60

Val Thr Glu Val Lys Thr Asp Ile Phe Val Thr Ser Phe Gly Pro Val
65                  70                  75                  80

Ser Asp His Asp Met Glu Tyr Thr Ile Asp Val Phe Phe Arg Gln Ser
                85                  90                  95

Trp Lys Asp Glu Arg Leu Lys Phe Lys Gly Pro Met Thr Val Leu Arg
            100                 105                 110

Leu Asn Asn Leu Met Ala Ser Lys Ile Trp Thr Pro Asp Thr Phe Phe
        115                 120                 125

His Asn Gly Lys Lys Ser Val Ala His Asn Met Thr Met Pro Asn Lys
    130                 135                 140

Leu Leu Arg Ile Thr Glu Asp Gly Thr Leu Leu Tyr Thr Met Arg Leu
145                 150                 155                 160

Thr Val Arg Ala Glu Cys Pro Met His Leu Glu Asp Phe Pro Met Asp
                165                 170                 175

Ala His Ala Cys Pro Leu Lys Phe Gly Ser Tyr Ala Tyr Thr Arg Ala
            180                 185                 190

Glu Val Val Tyr Glu Trp Thr Arg Glu Pro Ala Arg Ser Val Val Val
        195                 200                 205

Ala Glu Asp Gly Ser Arg Leu Asn Gln Tyr Asp Leu Leu Gly Gln Thr
    210                 215                 220
```

-continued

```
Val Asp Ser Gly Ile Val Gln Ser Ser Thr Gly Glu Tyr Val Val Met
225                 230                 235                 240

Thr Thr His Phe His Leu Lys Arg Lys Ile Gly Tyr Phe Val Ile Gln
                245                 250                 255

Thr Tyr Leu Pro Cys Ile Met Thr Val Ile Leu Ser Gln Val Ser Phe
            260                 265                 270

Trp Leu Asn Arg Glu Ser Val Pro Ala Arg Thr Val Phe Gly Val Thr
        275                 280                 285

Thr Val Leu Thr Met Thr Thr Leu Ser Ile Ser Ala Arg Asn Ser Leu
    290                 295                 300

Pro Lys Val Ala Tyr Ala Thr Ala Met Asp Trp Phe Ile Ala Val Cys
305                 310                 315                 320

Tyr Ala Phe Val Phe Ser Ala Leu Ile Glu Phe Ala Thr Val Asn Tyr
                325                 330                 335

Phe Thr Lys Arg Gly Tyr Ala Trp Asp Gly Lys Ser Val Val Pro Glu
            340                 345                 350

Lys Pro Lys Lys Val Lys Asp Pro Leu Ile Lys Lys Asn Asn Thr Tyr
        355                 360                 365

Ala Pro Thr Ala Thr Ser Tyr Thr Pro Asn Leu Ala Arg Gly Asp Pro
    370                 375                 380

Gly Leu Ala Thr Ile Ala Lys Ser Ala Thr Ile Glu Pro Lys Glu Val
385                 390                 395                 400

Lys Pro Glu Thr Lys Pro Pro Glu Pro Lys Lys Thr Phe Asn Ser Val
                405                 410                 415

Ser Lys Ile Asp Arg Leu Ser Arg Ile Ala Phe Pro Leu Leu Phe Gly
            420                 425                 430

Ile Phe Asn Leu Val Tyr Trp Ala Thr Tyr Leu Asn Arg Glu Pro Gln
        435                 440                 445

Leu Lys Ala Pro Thr Pro His Gln
    450                 455
```

<210> SEQ ID NO 70
<211> LENGTH: 3440
<212> TYPE: DNA
<213> ORGANISM: Homo sapiens

<400> SEQUENCE: 70

```
agcggagcgg gcgagcaagg gagcgagcag gacaggagcc tgatcccaca gctgctgctc     60

cagcccgcga tgaggaaaag tccaggtctg tctgactgtc tttgggcctg gatcctcctt    120

ctgagcacac tgactggaag aagctatgga cagccgtcat tacaagatga acttaaagac    180

aataccactg tcttcaccag gattttggac agactcctag atggttatga caatcgcctg    240

agaccaggat tgggagagcg tgtaaccgaa gtgaagactg atatcttcgt caccagtttc    300

ggacccgttt cagaccatga tatggaatat acaatagatg tatttttccg tcaaagctgg    360

aaggatgaaa ggttaaaatt taaaggacct atgacagtcc tccggttaaa taacctaatg    420

gcaagtaaaa tctggactcc ggacacattt ttccacaatg gaaagaagtc agtggcccac    480

aacatgacca tgcccaacaa actcctgcgg atcacagagg atggcacctt gctgtacacc    540

atgaggctga cagtgagagc tgaatgtccg atgcatttgg aggacttccc tatggatgcc    600

catgcttgcc cactaaaatt tggaagttat gcttatacaa gagcagaagt tgtttatgaa    660

tggaccagag agccagcacg ctcagtggtt gtagcagaag atggatcacg tctaaaccag    720

tatgaccttc ttggacaaac agtagactct ggaattgtcc agtcaagtac aggagaatat    780
```

-continued

```
gttgttatga ccactcattt ccacttgaag agaaagattg gctactttgt tattcaaaca    840
tacctgccat gcataatgac agtgattctc tcacaagtct ccttctggct caacagagag    900
tctgtaccag caagaactgt ctttggagta acaactgtgc tcaccatgac aacattgagc    960
atcagtgcca gaaactccct ccctaaggtg gcttatgcaa cagctatgga ttggtttatt   1020
gccgtgtgct atgcctttgt gttctcagct ctgattgagt ttgccacagt aaactatttc   1080
actaagagag gttatgcatg ggatggcaaa agtgtggttc cagaaaagcc aaagaaagta   1140
aaggatcctc ttattaagaa aaacaacact tacgctccaa cagcaaccag ctacacccct   1200
aatttggcca ggggcgaccc gggcttagcc accattgcta aaagtgcaac catagaacct   1260
aaagaggtca agcccgaaac aaaaccacca gaacccaaga aaacctttaa cagtgtcagc   1320
aaaattgacc gactgtcaag aatagccttc ccgctgctat ttggaatctt taacttagtc   1380
tactgggcta cgtatttaaa cagagagcct cagctaaaag cccccacacc acatcaatag   1440
atcttttact cacattctgt tgttcagtcc tctgcactgg gaatttattt atgttctcaa   1500
cgcagtaatt cccatctgct ttattgcctc tgtcttaaag aatttgaaag tttccttatt   1560
ttcataattc atttaagaac aagagacccc tgtctggcag tctggagcaa agcagactat   1620
gcagcttgga gacaggattc tgacagagca agcgaaagag caaagtcatg tcagaaggag   1680
acagaatgag agagaaaaga gggggaagat ggttcaaaga tacaagaaaa agtagaaaaa   1740
aaaataacac ttaactaaaa cccctaggtc atttgtagat atatatttcc aaatattcta   1800
aaaaagatac tgtatatgtc aaaaatattt ttatgtgaag gtgtttcaaa gggtaaatta   1860
taaatgtttc atgaagaaaa aattttaaaa atctacgtct ttattacaca aactatggtg   1920
tgcttatgtt tttgttttgc tttttaaact gatgtatagc tttaacattt tgtttccaaa   1980
gctgaagatc cccattcttt ctctttgaaa aaaaaaaagg cctaatgcat tattttgtca   2040
taaaatgcta ttttaaaatt catggaactt tcatacgtaa aggtgcagtt gctcattgta   2100
gagcacattt agtccaatga agataaatgc tttaaatagt ttacttcact ttcatctgag   2160
cttttaccac tagactcaag gaagaataat tttaacagac atgtatactc catagaaact   2220
aaattaaaat agtttaaaaa tattcccttt ttcaccctat tttcagatag cacatgagcc   2280
caacactcac ttaattctca ttatgaagat gtttttagag gggcaaaaat attttgcaag   2340
ctctggaatt gttgaatgta ttcttttata taactacatt aaaagcttta gattgaaatt   2400
tatgactagc aaacaaaaat agaatatata aacgatatat gtaaatatac agcatgagat   2460
tgtacatttt ttactttttt aaaattgtgt tcttaaaata ttgtgtaaga atcactgcac   2520
ttagctgttg gaatgttgtt aaatgctatg gaaatacatt tagaacctgc atttaagaac   2580
agaacagcaa gtatgaacca catggaactt aaaacatatg ggtgtgaagt ccacttatgt   2640
agacaaaact tataatttcc aaactgttgt ctagtataca gtgatcagtt gctctctgtt   2700
caagtcattc cacacatttc cctattttag gctattataa tatagaaaga aaatgggaag   2760
cattagttgg agctagaaaa tgaactgtat attattgcta tatttgctaa taccaactat   2820
ttcaataagt gttgtaccat atgtagcatt aaatataaaa tacataaaag aatgtacaga   2880
aaatagcttt tattgagtaa tattacattt catttatact gtagcaatat atttgtaggt   2940
atactatgta agggctttaa ataaaagagg tccattaata cttccttata aaaattctag   3000
tctgtttcat tactgcccag atgttttaga gataaatatt tatgcagaag gtatttttga   3060
agtctccttt tgtctgatag agtttaacag atatttaaat ttagtgctca gaatccacaa   3120
gtcacggtct aaacacactt agaatactac agcataaatc tgttagcatt attgccaaat   3180
```

-continued

| | |
|---|---|
| aagacagttg ggatccaaac ccaagtcttg agcaatgttt ttctcaaaaa gctgctatcc | 3240 |
| aatgatatag gaaaatacat tgtgttttcc taaacacact tttcttttta aatgtgcttc | 3300 |
| attgtttgat ttggtcctgc ctaaatttca caagctaggc caatgaaggc tgaatcaaag | 3360 |
| acatttcatc caccaatatc atgtgtagat attatgtata gaaaataaaa taaattatgg | 3420 |
| ctccaaaaaa aaaaaaaaaa | 3440 |

COMPOSITIONS AND METHODS FOR NEURALGENESIS

RELATED APPLICATIONS

This application is a continuation application, filed under 35 U.S.C. § 120, of U.S. application Ser. No. 16/077,411, filed on Aug. 10, 2018, which is a national stage application, filed under 35 U.S.C. § 371, of International Stage Application No. PCT/US2017/017464, filed on Feb. 10, 2017, which claims the benefit of priority under 35 U.S.C. § 119(e) to U.S. Provisional Application No. 62/294,112, filed Feb. 11, 2016, all of which are incorporated herein by reference in their entireties.

STATEMENT AS TO FEDERALLY SPONSORED RESEARCH

The invention was made with government support under the following grant awarded by the National Institute of Health (NIH): U18TR000547. The government has certain rights in the invention.

SEQUENCE LISTING

The instant application contains a Sequence Listing which has been submitted electronically in ASCII format and is hereby incorporated by reference in its entirety. Said ASCII copy, created on Oct. 10, 2020, is named 048317-518C01US_SL.txt and is 329,101 bytes in size.

BACKGROUND OF THE INVENTION

Simple neural in vitro systems do not reflect the physiology, cellular interactions, or genetics of mammalian brain tissue. Accordingly, there is an unmet need to develop human models of brain disorders and/or diseases.

SUMMARY OF THE INVENTION

The present invention provides brain microphysiological systems (BMPS) that can be produced from induced pluripotent stem cells (iPSCs). Furthermore, the invention provides for reproducible BMPS that differentiate into mature neurons and glial cells (astrocytes and oligodendrocytes) in the central nervous system. This model is electrophysiologically active in a spontaneous manner and may be reproduced with patient cells. The derivation of 3D BMPS from iPSCs has applications in the study and treatment of neurological diseases.

In an aspect, the disclosure provides an in vitro brain microphysiological system (BMPS), comprising two or more neural cell types aggregated into a spheroid mass, wherein the spheroid mass has a diameter that is less than about 500 μm and the in vitro BMPS is electrophysiologically active in a spontaneous manner.

In an embodiment, the two or more neural cell types comprise at least a mature neuron and glial cell.

In an embodiment, the two or more neural cell types further comprise cells selected from the group consisting of astrocytes, polydendrocytes, oligodendrocytes, and combinations thereof.

In an embodiment, the in vitro BMPS has neural characteristics selected from the group consisting of synaptogenesis, neuron-neuron interactions, neuronal-glial interactions, axon myelination, and combinations thereof.

In an embodiment, two or more neural cell types of the in vitro BMPS express one or more biomarker selected from the group consisting of GRIN1, GAD1, GABA, TH, LMX1A, FOXO1, FOXA2, FOXO4, CNP, MBP, TH, TUBIII, NEUN, SLC1A6, and any combination thereof.

In an aspect, the disclosure provides a synthetic neurological organ comprising two or more neural cell types aggregated into a spheroid mass, wherein the spheroid mass has a diameter that is less than 500 μm and the in vitro BMPS is electrophysiologically active in a spontaneous manner.

In an embodiment, the two or more neural cell types comprise at least a mature neuron and glial cells.

In an embodiment, the mature neuron and glial cells further comprise cells selected from the group consisting of astrocytes, polydendrocytes, oligodendrocytes, and combinations thereof.

In an embodiment, the synthetic neurological organ further comprises neural characteristics selected from the group consisting of synaptogenesis, neuron-neuron interactions, neuronal-glial interactions, axon myelination, and combinations thereof.

In an embodiment, the synthetic neurological organ mimics the microenvironment of the central nervous system (CNS).

In an aspect, the disclosure provides a method of reproducibly producing an in vitro brain microphysiological system (BMPS), comprising: inducing one or more pluripotent stem cell (PSC) types; differentiating the one or more PSC types to form one or more neural progenitor cell (NPC) types; exposing the one or more NPC types to gyratory shaking or stirring; and differentiating the one or more NPC types into one or more neural cell types aggregated into a spheroid mass, wherein the spheroid mass has a diameter that is less than 500 μm.

In an embodiment, the one or more pluripotent stem cells are selected from the group consisting of human or animal embryonic stem cells, iPSC, adult stem cells, fibroblasts, embryonic fibroblasts, peripheral blood mononuclear cells, neuronal precursor cells, mesenchymal stem cells, and combinations thereof.

In an embodiment, inducing further comprises: adding micro-glia or micro-glia precursor cells.

In an embodiment, the micro-glia or micro-glia precursor cells are selected from the group consisting of monocytes, human monocytes, pro-monocyte cell lines, iPSC-derived monocytes, hematopoetic stem cells, isolated microglia, immortalized microglia, and combinations thereof.

In an embodiment, gyratory shaking comprises constant or regular gyratory shaking or stirring for 2 or more, 3 or more, 4 or more, 5 or more, 6 or more, 7 or more, or 8 or more weeks.

In an embodiment, the one or more growth factors are selected from the group consisting of GDNF, BDNF, GM-CSF, B27, basic FGF, basic EGF, NGF, CNTF, and any combination thereof.

In an aspect, the disclosure provides a method of cryopreserving an in vitro brain microphysiological system (BMPS), comprising: differentiating BMPS aggregates into one or more mature neurons; incubating the aggregates in a cryopreserving medium; and exposing the aggregates to freezing temperatures of −60° C. or colder.

In an embodiment, differentiating further comprises: inducing differentiation of one or more pluripotent stem cell types by incubation with one or more growth factors.

In an embodiment, the one or more pluripotent stem cells are selected from a group consisting of human or animal embryonic stem cells, iPSC, adult stem cells, fibroblasts, embryonic fibroblasts, peripheral blood mononuclear cells, neuronal precursor cells, mesenchymal stem cells, and combinations thereof.

In an embodiment, inducing further comprises: adding micro-glia precursor cells.

In an embodiment, micro-glia precursor cells are selected from the group consisting of monocytes, human monocytes, iPSC-derived monocytes, hematopoetic stem cells, promonocyte cell lines, isolated microglia, immortalized microglia, and combinations thereof.

In an embodiment, the one or more growth factors are selected from the group consisting of GDNF, BDNF, GM-CSF, B27, basic FGF, basic EGF, NGF, CNTF, and any combination thereof.

In an embodiment, the cryopreserving medium is a medium selected from the group consisting of regular cryopreservation medium (95% FBS and 5% DMSO), STEMdiff Neural Progenitor Freezing Medium (Stem Cells Technologies), solutions with cryoprotectants, and combinations thereof.

In an embodiment, exposing the aggregates to freezing temperatures further comprises freezing aggregates over a temperature gradient of about 1° C. per hour to below −60° C. over up to 48 hours.

In an embodiment, cryopreserving further comprises additives selected from the group consisting of DMSO, HES, glycerol, serum, and any combination or derivative thereof.

In an aspect, the disclosure provides a method of transporting a brain microphysiological system (BMPS) or mini-brain, comprising: producing the BMPS or mini-brain of claim 1, incubating the BMPS or mini-brain at 37° C., and maintaining the temperature at 37° C. with constant application of heat while moving the BMPS or mini-brain.

In an embodiment, maintaining the temperature comprises use of heating pads, heaters, insulation, insulated boxes, heat packs, electric blankets, chemical pads, and combinations thereof.

In an aspect, the disclosure provides a method of studying a neurological disease or disorder comprising: producing an in vitro brain microphysiological system (BMPS); exposing the in vitro BMPS to conditions that replicate or induce the neurological disease or disorder; adding an agent to treat the neurological disease or disorder; and assessing the effect of the agent on the neurological disease or disorder.

In an embodiment, the neurological disease or disorder is selected from the group consisting of neurodegenerative disorder, muscular dystrophy, Parkinson's Disease, Huntington's Disease, Autism Spectrum Disorder and other neurodevelopmental disorders, Down's Syndrome, Multiple Sclerosis, Amyotrophic lateral sclerosis, brain cancer, encephalitis, infection, trauma, stroke, and paralysis.

In an aspect, the disclosure provides a method of treating a patient having a neurological disease or disorder, comprising: extracting a stem cell from the patient with a genetic background pre-disposed for the neurological disease or disorder; producing a brain microphysiological system (BMPS) or mini-brain with the genetic background; treating the BMPS or mini-brain with an agent targeting the neurological disease or disorder; and assessing the effect of the agent on the BMPS or mini-brain.

In an embodiment, the neurological disease or disorder is selected from the group consisting of neurodegenerative disorder, muscular dystrophy, Parkinson's Disease, Huntington's Disease, Autism Spectrum Disorder and other neurodevelopmental disorders, Down's Syndrome, Multiple Sclerosis, Amyotrophic lateral sclerosis, brain cancer, encephalitis, infection, trauma, stroke, and paralysis.

In an embodiment, the BMPS includes two or more neuronal cell types that include one or more genetically modified cells. The BMPS wherein the one or more genetically modified cells include one or more reporter genes. The BMPS further comprises one or more endothelial cells capable of forming a blood-brain-barrier.

In an embodiment, the synthetic neurological organ may include two or more neural cell types that include one or more genetically modified cells. The synthetic neurological organ including one or more genetically modified cells that include one or more reporter genes. The synthetic neurological organ further comprising one or more endothelial cells capable of forming a blood-brain-barrier.

In an aspect, the disclosure provides a method of reproducibly producing an in vitro brain microphysiological system (BMPS), comprising: exposing one or more NPC types to gyratory shaking or stirring; and differentiating the one or more NPC types into one or more neural cell types aggregated into a spheroid mass, wherein the spheroid mass has a diameter that is less than 500 μm.

In an embodiment, the spheroid mass has a diameter that is less than about 450 μm, 400 μm, 350 μm, or 300 μm, or a diameter that is between about 350 μm and about 300 μm, or a diameter that is between about 330 μm and about 300 μm, or a diameter that is about 310 μm.

In an embodiment, the two or more neural cell types of the in vitro BMPS express one or more biomarker selected from the group consisting of GRIN1, GAD1, GABA, TH, LMX1A, FOXO1, FOXA2, FOXO4, CNP, MBP, TH, TUBIII, NEUN, SLC1A6, and any combination thereof.

In an embodiment, the two or more neural cell types of the in vitro BMPS express one or more biomarker selected from the group consisting of GRIN1, GAD1, GABA, TH, LMX1A, FOXO1, FOXA2, FOXO4, CNP, MBP, TH, TUBIII, NEUN, SLC1A6, and any combination thereof.

In an embodiment, the two or more neural cell types of the in vitro BMPS express one or more biomarker selected from the group consisting of GRIN1, GAD1, GABA, TH, LMX1A, FOXO1, FOXA2, FOXO4, CNP, MBP, TH, TUBIII, NEUN, SLC1A6, and any combination thereof.

In an embodiment, inducing comprises a single PSC.

In an embodiment, the an in vitro brain microphysiological system (BMPS) may be produced according to the above described method.

It is also contemplated within the scope of the invention that the addition of other cells inside (see e.g., FIG. 6) and outside (see e.g., FIG. 7) the BMPS may be used to modify the structure/composition of the BMPS, such as, e.g., by forming a blood-brain-barrier. It is also contemplated that the BMPS described herein may include genetically modified pluripotent stem cells, or be combined with other organoids (see e.g., Example 11).

Definitions

By "agent" is meant any small compound, antibody, nucleic acid molecule, or polypeptide, or fragments thereof.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels.

By "ameliorate" is meant decrease, suppress, attenuate, diminish, arrest, or stabilize the development or progression of a disease.

In this disclosure, "comprises," "comprising," "containing," and "having" and the like may have the meaning ascribed to them in U.S. Patent law and may mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected.

By "effective amount" is meant the amount of an agent needed to ameliorate the symptoms of a neurological disease relative to an untreated patient. The effective amount of active agent(s) used to practice the present invention for therapeutic treatment of a neurological disease varies depending upon the manner of administration, the age, body weight, and general health of the subject. Ultimately, the attending physician or veterinarian will decide the appropriate amount and dosage regimen. Such amount is referred to as an "effective" amount.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, 100, 200, 300, 400, 500, 600, 700, 800, 900, or 1000 nucleotides or amino acids, or more.

By "gene" is meant a locus (or region) of DNA that encodes a functional RNA or protein product, and is the molecular unit of heredity.

By "marker" is meant any protein or polynucleotide having an alteration in expression level or activity that is associated with a disease or disorder.

By "modulate" is meant alter (increase or decrease). Such alterations are detected by standard art known methods such as those described herein.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

By "reduces" is meant a negative alteration of at least 10%, 25%, 50%, 75%, or 100%.

By "reference" is meant a standard or control condition.

By "pluripotency" is meant stem cells with the potential to differentiate into any of the three germ layers: endoderm (e.g., interior stomach lining, gastrointestinal tract, the lungs), mesoderm (e.g., muscle, bone, blood, urogenital), or ectoderm (e.g., epidermal tissues and nervous system). However, one of skill in the art will understand that cell pluripotency is a continuum, ranging from the completely pluripotent cell that can form every cell of the embryo proper, e.g., embryonic stem cells and iPSCs (see below), to the incompletely or partially pluripotent cell that can form cells of all three germ layers but that may not exhibit all the characteristics of completely pluripotent cells. Induced pluripotent stem cells, commonly abbreviated as iPS cells or iPSCs are a type of pluripotent stem cell artificially derived from a non-pluripotent cell, typically an adult somatic cell, by inducing a "forced" expression of certain genes and transcription factors. These transcription factors play a key role in determining the state of these cells and also highlight the fact that these somatic cells do preserve the same genetic information as early embryonic cells. The ability to induce cells into a pluripotent state was initially pioneered using mouse fibroblasts and four transcription factors, Oct4, Sox2, Klf4 and c-Myc; —a process called reprogramming. The successful induction of human iPSCs derived from human dermal fibroblasts has been performed using methods similar to those used for the induction of mouse cells. These induced cells exhibit similar traits to those of embryonic stem cells (ESCs) but do not require the use of embryos. Some of the similarities between ESCs and iPSCs include pluripotency, morphology, self-renewal ability, a trait that implies that they can divide and replicate indefinitely, and gene expression.

By "stem cells" is meant undifferentiated biological cells that can differentiate into specialized cells and can divide (through mitosis) to produce more stem cells. They are found in multicellular organisms. In mammals, there are two broad types of stem cells: embryonic stem cells, which are isolated from the inner cell mass of blastocysts, and adult stem cells, which are found in various tissues. In adult organisms, stem cells and progenitor cells act as a repair system for the body, replenishing adult tissues. In a developing embryo, stem cells can differentiate into all the specialized cells—ectoderm, endoderm and mesoderm (see induced pluripotent stem cells)—but also maintain the normal turnover of regenerative organs, such as blood, skin, or intestinal tissues. There are three known accessible sources of autologous adult stem cells in humans: 1. Bone marrow, which requires extraction by harvesting, that is, drilling into bone (typically the femur or iliac crest). 2. Adipose tissue (lipid cells), which requires extraction by liposuction. 3. Blood, which requires extraction through apheresis, wherein blood is drawn from the donor (similar to a blood donation), and passed through a machine that extracts the stem cells and returns other portions of the blood to the donor. Stem cells can also be taken from umbilical cord blood just after birth. Of all stem cell types, autologous harvesting involves the least risk. By definition, autologous cells are obtained from one's own body.

By "subject" is meant a mammal, including, but not limited to, a human or non-human mammal, such as a bovine, equine, canine, ovine, or feline.

As used herein, the terms "treat," treating," "treatment," and the like refer to reducing or ameliorating a neurological disorder and/or symptoms associated therewith. It will be appreciated that, although not precluded, treating a disorder or condition does not require that the disorder, condition or symptoms associated therewith be completely eliminated.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

Unless specifically stated or obvious from context, as used herein, the term "or" is understood to be inclusive. Unless specifically stated or obvious from context, as used herein, the terms "a," "an," and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

A "therapeutically effective amount" is an amount sufficient to effect beneficial or desired results, including clinical results. An effective amount can be administered in one or more administrations.

By "GRIN1 polypeptide" (or glutamate ionotropic receptor NMDA type subunit 1) is meant a polypeptide or fragment thereof having at least about 85% amino acid identity to NCBI Accession No. Q05586.

```
                                                   (SEQ ID NO: 1)
  1  mstmrlltla llfscsvara acdpkivnig avlstrkheq mfreavnqan krhgswkiql

 61  natsvthkpn aiqmalsvce dlissqvyai lvshpptpnd hftptpvsyt agfyripvlg

121  lttrmsiysd ksihlsflrt vppyshqssv wfemmrvysw nhiillvsdd hegraaqkrl

181  etlleeresk aekvlqfdpg tknvtallme akelearvii lsaseddaat vyraaamlnm

241  tgsgyvwlvg ereisgnalr yapdgilglq lingknesah isdavgvvaq avhelleken

301  itdpprgcvg ntniwktgpl fkrvlmssky adgvtgrvef nedgdrkfan ysimnlqnrk

361  lvqvgiyngt hvipndrkii wpggetekpr gyqmstrlki vtihqepfvy vkptlsdgtc

421  keeftvngdp vkkvictgpn dtspgsprht vpqccygfci dlliklartm nftyevhlva

481  dgkfgtqerv nnsnkkewng mmgellsgqa dmivapltin neraqyiefs kpfkyqglti

541  lvkkeiprst ldsfmqpfqs tlwllvglsv hvvavmlyll drfspfgrfk vnseeeeeda

601  ltlssamwfs wgvllnsgig egaprsfsar ilgmvwagfa miivasytan laaflvldrp

661  eeritgindp rlrnpsdkfi yatvkqssvd iyfrrqvels tmyrhmekhn yesaaeaiqa

721  vrdnklhafi wdsavlefea sqkcdlvttg elffrsgfgi gmrkdspwkq nvslsilksh

781  engfmedldk twvryqecds rsnapatltf enmagvfmlv aggivagifl ifieiaykrh

841  kdarrkqmql afaavnvwrk nlqdrksgra epdpkkkatf raitstlass fkrrrsskdt

901  stgggrgalq nqkdtvlprr aiereegqlq lcsrhres
```

By "GRIN1 nucleic acid molecule" (or glutamate ionotropic receptor NMDA type subunit 1) is meant a polynucleotide encoding an GRIN1 polypeptide. An exemplary GRIN1 nucleic acid molecule (e.g., mRNA) is provided at NCBI Accession No. NM_007327.

```
                                                   (SEQ ID NO: 2)
  1  gtcgccgcag cgtccggacc ggaaccagcg ccgtccgcgg agccgccgcc gccgccgccg

 61  ggccctttcc aagccgggcg ctcggagctg tgcccggccc cgcttcagca ccgcggacag

121  cgccggccgc gtggggctga gccccgagcc cccgcgcacg cttcagcgcc ccttccctcg

181  gccgacgtcc cgggaccgcc gctccggggg agacgtggcg tccgcagccc gcggggccgg

241  gcgagcgcag gacggcccgg aagccccgcg ggggatgcgc cgagggcccc gcgttcgcgc

301  cgcgcagagc caggcccgcg gcccgagccc atgagcacca tgcgcctgct gacgctcgcc

361  ctgctgttct cctgctccgt cgcccgtgcc gcgtgcgacc ccaagatcgt caacattggc

421  gcggtgctga gcacgcggaa gcacgagcag atgttccgcg aggccgtgaa ccaggccaac

481  aagcggcacg gctcctggaa gattcagctc aatgccacct ccgtcacgca caagcccaac

541  gccatccaga tggctctgtc ggtgtgcgag gacctcatct ccagccaggt ctacgccatc

601  ctagttagcc atccacctac ccccaacgac cacttcactc ccacccctgt ctcctacaca

661  gccggcttct accgcatacc cgtgctgggg ctgaccaccc gcatgtccat ctactcggac

721  aagagcatcc acctgagctt cctgcgcacc gtgccgccct actcccacca gtccagcgtg

781  tggtttgaga tgatgcgtgt ctacagctgg aaccacatca tcctgctggt cagcgacgac
```

-continued

```
841   cacgagggcc gggcggctca gaaacgcctg gagacgctgc tggaggagcg tgagtccaag
901   gcagagaagg tgctgcagtt tgacccaggg accaagaacg tgacggccct gctgatggag
961   gcgaaagagc tggaggcccg ggtcatcatc ctttctgcca gcgaggacga tgctgccact
1021  gtataccgcg cagccgcgat gctgaacatg acgggctccg ggtacgtgtg gctggtcggc
1081  gagcgcgaga tctcggggaa cgccctgcgc tacgccccag acggcatcct cgggctgcag
1141  ctcatcaacg gcaagaacga gtcggcccac atcagcgacg ccgtgggcgt ggtggcccag
1201  gccgtgcacg agctcctcga gaaggagaac atcaccgacc cgccgcgggg ctgcgtgggc
1261  aacaccaaca tctggaagac cgggccgctc ttcaagagag tgctgatgtc ttccaagtat
1321  gcggatgggg tgactggtcg cgtggagttc aatgaggatg gggaccggaa gttcgccaac
1381  tacagcatca tgaacctgca gaaccgcaag ctggtgcaag tgggcatcta caatggcacc
1441  cacgtcatcc ctaatgacag gaagatcatc tggccaggcg gagagacaga gaagcctcga
1501  gggtaccaga tgtccaccag actgaagatt gtgacgatcc accaggagcc cttcgtgtac
1561  gtcaagccca cgctgagtga tgggacatgc aaggaggagt tcacagtcaa cggcgaccca
1621  gtcaagaagg tgatctgcac cgggcccaac gacacgtcgc cgggcagccc ccgccacacg
1681  gtgcctcagt gttgctacgg cttttgcatc gacctgctca tcaagctggc acggaccatg
1741  aacttcacct acgaggtgca cctggtggca gatggcaagt tcggcacaca ggagcgggtg
1801  aacaacagca acaagaagga gtggaatggg atgatgggcg agctgctcag cgggcaggca
1861  gacatgatcg tggcgccgct aaccataaac aacgagcgcg cgcagtacat cgagttttcc
1921  aagcccttca agtaccaggg cctgactatt ctggtcaaga aggagattcc ccggagcacg
1981  ctggactcgt tcatgcagcc gttccagagc acactgtggc tgctggtggg gctgtcggtg
2041  cacgtggtgg ccgtgatgct gtacctgctg gaccgcttca gccccttcgg ccggttcaag
2101  gtgaacagcg aggaggagga ggaggacgca ctgaccctgt cctcggccat gtggttctcc
2161  tggggcgtcc tgctcaactc cggcatcggg gaaggcgccc ccagaagctt ctcagcgcgc
2221  atcctgggca tggtgtgggc cggctttgcc atgatcatcg tggcctccta caccgccaac
2281  ctggcggcct tcctggtgct ggaccggccg gaggagcgca tcacgggcat caacgaccct
2341  cggctgagga acccctcgga caagtttatc tacgccacgg tgaagcagag ctccgtggat
2401  atctacttcc ggcgccaggt ggagctgagc accatgtacc ggcatatgga gaagcacaac
2461  tacgagagtg cggcggaggc catccaggcc gtgagagaca acaagctgca tgccttcatc
2521  tgggactcgg cggtgctgga gttcgaggcc tcgcagaagt gcgacctggt gacgactgga
2581  gagctgtttt tccgctcggg cttcggcata ggcatgcgca aagacagccc ctggaagcag
2641  aacgtctccc tgtccatcct caagtcccac gagaatggct tcatggaaga cctggacaag
2701  acgtgggttc ggtatcagga atgtgactcg cgcagcaacg cccctgcgac ccttactttt
2761  gagaacatgg ccggggtctt catgctggta gctgggggca tcgtggccgg gatcttcctg
2821  attttcatcg agattgccta caagcggcac aaggatgctc gccggaagca gatgcagctg
2881  gcctttgccg ccgttaacgt gtggcggaag aacctgcagg atagaaagag tggtagagca
2941  gagcctgacc ctaaaaagaa agccacattt agggctatca cctccaccct ggcttccagc
3001  ttcaagaggc gtaggtcctc caaagacacg agcaccgggg gtggacgcgg cgctttgcaa
3061  aaccaaaaag acacagtgct gccgcgacgc gctattgaga gggaggaggg ccagctgcag
3121  ctgtgttccc gtcataggga gagctgagac tccccgcccg ccctcctctg ccccctcccc
3181  cgcagacaga cagacagacg gacgggacag cggcccggcc cacgcagagc cccggagcac
3241  cacggggtcg gggaggagc acccccagcc tcccccaggc tgcgcctgcc cgcccgccgg
```

-continued

```
3301 ttggccggct ggccggtcca ccccgtcccg gccccgcgcg tgcccccagc gtggggctaa
3361 cgggcgcctt gtctgtgtat ttctattttg cagcagtacc atcccactga tatcacgggc
3421 ccgctcaacc tctcagatcc ctcggtcagc accgtggtgt gaggcccccg gaggcgccca
3481 cctgcccagt tagcccggcc aaggacactg atgggtcctg ctgctcggga aggcctgagg
3541 gaagcccacc cgccccagag actgcccacc ctgggcctcc cgtccgtccg cccgcccacc
3601 ccgctgcctg gcgggcagcc cctgctggac caaggtgcgg accggagcgg ctgaggacgg
3661 ggcagagctg agtcggctgg gcagggccgc agggcgctcc ggcagaggca gggccctggg
3721 gtctctgagc agtggggagc gggggctaac tggccccagg cggaggggct tggagcagag
3781 acggcagccc catccttccc gcagcaccag cctgagccac agtggggccc atggccccag
3841 ctggctgggt cgcccctcct cgggcgcctg cgctcctctg cagcctgagc tccaccctcc
3901 cctcttcttg cggcaccgcc cacccacacc ccgtctgccc cttgacccca cacgccgggg
3961 ctggccctgc cctcccccac ggccgtccct gacttcccag ctggcagcgc ctcccgccgc
4021 ctcgggccgc ctcctccaga ctcgagaggg ctgagcccct cctctcctcg tccggcctgc
4081 agcccagaac gggcctcccc gggggtcccc ggacgctggc tcgggactgt cttcaaccct
4141 gccctgcacc ttgggcacgg gagagcgcca cccgcccgcc cccgccctcg ctccgggtgc
4201 gtgaccggcc cgccaccttg tacagaacca gcactcccag ggcccgagcg cgtgccttcc
4261 ccgtgcggcc cgtgcgcagc cgcgctctgc ccctccgtcc ccagggtgca ggcgcgcacc
4321 gcccaacccc cacctcccgg tgtatgcagt ggtgatgcct aaaggaatgt cacgcagttt
4381 tcaaaaaaaa aaaaaaaaaa
```

By “GAD1 polypeptide” (or glutamate decarboxylase 1) is meant a polypeptide or fragment thereof having at least about 85% amino acid identity to NCBI Accession No. Q99259.

```
                                                    (SEQ ID NO: 3)
  1  masstpsssa tssnagadpn ttnlrpttyd twcgvahgct rklglkicgf lqrtnsleek
 61  srlvsafker qssknllsce nsdrdarfrr tetdfsnlfa rdllpaknge eqtvqfllev
121  vdillnyvrk tfdrstkvld fhhphqlleg megfnlelsd hpesleqilv dcrdtlkygv
181  rtghprffnq lstgldiigl agewltstan tnmftyeiap vfvlmeqitl kkmreivgws
241  skdgdgifsp ggaisnmysi maarykyfpe vktkgmaavp klvlftseqs hysikkagaa
301  lgfgtdnvil ikcnergkii padfeakile akqkgyvpfy vnatagttvy gafdpiqeia
361  dicekynlwl hvdaawgggl lmsrkhrhkl ngieransvt wnphkmmgvl lqcsailvke
421  kgilqgcnqm cagylfqpdk qydvsydtgd kaiqcgrhvd ifkfwlmwka kgtvgfenqi
481  nkclelaeyl yakiknreef emvfngepeh tnvcfwyipq slrgvpdspq rreklhkvap
541  kikalmmesg ttmvgyqpqg dkanffrmvi snpaatqsdi dflieeierl gqdl
```

By “GAD1 nucleic acid molecule” (or glutamate decarboxylase 1) is meant a polynucleotide encoding an GAD1 polypeptide. An exemplary GAD1 nucleic acid molecule (e.g., mRNA) is provided at NCBI Accession No. BC036552.

```
                                                    (SEQ ID NO: 4)
  1  agcgtgtggt agaggagaaa cgctgaaacc ggaccgaaac ctcgccctag gcttagcgat
 61  ggctaaaaac cggctgggac aagagggagg caagcaacat tccgactcgc tgctttctgg
```

-continued

```
121   ctgtctggag tgcaaggtga ctgtggttct tctctggcca agtccgaggg agaacgtaaa
181   gatatgggcc tttttccccc tctcaccttg tctcaccaaa gtccctagtc cccggagcag
241   ttagcctctt tctttccagg gaattagcca gacacaacaa cgggaaccag acaccgaacc
301   agacatgccc gccccgtgcg ccctcccccc gctggcccac acgccggctg ctgagtgccc
361   aatggggctt gtagcggctc ggctggaaaa tcgctcactg agcgctcccc tgtgctccta
421   gcccagtccc ccacaccctt gcgtcttgta ctggccttgg acccccaccc cgaccccgac
481   cccgcctcgt ctcggcgctt cactccaggt cgcgccgatg caccgccaga ctcgagagcg
541   gcccagggct acgctccctg cgccccagta ccggagctag cgcgcacgtc tcctccgctg
601   cccccacccc tgcgcacccc taccaggcag gctcgctgcc tttcctccct cttgtctctc
661   cagagccgga tcttcaaggg gagcctccgt gcccccggct gctcagtccc tccggtgtgc
721   aggaccccgg aagtcctccc cgcacagctc tcgcttctct ttgcagcctg tttctgcgcc
781   ggaccagtcg aggactctgg acagtagagg ccccgggacg accgagctga tggcgtcttc
841   gaccccatct tcgtccgcaa cctcctcgaa cgcgggagcg gaccccaata ccactaacct
901   gcgccccaca acgtacgata cctggtgcgg cgtggcccat ggatgcacca gaaaactggg
961   gctcaagatc tgcggcttct tgcaaaggac caacagcctg gaagagaaga gtcgccttgt
1021  gagtgccttc aaggagaggc aatcctccaa gaacctgctt tcctgtgaaa acagcgaccg
1081  ggatgcccgc ttccggcgca cagagactga cttctctaat ctgtttgcta gagatctgct
1141  tccggctaag aacggtgagg agcaaaccgt gcaattcctc ctggaagtgg tggacatact
1201  cctcaactat gtccgcaaga catttgatcg ctccaccaag gtgctggact ttcatcaccc
1261  acaccagttg ctggaaggca tggagggctt caacttggag ctctctgacc accccgagtc
1321  cctggagcag atcctggttg actgcagaga caccttgaag tatggggttc gcacaggtca
1381  tcctcgattt ttcaaccagc tctccactgg attggatatt attggcctag ctggagaatg
1441  gctgacatca acggccaata ccaacatgtt tacatatgaa attgcaccag tgtttgtcct
1501  catggaacaa ataacactta agaagatgag agagatagtt ggatggtcaa gtaaagatgg
1561  tgatgggata ttttctcctg gggcgccat atccaacatg tacagcatca tggctgctcg
1621  ctacaagtac ttcccggaag ttaagacaaa gggcatggcg gctgtgccta aactggtcct
1681  cttcacctca gaacagagtc actattccat aaagaaagct ggggctgcac ttggctttgg
1741  aactgacaat gtgattttga taaagtgcaa tgaaaggggg aaaataattc cagctgattt
1801  tgaggcaaaa attcttgaag ccaaacagaa gggatatgtt ccccttttatg tcaatgcaac
1861  tgctggcacg actgtttatg gagcttttga tccgatacaa gagattgcag atatatgtga
1921  gaaatataac ctttggttgc atgtcgatgg atttaacttc tcacaattgg ccaataggat
1981  catctgcctt gctactgaac taatgactaa caaaggctgt gtcacgtggc atcccaacta
2041  ttcagtaaac atgcatcatg gctgcctggg gaggtgggct gctcatgtcc aggaagcacc
2101  accataaact caacggcata gaaagggcca actcagtcac ctggaaccct cacaagatga
2161  tgggcgtgct gttgcagtgc tctgccattc tcgtcaagga aaagggtata ctccaaggat
2221  gcaaccagat gtgtgcagga tacctcttcc agccagacaa gcagtatgat gtctcctacg
2281  acaccgggga caaggcaatt cagtgtggcc gccacgtgga tatcttcaag ttctggctga
2341  tgtggaaagc aaagggcaca gtgggatttg aaaaccagat caacaaatgc ctggaactgg
2401  ctgaatacct ctatgccaag attaaaaaca gagaagaatt tgagatggtt ttcaatggcg
2461  agcctgagca cacaaacgtc tgtttttggt atattccaca aagcctcagg ggtgtgccag
```

-continued

```
2521 acagccctca acgacgggaa aagctacaca aggtggctcc aaaaatcaaa gccctgatga
2581 tggagtcagg tacgaccatg gttggctacc agccccaagg ggacaaggcc aacttcttcc
2641 ggatggtcat ctccaaccca gccgctaccc agtctgacat tgacttcctc attgaggaga
2701 tagaaagact gggccaggat ctgtaatcat ccttcgcaga acatgagttt atgggaatgc
2761 cttttccctc tggcactcca gaacaaacct ctatatgttg ctgaaacaca caggccattt
2821 cattgaggga aaacataata tcttgaagaa tattgttaaa accttactta aagcttgttt
2881 gttctagtta gcaggaaata gtgttctttt taaaaagttg cacattagga acagagtata
2941 tatgtacagt tatacatacc tctctctata tatacatgta tagtgagtgt ggcttagtaa
3001 tagatcacgg catgtttccc gctccaagag aattcacttt accttcagca gttaccgagg
3061 agctaaacat gctgccaacc agcttgtcca acaactccag gaaaactgtt tttcaaaacg
3121 ccatgtccta ggggccaagg gaaatgctgt tggtgagaat cgacctcact gtcagcgttt
3181 ctccacctga agtgatgatg gatgagaaaa aacaccacca aatgacaagt cacaccctcc
3241 ccattagtat cctgttaggg gaaaatagta gcagagtcat tgttacaggt gtactatggc
3301 tgtattttta gagattaatt tgtgtagatt gtgtaaattc ctgttgtctg accttggtgg
3361 tgggaggggg agactatgtg tcatgatttc aatgattgtt taattgtagg tcaatgaaat
3421 atttgcttat ttatattcag agatgtacca tgttaaagag gcgtcttgta ttttcttccc
3481 atttgtaatg tatcttattt atatatgaag taagttctga aaactgttta tggtattttc
3541 gtgcatttgt gagccaaaga gaaaagatta aaattagtga gatttgtatt tatattagag
3601 tgcccttaaa ataatgattt aagcatttta ctgtctgtaa gagaattcta agattgtaca
3661 taaagtcata tatatggaaa tcctgttact taaatagcat ctgctcttct cttacgctct
3721 ctgtctggct gtacgtctgg tgttctcaat gcttttctag caactgttgg ataataacta
3781 gatctcctgt aattttgtag tagttgatga ccaatctctg ttactcgctt agctgaaacc
3841 taaggcaaca tttccgaaga ccttctgaag atctcagata aagtgaccag gctcacaact
3901 gtttttgaag aagggaaatt cacactgtgc gttttagagt atgcaagaag aatataaata
3961 aataaaaata ttctccatgg agaatttgaa caaaaaaaaa aaaaaaa
```

By "GABA polypeptide" (or gamma-Aminobutyric acid) is meant a polypeptide or fragment thereof having at least about 85% amino acid identity to NCBI Accession No. P30531.

(SEQ ID NO: 5)

```
  1 matngskvad gqistevsea pvandkpktl vvkvqkkaad lpdrdtwkgr fdflmscvgy
 61 aiglgnvwrf pylcgknggg aflipyfltl ifagvplfll ecslgqytsi gglgvwklap
121 mfkgvglaaa vlsfwlniyy iviiswaiyy lynsftttlp wkqcdnpwnt drcfsnysmv
181 nttnmtsavv efwernmhqm tdgldkpgqi rwplaitlai awilvyfciw kgvgwtgkvv
241 yfsatypyim liilffrgvt lpgakegilf yitpnfrkls dsevwldaat qiffsyglgl
301 gslialgsyn sfhnnvyrds iivccinsct smfagfvifs ivgfmahvtk rsiadvaasg
361 pglaflaype avtqlpispl wailffsmll mlgidsqfct vegfitalvd eyprllrnrr
421 elfiaavcii syliglsnit qggiyvfklf dyysasgmsl lflvffecvs iswfygvnrf
481 ydniqemvgs rpciwwklcw sfftpiivag vfifsavqmt pltmgnyvfp kwgqgvgwlm
541 alssmvlipg ymaymfltlk gslkqriqvm vqpsedivrp engpeqpqag sstskeayi
```

By "GABA nucleic acid molecule" (or gamma-Aminobutyric acid) is meant a polynucleotide encoding an GABA polypeptide. An exemplary GABA nucleic acid molecule (e.g., mRNA) is provided at NCBI Accession No. U76343.

(SEQ ID NO: 6)

```
1     gtagcttcac taaggtggga tggatagcag ggtctcaggc acaaccagta atggagagac
61    aaaaccantg tatcacaaga tggagtttgt gctgtcagtg gctggggaga tcattggctt
121   aggcaacgtc tggaggtttc cctatctctg ctacaaaaat gggggaggtg ccttcttcat
181   cccctacctc gtcttcctct ttacctgtgg cattcctgtc ttccttctgg agacagcact
241   aggccagtac actagccagg gaggcgtcac agcctggagg aagatctgcc ccatctttga
301   gggcattggc tatgcctccc agatgatcgt catcctcctc aacgtctact acatcattgt
361   gttggcctgg gccctgttct acctcttcag cagcttcacc atcgacctgc cctggggcgg
421   ctgctaccat gagtggaaca cagaacactg tatggagttc cagaagacca acggctccct
481   gaatggtacc tctgagaatg ccacctctcc tgtcatcgag ttctgggagc ggcgggtctt
541   gaagatctct gatgggatcc agcacctggg ggccctgcgc tgggagctgg ctctgtgcct
601   cctgctggcc tgggtcatct gctacttctg catctggaag gggtgaagt ccacaggcaa
661   ggtggtgtac ttcacggcca catttcctta cctcatgctg gtggtcctgt taattcgagg
721   ggtgacgttg cctggggcag cccaaggaat tcagttttac ctgtacccaa acctcacgcg
781   tctgtgggat ccccaggtgt ggatggatgc aggcacccag atattcttct ccttcgccat
841   ctgtcttggg tgcctgacag ccctgggcag ctacaacaag taccacaaca actgctacag
901   cggcaccagc tttgtggccg gctttgccat cttctccatc ctgggcttca tgtctcagga
961   gcagggggtg cccatttctg aggtggccga gtcaggccct ggcctggctt tcatcgctta
1021  cccgcgggct gtggtgatgc tgcccttctc tcctctctgg gcctgctgtt tcttcttcat
1081  ggtcgttctc ctgggactgg atagccagtt tgtgtgtgta gaaagcctgg tgacagcgct
1141  ggtggacatg taccctcacg tgttccgcaa gaagaaccgg agggaagtcc tcatccttgg
1201  agtatctgtc gtctccttcc ctgtggggct gatcatgctc acagagggcg gaatgtacgt
1261  gttccagctc tttgactact atgcggccag tggcatgtgc ctcctgttcg tggccatctt
1321  cgagtccctc tgtgtggctt gggtttacgg agccaagcgc ttctacgaca acatcgaaga
1381  catgattggg tacaggccat ggcctcttat caaatactgt tggctcttcc tcacaccagc
1441  tgtgtgcaca gccacctttc tcttctccct gataaagtac actccgctga cctacaacaa
1501  gaagtacacg tacccgtggt ggggcgatgc cctgggctgg ctcctggctc tgtcctcctg
1561  gtctgcattc ctgcctggag cctctacaga ctcggaaccc tcaagggccc cttcagagag
1621  agaatccgtc agctcatgtg cccagccgag gacctgcccc agcggaaccc agcaggaccc
1681  tcggctcccg ccacccccag gacctcactg ctcagactca cagagctaga gtctcactgc
1741  taggggcag gcccttggat ggtgcctgtg tgcctggcct tggggatggc tgtggaggga
1801  acgtggcaga agcagcccca tgtgttccct gcccccgacc tggagtggat aagacaagag
1861  gggtattttg gagtccacct gctgagctgg aggcctccca ctgcaacttt tcagctcagg
1921  ggttgttgaa cagatgtgaa aaggccagtg ccaagagtgt ccctcggaga cccttgaagg
1981  c
```

By "TH polypeptide" (or Tyrosine Hydroxylase) is meant a polypeptide or fragment thereof having at least about 85% amino acid identity to NCBI Accession No. NP_002692.

(SEQ ID NO: 7)

```
1     mptpdattpq akgfrravse ldakqaeaim vrgqgapgps ltgspwpgta apaasytptp
61    rsprfigrrq sliedarker eaavaaaaaa vpsepgdple avafeekegk avlnllfspr
```

-continued

```
121    atkpsalsra vkvfetfeak ihhletrpaq rpraggphle yfvrlevrrg dlaallsgvr

181    qvsedvrspa gpkvpwfprk vseldkchhl vtkfdpdldl dhpgfsdqvy rqrrkliaei

241    afqyrhgdpi prveytaeei atwkevyttl kglyathacg ehleafalle rfsgyredni

301    pqledvsrfl kertgfqlrp vagllsardf laslafrvfq ctqyirhass pmhspepdcc

361    hellghvpml adrtfaqfsq diglaslgas deeieklstl ywftvefglc kqngevkayg

421    agllssygel lhclseepei rafdpeaaav qpyqdqtyqs vyfvsesfsd akdklrsyas

481    riqrpfsvkf dpytlaidvl dspqavrrsl egvqdeldtl ahalsaig
```

By "TH nucleic acid molecule" (or Tyrosine Hydroxylase) is meant a polynucleotide encoding an TH polypeptide. An exemplary TH nucleic acid molecule is provided at NCBI Accession No. NG_008128.

(SEQ ID NO: 8)

```
1    gcgggggggc agtgtgtgct ccagcatgtg tgtgtgtgtg tgcatgtaca cgtgtgcacc

61    tgtatcgcct gtgtgtgtgc atgtgatgtg tacacgtgtc atgcatgcac gcacatgtgt

121    agtgtgtgct cgtgtgtggt gtgtgcctgt gtcatgtatg agcacacttg tatatgttgt

181    gtgtactgtg tcatatatga gtgtgtttgc ctgtgtagtg catgcacatc cgtgtgtgca

241    tctggtgtgt ccgtgggtca ttacgagtgc atcgtatgtg tatcgtgtac atgagtacac

301    ttgtatgtgt ggtgtgtaca ggtgccatgt aagtgtgctt gtacatatat gcatgcatgt

361    gtcatatgca tctgtgtgtg catgtgtgtg gtgcacacat gtgttatgtc tgagtgtgcc

421    tgtatgtgtg ctatgtacac gtcatgtgtg agtgtgcttg catgtgcagt gtgtggatgc

481    tgcttgtacc tgtggtgtgt acctgtgtca tgggtgctca cacgtgcatg gagtgttgtg

541    tgtgtgcttg tgtgccccat gtgtgcatgt gtgtgtgcct cacacagatg cctgcatttg

601    cctaggcact tgcaagagga caccatgctg gctctcaaag atcacagggc cacctgagcc

661    ctgtgcacac cacagccagg ccatggctag accctgcaga gccacagggc gatgcctgtc

721    agccagggga cccagaacac ctcctgggct cctccccagc acatggctgg gctcctccag

781    caggcctgga tttgggaagg gcccgtggtg ggcaaggctg gtgctgggga gcaggcctgg

841    tggcctcaga gactcgccct gtgggcggag cagcctcaca gccaggtcga agtcagcact

901    ctgaccctgc cccacgcggg gagtgggcac cagtcccagg gcacagacgt gctgggtgat

961    taatctgggt gattaagcct cgggctgaga ggctgttgag agagaacacg ctccattgtg

1021    gagctggctc agcattcctt acggccatgg tggcaggggc tgtaaccaca gggacggcgg

1081    aagtggtgga gggtggtggg gtatggaggg aagcccagag ggctccgtgc aggaaggtgg

1141    agcctggtgc aatggagggg acagcaaggg ctcctcagac ctctgcgggg cccccactcc

1201    cctggtcacc tgttttgtct ctgatctggc ctgggtcggc cctcactcct ggccccacct

1261    catagccccc cctggtgggg ctccgctcca gcccttctcc ttcccagggg ccagtatgct

1321    ggccccaggg gtctcttggg gcgtgacctc ggcctccaga gaaccctgtc ccagctctgc

1381    ccttccctct ggggtctctg tagatgggac gctggtcaca gcagcctgtc tgatttgttc

1441    cctgtggcct aggttcctga gccccacagt gccaggggat ggatgccacc ggatctttga

1501    aagaccagtg tcaggccggg cgcagtggct cacgcctgta atcccagcac tttgggaggc

1561    cgaggtgggc ggatcacgaa gtcaggagat cgagaccatc ctggctaaca cagtgaaacc

1621    ccgtctccac taaaaataca aaaagttagc tgggcgtggt ggtgggcgcc tgtagtccca

1681    gctacttggg aggctgaggc aggagaatgg cgtgaaccgg ggaggcggag cttgcagtga

1741    gccgagatcg cgccattgca ctccagcctg ggtgacagag cgagactcgg tctcaaaaaa
```

-continued

```
1801   aaagaaaaaa aggaaagacc agtgtcttgg gagttgggaa acctgggctg gagactcact
1861   gcatgacccc tgagaagttg cacctcagaa cctcagtcct cgcatctgca gaatgggtct
1921   gtgaacacct cagctgcccg aacgtggatg ccgcaggctg acccagcact gagctctacc
1981   aagaccaggg gccagccgtg tgctccctcc aggcctgtgc ccagcgtgga gaggcctcgt
2041   cccgtgggcg ctggagtgga gccttcctgg tgtttgtgga catctctgga gagggccaga
2101   ggcaggtggg tgacacgggg catggctcaa tcatgggtgg tccagactgg agaggtaccc
2161   tcgggctggg agcggggagg ctggccaggg tagacttttg gggcctccat ggataccctc
2221   accatctgga atcggagagg ggcacggcac aaaggagggc ggggccaggg ccaggactgg
2281   agtcgggggc acctctgtgc caacaggggc cttggatctg ggtacagca tggttccccg
2341   gccctgaagg ggctggcgtg tgggacaggc ttcccaggaa tggataggca gggatggatg
2401   ctgcctgatt ggggcgggag gctggaggca gggcaggtgc aggcacctga gggcagcact
2461   cacctccaca ggggtccagg ggcctcccca gcctcagcac ctggcctggg ctcctgcctc
2521   cagagagcct ggccccaagg aagagtctag taagcttagt tcccatcggg cttccatgaa
2581   agcacaactg gcccggcagg aaaccgaatt aaaaagcaat atttgtatca gtggaagaca
2641   tttgctgaaa ggttaaatcc acatccggca gtgtgggcca tgagcctccg gcgtggtgtt
2701   catcaggcat gtctctcctc ctggcctggg cacctgagca ctggggccgc cctgggcaga
2761   gctggggcgg ggtgctgggg ggcctggagc tgcctcaccg agggatcctc agcagccgac
2821   cctgggggag gcaaatgaga ctctttctgg ggaccttgag gggagctcgg gggagccatg
2881   cagagcttca ccaggcctgg acactgggca tggaggctgg gccacccaag ggccatcacc
2941   agggactcag gtgggtgggc ctcagccctg ggtgacagaa gctcacgggc cgcagggcga
3001   ggccagaggc tgagccttca ggctgaggtc ttggaggcaa atccctccaa cgcccttctg
3061   agcaggcacc cagacctact gtgggcagga cccacaggag gtggaggcct ttggggaaca
3121   ctgtggaggg gcatagcatc tccgagagag gacagggtct gcactgggtg ctgagagaca
3181   gcaggggccg agcggtaggc ttccctgccc ccagggatgt tccagaggag cgcaagggag
3241   gggcattaat atcgtggcaa gaaagggcag gcattgcaga gtgagcagcg acggaactgg
3301   gttttgtggg atgcatagga gttcacccgg ataagaggtg ggtgaggaat gacactgcaa
3361   accggggatc acggagcccc aaatccttct gggccaggaa gtgggaaggg ttgggggggtc
3421   ttccctttgc tttgactgag cactcagcct gcctgcagag ggcagcgagg agccacggag
3481   gggtgtggga cagggatgcc atggctgaag cagttttagg aaaggtccca ggggctattg
3541   ttgaagagag aacggggagc ggggagtccc acagctgaca ggagcagagt gggccctgag
3601   agatgccagc tctggctgcc acagtgacca gccggggtag gccttcgaga agtcagggag
3661   cgtctagggc ttctggctcc tgctgggccc agggtgtcat cttgggctgc caacaccaga
3721   aagcccagca gatacaggaa gccccaagcc ctgtcggaaa cggttcttct ccaggaggga
3781   cagcggtggc agcgttcagc cgcaggccat gcactctggg gccacgtcct tccctctgta
3841   cagtccagca ttgtcaaggc aggctctggc catctctgct gaccccagag ggatggggag
3901   gcctcccctt ccaccagaag ggccagaagc caccctgggc aggggcatca ctctccctgg
3961   gtggggcagc ggctgggagc aggaggtgcc agtgggcgtg ggctggatgc gggtgcctgc
4021   ggggcggaca tggaacttgg gggaggctct aggctggggt tgtcctcaag ggagttctca
4081   ggtcacccca gggtcaccct caacccgggg cctggtgggg tagaggagaa actgcaaagg
4141   tctctccaag gggaaggcat cagggccctc agcactgagg gacgtgcgtg ctctttaaag
4201   aaggggccac aggaccccga gggaagccag gagctagcag tggccatag aggggctgag
```

-continued

```
4261   tggggtgggt ggaagccgtc cctggccctg gtcgccctgg caaccctggt ggggactgtg
4321   atgcaggagg tggcagccat ttggaaacgc gtggcgtctc cttagagatg tcttcttcag
4381   cctcccaggg tcctccacac tggacaggtg ggccctcctg ggacattctg gaccccacgg
4441   ggcgagcttg ggaagccgct gcaagggcca cacctgcagg gcccgggggc tgtgggcaga
4501   tggcactcct aggaaccacg tctatgagac acacggcctg gaatcttctg gagaagcaaa
4561   caaattgcct cctgacatct gaggctggag gctggattcc ccgtcttggg gctttctggg
4621   tcggtctgcc acgaggttct ggtgttcatt aaaagtgtgc ccctgggctg ccagaaagcc
4681   cctccctgtg tgctctcttg agggctgtgg ggccaagggg accctggctg tctcagcccc
4741   ccgcagagca cgagcccctg gtccccgcaa gcccgcgggc tgaggatgat tcagacaggg
4801   ctggggagtg aaggcaatta gattccacgg acgagccctt tctcctgcgc ctccctcctt
4861   cctcacccac ccccgcctcc atcaggcaca gcaggcaggg gtgggggatg taaggagggg
4921   aaggtggggg acccagaggg ggctttgacg tcagctcagc ttataagagg ctgctgggcc
4981   agggctgtgg agacggagcc cggacctcca cactgagcca tgcccacccc cgacgccacc
5041   acgccacagg ccaagggctt ccgcagggcc gtgtctgagc tggacgccaa gcaggcagag
5101   gccatcatgg taagagggca ggtaggtgcc cggcggccgc agtggaccgg agcccagggc
5161   tggtgccagc tgcctctgct actccccagc ctggctggca gccccaggct cagggtccat
5221   gcaaacccct gggacgcggc gtggatgtgg aggcctgggc acagcggcat cccctgtgcc
5281   tggtgtttga gtccctgttg gggagggtg  aggtgatgcc tgtccctgtg tgtgcccctc
5341   ttaggccgac ctctctcggg ggtcgtgtgg gtctctgtgt cttgtttcat cttgaatctt
5401   aacgatcgga atgtggaaac aaatccatcc aaaaaatcca agatggccag aggtccccgg
5461   ctgctgcacc cagcccccac cctactccca cctgcccctg cctccctctg ccccagctgc
5521   cctagtcagc accccaacca gcctgcctgc ttggggaggc agccccaagg cccttcccag
5581   gctctagcag cagctcatgg tggggggtcc tgggcaaata gggggcaaaa ttcaaagggt
5641   atctgggctc tggggtgatt cccattggcc tgttcctccc ttatttccct cattcattca
5701   ttcattcatt cattcattca ccatggagtc tgtgttccct gtgacctgca ctcggaagcc
5761   ctgtgtacag gggactgtgt gggccaggct ggataatcgg gagcttttca gcccacagga
5821   ggggtcttcg gtgcctcctt gggcactcag aaccttgggc tccctggcac atttaaaatg
5881   ggtttttatt tatggacctt gattgaaatg tggtgtgagt tgtagcagtg tcatttccag
5941   gtaccttctc agggacacag ggcgccctcc cccgtcctcc cccgccctcc cctaccctcc
6001   cccaccaggc tccccatcag gcatcccctc cccagggcgc cccggggccc agcctcacag
6061   gctctccgtg gcctggaact gcagccccag ctgcatccta cacccccacc ccaagggtaa
6121   gtaagagggg actctgggag gggcttctgc tgctcccctt catgttccac aaccctggaa
6181   gctcaggatg aagctgattc ttctcttaca aggggcccag agccttcttg ggagttcagc
6241   tccaaggat  gagccccagg tgtctgccaa gtccccctct gtccaggcct gggacggctc
6301   tgggatcgag ggggtcagagg cgctgagccc agggagagac acctgcgccc agagctatga
6361   caaagggtgg agggatgaca aggcagccag gagcgggcgc ctgcggggtg gcacagaggg
6421   gcagggcccg aggacaggtg tcctgatggg agtgtgagaa agggtcccct gtgcggcagc
6481   caggagggta ggggggttgt tcactggggc cctgtggggg cagctccttc ctgagctgcc
6541   gttccctccc cggcagccga tgccactgtc catcaagaca tcgccctctt cccatcacta
6601   atccagttag cgcctggcct ggggatgagt gacacagcgt ctctgtctgt ctgctcgcca
6661   cagagtgggg agcaggcgag caccttccca gcccccactc ctcccccacc accactgctt
```

-continued

```
6721 ctgactgggc tgcccccatc gggaagggcg tgcaatgccc gcaggcacct cggctagcat
6781 ctgccccagc aggcacacag taggcgctca aaaacgtgct ctcatcccct gcctctgtgt
6841 gccatcagcg ctgcccgact gtgggaccag ctgtgggtgg aggtccccgg gtctcagcag
6901 gtggaggagg catgggtgcc ccttgtcccc acagtccccg cggttcattg ggcgcaggca
6961 gagcctcatc gaggacgccc gcaaggagcg ggaggcggcg gtggcagcag cggccgctgc
7021 agtcccctcg gagcccgggg acccccctgga ggctgtggcc tttgaggaga aggaggggaa
7081 ggccgtgcta aacctgctct tctccccgag ggccaccaag ccctcggcgc tgtcccgagc
7141 tgtgaaggtg tttgaggtga gctggtggcc ttcgtgtccc tggggcaagt tcacctgtgg
7201 gtggggctgt gtgggctgag ttcctgaccc ctctatagca gaggtgcagc tgcccaggcc
7261 cccgaggccg gcacaggatg cagcagggga gtctcaggcc tcagctcagc cccccatggca
7321 tctagccaca cccccgtgtt tttgagggat cctgagccca cccctagggc tgaggctacc
7381 aagccccact gtgcctcttg ccttgcccat cccctggatc cccctcaccc accatttccc
7441 acgtgggggg ctcccagcag ggcagcacaa gaggcagggg cagggcagtg tgccctctcc
7501 cacccaccca gcacagtggc tcaggtgacc actgattgca ttagtcactc cggccccact
7561 gtgccccggg aggcaggtga cccagctccc ggaagaagct cccaaatgac attaaagcca
7621 gactccccgc cccccagctc ccagagccag ttttgtggcc cgagggccac tgcgacccac
7681 cgcccttgtt gctaggcaac aggaggtggg ggtggagcgg acccttctgg ccagtgtcct
7741 ggacgctcag gggccagtga gactcagggc ccatcctaca aacctggatg aggccaccag
7801 ggttgggggc accttctgac cagtggctga ggagccggac tgtgtggcat ggccttggga
7861 cacacacacc gagccgccca gaaccaggtt aagcctcaag cggtgacaac tcctggttag
7921 gcacgtaaca caaaatccaa cttgccagtg gcaaaccctg gcctggtggc cgacagctga
7981 cctgagcctg gaagaacggg atctgtgtgc tgctagcaca aaagtcaagg gcagggcctg
8041 gccagccagc cagatgtgcc tcctccccgc ccaccccacc ctctctctcc atctctgtct
8101 ctttctcctt ctctctctct tcctgctttt gctccctaag acgtttgaag ccaaaatcca
8161 ccatctagag acccggcccg cccagaggcc gcgagctggg ggcccccacc tggagtactt
8221 cgtgcgcctc gaggtgcgcc gaggggacct ggccgccctg ctcagtggtg tgcgccaggt
8281 gtcagaggac gtgcgcagcc ccgcggggcc caagggtgag gcggttttct gtccttgagg
8341 gccaccaaat gaccttgaga ggctggggtg caggggctcc tgcaggggga ccctacagtg
8401 accacgtggt ggtggcctgg ttccctctct gcgggctcca ctccgcaccc cgttttgcta
8461 cacatccgtg tccgggcctg gggccactcc aggatccccc cgcagctctc acagccccgg
8521 ctgcctctgc cccccggaag tcttgtaggg gaggctgctt caaggtgggt gacacagccc
8581 cacggctccg agctcaccaa gatctcttcc tccatcaccc ataaagtccc ctggttccca
8641 agaaaagtgt cagagctgga caagtgtcat cacctggtca ccaagttcga ccctgacctg
8701 gacttggacc acccggtgag tggtgcgccc ctcactcagg cctcctgccc ctgatcacat
8761 cccctaccct tagcccaacc ctggacagga gtctgtcggc tccaggagcc tccgtggcct
8821 gtgcccccac cccagcacag cctcctgacc cgtgcatccc ctctgccctc agggcttctc
8881 ggaccaggtg taccgccagc gcaggaagct gattgctgag atcgccttcc agtacaggca
8941 gtgaggggcc cctgcgctcg ggacccagac tccgtcctgc aggctgacgc tggacctggg
9001 gggtgggagg gaaggacaaa ggggaggacc catcttgtca ccagcatcag tgcctcctgc
9061 caggcagctc tgctccaggg ctttccatgt ccccaaatcc cagtggggaa actgaggccc
9121 agggggggcta gagcaacctg ccgaggccac atagccggct cacggcacag tcagctgggg
```

-continued

```
9181  tgcaccctcc tgtccatcct ccaacccaaa ggcctcgctg cactaggcgg gtgtggacct
9241  gtgcccagtg aagctccctc cctccctcct gcccttctca ctccccgagg ggacctgctg
9301  accactggcc ccctccccag cggcgacccg attccccgtg tggagtacac cgccgaggag
9361  attgccacct ggtgagacct ccgtgcagct aggggctggg gaggagcccg ggggatgcct
9421  cctggaatcc tggcgtgtga gggccgcctc cagggacctt ggcacaacag gagagactaa
9481  ggccgggaag aagagggact tgcagggctc agaatgttgg gttgggagga agaggctacc
9541  catcctgtcg ggccatcccc agtgtgctga gggaccgccc ctcatggccc cctatcccct
9601  gggattccct aaagccacca gcaaaagccc ctcccggggg cctgggtctt caggggtccc
9661  caagaggcct gcgttggtag gggctcaggc aggcagaggc acccacagtt caggaggggg
9721  gtttcgggca ctggggtggg gcattagagg gccctgagcc tggctgcccg caggaaggag
9781  gtctacacca cgctgaaggg cctctacgcc acgcacgcct gcggggagca cctggaggcc
9841  tttgctttgc tggagcgctt cagcggctac cgggaagaca atatccccca gctggaggac
9901  gtctcccgct tcctgaaggg tgtgcccaga cgggaggggc gcagagccgg ggggccgggg
9961  atggtcagcc aagcgcccca ccccagcgcg gctccagccc gtcccggctc ggcagtgacc
10021 cgcgtggccc cttgcagagc gcacgggctt ccagctgcgg cctgtggccg gcctgctgtc
10081 cgcccgggac ttcctggcca gcctggcctt ccgcgtgttc cagtgcaccc agtatatccg
10141 ccacgcgtcc tcgcccatgc actcccctga gccgtgagtg cgcgccctgg ccgccagccc
10201 gagggtgggg ggtgcgacgg gcggcccctc agccccctc tccctcctac gcgcagggac
10261 tgctgccacg agctgctggg gcacgtgccc atgctggccg accgcacctt cgcgcagttc
10321 tcgcaggtac gccgcggcct cggagggagc cggggtcacc caggggctgg cttggcgccg
10381 ggggcgggcg gggatcgatg tgcgggtggg tgaagtgtgc tgcctgctcc cgggccccgc
10441 caaggaggct cggcgccccg agggtcgcgc ggcatagggc ggggctggag cggagcctcc
10501 cacggcctgt gctgccacct gccggctacc tgggaacggc gcccacgggc ttaggaatgt
10561 ggtcaaggag ggctgcctgg aggaggaggc ccggtggagg tgcggatcct gggcggccag
10621 ggaaggtctc tgccgccagg gaagtgtccc agagacccct ggaggggctg ctgacacccc
10681 cggtgccccc acctcgagca tgacccaggg ctgcctctcc ccatccttca tcctccctgc
10741 tccacaggac attggcctgg cgtccctggg ggcctcggat gaggaaattg agaagctgtc
10801 cacggtgggt tgacccctcc ctgcagggcc tggggtgtgg gtttgggggt ctgaatccag
10861 gcctcaccct cttgccgtcc aggctgaggc ctctccttcc acccacgaat tgtgaccctc
10921 accctggcct gcctgcatcc tggcctggcc tccctggggg tggtatcctg gtcacgggtg
10981 accaggggct gcccggtggg cggcagctgt ctctgggctg atgctgcccg gcttccccgc
11041 agctgtactg gttcacggtg gagttcgggc tgtgtaagca gaacggggag gtgaaggcct
11101 atggtgccgg gctgctgtcc tcctacgggg agctcctggt gagagtctct ccttgctgca
11161 gcccccagca gaggggcagg gctgggggac ggtgcaggga ggggacaggc tcccagtggg
11221 aggaaactga ggcctggacc tccaggactc aggctctgtt tgggagaagg cttgtctctg
11281 cccagtcctc accccacatt atcccaggcc tccgaaggcc cggcgggggga gatgggggtg
11341 actctaccca aggaacccac ccagcgtcag gccacggtgc cccagttccc tcggggacct
11401 gggtgcagtg gagtcagtga tgccattggc ctcctgccag cactgcctgt ctgaggagcc
11461 tgagattcgg gccttcgacc ctgaggctgc ggccgtgcag ccctaccaag accagacgta
11521 ccagtcagtc tacttcgtgt ctgagagctt cagtgacgcc aaggacaagc tcaggtgggc
11581 taggctgcta gggcaagccc cccatggtgc cccccaaactg ggccagccag gccttccttc
```

-continued 11641 tggccttgag cagggctgga cctgtgagcc caggtcacag atgagaaaac cgacccctgg 11701 ttgcagcagc ccccacacag cagggacacc atccgtgaga aggaccccag cgtctgggga 11761 ggggcagacc tacaggactg gggctgctg ggtggccggg tcaaggccag tcttggaggt 11821 gctgacagag cctgagcttt gtgaggacgt cctgtggaac ctgtcccggc cccctgccct 11881 gggatgggga gaagtcaggg ggatagacag agtcaaggtg ggggacaggg cgggagtggg 11941 gtccccaggg ctgggggcct ttggtgcagt gaccagagtg tcaggagagg ggagcaaagc 12001 cctctagcct catcctcata aaaggtctca tcattttccc tccagcctct tatgcactgg 12061 ggaaactgag gccaggggct atgtgtccag cggacagggg tgctgaattc cacccacagg 12121 cttagggata tggtcaagga aagcttcctg gaggaggccc agtggaggtt cagggaggga 12181 tggggtgccc ggcagtctct agtggaaaag gcgcctagcc tatctccccc atgaaccccc 12241 tcacccagcc ctggaagagg cctcagtgtc ccgcctgtga ccagttggct cagaaaagcc 12301 ctgggagctc tgagccactg tgaaggtgga aacgcggccc ctggcctccc ctctcctgga 12361 ggctgcagac tctgcccgcc agttgacgag ggctctgccg ctctcctccc caggagctat 12421 gcctcacgca tccagcgccc cttctccgtg aagttcgacc cgtacacgct ggccatcgac 12481 gtgctggaca gcccccaggc cgtgcggcgc tccctggagg gtgtccagga tgagctggac 12541 acccttgccc atgcgctgag tgccattggc taggtgcacg gcgtccctga gggcccttcc 12601 caacctcccc tggtcctgca ctgtcccgga gctcaggccc tggtgagggg ctgggtcccg 12661 ggtgcccccc atgccctccc tgctgccagg ctcccactgc ccctgcacct gcttctcagc 12721 gcaacagctg tgtgtgcccg tggtgaggtt gtgctgcctg tggtgaggtc ctgtcctggc 12781 tcccagggtc ctgggggctg ctgcactgcc ctccgccctt ccctgacact gtctgctgcc 12841 ccaatcaccg tcacaataaa agaaactgtg gtctctacac ctgcctggcc ccacatctgt 12901 gccacagaga cagaccctgg gatcctcaga ctcccacacc cccaccccag cctcactcag 12961 aggtttcgcc ctggcctcct tcctcctctg ggagatggct ggccgccctg gccaggcagc 13021 tggcccctcc gggcctggtt tccccgctca ccctgaggcc ccgcccagct ctgagcccca 13081 agcagctcca gaggctcggg caccctggcc gagctgcccc atctccgtgg ggtgccctcc 13141 caaggtgggg agccacgtga cagtgggagg gcctctctca ggcctggcag ggagcagggg 13201 tcacaaactg tgctggctgg gggtggtctc agaggtgggc ctgcaggcct aaccctccct 13261 gctgacaggg ctcccagccc ttgagagaaa cagggatgga ggaacagctg ccctgatgcc 13321 ctcacccacc cggagcaggc cctgcgaacc aaggggaacc tcagtgtggc cccagcatg 13381 tgtgctgatg gggagggtct ggctgagctg gtgcccaggc agatggtctg ggcctgtctc 13441 cccagcgagg caggatgggg gctggatttc agactctgta agatgcccct ggcttactcg 13501 aggggcctgg acattgccct ccagagagag cacccaacac cctccaggct tgaccggcca 13561 gggtgtcccc ttcctacctt ggagagagca gccccagggc atcctgcagg gggtgctggg 13621 acaccagctg gccttcaagg tctctgcctc cctccagcca ccccactaca cgctgctggg 13681 atcctggatc tcagctcccc ggccgacaac actggcaaac tcctactcat ccacgaaggc 13741 cctcctgggc atggtggtcc ttcccagcct ggcagtctgt tcctcacaca ccttgttagt 13801 gcccagcccc tgaggttgca gctgggggtg tctctgaagg gctgtgagcc cccaggaagc 13861 cctggggaag tgcctgcctt gcctcccccc ggccctgcca gcgcctggct ctgccctcct 13921 acctgggctc cccccatcca gcctccctcc ctacacactc ctctcaagga ggcacccatg 13981 tcctctccag ctgccgggcc tcagagcact gtggcgtcct ggggcagcca ccgcatgtcc 14041 tgctgtggca tggctcaggg tggaaagggc ggaagggagg ggtcctgcag atagctggtg -continued 14101 cccactacca aacccgctcg gggcaggaga gccaaaggct gggtgtgtgc agagcggccc 14161 cgagaggttc cgaggctgag gccagggtgg gacataggga tgcgaggggc cggggcacag 14221 gatactccaa cctgcctgcc cccatggtct catcctcctg cttctgggac ctcctgatcc 14281 tgcccctggt gctaagaggc aggtaggggc tgcaggcagc agggctcgga gcccatgccc 14341 cctcaccatg ggtcaggctg gacctccagg tgcctgttct ggggagctgg gagggccgga 14401 ggggtgtacc ccaggggctc agcccagatg acactatggg ggtgatggtg tcatgggacc 14461 tggccaggag aggggagatg ggctcccaga agaggagtgg gggctgagag ggtgcctggg 14521 gggccaggac ggagctgggc cagtgcacag cttcccacac ctgcccaccc ccagagtcct 14581 gccgccaccc ccagatcaca cggaagatga ggtccgagtg gcctgctgag gacttgctgc 14641 ttgtccccag gtccccaggt catgccctcc ttctgccacc ctggggagct gagggcctca 14701 gctggggctg ctgtcctaag gcagggtggg aactaggcag ccagcaggga ggggacccct 14761 ccctcactcc cactctccca cccccaccac cttggcccat ccatggcggc atcttgggcc 14821 atccgggact ggggacaggg gtcctgggga caggggtgtg gggacagggg tcctggg By “LMX1A polypeptide” (or LIM homeobox transcription factor 1-alpha) is meant a polypeptide or fragment thereof having at least about 85% amino acid identity to NCBI Accession No. Q8TE12.

(SEQ ID NO: 9)

1 mldglkmeen fqsaidtsas fssllgravs pksvcegcqr vildrfllrl ndsfwheqcv 61 qcasckeple ttcfyrdkkl yckydyeklf avkcggcfea iapnefvmra qksvyhlscf 121 cccvcerqlq kgdefvlkeg qllckgdyek erellslvsp aasdsgksdd eeslcksahg 181 agkgtaeegk dhkrpkrprt ilttqqrraf kasfevsskp crkvretlaa etglsvrvvq 241 vwfqnqrakm kklarrqqqq qqdqqntqrl ssaqtngggs agmegimnpy talptpqqll 301 aieqsvyssd pfrqgltppq mpgdhmhpyg aeplfhdlds ddtslsnlgd cflatseagp 361 lqsrvgnpid hlysmqnsyf ts By “LMX1A nucleic acid molecule” (or LIM homeobox transcription factor 1-alpha) is meant a polynucleotide encoding an LMX1A polypeptide. An exemplary LMX1A nucleic acid molecule is provided at NCBI Accession No. AH011517.

(SEQ ID NO: 10)

1 gtataggttg gggcggagtc ggattcggga tggaaaacct ggggcaaggg atgtaggtgg 61 gggtgagggg ggcaggagaa ggagaaacgc agttgggggg cggaggccta agtacataac 121 gtgttgactt caagtgaaat cagatcagcc agagcagttc gctgtgactg atctctcctc 181 ccaccctaca ttctcttggc tggaccctat cctcctggct gattctggtc gccctggaca 241 ctccctcagt tctttcccag gagtgcggtg gctgctggcg ccgagtccca gcgggcacgg 301 acgtcagacg catcgtttct tctcctctac aggtcctccc ggcccggccc gaacatgctg 361 gacggcctaa agatggagga gaacttccaa agcgcgatcg acacctcggc ctccttctcc 421 tcgctgctgg gtgagtgttc aggccgtgcg tcctgggcgc actctctttc cgcttggcgc 481 tgagctctgg agccccgctc tctgggacct ggtccgcgat agggaagcta gcgcccctct 541 tcatacacta aattgagccc catcactatc tgtccgtcag tgcttgtggg tcgtccctac 601 ccaaataaat ccaacaagcc gccccaggcc tcacgcactg ggcaccgaat tccccaaagc -continued

```
661 cgcgaggggc gggcgagctt gttcgtaggc gtctgagtgg caagtgatta aaaataccca

721 gggctggatt tttaatctcg gagctgatcg acgtctcata aatgccgccc tcttctcgcg

781 gcctagaggc aatagcatcc gagacccgag gcctggagcg cccaagttcg aggaggcttc

841 tctcccccac caactccagc cccaatttca gccatgggca aggccgagag agacttttct

901 nnnnnnnnnn nnnnnnnnnn nnnnnnnnnn nnnnnnnnnn nnnnnnnnnn nnnnnnnnnn

961 nnnnnnnnnn nnnnnnnnnn nnnnnnnnnn nnnnnnnnnn gggtcccggc caggtttggc

1021 atggtctacc tgcccgggct gctcacccgc caacgtctgt tgtggctaca ggcagagcgg

1081 tgagccccaa gtctgtctgc gagggctgtc agcgggtcat cttggacagg tttctgctgc

1141 ggctcaacga cagcttctgg catgagcagt gcgtgcagtg cgcctcctgc aaagagcccc

1201 tggagaccac ctgcttctac cgggacaaga agctgtactg caagtatgac tacgagaagt

1261 aagtggccgc accccccgcag cgctccccgc gcactggcat nnnnnnnnnn nnnnnnnnnn

1321 nnnnnnnnnn nnnnnnnnnn nnnnnnnnnn nnnnnnnnnn nnnnnnnnnn nnnnnnnnnn

1381 nnnnnnnnnn nnnnnnnnnn atcccagttc ttgaagttcc ttttgctgtt gacttcaggg

1441 gagacccagg accaagccag attttactca tggtgcatgt acttcctttc tccctgctgc

1501 caggctgttt gctgttaaat gtgggggctg cttcgaggcc atcgctccca atgagtttgt

1561 tatgcgggcc cagaagagtg tataccacct gagctgcttc tgctgctgtg tctgcgagcg

1621 acagcttcag aagggtgatg agtttgtcct gaaggagggg cagctgctct gcaaagggga

1681 ctatgagaag gagcgggagc tgctcagcct ggtgagccca gcagcctcag actcaggtga

1741 gtgccaggtg gtgggcaggg ctgcggtggg gtgggtagag tggagttggg tggctgtctg

1801 cattgtttct tccctagatg nnnnnnnnnn nnnnnnnnnn nnnnnnnnnn nnnnnnnnnn

1861 nnnnnnnnnn nnnnnnnnnn nnnnnnnnnn nnnnnnnnnn nnnnnnnnnn nnnnnnnnnn

1921 catacagctc caggaactgg ctttcaggga ctcacaacat tgtcttttgc ttctttcagg

1981 taaaagtgat gatgaagaaa gtctctgcaa gtcagcccat ggggcaggga aaggaactgc

2041 tgaggaaggc aaggaccata agcgccccaa acgtccgaga accatcttga caactcaaca

2101 gaggcgagca ttcaaggcct catttgaagt atcctccaag ccctgcagga aggtatagga

2161 gggagcaggg aggaaaagga gctgggcccc acttctctgt gtgcactcag acccctctgg

2221 gatctcagtg ggcattgggg gtcacagtgg tgaggaaggc tgttcagaca gagcctgcac

2281 aggcggctca agcctgttgg agactccaga gatcactaag ctgtggccag ggtgtgatag

2341 actctcctga agctttcatg catgcacacc aactccaaat ggcccctgtc acacctttca

2401 tttcatagag cacaatggga acagtaataa tgataggtgt ccattgtggt gtagacccag

2461 atgctgtaaa gcaaagagta taaaaacaca gtggcttgca gtactctttt ttgagtctgg

2521 ctttttccac ttggtgtggt ggtttgggga ttcattcatt cctatttcag cattccactg

2581 tataggtgtg ccatgattgg tttgtccatg cacctgttga tgggtgtttg ggttgtttc

2641 tagtttggga ctgtttcaaa taggactgct atggacattc atgtaaaaaa aaatacagtg

2701 gtttaatgag acaggagttt attctcttct gtcacagtcc agaggtgagc aaggcaaggc

2761 tggtgggtgg ctctgttatc catctcctgt gtccaagcga ctgctccagt tgtcaccatg

2821 tttccagtca ccaggtagag aaagaggaaa tggagggcaa gcgccctgct ttttaaggat

2881 nnnnnnnnnn nnnnnnnnnn nnnnnnnnnn nnnnnnnnnn nnnnnnnnnn nnnnnnnnnn

2941 nnnnnnnnnn nnnnnnnnnn nnnnnnnnnn nnnnnnnnnn atgcatatgc atggcttata

3001 gctaaagcac aacaatagac taaagtctaa accacttgaa ggcctaattt ccagagcaag

3061 agaaatccag aaacacctct tgggaatgca catgtaaatt aataattatt attttgtttc
```

-continued

```
3121 tttacctggt gaaggacttt ctttctacct gaagggaagc aatgttctcg tgtttgtgtg
3181 tatgctcaac attaaaaact attcagctcc taaagcagat acagtctttt ggcctcctca
3241 agtattatat aggagatgtt ctacctccta ccctgagatg ccagtgtgtc tacatttctc
3301 gttcaatttt tccaaggtga gagagactct ggctgcagag acagggctga gtgtccgtgt
3361 cgtccaggtg tggttccaaa accagagagc gaaggtaacc tgcttcttac ttttatctgt
3421 ccccatgttg ctggtttcct gaaataatca cagtaggaca nnnnnnnnnn nnnnnnnnnn
3481 nnnnnnnnnn nnnnnnnnnn nnnnnnnnnn nnnnnnnnnn nnnnnnnnnn nnnnnnnnnn
3541 nnnnnnnnnn nnnnnnnnnn agccctctcc cggggaaggt gtcacttcca ggccccccct
3601 tactttgtga acatgctgca ggccacctga cttctaatcc tatggtcctc tccttatcag
3661 atgaagaagc tggccaggcg acagcagcag cagcagcaag atcagcagaa cacccagagg
3721 ctgagctctg gtaagctggt gcctcctccc aggcagttct ggctggaatc caggctgttc
3781 ctaccagagg cctcccacta cccagctctt tggatgacat atctggactc agtgaagcct
3841 agaccacacc cactggagaa ataaggcctt caagggaaga ctgagccacg aggaacttgt
3901 gagagggttg agggctcctg agctgcaggc ttagaactgc tgattgggga tggcactgac
3961 cttatccaca gcgtccaggc ctggatccca ccacagcgtc agggactgct tgcagagtca
4021 cagatacgtt cagtttctca tcttgcttag ttctccttcc aggctaattg atttaataga
4081 agacacctcg gtgacttggc tctttccaaa ataacataaa gtagtaaaaa taatgatagt
4141 aaaataacaa tgccttcctt tgttgaacac tcttatagat tggtgttctc atacatgctg
4201 acttgacttt tacaacaccc attcctggag gcgagtggag aagttgttat tatccctatg
4261 tcacagatga gcaaacaaag gctctgcaag attgaatgtg gccctagatc ggtaagggca
4321 gggggctggg actagaactc taactgtgtt ccacaggcca tgggccttct catctctacc
4381 cagatgtgct tttgaaaaag nnnnnnnnnn nnnnnnnnnn nnnnnnnnnn nnnnnnnnnn
4441 nnnnnnnnnn nnnnnnnnnn nnnnnnnnnn nnnnnnnnnn nnnnnnnnnn nnnnnnnnnn
4501 cacgttgaga atgacctggc ttcttctttg ttccacagct cagacaaacg gtggtgggag
4561 tgctgggatg gaaggaatca tgaaccccta cacggctctg cccaccccac agcagctcct
4621 ggccatcgag cagagtgtct acagctcaga tcccttccga cagggtctca ccccacccca
4681 gatgcctgga gaccacatgc acccttatgg taagagggac ttaagcccct cgggccctct
4741 cataacttgt gtgggtttct cattccctcc taaacacatc taggcagttc ccagatgctc
4801 nnnnnnnnnn nnnnnnnnnn nnnnnnnnnn nnnnnnnnnn nnnnnnnnnn nnnnnnnnnn
4861 nnnnnnnnnn nnnnnnnnnn nnnnnnnnnn nnnnnnnnnn aaatgagtca cttcttcaag
4921 accctcatgc cagtgtttca tctccatttc aggtgccgag ccccttttcc atgacctgga
4981 tagcgacgac acctccctca gtaacctggg tgattgtttc ctagcaacct cagaagctgg
5041 gcctctgcag tccagagtgg gaaaccccat tgaccatctg tactccatgc agaattctta
5101 cttcacatct tgagtcttcc cctagagttc tgtgactagg ctcccatatg gaacaaccat
5161 attctttgag ggtcactgg ctttaggaca gggaggccag ggaagaggtg ggttggggag
5221 ggagttttgt tggggatgct gttgtataat gatatggtgt agctcagcat ttccaaagac
5281 tgaatacatt atggattgca tagtttaatg
```

By "FOXO1 polypeptide" (or Forkhead box protein 01) is meant a polypeptide or fragment thereof having at least about 85% amino acid identity to NCBI Accession No. Q12778.

(SEQ ID NO: 11)

```
  1 maeapqvvei dpdfeplprp rsctwplprp efsqsnsats spapsgsaaa npdaaaglps
 61 asaaaysadf msnlsllees edfpqapgsv aaavaaaaaa aatgglcgdf qgpeagclhp
121 appqppppgp lsqhppvppa aagplagqpr kssssrrnaw gnlsyadlit kaiessaekr
181 ltlsqiyewm vksvpyfkdk gdsnssagwk nsirhnlslh skfirvqneg tgksswwmln
241 peggksgksp rrraasmdnn skfaksrsra akkkaslqsg qegagdspgs qfskwpaspg
301 shsnddfdnw stfrprtssn astisgrlsp imteqddlge gdvhsmvypp saakmastlp
361 slseisnpen menlldnlnl lssptsltvs tqsspgtmmq qtpcysfapp ntslnspspn
421 yqkytygqss msplpqmpiq tlqdnkssyg gmsqyncapg llkelltsds pphndimtpv
481 dpgvaqpnsr vlgqnvmmgp nsvmstygsq ashnkmmnps shthpghaqq tsavngrplp
541 htvstmphts gmnrltqvkt pvqvplphpm qmsalggyss vsscngygrm gllhqeklps
601 dldgmfierl dcdmesiirn dlmdgdtldf nfdnvlpnqs fphsvktttH swvsg
```

By "FOXO1 nucleic acid molecule" (or Forkhead box protein 01) is meant a polynucleotide (e.g., mRNA) encoding an FOXO1 polypeptide. An exemplary FOXO1 nucleic acid molecule is provided at NCBI Accession No. NM_002015.

(SEQ ID NO: 12)

```
   1 gcagccgcca cattcaacag gcagcagcgc agcgggcgcg ccgctgggga gagcaagcgg
  61 cccgcggcgt ccgtccgtcc ttccgtccgc ggccctgtca gctggagcgc ggcgcaggct
 121 ctgccccggc ccggcggctc tggccggccg tccagtccgt gcggcggacc ccgaggagcc
 181 tcgatgtgga tggccccgcg aagttaagtt ctgggctcgc gcttccactc cgccgcgcct
 241 tcctcccagt ttccgtccgc tcgccgcacc ggcttcgttc ccccaaatct cggaccgtcc
 301 cttcgcgccc cctccccgtc cgcccccagt gctgcgttct ccccctcttg gctctcctgc
 361 ggctggggga ggggcggggg tcaccatggc cgaggcgcct caggtggtgg agatcgaccc
 421 ggacttcgag ccgctgcccc ggccgcgctc gtgcacctgg ccgctgccca ggccggagtt
 481 tagccagtcc aactcggcca cctccagccc ggcgccgtcg ggcagcgcgg ctgccaaccc
 541 cgacgccgcg gcgggcctgc cctcggcctc ggctgccgct gtcagcgccg acttcatgag
 601 caacctgagc ttgctggagg agagcgagga cttcccgcag gcgcccggct ccgtggcggc
 661 ggcggtggcg gcggcggccg ccgcggccgc caccgggggg ctgtgcgggg acttccaggg
 721 cccggaggcg ggctgcctgc acccagcgcc accgcagccc ccgccgcccg ggccgctgtc
 781 gcagcacccg ccggtgcccc ccgccgccgc tgggccgctc gcggggcagc cgcgcaagag
 841 cagctcgtcc cgccgcaacg cgtggggcaa cctgtcctac gccgacctca tcaccaaggc
 901 catcgagagc tcggcggaga agcggctcac gctgtcgcag atctacgagt ggatggtcaa
 961 gagcgtgccc tacttcaagg ataagggtga cagcaacagc tcggcgggct ggaagaattc
1021 aattcgtcat aatctgtccc tacacagcaa gttcattcgt gtgcagaatg aaggaactgg
1081 aaaaagttct tggtggatgc tcaatccaga gggtggcaag agcgggaaat ctcctaggag
1141 aagagctgca tccatggaca acaacagtaa atttgctaag agccgaagcc gagctgccaa
1201 gaagaaagca tctctccagt ctggccagga gggtgctggg gacagccctg gatcacagtt
1261 ttccaaatgg cctgcaagcc ctggctctca cagcaatgat gactttgata actggagtac
1321 atttcgccct cgaactagct caaatgctag tactattagt gggagactct cacccattat
```

-continued 1381 gaccgaacag gatgatcttg gagaagggga tgtgcattct atggtgtacc cgccatctgc 1441 cgcaaagatg gcctctactt tacccagtct gtctgagata agcaatcccg aaaacatgga 1501 aaatcttttg gataatctca accttctctc atcaccaaca tcattaactg tttcgaccca 1561 gtcctcacct ggcaccatga tgcagcagac gccgtgctac tcgtttgcgc caccaaacac 1621 cagtttgaat tcacccagcc caaactacca aaaatataca tatggccaat ccagcatgag 1681 ccctttgccc cagatgccta tacaaacact tcaggacaat aagtcgagtt atggaggtat 1741 gagtcagtat aactgtgcgc ctggactctt gaaggagttg ctgacttctg actctcctcc 1801 ccataatgac attatgacac cagttgatcc tggggtagcc cagcccaaca gccgggttct 1861 gggccagaac gtcatgatgg gccctaattc ggtcatgtca acctatggca gccaggcatc 1921 tcataacaaa atgatgaatc ccagctccca tacccaccct ggacatgctc agcagacatc 1981 tgcagttaac gggcgtcccc tgccccacac ggtaagcacc atgccccaca cctcgggtat 2041 gaaccgcctg acccaagtga agacacctgt acaagtgcct ctgccccacc ccatgcagat 2101 gagtgccctg gggggctact cctccgtgag cagctgcaat ggctatggca gaatgggcct 2161 tctccaccag gagaagctcc caagtgactt ggatggcatg ttcattgagc gcttagactg 2221 tgacatggaa tccatcattc ggaatgacct catggatgga gatacattgg attttaactt 2281 tgacaatgtg ttgcccaacc aaagcttccc acacagtgtc aagacaacga cacatagctg 2341 ggtgtcaggc tgagggttag tgagcaggtt acacttaaaa gtacttcaga ttgtctgaca 2401 gcaggaactg agagaagcag tccaaagatg tctttcacca actccctttt agttttcttg 2461 gttaaaaaaa aaaacaaaaa aaaaaaccct cctttttcc tttcgtcaga cttggcagca 2521 aagacatttt tcctgtacag gatgtttgcc caatgtgtgc aggttatgtg ctgctgtaga 2581 taaggactgt gccattggaa atttcattac aatgaagtgc caaactcact acaccatata 2641 attgcagaaa agattttcag atcctggtgt gctttcaagt tttgtatata agcagtagat 2701 acagattgta tttgtgtgtg tttttggttt ttctaaatat ccaattggtc caaggaaagt 2761 ttatactctt tttgtaatac tgtgatgggc ctcatgtctt gataagttaa acttttgttt 2821 gtactacctg ttttctgcgg aactgacgga tcacaaagaa ctgaatctcc attctgcatc 2881 tccattgaac agccttggac ctgttcacgt tgccacagaa ttcacatgag aaccaagtag 2941 cctgttatca atctgctaaa ttaatggact tgttaaactt ttggaaaaaa aaagattaaa 3001 tgccagcttt gtacaggtct tttctatttt tttttgttta ttttgttatt tgcaaatttg 3061 tacaaacatt taaatggttc taatttccag ataaatgatt tttgatgtta ttgttgggac 3121 ttaagaacat ttttggaata gatattgaac tgtaataatg ttttcttaaa actagagtct 3181 actttgttac atagtcagct tgtaaatttt gtggaaccac aggtatttgg ggcagcattc 3241 ataattttca ttttgtattc taactggatt agtactaatt ttatacatgc ttaactggtt 3301 tgtacacttt gggatgctac ttagtgatgt ttctgactaa tcttaaatca ttgtaattag 3361 tacttgcata ttcaacgttt caggccctgg ttgggcagga aagtgatgta tagttatgga 3421 cactttgcgt ttcttattta ggataactta atatgttttt atgtatgtat tttaaagaaa 3481 tttcatctgc ttctactgaa ctatgcgtac tgcatagcat caagtcttct ctagagacct 3541 ctgtagtcct gggaggcctc ataatgtttg tagatcagaa aagggagatc tgcatctaaa 3601 gcaatggtcc tttgtcaaac gagggatttt gatccacttc accattttga gttgagcttt 3661 agcaaaagtt tcccctcata attctttgct cttgtttcag tccaggtgga ggttggtttt 3721 gtagttctgc cttgaggaat tatgtcaaca ctcatacttc atctcattct cccttctgcc 3781 ctgcagatta gattacttag cacactgtgg aagtttaagt ggaaggaggg aatttaaaaa -continued

```
3841 tgggacttga gtggtttgta gaatttgtgt tcataagttc agatgggtag caaatggaat
3901 agaacttact taaaaattgg ggagatttat ttgaaaacca gctgtaagtt gtgcattgag
3961 attatgttaa aagccttggc ttaagaattt gaaaatttct ttagcctgta gcaacctaaa
4021 ctgtaattcc tatcattatg ttttattact ttccaattac ctgtaactga cagaccaaat
4081 taattggctt tgtgtcctat ttagtccatc agtattttca agtcatgtgg aaagcccaaa
4141 gtcatcacaa tgaagagaac aggtgcacag cactgttcct cttgtgttct tgagaaggat
4201 ctaatttttc tgtatatagc ccacatcaca cttgctttgt cttgtatgtt aattgcatct
4261 tcattggctt ggtatttcct aaatgtttaa caagaacaca agtgttcctg ataagatttc
4321 ctacagtaag ccagctctat tgtaagcttc ccactgtgat gatcattttt ttgaagattc
4381 attgaacagc caccactcta tcatcctcat tttggggcag tccaagacat agctggtttt
4441 agaaacccaa gttcctctaa gcacagcctc ccgggtatgt aactgaactt ggtgccaaag
4501 tacttgtgta ctaatttcta ttactacgta ctgtcacttt cctcccgtgc cattactgca
4561 tcataataca aggaacctca gagcccccat ttgttcatta aagaggcaac tacagccaaa
4621 atcactgtta aaatcttact acttcatgga gtagctctta ggaaaatata tcttcctcct
4681 gagtctgggt aattatacct ctcccaagcc cccattgtgt gttgaaatcc tgtcatgaat
4741 ccttggtagc tctctgagaa cagtgaagtc cagggaaagg catctggtct gtctggaaag
4801 caaacattat gtggcctctg gtagtttttt tcctgtaaga atactgactt tctggagtaa
4861 tgagtatata tcagttattg tacatgattg ctttgtgaaa tgtgcaaatg atatcaccta
4921 tgcagccttg tttgatttat tttctctggt ttgtactgtt attaaaagca tattgtatta
4981 tagagctatt cagatatttt aaatataaag atgtattgtt tccgtaatat agacgtatgg
5041 aatatattta ggtaatagat gtattacttg gaaagttctg ctttgacaaa ctgacaaagt
5101 ctaaatgagc acatgtatcc cagtgagcag taaatcaatg gaacatccca agaagaggat
5161 aaggatgctt aaaatggaaa tcattctcca acgatataca aattggactt gttcaactgc
5221 tggatatatg ctaccaataa ccccagcccc aacttaaaat tcttacattc aagctcctaa
5281 gagttcttaa tttataacta attttaaaag agaagtttct tttctggttt tagtttggga
5341 ataatcattc attaaaaaaa atgtattgtg gtttatgcga acagaccaac ctggcattac
5401 agttggcctc tccttgaggt gggcacagcc tggcagtgtg gccaggggtg gccatgtaag
5461 tcccatcagg acgtagtcat gcctcctgca tttcgctacc cgagtttagt aacagtgcag
5521 attccacgtt cttgttccga tactctgaga agtgcctgat gttgatgtac ttacagacac
5581 aagaacaatc tttgctataa ttgtataaag ccataaatgt acataaatta tgtttaaatg
5641 gcttggtgtc tttcttttct aattatgcag aataagctct ttattaggaa ttttttgtga
5701 agctattaaa tacttgagtt aagtcttgtc agccacaa
```

By “FOXA2 polypeptide” (or Forkhead box protein A2) is meant a polypeptide or fragment thereof having at least about 85% amino acid identity to NCBI Accession No. Q9Y261.

(SEQ ID NO: 13)

```
  1 mlgavkmegh epsdwssyya epegyssysn mnaglgmngm ntymsmsaaa mgsgsgnmsa
 61 gsmnmssyvg agmspslagm spgagamagm ggsagaagva gmgphlspsl splggqaaga
121 mgglapyanm nsmspmygqa glsrardpkt yrrsythakp pysyislitm aiqqspnkml
181 tlseiyqwim dlfpfyrqnq qrwqnsirhs lsfndcflkv prspdkpgkg sfwtlhpdsg
```

-continued

```
241 nmfengcylr rqkrfkcekq lalkeaagaa gsgkkaaaga qasqaqlgea agpasetpag
301 tesphssasp cqehkrgglg elkgtpaaal sppepapspg qqqqaaahll gpphhpglpp
361 eahlkpehhy afnhpfsinn lmsseqqhhh shhhhqphkm dlkayeqvmh ypgygspmpg
421 slamgpvtnk tgldasplaa dtsyyqgvys rpimnss
```

By "FOXA2 nucleic acid molecule" (or Forkhead box protein A2) is meant a polynucleotide (e.g., mRNA) encoding an FOXA2 polypeptide. An exemplary FOXA2 nucleic acid molecule is provided at NCBI Accession No. NM_021784.

(SEQ ID NO: 14)

```
   1 cccgcccact tccaactacc gcctccggcc tgcccaggga gagagaggga gtggagccca
  61 gggagaggga gcgcgagaga gggagggagg aggggacggt gctttggctg actttttttt
 121 aaaagagggt gggggtgggg ggtgattgct ggtcgtttgt tgtggctgtt aaattttaaa
 181 ctgccatgca ctcggcttcc agtatgctgg gagcggtgaa gatggaaggg cacgagccgt
 241 ccgactggag cagctactat gcagagcccg agggctactc ctccgtgagc aacatgaacg
 301 ccggcctggg gatgaacggc atgaacacgt acatgagcat gtcggcggcc gccatgggca
 361 gcggctcggg caacatgagc gcgggctcca tgaacatgtc gtcgtacgtg ggcgctggca
 421 tgagcccgtc cctggcgggg atgtccccgg gcgcgggcgc catggcgggc atgggcggct
 481 cggccggggc ggccggcgtg gcgggcatgg ggccgcactt gagtcccagc ctgagcccgc
 541 tcggggggca ggcggccggg gccatgggcg gcctggcccc ctacgccaac atgaactcca
 601 tgagccccat gtacgggcag gcgggcctga gccgcgcccg cgaccccaag acctacaggc
 661 gcagctacac gcacgcaaag ccgccctact cgtacatctc gctcatcacc atggccatcc
 721 agcagagccc caacaagatg ctgacgctga gcgagatcta ccagtggatc atggacctct
 781 tccccttcta ccggcagaac cagcagcgct ggcagaactc catccgccac tcgctctcct
 841 tcaacgactg tttcctgaag gtgccccgct cgcccgacaa gcccggcaag ggctccttct
 901 ggaccctgca ccctgactcg ggcaacatgt tcgagaacgg ctgctacctg cgccgccaga
 961 agcgcttcaa gtgcgagaag cagctggcgc tgaaggaggc cgcaggcgcc gccggcagcg
1021 gcaagaaggc ggccgccgga gcccaggcct cacaggctca actcggggag gccgccgggc
1081 cggcctccga gactccggcg ggcaccgagt cgcctcactc gagcgcctcc ccgtgccagg
1141 agcacaagcg agggggcctg ggagagctga aggggacgcc ggctgcggcg ctgagccccc
1201 cagagccggc gccctctccc gggcagcagc agcaggccgc ggcccacctg ctgggcccgc
1261 cccaccaccc gggcctgccg cctgaggccc acctgaagcc ggaacaccac tacgccttca
1321 accacccgtt ctccatcaac aacctcatgt cctcggagca gcagcaccac cacagccacc
1381 accaccacca accccacaaa atggacctca aggcctacga acaggtgatg cactaccccg
1441 gctacggttc cccatgcct ggcagcttgg ccatgggccc ggtcacgaac aaaacgggcc
1501 tggacgcctc gcccctggcc gcagatacct cctactacca gggggtgtac tcccggccca
1561 ttatgaactc ctcttaagaa gacgacggct tcaggcccgg ctaactctgg caccccggat
1621 cgaggacaag tgagagagca agtgggggtc gagactttgg ggagacggtg ttgcagagac
1681 gcaagggaga agaaatccat aacaccccca ccccaacacc cccaagacag cagtcttctt
1741 cacccgctgc agccgttccg tcccaaacag agggccacac agatacccca cgttctatat
1801 aaggaggaaa acgggaaaga atataaagtt aaaaaaaagc ctccggtttc cactactgtg
1861 tagactcctg cttcttcaag cacctgcaga ttctgatttt tttgttgttg ttgttctcct
```

-continued

```
1921 ccattgctgt tgttgcaggg aagtcttact taaaaaaaaa aaaaaatttt gtgagtgact
1981 cggtgtaaaa ccatgtagtt ttaacagaac cagagggttg tactattgtt taaaaacagg
2041 aaaaaaaata atgtaagggt ctgttgtaaa tgaccaagaa aaagaaaaaa aaagcattcc
2101 caatcttgac acggtgaaat ccaggtctcg ggtccgatta atttatggtt tctgcgtgct
2161 ttatttatgg cttataaatg tgtattctgg ctgcaagggc cagagttcca caaatctata
2221 ttaaagtgtt atacccggtt ttatcccttg aatcttttct tccagatttt tcttttcttt
2281 acttggctta caaaatatac aggcttggaa attatttcaa gaaggaggga gggataccct
2341 gtctggttgc aggttgtatt ttattttggc ccagggagtg ttgctgtttt cccaacattt
2401 tattaataaa attttcagac ataaaaaa
```

By "FOXO4 polypeptide" (or Forkhead box protein 04) is meant a polypeptide or fragment thereof having at least about 85% amino acid identity to NCBI Accession No. P98177.

```
                                                    (SEQ ID NO: 15)
  1 mdpgnensat eaaaiidldp dfepqsrprs ctwplprpei anqpseppev epdlgekvht
 61 egrsepillp srlpepaggp qpgilgavtg prkggsrrna wgnqsyaeli sqaiesapek
121 rltlaqiyew mvrtvpyfkd kgdsnssagw knsirhnlsl hskfikvhne atgksswwml
181 npeggksgka prrraasmds ssklllrgrsk apkkkpsvlp appegatpts pvghfakwsg
241 spcsrnreea dmwttfrprs ssnassystr lsplrpesev laeeipasvs syaggvpptl
301 neglelldgl nitsshslls rsglsgfslq hpgvtgplht yssslfspae gplsagegcf
361 sssqaleall tsdtppppad vlmtqvdpil sqaptllllg glpssskklat gvglcpkple
421 apgpsslvpt lsmiapppvm asapipkalg tpvltpptea asqdrmpqdl dldmymenle
481 cdmdniisdl mdegegldfn fepdp
```

By "FOXO4 nucleic acid molecule" (or Forkhead box protein 04) is meant a polynucleotide (e.g., mRNA) encoding an FOXO4 polypeptide. An exemplary FOXO4 nucleic acid molecule is provided at NCBI Accession No. NM_005938.

```
                                                    (SEQ ID NO: 16)
  1 aaaaggggga gggaactgcg gctaaggaga cgttcggtga tgggagcgca atatatgagg
 61 ggatacagtg cctcaggttt aaaagagcag gaagctgagt gagaggttgc agaaaaagtg
121 tcttcgctcg gcagaggtta caggtggcat ctcagaaaga gctttgaggc tacaggctgt
181 agtcgggaag gggatcggag aactgtgtga agggacagct tagggactag cgtcctggga
241 ctagggggaa gttcgcgact ttctgaagac tggcaggaat gtgcctcctg gccctcgatg
301 cttcccccct gaggggaggc atcgtgaggg actgtggcag gcttcactga acgctgagcc
361 ggggaggtcc aactccacgt atggatccgg ggaatgagaa ttcagccaca gaggctgccg
421 cgatcataga cctagatccc gacttcgaac cccagagccg tccccgctcc tgcacctggc
481 cccttccccg accagagatc gctaaccagc cgtccgagcc gcccgaggtg gagccagatc
541 tgggggaaaa ggtacacacg gaggggcgct cagagccgat cctgttgccc tctcggctcc
601 cagagccggc cgggggcccc cagcccggaa tcctgggggc tgtaacaggt cctcggaagg
661 gaggctcccg ccggaatgcc tggggaaatc agtcatatgc agaactcatc agccaggcca
721 ttgaaagcgc cccggagaag cgactgacac ttgcccagat ctacgagtgg atggtccgta
```

-continued

```
781 ctgtacccta cttcaaggac aagggtgaca gcaacagctc agcaggatgg aagaactcga
841 tccgccacaa cctgtccctg cacagcaagt tcatcaaggt tcacaacgag gccaccggca
901 aaagctcttg gtggatgctg aaccctgagg gaggcaagag cggcaaagcc ccccgccgcc
961 gggccgcctc catggatagc agcagcaagc tgctccgggg ccgcagtaaa gcccccaaga
1021 agaaaccatc tgtgctgcca gctccacccg aaggtgccac tccaacgagc cctgtcggcc
1081 actttgccaa gtggtcaggc agcccttgct ctcgaaaccg tgaagaagcc gatatgtgga
1141 ccaccttccg tccacgaagc agttcaaatg ccagcagtgt cagcacccgg ctgtccccct
1201 tgaggccaga gtctgaggtg ctggcggagg aaataccagc ttcagtcagc agttatgcag
1261 ggggtgtccc tcccaccctc aatgaaggtc tagagctgtt agatgggctc aatctcacct
1321 cttcccattc cctgctatct cggagtggtc tctctggctt ctctttgcag catcctgggg
1381 ttaccggccc cttacacacc tacagcagct ccctttttcag cccagcagag gggcccctgt
1441 cagcaggaga agggtgcttc tccagctccc aggctctgga ggccctgctc acctctgata
1501 cgccaccacc ccctgctgac gtcctcatga cccaggtaga tcccattctg tcccaggctc
1561 cgactcttct gttgctgggg gggcttcctt cctccagtaa gctggccacg ggcgtcggcc
1621 tgtgtcccaa gcccctagag gctccaggcc ccagcagtct ggttcccacc ctttctatga
1681 tagcaccacc tccagtcatg gcaagtgccc ccatccccaa ggctctgggg actcctgtgc
1741 tcacaccccc tactgaagct gcaagccaag acagaatgcc tcaggatcta gatcttgata
1801 tgtatatgga gaacctggag tgtgacatgg ataacatcat cagtgacctc atggatgagg
1861 gcgagggact ggacttcaac tttgagccag atccctgagt catgcctgga agctttgtcc
1921 cctgcttcag atgtggagcc aggcgtgttc atatctactc tttacccttg agccctcccc
1981 aggaatttgg gaccctgctt tagagctagg gtggggtctg gtcacacaca ggtgttgaag
2041 aaattataaa gataaagctg ccccatctgg ggacgatatg gggagggaga tgggagggga
2101 aaggggagag ggtttttctc actgtgccaa ttagggggta aggccccctc tcaggagcca
2161 tcatcggctt tccccattcc tacccactta ggctttgtag caagatgagc aatgctgttg
2221 gaaatgtgaa gtcaccagtg gccttacccc tgcctttggg agcaggattt ttttgtagag
2281 agtcttatct gagctgagcc aggctagctg gagcctggga tttctatgca gtggcccctt
2341 aggccagtga tgtgcggtgg gtgggctgtt taggggatct ggaagggcca aggtctgagc
2401 actggagtgg ctcgccaggc caaatcaccc ttagaaggct gcagataaca gaaaggcttt
2461 ttataaactt ttaaagaaat ataaacacaa atatagagat tttttaacca tggcagggtg
2521 ctagtggtgg gcagaatgct ttttttttctt tctgaaggct ttgtgatagt gacatgatac
2581 aaacactaca gacaataaat attaggagac acagggaagt ggggagaggt ggggagtaat
2641 agtaaacaca gggaagagct cccctacgga ccaggtatag agaaaggtct atgcagaaat
2701 aggttagagt ttccctaaca aaaaagctaa cccaggtccc ctcattcctt caacttgtgc
2761 ctgggagtgt gtggtgttag ggtgcagcca cactcttcta tgacccagca tgggttagtg
2821 ctatggtggg agagtacatt gaaggcctgg aattagcttg gggccaggga agggactggg
2881 aggggagaga agagaaggag ggaaggattt aggatggtaa agttaggtac agagacctcc
2941 ctgttcaagg cccctgacag ctgtccctgc ccttcttccc cttccctgac tgcaggggtt
3001 atgtggaagt gtgtgtggca gcaggcagcg gggaggggag gaacagggaa gggggagctg
3061 gggagcttgg ctgagggtct gggaaatgag cagggatggg gggggatgtg gatcaggttt
3121 actagcacct gccagggagg ccatctgggg ctccttctcc accccagccc ccaaagcagc
3181 ccttccccca gtgccctttg catcgtcccc tcccccaccc ctgctgtggg ttcccatcat
```

-continued 3241 ttcctgtgtc agcgcctggc ctacccagat tgtatcatgt gctagattgg agtggggaag 3301 tgtgtcaaat caataaatga ataaattcaa taaatgccta taaccagcaa aaaaaaaaaa 3361 aaaaa By “CNP polypeptide” (or 2',3'-cyclic-nucleotide 3'-phosphodiesterase) is meant a polypeptide or fragment thereof having at least about 85% amino acid identity to NCBI Accession No. P09543.

(SEQ ID NO: 17)

1 mnrgfsrksh tflpkiffrk msssgakdkp elqfpflqde dtvatlleck tlfilrglpg 61 sgkstlarvi vdkyrdgtkm vsadaykitp gargafseey krldedlaay crrrdirilv 121 lddtnherer leqlfemadq yqyqvvlvep ktawrldcaq lkeknqwqls addlkklkpg 181 lekdflplyf gwfltkksse tlrkagqvfl eelgnhkafk kelrqfvpgd eprekmdlvt 241 yfgkrppgvl hcttkfcdyg kapgaeeyaq qdvlkksysk aftltisalf vtpkttgary 301 elseqqlqlw psdvdklspt dnlprgsrah itlgcaadve avqtgldlle ilrqekggsr 361 geevgelsrg klyslgngrw mltlaknmev raiftgyygk gkpvptqgsr kggalqscti 421 i By “CNP nucleic acid molecule” (or 2',3'-cyclic-nucleotide 3'-phosphodiesterase) is meant a polynucleotide (e.g., mRNA) encoding an CNP polypeptide. An exemplary CNP nucleic acid molecule is provided at NCBI Accession No. BC011046.

(SEQ ID NO: 18)

1 ctccgcgcag gcgggcggcc ccggagcgct ggtgccggca gaggcggcga cggtggcgcc 61 cctcctcatc atgaggcttc tcccgaaaaa gccacacatt cctgcccaag atcttcttcc 121 gcaagatgtc atcctcaggg gccaaggaca agcctgagct gcagtttccc ttccttcagg 181 atgaggacac agtggccacg ctgctagagt gcaagacgct cttcatcttg cgcggcctgc 241 caggaagcgg caagtccacg ctggcacggg tcatcgtgga caagtaccgt gatggcacca 301 agatggtgtc ggctgacgct tacaagatca cccccggcgc tcgaggagcc ttctccgagg 361 agtacaagcg gctcgatgag gacctggctg cctactgccg ccgccgggac atcagaattc 421 ttgtgcttga tgacaccaac cacgaacggg aacggctgga gcagctcttt gaaatggccg 481 accagtacca gtaccaggtg gtgctggtgg agcccaagac ggcgtggcgg ctggactgtg 541 cccagctcaa ggagaagaac cagtggcagc tgtcggctga tgacctgaag aagctgaagc 601 ctgggctgga gaaggacttc ctgccgctct acttcggctg gttcctgacc aagaagagct 661 ctgagaccct ccgcaaagcc ggccaggtct tcctggaaga gctggggaac cacaaggcct 721 tcaagaagga gctgcgacaa ttcgtccctg gggatgagcc cagggagaag atggacttgg 781 tcacctactt tggaaagaga cccccaggcg tgctgcattg cacaaccaag ttttgtgact 841 acgggaaggc tcccggggca gaggagtacg ctcaacaaga tgtgttaaag aaatcttact 901 ccaaggcctt cacgctgacc atctctgccc tctttgtgac acccaagacg actggggccc 961 gggtggagtt aagcgagcag caactgcagt tgtggccgag tgatgtggac aagctgtcac 1021 ccactgacaa cctgccgcgg gggagccgcg cccacatcac cctcggctgt gcagctgacg 1081 tagaggccgt gcagacgggc cttgacctct tagagattct gcggcaggag aagggggggca 1141 gccgaggcga ggaggtgggc gagctaagcc ggggcaagct ctattccttg ggcaatgggc -continued

```
1201 gctggatgct gaccctggcc aagaacatgg aggtcagggc catcttcacg ggtactacg
1261 ggaaaggcaa acctgtgccc acgcaaggta gccggaaggg gggcgccttg cagtcctgca
1321 ccatcatatg agtgttctca ccaccactta tgcccctaga agggaagggg agagggaaac
1381 gtgccctctg tttgatcctt gttttgtgac attttttttt ttttttttt tactcaaagt
1441 taacctacct gtaacttttt aaaaacttgt aaaataactg accctccctt cctgtccgcc
1501 ctcttcccct ctaatgctca cgctcccaac acaaggtggg cagggaggca ccattcagga
1561 acctggacca aagctgacga ggctgggcca agccagggat ggggccacag ccagaacccc
1621 gagccctact tccaggttct ggttagctca gccccagccc agcccagctg ctctgcccag
1681 agctgggtga gtggggagac acctcagagc cccgcaaaac ccactgaccg gaggcaaaag
1741 gcagtggggc tgggggtagt tttccatggt cacagagaac tagtggtggc tctgagaagg
1801 ggaggacctc tgggctttga ttccatctcc ttgtcttttt tctttgtttt tagagacagg
1861 gtcctgctat ttcccaagct ggagtgcagt ggtgcgatca tggctcactg cagcctcgaa
1921 ctcctgggct caagcaatcc tcctgagtga tcccatttct taatcagtgt agccccaaga
1981 aggctggggc tatttaccag ggtagaaaaa ggagcttacc tcccaccttt ggtcctaagt
2041 ccctgccccc tccccttcac accataacta ggtaacagtt tgataactag ggaagaaagc
2101 agaacagtta agcagccgcc acatccccgc tggctggggg cctcactcca ggaaggggct
2161 ggactggctg tcctttccag tggcctggct ccgctgtgtg gatggggaga tcggggccag
2221 aggcagaacc ctggtgagga agctccagtc ctgctctcta cccagcccat cttgcctcca
2281 tggtgcctct ggaggcctct gggcctcctc taacaggggc tggtgggcac caagagccaa
2341 tggagtagac ccctggctgg taagggccaa gtcccaccgg ttgcttctgg gaaggggttt
2401 ctaacactag tctgtgtgct gtggttcctg ggtgccctc cactgccctc tgttcagtaa
2461 cagggccttg ctaatcgggt tgtcactcaa caaaagtgct ttggatttaa gttactatcc
2521 tggctttgcc caacctcagc aacctgtaag actgataatg aaataaatca tgttaatcct
2581 agcaaaaaaa aaaaaaaa
```

By “MBP polypeptide” (or myelin basic protein) is meant a polypeptide or fragment thereof having at least about 85% amino acid identity to NCBI Accession No. P02686.

```
(SEQ ID NO: 19)
  1 mgnhagkrel naekastnse tnrgesekkr nlgelsrtts ednevfgead anqnngtssq
 61 dtavtdskrt adpknawqda hpadpgsrph lirlfsrdap grednttfkdr psesdelqti
121 qedsaatses ldvmasqkrp sqrhgskyla tastmdharh gflprhrdtg ildsigrffg
181 gdrgapkrgs gkdshhpart ahygslpqks hgrtqdenpv vhffknivtp rtpppsqgkg
241 rglslsrfsw gaegqrpgfg yggrasdyks ahkgfkgvda qgtlskifkl ggrdsrsgsp
301 marr
```

By “MBP nucleic acid molecule” (or myelin basic protein) is meant a polynucleotide (e.g., mRNA) encoding an MBP polypeptide. An exemplary MBP nucleic acid molecule is provided at NCBI Accession No. M13577.

```
(SEQ ID NO: 20)
  1 gaaaacagtg cagccacctc cgagagcctg gatgtgatgg cgtcacagaa gagaccctcc
 61 cagaggcacg gatccaagta cctggccaca gcaagtacca tggaccatgc caggcatggc
121 ttcctcccaa ggcacagaga cacgggcatc cttgactcca tcgggcgctt ctttggcggt
181 gacaggggtg cgccaaagcg gggctctggc aaggactcac accacccggc aagaactgct
```

-continued 241 cactatggct ccctgcccca gaagtcacac ggccggaccc aagatgaaaa ccccgtagtc 301 cacttcttca agaacattgt gacgcctcgc acaccacccc cgtcgcaggg aaaggggaga 361 ggactgtccc tgagcagatt tagctggggg gccgaaggcc agagaccagg atttggctac 421 ggaggcagag cgtccgacta taaatcggct cacaagggat tcaagggagt cgatgcccag 481 ggcacgcttt ccaaaatttt taagctggga ggaagagata gtcgctctgg atcacccatg 541 gctagacgct gaaaacccac ctggttccgg aatcctgtcc tcagcttctt aatataactg 601 ccttaaaact ttaatcccac ttgcccctgt tacctaatta gagcagatga cccctcccct 661 aatgcctgcg gagttgtgca cgtagtaggg tcaggccacg gcagcctacc ggcaatttcc 721 ggccaacagt taaatgagaa catgaaaaca gaaaacggtt aaaactgtcc ctttctgtgt 781 gaagatcacg ttccttcccc cgcaatgtgc cccagacgc acgtgggtct tcagggggcc 841 aggtgcacag acgtccctcc acgttcaccc ctccaccctt ggactttctt ttcgccgtgg 901 ctcggcaccc ttgcgctttt gctggtcact gccatggagg cacacagctg cagagacaga 961 gaggacgtgg gcggcagaga ggactgttga catccaagct tcctttgttt ttttttcctg 1021 tccttctctc acctcctaaa gtagacttca tttttcctaa caggattaga cagtcaagga 1081 gtggcttact acatgtggga gctttttggt atgtgacatg cgggctgggc agctgttaga 1141 gtccaacgtg gggcagcaca gagagggggc cacctcccca ggccgtggct gcccacacac 1201 cccaattagc tgaattcgcg tgtggcagag ggaggaaaag gaggcaaacg tgggctgggc 1261 aatggcctca cataggaaac agggtcttcc tggagatttg gtgatggaga tgtcaagcag 1321 gtggcctctg gacgtcaccg ttgccctgca tggtggcccc agagcagcct ctatgaacaa 1381 cctcgtttcc aaaccacagc ccacagccgg agagtccagg aagacttgcg cactcagagc 1441 agaagggtag gagtcctcta gacagcctcg cagccgcgcc agtcgcccat agacactggc 1501 tgtgaccggg cgtgctggca gcggcagtgc acagtggcca gcactaaccc tccctgagaa 1561 gataaccggc tcattcactt cctcccagaa gacgcgtggt agcgagtagg cacaggcgtg 1621 cacctgctcc cgaattactc accgagacac acgggctgag cagacggccc ctgtgatgga 1681 gacaaagagc tcttctgacc atatccttct taacacccgc tggcatctcc tttcgcgcct 1741 ccctccctaa cctactgacc cacctttga ttttagcgca cctgtgattg ataggccttc 1801 caaagagtcc cacgctggca tcaccctccc cgaggacgga gatgaggagt agtcagcgtg 1861 atgccaaaac gcgtcttctt aatccaattc taattctgaa tgtttcgtgt gggcttaata 1921 ccatgtctat taatatatag cctcgatgat gagagagtta caaagaacaa aactccagac 1981 acaaacctcc aaatttttca gcagaagcac tctgcgtcgc tgagctgagg tcggctctgc 2041 gatccatacg tggccgcacc cacacagcac gtgctgtgac gatggctgaa cggaaagtgt 2101 acactgttcc tgaatattga aataaaacaa taaactttt By “TUBIII polypeptide” (or TUBB3, tubulin beta chain 3) is meant a polypeptide or fragment thereof having at least about 85% amino acid identity to NCBI Accession No. NP_001184110.

(SEQ ID NO: 21)

1 mdsvrsgafg hlfrpdnfif gqsgagnnwa kghytegael vdsvldvvrk ecencdclqg 61 fqlthslggg tgsgmgtlli skvreeypdr imntfsvvps pkvsdtvvep ynatlsihql 121 ventdetyci dnealydicf rtlklatpty gdlnhlvsat msgvttslrf pgqlnadlrk 181 lavnmvpfpr lhffmpgfap ltargsqqyr altvpeltqq mfdaknmmaa cdprhgrylt -continued 241 vatvfrgrms mkevdeqmla iqsknssyfv ewipnnvkva vcdipprglk msstfignst 301 aiqelfkris eqftamfrrk aflhwytgeg mdemefteae snmndlvsey qqyqdataee 361 egemyeddee eseaqgpk By "TUBIII nucleic acid molecule" (or TUBB3, tubulin beta chain 3) is meant a polynucleotide (e.g., mRNA) encoding an TUBIII polypeptide. An exemplary TUBIII nucleic acid molecule is provided at NCBI Accession No. BC000748.

(SEQ ID NO: 22)

1 gcccggcccg cccgcgcccg tccgcagccg cccgccagac gcgcccagta tgagggagat 61 cgtgcacatc caggccggcc agtgcggcaa ccagatcggg gccaagttct gggaagtcat 121 cagtgatgag catggcatcg accccagcgg caactacgtg ggcgactcgg acttgcagct 181 ggagcggatc agcgtctact acaacgaggc ctcttctcac aagtacgtgc ctcgagccat 241 tctggtggac ctggaacccg gaaccatgga cagtgtccgc tcaggggcct ttggacatct 301 cttcaggcct gacaatttca tctttggtca gagtggggcc ggcaacaact gggccaaggg 361 tcactacacg gagggggcgg agctggtgga ttcggtcctg gatgtggtgc ggaaggagtg 421 tgaaaactgc gactgcctgc agggcttcca gctgacccac tcgctggggg gcggcacggg 481 ctccggcatg ggcacgttgc tcatcagcaa ggtgcgtgag gagtatcccg accgcatcat 541 gaacaccttc agcgtcgtgc cctcacccaa ggtgtcagac acggtggtgg agccctacaa 601 cgccacgctg tccatccacc agctggtgga gaacacggat gagacctact gcatcgacaa 661 cgaggcgctc tacgacatct gcttccgcac cctcaagctg gccacgccca cctacgggga 721 cctcaaccac ctggtatcgg ccaccatgag cggagtcacc acctccttgc gcttcccggg 781 ccagctcaac gctgacctgc gcaagctggc cgtcaacatg gtgcccttcc cgcgcctgca 841 cttcttcatg cccggcttcg ccccccctcac agcccggggc agccagcagt accgggccct 901 gaccgtgccc gagctcaccc agcagatgtt cgatgccaag aacatgatgg ccgcctgcga 961 cccgcgccac ggccgctacc tgacggtggc caccgtgttc cggggccgca tgtccatgaa 1021 ggaggtggac gagcagatgc tggccatcca gagcaagaac agcagctact tcgtggagtg 1081 gatccccaac aacgtgaagg tggccgtgtg tgacatcccg ccccgcggcc tcaagatgtc 1141 ctccaccttc atcgggaaca gcacggccat ccaggagctg ttcaagcgca tctccgagca 1201 gttcacggcc atgttccggc gcaaggcctt cctgcactgg tacacgggcg agggcatgga 1261 cgagatggag ttcaccgagg ccgagagcaa catgaacgac ctggtgtccg agtaccagca 1321 gtaccaggac gccacggccg aggaagaggg cgagatgtac gaagacgacg aggaggagtc 1381 ggaggcccag ggccccaagt gaagctgctc gcagctggag tgagaggcag gtggcggccg 1441 gggccgaagc cagcagtgtc taaacccccg gagccatctt gctgccgaca ccctgctttc 1501 ccctcgccct agggctccct tgccgccctc ctgcagtatt tatggcctcg tcctccccac 1561 ctaggccacg tgtgagctgc tcctgtctct gtcttattgc agctccaggc ctgacgtttt 1621 acggttttgt tttttactgg tttgtgttta tattttcggg gatacttaat aaatctattg 1681 ctgtcagata cccttaaaaa aaaaaaaaaa aaaaaaaaaa By "NEUN polypeptide" (or Feminizing Locus on X-3, Fox-3, RNA-binding protein fox-1 homolog 3, or Hexaribonucleotide Binding Protein-3) is meant a polypeptide or fragment thereof having at least about 85% amino acid identity to NCBI Accession No. NP_001076044.

```
                                                    (SEQ ID NO: 23)
  1 maqpyppaqy ppppqngipa eyapppphpt qdysgqtpvp tehgmtlytp aqthpeqpgs

 61 eastqpiagt qtvpqtdeaa qtdsqplhps dptekqqpkr lhvsnipfrf rdpdlrqmfg

121 qfgkildvei ifnergskgf gfvtfetssd adrarekln g tivegrkiev nnatarvmtn

181 kktgnpytng wklnpvvgav ygpefyavtg fpypttgtav ayrgahlrgr gravyntfra

241 apppppipty gavvyqdgfy gaeiyggyaa yryaqpaaaa aaysdsygrv yaaadpyhht

301 igpaatysig tm
```

By "NEUN nucleic acid molecule" (or Feminizing Locus on X-3, Fox-3, RNA-binding protein fox-1 homolog 3, or Hexaribonucleotide Binding Protein-3) is meant a polynucleotide (e.g., mRNA) encoding an NEUN polypeptide. An exemplary NEUN nucleic acid molecule is provided at NCBI Accession No. NM_001082575.

```
                                                     (SEQ ID NO: 24)
   1 gatacagcag cagctggtgc tcctggccag gctgtgcgtg ctctctctgc ctctctctct

  61 cggactctct gctctctctc tctgactctc tcctctctct ctgttggcct ggtgaaatgt

 121 tcttggctgt aggcacacag agccttggac tcaaggctgt tggagtcgag gacaccttga

 181 cttcggtcct ggaggttgaa attctgcctc tgagaagcta acagtcttcc tgtggtcgcc

 241 actcctcccc agcagccccc tccttgccaa ggacggtcca gaaggagccc cactggggcc

 301 tccccgctca gcaaagcaga cctcacctcc cactaccagc ttgaagtcac agcagccaga

 361 ggaaattctg ccaccatttt cccaggtctg cagcccctcc agctgggaac ctgctcctgg

 421 agccatccct ctgcaaacag agagcccaga gtgcctcggg gaaaattggc tgaataaaag

 481 agcgatcagg acgccacggc tccgcctgaa gcgatggccc agccctaccc ccccgcccag

 541 taccccccctc cgccacagaa cggcatccct gccgagtacg ccccgccccc accgcacccc

 601 acgcaggact actccggcca gaccccggtc cccacagagc atggcatgac cctgtacaca

 661 ccagcacaga cccaccccga gcagccaggc tccgaggcca gcacacagcc catcgccggg

 721 acccagacag tgccgcagac agacgaggcg gcacagacgg acagccagcc gctccacccc

 781 tccgacccta cagagaagca gcagcccaag cggctacacg tctccaacat ccccttccgg

 841 ttcagggacc ccgacttgcg gcaaatgttc gggcaattcg gaaaaatttt agacgtggag

 901 atcattttta acgagcgggg ctccaagggt tttgggtttg taacttttga aactagctca

 961 gatgctgacc gagcccggga gaagctgaat gggacgatcg tagagggacg gaaaattgag

1021 gtcaataatg ccacggcccg agtgatgacc aacaagaaga cggggaaccc ctacaccaac

1081 ggctggaagc taaatccagt ggtcggcgca gtctacgggc ctgaattcta tgcagtgacg

1141 gggttcccct accccaccac cggcacagcc gttgcctacc ggggcgcaca tcttcggggc

1201 cggggccggg ccgtgtataa tacatttcgg gctgcgccac ccccaccccc catcccgact

1261 tacggagcgg tcgtgtatca ggatggattt tatggtgctg agatttatgg aggctacgca

1321 gcctacagat acgctcagcc cgctgcagcg gcggcagcct acagcgacag ttacggcaga

1381 gtctacgcag ctgccgaccc gtaccatcac accatcgggc ccgcggcgac ctacagcatt

1441 ggaaccatgt gaaaccttcc accgtttcct tctcggacca tgaagggcaa aaacaaaaaa

1501 acaaaaaaaa tcacaaaaca aaaaaaacaa aaaaagatgt taagatccaa gcaacaaaaa

1561 aaaaaccaac caaaccaaga ggcatccaac caagtccaag tcccgcgtcc tggccacacg
```

-continued

```
1621 cccgcaccga gggagcacgc cggcaggggc gccgaggagc ggccccagga caggacggcc
1681 ccaccgcgtc ctggctggca gcacagtggg aacacgcccc tccgtctcag gcagtggggg
1741 agttggaggg gaaggggcct cccttgtggg acccgtgggg ggctctgttt tccatccagt
1801 cttcctttcc cagcccccaa ctcccaagac agacagtgtg gagcccagcg gcggcggagc
1861 aggcccgggc ctgagcaggc aggcgctgct agcaagactt gatctttgtg gccagctgtg
1921 ccagggggcc ggcggggctg aggggtgcgg gcagctttca tcccaggggc tccactgggc
1981 cccgtcaccc tcctgtcgcg tcccctgcgt cccacctccc tcctgcccgg cagtcccgcc
2041 cgtgccccca gcctggcgag gaagccgtcc aacagtagcc ccggggccag ctcccaacag
2101 aaagggctga cgtggctcca ggactcaggg gcgctccatg ggaggacgaa ggaagcccag
2161 ccagccagga gccactcctc acacctccaa gtgtggccaa gtgggccctg aggccaagga
2221 cttacttgct cttcctggcc atctctccct ttctggagga ggcccggggc ctgtgtacac
2281 caaggctgac ctcgtgctgc ctgctgggac ccagccctcc ctgccgctcc cctgtgagcc
2341 cagtccaccg tgggcgccca gggccaggga cgggccagcg cccggctgca tcgcgaggtt
2401 gggagtcaca gtggctgtgg gcctggacgg gcacagccag agcaggggcc catgggaagg
2461 gcaagggatg gggaagcctg ggccggcccc ttccctgctc ccaaggcagg tgtccaggtg
2521 gcgggagcag caccaaggac agccaggctt acccggtggg aggagcagga gcagagcagg
2581 tggcagggag gaacccctgg cgaggcaggg agcactgaag tagggaagca gcaaaaaata
2641 caggctccca acgtggctcc actgtctcat gaagtgtcaa aaatttaaaa atacacctca
2701 ctttctattc agcatcagct attgaaatgg aattctcctt ttctattccc gttgtacata
2761 gccccacgcc ctgcctccgg ctttgtcctc tgtacagagc cccctgtccc ctctgctgtt
2821 ccggaccctt ttcttgcagc agctcaaccc cccgactcac tcagatcccc aggactgcag
2881 ccgagccccg ggcttccttt cttaccattc tgtatgcttc caaggtgtga ccattcaaac
2941 taacagtatt attaagatta ttaataaaga tttctttctt caaaccagga aaaaaaaaaa
3001 aaaaaaa
```

By "SLC1A6 polypeptide" (or Excitatory amino acid transporter 4; Sodium-dependent glutamate/aspartate transporter; Solute carrier family 1 member 6) is meant a polypeptide or fragment thereof having at least about 85% amino acid identity to NCBI Accession No. P48664.

(SEQ ID NO: 25)

```
  1 msshgnslfl resgqrlgry gwlqrlqesl qqralrtrlr lqtmtlehvl rflrrnafil
 61 ltvsavvigv slafalrpyq ltyrqikyfs fpgellmrml qmlvlplivs slvtgmasld
121 nkatgrmgmr aavyymvtti iavfigilmv tiihpgkgsk eglhregrie tiptadafmd
181 lirnmfppnl veacfkqfkt qystrvvtrt mvrtengsep gasmpppfsv engtsflenv
241 tralgtlqem lsfeetvpvp gsanginalg lvvfsvafgl viggmkhkgr vlrdffdsln
301 eaimrlvgii iwyapvgilf liagkileme dmavlggqlg mytltvivgl flhagivlpl
361 iyflvthrnp fpfiggmlqa litamgtsss satlpitfrc leeglgvdrr itrfvlpvga
421 tvnmdgtaly ealaaifiaq vnnyelnlgq ittisitata asvgaagipq aglvtmvivl
481 tsvglptedi tliiavdwfl drlrtmtnvl gdsigaavie hlsqrelelq eaeltlpslg
541 kpykslmaqe kgasrgrggn esam
```

By "SLC1A6 nucleic acid molecule" (or Excitatory amino acid transporter 4; Sodium-dependent glutamate/aspartate transporter; Solute carrier family 1 member 6) is meant a polynucleotide (e.g., mRNA) encoding an SLC1A6 polypeptide. An exemplary SLC1A6 nucleic acid molecule is provided at NCBI Accession No. BC040604.

(SEQ ID NO: 26)

1 ggcatagcgc gtcccggctc cgcgccggtg cctccacggt ccggtccccg cgccggtgct
61 gcacagtccc tggcgggtcc ccgcggcccc ggccgggcgc ttcgccgggc tccggctcct
121 gcatccgggc gcagcgcgca ggccgaggcg cgggcaggcc gcccccgccg ctccggacgc
181 cgggatgtaa gaggctccga aaagcagccc acgcatctca tcagatctaa gtgtctagag
241 gtcgggagaa ccaagtggga aagacccacc ctcacccctc accttgtaga aactgggaac
301 actagaaggg acattttctg agcaggaaac ccaagagaca gggttttacg ctgtcaccca
361 agttggagtg cagtggtacg atcatagctc attgcagcct caaactcctg ggttcaagcg
421 atcctcctgc tttagcctct tgagtagcta ggactacagg cacaggccac cgtgcctggc
481 taatttttaa tttttaaaaa agagacaggg tctggctatg ttgcccaggc tggccatgaa
541 ctcctgggct caagcggttc tccagccttc acctcccaaa gtgttgggat tgcaggcatg
601 agccactgcg tctggcccac agatgctaag tgctgtctgc tcttctccag gggtcagcaa
661 attttttcag caaatggccc aagagtaaat attttgagct ttgtggcccg tacaatctct
721 gtcccaacaa ctcaactcag gcattgtagc ttgaaagcag ctgtagacaa taggtaatcc
781 atgagtgtgg ctgtgtgcca ataaaacttt atttacaaaa acaagcagta ggctgaattt
841 gactagcaga ccatagtttg tcaataccgt attatgtctt gtaaggaaga gaaaggaacc
901 agacaaaact ctagcctcgg gagttttcct gactgttcag atcttagctg aatgatctcc
961 cttggtatct acaggcaact tcctgctgtg gcttagggac tggaaacata atatcccaga
1021 gggattccct gtgtagtctg tggttcactc tttgggattt tttttttttt tttcacagca
1081 aggagaagca gcattgtggt ttcaggagat gggtccattt ggagcaggat cctaagtggg
1141 gcttggcatt gggaatttgg attagctcta gaggacgcag gatctggaaa atcagggcag
1201 atttcccatc ccttggatat ggtggggagt tgaggagggc aaggaagatc ccagaaaagc
1261 cagtggcagc aaaacacaaa ggccagggac ctacgtactg gtaaaactga gacctccaag
1321 aaacctgcag ctcgacctgg ttgaattcag atagaccatg agcagccatg gcaacagcct
1381 gttccttcgg gagagcggcc agcggctggg ccgggtgggc tggctgcagc ggctgcagga
1441 aagcctgcag cagagagcac tgcgcacgcg cctgcgcctg cagaccatga ccctcgagca
1501 cgtgctgcgc ttcctgcgcc gaaacgcctt cattctgctg acggtcagcg ccgtggtcat
1561 tggggtcagc ctggcctttg ccctgcgccc atatcagctc acctaccgcc agatcaagta
1621 cttctctttt cctggagagc ttctgatgag gatgctgcag atgctggtgt tacctctcat
1681 tgtctccagc ctggtcacag gtatggcatc cctggacaac aaggccacgg ggcggatggg
1741 gatgcgggca gctgtgtact acatggtgac caccatcatc gcggtcttca tcggcatcct
1801 catggtcacc atcatccatc ccgggaaggg ctccaaggag gggctgcacc gggagggccg
1861 gatcgagacc atccccacag ctgatgcctt catggacctg atcagaaata tgtttccacc
1921 aaaccttgtg gaggcctgct tcaaacagtt caagacgcag tacagcacga gggtggtaac
1981 caggaccatg gtgaggacag agaacgggtc tgagccgggt gcctccatgc ctcctccatt
2041 ctcagtggag aacggaacca gcttcctgga aaatgtcact cgggccttgg gtaccctgca
2101 ggagatgctg agctttgagg agactgtacc cgtgcctggc tccgccaatg gcatcaacgc
2161 cctgggcctc gtggtcttct ctgtggcctt tgggctggtc attggtggca tgaaacacaa
2221 gggcagagtc ctcagggact tcttcgacag cctcaatgag gctattatga ggctggtggg
2281 catcattatc tggtgagtcc tggtctgtgc ccacgggaag gtggagccag agctgggaag
2341 tcaggctgtg gggaagctgc cgaagggctt gctggggacc tttggtcatt catttacgta -continued

```
2401 ttgggtgatt cacttaccca ctcaccaact cattcattca tgtctttctg ggatgatttc

2461 atcactagtt cacttccttg ttcatctgtt cattcattca ttcttctatg cattggttag

2521 ttcatggaat atctcactct ttcattcatt catgtccttc tgcaatgatt cattcactgc

2581 tttgttcatc tgttcattca ctcattcttc tatgcattga tgaaatcact cattcagtga

2641 tttattcatc tatactcatg cttcaatgca ttgatttact catttcctca tgcatttatt

2701 cattcatcta tgcattggtt aaatcactgg ccaactcact aactcattca ttcattcaca

2761 cttttctgca atgatttgtt cacttgttca ctcccttgct tatctgttca ttcactcatt

2821 cttcaataca ttgaccaagc cattcactga catttattca gctacattta ttctttcatg

2881 cattggtctg gatttatttg gtcattcatt tatttatttt gcaaaattaa tgtattttta

2941 attgacaaat aaaaactgta tatttttca tgtgcaaaaa aaaaaaaaaa
```

By "NOGOA polypeptide" (or neurite outgrowth inhibitor A; neurite outgrowth inhibitor isoform A; human reticulon-4; human reticulon-4 isoform A) is meant a polypeptide or fragment thereof having at least about 85% amino acid identity to NCBI Accession No. NP_065393.

(SEQ ID NO: 27)
```
   1 medldqsplv sssdspprpq pafkyqfvre pedeeeeeee eeedededle elevlerkpa

  61 aglsaapvpt apaagaplmd fgndfvppap rgplpaappv aperqpswdp spvsstvpap

 121 splsaaaysp sklpeddepp arpppppppas vspqaepvwt ppapapaapp stpaapkrrg

 181 ssgsvdetlf alpaasepvi rssaenmdlk eqpgntisag qedfpsvlle taaslpslsp

 241 lsaasfkehe ylgnlstvlp tegtlqenvs easkevseka ktllidrdlt efseleysem

 301 gssfsyspka esavivanpr eeiivknkde eeklvsnnil hnqqelptal tklykedevv

 361 ssekakdsfn ekrvaveapm reeyadfkpf ervwevkdsk edsdmlaagg kiesnleskv

 421 dkkcfadsle qtnhekdses snddtsfpst pegikdrsga yitcapfnpa atesiatnif

 481 pllgdptsen ktdelddeek kaqivteknt stktsnpflv aaqdsetdyv ttdnitkvte

 541 evvanmpegl tpdlvqeace selnevtgtk iayetkmdlv qtsevmqesl ypaaqlcpsf

 601 eeseatpspv lpdivmeapl nsavpsagas viqpsssple assvnyesik hepenpppye

 661 eamsyslkkv sgikeeikep eninaalqet eapyisiacd liketklsae papdfsdyse

 721 makveqpvpd hselvedssp dsepvdlfsd dsipdvpqkq detvmlvkes ltetsfesmi

 781 eyenkeklsa lppeggkpyl esfklsldnt kdtllpdevs tlskkekipl qmeelstavy

 841 snddlfiske aqiretetfs dsspieiide fptlissktd sfsklareyt dlevshksei

 901 anapdgagsl pctelphdls lkniqpkvee kisfsddfsk ngsatskyll lppdvsalat

 961 qaeiesivkp kvlvkeaekk lpsdtekedr spsaifsael sktsvvdlly wrdikktgvv

1021 fgaslfllls ltvfsivsvt ayialallsv tisfriykgv iqaiqksdeg hpfraylese

1081 vaiseelvqk ysnsalghvn ctikelrrlf lvddlvdslk favlmwvfty vgalfngltl

1141 lilalislfs vpviyerhqa qidhylglan knvkdamaki qakipglkrk ae
```

By "NOGOA nucleic acid molecule" (or neurite outgrowth inhibitor A; neurite outgrowth inhibitor isoform A; human reticulon-4; human reticulon-4 isoform A) is meant a polynucleotide encoding an NOGOA polypeptide. An exemplary NOGOA nucleic acid molecule (e.g., mRNA) is provided at NCBI Accession No. NM_020532.

(SEQ ID NO: 28)
```
  1 agtccctgcc ctcccctggg gagggtgagt cacgccaaac tgggcggaga gtccgctggc

 61 ctcactccta gctcatctgg gcggcggcgg caagtgggga cagggcgggt ggcgcatcac
```

-continued

```
 121 cggcgcggag gcaggaggag cagtctcatt gttccgggag ccgtcaccac agtaggtccc
 181 tcggctcagt cggcccagcc cctctcagtc ctccccaacc cccacaaccg cccgcggctc
 241 tgagacgcgg ccccggcggc ggcggcagca gctgcagcat catctccacc ctccagccat
 301 ggaagacctg gaccagtctc ctctggtctc gtcctcggac agcccacccc ggccgcagcc
 361 cgcgttcaag taccagttcg tgagggagcc cgaggacgag gaggaagaag aggaggagga
 421 agaggaggac gaggacgaag acctggagga gctggaggtg ctggagagga agcccgccgc
 481 cgggctgtcc gcggccccag tgcccaccgc ccctgccgcc ggcgcgcccc tgatggactt
 541 cggaaatgac ttcgtgccgc cggcgccccg gggacccctg ccggccgctc cccccgtcgc
 601 cccggagcgg cagccgtctt gggacccgag cccggtgtcg tcgaccgtgc ccgcgccatc
 661 cccgctgtct gctgccgcag tctcgccctc caagctccct gaggacgacg agcctccggc
 721 ccggcctccc cctcctcccc cggccagcgt gagcccccag gcagagcccg tgtggacccc
 781 gccagccccg gctcccgccg cgcccccctc caccccggcc gcgcccaagc gcaggggctc
 841 ctcgggctca gtggatgaga ccctttttgc tcttcctgct gcatctgagc ctgtgatacg
 901 ctcctctgca gaaaatatgg acttgaagga gcagccaggt aacactattt cggctggtca
 961 agaggatttc ccatctgtcc tgcttgaaac tgctgcttct cttccttctc tgtctcctct
1021 ctcagccgct tctttcaaag aacatgaata ccttggtaat ttgtcaacag tattacccac
1081 tgaaggaaca cttcaagaaa atgtcagtga agcttctaaa gaggtctcag agaaggcaaa
1141 aactctactc atagatagag atttaacaga gttttcagaa ttagaatact cagaaatggg
1201 atcatcgttc agtgtctctc caaaagcaga atctgccgta atagtagcaa atcctaggga
1261 agaaataatc gtgaaaaata aagatgaaga agagaagtta gttagtaata acatccttca
1321 taatcaacaa gagttaccta cagctcttac taaattggtt aaagaggatg aagttgtgtc
1381 ttcagaaaaa gcaaaagaca gttttaatga aaagagagtt gcagtggaag ctcctatgag
1441 ggaggaatat gcagacttca aaccatttga gcgagtatgg gaagtgaaag atagtaagga
1501 agatagtgat atgttggctg ctggaggtaa aatcgagagc aacttggaaa gtaaagtgga
1561 taaaaaatgt tttgcagata gccttgagca aactaatcac gaaaaagata gtgagagtag
1621 taatgatgat acttctttcc ccagtacgcc agaaggtata aaggatcgtt caggagcata
1681 tatcacatgt gctcccttta acccagcagc aactgagagc attgcaacaa acatttttcc
1741 tttgttagga gatcctactt cagaaaataa gaccgatgaa aaaaaaatag aagaaaagaa
1801 ggcccaaata gtaacagaga agaatactag caccaaaaca tcaaaccctt ttcttgtagc
1861 agcacaggat tctgagacag attatgtcac aacagataat ttaacaaagg tgactgagga
1921 agtcgtggca aacatgcctg aaggcctgac tccagattta gtacaggaag catgtgaaag
1981 tgaattgaat gaagttactg gtacaaagat tgcttatgaa acaaaaatgg acttggttca
2041 aacatcagaa gttatgcaag agtcactcta tcctgcagca cagctttgcc catcatttga
2101 agagtcagaa gctactcctt caccagtttt gcctgacatt gttatggaag caccattgaa
2161 ttctgcagtt cctagtgctg gtgcttccgt gatacagccc agctcatcac cattagaagc
2221 ttcttcagtt aattatgaaa gcataaaaca tgagcctgaa aaccccccac catatgaaga
2281 ggccatgagt gtatcactaa aaaaagtatc aggaataaag gaagaaatta aagagcctga
2341 aaatattaat gcagctcttc aagaaacaga agctccttat atatctattg catgtgattt
2401 aattaaagaa acaaagcttt ctgctgaacc agctccggat ttctctgatt attcagaaat
2461 ggcaaaagtt gaacagccag tgcctgatca ttctgagcta gttgaagatt cctcacctga
2521 ttctgaacca gttgacttat ttagtgatga ttcaatacct gacgttccac aaaaacaaga
```

-continued

```
2581 tgaaactgtg atgcttgtga aagaaagtct cactgagact tcatttgagt caatgataga
2641 atatgaaaat aaggaaaaac tcagtgcttt gccacctgag ggaggaaagc catatttgga
2701 atcttttaag ctcagtttag ataacacaaa agataccctg ttacctgatg aagtttcaac
2761 attgagcaaa aaggagaaaa ttcctttgca gatggaggag ctcagtactg cagtttattc
2821 aaatgatgac ttatttattt ctaaggaagc acagataaga gaaactgaaa cgttttcaga
2881 ttcatctcca attgaaatta tagatgagtt ccctacattg atcagttcta aaactgattc
2941 attttctaaa ttagccaggg aatatactga cctagaagta tcccacaaaa gtgaaattgc
3001 taatgccccg gatggagctg ggtcattgcc ttgcacagaa ttgccccatg acctttcttt
3061 gaagaacata caacccaaag ttgaagagaa aatcagtttc tcagatgact tttctaaaaa
3121 tgggtctgct acatcaaagg tgctcttatt gcctccagat gtttctgctt tggccactca
3181 agcagagata gagagcatag ttaaacccaa agttcttgtg aaagaagctg agaaaaaact
3241 tccttccgat acagaaaaag aggacagatc accatctgct atattttcag cagagctgag
3301 taaaacttca gttgttgacc tcctgtactg gagagacatt aagaagactg gagtggtgtt
3361 tggtgccagc ctattcctgc tgctttcatt gacagtattc agcattgtga gcgtaacagc
3421 ctacattgcc ttggccctgc tctctgtgac catcagcttt aggatataca agggtgtgat
3481 ccaagctatc cagaaatcag atgaaggcca cccattcagg gcatatctgg aatctgaagt
3541 tgctatatct gaggagttgg ttcagaagta cagtaattct gctcttggtc atgtgaactg
3601 cacgataaag gaactcaggc gcctcttctt agttgatgat ttagttgatt ctctgaagtt
3661 tgcagtgttg atgtgggtat ttacctatgt tggtgccttg tttaatggtc tgacactact
3721 gattttggct ctcatttcac tcttcagtgt tcctgttatt tatgaacggc atcaggcaca
3781 gatagatcat tatctaggac ttgcaaataa gaatgttaaa gatgctatgg ctaaaatcca
3841 agcaaaaatc cctggattga agcgcaaagc tgaatgaaaa cgcccaaaat aattagtagg
3901 agttcatctt taaaggggat attcatttga ttatacgggg gagggtcagg gaagaacgaa
3961 ccttgacgtt gcagtgcagt ttcacagatc gttgttagat ctttattttt agccatgcac
4021 tgttgtgagg aaaaattacc tgtcttgact gccatgtgtt catcatctta agtattgtaa
4081 gctgctatgt atggatttaa accgtaatca tatctttttc ctatctatct gaggcactgg
4141 tggaataaaa aacctgtata ttttactttg ttgcagatag tcttgccgca tcttggcaag
4201 ttgcagagat ggtggagcta gaaaaaaaaa aaaaaaagcc cttttcagtt tgtgcactgt
4261 gtatggtccg tgtagattga tgcagatttt ctgaaatgaa atgtttgttt agacgagatc
4321 ataccggtaa agcaggaatg acaaagcttg cttttctggt atgttctagg tgtattgtga
4381 cttttactgt tatattaatt gccaatataa gtaaatatag attatatatg tatagtgttt
4441 cacaaagctt agacctttac cttccagcca ccccacagtg cttgatattt cagagtcagt
4501 cattggttat acatgtgtag ttccaaagca cataagctag aagaagaaat atttctagga
4561 gcactaccat ctgttttcaa catgaaatgc cacacacata gaactccaac atcaatttca
4621 ttgcacagac tgactgtagt taattttgtc acagaatcta tggactgaat ctaatgcttc
4681 caaaaatgtt gtttgtttgc aaatatcaaa cattgttatg caagaaatta ttaattacaa
4741 aatgaagatt tataccattg tggtttaagc tgtactgaac taaatctgtg gaatgcattg
4801 tgaactgtaa aagcaaagta tcaataaagc ttatagactt aaaaaaaaaa aaaaaaaaaa
4861 aaaaaaaaaa a
```

By "oligodendrocyte 01 polypeptide" (or oligodendrocyte marker 01; oligodendrocyte transcription factor 1; olig1) is meant a polypeptide or fragment thereof having at least about 85% amino acid identity to NCBI Accession No. Q8TAK6.

```
                                                  (SEQ ID NO: 29)
  1 myyavsqarv navpgtmlrp qrpgdlqlga slyelvgyrq ppssssssts stsstsssst

 61 tapllpkaar ekpeapaepp gpgpgsgahp ggsarpdake eqqqqlrrki nsrerkrmqd

121 lnlamdalre vilpysaahc qgapgrklsk iatlllarny illlgsslqe lrralgegag

181 paaprlllag lpllaaapgs vllapgavgp pdalrpakyl slaldeppcg qfalpgggag

241 gpglctcavc kfphlvpasl glaavqaqfs k
```

By "oligodendrocyte 01 nucleic acid molecule" (or oligodendrocyte marker 01; oligodendrocyte transcription factor 1; olig1) is meant a polynucleotide encoding an oligodendrocyte 01 polypeptide. An exemplary oligodendrocyte 01 nucleic acid molecule (e.g., mRNA) is provided at NCBI Accession No. NM_138983.

```
                                                   (SEQ ID NO: 30)
   1 gttctagatc gtttccccgc gcgcaggtcc gcggggaggg gcggcctgcc gaccggccca

  61 ccccagggcg ttcctgaagg gcgtcctcgg ccgcccccac cgcctcccag atgtactatg

 121 cggtttccca ggcgcgcgtg aacgcggtcc ccgggaccat gctgcggcca cagcggcccg

 181 gagacttgca gctcggggcc tccctctacg agctggtggg ctacaggcag ccgcccctcct

 241 cctcctcctc ctccacctcc tccacctcct ccacttcctc ctcctccacg acggcccccc

 301 tcctccccaa ggctgcgcgc gagaagccgg aggcgccggc cgagcctcca ggccccgggc

 361 ccgggtcagg cgcgcacccg ggcggcagcg cccggccgga cgccaaggag gagcagcagc

 421 agcagctgcg gcgcaagatc aacagccgcg agcggaagcg catgcaggac ctgaacctgg

 481 ccatggacgc cctgcgcgag gtcatcctgc cctactcagc ggcgcactgc cagggcgcgc

 541 ccggccgcaa gctctccaag atagccacgc tgctgctcgc ccgcaactac atcctactgc

 601 tgggcagctc gctgcaggag ctgcgccgcg cgctgggcga gggcgccggg cccgccgcgc

 661 cgcgcctgct gctggccggg ctgcccctgc tcgccgccgc gcccggctcc gtgctgctgg

 721 cgcccggcgc cgtaggaccc cccgacgcgc tgcgcccccgc caagtacctg tcgctggcgc

 781 tggacgagcc gccgtgcggc cagttcgctc tccccggcgg cggcgcaggc ggcccccggcc

 841 tctgcacctg cgccgtgtgc aagttcccgc acctggtccc ggccagcctg ggcctggccg

 901 ccgtgcaggc gcaattctcc aagtgagggc gggtctgggc ctggggcgcg acctcggccc

 961 ggcctccctt cgctcagctt ctccgcgccc ctgctccctg cgtctgggag agcgaggccg

1021 agcaaggaaa gcatttcgaa ccttccagtc cagaggaagg gactgtcggg caccccccttc

1081 cccgccccca cccctgggac gttaaagtga ccagagcgga tgttcgatgg cgcctcgggg

1141 cagtttgggg ttctgggtcg gttccagcgg ctttaggcag aaagtgctcg ctctcaccca

1201 gcacatctct ctccttgtcc ctggagttgc gcgcttcgcg gggccgatgt agaacttagg

1261 gcgccttgcc gtggttggcg cgccccgggt gcagcgagag gccatccccg agcgctacct

1321 ccccggagcg gagcacgcgg gctcccagta ctaggggctg cgctcgagca gtggcggggg

1381 cggaggggtg gttcttttcc ttctcctccg ccagaggcca cgggcgccct tgttcccgcc

1441 ggccaggtcc tatcaaagga ggctgccgga actcaagagg cagaaaaaga ccagttaggc

1501 ggtgcagacg gtctgggacg tggcagacgg acggaccctc ggcggacagg tggtcggcgt

1561 cggggtgcgg tgggtagggg cgaggacaac gcagggtgcg ctgggttggg acgtgggtcc

1621 acttttgtag accagctgtt tggagagctg tatttaagac tcgcgtatcc agtgttttgt
```

-continued

```
1681 cgcagagagt tttcactctt aaatcctggg ggtttcttag aaagcaactt agaactcgag
1741 attcaccttt cgtttccctt tccccaaaag tagcgtaacc aacatttaag cttgcttaaa
1801 aacgaaaacc aaccgccttg catccagtgt tcccgattta ctaaaatagg taaccaggcg
1861 tctcacagtc gccgtcctgt caagagcgct aatgaacgtt ctcattaaca cgcaggagta
1921 ccgggagccc tgaaccgccc gctgctcggc ggatcccagc tgcggtggcg acggcgggaa
1981 ggcgctttcc gctgttcctc agcgggccgg gcccttgacc agcgcggccc gcaggtcttc
2041 cttctcgccg tcttgcagtt gaagagctac atacgtagtc agtttcgatt tgttacagac
2101 gttaacaaat tcctttaccc aaggttatgc tatgaccttt ccgcagttta ctttgatttt
2161 ctatgtttaa ggttttggtt gttggtagta gccgaattta actggcactt tattttactt
2221 ctaaccttgt ttcctgacgg tgtacagaat caacaaaata aaacatttaa agtctgattt
2281 tttaaaaaaa aaaaaaaa
```

By "oligodendrocyte 02 polypeptide" (or oligodendrocyte marker 02; oligodendrocyte transcription factor 2; olig2) is meant a polypeptide or fragment thereof having at least about 85% amino acid identity to NCBI Accession No. Q13516.

```
                                                (SEQ ID NO: 31)
  1 mdsdaslvss rpsspepddl flparskgss gsaftggtvs sstpsdcppe lsaelrgamg
 61 sagahpgdkl ggsgfkssss stssstssaa asstkkdkkq mtepelqqlr lkinsrerkr
121 mhdlniamdg lrevmpyahg psvrklskia tlllarnyil mltnsleemk rlvseiyggh
181 hagfhpsacg glahsaplpa atahpaaaah aahhpavhhp ilppaaaaaa aaaaaaavss
241 aslpgsglps vgsirpphgl lkspsaaaaa plggggggsg asggfqhwgg mpcpcsmcqv
301 ppphhhvsam gagslprlts dak
```

By "oligodendrocyte 02 nucleic acid molecule" (or oligodendrocyte marker 02; oligodendrocyte transcription factor 2; olig2) is meant a polynucleotide encoding an oligodendrocyte 02 polypeptide. An exemplary oligodendrocyte 02 nucleic acid molecule (e.g., mRNA) is provided at NCBI Accession No. NM_005806.

```
                                                (SEQ ID NO: 32)
  1 gggtgcttat tatagatcga cgcgacacca gcgcccggtg ccaggttctc ccctgaggct
 61 tttcggagcg agctcctcaa atcgcatcca gagtaagtgt ccccgcccca cagcagccgc
121 agcctagatc ccagggacag actctcctca actcggctgt gacccagaat gctccgatac
181 agggggtctg gatccctact ctgcgggcca tttctccaga gcgactttgc tcttctgtcc
241 tccccacact caccgctgca tctccctcac caaaagcgag aagtcggagc gacaacagct
301 ctttctgccc aagccccagt cagctggtga gctccccgtg gtctccagat gcagcacatg
361 gactctgggc cccgcgccgg ctctgggtgc atgtgcgtgt gcgtgtgttt gctgcgtggt
421 gtcgatggag ataaggtgga tccgtttgag gaaccaaatc attagttctc tatttagatc
481 tccattctcc ccaaagaaag gccctcactt cccactcgtt tattccagcc cgggggctca
541 gtttcccac acctaactga aagcccgaag cctctagaat gccacccgca ccccgagggt
601 caccaacgct ccctgaaata acctgttgca tgagagcaga ggggagatag agagagctta
661 attataggta cccgcgtgca gctaaaagga gggccagaga tagtagcgag ggggacgagg
721 agccacgggc cacctgtgcc gggaccccgc gctgtggtac tgcggtgcag gcgggagcag
781 cttttctgtc tctcactgac tcactctctc tctctctccc tctctctctc tctcattctc
841 tctcttttct cctcctctcc tggaagtttt cgggtccgag ggaaggagga ccctgcgaaa
```

-continued

```
901 gctgcgacga ctatcttccc ctggggccat ggactcggac gccagcctgg tgtccagccg
961 cccgtcgtcg ccagagcccg atgacctttt tctgccggcc cggagtaagg gcagcagcgg
1021 cagcgccttc actgggggca ccgtgtcctc gtccaccccg agtgactgcc cgccggagct
1081 gagcgccgag ctgcgcggcg ctatgggctc tgcgggcgcg catcctgtgg acaagctagg
1141 aggcagtggc ttcaagtcat cctcgtccag cacctcgtcg tctacgtcgt cggcggctgc
1201 gtcgtccacc aagaaggaca agaagcaaat gacagagccg gagctgcagc agctgcgtct
1261 caagatcaac agccgcgagc gcaagcgcat gcacgacctc aacatcgcca tggatggcct
1321 ccgcgaggtc atgccgtacg cacacggccc ttcggtgcgc aagctttcca agatcgccac
1381 gctgctgctg gcgcgcaact acatcctcat gctcaccaac tcgctggagg agatgaagcg
1441 actggtgagc gagatctacg gggccacca cgctggcttc cacccgtcgg cctgcggcgg
1501 cctggcgcac tccgcgcccc tgcccgccgc caccgcgcac ccggcagcag cagcgcacgc
1561 cgcacatcac cccgcggtgc accaccccat cctgccgccc gccgccgcag cggctgctgc
1621 cgccgctgca gccgcggctg tgtccagcgc ctctctgccc ggatccgggc tgccgtcggt
1681 cggctccatc cgtccaccgc acggcctact caagtctccg tctgctgccg cggccgcccc
1741 gctgggggc gggggcggcg gcagtggggc gagcgggggc ttccagcact ggggcggcat
1801 gccctgcccc tgcagcatgt gccaggtgcc gccgccgcac caccacgtgt cggctatggg
1861 cgccggcagc ctgccgcgcc tcacctccga cgccaagtga gcctactggc gccggcgcgt
1921 tctggcgaca ggggagccag gggccgcggg gaagcgagga ctggcctgcg ctgggctcgg
1981 gagctctgtc gcgaggaggg gcgcaggacc atggactggg ggtggggcat ggtggggatt
2041 tcagcatctg cgaacccaag caatgggggc gcccacagag cagtggggag tgaggggatg
2101 ttctctccgg gacctgatcg agcgctgtct ggctttaacc tgagctggtc cagtagacat
2161 cgttttatga aaaggtaccg ctgtgtgcat tcctcactag aactcatccg acccccgacc
2221 cccacctccg ggaaaagatt ctaaaaactt ctttccctga gagcgtggcc tgacttgcag
2281 actcggcttg ggcagcactt cggggggga gggggtgtta tgggaggggg acacattggg
2341 gccttgctcg tcttcctcct ttcttggcgg gtgggagact ccgggtagcc gcactgcaga
2401 agcaacagcc cgaccgcgcc ctccagggtc gtccctggcc caaggccagg ggccacaagt
2461 tagttggaag ccggcgttcg gtatcagaag cgctgatggt catatccaat ctcaatatct
2521 gggtcaatcc acaccctctt agaactgtgg ccgttcctcc ctgtctctcg ttgatttggg
2581 agaatatggt tttctaataa atctgtggat gttccttctt caacagtatg agcaagttta
2641 tagacattca gagtagaacc acttgtggat tggaataacc caaaactgcc gatttcaggg
2701 gcgggtgcat tgtagttatt attttaaaat agaaactacc ccaccgactc atctttcctt
2761 ctctaagcac aaagtgattt ggttattttg gtacctgaga acgtaacaga attaaaaggc
2821 agttgctgtg gaaacagttt gggttatttg gggttctgt tggcttttta aaattttctt
2881 ttttggatgt gtaaatttat caatgatgag gtaagtgcgc aatgctaagc tgtttgctca
2941 cgtgactgcc agccccatcg gagtctaagc cggctttcct ctattttggt ttatttttgc
3001 cacgtttaac acaaatggta aactcctcca cgtgcttcct gcgttccgtg caagccgcct
3061 cggcgctgcc tgcgttgcaa actgggcttt gtagcgtctg ccgtgtaaca cccttcctct
3121 gatcgcaccg cccctcgcag agagtgtatc atctgtttta tttttgtaaa aacaaagtgc
3181 taaataatat ttattacttg tttggttgca aaaacggaat aaatgactga gtgttgagat
3241 tttaaataaa atttaaagca aaaaaaaaaa aaaaa
```

By "oligodendrocyte 04 polypeptide" (or oligodendrocyte marker 04; oligodendrocyte transcription factor 4; olig4) is meant a polypeptide or fragment thereof having at least about 85% amino acid identity to NCBI Accession No. Q05586.

By "oligodendrocyte 04 nucleic acid molecule" (or oligodendrocyte marker 04; oligodendrocyte transcription factor 4; olig4) is meant a polynucleotide encoding an oligodendrocyte 04 polypeptide. An exemplary oligodendrocyte 04 nucleic acid molecule (e.g., mRNA) is provided at NCBI Accession No. NM_007327.

By "GFAP" (or Glial fibrillary acidic protein) is meant a polypeptide or fragment thereof having at least about 85% amino acid identity to NCBI Accession No. P14136.

```
                                                          (SEQ ID NO: 33)
  1 merrritsaa rrsyvssgem mvgglapgrr lgpgtrlsla rmppplptry dfslagalna

 61 gfketraser aemmelndrf asyiekvrfl eqqnkalaae lnqlrakept kladvyqael

121 relrlrldql tansarleve rdnlaqdlat vrqklqdetn lrleaennla ayrqeadeat

181 larldlerki esleeeirfl rkiheeevre lqeqlarqqv hveldvakpd ltaalkeirt

241 qyeamassnm heaeewyrsk fadltdaaar naellrqakh eandyrrqlq sltcdleslr

301 gtneslerqm reqeerhvre aasyqealar leeegqslkd emarhlqeyq dllnvklald

361 ieiatyrkll egeenritip vqtfsnlqir etsldtksys eghlkrnivv ktvemrdgev

421 ikeskqehkd vm
```

By "GFAP nucleic acid molecule" (or Glial fibrillary acidic protein) is meant a polynucleotide encoding an GFAP polypeptide. An exemplary GFAP nucleic acid molecule (e.g., mRNA) is provided at NCBI Accession No. NM_002055.

```
                                                          (SEQ ID NO: 34)
   1 gcaggatgga gaggagacgc atcacctccg ctgctcgccg ctcctacgtc tcctcagggg

  61 agatgatggt gggggcctg gctcctggcc gccgtctggg tcctggcacc cgcctctccc

 121 tggctcgaat gccccctcca ctcccgaccc gagtggattt ctccctggct ggggcactca

 181 atgctggctt caaggagacc cgggccagtg agcgggcaga gatgatggag ctcaatgacc

 241 gctttgccag ctacatcgag aaggttcgct tcctggaaca gcaaaacaag gcgctggctg

 301 ctgagctgaa ccagctgcgg gccaaggagc ccaccaagct ggcagacgtc taccaggctg

 361 agctgcgaga gctgcggctg cggctcgatc aactcaccgc caacagcgcc cggctggagg

 421 ttgagaggga caatctggca caggacctgg ccactgtgag gcagaagctc caggatggaa

 481 ccaacctgag gctggaagcc gagaacaacc tggctgccta tagacaggaa gcagatgaag

 541 ccaccctggc ccgtctggat ctggagagga agattgagtc gctggaggag gagatccggt

 601 tcttgaggaa gatccacgag gaggaggttc gggaactcca ggagcagctg gcccgacagc

 661 aggtccatgt ggagcttgac gtggccaagc cagacctcac cgcagccctg aaagagatcc

 721 gcacgcagta tgaggcaatg gcgtccagca acatgcatga agccgaagag tggtaccgct

 781 ccaagtttgc agacctgaca gacgctgctg cccgcaacgc ggagctgctc cgccaggcca

 841 agcacgaagc caacgactac cggcgccagt tgcagtcctt gacctgcgac ctggagtctc

 901 tgcgcggcac gaacgagtcc ctggagaggc agatgcgcga gcaggaggag cggcacgtgc

 961 gggaggcggc cagttatcag gaggcgctgg cgcggctgga ggaagagggg cagagcctca

1021 aggacgagat ggcccgccac ttgcaggagt accaggacct gctcaatgtc aagctggccc

1081 tggacatcga gatcgccacc tacaggaagc tgctagaggg cgaggagaac cggatcacca

1141 ttcccgtgca gaccttctcc aacctgcaga ttcgagaaac cagcctggac accaagtctg

1201 tgtcagaagg ccacctcaag aggaacatcg tggtgaagac cgtggagatg cgggatggag

1261 aggtcattaa ggagtccaag caggagcaca aggatgtgat gtgaggcagg acccacctgg
```

-continued

```
1321 tggcctctgc cccgtctcat gaggggcccg agcagaagca ggatagttgc tccgcctctg

1381 ctggcacatt tccccagacc tgagctcccc accaccccag ctgctcccct ccctcctctg

1441 tccctaggtc agcttgctgc cctaggctcc gtcagtatca ggcctgcc
```

By "s110b" (or S-100 protein beta chain; S-100 protein subunit beta; S100 calcium-binding protein B) is meant a polypeptide or fragment thereof having at least about 85% amino acid identity to NCBI Accession No. P04271.

```
                                                       (SEQ ID NO: 35)
 1 mselekamva lidvfhqysg regdkhklkk selkelinne lshfleeike qevvdkvmet

61 ldndgdgecd fqefmafvam vttacheffe he
```

By "s100b nucleic acid molecule" (or S-100 protein beta chain; S-100 protein subunit beta; S100 calcium-binding protein B) is meant a polynucleotide encoding an s100b polypeptide. An exemplary s100b nucleic acid molecule (e.g., mRNA) is provided at NCBI Accession No. NM_006272.

```
                                                          (SEQ ID NO: 36)
   1 gggcagaggg aataagaggc tgcctctgcc caccagtcct gccgcccagg acccgcagca

  61 gagacgacgc ctgcagcaag gagaccagga aggggtgaga caaggaagag gatgtctgag

 121 ctggagaagg ccatggtggc cctcatcgac gttttccacc aatattctgg aagggaggga

 181 gacaagcaca agctgaagaa atccgaactg aaggagctca tcaacaatga gctttcccat

 241 ttcttagagg aaatcaaaga gcaggaggtt gtggacaaag tcatggaaac actggacaat

 301 gatggagacg gcgaatgtga cttccaggaa ttcatggcct ttgttgccat ggttactact

 361 gcctgccacg agttctttga acatgagtga gattagaaag cagccaaacc tttcctgtaa

 421 cagagacggt catgcaagaa agcagacagc aagggcttgc agcctagtag gagctgagct

 481 ttccagccgt gttgtagcta attaggaagc ttgatttgct ttgtgattga aaaattgaaa

 541 acctctttcc aaaggctgtt ttaacggcct gcatcattct ttctgctata ttaggcctgt

 601 gtgtaagctg actggcccca gggactcttg ttaacagtaa cttaggagtc aggtctcagt

 661 gataaagcgt gcaccgtgca gcccgccatg gccgtgtaga ccctaacccg gagggaaccc

 721 tgactacaga aattaccccg gggcaccctt aaaacttcca ctacctttaa aaaacaaagc

 781 cttatccagc attatttgaa aacactgctg ttctttaaat gcgttcctca tccatgcaga

 841 taacagctgg ttggccggtg tggccctgca agggcgtggt ggcttcggcc tgcttcccgg

 901 gatgcgcctg atcaccaggt gaacgctcag cgctggcagc gctcctggaa aaagcaactc

 961 catcagaact cgcaatccga gccagctctg gggctccag cgtggcctcc gtgacccatg

1021 cgattcaagt cgcggctgca ggatccttgc ctccaacgtg cctccagcac atgcggcttc

1081 cgagggcact accgggggct ctgagccacc gcgagggcct gcgttcaata aaaag
```

By "SOX10 polypeptide" (or SRY-related HMG-box transcription factor) is meant a polypeptide or fragment thereof having at least about 85% amino acid identity to NCBI Accession No. NP_008872.1.

```
                                          (SEQ ID NO: 37)
MAEEQDLSEVELSPVGSEEPRCLSPGSAPSLGPDGGGGGSGLRASPGPGE

LGKVKKEQQDGEADDDKFPVCIREAVSQVLSGYDWTLVPMPVRVNGASKS
```

-continued

```
KPHVKRPMNAFMVWAQAARRKLADQYPHLHNAELSKTLGKLWRLLNESDK

RPFIEEAERLRMQHKKDHPDYKYQPRRRKNGKAAQGEAECPGGEAEQGGT

AAIQAHYKSAHLDHRHPGEGSPMSDGNPEHPSGQSHGPPTPPTTPKTELQ

SGKADPKRDGRSMGEGGKPHIDFGNVDIGEISHEVMSNMETFDVAELDQY

LPPNGHPGHVSSYSAAGYGLGSALAVASGHSAWISKPPGVALPTVSPPGV

DAKAQVKTETAGPQGPPHYTDQPSTSQIAYTSLSLPHYGSAFPSISRPQF
```

-continued

DYSDHQPSGPYYGHSGQASGLYSAFSYMGPSQRPLYTAISDPSPSGPQSH

SPTHWEQPVYTTLSRP

By "SOX10 nucleic acid molecule" (or SRY-related HMG-box transcription factor) is meant a polynucleotide encoding an SOX10 polypeptide. An exemplary SOX10 nucleic acid molecule (e.g., mRNA) is provided at NCBI Accession No. NM_006941.3.

(SEQ ID NO: 38)

1 gtccggccag ggtggttggt ggtaaggatt caggctccgt cctaacgagg ccgtggcctg 61 aggctcaggg ccccccgccc ctccctccca gcccaccagc gtcacctccc agccccgagc 121 tggaccgcac accttgggac acggttttcc acttcctaag gacgagcccc agactggagg 181 agaggtccga ggaggtgggc gttggactct ttgcgaggac cccggcggct ggcccggggg 241 aggcggccga ggcggcggcg gcggcggccg gggcgacat ggcggaggag caggacctat 301 cggaggtgga gctgagcccc gtgggctcgg aggagccccg ctgcctgtcc ccggggagcg 361 cgccctcgct agggcccgac ggcggcggcg gcggatcggg cctgcgagcc agcccggggc 421 caggcgagct gggcaaggtc aagaaggagc agcaggacgg cgaggcggac gatgacaagt 481 tccccgtgtg catccgcgag gccgtcagcc aggtgctcag cggctacgac tggacgctgg 541 tgcccatgcc cgtgcgcgtc aacggcgcca gcaaaagcaa gccgcacgtc aagcggccca 601 tgaacgcctt catggtgtgg gctcaggcag cgcgcaggaa gctcgcggac cagtacccgc 661 acctgcacaa cgctgagctc agcaagacgc tgggcaagct ctggaggctg ctgaacgaaa 721 gtgacaagcg cccctcatc gaggaggctg agcggctccg tatgcagcac aagaaagacc 781 acccggacta caagtaccag cccaggcggc ggaagaacgg gaaggccgcc cagggcgagg 841 cggagtgccc cggtggggag gccgagcaag gtgggaccgc cgccatccag gcccactaca 901 agagcgccca cttggaccac cggcacccag gagagggctc cccatgtca gatgggaacc 961 ccgagcaccc ctcaggccag agccatggcc cacccacccc tccaaccacc ccgaagacag 1021 agctgcagtc gggcaaggca gacccgaagc gggacgggcg ctccatgggg gagggcggga 1081 agcctcacat cgacttcggc aacgtggaca ttggtgagat cagccacgag gtaatgtcca 1141 acatggagac ctttgatgtg gctgagttgg accagtacct gccgcccaat gggcacccag 1201 gccatgtgag cagctactca gcagccggct atgggctggg cagtgccctg gccgtggcca 1261 gtggacactc cgcctggatc tccaagccac caggcgtggc tctgcccacg gtctcaccac 1321 ctggtgtgga tgccaaagcc caggtgaaga cagagaccgc ggggccccag gggcccccac 1381 actacaccga ccagccatcc acctcacaga tcgcctacac ctccctcagc ctgccccact 1441 atggctcagc cttcccctcc atctcccgcc cccagtttga ctactctgac catcagccct 1501 caggacccta ttatggccac tcgggccagg cctctggcct ctactcggcc ttctcctata 1561 tggggccctc gcagcggccc ctctacacgg ccatctctga ccccagcccc tcagggcccc 1621 agtcccacag ccccacacac tgggagcagc cagtatatac gacactgtcc cggccctaaa 1681 gggggccctg tcgccaccac cccccgccca gcccctgccc ccagcctgtg tgccctgttc 1741 cttgcccacc tcaggcctgg tggtggcagt ggaggaggct gaggaggctg aagaggctga 1801 caggtcgggg ggctttctgt ctggctcact gccctgatga cccacccgcc ccatccaggc 1861 tccagcagca aagccccagg agaacaggct ggacagagga gaaggaggtt gactgttgca 1921 cccacactga aagatgaggg gctgcacctt cccccaggaa tgaccctcta tcccaggacc 1981 tgagaagggc ctgctcaccc tcctcgggga ggggaagcac cagggttggt ggcatcggag 2041 gccttaccac tcctatgact cctgttttct ctctcacaga tagtgagggt ctgacatgcc 2101 catgccacct atgccacagt gcctaagggc taggccaccc agagactgtg cccggagctg -continued

```
2161 gccgtgtctc ccactcaggg gctgagagta gctttgagga gcctcattgg ggagtggggg
2221 gttcgaggga cttagtggag ttctcatccc ttcaatgccc cctccctttc tgaaggcagg
2281 aaggagttgg cacagaggcc ccctgatcca attctgtgcc aataacctca ttctttgtct
2341 gagaaacagc ccccagtcct cctccactac aacctccatg accttgagac gcatcccagg
2401 aggtgacgag gcaggggctc caggaaagga atcagagaca attcacagag cctccctccc
2461 tgggctcctt gccagctccc tcttccctta ctaggctcta tggcccctgc tcagtcagcc
2521 ccactccctg ggcttcccag agagtgacag ctgctcaggc cctaaccctt ggctccagga
2581 gacacagggc ccagcaccca ggttgctgtc ggcaggctga agacactaga atcctgacct
2641 gtacattctg cccttgcctc ttaccccttg cctcccagtg gtatttgaat aaagtatgta
2701 gctatatctg cccctatttt cctgttctgc agccccccaa atccacatgt aactcattac
2761 tgtctcctgt tatttatctc agtagtcccc tctcctagcc actctagccc ctattaactc
2821 tgcattaagc attccacata ataaaattaa aggttccggt taaaaaaaaa aaaaaaaaaa
2881 aa
```

By "SYN1 protein" (or Synaptin I protein) is meant a polypeptide or fragment thereof having at least about 85% amino acid identity to GenBank: AH006533.2.

(SEQ ID NO: 39)

```
MNYLRRRLSDSNFMANLPNGYMTDLQRPQPPPPPPGAHSPGATPGPGTAT
AERSSGVAPAASPAAPSPGSSGGGGFFSSLSNAVKQTTAAAAATFSEQVG
GGSGGAGRGGAASRVLLVIDEPHTDWAKYFKGKKIHGGIDIKVEQAEFSD
LNLVAHANGGFSVDMEVLRNGVKVVRSLKPDFVLIRQHAFSMARNGDYRS
LVIGLQYAGIPSVNSLHSVYNFCDKPWVFAQMVRLHKKLGTEEFPLIDQT
FYPNHKEMLSSTTYPVVVKMGHAHSGMGKVKVDNQHDFQDIASVVALTKT
YATAEPFIDAKYDVRVQKIGQNYKAYMRTSVSGNWKTNTGSAMLEQIAMS
```

-continued

```
DRYKLWVDTCSEIFGGLDICAVEALHGKDGRDHIIEVVGSSMPLIGDHQD
EDKQLIVELVVNKMAQALPRQRQRDASPGRGSHGQTPSPGALPLGRQTSQ
QPAGPPAQQRPPPQGGPPQPGPGPQRQGPPLQQRPPPQGQQHLSGLGPPA
GSPLPQRLPSPTSAPQQPASQAAPPTQGQGRQSRPVAGGPGAPPAARPPA
SPSPQRQAGPPQATRQTSVSGPAPPKASGAPPGGQQRQGPPQKPPGPAGP
TRQASQAGPVPRTGPPTTQQPRPSGPGPAGAPKPQLAQKPSQDVPPPATA
AAGGPPHPQLNKSQSLTNAFNLPEPAPPRPSLSQDEVKAETIRSLRKSFA
SLFSD
```

By "SYN1 nucleic acid molecule" (or synapsin I gene) is meant a polynucleotide encoding an SYN1 polypeptide. An exemplary SYN1 nucleic acid molecule (e.g., mRNA) is provided at GenBank: AH006533.2.

(SEQ ID NO: 40)

```
  1 ctcgagagag aaggagagga cattcctggc agaagttaca acacatgcaa aggtacagag
 61 gttgcccccct tcctacccct ctccttagag gtgggttaga gatgtatcct ttttacagat
121 gaggaaacca aatctcagaa agattaagtc actttcccaa gtgtatggtg gaggccccac
181 ttgaacccag gcactgtgtc tccagacccc acactattac tgccttgttt aaaccagcca
241 actgatttaa tgaataaagg atgaacaaat gaataagtgg atgagtcacc tgaaaattct
301 gcaggcaaag agactccata tctacttact tcttgcctat cttctgccac ctctcctagt
361 ccaccatcac tgctcactat ggtcaaggtc ctacccaatc tggcccctgc taccacaacc
421 cccttcagct tgttccagcc acattggcac tggatgtttc ctcttcctgg cacattctta
481 aaaaaatgtg ttgatcataa agtgaacatg accctttggg aattaactgg agttcttgta
541 ttccctcatc tgtaaaatag acattatatt atccacccca ctggattgtt gtgagggtgg
601 gatgaaatga tgcatgtaaa cacgcttagc ttaagagttg ggtacaatca gtgaacaaat
661 gattatgaat tagtgctttt attgtagtca gaatcataaa gatttgacag gttcccatat
721 cccacctctg cttggactac ctcatttgct catatgcaaa gattatttgg tacctactgt
781 gtgtgcacca tgggatgggc ctgcctctgt ggaaagttct tgggtgcagg gggagacagc
```

-continued

```
 841 catgggcact gatgacatca ggtagttatc gtgagttttg gcggtgtcca gagcaaaggg
 901 atggtggcgt atataccaag tgtgttctgg tgtgggggtg gacacgcacc agggctaggg
 961 ctgcagagaa tgtctgtgtt gcagatctag gtttctccat gatcatcggt gggaatgtgt
1021 tttgtctgca agtgtatgct catatgagtt tccctgggtc tctgtgtgtc agtgtgttac
1081 ctgtgtgtgt gggggtatgg gtgtatgcat gcatgtatgt aacatgccca tgtgtgttac
1141 tctggacttg tatgtctgta tgtataccta gattggcgtg tgttctgtct gtacatgccc
1201 tcgtatgttt cctcactttt gtgtgtgttt atatgtgtgt catttcttgt gtgccctcca
1261 ggcccccctt gccaccttgg gcaagggtgt gtacaccacc caagtgtcca cctccgcttg
1321 tctgatgctg tctgtgacgc cccgctctc tgcctagctg agcctgtgtg gatgtgggag
1381 actaatctcc ccgcgggcac tgcgtgtgac ctcacccccc tctgtgaggg ggttatttct
1441 ctactttcgt gtctctgagt gtgcttccag tgcccccctc cccccaaaaa atgccttctg
1501 agttgaatat caacactaca aaccgagtat ctgcagactg cagagggccc tgcgtatgag
1561 tgcaagtggg ttttaggacc aggatgaggc ggggtggggg tgcctacctg acgaccgacc
1621 ccgacccact ggacaagcac ccaaccccca ttccccaaat tgcgcatccc ctatcagaga
1681 gggggagggg aaacaggatg cggcgaggcg cgtcgcgact gccagcttca gcaccgcgga
1741 cagtgccttc gcccccgcct ggcggcgcgc gccaccgccg cctcagcact gaaggcgcgc
1801 tgacgtcact cgccggtccc ccgcaaactc cccttcccgg ccaccttggt cgcgtccgcg
1861 ccgccgccgg cccagccgga ccgcaccacg cgaggcgcga gatagggggg cacgggcgcg
1921 accatctgcg ctgcggcgcc ggcgactcag cgctgcctca gtctgcggtg ggcagcggag
1981 gagtcgtgtc gtgcctgaga gcgcagctgt gctcctgggc accgcgcagt ccgcccccgc
2041 ggctcctggc cagaccaccc ctaggacccc ctgccccaag tcgcagccat gaactacctg
2101 cggcgccgcc tgtcggacag caactttatg gccaatctgc caaatgggta catgacagac
2161 ctgcagcgtc cgcagccgcc cccaccgccg cccggtgccc acagccccgg agccacgccc
2221 ggtcccggga ccgccactgc cgagaggtcc tccggggtcg ccccagcggc ctctccggcc
2281 gcccctagcc ccgggtcctc ggggggcggt ggcttcttct cgtcgctgtc caacgcggtc
2341 aagcagacca cggcggcggc agctgccacc ttcagcgagc aggtgggcgg cggctctggg
2401 ggcgcaggcc gcgggggagc cgcctccagg gtgctgctgg tcatcgacga gccgcacacc
2461 gactggtaag
```

By "SYP protein" (or synaptophysin protein) is meant a polypeptide or fragment thereof having at least about 85% amino acid identity to NCBI Reference Sequence: NM_003179.2.

```
                                       (SEQ ID NO: 41)
MLLLADMDVVNQLVAGGQFRVVKEPLGFVKVLQWVFAIFAFATCGSYSGE

LQLSVDCANKTESDLSIEVEFEYPFRLHQVYFDAPTCRGGTTKVFLVGDY

SSSAEFFVTVAVFAFLYSMGALATYIFLQNKYRENNKGPMLDFLATAVFA
```

-continued

```
FMWLVSSSAWAKGLSDVKMATDPENIIKEMPVCRQTGNTCKELRDPVTSG

LNTSVVFGFLNLVLWVGNLWFVFKETGWAAPFLRAPPGAPEKQPAPGDAY

GDAGYGQGPGGYGPQDSYGPQGGYQPDYGQPAGSGGSGYGPQGDYGQQGY

GPQGAPTSFSNQM
```

By "SYP nucleic acid molecule" (or synaptophysin gene) is meant a polynucleotide encoding an SYN1 polypeptide. An exemplary SYP nucleic acid molecule (e.g., mRNA) is provided at NCBI Reference Sequence: NM_003179.2.

```
                                                         (SEQ ID NO: 42)
  1 gccccctgca ttgctgatgc tgctgctggc ggacatggac gtggtgaatc agctggtggc

 61 tgggggtcag ttccgggtgg tcaaggagcc cctcggcttt gtgaaggtgc tgcaatgggt

121 cttcgccatc ttcgcctttg ccacatgcgg cagctacagt ggggagctcc agctgagcgt
```

-continued

```
 181 ggattgtgcc aacaagaccg agagtgacct cagcatcgag gtcgagttcg agtacccctt
 241 caggctgcac caagtgtact ttgatgcacc cacctgccga gggggcacca ccaaggtctt
 301 cttagttggg gactactcct cgtcagccga attctttgtc accgtggccg tgtttgcctt
 361 cctctactcc atgggggctc tggccaccta catcttcctg cagaacaagt accgagagaa
 421 taacaaaggg cccatgctgg actttctggc cacggctgtg ttcgccttca tgtggctagt
 481 tagctcatcg gcatgggcca aggggctgtc agatgtgaag atggccacag acccagagaa
 541 cattatcaag gagatgcctg tctgccgcca gacagggaac acatgcaagg agctgagaga
 601 ccctgtgacc tcgggactca acacctcggt ggtgttcggc ttcctgaacc tggtgctctg
 661 ggtcggcaac ctgtggttcg tgtttaagga gacaggctgg gccgccccgt tcctgcgcgc
 721 gcctcccggc gcccccgaga aacaaccggc acccggggac gcctacggcg atgcaggcta
 781 cgggcagggc cccggcgggt acgggcccca ggattcctac gggcctcagg gcggctacca
 841 gcctgactat ggtcaaccag ccggcagcgg tggcagtggc tacgggcctc agggcgacta
 901 tgggcagcaa ggctacggcc cgcagggtgc acccacctcc ttctccaatc agatgtagtc
 961 tggtcagtga agcccaggag gacctggggg gggcaagagc tcaggagaag gcctgccccc
1021 cttcccaccc ctatacccta ggtctccacc cctcaagcca ggagaccctg tctttgctgt
1081 ttatatatat atatattata tataaatatc tatttatctg tctgagccct gccctcactc
1141 cactcccctc atccactagg tgcccagtct tgagtgggcc ccctctctta ccccgtccct
1201 ttccctgcat cccttggccc ctctctgttt accctccctg tcccctgagg ttaaggggat
1261 ctaaaaggag gacagggagg gaacagacct cggctgtgtg gggagggtgg gcgtgacttc
1321 agactctctc ctctctctcc ctccactcct cccaactctg gccttggttc ctccagcaat
1381 gcctgcctga acaaaggccg ttagggaaat ccaactccag ggttaaagaa aggcagagat
1441 tggggggggct tggggtagag aggacagttt aggacccaag gtggtcttgg agaggaggtg
1501 tggagtggag gggtcagcag gggggttggg ttccagacag agtggatctg gagtctgaag
1561 gagaggagtg cgctagagca ttctggggtg gggcttggaa gggcgctgag ggcagggttc
1621 tagaaggggc gaggctttaa gcgaggcaga atggtgggct ccagagtagg tgggtcttgg
1681 attggtacca gagcctatgg aaagggtgtg gcttggaaca tttgggagac tgagcttgat
1741 tctaaagggg acagatcttg agcaaggcaa gaagtgggat tcaggaatgg gccaagccag
1801 ggttccagac agggtggggc ttagaatggg gcttccatgg tggtttcaga aagggcagcc
1861 cctccccatg gtgcagtgaa gaaaatgttt tacaatggct gggtttgggc agtggagagg
1921 ggacttggat aggagcttcc agatgggttt tgttaggggt gggggagaat ggctctggct
1981 acgacttggg acggaagtgg cctgagaaga gtcgagtgat atggcttgta gggtgaggcg
2041 tgggatccag agagaagcac cccaccacac acacccttcc ccactcccgt gatgaaacag
2101 ctaggttaat aggaggacag aaccaacggg tctgtgggac tggcccaccc ctcttccccc
2161 ttcccctgcg ccctccctcc ctccacacct ccacccgtcc tggggtggtt ggaggcctgg
2221 tctggagccc ctatcctgca ccctctgcta tgtctgtgat gtcagtagtg cctgtgatcg
2281 tgtgttgcca ttttgtctgg ctgtggcccc tccttctccc ctccagaccc ctaccctttc
2341 ccaaaccctt cggtattgtt caaagaaccc ccctccccaa ggaagaacaa atatgattct
2401 cctctcccaa ataaactcct taaccaccta gtcaaaaaaa aaaaaaaaa
```

By "NOGOA polypeptide" (or neurite outgrowth inhibitor A; neurite outgrowth inhibitor isoform A; human reticulon-4; human reticulon-4 isoform A) is meant a polypeptide or fragment thereof having at least about 85% amino acid identity to NCBI Accession No. NP_065393.

(SEQ ID NO: 43)

```
   1 medldqsplv sssdspprpq pafkyqfvre pedeeeeeee eeedededle elevlerkpa
  61 aglsaapvpt apaagaplmd fgndfvppap rgplpaappv aperqpswdp spvsstvpap
 121 splsaaavsp sklpeddepp arppppppas vspqaepvwt ppapapaapp stpaapkrrg
 181 ssgsvdetlf alpaasepvi rssaenmdlk eqpgntisag qedfpsvlle taaslpslsp
 241 lsaasfkehe ylgnlstvlp tegtlqenvs easkevseka ktllidrdlt efseleysem
 301 gssfsvspka esavivanpr eeiivknkde eeklvsnnil hnqqelptal tklvkedevv
 361 ssekakdsfn ekrvaveapm reeyadfkpf ervwevkdsk edsdmlaagg kiesnleskv
 421 dkkcfadsle qtnhekdses snddtsfpst pegikdrsga yitcapfnpa atesiatnif
 481 pllgdptsen ktdekkieek kaqivteknt stktsnpflv aaqdsetdyv ttdnltkvte
 541 evvanmpegl tpdlvqeace selnevtgtk iayetkmdlv qtsevmqesl ypaaqlcpsf
 601 eeseatpspv lpdivmeapl nsavpsagas viqpssspl e assvnyesik hepenpppye
 661 eamsvslkkv sgikeeikep eninaalqet eapyisiacd liketklsae papdfsdyse
 721 makveqpvpd hselvedssp dsepvdlfsd dsipdvpqkq detvmlvkes ltetsfesmi
 781 eyenkeklsa lppeggkpyl esfklsldnt kdtllpdevs tlskkekipl qmeelstavy
 841 snddlfiske aqiretetfs dsspieiide fptlissktd sfsklareyt dlevshksei
 901 anapdgagsl pctelphdls lkniqpkvee kisfsddfsk ngsatskvll lppdvsalat
 961 qaeiesivkp kvlvkeaekk lpsdtekedr spsaifsael sktsvvdlly wrdikktgvv
1021 fgaslfllls ltvfsivsvt ayialallsv tisfriykgv iqaiqksdeg hpfraylese
1081 vaiseelvqk ysnsalghvn ctikelrrlf lvddlvdslk favlmwvfty vgalfngltl
1141 lilalislfs vpviyerhqa qidhylglan knvkdamaki qakipglkrk ae
```

By "NOGOA nucleic acid molecule" (or neurite outgrowth inhibitor A; neurite outgrowth inhibitor isoform A; human reticulon-4; human reticulon-4 isoform A) is meant a polynucleotide encoding an NOGOA polypeptide. An exemplary NOGOA nucleic acid molecule (e.g., mRNA) is provided at NCBI Accession No. NM_020532.

(SEQ ID NO: 44)

```
  1 agtccctgcc ctcccctggg gagggtgagt cacgccaaac tgggcggaga gtccgctggc
 61 ctcactccta gctcatctgg gcggcggcgg caagtgggga cagggcgggt ggcgcatcac
121 cggcgcggag gcaggaggag cagtctcatt gttccgggag ccgtcaccac agtaggtccc
181 tcggctcagt cggcccagcc cctctcagtc ctccccaacc cccacaaccg cccgcggctc
241 tgagacgcgg ccccggcggc ggcggcagca gctgcagcat catctccacc ctccagccat
301 ggaagacctg gaccagtctc ctctggtctc gtcctcggac agcccacccc ggccgcagcc
361 cgcgttcaag taccagttcg tgagggagcc cgaggacgag gaggaagaag aggaggagga
421 agaggaggac gaggacgaag acctggagga gctggaggtg ctggagagga agcccgccgc
481 cgggctgtcc gcggccccag tgcccaccgc ccctgccgcc ggcgcgcccc tgatggactt
541 cggaaatgac ttcgtgccgc cggcgccccg gggacccctg ccggccgctc cccccgtcgc
601 cccggagcgg cagccgtctt gggacccgag cccggtgtcg tcgaccgtgc ccgcgccatc
661 cccgctgtct gctgccgcag tctcgccctc caagctccct gaggacgacg agcctccggc
721 ccggcctccc cctcctcccc cggccagcgt gagcccccag gcagagcccg tgtggacccc
```

-continued 781 gccagccccg gctcccgccg cgccccccctc caccccggcc gcgcccaagc gcaggggctc 841 ctcgggctca gtggatgaga cccttttttgc tcttcctgct gcatctgagc ctgtgatacg 901 ctcctctgca gaaaatatgg acttgaagga gcagccaggt aacactattt cggctggtca 961 agaggatttc ccatctgtcc tgcttgaaac tgctgcttct cttccttctc tgtctcctct 1021 ctcagccgct tctttcaaag aacatgaata ccttggtaat ttgtcaacag tattacccac 1081 tgaaggaaca cttcaagaaa atgtcagtga agcttctaaa gaggtctcag agaaggcaaa 1141 aactctactc atagatagag atttaacaga gttttcagaa ttagaatact cagaaatggg 1201 atcatcgttc agtgtctctc caaaagcaga atctgccgta atagtagcaa atcctaggga 1261 agaaataatc gtgaaaaata aagatgaaga agagaagtta gttagtaata acatccttca 1321 taatcaacaa gagttaccta cagctcttac taaattggtt aaagaggatg aagttgtgtc 1381 ttcagaaaaa gcaaaagaca gttttaatga aaagagagtt gcagtggaag ctcctatgag 1441 ggaggaatat gcagacttca aaccatttga gcgagtatgg gaagtgaaag atagtaagga 1501 agatagtgat atgttggctg ctggaggtaa aatcgagagc aacttggaaa gtaaagtgga 1561 taaaaaatgt tttgcagata gccttgagca aactaatcac gaaaaagata gtgagagtag 1621 taatgatgat acttctttcc ccagtacgcc agaaggtata aaggatcgtt caggagcata 1681 tatcacatgt gctcccttta acccagcagc aactgagagc attgcaacaa acatttttcc 1741 tttgttagga gatcctactt cagaaaataa gaccgatgaa aaaaaaatag aagaaaagaa 1801 ggcccaaata gtaacagaga agaatactag caccaaaaca tcaaaccctt ttcttgtagc 1861 agcacaggat tctgagacag attatgtcac aacagataat ttaacaaagg tgactgagga 1921 agtcgtggca aacatgcctg aaggcctgac tccagattta gtacaggaag catgtgaaag 1981 tgaattgaat gaagttactg gtacaaagat tgcttatgaa acaaaaaatgg acttggttca 2041 aacatcagaa gttatgcaag agtcactcta tcctgcagca cagctttgcc catcatttga 2101 agagtcagaa gctactcctt caccagtttt gcctgacatt gttatggaag caccattgaa 2161 ttctgcagtt cctagtgctg gtgcttccgt gatacagccc agctcatcac cattagaagc 2221 ttcttcagtt aattatgaaa gcataaaaca tgagcctgaa aacccccccac catatgaaga 2281 ggccatgagt gtatcactaa aaaaagtatc aggaataaag gaagaaatta aagagcctga 2341 aaatattaat gcagctcttc aagaaacaga agctccttat atatctattg catgtgattt 2401 aattaaagaa acaaagcttt ctgctgaacc agctccggat ttctctgatt attcagaaat 2461 ggcaaaagtt gaacagccag tgcctgatca ttctgagcta gttgaagatt cctcacctga 2521 ttctgaacca gttgacttat ttagtgatga ttcaatacct gacgttccac aaaaacaaga 2581 tgaaactgtg atgcttgtga aagaaagtct cactgagact tcatttgagt caatgataga 2641 atatgaaaat aaggaaaaac tcagtgcttt gccacctgag ggaggaaagc catatttgga 2701 atcttttaag ctcagtttag ataacacaaa agataccctg ttacctgatg aagtttcaac 2761 attgagcaaa aaggagaaaa ttcctttgca gatggaggag ctcagtactg cagtttattc 2821 aaatgatgac ttatttattt ctaaggaagc acagataaga gaaactgaaa cgttttcaga 2881 ttcatctcca attgaaatta tagatgagtt ccctacattg atcagttcta aaactgattc 2941 attttctaaa ttagccaggg aatatactga cctagaagta tcccacaaaa gtgaaattgc 3001 taatgccccg gatggagctg ggtcattgcc ttgcacagaa ttgccccatg acctttcttt 3061 gaagaacata caacccaaag ttgaagagaa aatcagtttc tcagatgact tttctaaaaa 3121 tgggtctgct acatcaaagg tgctcttatt gcctccagat gtttctgctt tggccactca 3181 agcagagata gagagcatag ttaaacccaa agttcttgtg aaagaagctg agaaaaaact -continued

```
3241 tccttccgat acagaaaaag aggacagatc accatctgct atattttcag cagagctgag
3301 taaaacttca gttgttgacc tcctgtactg gagagacatt aagaagactg gagtggtgtt
3361 tggtgccagc ctattcctgc tgctttcatt gacagtattc agcattgtga gcgtaacagc
3421 ctacattgcc ttggccctgc tctctgtgac catcagcttt aggatataca agggtgtgat
3481 ccaagctatc cagaaatcag atgaaggcca cccattcagg gcatatctgg aatctgaagt
3541 tgctatatct gaggagttgg ttcagaagta cagtaattct gctcttggtc atgtgaactg
3601 cacgataaag gaactcaggc gcctcttctt agttgatgat ttagttgatt ctctgaagtt
3661 tgcagtgttg atgtgggtat ttacctatgt tggtgccttg tttaatggtc tgacactact
3721 gattttggct ctcatttcac tcttcagtgt tcctgttatt tatgaacggc atcaggcaca
3781 gatagatcat tatctaggac ttgcaaataa gaatgttaaa gatgctatgg ctaaaatcca
3841 agcaaaaatc cctggattga agcgcaaagc tgaatgaaaa cgcccaaaat aattagtagg
3901 agttcatctt taaaggggat attcatttga ttatacgggg gagggtcagg gaagaacgaa
3961 ccttgacgtt gcagtgcagt ttcacagatc gttgttagat ctttattttt agccatgcac
4021 tgttgtgagg aaaaattacc tgtcttgact gccatgtgtt catcatctta agtattgtaa
4081 gctgctatgt atggatttaa accgtaatca tatctttttc ctatctatct gaggcactgg
4141 tggaataaaa aacctgtata ttttactttg ttgcagatag tcttgccgca tcttggcaag
4201 ttgcagagat ggtggagcta gaaaaaaaaa aaaaaaagcc cttttcagtt tgtgcactgt
4261 gtatggtccg tgtagattga tgcagatttt ctgaaatgaa atgtttgttt agacgagatc
4321 ataccggtaa agcaggaatg acaaagcttg cttttctggt atgttctagg tgtattgtga
4381 cttttactgt tatattaatt gccaatataa gtaaatatag attatatatg tatagtgttt
4441 cacaaagctt agacctttac cttccagcca ccccacagtg cttgatattt cagagtcagt
4501 cattggttat acatgtgtag ttccaaagca cataagctag aagaagaaat atttctagga
4561 gcactaccat ctgttttcaa catgaaatgc cacacacata gaactccaac atcaatttca
4621 ttgcacagac tgactgtagt taattttgtc acagaatcta tggactgaat ctaatgcttc
4681 caaaaatgtt gtttgtttgc aaatatcaaa cattgttatg caagaaatta ttaattacaa
4741 aatgaagatt tataccattg tggtttaagc tgtactgaac taaatctgtg gaatgcattg
4801 tgaactgtaa aagcaaagta tcaataaagc ttatagactt aaaaaaaaaa aaaaaaaaaa
4861 aaaaaaaaaa a
```

By “GFAP” (or Glial fibrillary acidic protein) is meant a polypeptide or fragment thereof having at least about 85% amino acid identity to NCBI Accession No. P14136.

```
                                                      (SEQ ID NO: 45)
  1 merrritsaa rrsyvssgem mvgglapgrr lgpgtrlsla rmppplptrv dfslagalna
 61 gfketraser aemmelndrf asyiekvrfl eqqnkalaae lnqlrakept kladvyqael
121 relrlrldql tansarleve rdnlaqdlat vrqklqdetn lrleaennla ayrqeadeat
181 larldlerki esleeeirfl rkiheeevre lqeqlarqqv hveldvakpd ltaalkeirt
241 qyeamassnm heaeewyrsk fadltdaaar naellrqakh eandyrrqlq sltcdleslr
301 gtneslerqm reqeerhvre aasyqealar leeegqslkd emarhlqeyq dllnvklald
361 ieiatyrkll egeenritip vqtfsnlqir etsldtksvs eghlkrnivv ktvemrdgev
421 ikeskqehkd vm
```

By "GFAP nucleic acid molecule" (or Glial fibrillary acidic protein) is meant a polynucleotide encoding an GFAP polypeptide. An exemplary GFAP nucleic acid molecule (e.g., mRNA) is provided at NCBI Accession No. NM_002055.

```
                                                      (SEQ ID NO: 46)
   1 atcgccagtc tagcccactc cttcataaag ccctcgcatc ccaggagcga gcagagccag

  61 agcaggatgg agaggagacg catcacctcc gctgctcgcc gctcctacgt ctcctcaggg

 121 gagatgatgg tgggggcct ggctcctggc cgccgtctgg gtcctggcac ccgcctctcc

 181 ctggctcgaa tgcccctcc actcccgacc cgggtggatt tctccctggc tggggcactc

 241 aatgctggct tcaaggagac ccgggccagt gagcgggcag agatgatgga gctcaatgac

 301 cgctttgcca gctacatcga gaaggttcgc ttcctggaac agcaaaacaa ggcgctggct

 361 gctgagctga accagctgcg ggccaaggag cccaccaagc tggcagacgt ctaccaggct

 421 gagctgcgag agctgcggct gcggctcgat caactcaccg ccaacagcgc ccggctggag

 481 gttgagaggg acaatctggc acaggacctg gccactgtga ggcagaagct ccaggatgaa

 541 accaacctga ggctggaagc cgagaacaac ctggctgcct atagacagga agcagatgaa

 601 gccaccctgg cccgtctgga tctggagagg aagattgagt cgctggagga ggagatccgg

 661 ttcttgagga agatccacga ggaggaggtt cgggaactcc aggagcagct ggcccgacag

 721 caggtccatg tggagcttga cgtggccaag ccagacctca ccgcagccct gaaagagatc

 781 cgcacgcagt atgaggcaat ggcgtccagc aacatgcatg aagccgaaga gtggtaccgc

 841 tccaagtttg cagacctgac agacgctgct gcccgcaacg cggagctgct ccgccaggcc

 901 aagcacgaag ccaacgacta ccggcgccag ttgcagtcct tgacctgcga cctggagtct

 961 ctgcgcggca cgaacgagtc cctggagagg cagatgcgcg agcaggagga gcggcacgtg

1021 cgggaggcgg ccagttatca ggaggcgctg gcgcggctgg aggaagaggg gcagagcctc

1081 aaggacgaga tggcccgcca cttgcaggag taccaggacc tgctcaatgt caagctggcc

1141 ctggacatcg agatcgccac ctacaggaag ctgctagagg gcgaggagaa ccggatcacc

1201 attcccgtgc agaccttctc caacctgcag attcgagaaa ccagcctgga caccaagtct

1261 gtgtcagaag gccacctcaa gaggaacatc gtggtgaaga ccgtggagat gcgggatgga

1321 gaggtcatta aggagtccaa gcaggagcac aaggatgtga tgtgaggcag gacccacctg

1381 gtggcctctg ccccgtctca tgaggggccc gagcagaagc aggatagttg ctccgcctct

1441 gctggcacat ttccccagac ctgagctccc caccacccca gctgctcccc tccctcctct

1501 gtccctaggt cagcttgctg ccctaggctc cgtcagtatc aggcctgcca gacggcaccc

1561 acccagcacc cagcaactcc aactaacaag aaactcaccc ccaaggggca gtctggaggg

1621 gcatggccag cagcttgcgt tagaatgagg aggaaggaga gaaggggagg agggcggggg

1681 gcacctacta catcgccctc cacatccctg attcctgttg ttatggaaac tgttgccaga

1741 gatggaggtt ctctcggagt atctgggaac tgtgcctttg agtttcctca ggctgctgga

1801 ggaaaactga gactcagaca ggaaagggaa ggccccacag acaaggtagc cctggccaga

1861 ggcttgtttt gtcttttggt ttttatgagg tgggatatcc ctatgctgcc taggctgacc

1921 ttgaactcct gggctcaagc agtctaccca cctcagcctc ctgtgtagct gggattatag

1981 attggagcca ccatgcccag ctcagagggt tgttctccta gactgaccct gatcagtcta

2041 agatgggtgg ggacgtcctg ccacctgggg cagtcacctg cccagatccc agaaggacct

2101 cctgagcgat gactcaagtg tctcagtcca cctgagctgc catccaggga tgccatctgt

2161 gggcacgctg tgggcaggtg ggagcttgat tctcagcact tgggggatct gttgtgtacg
```

-continued

```
2221 tggagaggga tgaggtgctg ggagggatag agggggggctg cctggccccc agctgtgggt
2281 acagagaggt caagcccagg aggactgccc cgtgcagact ggaggggacg ctggtagaga
2341 tggaggagga ggcaattggg atggcgctag gcatacaagt aggggttgtg ggtgaccagt
2401 tgcacttggc ctctggattg tgggaattaa ggaagtgact catcctcttg aagatgctga
2461 aacaggagag aaaggggatg tatccatggg ggcagggcat gactttgtcc catttctaaa
2521 ggcctcttcc ttgctgtgtc ataccaggcc gccccagcct ctgagcccct gggactgctg
2581 cttcttaacc ccagtaagcc actgccacac gtctgaccct ctccacccca tagtgaccgg
2641 ctgcttttcc ctaagccaag ggcctcttgc ggtccccttct tactcacaca caaaatgtac
2701 ccagtattct aggtagtgcc ctattttaca attgtaaaac tgaggcacga gcaaagtgaa
2761 gacactggct catattcctg cagcctggag gccgggtgct cagggctgac acgtccaccc
2821 cagtgcaccc actctgcttt gactgagcag actggtgagc agactggtgg gatctgtgcc
2881 cagagatggg actgggaggg cccacttcag ggttctcctc tcccctctaa ggccgaagaa
2941 gggtccttcc ctctccccaa gacttggtgt cctttccctc cactccttcc tgccacctgc
3001 tgctgctgct gctgctaatc ttcagggcac tgctgctgcc tttagtcgct gaggaaaaat
3061 aaagacaaat gctgcgccct tccccaaaaa aaaaaaa
```

By “s110b” (or S-100 protein beta chain; S-100 protein subunit beta; S100 calcium-binding protein B) is meant a polypeptide or fragment thereof having at least about 85% amino acid identity to NCBI Accession No. P04271.

```
                                                    (SEQ ID NO: 47)
 1 mselekamva lidvfhqysg regdkhklkk selkelinne lshfleeike qevvdkvmet
61 ldndgdgecd fqefmafvam vttacheffe he
```

By “s100b nucleic acid molecule” (or S-100 protein beta chain; S-100 protein subunit beta; S100 calcium-binding protein B) is meant a polynucleotide encoding an s100b polypeptide. An exemplary s100b nucleic acid molecule (e.g., mRNA) is provided at NCBI Accession No. NM_006272.

```
                                                    (SEQ ID NO: 48)
  1 gggcagaggg aataagaggc tgcctctgcc caccagtcct gccgcccagg acccgcagca
 61 gagacgacgc ctgcagcaag gagaccagga aggggtgaga caaggaagag gatgtctgag
121 ctggagaagg ccatggtggc cctcatcgac gttttccacc aatattctgg aagggaggga
181 gacaagcaca agctgaagaa atccgaactg aaggagctca tcaacaatga gctttcccat
241 ttcttagagg aaatcaaaga gcaggaggtt gtggacaaag tcatggaaac actggacaat
301 gatggagacg gcgaatgtga cttccaggaa ttcatggcct ttgttgccat ggttactact
361 gcctgccacg agttctttga acatgagtga gattagaaag cagccaaacc tttcctgtaa
421 cagagacggt catgcaagaa agcagacagc aagggcttgc agcctagtag gagctgagct
481 ttccagccgt gttgtagcta attaggaagc ttgatttgct ttgtgattga aaaattgaaa
541 acctctttcc aaaggctgtt ttaacggcct gcatcattct ttctgctata ttaggcctgt
601 gtgtaagctg actggcccca gggactcttg ttaacagtaa cttaggagtc aggtctcagt
661 gataaagcgt gcaccgtgca gcccgccatg gccgtgtaga ccctaacccg gagggaaccc
721 tgactacaga aattaccccg gggcaccctt aaaacttcca ctacctttaa aaaacaaagc
781 cttatccagc attatttgaa aacactgctg ttctttaaat gcgttcctca tccatgcaga
841 taacagctgg ttggccggtg tggccctgca agggcgtggt ggcttcggcc tgcttcccgg
```

-continued

```
901 gatgcgcctg atcaccaggt gaacgctcag cgctggcagc gctcctggaa aaagcaactc
961 catcagaact cgcaatccga gccagctctg gggctccag cgtggcctcc gtgacccatg
1021 cgattcaagt cgcggctgca ggatccttgc ctccaacgtg cctccagcac atgcggcttc
1081 cgagggcact accgggggct ctgagccacc gcgagggcct gcgttcaata aaaag
```

By “PAX6 polypeptide” (or paired box protein PAX6) is meant a polypeptide or fragment thereof having at least about 85% amino acid identity to NCBI Accession No. AAK95849.1.

(SEQ ID NO: 49)

```
MQNSHSGVNQLGGVFVNGRPLPDSTRQKIVELAHSGARPCDISRILQVSN
GCVSKILGRYYETGSIRPRAIGGSKPRVATPEVVSKIAQYKRECPSIFAW
EIRDRLLSEGVCTNDNIPSVSSINRVLRNLASEKQQMGADGMYDKLRMLN
GQTGSWGTRPGWYPGTSVPGQPTQDGCQQQEGGGENTNSISSNGEDSDEA
```

-continued

```
QMRLQLKRKLQRNRTSFTQEQIEALEKEFERTHYPDVFARERLAAKIDLP
EARIQVWFSNRRAKWRREEKLRNQRRQASNTPSHIPISSSFSTSVYQPIP
QPTTPVSSFTSGSMLGRTDTALTNTYSALPPMPSFTMANNLPMQPPVPSQ
TSSYSCMLPTSPSVNGRSYDTYTPPHMQTHMNSQPMGTSGTTSTGLISPG
VSVPVQVPGSEPDMSQYWPRLQ
```

By “PAX6 polynucleotide” (or paired box protein PAX6) is meant a polynucleotide encoding an PAX6 polypeptide. An exemplary PAX6 nucleic acid molecule (e.g., mRNA) is provided at NCBI Accession No. AY047583.

(SEQ ID NO: 50)

```
1 aggggaaga ctttaactag gggcgcgcag atgtgtgagg ccttttattg tgagagtgga
61 cagacatccg agatttcaga gccccatatt cgagccccgt ggaatcccgc ggcccccagc
121 cagagccagc atgcagaaca gtcacagcgg agtgaatcag ctcggtggtg tctttgtcaa
181 cgggcggcca ctgccggact ccacccggca gaagattgta gagctagctc acagcggggc
241 ccggccgtgc gacatttccc gaattctgca ggtgtccaac ggatgtgtga gtaaaattct
301 gggcaggtat tacgagactg gctccatcag acccagggca atcggtggta gtaaaccgag
361 agtagcgact ccagaagttg taagcaaaat agcccagtat aagcgggagt gcccgtccat
421 ctttgcttgg gaaatccgag acagattact gtccgagggg gtctgtacca acgataacat
481 accaagcgtg tcatcaataa acagagttct tcgcaacctg gctagcgaaa agcaacagat
541 gggcgcagac ggcatgtatg ataaactaag gatgttgaac gggcagaccg gaagctgggg
601 cacccgccct ggttggtatc cggggacttc ggtgccaggg caacctacgc aagatggctg
661 ccagcaacag gaaggagggg gagagaatac caactccatc agttccaacg gagaagattc
721 agatgaggct caaatgcgac ttcagctgaa gcggaagctg caaagaaata gaacatcctt
781 tacccaagag caaattgagg ccctggagaa agagtttgag agaacccatt atccagatgt
841 gtttgcccga gaaagactag cagccaaaat agatctacct gaagcaagaa tacaggtatg
901 gttttctaat cgaagggcca aatggagaag agaagaaaaa ctgaggaatc agagaagaca
961 ggccagcaac acacctagtc atattcctat cagcagtagt ttcagcacca gtgtctacca
1021 accaattcca caacccacca caccggtttc ctccttcaca tctggctcca tgttgggccg
1081 aacagacaca gccctcacaa acacctacag cgctctgccg cctatgccca gcttcaccat
1141 ggcaaataac ctgcctatgc aacccccagt ccccagccag acctcctcat actcctgcat
1201 gctgcccacc agcccttcgg tgaatgggcg gagttatgat acctacaccc ccccacatat
1261 gcagacacac atgaacagtc agccaatggg cacctcgggc accacttcaa caggactcat
1321 ttcccctggt gtgtcagttc cagttcaagt tcccggaagt gaacctgata tgtctcaata
1381 ctggccaaga ttacagtaa
```

By "Nestin polypeptide" is meant a polypeptide or fragment thereof having at least about 85% amino acid identity to NCBI Accession No. NP_006608.1.

(SEQ ID NO: 51)
MEGCMGEESFQMWELNRRLEAYLARVKALEEQNELLSAELGGLRAQSADT
SWRAHADDELAALRALVDQRWREKHAAEVARDNLAEELEGVAGRCQQLRL
ARERTTEEVARNRRAVEAEKCARAWLSSQVAELERELEALRVAHEEERVG
LNAQAACAPRCPAPPRGPPAPAPEVEELARRLGEAWRGAVRGYQERVAHM
ETSLGQARERLGRAVQGAREGRLELQQLQAERGGLLERRAALEQRLEGRW
QERLRATEKFQLAVEALEQEKQGLQSQIAQVLEGRQQLAHLKMSLSLEVA
TYRTLLEAENSRLQTPGGGSKTSLSFQDPKLELQFPRTPEGRRLGSLLPV
LSPTSLPSPLPATLETPVPAFLKNQEFLQARTPTLASTPIPPTPQAPSPA
VDAEIRAQDAPLSLLQTQGGRKQAPEPLRAEARVAIPASVLPGPEEPGGQ
RQEASTGQSPEDHASLAPPLSPDHSSLEAKDGESGGSRVFSICRGEGEGQ
IWGLVEKETAIEGKVVSSLQQEIWEEEDLNRKEIQDSQVPLEKETLKSLG
EEIQESLKTLENQSHETLERENQECPRSLEEDLETLKSLEKENKELLKDV
EVVRPLEKEAVGQLKPTGKEDTQTLQSLQKENQELMKSLEGNLETFLFPG
TENQELVSSLQENLESLTALEKENQEPLRSPEVGDEEALRPLTKENQEPL
RSLEDENKEAFRSLEKENQEPLKTLEEEDQSIVRPLETENHKSLRSLEEQ
DQETLRTLEKETQQRRRSLGEQDQMTLRPPEKVDLEPLKSLDQEIARPLE

-continued

NENQEFLKSLKEESVEAVKSLETEILESLKSAGQENLETLKSPETQAPLW
TPEEINQGAMNPLEKEIQEPLESVEVNQETFRLLEEENQESLRSLGAWNL
ENLRSPEEVDKESQRNLEEEENLGKGEYQESLRSLEEEGQELPQSADVQR
WEDTVEKDQELAQESPPGMAGVENEDEAELNLREQDGFTGKEEVVEQGEL
NATEEVWIPGEGHPESPEPKEQRGLVEGASVKGGAEGLQDPEGQSQQVGA
PGLQAPQGLPEAIEPLVEDDVAPGGDQASPEVMLGSEPAMGESAAGAEPG
PGQGVGGLGDPGHLTREEVMEPPLEEESLEAKRVQGLEGPRKDLEEAGGL
GTEFSELPGKSRDPWEPPREGREESEAEAPRGAEEAFPAETLGHTGSDAP
SPWPLGSEEAEEDVPPVLVSPSPTYTPILEDAPGPQPQAEGSQEASWGVQ
GRAEALGKVESEQEELGSGEIPEGPQEEGEESREESEEDELGETLPDSTP
LGFYLRSPTSPRWDPTGEQRPPPQGETGKEGWDPAVLASEGLEAPPSEKE
EGEEGEEECGRDSDLSEEFEDLGTEAPFLPGVPGEVAEPLGQVPQLLLDP
AAWDRDGESDGFADEEESGEEGEEDQEEGREPGAGRWGPGSSVGSLQALS
SSQRGEFLESDSVSVSVPWDDSLRGAVAGAPKTALETESQDSAEPSGSEE
ESDPVSLEREDKVPGPLEIPSGMEDAGPGADIIGVNGQGPNLEGKSQHVN
GGVMNGLEQSEEVGQGMPLVSEGDRGSPFQEEEGSALKTSWAGAPVHLGQ
GQFLKFTQREGDRESWSSGED

By "Nestin polynucleotide" is meant a polynucleotide encoding an Nestin polypeptide. An exemplary Nestin nucleic acid molecule (e.g., mRNA) is provided at NCBI Accession No. NM_006617.

(SEQ ID NO: 52)
1 gctactccca ccccgccccg ccccgtcatt gtccccgtcg gtctcttttc tcttccgtcc
61 taaaagctct gcgagccgct cccttctccc ggtgccccgc gtctgtccat cctcagtggg
121 tcagacgagc aggatggagg gctgcatggg ggaggagtcg tttcagatgt gggagctcaa
181 tcggcgcctg gaggcctacc tggcccgggt caaggcgctg gaggagcaga atgagctgct
241 cagcgcggag ctcggggggc tccgggcaca atccgcggac acctcctggc gggcgcatgc
301 cgacgacgag ctggcggccc tgcgggccct cgttgaccaa cgctggcggg agaagcacgc
361 ggccgaggtg gcgcgcgaca acctggctga agagctggag ggcgtggcag gccgatgcca
421 gcagctgcgg ctggcccggg agcggacgac ggaggaggta gcccgcaacc ggcgcgccgt
481 cgaggcagag aaatgcgccc gggcctggct gagtagccag gtggcagagc tggagcgcga
541 gctagaggct ctacgcgtgg cgcacgagga ggagcgcgtc ggcctgaacg cgcaggctgc
601 ctgtgccccc cgctgccccg cgccgccccg cgggcctccc gcgccggccc cggaggtaga
661 ggagctggca aggcgactgg gcgaggcgtg gcgcggggca gtgcgcggct accaggagcg
721 cgtggcacac atggagacgt cgctgggcca ggcccgcgag cggctgggcc gggcggtgca
781 gggtgcccgc gagggccgcc tggagctgca gcagctccag gctgagcgcg gaggcctcct
841 ggagcgcagg gcagcgttgg aacagaggtt ggagggccgc tggcaggagc ggctgcgggc
901 tactgaaaag ttccagctgg ctgtggaggc cctggagcag gagaaacagg gcctacagag
961 ccagatcgct caggtcctgg aaggtcggca gcagctggcg cacctcaaga tgtccctcag
1021 cctggaggtg gccacgtaca ggaccctcct ggaggctgag aactcccggc tgcaaacacc
1081 tggcggtggc tccaagactt ccctcagctt tcaggacccc aagctggagc tgcaattccc
1141 taggacccca gagggccggc gtcttggatc tttgctccca gtcctgagcc caacttccct -continued 1201 cccctcaccc ttgcctgcta cccttgagac acctgtgcca gcctttctta agaaccaaga 1261 attcctccag gcccgtaccc ctaccttggc cagcaccccc atccccccca cacctcaggc 1321 accctctcct gctgtagatg cagagatcag agcccaggat gctcctctct ctctgctcca 1381 gacacagggt gggaggaaac aggctccaga gcccctgcgg gctgaagcca gggtggccat 1441 tcctgccagc gtcctgcctg gaccagagga gcctgggggc cagcggcaag aggccagtac 1501 aggccagtcc ccagaggacc atgcctcctt ggcaccaccc ctcagccctg accactccag 1561 tttagaggct aaggatggag aatccggtgg gtctagagtg ttcagcatat gccgagggga

1621 aggtgaaggg caaatctggg ggttggtaga gaaagaaaca gccatagagg gcaaagtggt 1681 aagcagcttg cagcaggaaa tatgggaaga agaggatcta aacaggaagg aaatccagga 1741 ctcccaggtt cctttggaaa aagaaaccct gaagtctctg ggagaggaga ttcaagagtc 1801 actgaagact ctggaaaacc agagccatga gacactagaa agggagaatc aagaatgtcc 1861 gaggtcttta gaagaagact tagaaacact aaaaagtcta gaaaaggaaa ataaagagct 1921 attaaaggat gtggaggtag tgagacctct agaaaaagag gctgtaggcc aacttaagcc 1981 tacaggaaaa gaggacacac agacattgca atccctgcaa aaggagaatc aagaactaat 2041 gaaatctctt gaaggtaatc tagagacatt tttatttcca ggaacggaaa atcaagaatt 2101 agtaagttct ctgcaagaga acttagagtc attgacagct ctggaaaagg agaatcaaga 2161 gccactgaga tctccagaag taggggatga ggaggcactg agacctctga caaaggagaa 2221 tcaggaaccc ctgaggtctc ttgaagatga gaacaaagag gcctttagat ctctagaaaa 2281 agagaaccag gagccactga agactctaga agaagaggac cagagtattg tgagacctct 2341 agaaacagag aatcacaaat cactgaggtc tttagaagaa caggaccaag agacattgag 2401 aactcttgaa aaagagactc aacagcgacg gaggtctcta ggggaacagg atcagatgac 2461 attaagaccc ccagaaaaag tggatctaga accactgaag tctcttgacc aggagatagc 2521 tagacctctt gaaaatgaga atcaagagtt cttaaagtca ctcaaagaag agagcgtaga 2581 ggcagtaaaa tctttagaaa cagagatcct agaatcactg aagtctgcgg gacaagagaa 2641 cctggaaaca ctgaaatctc cagaaactca agcaccactg tggactccag aagaaataaa 2701 tcaggggggca atgaatcctc tagaaaagga aattcaagaa ccactggagt ctgtggaagt 2761 gaaccaagag acattcagac tcctggaaga ggagaatcag gaatcattga gatctctggg 2821 agcatggaac ctggagaatt tgagatctcc agaggaggta gacaaggaaa gtcaaaggaa 2881 tctggaagag gaagagaacc tgggaaaggg agagtaccaa gagtcactga ggtctctgga 2941 ggaggaggga caggagctgc cgcagtctgc agatgtgcag aggtgggaag atacggtgga 3001 gaaggaccaa gaactggctc aggaaagccc tcctgggatg gctggagtgg aaaatgagga 3061 tgaggcagag ctgaatctga gggagcagga tggcttcact gggaaggagg aggtggtaga 3121 gcagggagag ctgaatgcca cagaggaggt ctggatccca ggcgaggggc acccagagag 3181 ccctgagccc aaagagcaga gaggcctggt tgagggagcc agtgtgaagg gaggggctga 3241 gggcctccag gaccctgaag ggcaatcaca acaggtgggg gccccaggcc tccaggctcc 3301 ccaggggctg ccagaggcga tagagcccct ggtggaagat gatgtggccc cagggggtga 3361 ccaagcctcc ccagaggtca tgttggggtc agagcctgcc atgggtgagt ctgctgcggg 3421 agctgagcca ggcccggggc agggggtggg agggctgggg gacccaggcc atctgaccag 3481 ggaagaggtg atggaaccac ccctggaaga ggagagtttg gaggcaaaga gggttcaggg 3541 cttggaaggg cctagaaagg acctagagga ggcaggtggt ctggggacag agttctccga 3601 gctgcctggg aagagcagag acccttggga gcctcccagg gagggtaggg aggagtcaga -continued

```
3661 ggctgaggcc cccaggggag cagaggaggc gttccctgct gagaccctgg gccacactgg
3721 aagtgatgcc ccttcacctt ggcctctggg gtcagaggaa gctgaggagg atgtaccacc
3781 agtgctggtc tcccccagcc caacgtacac cccgatcctg gaagatgccc ctgggcctca
3841 gcctcaggct gaagggagtc aggaggctag ctggggggtg caggggaggg ctgaagccct
3901 ggggaaagta gagagcgagc aggaggagtt gggttctggg gagatccccg agggccccca
3961 ggaggaaggg gaggagagca gagaagagag cgaggaggat gagctcgggg agacccttcc
4021 agactccact cccctgggct tctacctcag gtcccccacc tcccccaggt gggaccccac
4081 tggagagcag aggccacccc ctcaagggga gactggaaag gagggctggg atcctgctgt
4141 cctggcttcc gagggccttg aggccccacc ctcagaaaag gaggaggggg aggagggaga
4201 agaggagtgt ggccgtgact ctgacctgtc agaagaattt gaggacctgg ggactgaggc
4261 accttttctt cctggggtcc ctggggaggt ggcagaacct ctgggccagg tgccccagct
4321 gctactggat cctgcagcct gggatcgaga tggggagtcc gatgggtttg cagatgagga
4381 agaaagtggg gaggagggag aggaggatca ggaggagggg agggagccag ggctgggcg
4441 gtgggggcca gggtcttctg ttggcagcct ccaggccctg agtagctccc agagagggga
4501 attcctggag tctgattctg tgagtgtcag tgtcccctgg gatgacagct tgaggggtgc
4561 agtggctggt gcccccaaga ctgccctgga aacggagtcc caggacagtg ctgagccttc
4621 tggctcagag gaagagtctg accctgtttc cttggagagg gaggacaaag tccctggccc
4681 tctagagatc cccagtggga tggaggatgc aggcccaggg gcagacatca ttggtgttaa
4741 tggccagggt cccaacttgg aggggaagtc acagcatgtg aatgggggag tgatgaacgg
4801 gctggagcag tctgaggaag tggggcaagg aatgccgcta gtctctgagg gagaccgagg
4861 gagcccccttt caggaggagg aggggagtgc tctgaagacc tcttgggcag gggctcctgt
4921 tcacctgggc cagggtcagt tcctgaagtt cactcagagg gaaggagata gagagtcctg
4981 gtcctcaggg gaggactagg aaaagaccat ctgcccggca ctggggactt aggggtgcgg
5041 ggaggggaag gacgcctcca agcccgctcc ctgctcagga gcagcactct taacttacga
5101 tctcttgaca tatggtttct ggctgagagg cctggcccgc taaggtgaaa aggggtgtgg
5161 caaaggagcc tactccaaga atggaggctg taggaatata acctccccacc ctgcaaaggg
5221 aatctcttgc ctgctccatc tcataggcta agtcagctga atcccgatag tactaggtcc
5281 ccttccctcc gcatcccgtc agctggaaaa ggcctgtggc ccagaggctt ctccaaaggg
5341 agggtgacat gctggctttt gtgcccaagc tcaccagccc tgcgccacct cactgcagta
5401 gtgcaccatc tcactgcagt agcacgccct cctgggccgt ctggcctgtg gctaatggag
5461 gtgacggcac tcccatgtgc tgactccccc catccctgcc acgctgtggc cctgcctggc
5521 tagtccctgc ctgaataaag taatgcctcc gcttcaaaaa aaaaaaaaaa aaaaaaaaaa
5581 aaaaaaaaaa a
```

By “LHX6 polypeptide” (or LIM homeobox 6) is meant a polypeptide or fragment thereof having at least about 85% amino acid identity to NCBI Accession No. AAI03937.1.

(SEQ ID NO: 53)

```
MAQPGSGCKATTRCLEGTAPPAMAQSDAEALAGALDKDEGQASPCTPSTPS
VCSPPSAASSVPSAGKNICSSCGLEILDRYLLKVNNLIWHVRCLECSVCRT
SLRQQNSCYIKNKEIFCKMDYFSRFGTKCARCGRQIYASDWVRRARGNAYH
```

-continued

```
LACFACFSCKRQLSTGEEFGLVEEKVLCRIHYDTMIENLKRAAENGNGLTL
EGAVPSEQDSQPKPAKRARTSFTAEQLQVMQAQFAQDNNPDAQTLQKLADM
TGLSRRVIQVWFQNCRARHKKHTPQHPVPPSGAPPSRLPSALSDDIHYTPF
SSPERARMVTLHGYIESHPFSVLTLPALPHLPVGAPQLPLSR
```

By “LHX6 polynucleotide” (or LIM homeobox 6) is meant a polynucleotide encoding an LHX6 polypeptide. An exemplary LHX6 nucleic acid molecule (e.g., mRNA) is provided at NCBI Accession No. BC103936.

(SEQ ID NO: 54)

```
   1 cccgccaccg accaggtgat ggcccagcca gggtccggct gcaaagcgac cacccgctgt
  61 cttgaaggga ccgcgccgcc cgccatggct cagtctgacg ccgaggccct ggcaggagct
 121 ctggacaagg acgagggtca ggcctcccca tgtacgccca gcacgccatc tgtctgctca
 181 ccgccctctg ccgcctcctc cgtgccgtct gcaggcaaga acatctgctc cagctgcggc
 241 ctcgagatcc tggaccgata tctgctcaag gtcaacaacc tcatctggca cgtgcggtgc
 301 ctcgagtgct ccgtgtgtcg cacgtcgctg aggcagcaga acagctgcta catcaagaac
 361 aaggagatct tctgcaagat ggactacttc agccgattcg ggaccaagtg tgcccggtgc
 421 ggccgacaga tctacgccag cgactgggtg cggagagctc gcggcaacgc ctaccacctg
 481 gcctgcttcg cctgcttctc gtgcaagcgc cagctgtcca ctggtgagga gttcggcctg
 541 gtcgaggaga aggtgctctg ccgcatccac tacgacacca tgattgagaa cctcaagagg
 601 gccgccgaga acgggaacgg cctcacgttg gagggggcag tgccctcgga acaggacagt
 661 caacccaagc cggccaagcg cgcgcggacg tccttcaccg cggaacagct gcaggttatg
 721 caggcgcagt tcgcgcagga caacaacccc gacgctcaga cgctgcagaa gctggcggac
 781 atgacgggcc tcagccggag agtcatccag gtgtggtttc aaaactgccg ggcgcgtcat
 841 aaaaagcaca cgccgcaaca cccagtgccg ccctcggggg cgcccccgtc ccgccttccc
 901 tccgccctgt ccgacgacat ccactacacc ccgttcagca gccccgagcg ggcgcgcatg
 961 gtcaccctgc acggctacat tgagagtcat cctttttcag tactaacgct gccggcactt
1021 ccgcatctgc ccgtgggcgc cccacagctg cccctcagcc gctgagatcc agtgtccaag
1081 ctgcggccag gagtccaccc acctccgcat ccacccccgt ccgccatcct gcccaccacc
1141 aggtcggttc ccgaggcctg gcctttccct ctcctgctga gaaccagaac ccaccaggag
1201 caccacagag tcctcctctt ggaaggcaga actccctgaa atctggaatc agggtggaaa
1261 cagcctgttt ttcccattta aacaggagtc ctcttcaact tcagctgatt acaataacaa
1321 aaggcggaat tgaattgtgc gatgccaacg gccttctcat ttacaggttt ttttccccca
1381 cattggcctt tatttactac ttccttggaa ccatctctga attctgaata gctgacaacc
1441 cccaatgtta tccactctgt tgcttttgtc tggaaaactc tacagtgttt gtgggatgtc
1501 cccaaaggta agctatgttc taattttatc atttccatct gtctggttat gtcaagttaa
1561 ttcagaaaga gaagagacag tgaccaaccc tgagaggcct aatagggcag agatggaggc
1621 ctgcccagac taggaggcag cggggataga cagggaatgg ggagaagaaa gacccccatt
1681 ggtttggaaa tcaaggagag ggcggtgaca tattggacca gaagaggcac tagccatttt
1741 aaggagagga aagagaaaac tctggggtca gggagagacc ctacccccac ctaattatcc
1801 agcatatatg taagaaacat agcagcgatg gtattcgatc tgtgccatga ctcttctgaa
1861 tgtttggaca ggttagagtt ggggacccct gttggccact tgttgacctc tcatagtggt
1921 gcttgggcca ggtcttctca atggaagggg aatcccttat aggggagagg gaacagagcc
1981 cagtgaaatg gcagtcagaa tgttaaccct ggatccatct ctaagtagag agagggtgcc
2041 cattgcctag gtgagtgtgc caagctcagg attccaactg gtgcctctga gcttcccaat
2101 caatacttcc tggagccagc cccacccacc cctgagaaca gaggtcagac acagctgcgt
2161 aacatccatc ctgctacaac tcttccaccc caaacaaaag ggctcaggct acacacgacc
2221 atgatttatg ttttcagggg atgcccattt gtcccaagct tatcctgtaa ttctagaatt
2281 acctggtgtc ctgatgcatt ttccactaga ggttgctaat cagcatgttt tagcccaagt
2341 ccaccttcct gctgtggtta acctgttatg ttgcttttgg aaggagactc taagacaggg
```

-continued

```
2401 aaagcaagtt catggtacat acgcagccat tgtctctgtt tttacccatg gcagacattg

2461 ctaatcaatg gcagctctat ttcactgagt ctggataagg tttcagagtt caaatgcttg

2521 acgttggcac ttaacatgaa agcctatagg tcattcttgc tctgggatct acaggcaggg

2581 taggcacagg tgcagcctaa gaagggaacc tgcttcctct cccttccaaa gacagtgaca

2641 gctgactgag ggcaaagagc aggcaccact cagaacgtgg tgagtacagc tcagctcagc

2701 actcagtcag tggtaacttg tgcccagccc tgtgctaggc gctgacatta acaggagcaa

2761 ccagggccca attcctggcc ttggagctca aatctttcct ttgatttttg ctcctgatca

2821 tcaaggcccc agtgg
```

By "LHX8 polypeptide" (or LIM homeobox 8) is meant a polypeptide or fragment thereof having at least about 85% amino acid identity to NCBI Accession No. AAH40321.1.

(SEQ ID NO: 55)

```
MQILSRCQGLMSEECGRTTALAAGRTRKGAGEEGLVSPEGAGDEDSCSSS

APLSPSSSPRSMASGSGCPPGKCVCNSCGLEIVDKYLLKVNDLCWHVRCL

SCSVCRTSLGRHTSCYIKDKDIFCKLDYFRRYGTRCSRCGRHIHSTDWVR

RAKGNVYHLACFACFSCKRQLSTGEEFALVEEKVLCRVHYDCMLDNLKRE
```

-continued

```
VENGNGISVEGALLTEQDVNHPKPAKRARTSFTADQLQVMQAQFAQDNNP

DAQTLQKLAERTGLSRRVIQVWFQNCRARHKKHVSPNHSSSTPVTAAPPS

RLSPPMLEEMAYSAYVPQDGTMLTALHSYMDAHSPTTLGLQPLLPHSMTQ

LPISHT
```

By "LHX8 polynucleotide" (or LIM homeobox 8) is meant a polynucleotide encoding an LHX8 polypeptide. An exemplary LHX8 nucleic acid molecule (e.g., mRNA) is provided at NCBI Accession No. BC040321.

(SEQ ID NO: 56)

```
   1 agcggcaaga ggctagcggc tggaccactt gtgctggagt ggtaaagaac tatcatgaat

  61 ccatttactg aaagtgtcca tttctgaact caccctaaag aggacaaaca ccgcaaagta

 121 gttaaaagtc aggcattcgc gtcggacgtc tgggtttgaa ttctgccctg gcttgactgg

 181 aaacgcttcc cctatttctt ccgtagcgga ccgggagagc ttactggcgc tctgcgaacc

 241 ggctggaaag aaacaccgag tcactcgtac agactcttgg tcgcagaact tggctttccg

 301 ctattggtcc tccagaaccg cttgaaacaa ctggccccag ctggcgcatc agaccgcagt

 361 gaggaatgcc gcggggcggg tggcgaaggc agggtctgcc cgccagtgga ttcccgggtg

 421 tcccgcgtgg agcaggcttg cccagctggg aagcccatca aacctcagtc ttggcccaca

 481 gtgggagaga gaccagtggg tcccagacgg aggccatcgc ccgcttttgg cgacctccac

 541 tggcgtgaat aaaagcaccc ctctcttacc ctcagaaact gtgggtagca aggtataaaa

 601 cggagtctgg gaccggtaag tcccaaggtg agcccgtata cagctctgcc atctctgagg

 661 ggttatgcag attctgagca ggtgtcaggg gctcatgtca gaggagtgcg ggcggactac

 721 agccctggcg gccgggagga ctcgcaaagg cgccggggaa gagggactgg tgagccccga

 781 gggagcgggg gacgaggact cgtgctcctc ctcggccccg ctgtccccgt cgtcctcgcc

 841 ccggtccatg gcctcgggct ccggctgccc tcctggcaag tgtgtgtgca acagttgcgg

 901 cctggagatc gtggacaaat accttctcaa ggtgaatgac ctatgctggc atgtccggtg

 961 tctctcctgc agtgtttgca gaacctccct aggaaggcac accagctgtt atattaaaga

1021 caaagacatt ttctgcaaac ttgattattt cagaaggtat ggaactcgct gctctcgatg

1081 tgggagacac atccattcta ctgactgggt ccggagagcc aaggggaatg tctatcactt

1141 ggcatgcttt gcctgctttt cctgcaaaag gcaactttcc acaggagagg agtttgcttt

1201 ggtggaagag aaagtcctct gcagagtaca ttatgactgc atgctggata atttaaaaag

1261 agaagtagaa aatgggaatg ggattagtgt ggaaggtgcc ctcctcacag agcaagatgt

1321 taaccatcca aaaccagcaa aaagagctcg gaccagcttt acagcagatc agcttcaggt
```

-continued

```
1381 tatgcaagca caatttgctc aggacaacaa cccagatgca cagacactcc agaaattggc
1441 agaaaggaca ggcttgagca gacgtgtgat acaggtgtgg tttcagaatt gtagagcacg
1501 ccacaagaaa cacgtcagtc ctaatcactc atcctccacc ccagtcacag cagccccacc
1561 ctccaggctg tctccaccca tgttagaaga aatggcttat tctgcctacg tgccccaaga
1621 tggaacgatg ttaactgcgc tgcatagtta tatggatgct cattcaccaa caactcttgg
1681 actccagccc ttgttacccc attcaatgac acaactgcca ataagtcata cctaattctt
1741 ttttcaggga tagacttgat taaggatata aatttgtcat ttattatgta taaaatacca
1801 ttgaaaagat attactgtta atttttatt taacacctaa agcatttcca acatcacttt
1861 gctgcccagg tatgtatcta tagttggcct gcaagacact tttattaatt cttcattttt
1921 tgtaaaactt atgtttacaa gaagaaaaca aatcaaaaca tttttgtat tgtctggaaa
1981 tagttcactc tagtgtgtat ctgttaattt atttgtcatc aaaagagcac tttgcctaaa
2041 agaaaggact gacaagtgtg caaaatgttt acaatctttt gtgaaattgt agtttatcat
2101 tagtttgtat ctgtaagtta ttgtaataaa tattacctgt atttttgtt atatacaact
2161 ttatactttg aagcttgtat ctgtgaattt gcaactgaaa tttattttgc caatgttttc
2221 tgaatgaact gaataaagct tctgttgtag catgccatgc aaacacatta ttgtgtttgt
2281 ggttgatgaa ttatggctgt aaataacact atagtttaat aagcccacca ttctgagttt
2341 attaaacatt ttccattctt gtgaaaattt caaaaaaaaa aaaaaaaaaa aaagaaaaaa
2401 aaaaaaaaaa a
```

By “TBR1 polypeptide” (or T-box, brain 1 (TBR1)) is meant a polypeptide or fragment thereof having at least about 85% amino acid identity to NCBI Accession No. NP_006584.1.

(SEQ ID NO: 57)

```
MQLEHCLSPSIMLSKKFLNVSSSYPHSGGSELVLHDHPIISTTDNLERSS
PLKKITRGMTNQSDTDNFPDSKDSPGDVQRSKLSPVLDGVSELRHSFDGS
AADRYLLSQSSQPQSAATAPSAMFPYPGQHGPAHPAFSIGSPSRYMAHHP
VITNGAYNSLLSNSSPQGYPTAGYPYPQQYGHSYQGAPFYQFSSTQPGLV
PGKAQVYLCNRPLWLKFHRHQTEMIITKQGRRMFPFLSFNISGLDPTAHY
NIFVDVILADPNHWRFQGGKWVPCGKADTNVQGNRVYMHPDSPNTGAHWM
```

-continued

```
RQEISFGKLKLTNNKGASNNNGQMVVLQSLHKYQPRLHVVEVNEDGTEDT
SQPGRVQTFTFPETQFIAVTAYQNTDITQLKIDHNPFAKGFRDNYDTIYT
GCDMDRLTPSPNDSPRSQIVPGARYAMAGSFLQDQFVSNYAKARFHPGAG
AGPGPGTDRSVPHTNGLLSPQQAEDPGAPSPQRWFVTPANNRLDFAASAY
DTATDFAGNAATLLSYAAAGVKALPLQAAGCTGRPLGYYADPSGWGARSP
PQYCGTKSGSVLPCWPNSAAAAARMAGANPYLGEEAEGLAAERSPLPPGA
AEDAKPKDLSDSSWIETPSSIKSIDSSDSGIYEQAKRRRISPADTPVSES
SSPLKSEVLAQRDCEKNCAKDISGYYGFYSHS
```

By “TBR1 polynucleotide” (or T-box, brain 1 (TBR1)) is meant a polynucleotide encoding an TBR1 polypeptide. An exemplary TBR1 nucleic acid molecule (e.g., mRNA) is provided at NCBI Accession No. NM_006593.

(SEQ ID NO: 58)

```
  1 gtcgctacca ggagccaggt gattatccta attaatgtct atctaattaa attactgtca
 61 gcagctaacc aatggcagga gccgtttcat cggctgcaca agcagcaaga tcaaaagtga
121 gccttttctg attgctgcat agtgtcaatt ggccaatctc ttctcccagg gaaaaaaaaa
181 agtaaatcaa acctttgaga agcatttgct ggttgaagtg ctttctgtct agtgaggggg
241 tctgtggatt tctagtttat gataaatagg actttaaaaa ccagggacgg gagggcgagt
301 gttcaggttc tagagctatg cagctggagc actgcctttc tccttctatc atgctctcca
361 agaaatttct caatgtgagc agcagctacc cacattcagg cggatccgag cttgtcttgc
421 acgatcatcc cattatctcg accactgaca acctggagag aagttcacct ttgaaaaaaa
481 ttaccagggg gatgacgaat cagtcagata cagacaattt tcctgactcc aaggactcac
541 caggggacgt ccagagaagt aaactctctc ctgtcttgga cggggtctct gagcttcgtc
```

-continued 601 acagtttcga tggctctgct gcagatcgct acctcctctc tcagtccagc cagccacagt 661 ctgcggccac tgctcccagt gccatgttcc cgtaccccgg ccagcacgga ccggcgcacc 721 ccgccttctc catcggcagc cctagccgct acatggccca ccacccggtc atcaccaacg 781 gagcctacaa cagcctcctg tccaactcct cgccgcaggg ataccccacg gccggctacc 841 cctacccaca gcagtacggc cactcctacc aaggagctcc gttctaccag ttctcctcca 901 cccagccggg gctggtgccc ggcaaagcac aggtgtacct gtgcaacagg cccctttggc 961 tgaaatttca ccggcaccaa acggagatga tcatcaccaa acagggaagg cgcatgtttc 1021 ctttttttaag ttttaacatt tctggtctcg atcccacggc tcattacaat atttttgtgg 1081 atgtgatttt ggcggatccc aatcactgga ggtttcaagg aggcaaatgg gttccttgcg 1141 gcaaagcgga caccaatgtg caaggaaatc gggtctatat gcatccggat tcccccaaca 1201 ctggggctca ctggatgcgc caagaaatct cttttggaaa attaaaactt acgaacaaca 1261 aaggagcttc aaataacaat gggcagatgg tggttttaca gtccttgcac aagtaccagc 1321 cccgcctgca tgtggtggaa gtgaacgagg acggcacgga ggacactagc cagcccggcc 1381 gcgtgcagac gttcactttc cctgagactc agttcatcgc cgtcaccgcc taccagaaca 1441 cggatattac acaactgaaa atagatcaca acccttttgc aaaaggattt cgggataatt 1501 atgacacgat ctacaccggc tgtgacatgg accgcctgac cccctcgccc aacgactcgc 1561 cgcgctcgca gatcgtgccc ggggcccgct acgccatggc cggctctttc ctgcaggacc 1621 agttcgtgag caactacgcc aaggcccgct tccacccggg cgcgggcgcg ggccccgggc 1681 cgggtacgga ccgcagcgtg ccgcacacca acgggctgct gtcgccgcag caggccgagg 1741 acccgggcgc gccctcgccg caacgctggt ttgtgacgcc ggccaacaac cggctggact 1801 tcgcggcctc ggcctatgac acggccacgg acttcgcggg caacgcggcc acgctgctct 1861 cttacgcggc ggcgggcgtg aaggcgctgc cgctgcaggc tgcaggctgc actggccgcc 1921 cgctcggcta ctacgccgac ccgtcgggct ggggcgcccg cagtcccccg cagtactgcg 1981 gcaccaagtc gggctcggtg ctgccctgct ggcccaacag cgccgcggcc gccgcgcgca 2041 tggccggcgc caatccctac ctgggcgagg aggccgaggg cctggccgcc gagcgctcgc 2101 cgctgccgcc cggcgccgcc gaggacgcca agcccaagga cctgtccgat tccagctgga 2161 tcgagacgcc ctcctcgatc aagtccatcg actccagcga ctcggggatt tacgagcagg 2221 ccaagcggag gcggatctcg ccggccgaca cgcccgtgtc cgagagttcg tccccgctca 2281 agagcgaggt gctggcccag cgggactgcg agaagaactg cgccaaggac attagcggct 2341 actatggctt ctactcgcac agctaggccg cccctgcccg cccggccccg ccgcggcccg 2401 gacccccagc cagcccctca cagctcttcc ccagctccgc ctccccacac tcctccttgc 2461 gcacccactc attttatttg accctcgatg gccgtctgca gcgaataagt gcaggtctcc 2521 gagcgtgatt ttaacctttt ttgcacagca gtctctgcaa ttagctcacc gaccttcaac 2581 tttgctgtaa acctttttggt tttcctactt actcttcttc tgtggagtta tcctcctaca 2641 attcccctcc ccctcgtctt tctcttacct cctacttctc tttcttgtaa tgaaactctt 2701 cacctttagg agacctgggc agtcctgtca ggcagcagcg attccgaccc gccaagtctc 2761 ggcctccaca ttaaccatag gatgttgact ctagaacctg gacccaccca gcgcgtcctt 2821 tcttatcccc gagtggatgg atggatggat ggatggtagg gatgttaata attttagtgg 2881 aacaaagcct gtgaaatgat tgtacatagt gttaatttat tgtaacgaat ggctagtttt 2941 tattctcgtc aaggcacaaa accagttcat gcttaacctt tttttccttt cctttctttg 3001 cttttctttc tctcctctca tactttctct tctctctctt ttaattttct tgtgagataa -continued

```
3061 tattctaaga ggctctagaa acatgaaata ctcagtagtg atgggtttcc cacttctcct

3121 caatccgttg catgaaataa ttactatgtg ccctaatgca cacaaatagc taaggagaat

3181 ccacccaaac acctttaaag gataggtgtc tgttcatagg caagtcgatt aagtggcatg

3241 atgcctgcaa agcaaagtca actggagttg tatgttcccc ccaccttcta aatagaatag

3301 ctcgacatca gcaatattat tttgccttat ttgtttttcc ccaaagtgcc aaatccatta

3361 ctggtctgtg caggtgccaa atatgctgac aaactgtttc tgaatatctt tcagtacccc

3421 ttcaccttta tatgctgtaa atctttgtaa tgaatactct attaatgata tagatgactg

3481 aattgttggt aactatagtg tagtctagtg aagatgaatt gtgtgagttg tatattttac

3541 tgcattttag ttttgaaaat gacttcccca ccacctagaa acagctgaaa tttgacttcc

3601 ttgggagaac actagcatta atgcaagtaa gactgatttt cccctaagtc ttgttatatt

3661 tgataaggag cattaatccc cctggaaata gattagtagg atttctaatg ttgtgtagca

3721 aacctatact tttttgtatt taaaaattaa tgtgaaatat gcatcataca caatattcaa

3781 tctagattcc agtccatggg ggatttttc ctaataggaa ttcagggtct aaacgtgtgt

3841 atattttggc tcttctgtaa atctaatgtt gtgattttta tatttgtttc gttttgtctg

3901 tgaactgaat aatttataca agaacacact ccattgagaa acgttttgtt ttttgctcgt

3961 ttgtatcgtc tgtgtataac aagtaaaata aacctggtaa aaacgc
```

By "SLC1A3 polypeptide" (or solute carrier family 1; glial high affinity glutamate transporter member 3 (SLC1A3)) is meant a polypeptide or fragment thereof having at least about 85% amino acid identity to NCBI Accession No. BAG35230.1.

```
                                             (SEQ ID NO: 59)
MTKSNGEEPKMGGRMERFQQGVRKRTLLAKKKVQNITKEDVKSYLFRNAF

VLLTVTAVIVGTILGFTLRPYRMSYREVKYFSFPGELLMRMLQMLVLPLI

ISSLVTGMAALDSKASGKMGMRAVVYYMTTTIIAVVIGIIIVIIIHPGKG

TKENMHREGKIVRVTAADAFLDLIRNMFPPNLVEACFKQFKTNYEKRSFK

VPIQANETLVGAVINNVSEAMETLTRITEELVPVPGSVNGVNALGLVVFS
```

-continued

```
MCFGFVIGNMKEQGQALREFFDSLNEAIMRLVAVIMWYAPVGILFLIAGK

IVEMEDMGVIGGQLAMYTVTVIVGLLIHAVIVLPLLYFLVTRKNPWVFIG

GLLQALITALGTSSSSATLPITFKCLEENNGVDKRVTRFVLPVGATINMD

GTALYEALAAIFIAQVNNFELNFGQIITISITATAASIGAAGIPQAGLVT

MVIVLTSVGLPTDDITLIIAVDWFLDRLRTTTNVLGDSLGAGIVEHLSRH

ELKNRDVEMGNSVIEENEMKKPYQLIAQDNETEKPIDSETKM
```

By "SLC1A3 polynucleotide" (or solute carrier family 1; glial high affinity glutamate transporter member 3 (SLC1A3)) is meant a polynucleotide encoding an SLC1A3 polypeptide. An exemplary SLC1A3 nucleic acid molecule (e.g., mRNA) is provided at NCBI Accession No. AK312304.

```
                                                         (SEQ ID NO: 60)
  1 gatagtaact tgcagtttca gagcacatgc acactgtcag ggctagcctg cctgcttacg

 61 cgcgctgcgg attgttgctc cgttgtacct gctggggaat tcacctcgtt actgcttgat

121 atcttccacc ccttacaaaa tcagaaaagt tgtgttttct aataccaaag aggaggtttg

181 gctttctgtg ggtgattccc agacactgaa gtgcaaagaa gagaccctcc tagaaaagta

241 aaatatgact aaaagcaatg gagaagagcc caagatgggg ggcaggatgg agagattcca

301 gcagggagtc cgtaaacgca cacttttggc caagaagaaa gtgcagaaca ttacaaagga

361 ggatgttaaa agttacctgt ttcggaatgc ttttgtgctg ctcacagtca ccgctgtcat

421 tgtgggtaca atccttggat ttaccctccg accatacaga atgagctacc gggaagtcaa

481 gtacttctcc tttcctgggg aacttctgat gaggatgtta cagatgctgg tcttaccact

541 tatcatctcc agtcttgtca caggaatggc ggcgctagat agtaaggcat cagggaagat

601 gggaatgcga gctgtagtct attatatgac taccaccatc attgctgtgg tgattggcat

661 aatcattgtc atcatcatcc atcctgggaa gggcacaaag gaaaacatgc acagagaagg
```

-continued

```
 721 caaaattgta cgagtgacag ctgcagatgc cttcctggac ttgatcagga acatgttccc
 781 tccaaatctg gtagaagcct gctttaaaca gtttaaaacc aactatgaga agagaagctt
 841 taaagtgccc atccaggcca acgaaacgct tgtgggtgct gtgataaaca atgtgtctga
 901 ggccatggag actcttaccc gaatcacaga ggagctggtc ccagttccag gatctgtgaa
 961 tggagtcaat gccctgggtc tagttgtctt ctccatgtgc ttcggttttg tgattggaaa
1021 catgaaggaa caggggcagg ccctgagaga gttctttgat tctcttaacg aagccatcat
1081 gagactggta gcagtaataa tgtggtatgc ccccgtgggt attctcttcc tgattgctgg
1141 gaagattgtg gagatggaag acatgggtgt gattgggggg cagcttgcca tgtacaccgt
1201 gactgtcatt gttggcttac tcattcacgc agtcatcgtc ttgccactcc tctacttctt
1261 ggtaacacgg aaaaaccctt gggtttttat tggagggttg ctgcaagcac tcatcaccgc
1321 tctggggacc tcttcaagtt ctgccaccct acccatcacc ttcaagtgcc tggaagagaa
1381 caatggcgtg gacaagcgcg tcaccagatt cgtgctcccc gtaggagcca ccattaacat
1441 ggatgggact gccctctatg aggctttggc tgccatttc attgctcaag ttaacaactt
1501 tgaactgaac ttcggacaaa ttattacaat cagcatcaca gccacagctg ccagtattgg
1561 ggcagctgga attcctcagg cgggcctggt cactatggtc attgtgctga catctgtcgg
1621 cctgcccact gacgacatca cgctcatcat cgcggtggac tggttcctgg atcgcctccg
1681 gaccaccacc aacgtactgg gagactccct gggagctggg attgtggagc acttgtcacg
1741 acatgaactg aagaacagag atgttgaaat gggtaactca gtgattgaag agaatgaaat
1801 gaagaaacca tatcaactga ttgcacagga caatgaaact gagaaaccca tcgacagtga
1861 aaccaagatg tag
```

By “TH polypeptide” (or tyrosine hydroxylase) is meant a polypeptide or fragment thereof having at least about 85% amino acid identity to NCBI Accession No. AAI43612.1.

(SEQ ID NO: 61)

```
MPTPDATTPQAKGFRRAVSELDAKQAEAIMSPRFIGRRQSLIEDARKERE
AAVAAAAAAVPSEPGDPLEAVAFEEKEGKAVLNLLFSPRATKPSALSRAV
KVFETFEAKIHHLETRPAQRPRAGGPHLEYFVRLEVRRGDLAALLSGVRQ
VSEDVRSPAGPKVPWFPRKVSELDKCHHLVTKFDPDLDLDHPGFSDQVYR
QRRKLIAEIAFQYRHGDPIPRVEYTAEEIATWKEVYTTLKGLYATHACGE
```

-continued

```
HLEAFALLERFSGYREDNIPQLEDVSRFLKERTGFQLRPVAGLLSARDFL
ASLAFRVFQCTQYIRHASSPMHSPEPDCCHELLGHVPMLADRTFAQFSQD
IGLASLGASDEEIEKLSTLYWFTVEFGLCKQNGEVKAYGAGLLSSYGELL
HCLSEEPEIRAFDPEAAAVQPYQDQTYQSVYFVSESFSDAKDKLRSYASR
IQRPFSVKFDPYTLAIDVLDSPQAVRRSLEGVQDELDTLAHALSAIG
```

By “TH polynucleotide” (or tyrosine hydroxylase) is meant a polynucleotide encoding an TH polypeptide. An exemplary TH nucleic acid molecule (e.g., mRNA) is provided at NCBI Accession No. BC143611.

(SEQ ID NO: 62)

```
  1 acccagaggg ggctttgacg tcagctcagc ttataagagg ctgctgggcc agggctgtgg
 61 agacggagcc cggacctcca cactgagcca tgcccacccc cgacgccacc acgccacagg
121 ccaagggctt ccgcagggcc gtgtctgagc tggacgccaa gcaggcagag gccatcatgt
181 ccccgcggtt cattgggcgc aggcagagcc tcatcgagga cgcccgcaag gagcgggagg
241 cggcggtggc agcagcggcc gctgcagtcc cctcggagcc cggggacccc ctggaggctg
301 tggcctttga ggagaaggag gggaaggccg tgctaaacct gctcttctcc ccgagggcca
361 ccaagccctc ggcgctgtcc cgagctgtga aggtgtttga gacgtttgaa gccaaaatcc
421 accatctaga gacccggccc gcccagaggc cgcgagctgg gggccccac ctggagtact
481 tcgtgcgcct cgaggtgcgc cgaggggacc tggccgccct gctcagtggt gtgcgccagg
541 tgtcagagga cgtgcgcagc cccgcggggc ccaaggtccc ctggttccca agaaaagtgt
```

-continued

```
 601 cagagctgga caagtgtcat cacctggtca ccaagttcga ccctgacctg gacttggacc
 661 acccgggctt ctcggaccag gtgtaccgcc agcgcaggaa gctgattgct gagatcgcct
 721 tccagtacag gcacggcgac ccgattcccc gtgtggagta caccgccgag gagattgcca
 781 cctggaagga ggtctacacc acgctgaagg gcctctacgc cacgcacgcc tgcggggagc
 841 acctggaggc ctttgctttg ctggagcgct tcagcggcta ccgggaagac aatatccccc
 901 agctggagga cgtctcccgc ttcctgaagg agcgcacggg cttccagctg cggcctgtgg
 961 ccggcctgct gtccgcccgg gacttcctgg ccagcctggc cttccgcgtg ttccagtgca
1021 cccagtatat ccgccacgcg tcctcgccca tgcactcccc tgagccggac tgctgccacg
1081 agctgctggg gcacgtgccc atgctggccg accgcacctt cgcgcagttc tcgcaggaca
1141 ttggcctggc gtccctgggg gcctcggatg aggaaattga gaagctgtcc acgctgtact
1201 ggttcacggt ggagttcggg ctgtgtaagc agaacgggga ggtgaaggcc tatggtgccg
1261 ggctgctgtc ctcctacggg gagctcctgc actgcctgtc tgaggagcct gagattcggg
1321 ccttcgaccc tgaggctgcg gccgtgcagc cctaccaaga ccagacgtac cagtcagtct
1381 acttcgtgtc tgagagcttc agtgacgcca aggacaagct caggagctat gcctcacgca
1441 tccagcgccc cttctccgtg aagttcgacc cgtacacgct ggccatcgac gtgctggaca
1501 gcccccaggc cgtgcggcgc tccctggagg gtgtccagga tgagctggac acccttgccc
1561 atgcgctgag tgccattggc taggtgcacg gcgtccctga gggcccttcc caacctcccc
1621 tggtcctgc
```

By "Neurofilament 200 polypeptide" (or neurofilament heavy (NEFH)) is meant a polypeptide or fragment thereof having at least about 85% amino acid identity to NCBI Accession No. NP_066554.2.

```
                                        (SEQ ID NO: 63)
MMSFGGADALLGAPFAPLHGGGSLHYALARKGGAGGTRSAAGSSSGFHSW
TRTSVSSVSASPSRFRGAGAASSTDSLDTLSNGPEGCMVAVATSRSEKEQ
LQALNDRFAGYIDKVRQLEAHNRSLEGEAAALRQQQAGRSAMGELYEREV
REMRGAVLRLGAARGQLRLEQEHLLEDIAHVRQRLDDEARQREEAEAAAR
ALARFAQEAEAARVDLQKKAQALQEECGYLRRHHQEEVGELLGQIQGSGA
AQAQMQAETRDALKCDVTSALREIRAQLEGHAVQSTLQSEEWFRVRLDRL
SEAAKVNTDAMRSAQEEITEYRRQLQARTTELEALKSTKDSLERQRSELE
DRHQADIASYQEAIQQLDAELRNTKWEMAAQLREYQDLLNVKMALDIEIA
AYRKLLEGEECRIGFGPIPFSLPEGLPKIPSVSTHIKVKSEEKIKVVEKS
EKETVIVEEQTEETQVTEEVTEEEEKEAKEEEGKEEEGGEEEEAEGGEEE
```

-continued

```
TKSPPAEEAASPEKEAKSPVKEEAKSPAEAKSPEKEEAKSPAEVKSPEKA
KSPAKEEAKSPPEAKSPEKEEAKSPAEVKSPEKAKSPAKEEAKSPAEAKS
PEKAKSPVKEEAKSPAEAKSPVKEEAKSPAEVKSPEKAKSPTKEEAKSPE
KAKSPEKEEAKSPEKAKSPVKAEAKSPEKAKSPVKAEAKSPEKAKSPVKE
EAKSPEKAKSPVKEEAKSPEKAKSPVKEEAKTPEKAKSPVKEEAKSPEKA
KSPEKAKTLDVKSPEAKTPAKEEARSPADKFPEKAKSPVKEEVKSPEKAK
SPLKEDAKAPEKEIPKKEEVKSPVKEEEKPQEVKVKEPPKKAEEEKAPAT
PKTEEKKDSKKEEAPKKEAPKPKVEEKKEPAVEKPKESKVEAKKEEAEDK
KKVPTPEKEAPAKVEVKEDAKPKEKTEVAKKEPDDAKAKEPSKPAEKKEA
APEKKDTKEEKAKKPEEKPKTEAKAKEDDKTLSKEPSKPKAEKAEKSSST
DQKDSKPPEKATEDKAAKGK
```

By "Neurofilament 200 polynucleotide" (or neurofilament heavy (NEFH)) is meant a polynucleotide encoding an Neurofilament 200 polypeptide. An exemplary Neurofilament 200 nucleic acid molecule (e.g., mRNA) is provided at NCBI Accession No. NM_021076.

```
                                                  (SEQ ID NO: 64)
  1 aaaagggccg gcgccctggt gctgccgcag tgcctcccgc cccgtcccgg cctcgcgcac
 61 ctgctcaggc catgatgagc ttcggcggcg cggacgcgct gctgggcgcc ccgttcgcgc
121 cgctgcatgg cggcggcagc ctccactacg cgctagcccg aaagggtggc gcaggcggga
181 cgcgctccgc cgctggctcc tccagcggct tccactcgtg gacacggacg tccgtgagct
241 ccgtgtccgc ctcgcccagc cgcttccgtg gcgcaggcgc cgcctcaagc accgactcgc
301 tggacacgct gagcaacggg ccggagggct gcatggtggc ggtggccacc tcacgcagtg
```

-continued

```
 361 agaaggagca gctgcaggcg ctgaacgacc gcttcgccgg gtacatcgac aaggtgcggc
 421 agctggaggc gcacaaccgc agcctggagg gcgaggctgc ggcgctgcgg cagcagcagg
 481 cgggccgctc cgctatgggc gagctgtacg agcgcgaggt ccgcgagatg cgcggcgcgg
 541 tgctgcgcct gggcgcggcg cgcggtcagc tacgcctgga gcaggagcac ctgctcgagg
 601 acatcgcgca cgtgcgccag cgcctagacg acgaggcccg gcagcgagag gaggccgagg
 661 cggcggcccg cgcgctggcg cgcttcgcgc aggaggccga ggcggcgcgc gtggacctgc
 721 agaagaaggc gcaggcgctg caggaggagt gcggctacct gcggcgccac caccaggaag
 781 aggtgggcga gctgctcggc cagatccagg gctccggcgc cgcgcaggcg cagatgcagg
 841 ccgagacgcg cgacgccctg aagtgcgacg tgacgtcggc gctgcgcgag attcgcgcgc
 901 agcttgaagg ccacgcggtg cagagcacgc tgcagtccga ggagtggttc cgagtgaggc
 961 tggaccgact gtcggaggca gccaaggtga acacagacgc tatgcgctca gcgcaggagg
1021 agataactga gtaccggcgt cagctgcagg ccaggaccac agagctggag gcactgaaaa
1081 gcaccaagga ctcactggag aggcagcgct ctgagctgga ggaccgtcat caggccgaca
1141 ttgcctccta ccaggaagcc attcagcagc tggacgctga gctgaggaac accaagtggg
1201 agatggccgc ccagctgcga gaataccagg acctgctcaa tgtcaagatg gctctggata
1261 tagagatagc cgcttacaga aaactcctgg aaggtgaaga gtgtcggatt ggctttggcc
1321 caattccttt ctcgcttcca gaaggactcc ccaaaattcc ctctgtgtcc actcacataa
1381 aggtgaaaag cgaagagaag atcaaagtgg tggagaagtc tgagaaagaa actgtgattg
1441 tggaggaaca gacagaggag acccaagtga ctgaagaagt gactgaagaa gaggagaaag
1501 aggccaaaga ggaggagggc aaggaggaag aagggggtga agaagaggag gcagaagggg
1561 gagaagaaga aacaaagtct cccccagcag aagaggctgc atccccagag aaggaagcca
1621 agtcaccagt aaaggaagag gcaaagtcac cggctgaggc caagtcccca gagaaggagg
1681 aagcaaaatc cccagccgaa gtcaagtccc ctgagaaggc caagtctcca gcaaaggaag
1741 aggcaaagtc accgcctgag gccaagtccc cagagaagga ggaagcaaaa tctccagctg
1801 aggtcaagtc cccgagaag gccaagtccc cagcaaagga agaggcaaag tcaccggctg
1861 aggccaagtc tccagagaag gccaagtccc cagtgaagga agaagcaaag tcaccggctg
1921 aggccaagtc cccagtgaag gaagaagcaa aatctccagc tgaggtcaag tccccggaaa
1981 aggccaagtc tccaacgaag gaggaagcaa agtcccctga gaaggccaag tccccagaga
2041 aggaagaggc caagtcccct gagaaggcca agtccccagt gaaggcagaa gcaaagtccc
2101 ctgagaaggc caagtcccca gtgaaggcag aagcaaagtc ccctgagaag gccaagtccc
2161 cagtgaagga agaagcaaag tcccctgaga aggccaagtc cccagtgaag gaagaagcaa
2221 agtcccctga gaaggccaag tccccagtga aggaagaagc aaagaccccc gagaaggcca
2281 agtccccagt gaaggaagaa gctaagtccc cagagaaggc caagtcccca gagaaggcca
2341 agactcttga tgtgaagtct ccagaagcca agactccagc gaaggaggaa gcaaggtccc
2401 ctgcagacaa attccctgaa aaggccaaaa gccctgtcaa ggaggaggtc aagtccccag
2461 agaaggcgaa atctcccctg aaggaggatg ccaaggcccc tgagaaggag atcccaaaaa
2521 aggaagaggt gaagtcccca gtgaaggagg aggagaagcc ccaggaggtg aaagtcaaag
2581 agcccccaaa gaaggcagag gaagagaaag cccctgccac accaaaaaca gaggagaaga
2641 aggacagcaa gaaagaggag gcacccaaga aggaggctcc aaagcccaag gtggaggaga
2701 agaaggaacc tgctgtcgaa aagcccaaag aatccaaagt tgaagccaag aaggaagagg
2761 ctgaagataa gaaaaaagtc cccaccccag agaaggaggc tcctgccaag gtggaggtga
```

-continued 2821 aggaagacgc taaacccaaa gaaaagacag aggtagccaa gaaggaacca gatgatgcca 2881 aggccaagga acccagcaaa ccagcagaga agaaggaggc agcaccggag aaaaaagaca 2941 ccaaggagga gaaggccaag aagcctgagg agaaacccaa gacagaggcc aaagccaagg 3001 aagatgacaa gaccctctca aaagagccta gcaagcctaa ggcagaaaag gctgaaaaat 3061 cctccagcac agaccaaaaa gacagcaagc ctccagagaa ggccacagaa gacaaggccg 3121 ccaaggggaa gtaaggcagg gagaaaggaa catccggaac agccaaagaa actcagaaga 3181 gtcccggagc tcaaggatca gagtaacaca attttcactt tttctgtctt tatgtaagaa 3241 gaaactgctt agatgacggg gcctccttct tcaaacagga atttctgtta gcaatatgtt 3301 agcaagagag ggcactccca ggcccctgcc cccaggccct ccccaggcga tggacaatta 3361 tgatagctta tgtagctgaa tgtgatacat gccgaatgcc acacgtaaac acttgactat 3421 aaaaactgcc cccctccttt ccaaataagt gcatttattg cctctatgtg caactgacag 3481 atgaccgcaa taatgaatga gcagttagaa atacattatg cttgagatgt cttaacctat 3541 tcccaaatgc cttctgtttt ccaaaggagt ggtcaagccc ttgcccagag ctctctattc 3601 tggaagagcg gtccaggtgg ggccggggac tggccactga attatgccag ggcgcacttt 3661 ccactggagt tcactttcaa ttgcttctgt gcaataaaac caagtgctta taaaatgaaa 3721 a By "Map2" (or microtubule-associated protein 2) is meant a polypeptide or fragment thereof having at least about 85% amino acid identity to NCBI Accession No. AAH38857.1.

(SEQ ID NO: 65)

MADERKDEAKAPHWTSAPLTEASAHSHPPEIKDQGGAGEGLVRSANGFPY

REDEEGAFGEHGSQGTYSNTKENGINGELTSADRETAEEVSARIVQVVTA

EAVAVLKGEQEKEAQHKDQTAALPLAAEETANLPPSPPPSPASEQTVTVE

EAAGGESALAPSVFKQAKDKVSNSTLSKIPALQGSTKSPRYSSACPSTTK

RATFSDSLLIQPTSAGSTDRLPYSKSGNKDGVTKSPEKRSSLPRPSSILP

PRRGVSGDRDENSFSLNSSISSSARRTTRSEPIRRAGKSGTSTPTTPGST

-continued

AITPGTPPSYSSRTPGTPGTPSYPRTPHTPGTPKSAILVPSEKKVAIIRT

PPKSPATPKQLRLINQPLPDLKNVKSKIGSTDNIKYQPKGGQVRILNKKI

DFSKVQSRCGSKDNIKHSAGGGNVQIVTKKIDLSHVTSKCGSLKNIRHRP

GGGRVKIESVKLDFKEKAQAKVGSLDNAHHVPGGGNVKIDSQKLNFREHA

KARVDHGAEIITQSPGRSSVASPRRLSNVSSSGSINLLESPQLATLAEDV

TAALAKQGL

By "Map2 polynucleotide" (or microtubule-associated protein 2) is meant a polynucleotide encoding an Map2 polypeptide. An exemplary Map2 nucleic acid molecule (e.g., mRNA) is provided at NCBI Accession No. BC038857.

(SEQ ID NO: 66)

1 ggcgctcggg ctgcgcgggc tctgggcagc agcagcagca gcagcagcat cctctcttcc 61 tttacttccc ttccgcttct ttctcttcct tctccttctt tttccccccc ctccccttct 121 tcccctaacc cttctacccc tctccttttt ctccggaggg cgctaagtcc gtgagcggtg 181 gcagtcgcga ccgcgggtgc atccagtttc tgcgcccaga ttttattgat ctaatccaaa 241 gtatcttata acttctggct ggaattaaga ttcttcagct tgtctctaac cgaggaagca 301 ttgattggga gctactcatt cagaaaatta aaagaaagaa gccagaaaat attatcaacc 361 ctttgagaac acgacacaac gaactttata ttttaccact tccttgaata gttgcaggag 421 aaataacaag gcattgaaga atggcagatg aacggaaaga cgaagcaaag gcacctcact 481 ggacctcagc accgctaaca gaggcatctg cacactcaca tccacctgag attaaggatc 541 aaggcggagc aggggaagga cttgtccgaa gcgccaatgg attcccatac agggaggatg 601 aagagggtgc ctttggagag catgggtcac agggcaccta ttcaaatacc aaagagaatg 661 ggatcaacgg agagctgacc tcagctgaca gagaaacagc agaggaggtg tctgcaagga -continued

```
 721 tagttcaagt agtcactgct gaggctgtag cagtcctgaa aggtgaacaa gagaaagaag
 781 ctcaacataa agaccagact gcagctctgc ctttagcagc tgaagaaaca gctaatctgc
 841 ctccttctcc acccccatca cctgcctcag aacagactgt cacagtggag gaagcagcag
 901 gtggggaatc agctctggct cccagtgtat ttaaacaggc aaaggacaaa gtctctaatt
 961 ctaccttgtc aaagattcct gctttacagg gtagcacaaa gtccccaaga tacagctcag
1021 cctgccctag cacgactaaa agggctacat tttctgacag tttattaata cagcccacct
1081 cagcaggctc cacagaccgt ttgccatact caaaatcagg gaacaaggac ggagtaacca
1141 agagcccaga aaagcgctct tctctcccaa gaccttcctc cattctccct cctcggcgag
1201 gtgtgtcagg agacagagat gagaattcct tctctctcaa cagttctatc tcttcttcag
1261 cacggcggac caccaggtca gagccaattc gcagagcagg gaagagtggt acctcaacac
1321 ccactacccc tgggtctact gccatcactc ctggcacccc accaagttat tcttcacgca
1381 caccaggcac tcctggaacc cctagctatc ccaggacccc tcacacacca ggaaccccca
1441 agtctgccat cttggtgccg agtgagaaga aggtcgccat catacgtact cctccaaaat
1501 ctcctgcgac tcccaagcag cttcggctta ttaaccaacc actgccagac ctgaagaatg
1561 tcaaatccaa aatcggatca acagacaaca tcaaatacca gcctaaaggg ggcaggtta
1621 ggattttaaa caagaagatc gattttagca aagttcagtc cagatgtggt tccaaggata
1681 acatcaaaca ttcggctggg ggcggaaatg tacaaattgt taccaagaaa atagacctaa
1741 gccatgtgac atccaaatgt ggctctctga agaacatccg ccacaggcca ggtggcggac
1801 gtgtgaaaat tgagagtgta aaactagatt tcaaagaaaa ggcccaagct aaagttggtt
1861 ctcttgataa tgctcatcat gtacctggag gtggtaatgt caagattgac agccaaaagt
1921 tgaacttcag agagcatgct aaagcccgtg tggaccatgg ggctgagatc attacacagt
1981 ccccaggcag atccagcgtg gcatcacccc gacgactcag caatgtctcc tcgtctggaa
2041 gcatcaacct gctcgaatct cctcagcttg ccactttggc tgaggatgtc actgctgcac
2101 tcgctaagca gggcttgtga atatttctca tttagcattg aaataataat atttaggcat
2161 gagctcttgg caggagtggg ctctgagcag ttgttatatt cattctttat aaaccataaa
2221 ataaataatc tcatccccaa aaaaaaaaaa aaaaaaaaaa aaaaaaaaaa aaaaaaaaaa
2281 aaaaaa
```

By “DCX” (or doublecortin) is meant a polypeptide or fragment thereof having at least about 85% amino acid identity to NCBI Accession No. NP_835366.1.

```
(SEQ ID NO: 67)
MELDFGHFDERDKTSRNMRGSRMNGLPSPTHSAHCSFYRTRTLQALSNEK
KAKKVRFYRNGDRYFKGIVYAVSSDRFRSFDALLADLTRSLSDNINLPQG
VRYIYTIDGSRKIGSMDELEEGESYVCSSDNFFKKVEYTKNVNPNWSVNV
KTSANMKAPQSLASSNSAQARENKDFVRPKLVTIIRSGVKPRKAVRVLLN
```

-continued

```
KKTAHSFEQVLTDITEAIKLETGVVKKLYTLDGKQVTCLHDFFGDDDVFI
ACGPEKFRYAQDDFSLDENECRVMKGNPSATAGPKASPTPQKTSAKSPGP
MRRSKSPADSANGTSSSQLSTPKSKQSPISTPTSPGSLRKHKDLYLPLSL
DDSDSLGDSM
```

By “DCX polynucleotide” (or doublecortin) is meant a polynucleotide encoding an DCX polypeptide. An exemplary DCX nucleic acid molecule (e.g., mRNA) is provided at NCBI Accession No. NM_178153.

```
(SEQ ID NO: 68)
  1 ctggcaggaa tttcttgctt ggagctcaga caacaaaggc atagagagat tggttttctt
 61 tctctcagca tctccaccca accagcagaa aaccggtctc tgaggttcca ccaaaatatg
121 gaacttgatt ttggacactt tgacgaaaga gataagacat ccaggaacat gcgaggctcc
181 cggatgaatg ggttgcctag ccccactcac agcgcccact gtagcttcta ccgaaccaga
```

-continued

```
241 accttgcagg cactgagtaa tgagaagaaa gccaagaagg tacgtttcta ccgcaatggg
301 gaccgctact tcaaggggat tgtgtacgct gtgtcctctg accgttttcg cagctttgac
361 gccttgctgg ctgacctgac gcgatctctg tctgacaaca tcaacctgcc tcagggagtg
421 cgttacattt acaccattga tggatccagg aagatcggaa gcatggatga actggaggaa
481 ggggaaagct atgtctgttc ctcagacaac ttctttaaaa aggtggagta caccaagaat
541 gtcaatccca actggtctgt caacgtaaaa acatctgcca atatgaaagc cccccagtcc
601 ttggctagca gcaacagtgc acaggccagg gagaacaagg actttgtgcg ccccaagctg
661 gttaccatca tccgcagtgg ggtgaagcct cggaaggctg tgcgtgtgct tctgaacaag
721 aagacagccc actcttttga gcaagtcctc actgatatca cagaagccat caaactggag
781 accggggttg tcaaaaaact ctacactctg gatggaaaac aggtaacttg tctccatgat
841 ttctttggtg atgatgatgt gtttattgcc tgtggtcctg aaaaatttcg ctatgctcag
901 gatgattttt ctctggatga aatgaatgc cgagtcatga agggaaaccc atcagccaca
961 gctggcccaa aggcatcccc aacacctcag aagacttcag ccaagagccc tggtcctatg
1021 cgccgaagca agtctccagc tgactcagca aacggaacct ccagcagcca gctctctacc
1081 cccaagtcta agcagtctcc catctctacg cccaccagtc ctggcagcct ccggaagcac
1141 aaggacctgt acctgcctct gtccttggat gactcggact cgcttggtga ttccatgtaa
1201 aggaggggag agtgctcaga gtccagagta caaatccaag cctatcattg tagtagggta
1261 cttctgctca agtgtccaac agggctattg gtgctttcaa gtttttattt tgttgttgtt
1321 gttattttga aaaacacatt gtaatatgtt gggtttattt tcctgtgatt tctcctctgg
1381 gccactgatc cacagttacc aattatgaga gatagattga taaccatcct ttggggcagc
1441 attccaggga tgcaaaatgt gctagtccat gacctttcaa tggaaagctt aggtgcctgc
1501 gttatatttg ccctgtctaa ttttgcccat acagtcttcc ttctgtagag ggctgtttac
1561 atatacagca cttaaaatgt ttgtgtggga aaaaaaaaac tcattggcag atccaagaat
1621 gacaaacaca agtgcccctt ttctctggat ctcaagaatg gtggaggacc ctggaaggac
1681 agcaaggcag ctccccagcc tcactcttca ctcctgattg aggcccgggt ttgttgtcca
1741 gcaccaattc tggctgtcaa tggggagaaa taaaccaaca acttataatt gtgacaccag
1801 atgcttagga tcctggtgct gggttagcta agagaataga cagaattgga aaatactgca
1861 gacatttccg aagagtttat aaagcacagt gaattcctgg tcaatctctc cactgaggca
1921 atttggaatc aataagcaat tgataatagt ttggagtaag ggacttcata tacctgattc
1981 ctctagaagg ctgtctaaca taccacatga ttacatgaac tgtatggtat ccatctatct
2041 ctgttctatt gaatgccttg ttaacagcca acactgaaaa cactgtgaga atttgttttc
2101 aggtctgaca cctttcagtc tctttttata gcaagaaatc aatatccttt ttataaaaat
2161 tcatgtctgt atttcaggag caaactcttc aggctccttt tttataaact ggtgattttt
2221 cttttgtcta aaaaacacat gaagaaaatt taccaaaaaa aaaaaaaaaa gcagaagaat
2281 aatgtagttt agaaattatg ctgtcactgc caaacagtaa cctccaggag aaaacaagat
2341 gaatagcaga ggccaattca atagaatcag tttttgata gctttttaac agttatgctt
2401 gcattaataa tttcaatgtg gaccagacat tctaattata ttttaaatga aatgttacag
2461 catattttaa gcaactcttt ttatctataa tcctaatatt tcatactgaa gacacagaaa
2521 tctttcactt gtctttaaca ttagaaagga tttctcttta ctaaggactg atcatttgaa
2581 atagttttca gtcttttgag atacaggttt ataacactgc tttttttttt ctgtaatcat
2641 agcccataat ggcaaagaca actaaattta agtgaaggtc atgcatgcca attctgtgtt
```

-continued

```
2701 tgcttttagc agatatgaag atttccttat ttctttgtaa ttgtgcagat attttgaaag
2761 gcacagcatt cgaagccaag ctgctgtttg gctactgaat ggcttgcagt tgttcctcca
2821 ctctaaatgg aatgagcttg ctgtgtgtgt gtgtggtggt ggtgggaggg ggtggtgcat
2881 gtgtgtgtgt gtgtgtgcat ctgcagctgc ttcaaaatta ggaaatacta caggacaccc
2941 ctgtaatgga ttggtggcaa ctgggtggca ctgctgatgt gcactgtgta ggggggaacc
3001 cagtggtggt ggggtagctc agatgcccct agacaagctt cagatgtctg tagctaccag
3061 aaacattttc ggttcaggaa aagtgagatg atggtagtac tggtttctgg tgaaattgaa
3121 gaaccccaaa tgatgaggat ctctttttgc cccctctcct ttttttgtag acccattcaa
3181 aaccattaat aagcccattt tactaagccc ctatttcttt ctagaagctc agggttttct
3241 tagtgcctcc cagaacattt tgtagttaat tgggaaaaag tgatacttgg attagggggt
3301 gtgggcataa agaatggtgg gaggcctgat tttaaacttc aggccagaac cccaatgac
3361 tccacccata gtctcacttt aggtctcatt tagtccatca cctttatttt aagttgagga
3421 agtggaggct ggtaaagagc aggaccagag gaagaatcca gatttcctta tgcttgggcc
3481 tcacactagc tctctgagta tttccttgat tgcggtatat gtactactag aaaataccaa
3541 atggatatat tttctttagg ataacctttg aaccaacaat cttcaataac aatagtacat
3601 cttccatctt acttttaatc gagtataagg aaatgtttct ttatggccat tttggaggga
3661 gcaggggatg aggcttggca tagtccaaaa tttaagtctc caataattaa ttgcatttta
3721 aattggccca ctttcaaggc aatttttttt gtgtgtctgt aactgagctc ctccacccct
3781 gtcattcact tccaatttta cccaatccaa ttttagcact caagttccat tgtgttaatt
3841 tctgcacggt caacaaacat caagtcagca agcatttgcc accactccct atacttctcc
3901 ctccttctta cacacacaca cacacacaca cacacaatcc atctcttgct tgttcctacc
3961 tcctgatttt tcttccctac agaaatagaa atagggacaa agaaggggaa aatgtatata
4021 ttggggctgg gctgaacaac taacttcata agtagtatta actaggggta aattgagaga
4081 aaagctcctt ttctcttcac tgttttggaa aggatagcca ttagcatgac tgctttgtgt
4141 ccttatggac tttagtatta gcctagattg aattatagcg ttttctagct ggaaggaacc
4201 ttaagatcac atcatctact cctctactcc aaatttctca ttcttcaggc caggaaaccg
4261 agacacagag gtaaagtaat ttccccaagg tcacacagct ggctggggca ggattgggtt
4321 tacaacccac atctcctggc tcttattcca gggccttttc ccactaagta gtattgcctt
4381 ccattaggct cctgagagtt atttctcagg gtcatgttgc atcttggagc cacatgctgc
4441 tgccctgatc tcagtgggaa atccacccag caacctaata cagcccottt tccctgcatt
4501 cacctggttc ccatccacat gggttgcaga tgtccttgaa gagagtgagg cattgagggc
4561 caataggagc aatggggtcc ctggccttgt ccatctgatt caggagatca ctgctccatc
4621 gtgaggagcc ctctgaatag ccccccactg aatgcttgcc ttgcccaaat ggaatggagg
4681 aagattgatt ttctccatca gttcaccttg tgtcatctca taatggttgg tctttccagg
4741 ctgagggaaa tgtttcttgt ttccagagta gaaaaagaaa gagtggaaca atagctttgt
4801 tcatcctaac tttctgagat ggcttttcaa cattttaaaa aaactagtgt ggctaccatt
4861 cactggcaat gatttctttt agaatatggg agtaagatga gctagagaaa ataacctggt
4921 ctcactgtgg ttgccctcat ccacaatgtc cccaaagcca tcctgctctg atgaggacaa
4981 tttccaggta taagcaaggg gctttgtgac aaaaatgtac cctggctgat gttaaacatt
5041 ggctcctgtg tttgcaccaa aatagcaagc tgtgtgctct atacactctt cccatcgtct
5101 tgtgtacact gctcctgtgg ccttccacag cagaaaccag ggcaaaaggg tccaaacaca
```

-continued 5161 tggttttcct tgctgcaagg ctcttcctgg gaactaaggg ggtatttatt agttcagttc
5221 taagagacct ccttctgggc ttaccccact cctcaggtac ttctctctcc ttcctccttc
5281 tcctccacag tcacaagtaa ccaaggaacc tgaaagtgga tgtgtagcta tttgaagaag
5341 gcaaggaacc ctgagattct tctttgaatc ctctagtcca agtcttagac cagtgattgg
5401 tgcttacctt gaacaaaatt ttgtctgtgt tcctaatccc ttcaatactc tgggtacaat
5461 gctcccaatc accctgcaca tttgattcta aatggctttt atttttttaaa aatccatatc
5521 cctaggacaa gagaacagga tgcctatatc cccaaaatga gctccaggac actgatggga
5581 atgatcccaa agatcacccc acctcagaaa cgtctgtgcc aagagacttc cccagataga
5641 aacactggga cagtggtttg aacgacttct tttatggttg tccagtttgc tatggaaata
5701 aaaggcattg atttttttaaa aagatgattg gaacctgtct ttggccacat agggccactt
5761 ggatccattt ccaggcctta ctcatatatt gccttcactg aagggctttg gctttaagtc
5821 ccagactggt ctcccaagtg aaccataagt gttttggagc tcatctgggg tgaggcatga
5881 gaatgttgcc ccatctatcc cttcaggaaa aggtgccttc cctccctttc tcctaaagcc
5941 tggtccccag aaattgtttt tgtctccaaa agtctagtat ggtctttata cacccagact
6001 cttagtgttg cgtcctgcct tgtttccttg ttaaggatct atgcagacct cccgctttgg
6061 cttagctagc gtgacattgg ctatcatttg acaagactaa cttttttttt tttttttttt
6121 tgactgagtc tccctctgtc acctaggctg gagtgcagtg gcacaatctt ggctcgctgc
6181 aaccttcacc cttcacctcc caggtcgaag cgattctcct gcctcagtct cccgagtagc
6241 tgggattaca ggcgtgcgcc accaaatctg gctatttttt tattattatt atttttagta
6301 gagatggggt ttcaccatgt tggccagact ggtcttgaac tcttggcctc aaattatctg
6361 cccacctcgg cctcccaaag tgctgggatt acaggcatga gccaccatgc ccagctgaca
6421 agactaattt tttatccctt ggtttattgg cttcaacatc ttctggaatc agaggtgatt
6481 ttttcttacc ttggatgcct gagactaggg gagtatagaa ttccaattgg taattaaggc
6541 atctttctgc tcctgatcag aagggcaggt tagttgggag aggtcagatg gcacaacaga
6601 agtcaccttg taagtaaggc aaagacttga aggcattagc gtttctcatt actaggtcaa
6661 taacctgagg gaatcaatgg ctttttgccg ctctacctct tgtgtatctc tttgactttt
6721 ctttctctgt ctagtttcct ctgttctcag tttatattct atgttatcag tctctctttc
6781 cacagtacaa acatccatcc tttctcctgt gcaattctgt ctctccctct tattatcttt
6841 atttgtactt tttccttcct ccctgtctag gcattgggca tgtgcctctt cttagcctgt
6901 gattttgcct tgggactgat gataaattat ttccagattc aatcagccct ggtcctaccc
6961 cagtccaatc agaagtatgt tggtgggaat caacctgatc ctggcccttt cttcttctcc
7021 attttcattc gtaatccccc tcagcagatc tttacaagca gtttccttat agctcatgta
7081 tctttaggtc tttgccttcc aagcactgta cagaatactt tgtggttcct ttttagtctg
7141 acattttgtg gagcagtgaa gcgtgctcag agacataatc agctgaagag aaaaaatcca
7201 cccatggatt tatatcagct aaatactaat aattgatttt gtttgatgtg cccataattt
7261 ttaaagctgc aatataatat aatgagggac cacaggtaat ttctcctgtc atttgttttg
7321 gctggatggg ggtgggggag taattgctta aagttttacc attacacatt aaactctcta
7381 taataatctt gtttggggct tgctaactgt tgagctgttt taactaaact ggtaggcaat
7441 cggagttgat ttaaatgaaa agataattta acaaatctat actataaaaa gagacatttg
7501 cttaattgac atgtattttt tccttctgag tcacctaaac atttactctt gacaccaact
7561 gttcatgata ctgaatagac agtccatata agagaaatta gtggacctaa agaagccaga -continued

```
7621 ttgtaggtgt taatttatta aacagagtgc aaagcccttg gaaatgtcac tgcttggcaa
7681 taccatatgg aatgccaaaa tttacaatga cttttcttta taagttatcc aaaagggatt
7741 tgaacaagta agaggttatg ccaaaatgtc tccaatgtat ggtcctgtaa tatattgcag
7801 cttgaagcca atgatccctt atgacttgta tacaactaat gcatgtttta ttgaattttg
7861 catttcccac gtgtggtaag ttctttaaaa tgtttttgat caccttttttg tgccattaaa
7921 cttgtacaga aaatgttttt atggccattt tcaaagggag aaagtttaaa atggaaacag
7981 cccacccttt ctgccctata gctgtagtta gaattgagta cctgtagcaa aacagctgta
8041 attggtggtt gtagtgttag aggtgttagc ttgctagtga ctagctttgg agagtaaatg
8101 catggtattg tacatcacat ttcttaactc gttttaacct ctgaaaagaa tatattcttc
8161 tttgtagtcc ttcttcccac cccctgccc tctccctctc cctgctccca gttgtcttac
8221 agttgtaaat atctgatttg aggcccaata actcttgcca agtaaagtca gcaaacaaca
8281 aacaaaccaa aatgtgggga aaaggcattt ctcaaccatc tctcagcagt tattgatcat
8341 ttcttaagga acagcattgt gatcaaagac tcaactttac gtaaaaatca gtggtaaatt
8401 ggggttgtat ttggccattt gattacattt caggattgaa tagttttcag aatcacatgt
8461 aatccaaaga cagtaggtag tgatgtccct tatccctgca gctgttttaa gatagagacc
8521 tcagaagact ctgcttgacc gatgaccaat aattatttga aaaaaaaaga aaaaatgaga
8581 gaaataaaac agatatttaa gaactttagc cacctattta gaatagttat agccagaaaa
8641 aaaaacaagg gcatgagttc aaatgcatta ctatcagtgt cctaggcaat acctaaccta
8701 ctctgaaatt gtgattcaaa agcagtattt caagaggcat tctccttttt tggtttgctg
8761 accccacttg gactggtagg tttggtgagg cccccataaa ccagctggag cagacccttt
8821 tcatctcctg tgcctgtaac acccctcttc ccccaccccc tccgcaattc aatgagggct
8881 ttcttgggtc agaggacttc aaggttgtct agagaagttt gccatgtgtg taaggtgctg
8941 tgaactgtga gtgctgaaga ttcgcagcat tcaataccag gcagccaaag agctgctctt
9001 gcaattattt tggctctcaa gctctgttct tcatcgcatt ctcatttctg tgtacatttg
9061 caagatgtgt gtaatgtcat tttccaaaaa taaaatttga tttcaataaa aaaaaaaaaa
9121 aaaaaaaaaa aaaaa
```

By “GABRA1” (or gamma-aminobutyric acid (GABA) A receptor) is meant a polypeptide or fragment thereof having at least about 85% amino acid identity to NCBI Accession No. AAH30696.1.

(SEQ ID NO: 69)

```
MRKSPGLSDCLWAWILLLSTLTGRSYGQPSLQDELKDNTTVFTRILDRLL
DGYDNRLRPGLGERVTEVKTDIFVTSFGPVSDHDMEYTIDVFFRQSWKDE
RLKFKGPMTVLRLNNLMASKIWTPDTFFHNGKKSVAHNMTMPNKLLRITE
DGTLLYTMRLTVRAECPMHLEDFPMDAHACPLKFGSYAYTRAEVVYEWTR
EPARSVVVAEDGSRLNQYDLLGQTVDSGIVQSSTGEYVVMTTHFHLKRKI
```

-continued

```
GYFVIQTYLPCIMTVILSQVSFWLNRESVPARTVFGVTTVLTMTTLSISA
RNSLPKVAYATAMDWFIAVCYAFVFSALIEFATVNYFTKRGYAWDGKSVV
PEKPKKVKDPLIKKNNTYAPTATSYTPNLARGDPGLATIAKSATIEPKEV
KPETKPPEPKKTFNSVSKIDRLSRIAFPLLFGIFNLVYWATYLNREPQLK
APTPHQ
```

By “GABRA1 polynucleotide” (or gamma-aminobutyric acid (GABA) A receptor) is meant a polynucleotide encoding an GABRA1 polypeptide. An exemplary GABRA1 nucleic acid molecule (e.g., mRNA) is provided at NCBI Accession No. BC030696.

(SEQ ID NO: 70)

```
  1 agcggagcgg gcgagcaagg gagcgagcag gacaggagcc tgatcccaca gctgctgctc
 61 cagcccgcga tgaggaaaag tccaggtctg tctgactgtc tttgggcctg gatcctcctt
121 ctgagcacac tgactggaag aagctatgga cagccgtcat tacaagatga acttaaagac
```

-continued

```
181 aataccactg tcttcaccag gattttggac agactcctag atggttatga caatcgcctg
241 agaccaggat tgggagagcg tgtaaccgaa gtgaagactg atatcttcgt caccagtttc
301 ggacccgttt cagaccatga tatggaatat acaatagatg tatttttccg tcaaagctgg
361 aaggatgaaa ggttaaaatt taaaggacct atgacagtcc tccggttaaa taacctaatg
421 gcaagtaaaa tctggactcc ggacacattt ttccacaatg gaaagaagtc agtggcccac
481 aacatgacca tgcccaacaa actcctgcgg atcacagagg atggcacctt gctgtacacc
541 atgaggctga cagtgagagc tgaatgtccg atgcatttgg aggacttccc tatggatgcc
601 catgcttgcc cactaaaatt tggaagttat gcttatacaa gagcagaagt tgtttatgaa
661 tggaccagag agccagcacg ctcagtggtt gtagcagaag atggatcacg tctaaaccag
721 tatgaccttc ttggacaaac agtagactct ggaattgtcc agtcaagtac aggagaatat
781 gttgttatga ccactcattt ccacttgaag agaaagattg gctactttgt tattcaaaca
841 tacctgccat gcataatgac agtgattctc tcacaagtct ccttctggct caacagagag
901 tctgtaccag caagaactgt ctttggagta acaactgtgc tcaccatgac aacattgagc
961 atcagtgcca gaaactccct ccctaaggtg gcttatgcaa cagctatgga ttggtttatt
1021 gccgtgtgct atgcctttgt gttctcagct ctgattgagt ttgccacagt aaactatttc
1081 actaagagag gttatgcatg ggatggcaaa agtgtggttc cagaaaagcc aaagaaagta
1141 aaggatcctc ttattaagaa aaacaacact tacgctccaa cagcaaccag ctacacccct
1201 aatttggcca ggggcgaccc gggcttagcc accattgcta aaagtgcaac catagaacct
1261 aaagaggtca agcccgaaac aaaaccacca gaacccaaga aaacctttaa cagtgtcagc
1321 aaaattgacc gactgtcaag aatagccttc ccgctgctat ttggaatctt taacttagtc
1381 tactgggcta cgtatttaaa cagagagcct cagctaaaag cccccacacc acatcaatag
1441 atcttttact cacattctgt tgttcagtcc tctgcactgg gaatttattt atgttctcaa
1501 cgcagtaatt cccatctgct ttattgcctc tgtcttaaag aatttgaaag tttccttatt
1561 ttcataattc atttaagaac aagagacccc tgtctggcag tctggagcaa agcagactat
1621 gcagcttgga gacaggattc tgacagagca agcgaaagag caaagtcatg tcagaaggag
1681 acagaatgag agagaaaaga gggggaagat ggttcaaaga tacaagaaaa agtagaaaaa
1741 aaaataacac ttaactaaaa cccctaggtc atttgtagat atatatttcc aaatattcta
1801 aaaaagatac tgtatatgtc aaaaatattt ttatgtgaag gtgtttcaaa gggtaaatta
1861 taaatgtttc atgaagaaaa aattttaaaa atctacgtct ttattacaca aactatggtg
1921 tgcttatgtt tttgttttgc tttttaaact gatgtatagc tttaacattt tgtttccaaa
1981 gctgaagatc cccattcttt ctctttgaaa aaaaaaaagg cctaatgcat tattttgtca
2041 taaaatgcta ttttaaaatt catggaactt tcatacgtaa aggtgcagtt gctcattgta
2101 gagcacattt agtccaatga agataaatgc tttaaatagt ttacttcact ttcatctgag
2161 cttttaccac tagactcaag gaagaataat tttaacagac atgtatactc catagaaact
2221 aaattaaaat agtttaaaaa tattcccttt ttcaccctat tttcagatag cacatgagcc
2281 caacactcac ttaattctca ttatgaagat gtttttagag gggcaaaaat attttgcaag
2341 ctctggaatt gttgaatgta ttcttttata taactacatt aaaagcttta gattgaaatt
2401 tatgactagc aaacaaaaat agaatatata aacgatatat gtaaatatac agcatgagat
2461 tgtacatttt ttactttttt aaaattgtgt tcttaaaata ttgtgtaaga atcactgcac
2521 ttagctgttg gaatgttgtt aaatgctatg gaaatacatt tagaacctgc atttaagaac
2581 agaacagcaa gtatgaacca catggaactt aaaacatatg ggtgtgaagt ccacttatgt
```

-continued

```
2641 agacaaaact tataatttcc aaactgttgt ctagtataca gtgatcagtt gctctctgtt
2701 caagtcattc cacacatttc cctattttag gctattataa tatagaaaga aaatgggaag
2761 cattagttgg agctagaaaa tgaactgtat attattgcta tatttgctaa taccaactat
2821 ttcaataagt gttgtaccat atgtagcatt aaatataaaa tacataaaag aatgtacaga
2881 aaatagcttt tattgagtaa tattacattt catttatact gtagcaatat atttgtaggt
2941 atactatgta agggctttaa ataaaagagg tccattaata cttccttata aaaattctag
3001 tctgtttcat tactgcccag atgttttaga gataaatatt tatgcagaag gtatttttga
3061 agtctccttt tgtctgatag agtttaacag atatttaaat ttagtgctca gaatccacaa
3121 gtcacggtct aaacacactt agaatactac agcataaatc tgttagcatt attgccaaat
3181 aagacagttg ggatccaaac ccaagtcttg agcaatgttt ttctcaaaaa gctgctatcc
3241 aatgatatag gaaaatacat tgtgttttcc taaacacact tttcttttta aatgtgcttc
3301 attgtttgat ttggtcctgc ctaaatttca caagctaggc caatgaaggc tgaatcaaag
3361 acatttcatc caccaatatc atgtgtagat attatgtata gaaaataaaa taaattatgg
3421 ctccaaaaaa aaaaaaaaaa
```

Other features and advantages of the invention will be apparent to those skilled in the art from the following detailed description and claims.

BRIEF DESCRIPTION OF THE DRAWINGS

The patent or applicatin file contains at least one drawing executed in color. Copies of this patent or patent application publication with color drawings will be provided by the Office upon request and payent of the necessary fee.

FIGS. 1A-1D depict characterization of BMPS during differentiation. FIG. 1A depicts a diagram of a differentiation protocol. FIG. 1B depicts size of aggregates measured during the 3D neuronal differentiation. Negative days on the x-axis represent 3D cells cultured in NPC medium while positive days represent 3D cells cultured in differentiation medium. FIG. 1C1-C5 depicts BMPS mRNA and miRNA expression of different markers during differentiation. FIG. 1D depicts flow cytometry population analysis of BMPS at different stages of differentiation.

FIG. 2A depicts co-immunostaining of neurons with markers. MAP2+ neurons were co-immunostained with the maturation marker Nestin at 2, 4, and 8 weeks of differentiation, which showed progressive increase of MAP2+ neurons and decrease of Nestin+ cells over time (panels a, b, c), demonstrating neuronal maturation. Co-immunostaining of neurons (NF-H) with the myelin marker MBP at 2, 4, and 8 weeks of differentiation (d,e,f, respectively) showed progressive increase of MBP+ cells in association with axonal processes. An increasing number of MBP+ cells (oligodendrocytes) was observed in association with axons (panels d, e, f). FIG. 2B depicts neuronal and glial cell diversity was evaluated at 8 weeks. Neurons (MAP2, NF, SYP and SMI32) were visualized interacting with glia (GFAP and NOGOA). Neurons disclosed characteristic perykaria, dendrites (MAP2, panels a, b) and axons (NF, SMI32, panels c-f) associated with glia. Neurons exhibited diverse neurotransmitter identities shown by identification of glutamatergic VGLUT1+ (panels g, h), GABAergic CALB+ (panels i, j) and dopaminergic TH (panels k, 1) neurons. FIG. 2C depicts that GFAP+ astroglia and CNPase+, O1+ and MBP+ oligodendroglia were identified. Oligodendroglia appeared mixed among astrocytes (panels a, b). O1+ (panels c, d) and MBP+ (panels e, f) oligodendrocytes were associated with axonal processes. Astrocytes established relationships with oligodendrocytes and exhibited characteristic multipolar processes (panels g, h). MBP+ oligodendrocytes issued processes in association with axons (panel i) 3D-reconstruction demonstrated myelinating processes resembling human myelination (panels j, k). Electron microscopy analysis of BMPS at 4 and 8 weeks of differentiation identified morphology of axonal structures and cells (e.g., oligodendrocytes) (panel 1). Myelinating-like processes, which closely resembled cross-sections of myelinated axons of the CNS were identified at 8 weeks of differentiation (panel m).

FIG. 3A depicts heat map recordings from a 48-well plate. FIG. 3B depicts illustration of an active well showing spike morphology and FIG. 3C depicts spike activity. FIGS. 3D and 3E depicts phase-contrast imaging of the mini-brains on MEAs, electrode diameter is 40-50 μm and inter-electrode space is 350 μm. FIG. 3F depicts activity pattern recordings over 0.05 spikes/sec of the electrode over 10 min.

FIG. 4A depicts viability (resazurin assay) of BMPS after 24 hours rotenone exposure. FIG. 4B depicts ROS (OxiSelect™ In Vitro ROS/RNS Assay Kit) production of BMPS after 12 and 24 hours rotenone exposure. FIG. 4C depicts viability (resazurin assay) of BMPS after 24 hours MPP+ exposure. FIG. 4D depicts ROS (OxiSelect™ In Vitro ROS/RNS Assay Kit) production of BMPS after 12 and 24 hours MPP+ exposure. FIGS. 4E and 4F depict confocal images of BMPS exposed to different concentrations of rotenone and MPP+ for NF200 (Red), TH (Green) and Hoechst nucleus staining (Blue). FIG. 4G depicts expression of genes associated with oxidative stress and PD by real time RT-PCR. Graphs represent the relative expression of different markers compared to control (cells not treated) after 24 hours exposure to 5 μM rotenone and 1 mM MPP+. Genes of interest: mitochondrial complex 5 (ATP50, ATP5C1), mitochondrial complex 1 (NDUFB1), oxidative stress (KEAP1) and genes related to PD (TH, SNCA, TBR1, CASP1). Data are presented as mean±SD, of 3 independent experiments performed in 3 replicates. *$P<0.05$ comparing to control (untreated).

FIG. 5A depicts morphological characterization with immunostaining of neurons (MAP2, Syn1, TH, SYP), neural precursor cells (nestin) and glial cells (GFAP) at 8 weeks of differentiation. FIG. 5B depicts expression of genes in healthy BMPS vs. Down's Syndrome BMPS before and after treatment with 5 μM rotenone, after 24 hours exposure. Genes of interest include CNS markers (TH, OLIG2, NEFH), mitochondrial markers (ATP5C1, ATP5J, ATP50) and ROS markers (NFE2L2, SOD1) which were measured by comparing control with exposed cells to rotenone on both healthy and Down syndrome derived mini-brains. FIGS. 5C and 5D depict karyotyping of iPSCs derived from the patient with Down's Syndrome. aCGH+SNP results for Down syndrome iPSC line are shown.

FIG. 8A shows at 8 weeks, neuronal populations exhibited a diversity of neurotransmitter identities as shown by identification of dopaminergic TH+ (a,b), glutamatergic VGLUT1+ (c,d) and gabaergic calbindin+ (e,f) neurons. Neurons disclosed characteristic axons (NF) and synaptic proteins (SYN) (g,h). FIG. 8B depicts two distinctive glial populations were identified in close interaction with neuronal populations, GFAP+ astroglia and CNPase+, O1+, NOGOA+ oligodendroglia. O1+ oligodendrocytes were closely associated with axonal processes (NF) (a,b), CNPase+ oligodendroglia appeared mixed among GFAP+ astroglia (c,d) and exhibited the characteristic multipolar glial processes, which extended from the perykaria (e,f). NOGOA+ cells were associated with MAP+ neurons (g,h). FIG. 8C depicts example of custom algorithm created using the Cellomics Target Activation image-analysis software package to study astrocytes and oligodendrocytes (a,b,c,d). Quantification of cell populations as a percentage of the total nuclei count showed 3% NOGOA+ positive cells, 9% CNPase+ cells and 19% GFAP+ cells at 8 weeks (e). FIG. 8D shows Co-expression of mature oligodendroglia markers (MBP and O2). FIG. 8E shows expression of neuronal markers (VGLUT, TUJ1, SYN). Scale Bar: 10 μm.

FIG. 9A shows a diagram of μBS generation procedure under one embodiment. FIG. 8B provides a comparison between μBS and BS using different microglia markers (TMEM119, Mertk, Axl) and hematoxylin/eosin (HE). FIG. 9C provides confocial images of immunohistochemistry for the microglia marker IBA1 (green), the neuronal marker NF200 (red) and nuclear staining (Hoechst 33342, blue) in μBS. 48 h after microglia incorporation. FIG. 9D shows details of microglia aggregations in μBS. Green arrow indicated microglia cluster and red arrow indicates the BS. Bars represent 100 μm (FIG. 9B),m (FIG. 9C, upper panel), 20 μm (FIG. 9C, all other panels), and 50 μm (FIG. 9D).

FIG. 10A shows gene expression of IL6, IL10, IL1b, CCL2, and TNFa after LPS treatment on the different models (BS, μBS, and microglia cells). Data are shown as fold change of treated versus untreated up to an hour post treatment (3, 6, 12 and 24 h after treatment). FIG. 10B shows changes in cell cycle in percentage of the cells in G2 plus S phase in microglia cells, BS and μBS treated or non-treated with LPS. Each dot symbol represents a replicate sample of (N+3). FIG. 10C shows Annexim V Apoptosis Muse assay. Results show % live cells microglia, as μBS cells treated (+) or not treated (−) with LPS. Each symbol represent a replicate (n=3). Statistical analysis in FIG. 10A was performed using Dunnett test on ΔΔCt. The asterisks symbols represents *$P < 0.05$ and **$P < 0.01$ (two independent experiments and three boilogical replicates on each experiment).

FIG. 12A shows the growth kinetics of flaviviruses over time for the three models. The viral load (RNA ccopies/mL) are shown with standard deviation. FIG. 12B depicts changes in cell cycle shown as percentage of cells in G2/S phase in BS, μBS, and microglia treated or non-treated with the different viruses, FIG. 12C shown Annexin V Apoptosis Muse assay results. Results represent % live cells in BS, μBS, and microglia samples after the different flavivirus treatments. FIG. 12D shows gene expression relatvive quantification for TNFα, CCL2, and IL-6 over the time. Statistical analysis was performed using the Dunnett's Test (*mean eqqual p <0.05 and **P <0.01) for two independent experiments, three biological replicates on each experiment.

FIGS 13A-13C show an alternative protocol performed to incorporate microglia into BS 3D cultures. When $NPC_3$ reaches 95% confluence, 1 / $10^6$ microglia were added to the flask. After 24 h, the co-culture was detached mechanically with a cell scraper (Sarstedt, Newton, NC, United States, 2-position, Blade 25, 83.1830), re-pipetted for disaggregation, and counted using Countless Automated Cell Counter (Invitrogen, Carlsbad, CA, United States), 2+$10^6$ cells per well were then plated in non-treated 6-well plates and cultures as BS for 8 weeks. The dendity was chosen to have approximately 10% microglia cells. FIG. 13A shows a diagrammatic representation for the alternative protocol.

FIG 13B is immunohistochemistry showing microglia marker (IBA1) and neuronal marker (NF200). FIG. 13C shows immunohistopathology characterization of the microglia incorporation for this method of μBS generation markers are meentioned in Example.

DETAILED DESCRIPTION OF THE INVENTION

Figure 1A:
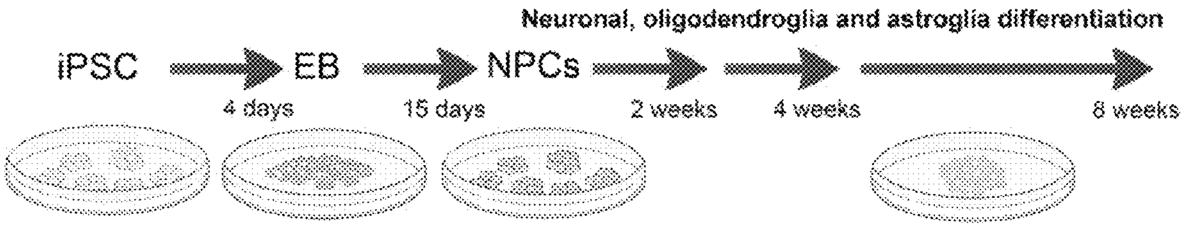

The present invention is based, at least in part, upon the discovery that brain microphysiological systems (BMPS) can be produced from induced pluripotent stem cells (iPSCs). Furthermore, the invention provides for reproducible BMPS that differentiate into mature neurons and glial cells (astrocytes and oligodendrocytes) in the central nervous system. This model is spontaneously electrophysiological active and may be reproduced with patient or genetically modified cells. The derivation of 3D BMPS from iPSCs has applications in the study and treatment of neurological and neurodevelopmental diseases. In some embodiments, the present disclosure provides for compositions and methods to study and/or treat neurodevelopmental and neurodegenerative disorders. In some cases, the neurodevelopmental and neurodegenerative disorders treated and/or studied by the present disclosure include, but are not limited to, autism, encephalitis, trauma, brain cancer, stroke, Amyotrophic lateral sclerosis, Huntington's Disease, muscular dystrophy, neurodegenerative disorder, neurodevelopmental disorder, Multiple Sclerosis, infection, Parkinson's Disease and Alzheimer's Disease.

As described herein, the present disclosure provides for the derivation of a multitude of identical brain microphysiological systems (BMPS) from stem cells, preferably of human origin, but including stem cells from animal origin. The preferred starting material are human induced pluripotent stem cells or embryonic stem cells, although other pluripotent stem cells such as, for example, neuronal precursor cells and mesenchymal stem cells may also be employed. Human in-vitro models of brain neurophysiology are needed to investigate molecular and cellular mechanisms associated with neurological disorders and neurotoxicity. The techniques herein provide a reproducible iPSC-derived human 3D BMPS that includes differentiated mature neurons and glial cells (astrocytes and oligodendrocytes) that reproduce neuronal-glial interactions and connectivity. BMPS mature over about eight weeks and show the critical elements of neuronal function including, but not limited to, synaptogenesis and neuron-to-neuron (e.g. spontaneous electric field potentials) and neuronal-glial interactions (e.g. myelination). Advantageously, the BMPS described herein include mature neurons (e.g., glutamatergic, dopaminergic and GABAergic neurons) and glial cells (e.g., astrocytes and oligodendrocytes). Quantification of the different cell types exhibited high reproducibility between experiments. Moreover, the BMPS disclosed herein present neuron and glial functions such as spontaneous electrical activity and axon myelination. The BMPS described herein are able to mimic the microenvironment of the central nervous system, which is a significant advance in the field of neurobiology as this ability has not been achieved at this level of functionality, reproducibility, and consistency in prior art in vitro systems.

In particular, the high amount of myelination of axons (up to 40%) in the disclosed BMPS represents a significant improvement over the prior art. Myelin pathology is a rather frequent condition in demyelinating and inflammatory disorders such as multiple sclerosis and post-infection diseases as well as other neurological diseases such as acute and post-traumatic brain injury, stroke and neurodegenerative disorders (see e.g., Fumagalli et al., 2016; Tse and Herrup, 2016). Moreover, the myelination process can be perturbed by exposure to chemicals and drugs (see e.g., Garcia et al., 2005; Brubaker et al., 2009; Creeley et al., 2013) during brain development and adulthood. For example, the BMPS disclosed herein show 40% overall myelination after 8 weeks of differentiation. Myelin was observed by immunohistochemistry and confirmed by confocal microscopy 3D reconstruction and electron microscopy. These findings are of particular relevance since myelin is crucial for proper neuronal function and development. The ability to assess oligodendroglia function and mechanisms associated with myelination in this BMPS model provide an excellent tool for future studies of neurological disorders such as multiple sclerosis and other demyelinating diseases. Thus, the BMPS provides a suitable and reliable model to investigate neuron-neuroglia function in neurotoxicology or other pathogenic mechanisms that has heretofore not been available in the prior art.

The method disclosed combines gyratory shaking or regular stirring and the addition of growth factors to obtain the basic model. Suitable conditions as to how to achieve reproducible brain composition are disclosed herein. In contrast to earlier models, identical units of BMPS are produced, which allow comparative testing for the purpose of product development or safety assessments.

According to the techniques herein, a number of additional measures complement the basic BMPS to increase their completeness in modeling the human brain and improve its usefulness for such testing, for example:

1. The addition of microglia: All stem-cell-derived brain models described so far lack micro-glia. The techniques herein provide that the addition of micro-glia precursor cells and suitable growth factors may allow microglia to be added to the model. Suitable cells may be monocytes (e.g., human monocytes), hematopoetic stem cells, respective (pro-) monocyte cell lines, and isolated microglia.

2. The addition of a blood-brain-barrier: The human brain is protected by a tight blood-brain-barrier that excludes many substances from the brain. For the first time, the techniques herein provide a method to form a blood-brain-barrier to the BMPS via cells such as, for example, human endothelial cells.

3. Addition of reporter and reporter cells: During the generation of the BMPS, cells carrying reporter for testing purposes may be used or added. These include, but are not limited to, fluorescent or luminescent markers to indicate a certain cell lineage or cell response. Genetic transient or permanent transfections are the primary, but not only, method of choice.

4. The BMPS may also be produced, entirely or in its components, from cells from a specific genetic background, e.g. from patients with a specific disease or after selective genetic manipulation of the cells.

5. The versatility of the BMPS may be improved by combining it with electrodes including, but not limited to, micro-electrode arrays (MEA).

6. The versatility of the BMPS may be improved by combining it with other MPS (organ models) platforms such as, for example, microfluidic human-on-chip systems, perfusion chambers and others.

7. Transportability of BMPS: Methods to cryopreserve BMPS were developed, which allow transport to other laboratories and testing or integration into multi-MPS platforms.

Simplified neural in vitro systems do not reflect physiology, interactions between different cell types, or human genetics. Induced pluripotent stem cells (iPSC)-derived human-relevant microphysiological systems (MPS) better mimic the organ level, but are too complex for chemical and drug screening. As described herein, a reproducible 3D brain MPS (BMPS) that differentiates into mature neurons and glial cells (astrocytes and oligodendrocytes), which reproduces the topology of neuronal-glial interactions and connectivity in the central nervous system was developed. BMPS from healthy donors or patients evolve from a period of differentiation to maturity over about 8 weeks, including synaptogenesis, neuron-neuron interactions (e.g. spontaneous electric field potentials) and neuronal-glial interactions (e.g. myelination of axons), which mimic the microenvironment of the central nervous system. Effects of substances on neurodevelopment may be studied during this phase of BMPS development. In an exemplary embodiment, the techniques herein were used to study Parkinson's disease (PD) by evaluating neurotoxicants with a link to PD pathogenesis. Exposure to 5 μM rotenone or 100 μM 1-methyl-4-phenylpyridinium (MPP+) (or 1 mM 1-methyl-4-phenylpyridinium (MPP+) for gene expression studies) disrupted dopaminergic neurons, as observed by immunohistochemistry and altered expression of PD-related genes (TH, TBR1, SNCA, KEAP1, NDUFB1, ATP5C1, ATP50 and CASP1), thus recapitulating hallmarks of PD pathogenesis linked to toxicant compounds in the respective animal models. The BMPS, as described herein, provide a suitable and reliable model to investigate neuron-neuroglia function in neurotoxicity or other pathogenic mechanisms.

There is growing concern about the continuing increase in neurodevelopmental and -degenerative disorders such as autism [1, 2], Parkinson's [3] and Alzheimer disease [4]. Although genetic factors play an important role, environmental factors such as pesticides, air pollution, cigarette smoke, and dietary toxicants appear to contribute [5, 6, 7]. Due to a lack of mechanistic understanding, it is difficult to study their contributions and interactions with respect to neurotoxicity and neurological disorders. The complexity of the CNS makes it challenging to find appropriate in vitro human-relevant models, ideally from different genetic backgrounds, that are able to recapitulate the relevant pathophysiology. The poor predictive ability of animal-based models for human health, which may fail to mimic human pathology as outlined in the costly and time-consuming current developmental neurotoxicity (DNT) guidelines, contributes to the lack of reliable information on DNT mechanisms [8]. At the same time, more than 90% of all drugs fail clinical trials after extensive animal testing [9] due, in part, to the fact that animal studies often do not reflect human physiology and inter-individual differences. Simple in vitro systems do not represent physiology and organ function [10], which creates a critical demand for better models in drug development, study of disease mechanisms and progression, bioengineering and toxicological testing.

Attempts to generate more complex organotypic cultures or microphysiological systems (MPS) [11, 12, 13, 14] have resulted in more physiological multicellular 3D co-culture models able to simulate a functional part of the brain [15, 16]. 3D MPS have shown increased cell survival, differentiation, cell-cell interactions and can reproduce the complexity of the organ more closely [18]. Recent US research programs by NIH, FDA, DARPA, and DTRA have initiated the systematic development of MPS, including the model presented here, and their combinations to human-on-a-chip technologies to assess the safety and efficacy of countermeasures to biological and chemical terrorism and warfare [19].

The discovery of induced pluripotent stem cells (iPSC) and new protocols to differentiate them into various cell types have boosted the development of human in vitro models [20, 21]. iPSC from healthy or patient donors with a specific disease [22, 23, 24, 12] used in MPS promise more human-representative models, e.g. the brain organoids by Lancaster et al. and Kadoshima et al., have been able to recapitulate features of human cortical development [15, 16]. These complex systems present novel tools to study biological mechanisms in the CNS, however, they have certain limitations: 1) an elaborate and complex protocol, 2) size differences between organoids, 3) necrosis in the center of the organoid, 4) low reproducibility in cell differentiation. The human BMPS described herein overcomes these limitations. The reproducible in vitro iPSC-derived human 3D brain microphysiological system (BMPS) is comprised of differentiated and mature neurons and glial cells (astrocytes and oligodendrocytes).

The techniques herein provide a reproducible BMPS that contains several different cell types of the human brain, such as glutamatergic, dopaminergic and GABAergic neurons, astrocytes and oligodendrocytes. Moreover, the system has shown neural functionality as observed by spontaneous electrical activity and myelination of axons. Furthermore, the BMPS is reproducible from batch to batch and displays differences between healthy and patient donors. In addition, the obtained results demonstrate the application of such BMPS to the study of neurological disorders such as, for example, Parkinson's Disease (PD).

The brain MPS described herein is a versatile tool for more complex testing platforms and strategies as well as research into neurotoxicity (e.g., developmental), CNS physiology and pathology. Some stem cell-derived brain microphysiological systems have been developed in the latest years showing the capability to recapitulate some of the in vivo biological process [36, 37, 38]. These models have an enormous advantage over the classical in vitro models to study various differentiation mechanisms, developmental processes and diseases [15]. However, they are mostly based on human embryonic stem cells raising ethical concerns and not allowing the use of patient cells. Moreover, they require complicated protocols that may reduce the reproducibility of the system and make it difficult to use in other fields such as chemical and drug screening. Some of these complex organoids have a large diameter, which can lead to extensive cell death, visible in the core of these tissues [15]. This may be due to insufficient diffusion of nutrients and oxygen in these non-vascularized systems, which may generate artifacts in toxicological and disease measurements and make it difficult to study different endpoints in a medium- to high-throughput manner. In addition, it will be challenging to adapt endpoints, established for relative simple 2D cultures, to such complex models. In the study described herein, the ability to generate a high number of viable (about 800 per batch), BMPS that are homogeneous in size (e.g., about 300 μm) and shape using iPSC by applying a constant or regular gyratory shaking or stirring technique as described earlier for rat re-aggregating brain cell cultures [40] is shown. Control of the size using specific shaker speed allowed the aggregates to be maintained below 350 μM in diameter (FIG. 1B) and avoid disparate morphology and/or necrosis in the middle of the organoids. Moreover, a spherical homogeneous shape facilitates fluorescent quantification and further imaging-based endpoints as well as reproducibility between aggregates. The BMPS had reproducible cell composition by immunomorphological quantification, assessment of imaging-based endpoints and neurophysiological testing.

Figure 1B:
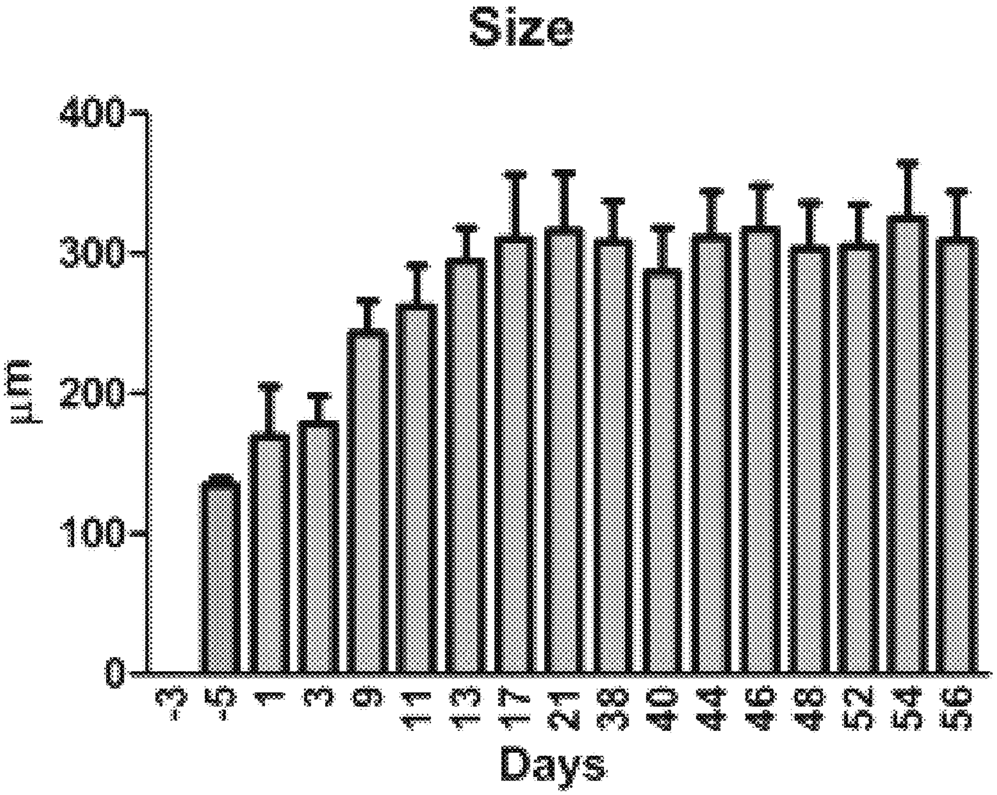
Figure 1D:
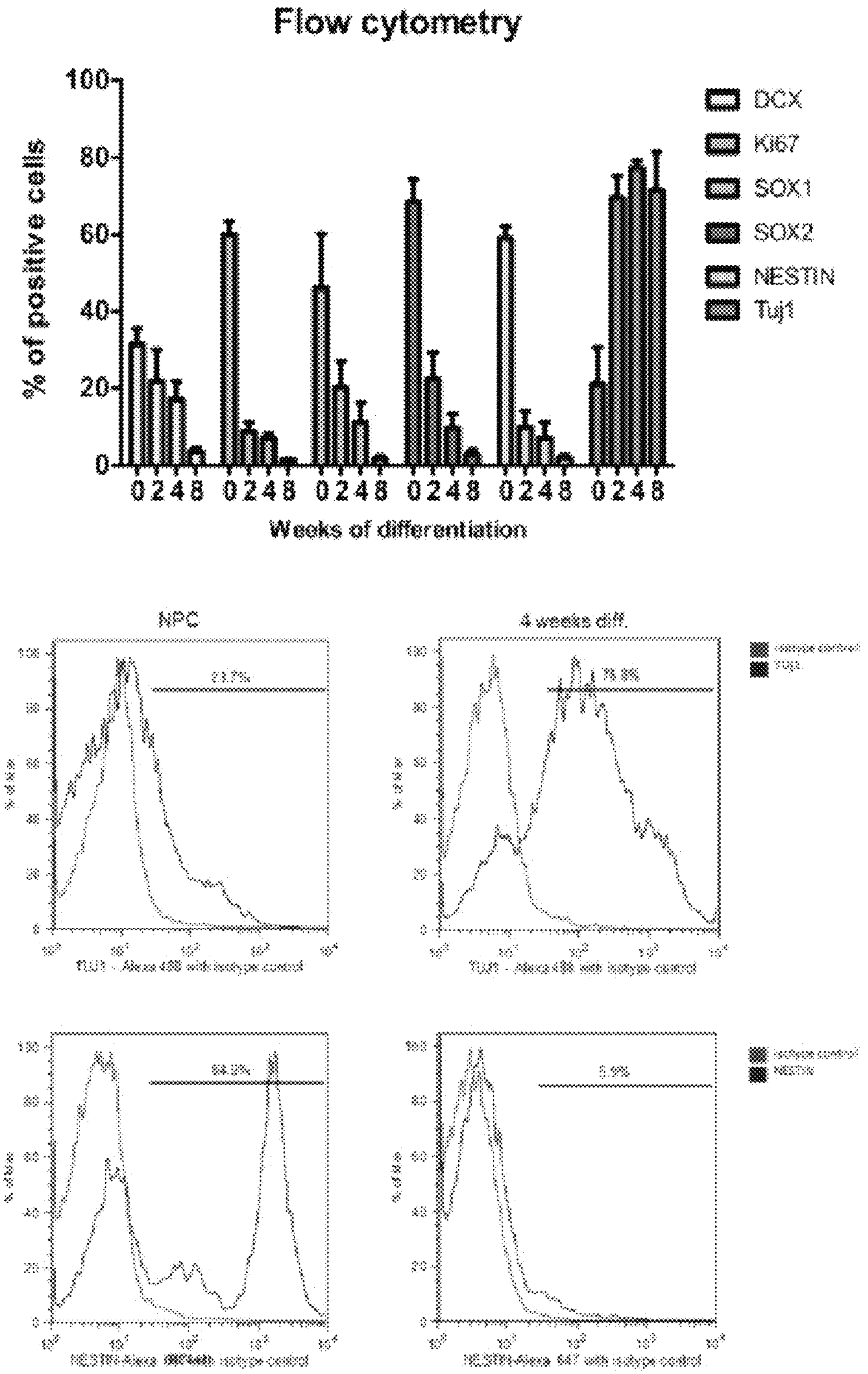
Figure 2A:
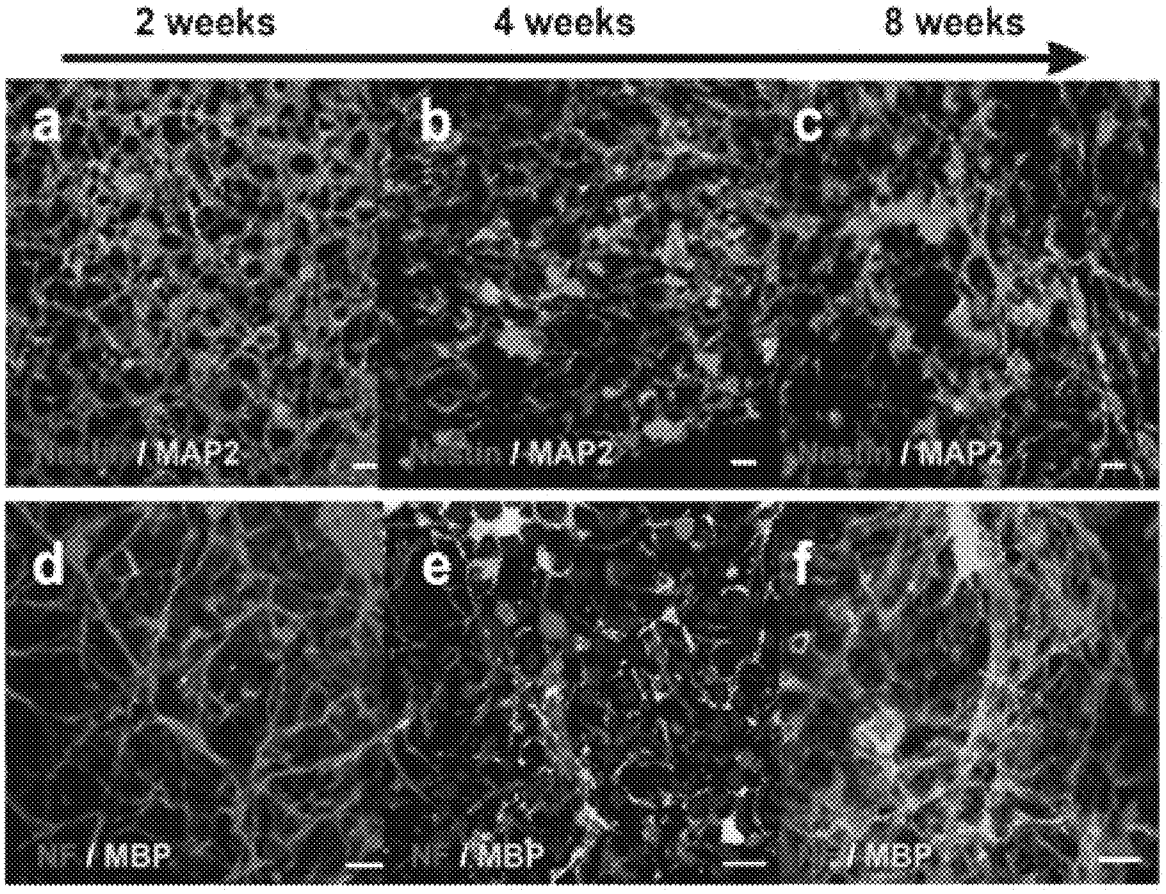
FIGS. 2A-2C depict morphological characterization of BMPS.
Figure 2B:
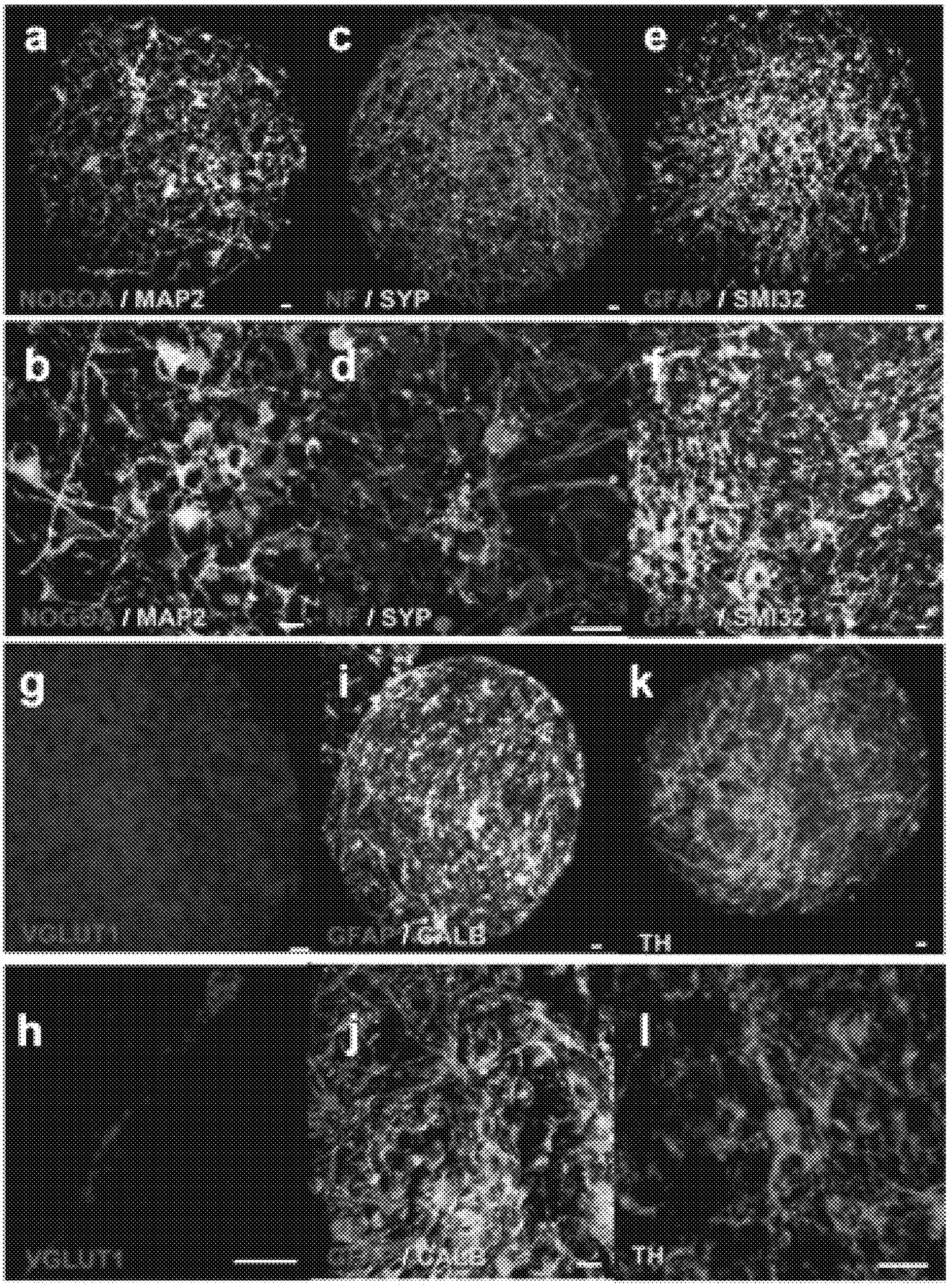

The 3D differentiation protocol described herein covered stages from neuronal precursors to different cell types of the mature CNS. After 2 weeks, BMPS consisted of an immature population of cells, showing minimal neuronal networks, low percentage of mature astrocytes and oligodendrocytes, with no myelin basic protein expression (FIG. 1C). Cell populations in the BMPS were further differentiated and matured over time (FIG. 2A). Evidence of iPSC differentiation into mature BMPS was supported by decreased Nestin expression over time. Nestin is normally expressed in embryonic tissue and its expression decreases with age in humans, therefore its decrement is a sign of maturation towards the adult phenotype [41, 42]. Also, the increasing presence of mature neuronal and glial markers such as MAP2, GFAP, Olig1 and MBP corroborate differentiation of the system. Different markers of pluripotency and proliferation decreased during the differentiation process, indicating maturing of the in vitro system (FIGS. 1C and 1D). Neuronal precursor markers such as Nestin, SOX1, SOX2 and the proliferation marker Ki67 decreased at the gene expression level and in flow cytometry measurements during the differentiation process (FIGS. 1C and 1D). Gene expression studies, flow cytometry, image analysis, immunostaining and miRNA studies have demonstrated an increase of cell maturation markers, which follows the BMPS differentiation (FIGS. 1A-1D, 2A-2H and 9A-9C). Obtained data demonstrate that this simple protocol is sufficient to generate representative CNS cell phenotypes that can reproduce various stages of differentiation. The presence of GABAergic neurons, dopaminergic neurons and glutamatergic neurons was observed by immunohistochemistry and real-time-PCR data (FIG. 1C and FIG. 2B). In addition, miRNAs such as mir-124, mir-132, mir-128, mir-137 and mir133b with a role in nervous system differentiation and neuronal degeneration [43, 44] increased during differentiation in patterns consistent with the in vivo situation. Moreover, the BMPS described herein produced spontaneous electrical activity (FIG. 3) confirming neuronal functionality of the system. However, further optimizations of the electrophysiological measurements using MEAs in 3D systems are needed.

Figure 2C:
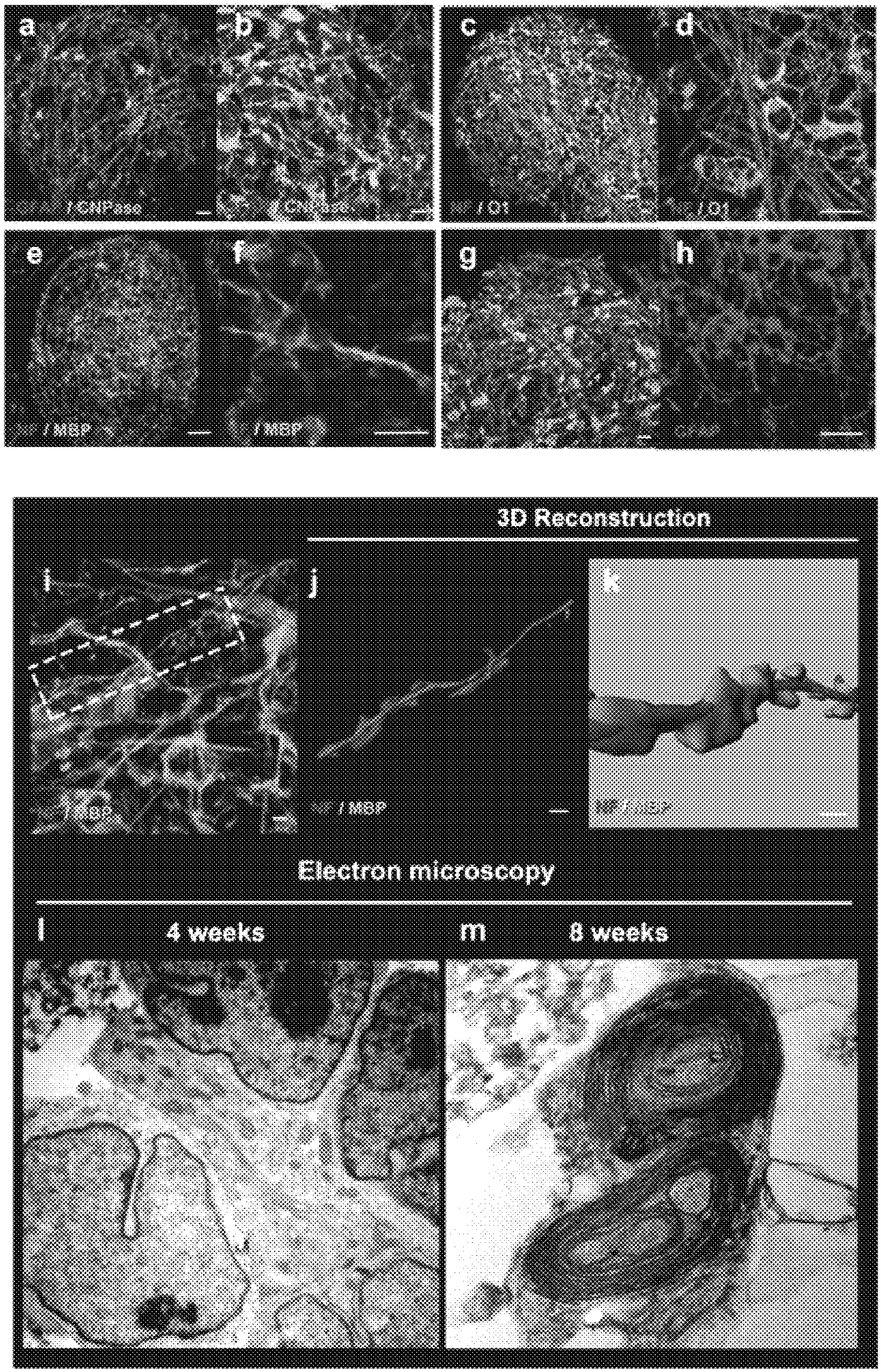

Most of the brain MPS published so far are entirely focused on neurons and not glia populations [45, 46]; the brain MPS described herein is the first 3D model with fully characterized mature human oligodendrocytes, astrocytes and neurons, derived from iPSC. Astrocytes and oligodendrocytes play an important role during neuronal development, plasticity and neuronal injury. Astrocytes have a role in protecting neurons, increasing neuronal viability and mitochondrial biogenesis from both exogenous (e.g. chemicals) or endogenous (such as glutamate-induced excitotoxicity or the Alzheimer related Aβ1-42) toxicity [47, 48, 49, 50]. Astrocytes have an especially important role in neuroprotection from oxidative stress. Oxidative stress is known to be involved in a number of neuropathological conditions (such as neurodegenerative diseases) [51, 52, 53]. Thus, the presence of astrocytes in a biological system to study disease is crucial due to their role in detoxification and neuronal protection. Immunochemistry results from the iPSC-derived BMPS showed low numbers of astrocytes (GFAP-positive cells) at 2 weeks of differentiation, which increased continuously throughout differentiation (FIG. 2F-2H, and FIG. 2A). Real-time RT-PCR data supports these findings, as a continuous increase in both s100b and GFAP mRNA levels could be observed from 2 weeks up to 8 weeks old BMPS. Immunohistochemistry and RT-PCR data results showed increasing numbers of astrocytes (GFAP-positive cells) in the BMPS model, reaching 19% astrocytes of the total cell population at 8 weeks. After 4 weeks of differentiation, astrocytes demonstrated increased positive staining for GFAP and the presence of glial network was observed (FIG. 2C, panels g, h). At the same time, the presence of oligodendrocytes and myelination of axons could be observed in the system described herein. This process is highly important, since it is known to be involved in many degenerative diseases such as multiple sclerosis [54], congenital hypomyelination [55], progressive multifocal leukoencephalopathy caused by JC virus infection [56], periventricular leukomalacia (PVL) [57] and Alzheimer's disease [58]. Moreover, several chemicals such as ethanol [59], tellurium [60] and lead [(61, 62, 63, 64, 65] have shown to have an effect on the myelination process.

The presence of astroglia and oligodendroglia in the model described herein brings the system closer to the in vivo brain physiology, which is a crucial component to study neurodegeneration and neurotoxicity. In addition, the system has shown functionality as seen by imaging of cell-cell junctions, myelination, a rich astroglial network and electrical activity (FIG. 3). These characteristics make the BMPS described herein a promising tool to study interactions between human neuronal cells in neurological diseases. The use of iPSCs makes it possible to study genetic factors and gene/environment interactions.

An assessment of the myelination process by quantification of MBP immunostaining along axons showed an increase over time reaching 42% of myelinated axons at 8 weeks (FIG. 2D). 3D reconstruction of confocal z-stacks images (FIGS. 2C and 2E) and electron microscopy confirmed the wrapping of axonal structures after 8 weeks of differentiation (FIG. 2C). These findings are of particular relevance since myelin is a critical element for proper neuronal function and development, the ensheathment of axons by myelin allows faster action potential transmission, reduces axonal energy consumption and protects the axons from degeneration[79]. Furthermore, recent evidence suggests that oligodendrocytes and myelin have a role in the metabolic support of axons independent of their role in action potential conduction, highlighting their importance in neuronal survival[80]. The ability of assessing oligodendroglia function and mechanisms associated with myelination in the BMPS model provide an excellent tool for future studies of neurological disorders such as multiple sclerosis and other demyelinating disorders.

Figures 3B, 3C, 3D, 3E, 3F:
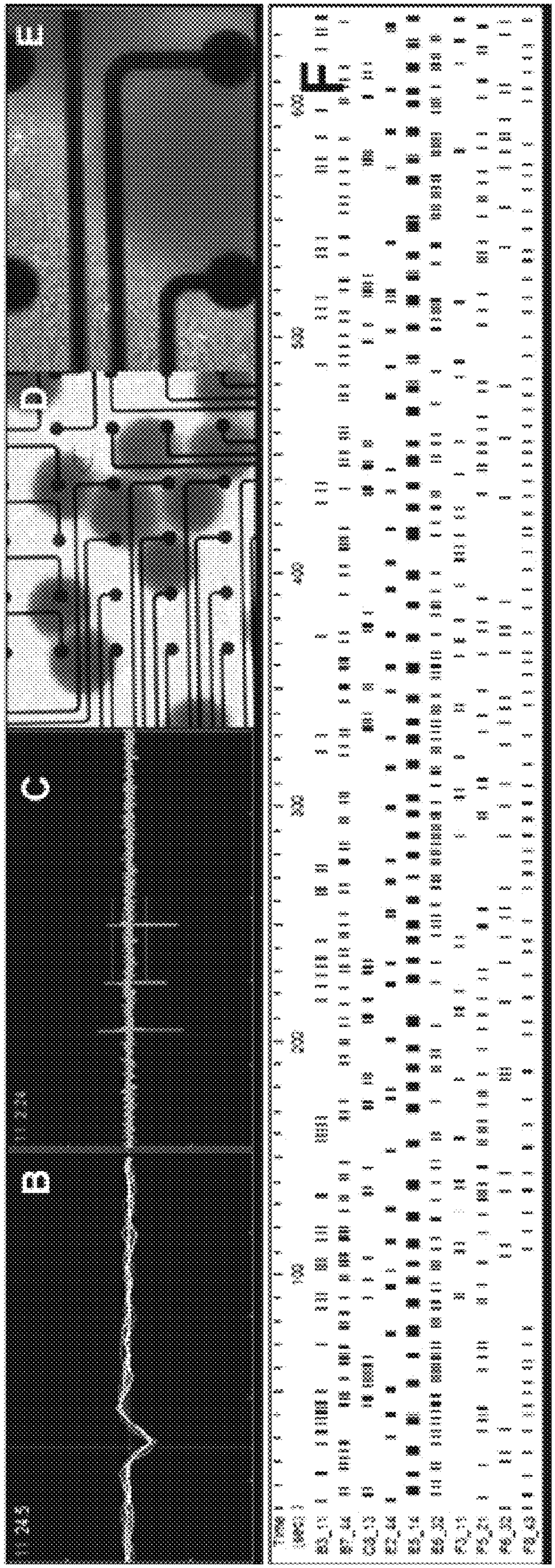
Figure 4A:
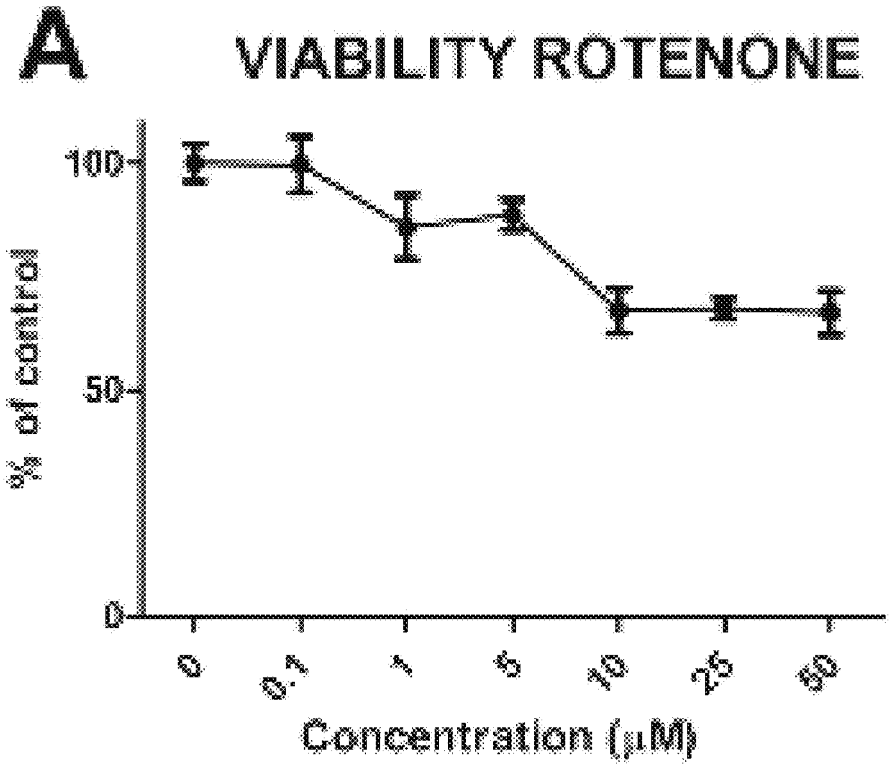
FIGS. 4A-4G depict Parkinson's disease (PD) application of BMPS. BMPS were differentiated for 4 weeks and exposed to rotenone and MPP+ for 12 and 24 hours.
Figure 4B:
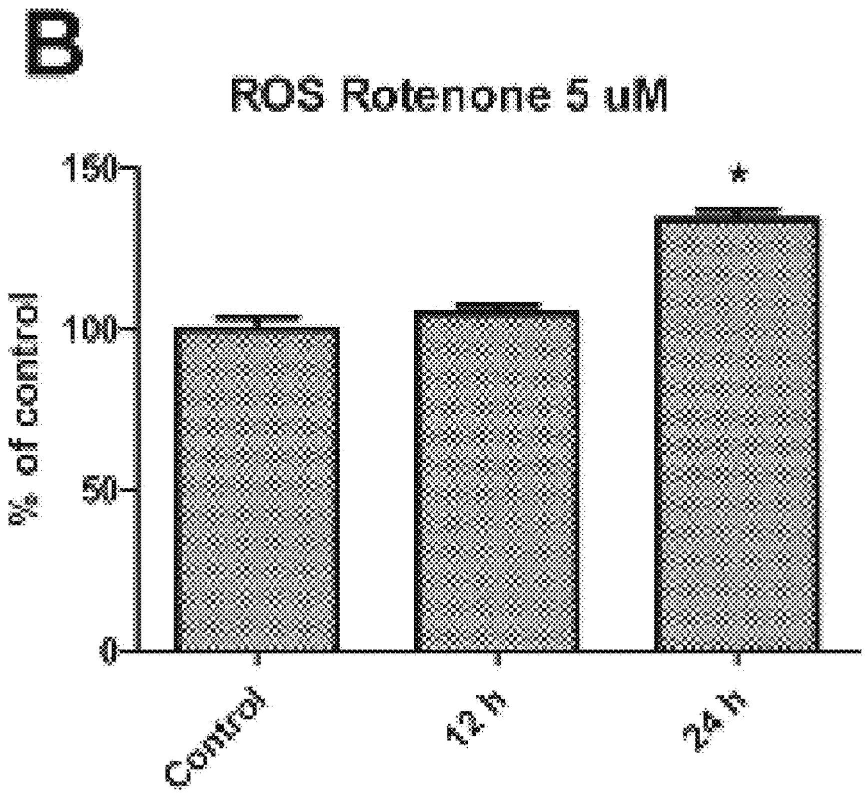
Figure 4C:
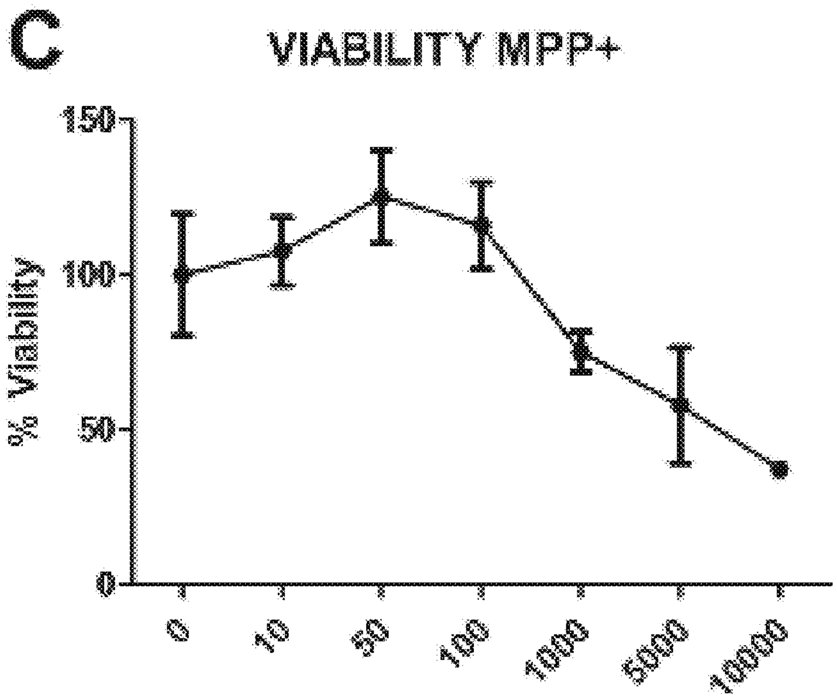
Figure 4D:
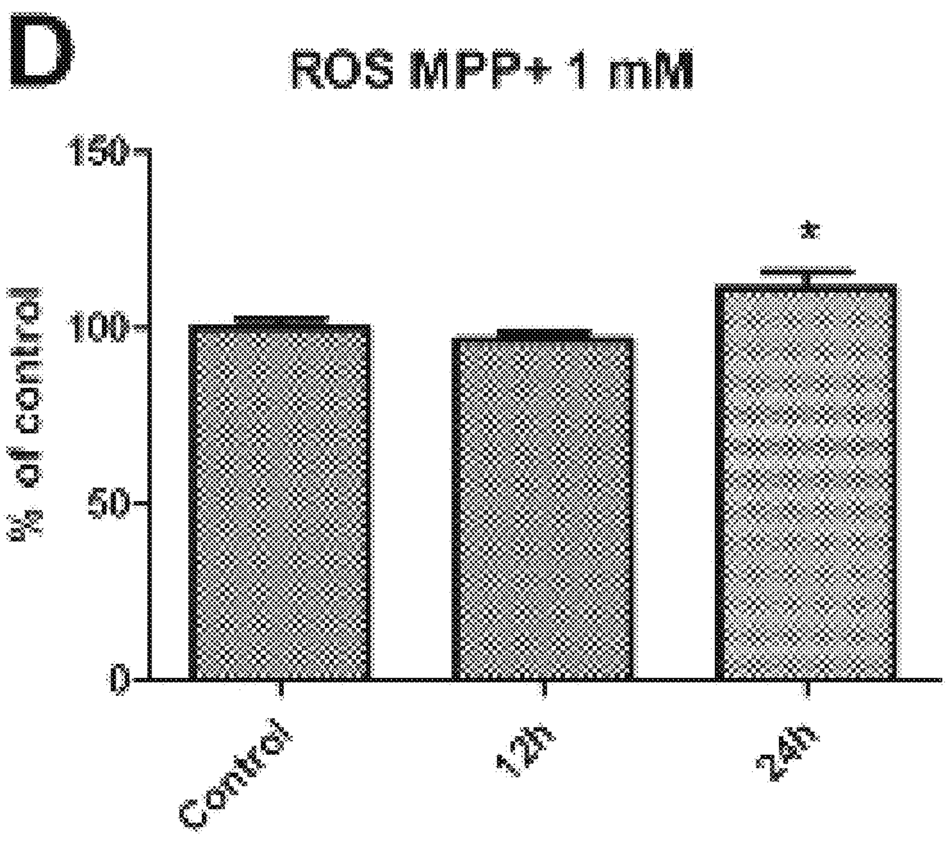
Figures 4E, 4F:
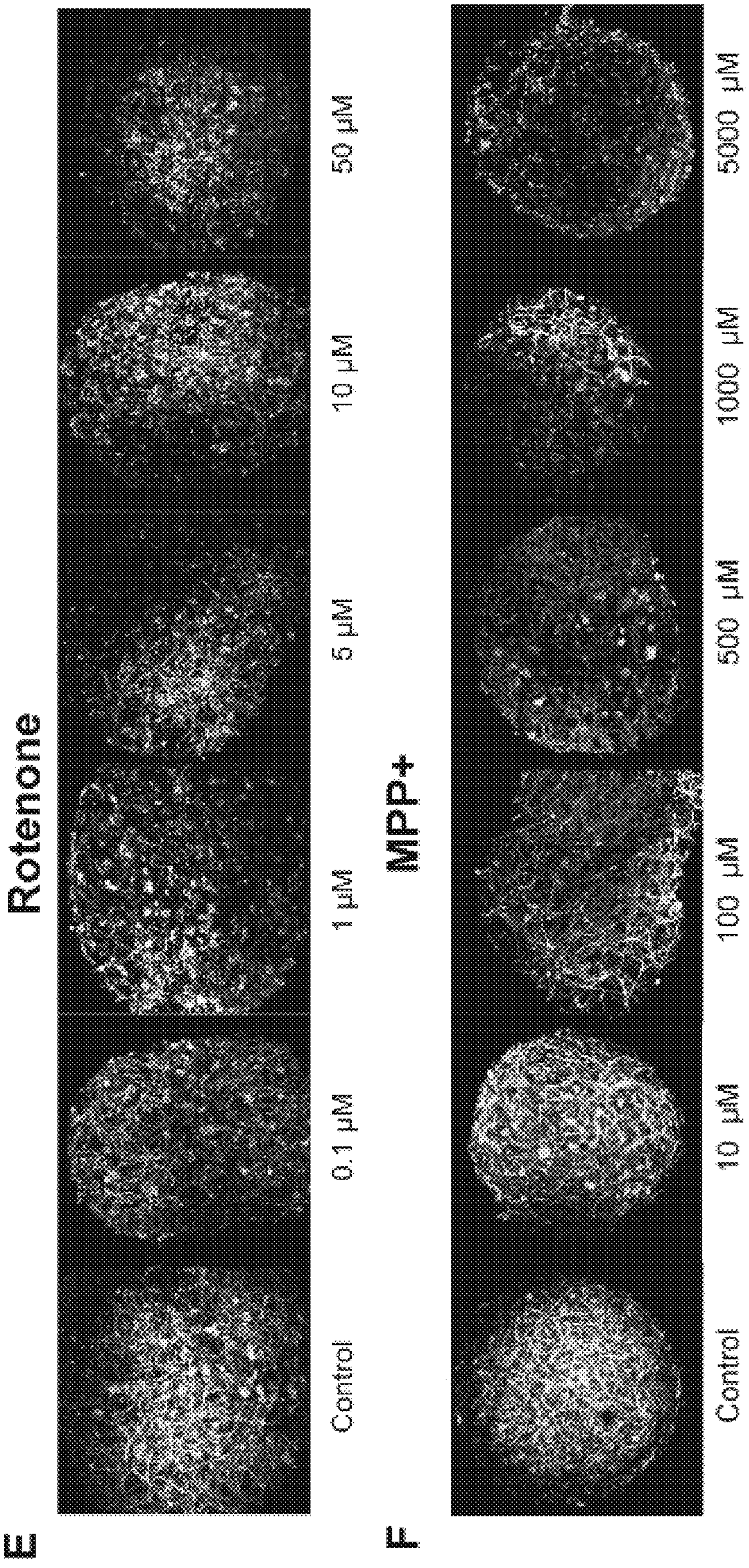
Figure 4G:
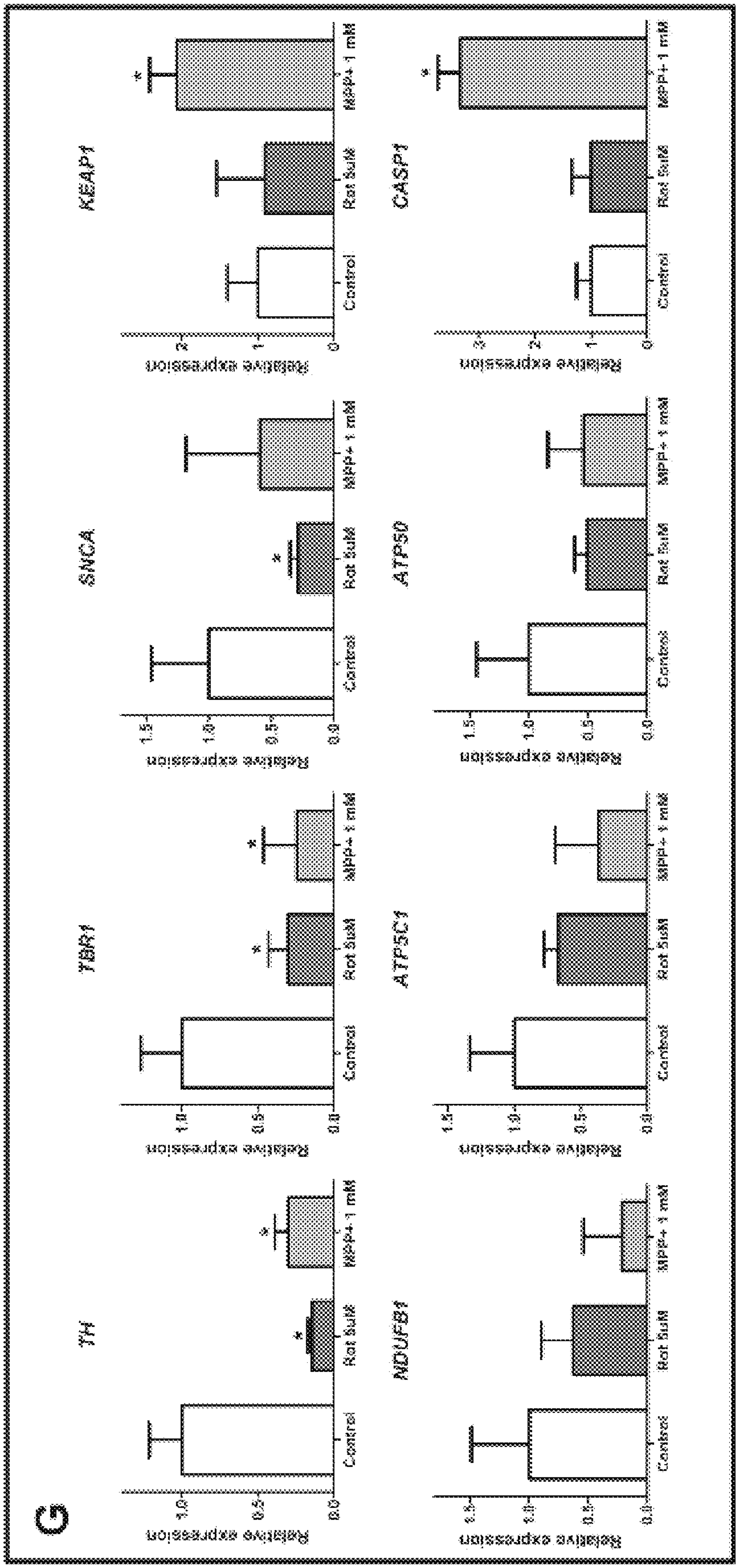
Figure 5A:
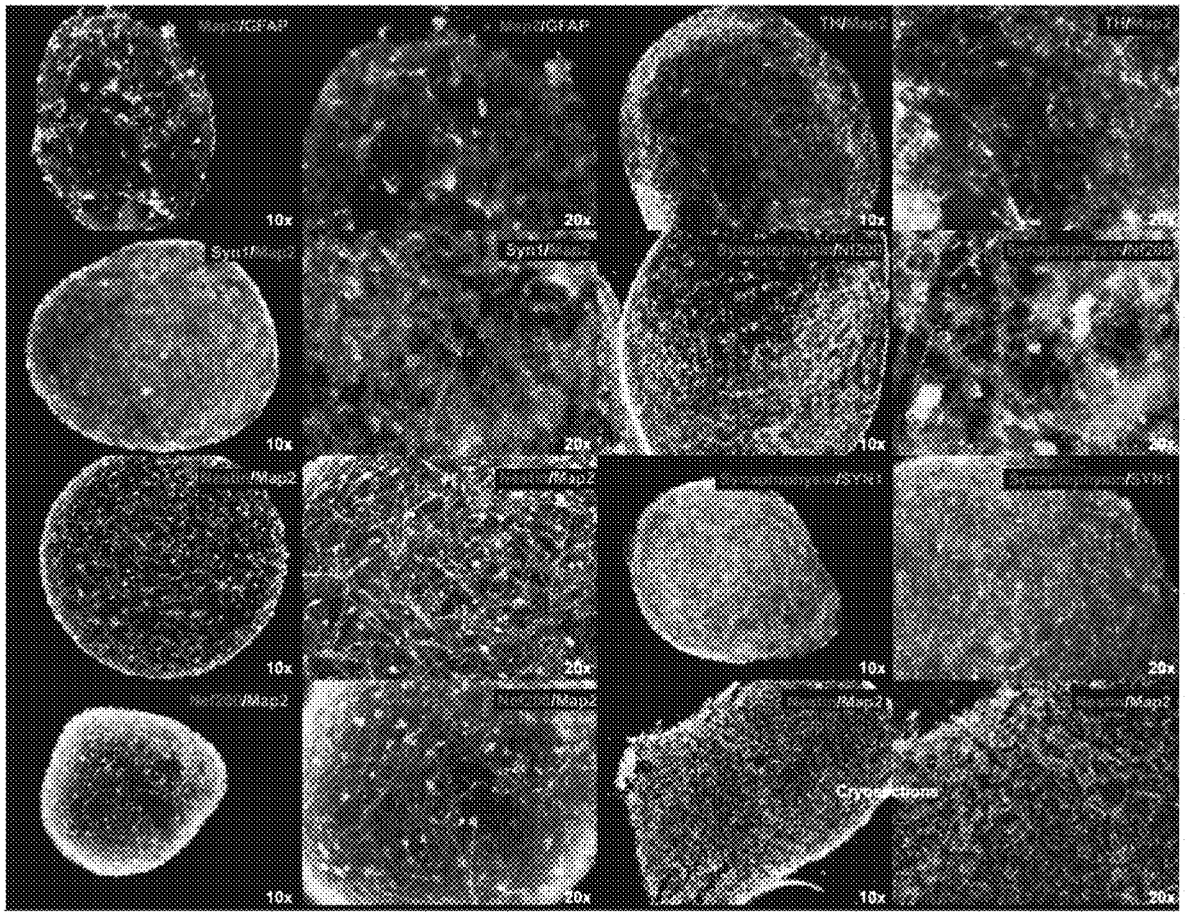
FIGS. 5A-5D depict Down's Syndrome application of BMPS. BMPS were produced with iPSCs derived from a patient with Down's Syndrome.
Figure 5B:
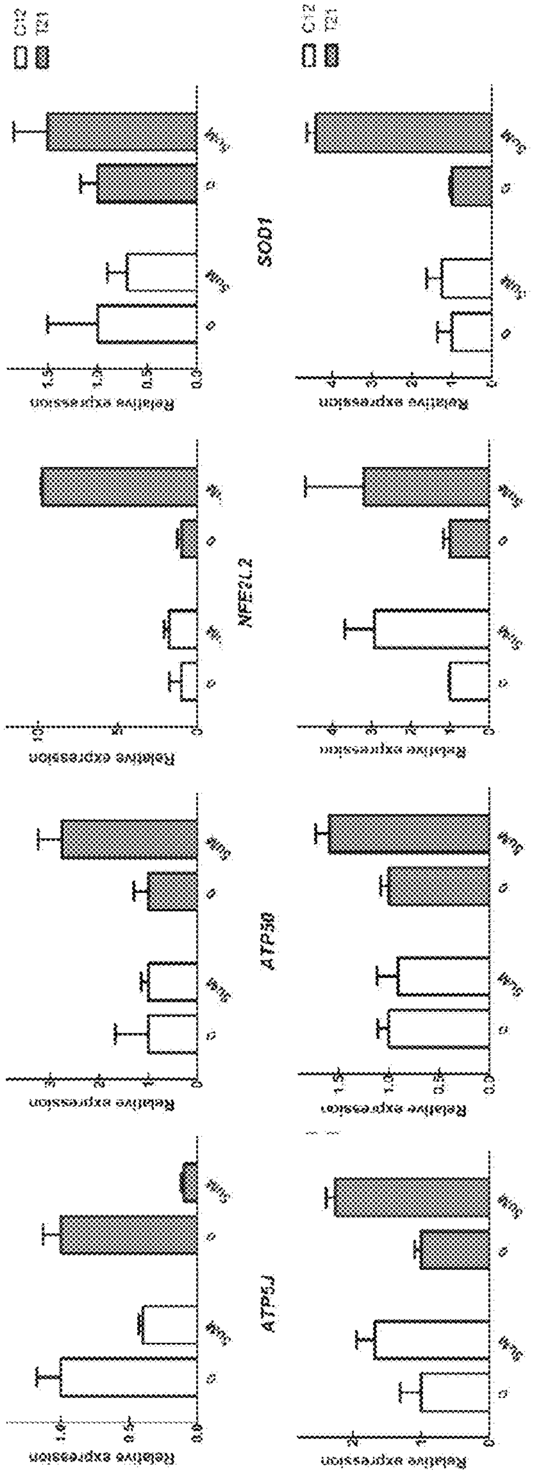
Figure 5C:
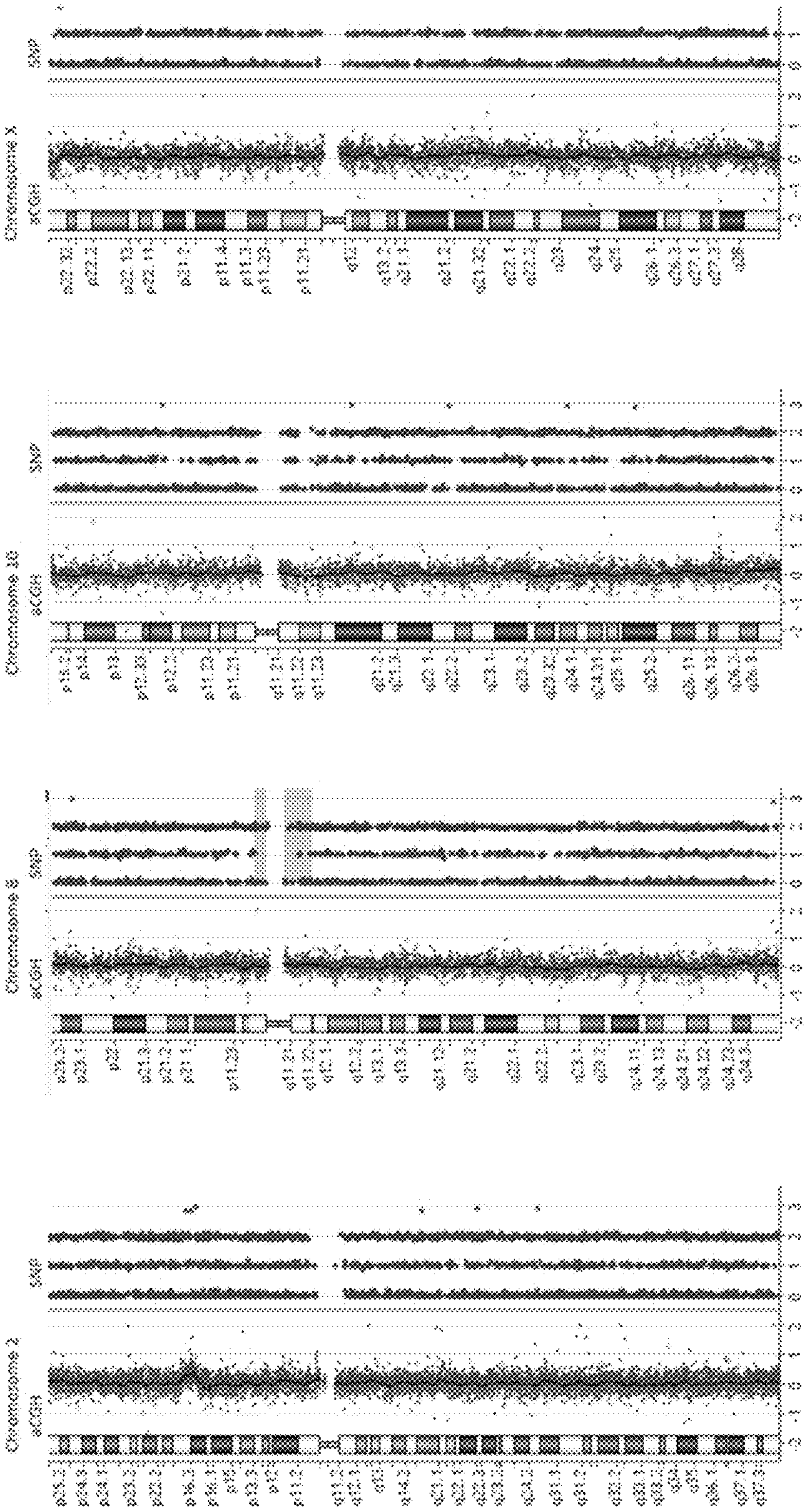
Figure 5D:
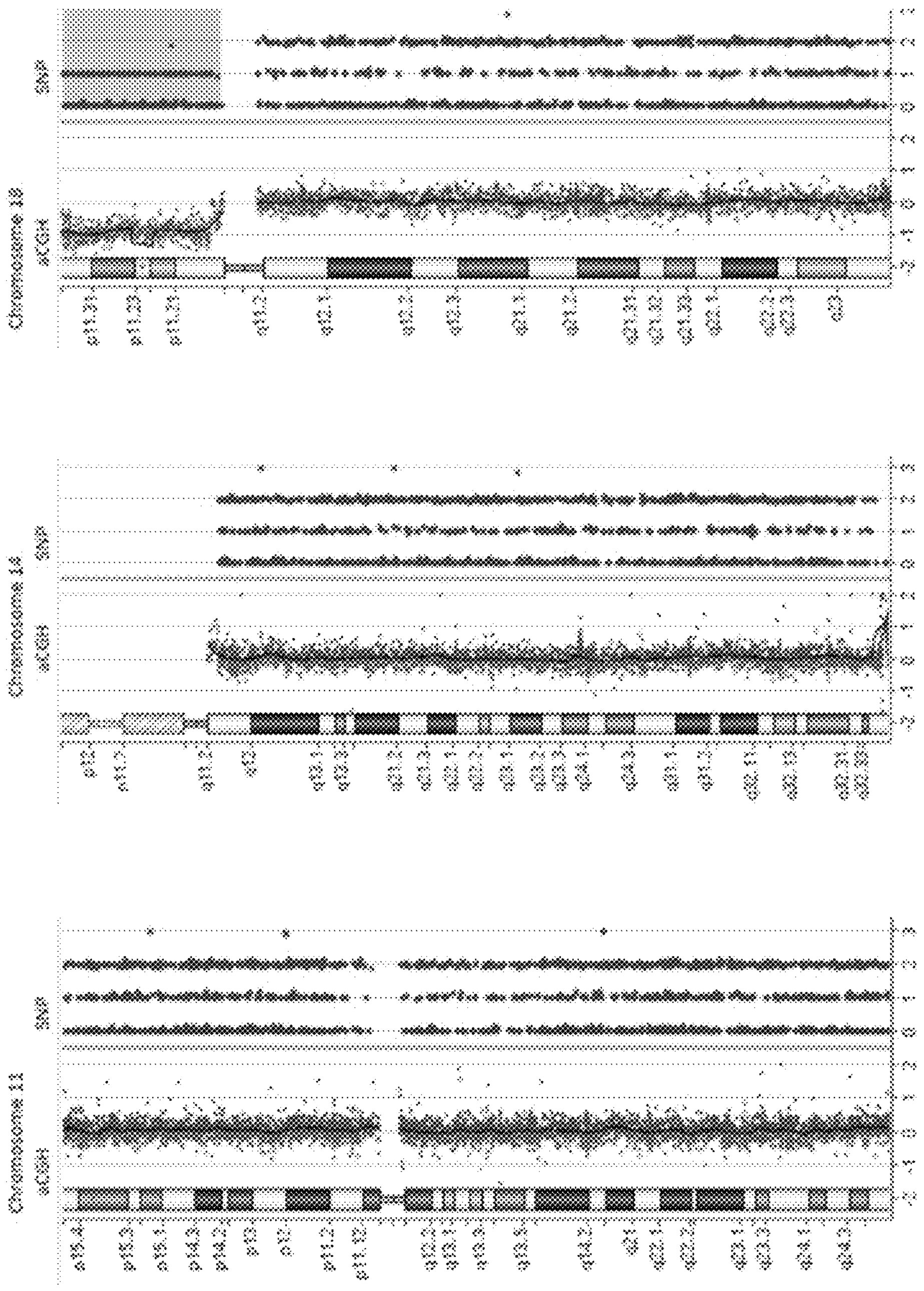

In one embodiment, the model described herein is useful for studying Parkinson's disease (PD). Traditionally, PD has been described as a pre-synaptic degenerative process that affects dopaminergic neurons and induces a fundamental motor disorder [66], however, non-motor symptoms can also be present [67]. Research in Parkinson's disease is experiencing an upswing at the moment, owing to a lack of curative drugs for the large number of patients. Drug testing is nearly exclusively performed in vivo in the so-called MPTP (the parent compound to the metabolite MPP+ used here), rotenone, methamphetamine and 6-hydroxydopamine models requiring tens of thousands of animals [68, 69, 70]. These model toxins are mainly used in mice and primates (and less in cell cultures) to model a disease state resembling PD. Human neurons, which would be most relevant, are not usually available and existing cell lines are only very poor substitutes. The model described herein shows that treatment with MPP+ or rotenone induced specific degeneration of dopaminergic neurons in agreement with Parkinson patients and current animal models of the disease (FIGS. 4E and 4F). The BMPS PD model has shown to recapitulate some of the molecular mechanisms of the human disease, e.g. increase in ROS production (FIGS. 4B and 3D) and changes in genes related to PD (FIG. 4G). BMPS treated with rotenone or MPP+ had decreased TH gene expression compared to controls, supporting the results presented in FIGS. 4E and 4F where the dopaminergic neuronal phenotype is altered after treatment with the two chemicals. TBR1 encodes a transcription factor involved in the regulation of developmental processes. It also plays a role in major neurological diseases such as Alzheimer Disease and PD [71]. This gene was down-regulated after treatment with non-cytotoxic concentrations of MPP+ and rotenone. At the same time, mRNA levels of SNAC were altered. α-Synucleinopathy (common in Parkinson) is a neurodegenerative disease, which consists of the abnormal accumulation of aggregates of alpha-synuclein protein in neurons, nerve fibers or glial cells [72]. Alpha-synuclein plays regulatory roles such as synaptic maintenance, mitochondrial homeostasis, proteasome function, dopamine metabolism [73]. Reduction of SNCA (the alpha-synuclein encoding gene) after treatment with 5 μM rotenone and to a lesser extent after 1 mM MPP+ exposure could be explained by the alteration of alpha-synuclein protein metabolism. However, it may be that longer exposure times are required to produce an increase in gene expression. Caspase-1 (CASP1) expression increased significantly after 24 h exposure to 1 NM MPP+. Recently, some studies have identified human enzyme caspase-1 as the protease that cleaves α-synuclein in vivo [74]. This cleavage generates α-synuclein fragments that are prone to toxic aggregate formation. Finally, effects upon genes related with mitochondrial function (such as NDUFB1, ATP5C1 and ATP50) were down-regulated, more strongly in BMPS treated with MPP+ than rotenone. Changes in NDUFB1, indicate an alteration in mitochondrial function, agreeing with the phenomena already described in Parkinson's disease. This downregulation is linked to the increase in KEAP1 expression (oxidative stress marker) after 24 h exposure to 1 mM MPP+. The high variability in some of the genes may be explained by the selective effects of these chemicals (especially MPP+) to dopaminergic neurons, which represent only a subpopulation within the BMPS. While rotenone and MPP+ alter gene expression of this cell population, the other populations presented in BMPS appear not to be affected. Further studies using cell sorting could identify cell-specific effects.

This disclosure provides for a description of a brain microphysiological system aiming to study various aspects of brain development, pathophysiology and disturbance by genetic and environmental factors. The possibilities to study developmental and neurodegenerative disorders, infections, toxicity and trauma are emerging with such a system. Furthermore, the potential to use iPSC from different donors adds a personalized component to these studies. The high reproducibility and relatively easy protocol, enables future higher throughput testing of chemicals, and drugs and their potential to induce or treat diseases.

Autism

Autism is a highly variable neurodevelopmental disorder that first appears during infancy or childhood, and generally follows a steady course without remission. Patients with autism may be severely impaired in some respects but normal, or even superior, in others. Overt symptoms gradually begin after the age of six months, become established by age two or three years, and tend to continue through adulthood, although often in more muted form. It is distinguished not by a single symptom, but by a characteristic triad of symptoms: impairments in social interaction; impairments in communication; and restricted interests and repetitive behavior. Other aspects, such as atypical eating, are also common but are not essential for diagnosis. Autism's individual symptoms occur in the general population and appear not to associate highly, without a sharp line separating pathologically severe from common traits.

While autism is highly heritable, researchers suspect both environmental and genetic factors as causes. In rare cases, autism is strongly associated with agents that cause birth defects. Controversies surround other proposed environmental causes; for example, the vaccine hypotheses have been disproven. Autism affects information processing in the brain by altering how nerve cells and their synapses connect and organize; how this occurs is not well understood. It is one of three recognized disorders in the autism spectrum (ASDs), the other two being Asperger syndrome, which lacks delays in cognitive development and language, and pervasive developmental disorder, not otherwise specified (commonly abbreviated as PDD-NOS), which is diagnosed when the full set of criteria for autism or Asperger syndrome are not met.

Globally, autism is estimated to affect 21.7 million people as of 2013. As of 2010, the number of people affected is estimated at about 1-2 per 1,000 worldwide. It occurs four to five times more often in boys than girls. About 1.5% of children in the United States (one in 68) are diagnosed with ASD as of 2014, a 30% increase from one in 88 in 2012. The rate of autism among adults aged 18 years and over in the United Kingdom is 1.1%. The number of people diagnosed has been increasing dramatically since the 1980s, partly due to changes in diagnostic practice and government-subsidized financial incentives for named diagnoses; the question of whether actual rates have increased is unresolved.

Autism has a strong genetic basis, although the genetics of autism are complex and it is unclear whether ASD is explained more by rare mutations with major effects, or by rare multigene interactions of common genetic variants. Complexity arises due to interactions among multiple genes, the environment, and epigenetic factors which do not change DNA but are heritable and influence gene expression. Studies of twins suggest that heritability is 0.7 for autism and as high as 0.9 for ASD, and siblings of those with autism are about 25 times more likely to be autistic than the general population. However, most of the mutations that increase autism risk have not been identified. Typically, autism cannot be traced to a Mendelian (single-gene) mutation or to a single chromosome abnormality, and none of the genetic syndromes associated with ASDs have been shown to selectively cause ASD. Numerous candidate genes have been located, with only small effects attributable to any particular gene. The large number of autistic individuals with unaffected family members may result from copy number variations-spontaneous deletions or duplications in genetic material during meiosis. Hence, a substantial fraction of autism cases may be traceable to genetic causes that are highly heritable but not inherited: that is, the mutation that causes the autism is not present in the parental genome.

Several lines of evidence point to synaptic dysfunction as a cause of autism. Some rare mutations may lead to autism by disrupting some synaptic pathways, such as those involved with cell adhesion. Gene replacement studies in mice suggest that autistic symptoms are closely related to later developmental steps that depend on activity in synapses and on activity-dependent changes. All known teratogens (agents that cause birth defects) related to the risk of autism appear to act during the first eight weeks from conception, and though this does not exclude the possibility that autism can be initiated or affected later, there is strong evidence that autism arises very early in development.

Exposure to air pollution during pregnancy, especially heavy metals and particulates, may increase the risk of autism. Environmental factors that have been claimed to contribute to or exacerbate autism, or may be important in future research, include certain foods, infectious diseases, solvents, diesel exhaust, PCBs, phthalates and phenols used in plastic products, pesticides, brominated flame retardants, alcohol, smoking, illicit drugs, vaccines, and prenatal stress, although no links have been found, and some have been completely disproven.

Autism does not have a clear unifying mechanism at either the molecular, cellular, or systems level; it is not known whether autism is a few disorders caused by mutations converging on a few common molecular pathways, or is (like intellectual disability) a large set of disorders with diverse mechanisms. Autism appears to result from developmental factors that affect many or all functional brain systems, and to disturb the timing of brain development more than the final product. Neuroanatomical studies and the associations with teratogens strongly suggest that autism's mechanism includes alteration of brain development soon after conception. This anomaly appears to start a cascade of pathological events in the brain that are significantly influenced by environmental factors. Just after birth, the brains of children with autism tend to grow faster than usual, followed by normal or relatively slower growth in childhood. It is not known whether early overgrowth occurs in all children with autism. It seems to be most prominent in brain areas underlying the development of higher cognitive specialization. Hypotheses for the cellular and molecular bases of pathological early overgrowth include the following: an excess of neurons that causes local over connectivity in key brain regions, disturbed neuronal migration during early gestation, unbalanced excitatory-inhibitory networks, and abnormal formation of synapses and dendritic spines, for example, by modulation of the neurexin-neuroligin cell-adhesion system, or by poorly regulated synthesis of synaptic proteins.

The immune system is thought to play an important role in autism. Children with autism have been found by researchers to have inflammation of both the peripheral and central immune systems as indicated by increased levels of pro-inflammatory cytokines and significant activation of microglia. Biomarkers of abnormal immune function have also been associated with increased impairments in behaviors that are characteristic of the core features of autism such as deficits in social interactions and communication. Interactions between the immune system and the nervous system begin early during the embryonic stage of life, and successful neurodevelopment depends on a balanced immune response. It is thought that activation of a pregnant mother's immune system such as from environmental toxicants or infection can contribute to causing autism through causing a disruption of brain development. This is supported by recent studies that have found that infection during pregnancy is associated with an increased risk of autism.

The relationship of neurochemicals to autism is not well understood; several have been investigated, with the most evidence for the role of serotonin and of genetic differences in its transport. The role of group I metabotropic glutamate receptors (mGluR) in the pathogenesis of fragile X syndrome, the most common identified genetic cause of autism, has led to interest in the possible implications for future autism research into this pathway. Some data suggests neuronal overgrowth potentially related to an increase in several growth hormones or to impaired regulation of growth factor receptors. Also, some inborn errors of metabolism are associated with autism, but probably account for less than 5% of cases.

The mirror neuron system (MNS) theory of autism hypothesizes that distortion in the development of the MNS interferes with imitation and leads to autism's core features of social impairment and communication difficulties. The MNS operates when an animal performs an action or observes another animal perform the same action. The MNS may contribute to an individual's understanding of other people by enabling the modeling of their behavior via embodied simulation of their actions, intentions, and emotions. Several studies have tested this hypothesis by demonstrating structural abnormalities in MNS regions of individuals with ASD, delay in the activation in the core circuit for imitation in individuals with Asperger syndrome, and a correlation between reduced MNS activity and severity of the syndrome in children with ASD. However, individuals with autism also have abnormal brain activation in many circuits outside the MNS and the MNS theory does not explain the normal performance of children with autism on imitation tasks that involve a goal or object.

The under connectivity theory of autism hypothesizes that autism is marked by under functioning high-level neural connections and synchronization, along with an excess of low-level processes. Evidence for this theory has been found in functional neuroimaging studies on autistic individuals and by a brainwave study that suggested that adults with ASD have local over connectivity in the cortex and weak functional connections between the frontal lobe and the rest of the cortex. Other evidence suggests the under connectivity is mainly within each hemisphere of the cortex and that autism is a disorder of the association cortex.

From studies based on event-related potentials, transient changes to the brain's electrical activity in response to stimuli, there is considerable evidence for differences in autistic individuals with respect to attention, orientation to auditory and visual stimuli, novelty detection, language and face processing, and information storage; several studies have found a preference for nonsocial stimuli. For example, magnetoencephalography studies have found evidence in children with autism of delayed responses in the brain's processing of auditory signals.

Relations have been found between autism and schizophrenia based on duplications and deletions of chromosomes; research showed that schizophrenia and autism are significantly more common in combination with 1q21.1 deletion syndrome. Research on autism/schizophrenia relations for chromosome 15 (15q13.3), chromosome 16 (16p13.1) and chromosome 17 (17p12) are inconclusive.

Diagnosis is based on behavior, not cause or mechanism. Under the DSM-5, autism is characterized by persistent deficits in social communication and interaction across multiple contexts, as well as restricted, repetitive patterns of behavior, interests, or activities. These deficits are present in early childhood, typically before age three, and lead to clinically significant functional impairment. Sample symptoms include lack of social or emotional reciprocity, stereotyped and repetitive use of language or idiosyncratic language, and persistent preoccupation with unusual objects. The disturbance must not be better accounted for by Rett syndrome, intellectual disability or global developmental delay. ICD-10 uses essentially the same definition. A pediatrician commonly performs a preliminary investigation by taking developmental history and physically examining the child. If warranted, diagnosis and evaluations are conducted with help from ASD specialists, observing and assessing cognitive, communication, family, and other factors using standardized tools, and taking into account any associated medical conditions. A pediatric neuropsychologist is often asked to assess behavior and cognitive skills, both to aid diagnosis and to help recommend educational interventions.

Clinical genetics evaluations are often done once ASD is diagnosed, particularly when other symptoms already suggest a genetic cause. Although genetic technology allows clinical geneticists to link an estimated 40% of cases to genetic causes, consensus guidelines in the US and UK are limited to high-resolution chromosome and fragile X testing. Metabolic and neuroimaging tests are sometimes helpful, but are not routine.

Many medications are used to treat ASD symptoms that interfere with integrating a child into home or school when behavioral treatment fails. More than half of US children diagnosed with ASD are prescribed psychoactive drugs or anticonvulsants, with the most common drug classes being antidepressants, stimulants, and antipsychotics. Antipsychotics, such as risperidone and aripiprazole, have been found to be useful for treating some conditions associated with autism, including irritability, repetitive behavior, and sleeplessness. A person with ASD may respond atypically to medications, the medications can have adverse effects, and no known medication relieves autism's core symptoms of social and communication impairments. Experiments in mice have reversed or reduced some symptoms related to autism by replacing or modulating gene function, suggesting the possibility of targeting therapies to specific rare mutations known to cause autism. Although many alternative therapies and interventions are available, few are supported by scientific studies. Some alternative treatments may place the child at risk. A 2008 study found that compared to their peers, autistic boys have significantly thinner bones if on casein-free diets; in 2005, botched chelation therapy killed a five-year-old child with autism. There has been early research looking at hyperbaric treatments in children with autism.

Parkinson's Disease

Parkinson's disease (PD, also known as idiopathic or primary parkinsonism, hypokinetic rigid syndrome (HRS), or paralysis agitans) is a degenerative disorder of the central nervous system mainly affecting the motor system. The motor symptoms of Parkinson's disease result from the death of dopamine-generating cells in the substantia nigra, a region of the midbrain. The causes of this cell death are poorly understood. Early in the course of the disease, the most obvious symptoms are movement-related; these include shaking, rigidity, slowness of movement and difficulty with walking and gait. Later, thinking and behavioral problems may arise, with dementia commonly occurring in the advanced stages of the disease, and depression is the most common psychiatric symptom. Other symptoms include sensory, sleep and emotional problems. Parkinson's disease is more common in older people, with most cases occurring after the age of 50; when it is seen in young adults, it is called young onset PD (YOPD).

The main motor symptoms are collectively called "parkinsonism," or a "parkinsonian syndrome." The disease can be either primary or secondary. Primary Parkinson's disease is referred to as idiopathic (having no known cause), although some atypical cases have a genetic origin, while secondary parkinsonism is due to known causes like toxins. The pathology of the disease is characterized by the accumulation of a protein into Lewy bodies in neurons, and insufficient formation and activity of dopamine in certain parts of the midbrain. Where the Lewy bodies are located is often related to the expression and degree of the symptoms of an individual. Diagnosis of typical cases is mainly based on symptoms, with tests such as neuroimaging being used for confirmation.

Diagnosis of Parkinson's disease involves a physician taking a medical history and performing a neurological examination. There is no lab test that will clearly identify the disease, but brain scans are sometimes used to rule out disorders that could give rise to similar symptoms. People may be given levodopa and resulting relief of motor impairment tends to confirm diagnosis. The finding of Lewy bodies in the midbrain on autopsy is usually considered proof that the person had Parkinson's disease. The progress of the illness over time may reveal it is not Parkinson's disease, and some authorities recommend that the diagnosis be periodically reviewed. Other causes that can secondarily produce a parkinsonian syndrome are Alzheimer's disease, multiple cerebral infarction and drug-induced parkinsonism. Parkinson plus syndromes such as progressive supranuclear palsy and multiple system atrophy must be ruled out. Anti-Parkinson's medications are typically less effective at controlling symptoms in Parkinson plus syndromes. Faster progression rates, early cognitive dysfunction or postural instability, minimal tremor or symmetry at onset may indicate a Parkinson plus disease rather than PD itself. Genetic forms are usually classified as PD, although the terms familial Parkinson's disease and familial parkinsonism are used for disease entities with an autosomal dominant or recessive pattern of inheritance.

The PD Society Brain Bank criteria require slowness of movement (bradykinesia) plus either rigidity, resting tremor, or postural instability. Other possible causes for these symptoms need to be ruled out prior to diagnosis with PD. Finally, three or more of the following features are required during onset or evolution: unilateral onset, tremor at rest, progression in time, asymmetry of motor symptoms, response to levodopa for at least five years, clinical course of at least ten years and appearance of dyskinesias induced by the intake of excessive levodopa. Accuracy of diagnostic criteria evaluated at autopsy is 75-90%, with specialists such as neurologists having the highest rates. Computed tomography (CT) and conventional magnetic resonance imaging (MRI) brain scans of people with PD usually appear normal. These techniques are nevertheless useful to rule out other diseases that can be secondary causes of parkinsonism, such as basal ganglia tumors, vascular pathology and hydrocephalus. A specific technique of MRI, diffusion MRI, has been reported to be useful at discriminating between typical and atypical parkinsonism, although its exact diagnostic value is still under investigation. Dopaminergic function in the basal ganglia can be measured with different PET and SPECT radiotracers. Examples are ioflupane (123I) (trade name DaTSCAN) and iometopane (Dopascan) for SPECT or fluorodeoxyglucose (18F) and DTBZ for PET. A pattern of reduced dopaminergic activity in the basal ganglia can aid in diagnosing PD.

Treatments, typically the medications L-DOPA and dopamine agonists, improve the early symptoms of the disease. As the disease progresses and dopaminergic neurons continue to be lost, these drugs eventually become ineffective at treating the symptoms and at the same time produce a complication marked by involuntary writhing movements. Surgery and deep brain stimulation have been used to reduce motor symptoms as a last resort in severe cases where drugs are ineffective. Although dopamine replacement alleviates the symptomatic motor dysfunction, its effectiveness is reduced as the disease progresses, leading to unacceptable side effects such as severe motor fluctuations and dyskinesias. Furthermore, there is no therapy that will halt the progress of the disease. Moreover, this palliative therapeutic approach does not address the underlying mechanisms of the disease.

The term parkinsonism is used for a motor syndrome whose main symptoms are tremor at rest, stiffness, slowing of movement and postural instability. Parkinsonian syndromes can be divided into four subtypes according to their origin: primary or idiopathic, secondary or acquired, hereditary parkinsonism, and Parkinson plus syndromes or multiple system degeneration. Usually classified as a movement disorder, PD also gives rise to several non-motor types of symptoms such as sensory deficits, cognitive difficulties or sleep problems. Parkinson plus diseases are primary parkinsonisms which present additional features. They include multiple system atrophy, progressive supranuclear palsy, corticobasal degeneration and dementia with Lewy bodies.

In terms of pathophysiology, PD is considered a synucleiopathy due to an abnormal accumulation of alpha-synuclein protein in the brain in the form of Lewy bodies, as opposed to other diseases such as Alzheimer's disease where the brain accumulates tau protein in the form of neurofibrillary tangles. Nevertheless, there is clinical and pathological overlap between tauopathies and synucleinopathies. The most typical symptom of Alzheimer's disease, dementia, occurs in advanced stages of PD, while it is common to find neurofibrillary tangles in brains affected by PD. Dementia with Lewy bodies (DLB) is another synucleinopathy that has similarities with PD, and especially with the subset of PD cases with dementia. However, the relationship between PD and DLB is complex and still has to be clarified. They may represent parts of a continuum or they may be separate diseases.

Mutations in specific genes have been conclusively shown to cause PD. These genes encode alpha-synuclein (SNCA), parkin (PRKN), leucine-rich repeat kinase 2 (LRRK2 or dardarin), PTEN-induced putative kinase 1 (PINK1), DJ-1 and ATP13A2. In most cases, people with these mutations will develop PD. With the exception of LRRK2, however, they account for only a small minority of cases of PD. The most extensively studied PD-related genes are SNCA and LRRK2. Mutations in genes including SNCA, LRRK2 and glucocerebrosidase (GBA) have been found to be risk factors for sporadic PD. Mutations in GBA are known to cause Gaucher's disease. Genome-wide association studies, which search for mutated alleles with low penetrance in sporadic cases, have now yielded many positive results.

The role of the SNCA gene is important in PD because the alpha-synuclein protein is the main component of Lewy bodies. The histopathology (microscopic anatomy) of the substantia nigra and several other brain regions shows neuronal loss and Lewy bodies in many of the remaining nerve cells. Neuronal loss is accompanied by death of astrocytes (star-shaped glial cells) and activation of the microglia (another type of glial cell). Lewy bodies are a key pathological feature of PD.

Alzheimer's Disease

Alzheimer's disease (AD) accounts for 60% to 70% of cases of dementia. It is a chronic neurodegenerative disease that often starts slowly, but progressively worsens over time. The most common early symptom is short-term memory loss. As the disease advances, symptoms include problems with language, mood swings, loss of motivation, disorientation, behavioral issues, and poorly managed self-care. Gradually, bodily functions are lost, ultimately leading to death. Although the speed of progression can vary, the average life expectancy following diagnosis is three to nine years. The cause of Alzheimer's disease is poorly understood. About 70% of the risk is believed to be genetic with many genes involved. Other risk factors include a history of head injuries, hypertension, or depression. The disease process is associated with plaques and tangles in the brain.

Alzheimer's disease is characterized by loss of neurons and synapses in the cerebral cortex and certain subcortical regions. This loss results in gross atrophy of the affected regions, including degeneration in the temporal lobe and parietal lobe, and parts of the frontal cortex and cingulate gyrus. Alzheimer's disease has been hypothesized to be a protein misfolding disease (proteopathy), caused by accumulation of abnormally folded A-beta and tau proteins in the brain. Plaques are made up of small peptides, 39-43 amino acids in length, called beta-amyloid (also written as A-beta or Aβ). Beta-amyloid is a fragment from a larger protein called amyloid precursor protein (APP), a transmembrane protein that penetrates through the neuron's membrane. APP is critical to neuron growth, survival and post-injury repair. In Alzheimer's disease, an unknown process causes APP to be divided into smaller fragments by enzymes through proteolysis. One of these fragments gives rise to fibrils of beta-amyloid, which form clumps that deposit outside neurons in dense formations known as senile plaques.

A probable diagnosis is based on the history of the illness and cognitive testing with medical imaging and blood tests to rule out other possible causes. Initial symptoms are often mistaken for normal ageing. Examination of brain tissue is needed for a definite diagnosis. Alzheimer's disease is diagnosed through a complete medical assessment. There is no one clinical test that can determine whether a person has Alzheimer's. Usually several tests are performed to rule out any other cause of dementia. The only definitive method of diagnosis is examination of brain tissue obtained from a biopsy or autopsy. Tests (such as blood tests and brain imaging) are used to rule out other causes of dementia-like symptoms. Laboratory tests and screening include: complete blood cell count; electrolyte panel; screening metabolic panel; thyroid gland function tests; vitamin B-12 folate levels; tests for syphilis and, depending on history, for human immunodeficiency antibodies; urinalysis; electrocardiogram (ECG); chest X-ray; computerized tomography (CT) head scan; and an electroencephalogram (EEG). A lumbar puncture may also be informative in the overall diagnosis.

There are no known medications or supplements that decrease risk of Alzheimer's. Additionally, no known treatments stop or reverse Alzheimer's progression, although some may temporarily improve symptoms.

This invention is further illustrated by the following examples, which should not be construed as limiting. The contents of all references, patents, and published patent applications cited throughout this application, as well as the figures, are incorporated herein by reference.

EXAMPLES

Example 1: Characterization of BMPS by Expression of Neural Specific Genes During Differentiation According to the techniques herein, the BMPS model established herein follows a stepwise differentiation protocol (FIG. 1A). In the final step, cells were differentiated into various neuronal and glial cell types during constant gyratory shaking. Briefly, the BMPS were established as follows: cells were differentiated, by addition of B27, GDNF and BDNF and withdrawal of stempro, basic FGF and EGF, into different neuronal and glial cell types with CNS functions during constant gyratory shaking. Advantageously, the techniques herein provide that the BMPS that were produced were of a spherical shape and a consistent size. For example, the BMPS showed spherical shapes and controlled sizes that were below 350 μm after 17 days in culture, a size that avoids necrosis in the center of the aggregate (FIG. 1B) that occurs in larger spheroids (e.g., >350 μm) due to nutrient and oxygen deprivation. Nutrient and oxygen deprivation-induced necrosis could produce artifacts in the different endpoints measured, especially in disease and toxicity studies. Five days after initiation of aggregation in NPC medium, spheres were on average 130±5 μm in diameter; the size increased to 300±40 μm during the first 17 days in differentiation medium. From day 17 onwards size remained constant around 310 μm. Advantageously, this technique significantly increases throughput of BMPS production by allowing simultaneous production of several batches with different conditions. Without the shaking condition, aggregates tend to stick together, grow in different shapes, attach to the bottom and in some point get necrotic in the middle of the sphere. Thus, constant gyratory shaking technology is a suitable method to control the shape and size of BMPS.

In order to characterize different stages of the differentiation and maturation process, BMPS were collected every week up to 8 weeks of differentiation (FIGS. 1C1-C5). Analysis of different neuronal and glial cell-specific genes by real-time reverse transcription polymerase chain reaction (RT-PCR) was performed to characterize the presence of neurons, astrocytes, oligodendrocytes and neural precursor cells (NPC). NPC are self-renewing and proliferating multipotent cells able to generate different cell types of the central nervous system. The differentiation of NPC in 3D was initiated by changing the medium to differentiation medium. Gene expression of the cell proliferation marker Ki67 decreased 95% after 2 weeks of differentiation (FIG. 1C1, proliferation and stem cell markers). The remaining Ki67 expression appears to be due to the presence of a small population of NPC and other proliferating cell types such as oligodendrocytes and astrocytes (FIG. 1C2, astroglia and oligodendroglia). Astrocyte-specific genes (S100B and GFAP) showed a constant increase after two weeks, while, differentiation of oligodendrocytes was induced later, after six weeks of differentiation as shown by OLIG2 gene expression (FIG. 1C2).

Gene expression of specific neurotransmitters or their receptors was used to characterize the identity of different neuronal populations and the differentiation patterns of the human iPSC derived BMPS (FIG. 1C4, neuronal markers; right y-axis relative quantification of GRIN1 and GABRA1; MBP, FOXA2, and SLC1A3). GRIN1 encodes the essential Glutamate [NMDA] receptor subunit zeta-1 [25] was increased at very early stages of differentiation (one week after induction of differentiation) and continued to increase up to 5 weeks when it reached a plateau (FIG. 1C4). Similarly, GAD1, a GABAergic neuronal gene marker which encodes the Glutamate decarboxylase 1, and catalyzes decarboxylation of glutamate to GABA, showed an increase in expression during the first 4 weeks of differentiation, reaching a plateau thereafter (FIG. 1C4). The expression of tyrosine hydroxylase (TH) a gene, which identifies dopaminergic neurons, was observed first after three weeks, showing delayed differentiation compared to glutamatergic neurons. The expression of TH increased constantly thereafter reaching an 86-fold increase at seven weeks compared to NPC (week 0; FIG. 1C4). GABRA1, which encodes the gamma-aminobutyric acid (GABA) receptor, showed a steady increase of expression after 2 weeks and reached its maximum increase of a 150-fold change at 8 weeks compared to week 0 (FIG. 1C4). Moreover other markers for specific part of the brain, such as ventral midbrain neuron marker LMX1A, FOXO1 and FOXA2 (Hedlund et al., 2016; Stott et al., 2013), cerebral cortex marker FOXO4, or markers for myelination CNP and MBP (Li and Richardson, 2008; Agrawal et al., 1994) and L-glutamate transport SLC1A6 (Sery et al., 2015) has been studied (FIG. 1D d). Based on the patterns of expression of neuronal genes, the iPSC-derived BMPS model closely represents the different neuronal populations of different cortical and subcortical areas of the human CNS, suggesting that some of the mechanisms implicated in the early stages of nervous system development are reflected.

To prove that BMPS can be generated from different IPCs, another healthy line (IPS IMR90) and Down syndrome line (DYP0730) were used (FIG. 1C5). Both lines were able to generate BMPS and differentiated to neurons (MAP2 marker), astrocytes (GFAP marker) and oligodendrocytes (OLIG1 marker).

Example 2: Characterization of BMPS by Flow Cytometry Analysis Shows Neuronal Maturation of the Human Induced Pluripotent Stem Cells Over Time In order to quantify cell populations in the iPSC-derived BMPS and verify the reproducibility between experiments and batches of the cell line (C1, CRL-2097), flow cytometry was performed using CNS-specific antibodies for identification of neural markers (Table 1). Flow cytometry allowed quantifying 60% of cells with proliferation marker (Ki67) at the NPCs stage (week 0), which was reduced during differentiation down to 9% at 2 weeks, 7% at 4 weeks and 1% at 8 weeks (FIG. 1D), indicating a fast reduction of proliferating cells after induction of differentiation. This confirms the gene expression data and indicates a fast reduction of proliferating cells after induction of differentiation. This result was confirmed by further analysis of NPC markers such as SOX1, SOX2 and Nestin. SOX1 and SOX2 are known to be involved in the maintenance of neural progenitor cell identity. The number of SOX1-, SOX2- and NES-positive (NPC marker) cells in the NPC population (week 0) was 46%, 68% and 60%, respectively. SOX1, SOX2 and NES expression was reduced dramatically with differentiation, showing very low positive populations at eight weeks (2%, 3% and 2%, respectively). This loss in the NPC population during differentiation was corroborated by Doublecortin (DCX), a microtubule-associated protein expressed in neuroblasts and immature neurons: the number of DCX-positive cells in NPC (week o) was around 30%, which reduced to 22% at two, 17% at four and 4% at eight weeks, respectively. On the other hand, the marker for mature neurons, Tuj1 (Neuron-specific class III beta-tubulin) presented the opposite pattern. Analysis showed low levels of Tuj1-positive cells at the NPC stage (week 0). The expression of this marker in the cell population increased to 70% after 2 weeks of differentiation and remained constant up to 8 weeks. These flow cytometry experiments indicate differentiation and maturation of the BMPS over time.

Quantification of the cell population in at least three independent experiments showed low variability between cultures, demonstrating the reproducibility of the system. The variation (standard deviation, SD) between experiments decreased with the cell differentiation process and was very small at the latest maturation stage (eight weeks); DCX SD 0.9%, Ki67 SD 0.2%, SOX1 SD 0.7%, SOX2 SD 1.2%, NES SD 0.7% and Tuj1 SD 9.8% (FIG. 1E). These results indicate that after eight weeks of differentiation the cellular composition is similar and shows high reproducibility between different BMPS experiments.

TABLE 1

Gene and miRNAs Taqman Assays. List of the primers used for the experiments.

| Assay ID | Assay Type | Availability | Catalog Number | Assay Name |
|---|---|---|---|---|
| Gene Expression Taqman Primers | | | | |
| Hs01060665 | TaqMan ® Gene Expression Assay | Inventoried | 4331182 | BACT |
| Hs99999901 | TaqMan ® Gene Expression Assay | Inventoried | 4331182 | 18S |
| Hs04187831 | TaqMan ® Gene Expression Assay | Inventoried | 4331182 | NES |
| Hs01032443 | TaqMan ® Gene Expression Assay | Inventoried | 4331182 | Ki67 |
| Hs01088112 | TaqMan ® Gene Expression Assay | Inventoried | 4331182 | PAX6 |
| Hs00909233 | TaqMan ® Gene Expression Assay | Inventoried | 4331182 | GFAP |
| Hs00300164 | TaqMan ® Gene Expression Assay | Inventoried | 4331182 | OLIG2 |
| Hs00902901 | TaqMan ® Gene Expression Assay | Inventoried | 4331182 | S100B |

TABLE 1-continued

Gene and miRNAs Taqman Assays. List of the primers used for the experiments.

| Assay ID | Assay Type | Availability | Catalog Number | Assay Name |
|---|---|---|---|---|
| Hs00609557 | TaqMan ® Gene Expression Assay | Inventoried | 4331182 | GRIN1 |
| Hs00165941 | TaqMan ® Gene Expression Assay | Inventoried | 4331182 | TH |
| Hs00971228 | TaqMan ® Gene Expression Assay | Inventoried | 4331182 | GABRA1 |
| Hs01065893 | TaqMan ® Gene Expression Assay | Inventoried | 4331182 | GAD1 |
| Hs00199577 | TaqMan ® Gene Expression Assay | Inventoried | 4331182 | SYN1 |
| Hs00232429 | TaqMan ® Gene Expression Assay | Inventoried | 4331182 | TBR1 |
| Hs01003383 | TaqMan ® Gene Expression Assay | Inventoried | 4331182 | SNCA |
| Hs01003430 | TaqMan ® Gene Expression Assay | Inventoried | 4331182 | KEAP1 |
| Hs00929425 | TaqMan ® Gene Expression Assay | Inventoried | 4331182 | NDUFB1 |
| Hs01101219 | TaqMan ® Gene Expression Assay | Inventoried | 4331182 | ATP5C1 |
| Hs00919163 | TaqMan ® Gene Expression Assay | Inventoried | 4331182 | ATP50 |
| Hs00354836 | TaqMan ® Gene Expression Assay | Inventoried | 4331182 | CASP1 |
| Hs00263981 | TaqMan ® Gene Expression Assay | Inventoried | 4331182 | CNP |
| Hs01054576 | TaqMan ® Gene Expression Assay | Inventoried | 4331182 | FOXO1 |
| Hs00188193 | TaqMan ® Gene Expression Assay | Inventoried | 4331182 | SLC1A3 |
| Hs00936217 | TaqMan ® Gene Expression Assay | Inventoried | 4331182 | FOXO4 |
| Hs00892663 | TaqMan ® Gene Expression Assay | Inventoried | 4331182 | LMX1A |
| Hs00232764 | TaqMan ® Gene Expression Assay | Inventoried | 4331182 | FOXA2 |
| miRNA Taqman Assays | | | | |
| 1182 | TaqMan ® microRNA Assay | Inventoried | 4427975 | mmu-miR-124a |
| 2216 | TaqMan ® microRNA Assay | Inventoried | 4427975 | hsa-miR-128a |
| 457 | TaqMan ® microRNA Assay | Inventoried | 4427975 | hsa-miR-132 |
| 2247 | TaqMan ® microRNA Assay | Inventoried | 4427975 | hsa-miR-133b |
| 1129 | TaqMan ® microRNA Assay | Inventoried | 4427975 | mmu-miR-137 |
| 1094 | Control miRNA Assay | Inventoried | 4427975 | RNU44 |

Example 3: MicroRNAs as Neuronal Differentiation Markers in Human iPSC-Derived BMPS MicroRNAs (miRNA), known as posttranscriptional regulators of developmental timing, have recently been established as markers to study the differentiation process [26]. Expression of neural-specific miRNAs showed strong induction of miRNAs involved in neurogenesis (FIG. 1C3, miRNA). mir-124, the most abundant brain miRNA, was strongly induced in the earlier stages of differentiation, then slightly down-regulated at eight weeks of differentiation. This finding correlates with previous studies, where mir-124 was shown to promote neuronal lineage commitment at earlier stages of neural stem cells specification by targeting anti-neuronal factors [26]. mir-128, a modulator of late neural differentiation, was strongly up-regulated after 5 weeks of differentiation. mir-137, the most induced miRNA over time in the system described herein, is known as a regulator of neural differentiation of embryonic stem cells (ESCs) [27]. mir-132 and mir-133b which are involved in regulation of dopaminergic neuron maturation and function, were induced in week three of differentiation, a finding which correlates with the expression pattern of TH. Moreover, mir-132 is involved in dendritic spine formation [28]. These results support the view of a coordinated mechanism of neuronal differentiation as reflected by the patterns of neuronal gene and miRNA expression and neuronal and neurotransmitter identity.

Figure 8A:
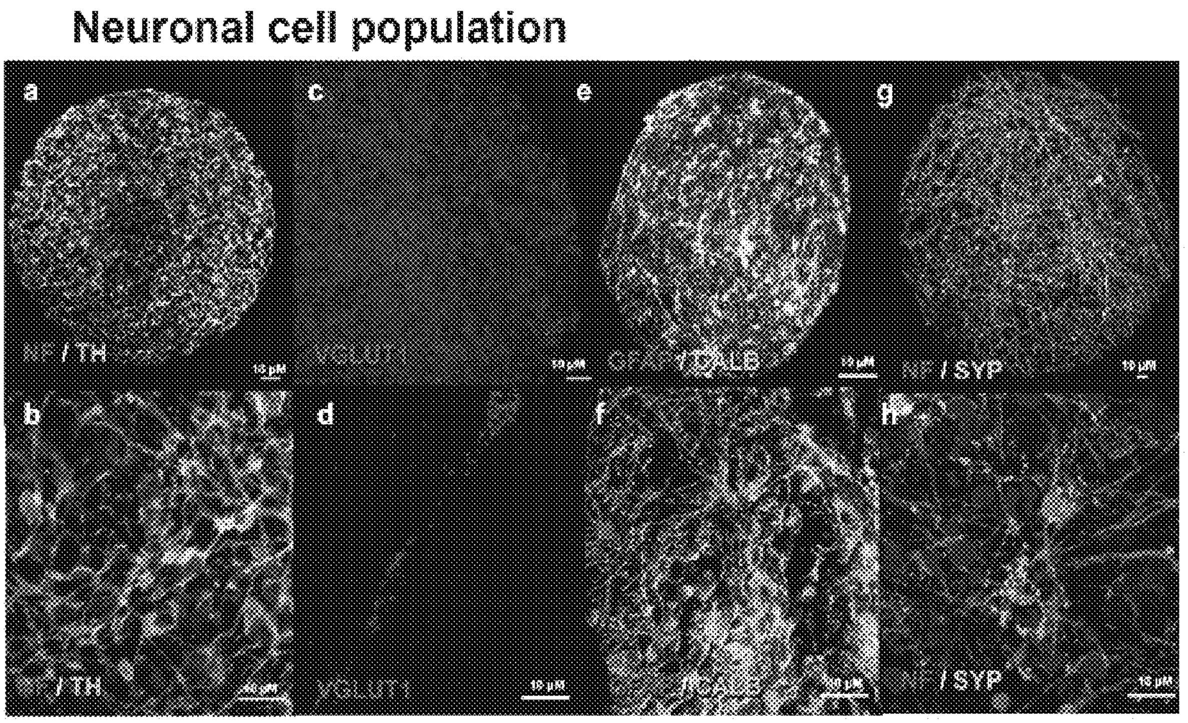
FIGS. 8A-8E depict morphologic characterization of mature human BMPS.

Example 4: Characterization of Human BMPS by Immunohistochemistry and Electron Microscopy Shows Evidence of Differentiation into Mature Brain Cell Types In order to assess the cellular composition and the process of maturation of the cells within the human BMPS, the expression of markers for different CNS cell populations including neurons and glial cells at 2, 4 and 8 weeks of differentiation were evaluated using immunohistochemistry and electron microscopy techniques. A reproducible pattern of expression consistent with maturation of the BMPS towards mature neural phenotypes was found. After 4 weeks of differentiation, the BMPS showed positive staining for mature neuronal markers such as microtubule-associated protein 2 (MAP2), neurofilament-heavy chain (NF, SMI32) and synaptophysin (FIG. 2A, 2B). Furthermore, different neuronal subtypes in the BMPS including dopaminergic (TH-positive neurons), glutamatergic (VGLUT1-positive neurons) and GABAergic interneurons (calbindin-positive neurons) (FIG. 2B, FIG. 8A) were observed. Moreover, the BMPS matured over time of differentiation as seen by decreased NES-positive cells (FIG. 2A) and increased cell-cell interactions (neuron-neuron and neuron glia) as subsets of neurons showed several processes, which resembled dendritic and axonal projections (FIG. 8A).

Figure 2D:
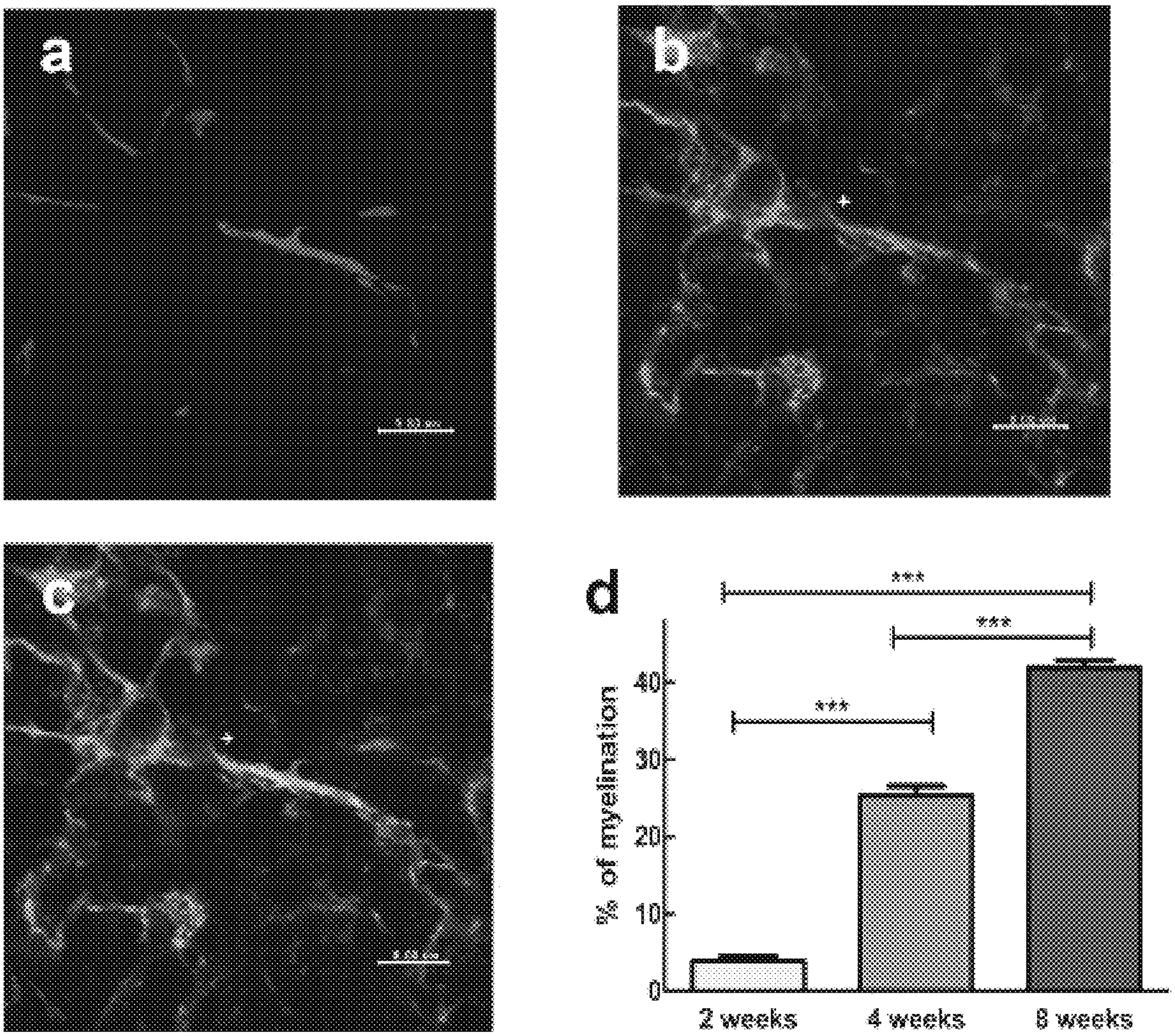
FIG. 2D depicts MBP+ oligodendrocytes issued processes in close association with axons and seemed to enwrap them at 8 weeks (a,b,c). Myelination calculated as the mean percentage MBP positive oligodendrocyte processes coverage of NF-H-positive axons (a,b,c) at 2, 4 and 8 weeks in at least 2 independent experiments showed significant increase of myelination observed with time of differentiation ($p<0.001$) (d).
Figure 2E:
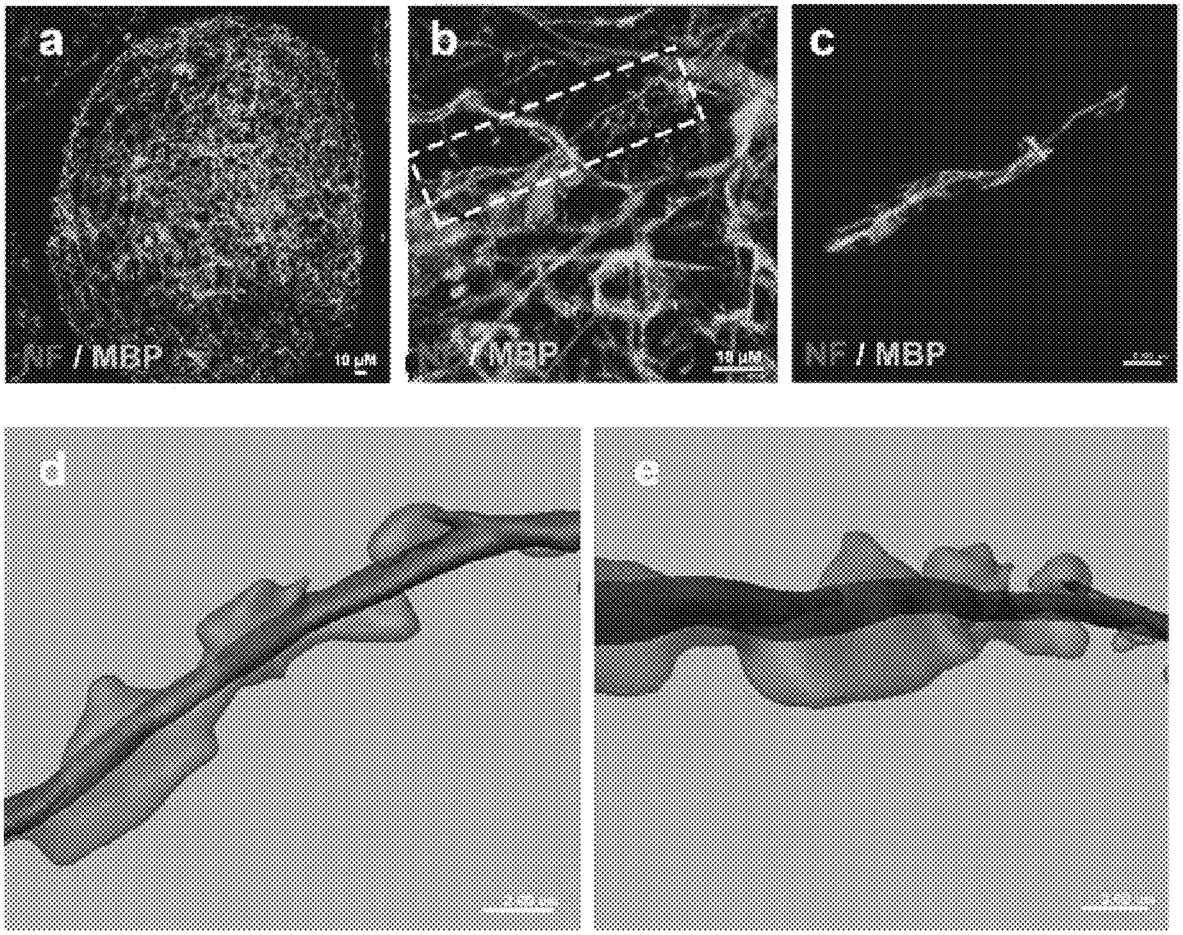
FIG. 2E depicts 3D-reconstruction based on confocal z-stacks at 8 weeks demonstrating a "wrapping" myelinating process, which resembled the myelination of axons in human CNS.
Figure 2F:
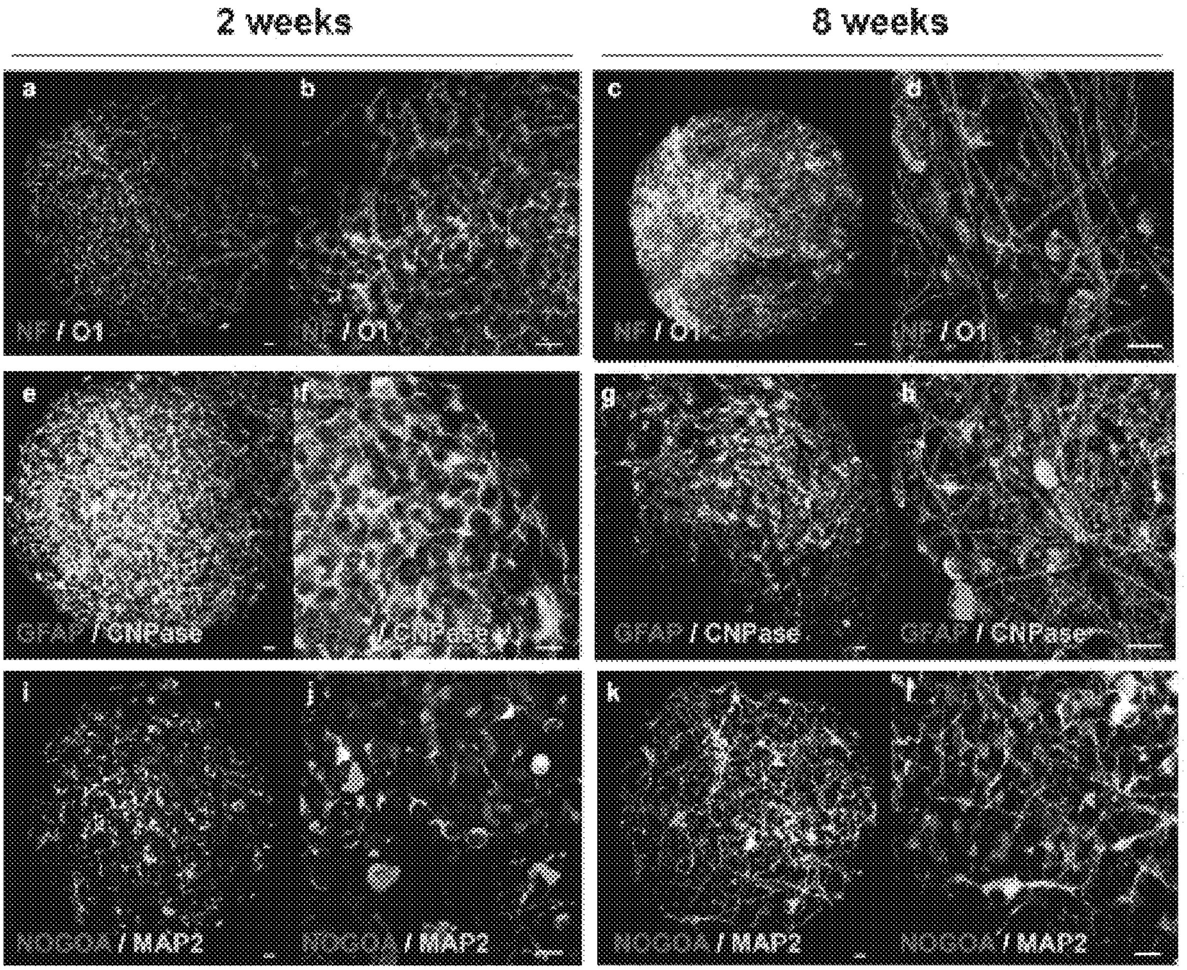
FIG. 2F depicts a comparison of expression of neuronal and glial markers at 2 and 8 weeks. At 2 weeks, oligodendrocytes (O1, CNPase, NOGOA) were identified without a preferential localization (a,b,e,f,i,j), later they resemble human oligodendrocytes and localize in close proximity with axons (c,d, g,h, k,l). At 2 weeks there are few MAP2-positive cells without identifiable neuronal shape (I,j) whereas at 8 weeks, the MAP2+ cells acquire a well-defined dendritic network (k,l). The amount of astrocytes and density of the astroglial network increases with time of differentiation (GFAP, g,h).
Figure 8B:
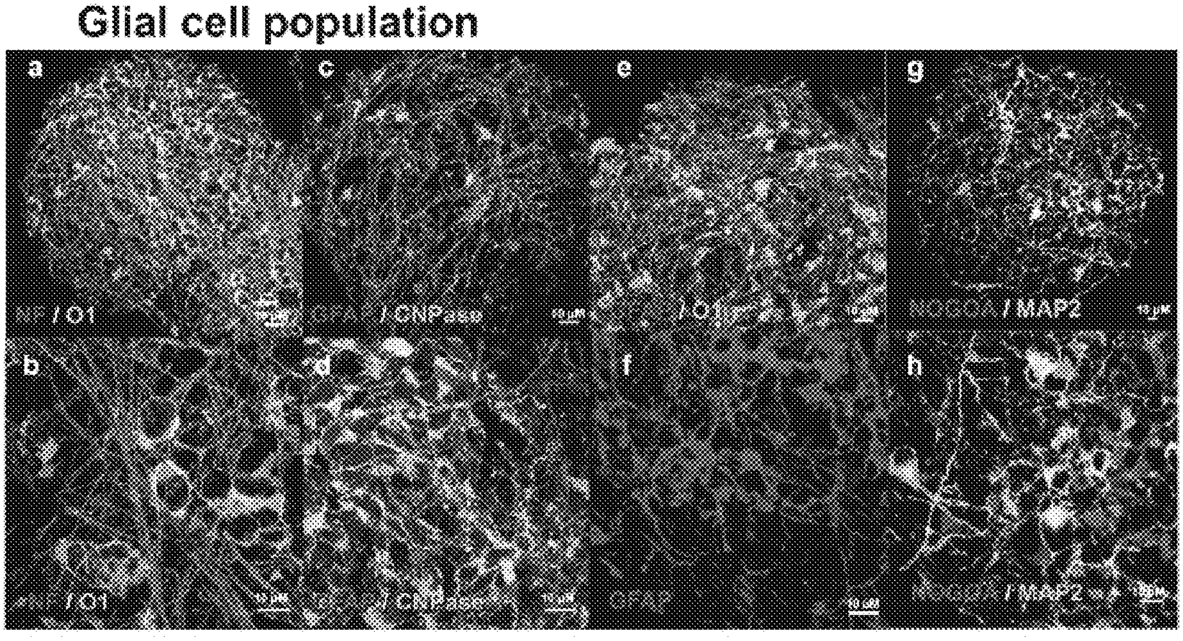

A subset of neuronal cells exhibited immunoreactivity for markers such as NOGOA, O1, O2, and CNPase (FIG. 8B, panels a-j; FIG. 1C5), which identifies the presence of mature oligodendrocytes in the BMPS [31, 33]. Automatic image quantification showed that oligodendrocytes (CNPase, NOGOA, and Olig1) comprised 3, 9, and 11% of the total cell population, respectively, at 8 weeks of differentiation (FIG. 8C; FIG. 1C5). Similar to the in vivo physiology, these cells were immunoreactive for myelin basic protein (MBP) (FIG. 2), which characterizes myelinating oligodendrocytes [32]. Moreover, they had morphological features of normal human oligodendrocytes in vivo and appeared in close contact with neuronal processes (FIG. 8*a-b*, FIG. 2C, 2D) Similarly, populations of neuroglia such as astrocytes and oligodendrocytes were identified using specific antibody markers. A subset of neuroglial cells exhibit immunoreactivity for markers such as NOGOA, Olig1 and CNPase (FIGS. 2C, panels a-f and 2C, panel i), which identify the presence of mature oligodendrocytes in the BMPS [29, 30, 31, 32]. This pattern of immunostaining suggests that oligodendrocytes within the BMPS are functional and myelinate axons. Similar to the in vivo physiology, these cells were also immunoreactive for myelin basic protein (MBP) (FIGS. 2C panel i and 2C panel j), which characterizes myelinating oligodendrocytes [33, 30]. These cells had morphological features of normal human oligodendrocytes and appeared in close contact with neuron processes, which resemble axonal structures (FIG. 2C, panels j-m). In addition, a high number of mature astrocytes (FIGS. 2Ca, 2Cb, 2Cg, 2Ch and 2F) at 4 and 8 weeks of differentiation were observed. Morphometric studies of neuronal processes identified by immunostaining with NF antibodies and MBP markers were used to estimate the percentage of myelinated axons within the BMPS with an average of 4% at 2 weeks, 25% at 4 weeks and 42% at 8 weeks of differentiation ($p<0.001$) (FIG. 2D). All analyzed BMPS showed similar extent of myelination at the same differentiation window. Percentages were calculated as the mean of at least 18 microscopy fields from at least 3 individual BMPS in 2 different experiments. Ultrastructural analysis by electron microscopy demonstrated cell projections, which enwrapped cell processes resembling axons after 8 weeks of differentiation (FIG. 2C).

Figure 8C:
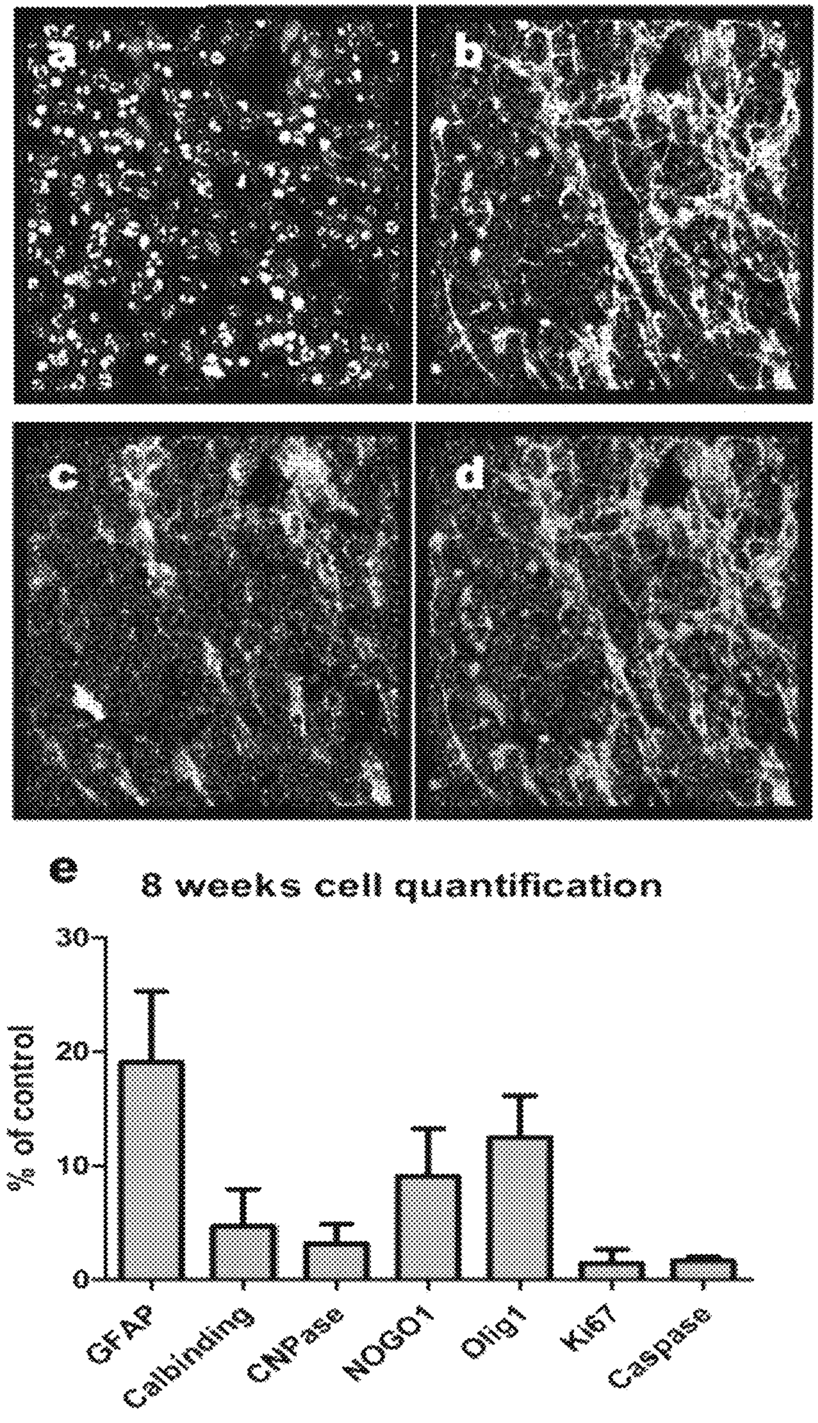

GFAP-positive cells formed numerous cell processes organized in a network typical for human astrocyte glial processes in vivo, which established contacts with other glial cells and neurons (FIG. 2Cg, 2Ch, 2F, and FIG. 8B). Image quantification revealed 19% of astrocytes in the total population (FIG. 8C). Altogether, the patterns of cell morphology, immunostaining and cell-cell interactions shown by neuronal and glial cell populations demonstrates that the BMPS recapitulates the cellular types and pattern of interactions seen in the human CNS and is, therefore, considered organotypic.

Figure 2G:
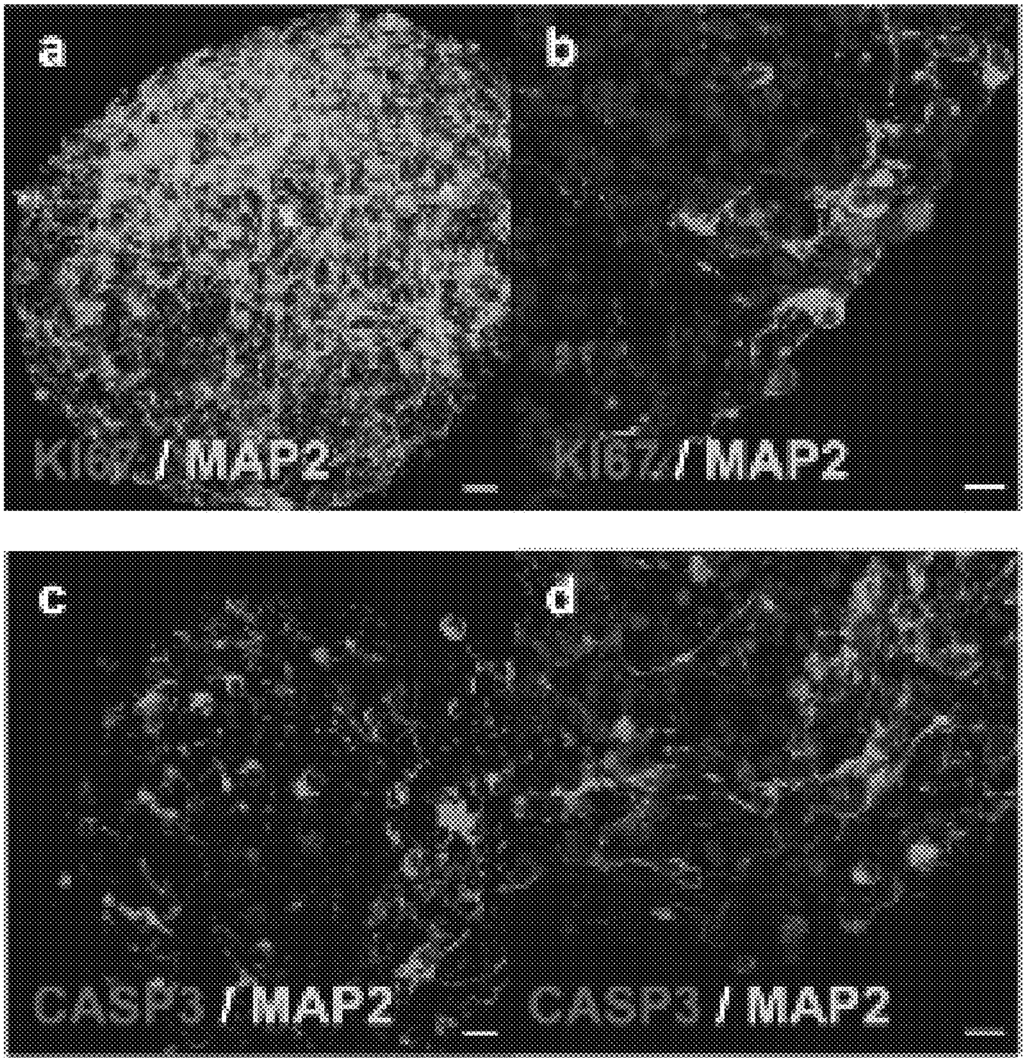
FIG. 2G depicts variation in the nuclear morphology. Co-immunostaining of neurons (MAP2) with cell-division marker KI67 showed that some cells are dividing (a,b), there was also a small degree of apoptosis demonstrated by positive staining with CASP3 (c). CASP 3-positive nuclei did not co-localize with mature neurons (d).
Figure 2H:
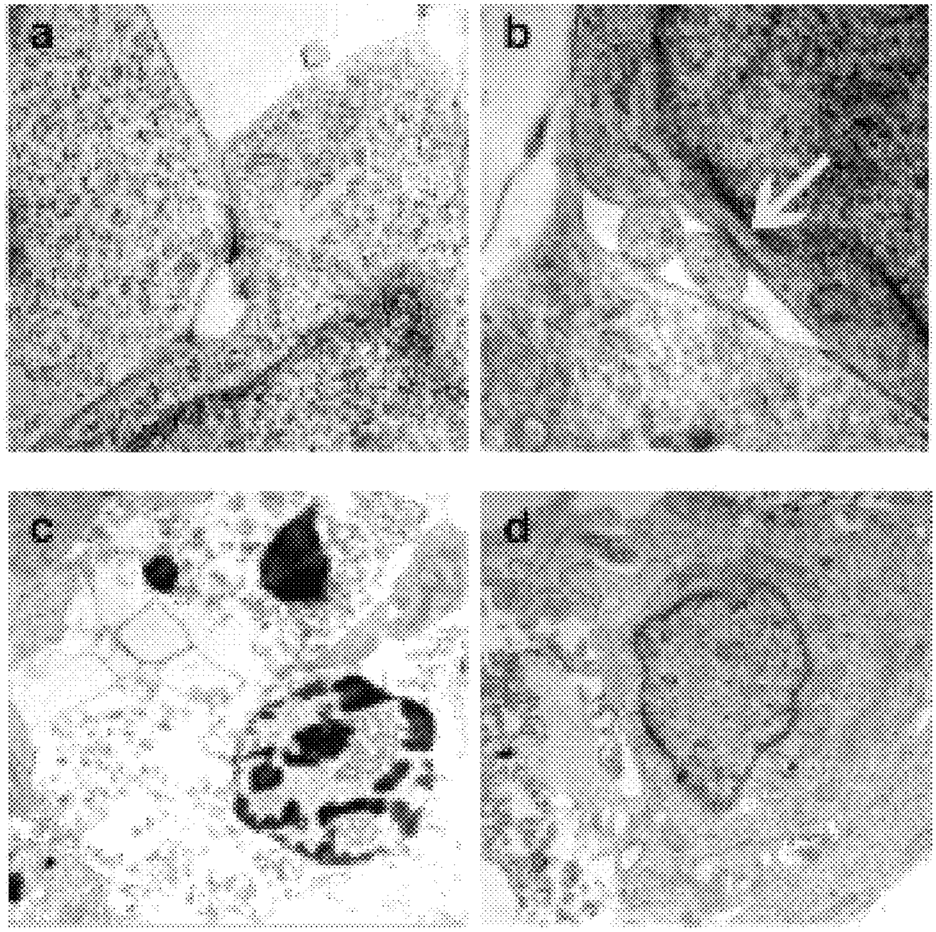
FIG. 2H depicts ultrastructure analysis by electron microscopy of 4 week BMPS showed evidence of cell to cell junctions demonstrating functional interactions between the cells (arrows, a,b). Nuclear variation was confirmed by the presence of a few apoptotic nuclei (c) and normal healthy nuclei (d). NF: Neurofilament-heavy-chain, MAP2: Microtubule-associated-protein 2, MBP: myelin-basic-protein, VGLUT1: Vesicular-glutamate-transporter 1, GFAP: Glial-fibrillary-acidic-protein, CALB: Calbindin, NOGOA: Neurite-outgrowth-inhibitor, SYP: Synaptophysin, SMI32: Nonphosphorylated-neurofilament, TH: Tyrosine-hydroxylase, O1: Olig1, CNPase: 2',3'-Cyclic-nucleotide-3'-phosphodiesterase. Scale Bar: 10 μm.
Figure 8D:
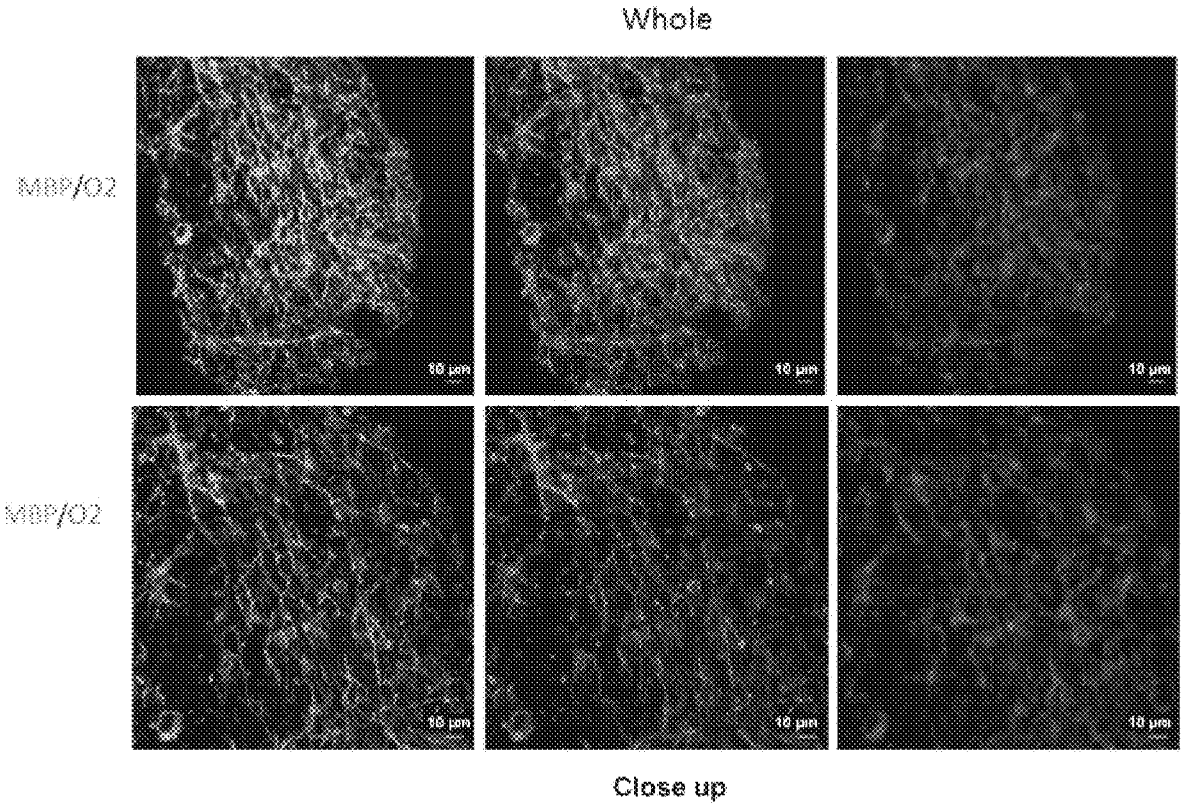
Figure 8E:
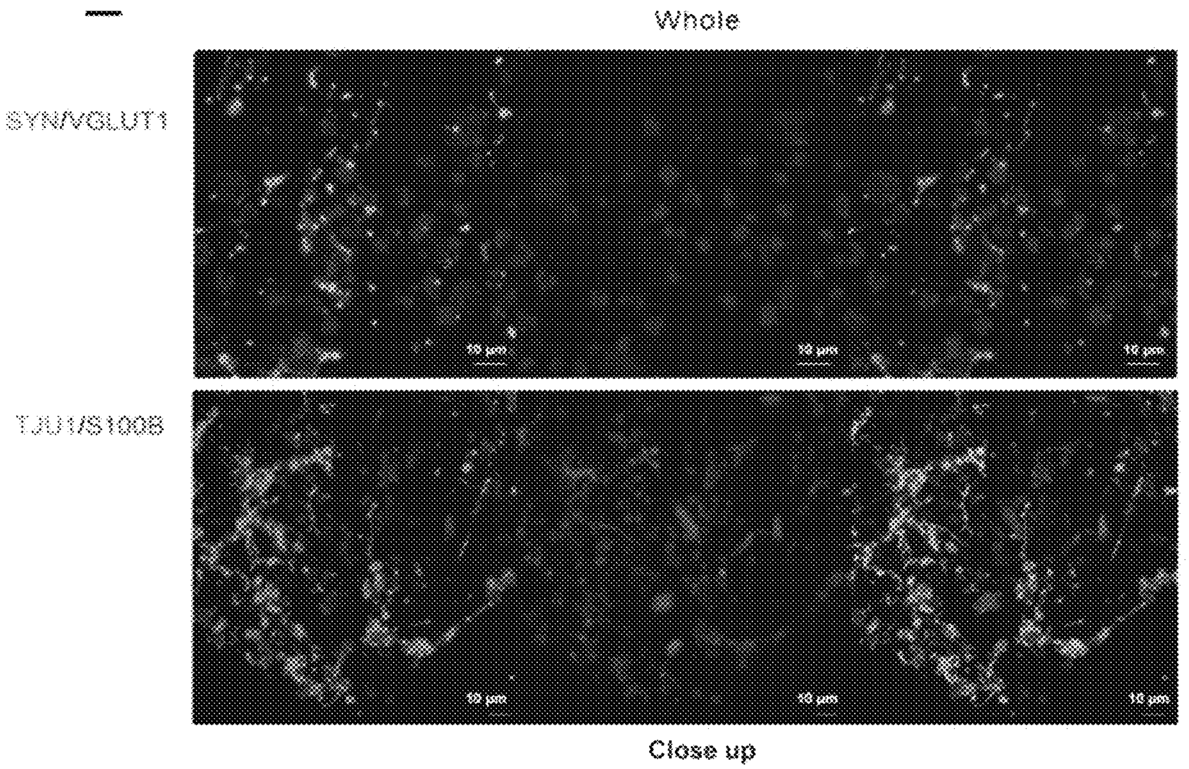
Figures 9A, 9B, 9C, 9D:
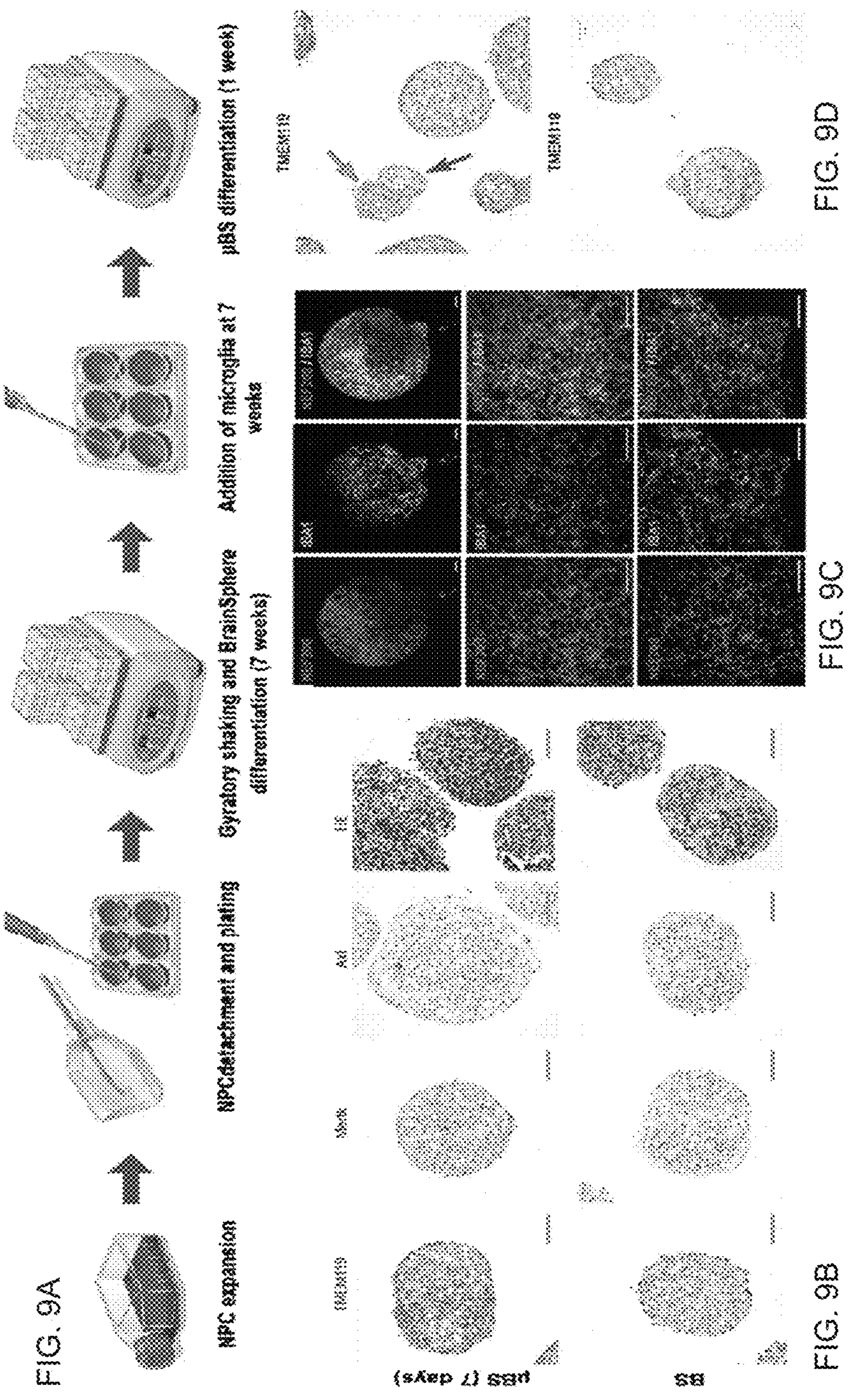
FIGS. 9A-9D depict the generation of microglia-containing BS (μBS). Immortalized Huma Microglia—SV40 were incorporated to 7 week differtiated BS by gravity.
Figure 10A:
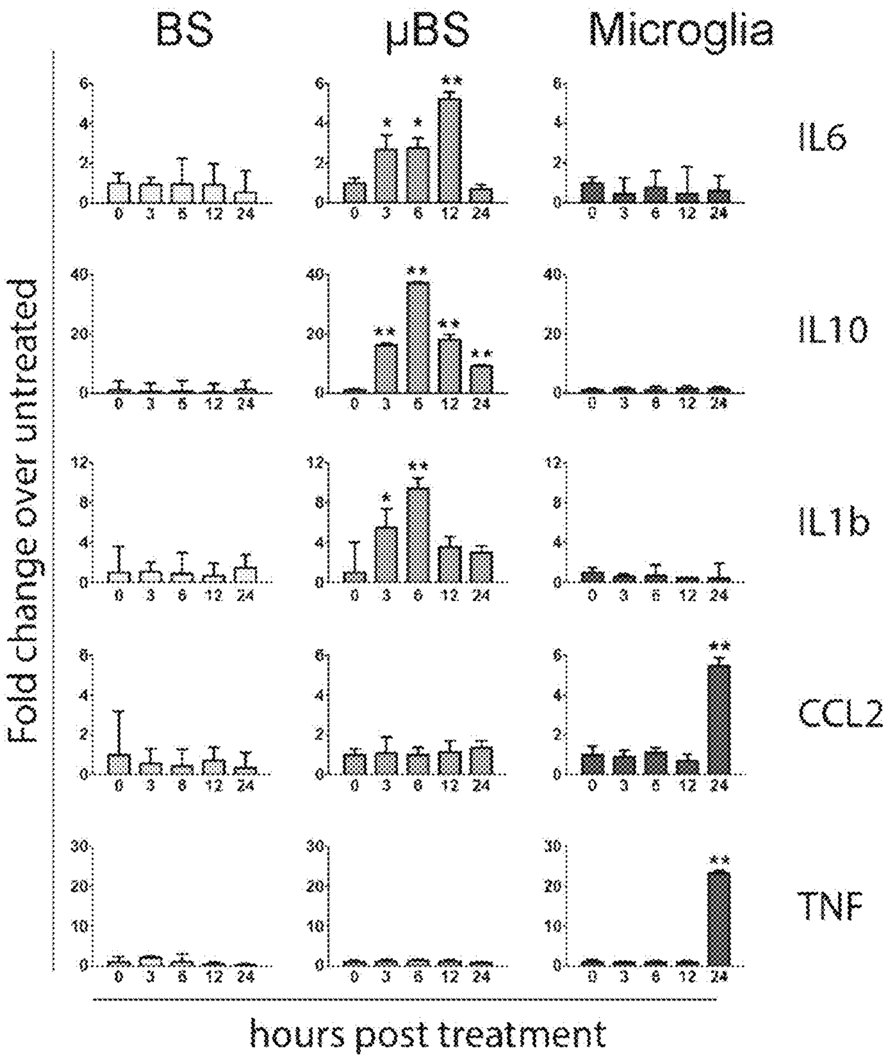
FIGS. 10A-10C depicts differences between BS, μBS, and microglia after LPS treatment. The microglia, BS, μBS, were exposed to 20 ng/mL LPS up to 24 h.
Figure 10B:
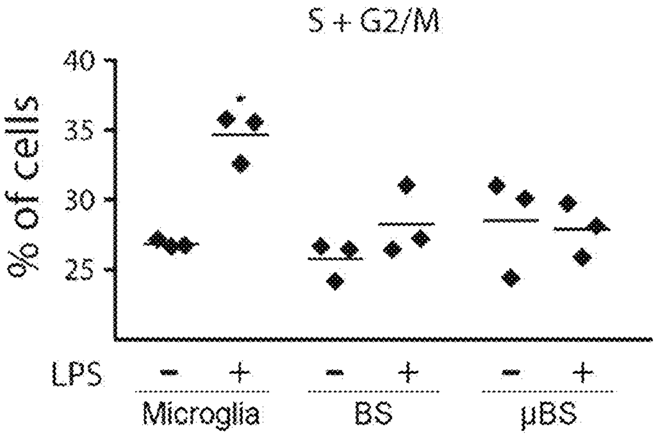
Figure 10C:
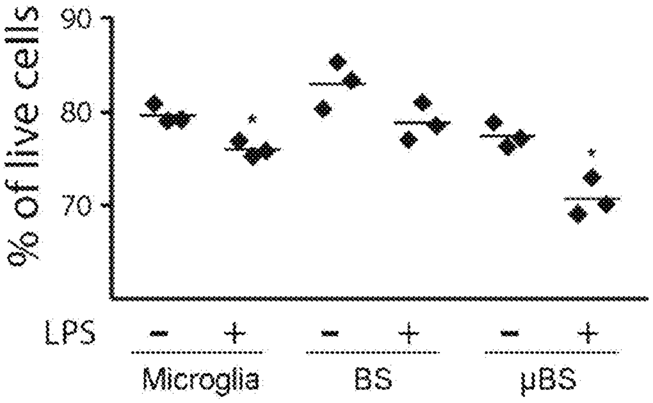
Figure 11:
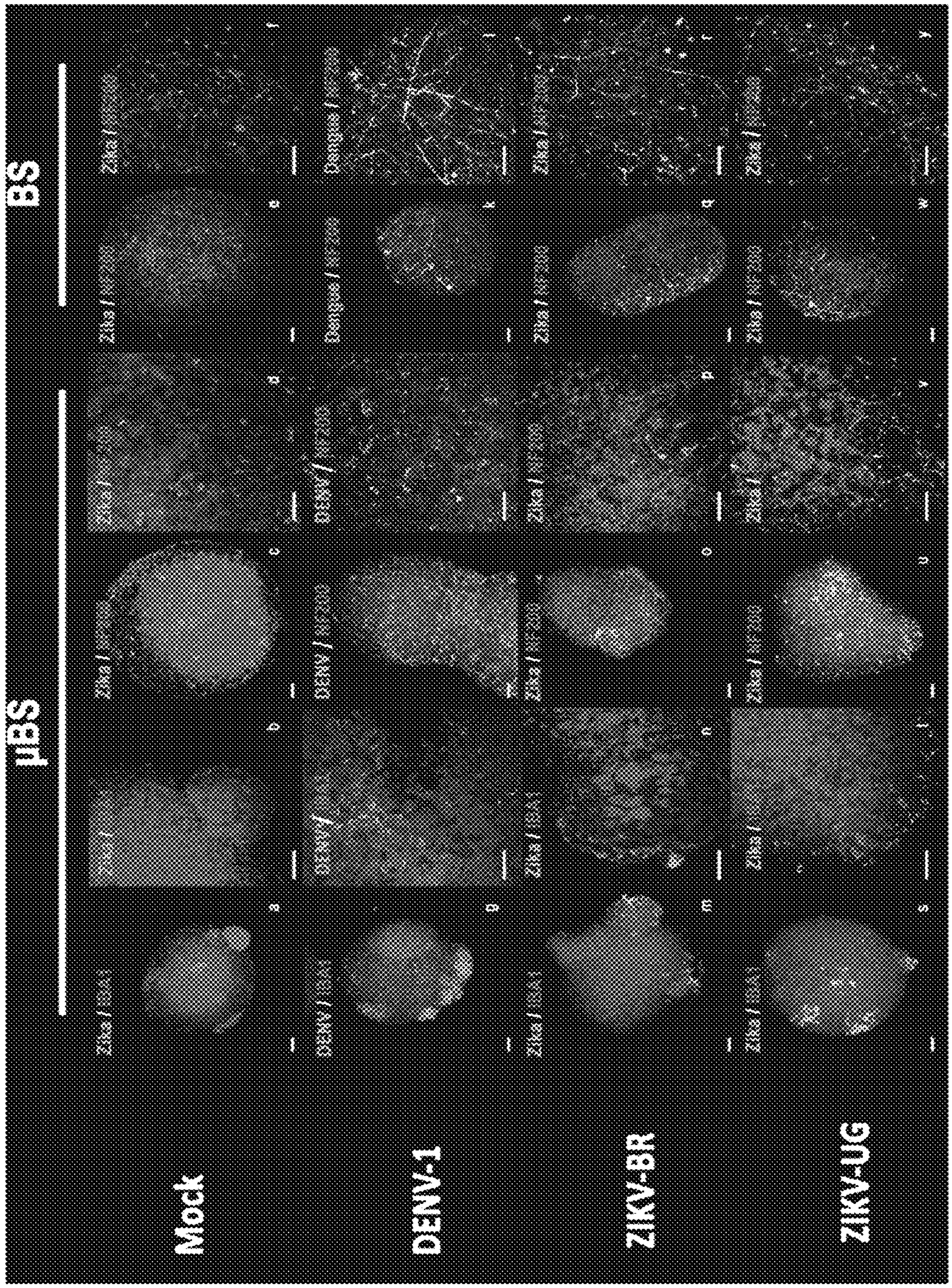
FIG. 11 shows virus infection by immunohistochemistry in BrainSpheres with μBS) and without microglia (BS). Green represents the Flavivirus marker for ZIKY (*NSI*) and DENV-L redrepresents microglia markers IBA1 abd NF200. Bard represent 50 μM (lower magnification) and 10 μm (higher magnification)
Figures 12A, 12B, 12C, 12D:
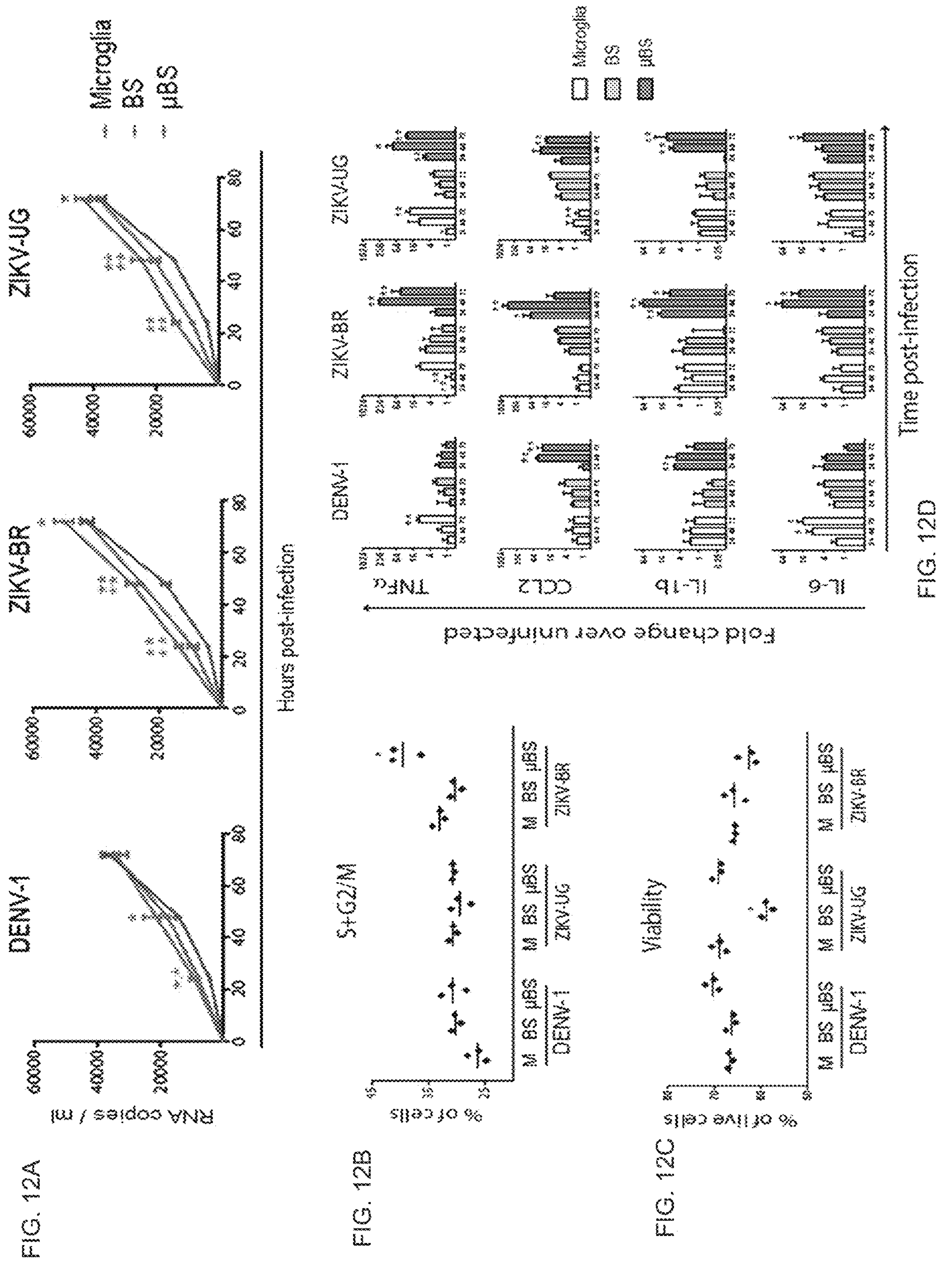
FIGS 12A-12D depict the effects of Flavivirus infection on 3D human iPSC-derived brain spheres (BrainSpheres, BS) without ot with microglia cells (μBS). The microglia cells, BS, and μBS wereinfected wirt Debgue, ZIKV-BR abd ZIKV-UG using MOI equal 0.1.

The morphology of cell nuclei observed by immunocytochemistry and electron microscopy showed some variation in nuclear morphology attributed to (i) cell proliferation as seen by positive staining for Ki67 and Nestin markers, and (ii) nuclear fragmentation likely associated with apoptosis as indicated by caspase 3 staining (FIG. 2G, 2H) was observed. These observations were also confirmed by electron microscopy studies at 4 and 8 weeks of differentiation (FIG. 2H). The variation of nuclei morphology likely reflects the active stages of cell differentiation that BMPS exhibited during all stages of development. The presence of apoptotic nuclei likely resemble stages of cell death seen in normal neurodevelopment [34, 35]. Importantly, Caspase 3-positive nuclei did not concentrate in the center of the spheres and BMPS did not present necrosis in the center of the 3D structures (FIG. 2G). Thus, Caspase3-positive nuclei do not appear linked to deprivation of oxygen or nutrients. Caspase has been quantified at eight weeks in BMPS (FIG. 8C). Additionally, FIGS. 8D and 8E depict co-expression of mature oligodendroglia markers (MBP and 02) and expression of neuronal markers (VGLUT, TUJ1, SYN), respectively.

Further analysis of neuronal cell populations and morphology presented a pattern of evolution that suggests BMPS maturation as seen by Nestin-positive cells decreasing over time of differentiation while MBP expressing cells increased (FIG. 2A). There was also evidence of cell-cell interactions as subsets of neurons showed several processes, which resemble dendritic and axonal projections that interact with other neurons as well as glial cells (FIG. 2B, FIG. 2H). Furthermore, cells immunostained with myelin binding protein (MBP) antibodies issued projections, which appear to enwrap neuronal processes, which resemble axons (FIGS. 2C, panels i-k, 2C, panel m). The pattern of immunostaining with MBP and its association with neuronal processes suggests that oligodendrocytes within the BMPS exhibit myelinating properties such as in the human CNS in vivo. Ultrastructural analysis by electron microscopy demonstrated cell projections, which enwrapped cell processes resembling axons (FIG. 2C, panel m).

Figure 3A:
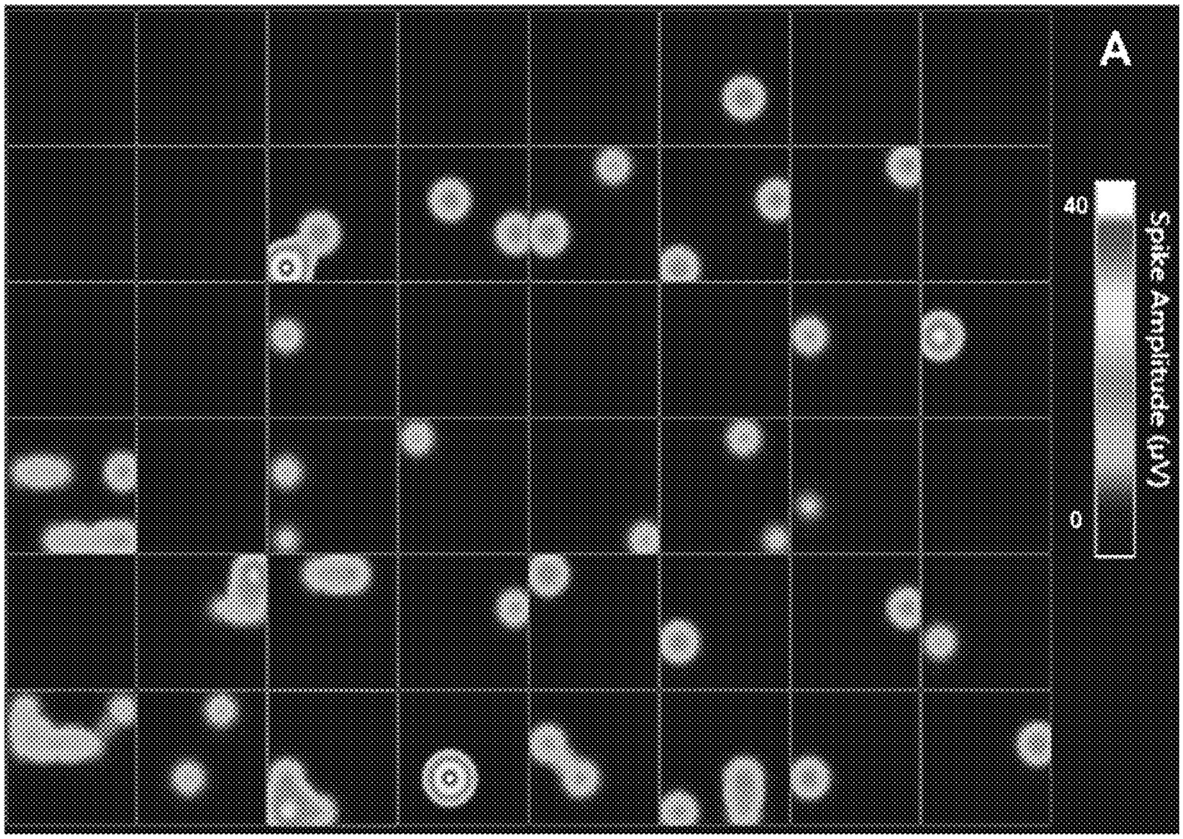
FIGS. 3A-3F depict electrical activity of BMPS. Cells were cultured in 3D for 8 weeks and then cultured in 12-well and 48-well MEA plates for 4 more weeks.

Example 5: Microelectrode Array Recording of Spontaneous Electrical Activity of BMPS To test the neurophysiological properties of the cells within the BMPS model, spontaneous electrical activity in BMPS was analyzed by micro-electrode array (MEA)(see FIG. 3 generally). BMPS were plated in 12-well or 48-well MEA plates at 8 weeks of differentiation. The aggregates were attached to the MEAs using Matrigel coating. Spontaneous electrical activity was measured starting one week after plating up to two weeks. The activity was measured for 20 minutes on 7 different days. Electrodes were considered active when the recorded activity was above 0.05 spikes/sec. FIG. 3A shows a representative heatmap of a 48-well MEA plate measurement from one 20 minute recording. The heatmap represents the spike amplitude (μV) with a minimum of 0 μV and maximum of 40 μV (FIG. 3A). The spikes showed a common waveform between different electrodes and measurements (FIG. 3B) and neurons were repeatedly firing. 25 electrodes, distributed over 19 wells, were included after the first step of data analysis. 20 to 40% of these 25 electrodes reached the threshold of 0.05 spikes/sec during each recording. FIG. 3F shows the spike events of active electrodes from one representative 20 minutes recording. These data show potential for the use of MEA to measure electrical activity of the 3D BMPS. Further optimization of the protocol may increase the measurement of the neuronal activity on the electrodes.

Example 6: A Human 3D Model to Study Parkinson's Disease

Due to the presence of TH-positive dopaminergic neurons in the iPSC-derived BMPS (FIG. 2B, panels k, l, and FIG. 8), the possibility of using this model to study Parkinson's Disease (PD), a neurodegenerative disorder known to specifically affect dopaminergic neurons, was further explored. Two well-known neurotoxicants, which induce pathogenic processes resembling the mechanism associated with neurodegeneration in PD: the illicit drug MPTP's toxic metabolite MPP+ and the broadly used pesticide rotenone, were selected. Both MPP+ and rotenone interfere with oxidative phosphorylation in mitochondria by inhibiting complex I [36]. Initially, cytotoxicity experiments were performed to estimate sub-cytotoxic concentrations of these two compounds affecting only dopaminergic neurons (FIGS. 4A and 4C). Selective disruption of dopaminergic neurons but not of any other cell types in the systems described herein were observed with immunohistochemistry after exposure to 1p M rotenone and 100 μM MPP+ for 24 h (FIGS. 4E and 4F). This effect was likely selective even at cytotoxic concentrations of 10 μM rotenone and 1000 μM MPP+ as these concentrations did not show any alterations in other neurofilament 200-positive neurons. Lower concentrations of these compounds may induce effects in dopaminergic neurons, however, the effect was not as obvious by immunocytochemistry. Higher concentrations of rotenone and MPP+ (up to 50 μM and 5000 μM, respectively) led to general cytotoxicity and affected also other neuronal types stained positive for neurofilament 200 (FIGS. 4E and F). 5 μM of rotenone and 1000 μM of MPP+ were selected for further studies as these concentrations induced clear and selective dopaminergic effects. Reactive oxygen species (ROS) were measured in the cellular medium using the OxiSelect™ In Vitro ROS/RNS Assay Kit (Cellbiolabs, San Diego, Calif.) as an indication of oxidative stress. Exposure to rotenone at 5 μM and MPP+ at 1000 μM showed an increase in ROS production after 24 hours exposure, while 12 hours showed no statistically significant changes. Real time RT-PCR was performed in order to determine effects of both chemicals on genes related to PD, mitochondrial dysfunction and oxidative stress. Tyrosine hydroxylase (TH, Dopaminergic neuronal marker) mRNA expression decreased by 84%±11 after exposure to 5 μM rotenone and 70%±9 after exposure to 1000 E M MPP+ for 24 hours. Additional genes related to PD also showed changes at sub-cytotoxic concentrations of MPP+ and rotenone. The expression of genes that encode T-box brain 1 (TBR1) and Alpha-synuclein (SNCA) protein decreased after 24 hours exposure. The reduction of TBR1 was 70±13% (rotenone) and 76±22% (MPP+) and the reduction of SNCA was 72±6% (rotenone) and 41±40% (MPP, however, BMPS exposed to 1 mM MPP+ led to no statistically significant changes in SNCA expression). Expression of genes related to mitochondrial function complex I (NDUFB1) or complex 0 (ATP5C1 or ATP50) tended to decrease in expression but these changes were not statistically significant. Caspase-1 gene expression, which has been related to SNCA, increased after 24 hours exposure to MPP+. These results demonstrate the potential of BMPS for studies elucidating molecular mechanisms of PD, lending itself to PD drug and neurotoxicity screening.

Example 7: Addition of Microglia

Peripheral blood mononuclear cells (PBMCs) are isolated from fresh or commercially available cryo-preserved whole blood of pooled healthy donors by Ficoll or Percoll gradient centrifugation. Monocyte populations are obtained by negative magnet-antibody selection after Ficoll or Percoll gradient and then re-suspend in RPMI 1640. Monocytes are cultured in macrophage serum-free medium, stimulated with a cocktail of cytokines, GM-CSF and IL-34. Monocytes may also be obtained by differentiation of iPSCs, hematopoetic or other stem cells. The microglia-like cells are combined with neuronal precursor cells in shaker cultures to preferably arrive at a final concentration of 5-8% microglia.

Primary monocytes or iPSC-derived monocytes may be incorporated into the system, both at early and later stages of BMPS differentiation. For the early stages, a number of $2\times10^6$ NPCs mixed with $2\times10^4$ monocytes are plated per 1 well (6 well-plate). Gyratory shaking is used at 88 rpms to generate spheres. After 2 days media are replaced with ½ CNS differentiation medial (Neurobasal® electro Medium (Gibco) supplemented with 5% B-27® Electrophysiology (Gibco), 1% glutamax (Gibco), 10 μg human recombinant GDNF (Gemini), 10 μg human recombinant BDNF (Gemini)) and ½ macrophage differentiation media (Dulbecco's modified Eagle's medium (Invitrogen) supplemented with 10% FCS, 0.055 mM β-mercaptoethanol, M-CSF (50 ng/ml), and IL-3 (25 ng/ml) (R&D Systems). The medium is replaced every 3 days.

Monocytes can also be incorporated after BMPS differentiation. For that, BMPS are differentiated up to 8 weeks. BMPS spheres are separated in 500 μl Eppendorf tubes. $2\times10^4$ monocytes are added to the Eppendorf with the BMPS. Tubes are shaking manually every hour, up to 8 hours. After that, BMPS-monocytes are collected and plated in 6 well plates. Cells are kept on constant shaking until use.

The characterization of the immune-competent human organoids can be carried out by immunocytochemically assessing the presence of markers such as HLA-DR, and the ionized calcium-binding adapter molecule 1 (Iba1), specific microglial markers. Measures of cytokines and chemokines release and expression of receptors associated with microglia function (e.g., CCL2 and CX3CL) demonstrates successful engrafting of the microglia cells. This modified model is more suitable to investigate the neuroimmunological component associated with many substance exposures and diseases.

Example 8: Addition of a Blood Brain Barrier

The blood brain barrier (BBB) has a crucial role in neurotoxicity, being the last barrier for substances before reaching the brain. Moreover, the BBB is the bottleneck in brain drug development and is the single most important factor limiting the future growth of neurotherapeutics [81]. Most of the in vitro models do not incorporate BBB.

Figure 7:
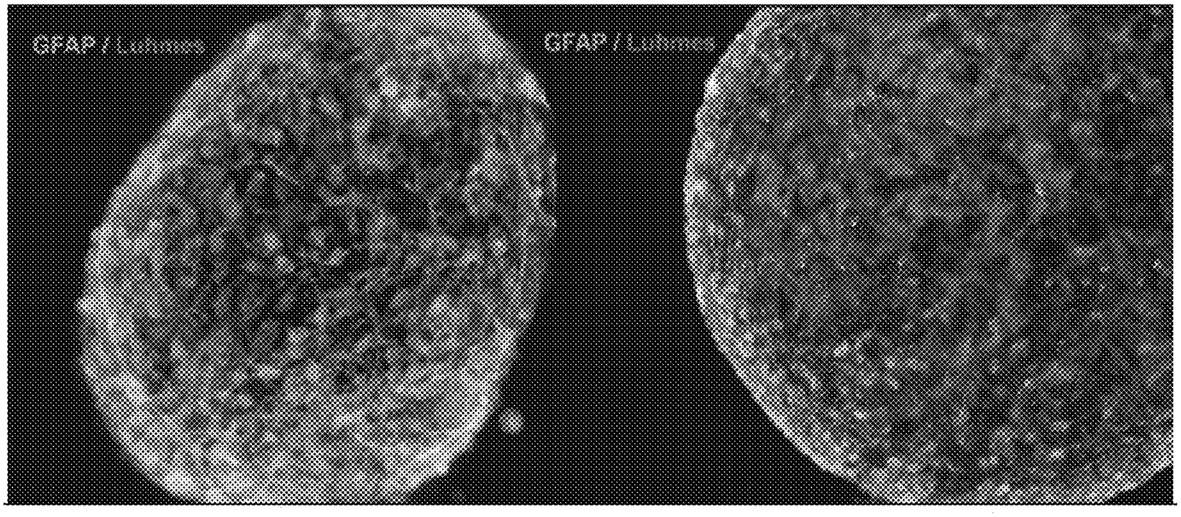
FIG. 7 depicts an example of a BMPS covered with other cell types. LUHMES fluorescent cells (red) were incorporated to a BMP using gravity systems to cover the surface of the aggregate.

Human brain microvascular endothelial cells (hBMECs) from human iPSCs are incorporated into the BMPS by two techniques. In the first approach, mature BBB endothelial cells and neuronal precursors cells (NPCs) are combined in a single cells suspension in a ratio of 1:5, gyratory shaking or stirring are used to generated spheroids and aggregates are cultured up to 8 weeks. In the second technique, mature BMPS (8 weeks of differentiation) are covered by BBB endothelial cells using gravity systems (aggrewell, gravity well or hanging drops). Cells may be covered as well with other cell types, such as fluorescent LUHMES cells (FIG. 7).

Example 9: Addition of Reporters

The BMPS gives the opportunity to develop cell-based assays allowing for high-content imaging (HCI) that can be adapted to high-throughput platforms, to evaluate the effects of toxicants on key cellular processes of neural development and physiology in the culture system.

Example of establishing fluorescent iPSC cell line: Creation of reporter cells lines greatly assists imaging efforts by allowing us to avoid complications associated with staining 3D cultures, to image subsets of cells, and to perform functional assays. Differentiated 3D aggregates from iPSC cultures spiked with 1-2% of iPSCs ubiquitously expressing fluorescent protein allow visualizing individual cells within the aggregates aiding quantification of phenotypic parameters, including neurite outgrowth and migration. Lines expressing markers allow measurement of synapse formation (PSD95, Synapsin 1), proliferation (Ki67), glial maturation (GFAP), and calcium signaling (GCaMP). Clustered Regularly Interspaced Short Palindromic Repeats/Cas (CRISPR) were used to create the various lines. Similar in function to the well-established zinc-finger (ZFNs) and TALEN nucleases, the Cas9-CRISPR system is a new entrant into the rapidly emerging field of genome engineering and has been quickly adopted and validated across a wide array of human stem cells. Gene-editing in hiPSCs has traditionally been a technically difficult task but with these advances it is now possible to generate reporter and mutant cell lines with genetically matched controls [83, 84, 85, 86]; essential tools not only for this project but also for the future success of using human iPSC-derived cells in quantitative live-cell phenotypic assays of toxicant testing.

Using the CRISPR-Cas9 system, fluorescent protein (FxP) reporter cell lines were generated by generating gRNAs targeting the gene of interested. In this system as described herein, an RNA guided Cas9 endonuclease is used in conjunction with customizable small guide RNAs (gRNAs) to target and cleave any DNA template with a GN21GG sequence; the first G is for the U6 polymerase promoter while the N21GG is for the protospacer adjacent motif (PAM) sequence requirement of Cas9 [86, 87, 89].

For reporter cell generation, homology-directed repair (HDR) guides the insertion of the appropriate DNA donor fragment into a target site at regions of homology between the donor fragment and the genomic DNA target. An ES line that ubiquitously expresses GFP was created by introducing CAG promoter-driven GFP into the AAVS1 safe harbor locus, and can use these constructs to transfect iPSC cells. For other reporters, constructs may be created that will direct the integration of a self-cleaving P2A peptide sequence [90] targeted fluorescent protein cassette in frame at the stop codon of the gene of interest. The P2A sequence engineered between the C-terminus of the endogenous protein and the fluorescent protein may minimize possible fusion protein functional defects. Plasmids encoding the Cas9 nuclease, the targeting gRNA, and appropriate donor DNA will be introduced by electroporation, recombinant hiPSC clones will be manually selected and screened for the desired insertion by PCR, and the genotype may be verified by sequencing. Reporter hiPSCs will be subjected to a differentiation protocol and expression of the reporter validated by examining expression patterns and through immunohistochemistry experiments where it may be determined whether the FxP expressing cells co-label with known markers.

Example 10: Using Cells with Specific Genetic Backgrounds

The use of iPSCs, as described herein, has created new opportunities to study human diseases and gene/environment interaction [20, 21]. Fibroblasts or other somatic cells from healthy and diseased individuals can be reprogrammed into iPSCs, and subsequently be differentiated into all neural cell types. Similarly, iPSC can be genetically modified before creating the BMPS. As a proof-of-principle, iPSCs were obtained from patients with Down's syndrome (FIGS. 1C5 and 5A-D), Rett Syndrome and from individuals with mutations in disrupted in schizophrenia 1 (DISC1). DISC1 may have some functional overlap with TSC-iPSCs as both are involved in the mTOR cell signaling pathway.

The Down's syndrome model is further characterized (see FIGS. 5A-5D). Down's syndrome iPSCs have been successfully differentiated into neural precursor cells (NPCs). Currently the cells are differentiated in 3D and characterization by gene expression and immunohistochemistry is being performed. The Down's syndrome model has been exposed to compounds that induce oxidative stress (rotenone and paraquat). The response was compared to the model from healthy donors, which were more sensitive to these compounds than the healthy model.

Example 11: Combining the BMPS with Other Organoids

In some embodiments, BMPS may be combined with other organs and/or organ model systems. Several groups have been developing organ-on-a-chip platforms for different organs by using microfluidic techniques. Those platforms are designed to mimic in-vivo fluidic flows in the organs by separating cell culture chambers and perfusion channels, and successfully demonstrate recapitulation of iPSC-based organ functions. Together with other organ models on these platforms, the BMPS can be integrated, which allow us to untwine the complex toxicology from organ interactions. Such platforms allow (1) in-situ and high-throughput production of mini-brains on chip, (2) in-vivo like fluidic flow around mini-brains with enough supply of nutrient and small molecule through diffusion, (3) a large number of parallel test of toxic materials, and (4) a real-time monitoring of electrophysiological activities from BMPS with integrated electrodes. Companies such as TissUse GmbH have designed microfluidics platform that allow culture of floating spheres like the BMPS as described herein.

Example 12: Cryopreservation and Other Modes of Transportability

Figure 6:
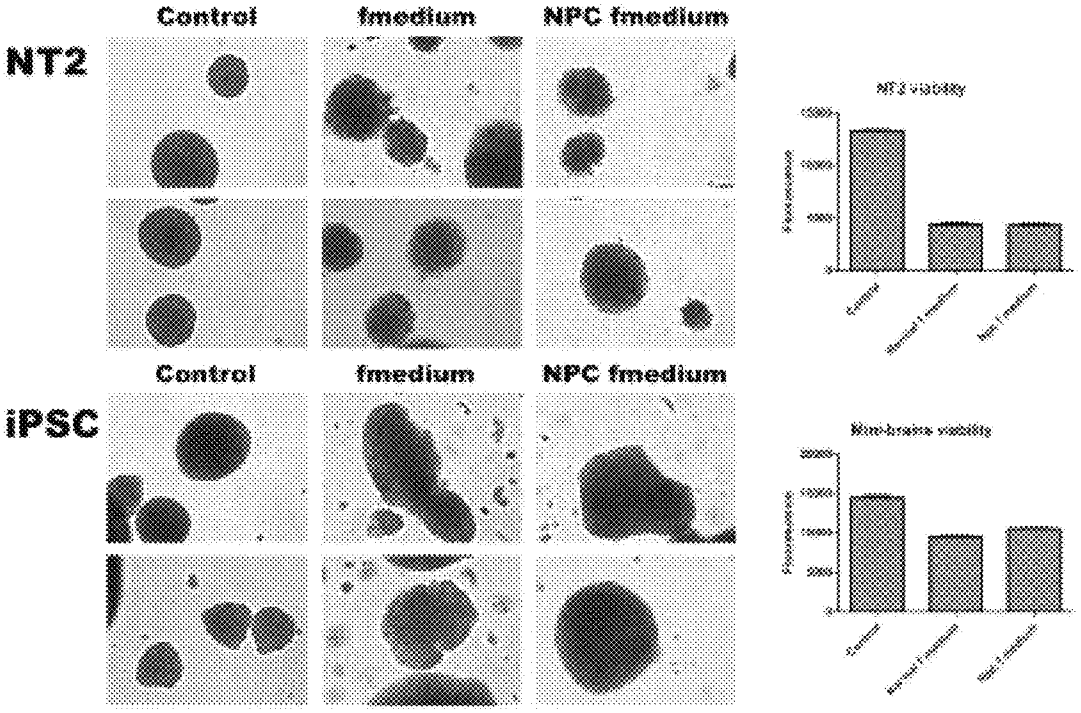
FIG. 6 depicts viability of pre-frozen NT2 human teratocarcinoma cell line and iPSC derived mini-brains. Fmedium corresponds to 95% FBS and 5% DMSO. NPC fmedium corresponds to STEMdiff™ Neural Progenitor Freezing Medium. Viability was measured by resazurin cell viability assay. Non-frozen cells at the same stage of differentiation were used as control aggregates.

In order to e.g. incorporate the BMPS into platforms or enable any use in other laboratories, transportability of the system was optimized. Preliminary studies have shown possible recovery of the neuronal 3D aggregates after cryopreservation (FIG. 6). A human embryonal carcinoma stem cell line, (hNT2), and iPSC derived-aggregates were differentiated into mature neurons (8 weeks of differentiation for each cell line) and then cryopreserved with regular cryopreservation medium (95% FBS and 5% DMSO) or STEMdiff™ Neural Progenitor Freezing Medium (Stem cells technologies). After 2 days in liquid nitrogen, cells were thawed. Freezing media was removed and fresh media was added. One day later, viability was measured using the resazurin cell viability assay. hNT2 aggregates presented a 70% decrease in viability in both freezing medias while iPSC derived mini-brains showed a 20%-35% reduction in viability (FIG. 6). However, viability recovery of the 3D aggregates is currently optimized using other viability and functional assays. Optimization of this protocol will vary additives (DMSO, HES, glycerol, serum etc.), the cooling temperature gradient as well as thawing protocol.

Human iPSC derived mini-brains are kept in culture at 37° C. In order to transport the live mini-brains, temperature must be controlled. Different methods can be used to control temperature during transport. Heating pads combined with an insulated box have been used to transport live biological material. Disposable chemical pads employ a one-time exothermic chemical reaction such as catalyzed rusting of iron, or dissolving calcium chloride. The most common reusable heat pads are based on a chemical reaction that transforms a liquid into a solid thus releasing energy. Some new heating pads (such as Deltaphase Isothermal Pad 3SET, from Braintree Scientific, Inc.) have been able to maintain 37° C. for more than 6 hours. 3D mini-brains cultured up to 8 weeks are sent in an insulated material box with heating pads. After transport, viability may be measured.

Example 13: Overview

The techniques herein provide a human BMPS model that is a versatile tool for more complex testing platforms, as well as for research into CNS physiology, mechanisms associated with (developmental) neurotoxicity, and pathogenesis of neurological disorders. Prior art stem cell-derived brain model systems developed in the past few years have shown the capability to recapitulate some of the in vivo biological processes (Juraver-Geslin and Durand, 2015; Nakano et al., 2012; Krug et al., 2014) and have an advantage over other classical in vitro models as they facilitate the study of various differentiation mechanisms, developmental processes and diseases (Lancaster et al., 2013). Unfortunately, these prior art systems require complicated protocols that reduce the reproducibility of the system and make it difficult to use in other fields such as chemical toxicity and drug screening. Additionally, these prior art models are also limited by large diameters, which lead to extensive cell death in the interior regions due to insufficient diffusion of oxygen and nutrients (Lancaster et al., 2013) and other artifacts.

The techniques herein overcome the limitations of the prior art by developing a human in vitro model by the gyratory shaking technique that enables reliably generation of a high number (about 500 per six-well plate) of viable BMPS that are homogeneous in size and shape. Control of size makes it possible to keep cell aggregates below 350 μM in diameter (FIG. 1C) and thereby avoid disparate morphology and/or necrosis in the center of the spheres. Moreover, the BMPS showed reproducible cell composition by immunomorphological quantification, assessment of imaging-based endpoints and flow cytometry analysis.

As described herein, the 3D differentiation protocol for the BMPS covers stages from neuronal precursors to different cell types of the mature CNS. As discussed in detail above, at two weeks, BMPS consisted of an immature population of cells, showing minimal neuronal networks, a low percentage of mature astrocytes and oligodendrocytes, and minimal but early stages of myelin basic protein (MBP) expression. iPSC differentiation into mature BMPS was indicated by decreasing NES expression over time and a progressive expression of mature neuronal and glial markers such as MAP2, GFAP, 01 and MBP. Gene expression studies, flow cytometry, image analysis, immunostaining and miRNA studies have shown increase of cell maturation markers, which follow the BMPS differentiation. The presence of GABAergic neurons, dopaminergic neurons and glutamatergic neurons was documented by immunohistochemistry and real-time PCR data. Moreover, the BMPS showed spontaneous electrical activity, indicating neuronal functionality of the system.

Since astrocytes and oligodendrocytes play important roles during neuronal development, plasticity and injury, the presence of glial cell populations in the presently disclosed BMPS model provides an excellent opportunity for the evaluation of neuronal-glial interactions and the role of glia in pathogenesis and toxicity processes. Astrocytes have an important role in protecting neurons, increasing neuronal viability and mitochondrial biogenesis from both exogenous (e.g. chemicals) and endogenous toxicity (Shinozaki et al., 2014; Aguirre-Rueda et al., 2015), especially against oxidative stress (Shao et al., 1997; Schwab and McGeer, 2008). Thus, their presence in a biological system to study disease and neurotoxicity is crucial. Immunohistochemistry and RT-PCR results showed increasing numbers of astrocytes (GFAP-positive cells) in the BMPS model reaching 19% astrocytes of the total cell population at eight weeks, which is earlier than in previously described cortical spheroids, where similar proportions of GFAP-positive cells were observed first at day 181, at day 86 the number of GFAP+ cells was below 10% (Pasca et al., 2015).

The most novel element of this BMPS is the presence of mature human oligodendrocytes with myelination properties, which has not been achieved in the prior art. Immunocytochemical and ultrastructural studies confirmed the morphological identity of these cells (FIG. 2D) as multiple markers for mature oligodendrocytes were expressed by rounded cells with branching processes and membrane sheaths that are similar to the ones found in humans in vivo. The structure and morphology was further confirmed by electron microscopy. Quantitative assessment of the myelination process of MBP immunostaining along axons showed an increase over time of differentiation reaching 42% of myelinated axons at eight weeks (FIG. 2D). 3D reconstruction of confocal z-stacks images (FIG. 2A) and electron microscopy confirmed the wrapping of axonal structures after eight weeks of differentiation (FIG. 2C). These findings are of particular relevance since myelin is a critical element for proper neuronal function and development, and the covering of axons by myelin allows faster action potential transmission, reduces axonal energy consumption and protects the axons from degeneration (Nave, 2010). Furthermore, recent evidence suggests that oligodendrocytes and myelin have a role in the metabolic support of axons independent of their role in action potential conduction, highlighting their importance in neuronal survival (Saab et al., 2013). This is the first time that a 3D human microphysiological system, consisting of different types of neurons and glial cells, has achieved such a high percentage of myelination. The ability to assess oligodendroglia function and mechanisms associated with myelination in this BMPS model provides an excellent tool for future studies of neurological disorders such as multiple sclerosis and other demyelinating disorders. As an illustration it was recently discovered that astroglia cells could promote oligodendrogenesis via secreted molecules (Jiang et al., 2016). A human BMPS that consist of neurons, astrocytes and oligodendrocytes is essential to evaluate this mechanism further and to develop a potential therapy for demyelinating disorders.

In conclusion, the techniques herein provide a BMPS that replicates crucial aspects of brain physiology and functionality. The potential for studying developmental and neurodegenerative disorders, brain infections, toxicity and trauma with such a system is growing. Furthermore, the potential to use iPSCs from different donors adds a personalized component to these studies. The high reproducibility and relatively simple protocol, enables future medium-throughput (96-well format) testing of chemicals, drugs and their potential to induce or treat diseases.

Methods and Materials

Chemicals

Rotenone and MPP+ were supplied from Sigma-Aldrich (St. Louis, Mo.). A 10 mM rotenone stock was prepared in DMSO Hybri-Max (Sigma) while MPP+ was diluted in water to a concentration of 30 mM.

iPSC Generation

CCD1079Sk (ATCC® CRL2097™), IPS IMR90 (WiCELL) and ATCCDYP0730 Human (IPS) Cells (ATCC® ACS1003™) fibroblasts were originally purchased from ATCC. All studies followed institutional IRB protocols approved by the Johns Hopkins University School of Medicine. Human fibroblasts and mouse embryonic fibroblasts (MEFs) were cultured in Dulbecco's modified Eagle's medium (DMEM, Mediatech Inc.) supplemented with 10% fetal bovine serum (FBS, HyClone) and 2 mM L-glutamine (Invitrogen). MEFs were derived from E13.5 CF-1 mouse embryos. Human iPCS cells were generated with the EBV-based vectors as previously described [75]. iPSC from other sources were used as well. Colonies of iPSCs were manually picked after 3-6 weeks for further expansion and characterization. iPSCs (passage ≤20) were cultured on irradiated MEFs in human embryonic stem cell (hESC) medium comprising D-MEM/F12 (Invitrogen), 20% Knockout Serum Replacement (KSR, Invitrogen), 2 mM L-glutamine (Invitrogen), 100 μM MEM NEAA (Invitrogen), 100 μM β-mercaptoethanol (Invitrogen), and 10 ng/mL human basic FGF (bFGF, PeproTech). Media were changed daily and iPSC lines were passaged using collagenase (Invitrogen, 1 mg/ml in D-MEM/F12 for 1 hr at 37° C.). These iPSC lines have been previously fully characterized [75].

Neuronal Progenitor Cells (NPC) Production

NPC generated followed the previous published protocol [75]. Briefly, iPSCs colonies were detached from the feeder layer with collagenase (1 mg/ml) treatment for 1 hr and suspended in EB medium, comprising of FGF-2-free hESC medium supplemented with Dorsomorphin (2 μM) and A-83 (2 μM), in non-treated polystyrene plates for 4 days with a daily medium change. After 4 days, EB medium was replaced by neural induction medium (hNPC medium) comprising of DMEM/F12, N2 supplement, NEAA, heparin (2 μg/ml) for 15 more days. The floating neurospheres were then dissociated to single cells in Accutase and plated in 175 mm flasks and were allowed to expand for 7 days. NPCs were expanded in poly-1-ornithine and laminin-coated 175 mm flask on StemPro® NSC SFM (Life Technologies). Half of the media was changed every day. Cultures were maintained at 37° C. in an atmosphere of 5% $CO_2$. After NPC generation, iPSCs colonies were detached and NPCs were expanded in poly-1-ornithine and laminin-coated 175 mm flask in StemPro® NSC SFM (Life Technologies). Half of the media was changed every day. Cultures were maintained at 37° C. in an atmosphere of 5% CO2.

BMPS Differentiation

At 100% confluence NPCs were detached mechanically and counted. $2\times10^6$ cells per well were plated in 2 ml of medium in non-treated 6 well-plates. Cells were grown in NPC media for two days under constant gyratory shaking. Subsequently, medium was changed to differentiation medium (Neurobasal® electro Medium (Gibco) supplemented with 5% B-27® Electrophysiology (Gibco), 1% glutamax (Gibco), 0.02 μg/ml human recombinant GDNF (Gemini), 0.02 μg/ml human recombinant BDNF (Gemini)). Cultures were maintained at 37° C., 5% $CO_2$ under constant gyratory shaking for up to 8 weeks. Differentiation medium was routinely changed every 2 days.

Size Measurement

Aggregates (n=20) from 3 independent experiments were randomly selected per time point for obtaining pictures and measuring size using SPOT software 5.0. Results were expressed as mean±SD. Cells were kept two days in NPC medium, indicated as NPC med. 2d in FIG. 1B.

RNA and miRNA Extraction

Total RNA was extracted from aggregates every week up to 8 weeks of differentiation using Tripure (Roche, Switzerland) according to Chomczynski and Sacchi (1987) [76]. The same RNA extraction method was used to isolate RNA after toxicant treatment. RNA quantity and purity was determined using NanoDrop 2000c (Thermo Scientific). One microgram of RNA was reverse-transcribed using the M-MI V Promega Reverse Transcriptase (Promega) according to the manufacturer's recommendations. For miRNA reverse-transcription 60 ng of RNA were reverse transcribed using TaqMan microRNA Reverse transcription kit in combination with miRNA specific stem-loop primers, which are a part of TaqMAn microRNA expression assay. Upto eight stem-loop primers were multiplexed in one reaction.

Quantitative RT-PCR

The expression of genes was evaluated using specific Taqman® gene expression assays (Life Technologies). miRNA expression was analyzed using TaqMAn microRNA expression assay in combination with TaqMan miRNA Reverse Transcription kit using protocol described in [77]. Table 1 shows a summary of the genes assayed. Real time RT-PCRs were performed using a 7500 Fast Real Time system machine (Applied Biosystems). Fold changes were calculated using the 2(−ΔΔCt) method [78]. β-actin and 18s were used as a housekeeping genes for mRNA and RNU44 for miRNA. There were no statistically significant differences in expression for β-actin, 18s, and RNU44. Data were presented as mean±SD, normalized to housekeeping genes and week 0.

Immunocytochemistry of the BMPS

BMPS aggregates were collected at 2, 4 and 8 weeks. BMPS were fixed in 4% paraformaldehyde for 1 hour, washed 3 times in PBS, then incubated for 1 hour in blocking solution consisting of 5% normal goat serum (NGS) in PBS with 0.4% TritonX (Sigma). BMPS were then incubated at 4° C. for 48 hours with a combination of primary antibodies (Table 2) diluted in PBS containing 3% NGS and 0.1% TritonX. BMPS were washed in PBS 3 times after which they were incubated with the appropriate fluorophore-tagged secondary antibody for 1 hour in PBS with 3% NGS at room temperature. Double immunostaining was visualized using the proper combination of secondary antibodies (e.g., goat anti-rabbit secondary antibody conjugated with Alexa 594 and goat anti-mouse secondary antibody conjugated with Alexa 488 (Molecular Probes). Nuclei were counterstained with DRAQ5 dye (Cell Signaling; 1:5000 in 1×PBS) or NucRed Live (Molecular Probes) for 15 minutes before mounted on slides with coverslips and Prolong Gold antifade reagent (Molecular Probes); BMPS used as negative controls for immunostaining were processed omitting the primary antibody. Images were taken using a Zeiss UV-LSM 510 confocal microscope. The experiments were performed in duplicates; at least three different fields of view were analyzed for each combination of antibodies. 3D reconstruction was done using Imaris 7.6.4 software for scientific imaging.

TABLE 2

Primary Antibodies.

| Antibody | Host | Type | Source | Dilution |
|---|---|---|---|---|
| NF-H | Rabbit | Polyclonal | Enzo | 1:1000 |
| GFAP | Rabbit | Polyclonal | Dako | 1:500 |
| Olig1 | Mouse | Monoclonal | Millipore | 1:500 |
| CNPase | Mouse | Monoclonal | Millipore | 1:500 |
| Calbindin | Mouse | Monoclonal | SIGMA | 1:500 |
| NOGO-A | Rabbit | Polyclonal | Santa Cruz | 1:500 |
| Map2 | Mouse | Monoclonal | Chemicon | 1:1000 |
| MBP/SMI99 | Mouse | Monoclonal | COVANCE | 1:1000 |
| SMI-32 | Mouse | Monoclonal | Stenberger Monoclonals | 1:2000 |
| Synaptophysin | Mouse | Monoclonal | SIGMA | 1:500 |
| VGLUT1 | Rabbit | Polyclonal | Alpha Diagnostic | 1:500 |
| TH | Mouse | Monoclonal | Millipore | 1:250 |
| Nestin | Rabbit | Polyclonal | Millipore | 1:200 |
| Ki67 | Rabbit | Polyclonal | abcam | 1:100 |
| Caspase3 | Rabbit | Polyclonal | R&D | 0.2 μg/ml |
| OLIG1 | Mouse | Monoclonal | Millipore | 1:200 |
| TUJ1 | Mouse | Monoclonal | Stemcell technologies | 1:200 |
| S100B | Rabbit | Polyclonal | Santa Cruz | 1:200 |

Automated Quantitation of Cell Types

BMPS was differentiated for 8 weeks. Randomly selected pictures from three experiments were acquired by confocal imaging and then analyzed with a custom algorithm created with the Cellomics TargetActivation (Thermo Fisher Scientific, Pittsburgh, Pa.) image-analysis software package. With this algorithm, cells were identified based on DRAQ5 stained nucleus and quantified oligodendrocytes and astrocytes based on staining of CNPase, NOGO1 and GFAP.

Myelination Assessment and Quantification

To calculate the percentage of axonal myelination, a semi-automated computer platform was used, termed computer-assisted evaluation of myelin formation (CEM) [82], which uses NIH Image J built-in tools as well as a Math lab processing functions. The results were generated as pixel counts and percent values. The percent of myelinated axons was calculated by dividing the pixel count for myelin by the pixel count for axons after cell body removal and multiplying by 100. For each time point at least 18 fields from at least two independent experiments were analyzed.

Electron Microscopy

BMPS aggregates were collected at 2, 4 and 8 weeks and were fixed in 2% glutaraldehyde and 4% formaldehyde in 0.1M Sodium Cacodylate buffer (EMS, electron microscopy sciences) pH 7.4 with 3% sucrose and 3 mM $CaCl_2$. Post-fixation was done with 2% osmium for 2 hours. The BMPS aggregates were then stained en bloc with 2% uranyl acetate in distilled water for 30 min and subsequently dehydrated in graded ethanol. Embed 812 (EMS) was used as the embedding media. Thin sections (70-80 nm) were cut on a Reichert Jung Ultracut E microtome and placed on formvar coated 100 mesh copper grids. The grids were stained with uranyl acetate and followed by lead citrate. All imaging was performed on a Zeiss Libra 120 electron microscope with a Veleta (Olympus) camera.

Treatment and Cytotoxicity Assay

BMPS was exposed to different concentrations of rotenone and MPP+ for 24 and 48 hours after 4 weeks of differentiation. Rotenone working solutions were prepared in differentiation medium from 10 nM or 100 μM stocks to reach final concentrations of 0.1, 1, 10, 25 and 50 μM. DMSO was used as vehicle control. MPP+ working solutions were prepared in differentiation medium from 30 mM stocks to reach final concentrations of 10, 50, 100, 500, 1,000, 5,000 and 10,000 μM. Four independent experiments in 3 replicates were performed for each experimental condition (control and toxicant exposure for the different time points). Resazurin reduction assay was performed in order to determine cell viability after rotenone and MPP+ treatment. Resazurin (7-Hydroxy-3H-phenoxazin-3-one 10-oxide) is a blue dye that is reduced into red fluorescent resorufin by redox reactions in viable cells. 100 μl Resazurin (2 mg/ml stock) were added directly to the 6 well plates (2 ml/well). Plates were incubated for 3 h at 37° C., 5% $CO_2$. Subsequently, 50 μl of medium were transferred from each well in triplicates to a 96-well plate and fluorescence was measured at 530 nm/590 nm (excitation/emission) using a multi-well fluorometric reader CytoFluor series 4000 (PerSeptive Biosystems, Inc). Data were presented as mean±SD. Statistical analysis was performed using Dunnett's test.

Reactive Oxygen Species Measurement

Reactive oxygen species (ROS) were measured in cell media collected 24 hours after treatment with 5 μM rotenone or 1,000 μM MPP+ using the OxiSelect™ In Vitro ROS/RNS Assay Kit (Cell Biolabs, San Diego, Calif.). This is a fluorescence-based assay measuring the presence of total free radicals within a sample and was used according to the manufacturer's protocol. The quenched fluorogenic dye dichlorodihydrofluorescin-DiOxyQ (DCFH-DiOxyQ) which is similar to the popular 2',7'-dichlorodihydrofluorescein diacetate (DCFH-DA) is first primed with a quench removal reagent. The resulted highly reactive non-fluorescent DCFH can react with present ROS species in the cell supernatant and is then oxidized to the highly fluorescent DCF (2',7'-dichlorodihydroxyfluorescein). At every time point, 50 μl of the cell supernatant was added to a 96-well plate in triplicates and was mixed and incubated with the DCFH-DiOxyQ for 45 minutes. The fluorescence intensity was measured with a fluorescence microplate reader at 480 nm/530 nm (excitation/emission) and was proportional to the total ROS/RNS levels within the sample.

Flow Cytometry

In order to quantify percentage of NPCs, and neurons within the aggregates, flow cytometry with NPC and neuronal markers was performed. Flow cytometry was performed according to previously published protocol [77] with some optimization steps for 3D cultures. Aggregates were washed once with PBS/1 mM EDTA and trypsinized directly in the well using TrypLE Express containing 4 units/ml DNAse for 30 min at 37° C. on the shaker. Pipetting the aggregates up and down with a 1 ml syringe and a 26G3/8 needle ensured generation of single cell suspension. Cells were counted, washed once with PBS/1 mM EDTA, fixed with 2% PFA for 20 min at 4° C., washed twice with PBS/1% BSA (wash solution I, WS I) and blocked for 30 min in blocking solution (PBS/1% BSA/0.15% saponin/10% NGS). $1\times10^6$ cells were stained for one hour at 4° C. with fluorochrome-conjugated antibodies dissolved in blocking solution (Table 3). Unstained cells as well as cells incubated with isotype controls were used as negative controls to set the gates for measurements. Cells were washed twice with PBS/1% BSA/0.15% saponin, once with PBS/1% BSA. Flow cytometry was performed using a Becton Dickinson FACSCalibur system by measuring $10^4$ gating events per measurement. Data was analyzed using FlowJo v10 software.

TABLE 3

Antibodies for flow cytometry analysis

| Antibodies | Host | type | Source | Dilution |
|---|---|---|---|---|
| Alexa Fluor ® 647 Nestin | Mouse | Monoclonal, clone 25 | BD Pharmingen | 1:05 |
| Alexa Fluor ® 488 β-III-Tubulin | Mouse | Monoclonal, clone TUJ1 | BD Pharmingen | 1:05 |
| PerCP-Cy ™ 5.5 Sox2 | Mouse | Monoclonal, clone 030-678 | BD Pharmingen | 1:20 |
| PerCP-Cy ™ 5.5 Sox1 | Mouse | Monoclonal, clone N23-844 | BD Pharmingen | 1:20 |
| PE Doublecortin | Mouse | Monoclonal, clone 30 | BD Pharmingen | 1:20 |
| Alexa Fluor ® 647 Ki67 | Mouse | Monoclonal, clone B56 | BD Pharmingen | 1:20 |

Microelectrode Array (MEA) Recordings

After 8 weeks of differentiation, BMPS were plated on 48-well MEA plates previously coated with Matrigel. During two weeks spontaneous electrical activity was recorded using the ‘Maestro’ MEA platform and Axion’s Integraded Studio (AXIS) software [Axion Biosystems inc.; Atlanta, US]. Each well of the 48-well MEA plate contains 16 individual microelectrodes (~40-50 μm diameter, center-to-center spacing 350 μm) with integrated ground electrodes, resulting in a total of 768 electrodes/plate. The ‘Maestro’ MEA platform has an integrated heating system, which can be controlled by AXIS software. All recordings were performed at a constant temperature of 37° C. Prior to a twenty minutes recording, the MEA plates were placed in the Maestro MEA platform and equilibrated for five min. AXIS software was used to control heating system and monitor the recordings, which includes simultaneously sampling of the channels at 12.5 kHz/channel with a gain of 1200× and a band pass filter of 200-5000 Hz. The recordings were converted into RAW files. After a recording the RAW-files were re-recorded with AXIS to convert the data into a spike file, which includes spike timing and profile information. A variable threshold spike detector was used for the spike-file, it was set at 6 times standard deviations of the rms-noise on each channel. The spike file was later used for data analysis with NeuroExplorer® [Nex Technologies, Madison (AL), US] to convert data into Microsoft Excel files. Using the function rate histogram, a summary of the spikes of all electrodes of one plate was put into one Excel sheet. Only electrodes that recorded activity higher than 0.05 spikes/sec at least once over the time measured were included for data analysis.

Statistical Analysis

Statistical analysis was performed using GraphPad InStat 3. The Dunnett’s test was applied to all the experiments shown here that compare to a control group. Statistically significant values ($p<0.01$) are marked with an asterisk (*). For myelination quantification at the different time points, a Kruskal-Wallis test was employed, statistical significance was considered for p values $<0.05$.

REFERENCES

1. K. Y. Liu, M. King, P. S. Bearman. Social influence and the autism epidemic. *AJS* 115, 1387-434 (2010).
2. M. Rutter. Incidence of autism spectrum disorders: changes over time and their meaning. *Acta. Paediatr.* 94, 2-15 (2005).
3. S. K. Van Den Eeden, C. M. Tanner, A. L. Bernstein, R. D. Fross, A. Leimpeter, D. A. Bloch, L. M. Nelson. Incidence of Parkinson’s disease: variation by age, gender, and race/ethnicity. *Am. J. Epidemiol.* 157, 1015-22 (2003).
4. W, A. Kukull, R. Higdon, J. D. Bowen, W. C. McCormick, L. Teri, G. D. Schellenberg, G. van Belle, L. Jolley, E. B. Larson. Dementia and Alzheimer disease incidence: a prospective cohort study. *Arch. Neurol.* 59, 1737-46 (2002).
5. C. Mo, A. J. Hannan, T. Renoir. Environmental factors as modulators of neurodegeneration: Insights from gene-environment interactions in Huntington’s disease. *Neurosci. Biobehav. Rev.* 52, 178-192 (2015).
6. S. Karama, S. Ducharme, J. Corley, F. Chouinard-Decorte, J. M. Starr, J. M. Wardlaw, M. E. Bastin, I. J. Deary. Cigarette smoking and thinning of the brain’s cortex. *Mol. Psychiatry*. In press (2015).
7. O. van de Rest, A. A. Berendsen, A. Haveman-Nies, L. C. de Groot. Dietary Patterns, Cognitive Decline, and Dementia: A Systematic Review. *Adv. Nutr.* 13, 154-168. (2015)
8. L. Smirnova H. T. Hogberg, M. Leist and T. Hartung. Developmental neurotoxicity—challenges in the 21st century and in vitro opportunities. *ALTEX* 31, 129-156 (2014),
9. T. Hartung. Look back in anger—what clinical studies tell us about preclinical work. *ALTEX.* 30, 275-91 (2013)
10. T. Hartung. Food for thought . . . on cell culture. *ALTEX.* 24, 143-52 (2007)
11. D. Huh, D. C. Leslie, B. D. Matthews, J. P. Fraser, S. Jurek, G. A. Hamilton, K. S. Thorneloe, M. A. McAlexander, D. E. Ingber. A human disease model of drug toxicity-induced pulmonary edema in a lung-on-a-chip microdevice. *Sci. Transl. Med.* 7, 4(159):159ra147 (2012).
12. D. Pamies, T. Hartung, H. T. Hogberg. Biological and medical applications of a brain-on-a-chip. *Exp. Biol. Med.* 239, 1096-107 (2014)
13. A. Agarwal, J. A. Goss, A. Cho, M. L. McCain, K. K. Parker. Microfluidic heart on a chip for higher throughput pharmacological studies. *Lab on a chip* 13, 3599-3608 (2013).

14. H. T. Hogberg, J. Bressler, K. M. Christian, G. Harris, G. Makri, C. O'Driscol, D. Pamies, L. Smirnova, Z. Wen, T. Hartung. Toward a 3D model of human brain development for studying gene/environment interactions. *Stem. Cell. Res*. Ther. 4 Suppl 1:S4 (2013).

15. M. A. Lancaster, M. Renner, C. A. Martin, D. Wenzel, L. S. Bicknell, M. E. Hurles, T. Homfray, J. M. Penninger, A. P. Jackson, J. A. Knoblich. Cerebral organoids model human brain development and microcephaly. *Nature* 19, 373-9 (2013).

16. Kadoshima T, Sakaguchi H, Nakano T, Soen M, Ando S, Eiraku M, Sasai Y. Self-organization of axial polarity, inside-out layer pattern, and species-specific progenitor dynamics in human ES cell-derived neocortex. *Proc. Natd. Acad. Sci. USA*. 110, 20284-9 (2013).

17. D. Huh, H. J. Kim, J. P. Fraser, D. E. Shea, M. Khan, A. Bahinski, G. A. Hamilton, D. E. Ingber. Microfabrication of human organs-on-chips. *Nat. Protoc.* 8, 2135-57 (2013).

18. N. Aldpde, A. Bahinski, M. Daneshian, B. De Wever, E. Fritsche, A. Goldberg, J. Hansmann, T. Hartung, J. Haycock, H. Hogberg, L. Hoelting, J. M. Kelm, S. Kadereit, E. McVey, R. Landsiedel, M. Leist, M. Lubberstedt, F. Noor, C. Pellevoisin, D. Petersohn, U. Pfannenbecker, K. Reisinger, T. Ramirez, B. Rothen-Rutishauser, M. Schäfer-Korting, K. Zeilinger, M. G. Zurich. State-of-the-art of 3D cultures (organs-on-a-chip) in safety testing and pathophysiology. *ALTEX*. 31, 441-77 (2014).

19. T. Hartung, J. Zurlo. Alternative approaches for medical countermeasures to biological and chemical terrorism and warfare. *ALTEX*. 29, 251-60 (2012).

20. K. Takahashi, K. Tanabe, M. Ohnuki, M. Narita, T. Ichisaka, K. Tomoda, S. Yamanaka. Induction of pluripotent stem cells from adult human fibroblasts by defined factors. *Cell* 131: 861-872 (2007).

21. J. Yu, M. A. Vodyanik, K. Smuga-Otto, J. Antosiewicz-Bourget, J. L. Frane, S. Tian, J. Nie, G. A. Jonsdottir, V. Ruotti, R. Stewart, I. I. Slukvin, J. A. Thomson. Induced pluripotent stem cell lines derived from human somatic cells. *Science* 318: 1917-1920 (2007)

22. Y. Tsai, B. Lu, B. Bakondi, S. Girman, A. Sahabian, D. Sareen, C. N. Svendsen, S. Wang. Human iPSC-Derived Neural Progenitors Preserve Vision in an AMD-like Model. *Stem. Cells*. In press (2015).

23. K. Nieweg, A. Andreyeva, B. van Stegen, G. Tanriöver, K. Gottmann. Alzheimer's disease-related amyloid-β induces synaptotoxicity in human iPS cell-derived neurons. *Cell. Death. Dis*. In press. (2015)

24. S. Raitano, L. Ordovàs, L. De Muynck, W. Guo, I. Espuny-Camacho, M. Geraerts, S. Khurana, K. Vanuytsel, B. I. Tóth, T. Voets, R. Vandenberghe, T. Cathomen, L. Van Den Bosch, P. Vanderhaeghen, P. Van Damme, C. M. Verfaillie. Restoration of progranulin expression rescues cortical neuron generation in an induced pluripotent stem cell model of frontotemporal dementia. *Stem Cell Reports*. 13, 16-24 (2015).

25. H. Monyer, R. Sprengel, R. Schoepfer, A. Herb, M. Higuchi, H. Lomeli, N. Bumashev, B. Sakmann, P. H. Seeburg. Heteromeric NMDA receptors: molecular and functional distinction of subtypes. *Science* 256, 1217-1221 (1992).

26. X. Li, P. Jin. Roles of small regulatory RNAs in determining neuronal identity. *Nat. Rev. Neurosci.* 11, 329-38 (2010).

27. C. Tarantino, G. Paolella, L. Cozzuto, G. Minopoli, L. Pastore, S. Parisi, T. Russo. miRNA 34a, 100, and 137 modulate differentiation of mouse embryonic stem cells. *FASEB Journal* 24, 3255-3263 (2010).

28. D. Yang, T. Li, Y. Wang, Y. Tang, H. Cui, X. Zhang, D. Chen, N. Shen, W. Le W. miR-132 regulates the differentiation of dopamine neurons by directly targeting Nurr1 expression. *Journal of Cell Science* 125, 1673-1682 (2012).

29. D. Edbauer, J. R. Neilson, K. A. Foster, C. F. Wang, D. P. Seeburg, M. N. Batterton, T. Tada, B. M. Dolan, P. A. Sharp, M. Sheng. Regulation of synaptic structure and function by FMRP-associated microRNAs miR-125b and miR-132. *Neuron* 65, 373-384 (2010).

30. S. U. Kim, F. A. McMorris, T. J. Sprinkle. Immunofluorescence demonstration of 2':3'-cyclic-nucleotide 3'-phosphodiesterase in cultured oligodendrocytes of mouse, rat, calf and human. *Brain Res.* 300, 195-9 (1984).

31. W. Deng, R. D. Poretz. Oligodendroglia in developmental neurotoxicity. *Neurotoxicology*. 24, 161-78 (2003).

32. S. P. Fancy, J. R. Chan, S. E. Baranzini, R. J. Franklin, D. H. Rowitch. Myelin Regeneration: A recapitulation of development? *Annu. Rev. Neurosci.* 34, 21-43 (2011)

33. M. E. Schwab. Functions of Nogo proteins and their receptors in the nervous system. *Nat. Rev. Neurosci.* 11, 799-811 (2010).

34. D. H. Meijer, M. F. Kane, S. Mentha, H. Liu, E. Harrington, C. M. Taylor, C. D. Stiles, D. H. Rowitch. Separated at birth? The functional and molecular divergence of OLIG1 and OLIG2. *Nat. Rev. Neurosci.* 13, 819-31 (2012).

35. Y. Yamaguchi, M. Miura. Programmed cell death in neurodevelopment. *Dev. Cell.* 32, 478-90 (2015).

36. H. A. Juraver-Geslin, B. C. Durand. Early development of the neural plate: new roles for apoptosis and for one of its main effectors caspase-3. *Genesis*. 53, 203-24 (2015).

37. A. K. Krug, S. Gutbier, L. Zhao, D. Pöltl, C. Kullmann, V. Ivanova, S. Förster, S. Jagtap, J. Meiser, G. Leparc, S. Schildknecht, M. Adam, K. Hiller, H. Farhan, T. Brunner, T. Hartung, A. Sachinidis, M. Leist. Transcriptional and metabolic adaptation of human neurons to the mitochondrial toxicant MPP(+). *Cell Death Dis.* 5, e1222 (2014).

38. T. Nakano, S. Ando, N. Takata, M. Kawada, K. Muguruma, K. Sekiguchi, K. Saito, S. Yonemura, M. Eiraku, Y. Sasai. Self-formation of optic cups and storable stratified neural retina from human ESCs. *Cell Stem Cell.* 14, 771-85 (2012)

39. M. Eiraku, N. Takata, H. Ishibashi, M. Kawada, E. Sakakura, S. Okuda, K. Sekiguchi, T. Adachi, Y. Sasai. Self-organizing optic-cup morphogenesis in three-dimensional culture. *Nature*. 472, 51-6 (2012).

40. H. Suga, T. Kadoshima, M. Minaguchi, M. Ohgushi, M. Soen, T. Nakano, N. Takata, T. Wataya, K. Muguruma, H. Miyoshi, S. Yonemura, Y. Oiso, Y. Sasai. Self-formation of functional adenohypophysis in three-dimensional culture. *Nature*. 480, 57-62 (2011).

41. E. van Vliet, S. Morath, C. Eskes, J. Linge, J. Rappsilber, P. Honegger, T. Hartung, S. Coecke. A novel in vitro metabolomics approach for neurotoxicity testing, proof of principle for methyl mercury chloride and caffeine. *Neurotoxicology*. 29, 1-12 (2008).

42. J. Kim, K. Inoue, J. Ishii, W. B. Vanti, S. V. Voronov, E. Murchison, G. Hannon, A. Abeliovich. A MicroRNA feedback circuit in midbrain dopamine neurons. *Science* 317, 1220-1224 (2007).

43. C. Wiese, A. Rolletschek, G. Kania, P. Blyszczuk, K. V. Tarasov, Y. Tarasova, R. P. Wersto, K. R. Boheler, A. M. Wobus. Nestin expression—a property of multi-lineage progenitor cells? *Cell. Mol. Life. Sci.* 61, 2510-22 (2004).

44. C. Lépinoux-Chambaud, J. Eyer. Review on intermediate filaments of the nervous system and their pathological alterations. Histochem. Cell. Biol. 140, 13-22 (2013).
45. J. Park, B. K. Lee, G. S. Jeong, J. K. Hyun, C. J. Lee, S. H. Lee. Three-dimensional brain-on-a-chip with an interstitial level of flow and its application as an in vitro model of Alzheimer's disease. *Lab Chip.* 15, 141-50 (2015).
46. J. P. Dollé, B. Morrison, R. S. Schloss, M. L. Yarmush. Brain-on-a-chip microsystem for investigating traumatic brain injury: Axon diameter and mitochondrial membrane changes play a significant role in axonal response to strain injuries. *Technology* (*Singap. World. Sci.*). 2,106 (2014).
47. S. J. Mullett, D. A. Hinkle. DJ-1 knock-down in astrocytes impairs astrocyte-mediated neuroprotection against rotenone. *Neurobiol. Dis.* 33, 28-36 (2009).
48. Y. Shinozaki, M. Nomura, K. Iwatsuki, Y. Moriyama, C. Gachet, S. Koizumi. Microglia trigger astrocyte-mediated neuroprotection via purinergic gliotransmission. *Sci. Rep.* 4, 4329 (2014).
49. D. Aguirre-Rueda, S, Guerra-Ojeda, M. Aldasoro, A. Iradi, E. Obrador, A. Ortega, M. D. Mauricio, J. M. Vila, S. L. Valles. Astrocytes protect neurons from Aβ1-42 peptide-induced neurotoxicity increasing TFAM and PGC-1 and decreasing PPAR-γ and SIRT-1. *Int. J. Med. Sci.* 12, 48-56. (2015).
50. R. Sattler, M. Tymianski. Molecular mechanisms of glutamate receptormediated excitotoxic neuronal cell death. *Mol. Neurobiol.* 24, 107-129 (2001).
51. Y. Shao, M. Gearing, S. S. Mirra. Astrocyte-apolipoprotein E associations in senile plaques in Alzheimer disease and vascular lesions: a regional immunohistochemical study. *J. Neuropathol. Exp. Neurol.* 56, 376-381 (1997)
52. C. Schwab, P. L. McGeer. Inflammatory aspects of Alzheimer disease and other neurodegenerative disorders. *J. Alzheimers. Dis.* 13, 359-369 (2008).
53. P. Damier, E. C. Hirsch, P. Zhang, Y. Agid, F. Javoy-Agid. Glutathione peroxidase, glial cells and Parkinson's disease. *Neuroscience* 52, 1-6 (1993).
54. C. Xie, Y. Q. Liu, Y. T. Guan, G. X. Zhang. Induced Stem Cells as a Novel Multiple Sclerosis Therapy. *Curr Stem Cell Res Ther.* In press (2015).
55. S. Wang, J. Bates, X. Li, S. Schanz, D. Chandler-Militello, C. Levine, N. Maherali, L. Studer, K. Hochedlinger, M. Windrem, S. A. Goldman. Human iPSC-derived oligodendrocyte progenitor cells can myelinate and rescue a mouse model of congenital hypomyelination. *Cell Stem Cell.* 12, 252-64 (2013)
56. M. Pinto, S. Dobson. BK and JC virus: a review. *J. Infect.* 68 Suppl 1:S2-8 (2014).
57. X. B. Liu, Y. Shen, J. M. Plane, W. Deng. Vulnerability of premyelinating oligodendrocytes to white-matter damage in neonatal brain injury. *Neurosci. Bull.* 29, 229-38 (2013).
58. G. Bartzokis. Age-related myelin breakdown: a developmental model of cognitive decline and Alzheimer's disease. *Neurobiol. Aging.* 25, 5-18 (2004).
59. H. Okamoto, T. Miki, K. Y. Lee, T. Yokoyama, H. Kuma, Z. Y. Wang, H. Gu, H. P. Li, Y. Matsumoto, S. Irawan, K. S. Bedi, Y. Nakamura, Y. Takeuchi. Oligodendrocyte myelin glycoprotein (OMgp) in rat hippocampus is depleted by chronic ethanol consumption. *Neurosci. Lett.* 406, 76-80 (2006).
60. T. W. Bouldin, G. Samsa, T. S. Earnhardt, M. R. Krigman. Schwann cell vulnerability to demyelination is associated with intemodal length in tellurium neuropathy. J. *Neuropathol. Exp. Neurol.* 47, 41-47 (1988).
61. P. David, K. Subramaniam. Prenatal alcohol exposure and early postnatal changes in the developing nerve-muscle system. *Birth Defects Res. A. Clin. Mol. Teratol.* 73, 897-903 (2005).
62. G. J. Harry, A. D. Toews, M. R. Krigman, P. Morell. The effect of lead toxicity and milk deprivation of myelination in the rat. *Toxicol. Appl. Pharmacol.* 77, 458-464 (1985).
63. S. J. Rothenberg, A. Poblano, S. Garza-Morales. Prenatal and perinatal low level lead exposure alters brainstem auditory evoked responses in infants. *Neurotoxicology* 15, 695-699 (1994).
64. E. Tiffany-Castiglioni, J. Zmudzki, G. R. Bratton. Cellular targets of lead neurotoxicity: in vitro models. *Toxicology* 42, 303-315 (1986).
65. E. Tiffany-Castiglioni. Cell culture models for lead toxicity in neuronal and glial cells. *Neurotoxicology.* 14, 513-36 (1993).
66. J. Parkinson. An essay on the shaking palsy. 1817. J. Neuropsychiatry *Clin. Neurosci.* 14:223-36 (2002)
67. K. R. Chaudhuri, P. Odin. The challenge of non-motor symptoms in Parkinson's disease. *Prog. Brain. Res.* 184, 325-41 (2010).
68. P. McGonigle. Animal models of CNS disorders. *Biochem. Pharmacol.* 87, 140-9 (2014).
69. K. Tieu. A guide to neurotoxic animal models of Parkinson's disease. Cold. Spring. Harb. Perspect. Med. In press (2011).
70. S. E. Cavanaugh, J. J. Pippin, N. D. Barnard. Animal models of Alzheimer disease: historical pitfalls and a path forward. *ALTEX.* 31, 279-302 (2014).
71. A. Pombero, C. Bueno, L. Saglietti, M. Rodenas, J. Guimera, A. Bulfone, S. Martinez. Pallial origin of basal forebrain cholinergic neurons in the nucleus basalis of Meynert and horizontal limb of the diagonal band nucleus. *Development.* 138, 4315-26 (2011).
72. H. McCann, C. H. Stevens, H. Cartwright, G. M. Halliday. α-Synucleinopathy phenotypes. *Parkinsonism. Relat. Disord.* 20 Suppl 1, S62-7 (2014).
73. V. N. Uversky. A protein-chameleon: conformational plasticity of alphasynuclein, a disordered protein involved in neurodegenerative disorders. *J. Biomol. Struct. Dyn.* 21, 211-34 (2003)
74. G. A. Petsko and D. Ringer. Ice cleaved alpha-synuclein a biomarker. Patent WO2012061786 A1. (2012)
75. Wen Z, Nguyen H N, Guo Z, Lalli M A, Wang X, Su Y, Kim N S, Yoon K J, Shin J, Zhang C, Makri G, Nauen D, Yu H, Guzman E, Chiang C H, Yoritomo N, Kaibuchi K, Zou J, Christian K M, Cheng L, Ross C A, Margolis R L, Chen G, Kosik K S, Song H, Ming G L. Synaptic dysregulation in a human iPS cell model of mental disorders. *Nature.* 2014 Nov. 20; 515(7527):414-8.
76. P. Chomczynski, N. Sacchi N. Single-step method of RNA isolation by acid guanidinium thiocyanate-phenol-chloroform extraction. *Ana.l Biochem.* 162, 156-9 (1987).
77. L. Smirnova, A. E. M. Seiler, A. Luch. microRNA profiling as tool for developmental neurotoxicity testing (DNT). *Toxicol.* 64:20.9.1-20.9.22, 2015
78. K. J. Livak, T. D. Schmittgen. Analysis of relative gene expression data using real-time quantitative PCR and the 2(−Delta Delta C(T)) Method. *Methods.* 25, 402-8 (2001).
79. Nave, K. A. Myelination and support of axonal integrity by glia. *Nature* 468, 244-252, (2010).
80. Saab, A. S., Tzvetanova, I. D. & Nave, K. A. The role of myelin and oligodendrocytes in axonal energy metabolism. *Current opinion in neurobiology* 23, 1065-1072, (2013).

81. Pardridge, W. M. Crossing the blood brain barrier: are we getting it right? *Drug Disc. Today* January 1; 6(1): 1-2, (2001).
82. Kerman, B. E. et al. *In vitro myelin formation using embryonic stem cells. Development* 142, 2213-2225, (2015)
83. Gaj T, Gersbach C A, Barbas C F 3rd. ZFN, TALEN, and CRISPR/Cas-based methods for genome engineering. *Trends Biotechnol*. July; 31(7):397-405, (2013).
84. Hockemeyer D, Soldner F, Beard C, Gao Q, Mitalipova M, DeKelver R C, Katibah G E, Amora R, Boydston E A, Zeitler B, Meng X, Miller J C, Zhang L, Rebar E J, Gregory P D, Urnov F D, Jaenisch R. Efficient targeting of expressed and silent genes in human ESCs and iPSCs using zinc-finger nucleases. *Nat Biotechnol*. September; 27(9):851-7, (2009).
85. Hockemeyer D, Wang H, Kiani S, Lai C S, Gao Q, Cassady J P, Cost G J, Zhang L, Santiago Y, Miller J C, Zeitler B, Cherone J M, Meng X, Hinkley S J, Rebar E J, Gregory P D, Urnov F D, Jaenisch R. Genetic engineering of human pluripotent cells using TALE nucleases. *Nat Biotechnol*. July 7; 29(8):731-4, (2011).
86. Mali P, Aach J, Stranges P B, Esvelt K M, Moosburner M, Kosuri S, Yang L, Church G M. CAS9 transcriptional activators for target specificity screening and paired nickases for cooperative genome engineering. *Nat Biotechnol*. September; 31(9):833-8, (2013).
87. Chang N, Sun C, Gao L, Zhu D, Xu X, Zhu X, Xiong J W, Xi J J. Genome editing with RNA-guided Cas9 nuclease in zebrafish embryos. *Cell Res*. April; 23(4):465-72, (2013).
88. Cong L, Ran F A, Cox D, Lin S, Barretto R, Habib N, Hsu P D, Wu X, Jiang W, Marraffini L A, Zhang F. Multiplex genome engineering using CRISPR/Cas systems. *Science*. February 15; 339(6121):819-23, (2013).
89. Ran F A, Hsu P D, Wright J, Agarwala V, Scott D A, Zhang F. Genome engineering using the CRISPR-Cas9 system. *Nat Protoc*. November; 8(11):2281-308, (2013).
90. Kim W R, Sun W. 2011. Programmed cell death during postnatal development of the rodent nervous system. *Development, growth & differentiation* 53: 225-235, (2011).

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. An in vitro brain microphysiological system (BMPS), comprising

A. an induced pluripotent stem cell (iPSC) wherein the iPSC is configured to differentiate into at least one neural cell type aggregated into a spheroid mass; and a population of microglia-like cells, wherein B. the in vitro BMPS is electrophysiologically active in a spontaneous manner.

2. The BMPS of claim 1, wherein the micro-glia like cells comprise microglia, microglia precursor cells, or a combination thereof.

3. The BMPS of claim 1, wherein the micro-glia like cells comprise monocytes, human monocytes, pro-monocyte cell lines, hematopoietic stem cells, isolated microglia, immortalized microglia, or combinations thereof.

4. The BMPS of claim 3, where the monocytes comprise adult cell-derived monocytes, embryonic cell-derived monocytes, or a combination thereof.

5. The BMPS of claim 4, wherein the monocytes comprise embryonic stem cell (ESC)-derived monocytes, induced pluripotent stem cell (iPSC)-derived monocytes, or a combination thereof.

6. The BMPS of claim 3, wherein the isolated microglia comprise adult microglia, fetal microglia, or a combination thereof.

7. The BMPS of claim 3, wherein the microglia-like cells are derived from somatic cells, neuronal cells, myeloid progenitor cells, or a combination thereof.

8. The BMPS of claim 1, wherein the microglia-like cells express one or more of the following biomarkers: HLA-DR, Iba1, CD14, CX3CR1, F4/80, CD80, CD86, CD36, iNOS, COX2, ARG1, PPARγ, SOCS-3, TMEM119, Mertk, Ax1, CD11b, CD11c, P2RY12, CD45, CD68, CD40, B7, ICAM-1, or any combination thereof.

9. The BMPS of claim 1, wherein the BMPS expresses receptors associated with microglia function.

10. The BMPS of claim 9, wherein the receptors associated with microglia function comprise CCL2, CX3CL, RAGE, NLRP3, SR-AI, TREM2, FPRL1/FPR2, CD36, CD33, C5a, CR1, CR3/Mac-1, FcRs, FPRs, TLRs, or a combination thereof.

11. The BMPS of claim 1, wherein the BMPS is configured to elicit a pro-inflammatory response, an anti-inflammatory response, or a combination thereof in response to a stimulus.

12. The BMPS of claim 10, the BMPS being configured to elicit a pro-inflammatory response, and the stimulus comprises viral infection, LPS exposure, or a combination thereof.

13. The BMPS of claim 10, the BMPS being configured to elicit an anti-inflammatory response, and the stimulus comprises IL-3, IL-4, IL-10, IL-13, IL-1β, IL-6, TNF-α, TGF-β, or a combination thereof.

14. The BMPS of claim 10, wherein the microglia-like cells comprise about 20% or less of the BMPS.

15. The BMPS of claim 10, wherein the at least one neural cell type comprises a mature neuron, a glial cell, or a combination thereof.

16. The BMPS of claim 15, wherein the at least one neural cell type further comprises astrocytes, polydendrocytes, oligodendrocytes, or combinations thereof.

17. The BMPS of claim 10, wherein the in vitro BMPS has neural characteristics selected from the group consisting of synaptogenesis, neuron-neuron interactions, neuronal-glial interactions, axon myelination, cell migration, neurological development, disease phenotypes, and combinations thereof.

18. The BMPS of claim 17, wherein disease process phenotypes comprise autophagy, integrated stress response, non-sense mediated decay, lesions, amyloid deposition, plaque formation, protein aggregation, or combinations thereof.

19. The BMPS of claim 10, wherein the at least one neural cell type express one or more biomarker selected from the group consisting of MBP, PLP, NG2, Olig1, Olig2, Olig 3, OSP, MOG, SOX10, neurofilament 200 (NF200), GRIN1, GAD1, GABA, TH, LMX1A, FOXO1, FOXA2, FOXO4, CNP, TH, TUBIII, NEUN, SLC1A6, and any combination thereof.

20. The in vitro BMPS of claim 10, wherein the spheroid mass comprises a diameter that is about 1000 μm or less.

21. The in vitro BMPS of claim 20, wherein the spheroid mass comprises a diameter that is about 500 μm or less.

22. The BMPS of claim 10, further comprising one or more endothelial cells, pericytes, or a combination thereof capable of forming a blood-brain-barrier.

* * * * *